(12) United States Patent
Donner et al.

(10) Patent No.: US 9,464,082 B2
(45) Date of Patent: Oct. 11, 2016

(54) ARYL AND ARYLALKYL SUBSTITUTED PYRAZOLYL AND PYRIMIDINYL TRICYCLIC ENONES AS ANTIOXIDANT INFLAMMATION MODULATORS

(71) Applicants: AbbVie Inc., North Chicago, IL (US); Reata Pharmaceuticals, Inc., Irving, TX (US)

(72) Inventors: Pamela Donner, Mundelein, IL (US); Rolf Wagner, Antioch, IL (US); Jason Shanley, Chicago, IL (US); Howard Heyman, Deerfield, IL (US); Allan Krueger, Gurnee, IL (US); Hui-Ju Chen, Grayslake, IL (US); Michael Rozema, Kenosha, WI (US); David Grampovnik, Waukegan, IL (US); Melean Visnick, Irving, TX (US); Eric Anderson, Southlake, TX (US); Xin Jiang, Coppell, TX (US); Christopher F. Bender, Garland, TX (US); Gary Louis Bolton, Ann Arbor, MI (US); Bradley William Caprathe, Livonia, MI (US); Chitase Lee, Ann Arbor, MI (US); William Howard Roark, Ann Arbor, MI (US)

(73) Assignees: AbbVie Inc., North Chicago, IL (US); Reata Pharmaceuticals, Inc., Irving, TX (US)

( * ) Notice: Subject to any disclaimer, the term of this patent is extended or adjusted under 35 U.S.C. 154(b) by 0 days.

(21) Appl. No.: 14/604,129

(22) Filed: Jan. 23, 2015

(65) Prior Publication Data
US 2015/0225397 A1    Aug. 13, 2015

Related U.S. Application Data

(60) Provisional application No. 61/931,291, filed on Jan. 24, 2014.

(51) Int. Cl.

| | | |
|---|---|---|
| *C07D 231/54* | (2006.01) | |
| *C07D 239/70* | (2006.01) | |
| *C07D 239/72* | (2006.01) | |
| *C07D 401/04* | (2006.01) | |
| *C07D 403/04* | (2006.01) | |
| *C07D 417/04* | (2006.01) | |
| *C07D 471/04* | (2006.01) | |
| *C07D 413/04* | (2006.01) | |

(52) U.S. Cl.
CPC .......... *C07D 471/04* (2013.01); *C07D 231/54* (2013.01); *C07D 239/70* (2013.01); *C07D 239/72* (2013.01); *C07D 401/04* (2013.01); *C07D 403/04* (2013.01); *C07D 413/04* (2013.01); *C07D 417/04* (2013.01)

(58) Field of Classification Search
CPC  C07D 231/54; C07D 239/70; C07D 239/72; C07D 401/04; C07D 403/04; C07D 413/04; C07D 417/04; C07D 471/04
See application file for complete search history.

(56) References Cited

U.S. PATENT DOCUMENTS

| 2002/0115856 A1 | 8/2002 | Sakya |
| 2003/0125361 A1 | 7/2003 | Clare et al. |

FOREIGN PATENT DOCUMENTS

| WO | WO-2011130302 A2 | 10/2011 | | |
| WO | WO 2012083306 | * | 6/2012 | .......... C07D 231/54 |
| WO | WO-2012083306 A2 | 6/2012 | | |

OTHER PUBLICATIONS

Abraham N.G., et al., "Heme Oxygenase and the Cardiovascular-renal System.," Free Radical Biology & Medicine, 2005 , vol. 39 (1), pp. 1-25.
Ahmad R., et al., "Triterpenoid Cddo-me Blocks the Nf-kappab Pathway by Direct inhibition of Ikkbeta on Cys-179.," The Journal of Biological Chemistry, 2006, vol. 281 (47), pp. 35764-35769.
Ahmad R., et al., "Triterpenoid Cddo-methyl Ester inhibits the Janus-activated Kinase-1 (jak1)->signal Transducer and Activator of Transcription-3 (stat3) Pathway by Direct inhibition of Jak1 and Stat3.," Cancer Research, 2008, vol. 68 (8), pp. 2920-2926.
Araujo J.A., et al., "Systemic Rather than Local Heme Oxygenase-1 Overexpression Improves Cardiac Allograft Outcomes in a New Transgenic Mouse.," Journal of Immunology , 2003 , vol. 171 (3), pp. 1572-1580.
Bach F.H., "Heme Oxygenase-1 and Transplantation tolerance.," Human Immunology, 2006 , vol. 67 (6), pp. 430-432.
Berge S.M., et al., "Pharmaceutical Salts," Journal of Pharmaceutical Sciences, 1977, vol. 66 (1), pp. 1-19.
Cai D., et al., "Local and Systemic insulin Resistance Resulting from Hepatic Activation of Ikk-beta and Nf-kappab.," Nature Medicine, 2005, vol. 11 (2), pp. 183-190. 0.

(Continued)

*Primary Examiner* — Erich A Leeser

(57) ABSTRACT

The present application relates to: (a) compounds of Formula (I):

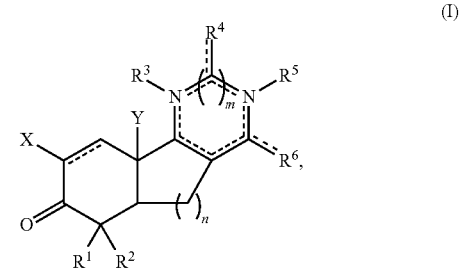

and salts thereof, wherein $R^1$, $R^2$, $R^3$, $R^4$, $R^5$, $R^6$, m, n, X and Y are as defined in the specification; (b) compositions comprising such compounds and salts; and (c) methods of use of such compounds, salts, and compositions, particularly use for the treatment and prevention of diseases such as those associated with oxidative stress and inflammation.

24 Claims, No Drawings

(56) References Cited

OTHER PUBLICATIONS

Chauhan A., et al., "Oxidative Stress in Autism.," Pathophysiology, 2006, vol. 13 (3), pp. 171-181.

Dickerson F., et al., "Elevated Serum levels of C-reactive Protein are Associated with Mania Symptoms in Outpatients with Bipolar Disorder.," Progress in Neuro-psychopharmacology & Biological Psychiatry, 2007, vol. 31 (4), pp. 952-955.

Dinkova-Kostova A.T., et al., "Extremely Potent Triterpenoid inducers of the Phase 2 Response: Correlations of Protection Against Oxidant and inflammatory Stress.," Proceedings of the National Academy of Sciences of the United States of America, 2005, vol. 102 (12), pp. 4584-4589.

Forstermann U., "Janus-faced Role of Endothelial no Synthase in Vascular Disease: Uncoupling of Oxygen Reduction from No Synthesis and Its Pharmacological Reversal.," Biological Chemistry, 2006, vol. 387 (12), pp. 1521-1533.

Greene T.W., et al., in: Protective Groups in Organic Synthesis, 3rd Edition, John Wiley and Sons, Inc., 1999, Preface, Table of Contents, Abbreviations.

Hanson D.R., et al., "Theories of Schizophrenia: A Genetic-inflammatory-vascular Synthesis.," BMC Medical Genetics, 2005, vol. 6 (7).

Honda T., et al., "A Novel Dicyanotriterpenoid, 2-cyano-3,12-dioxooleana-1,9(11)-dien-28-onitrile, Active at Picomolar Concentrations for inhibition of Nitric Oxide Production.," Bioorganic & Medicinal Chemistry Letters, 2002, vol. 12 (7), pp. 1027-1030.

Honda T., et al., "Design and Synthesis of 2-cyano-3,12-dioxoolean-1,9-dien-28-oic Acid, a Novel and Highly Active inhibitor of Nitric Oxide Production in Mouse Macrophages.," Bioorganic & Medicinal Chemistry Letters, 1998, vol. 8 (19), pp. 2711-2714.

Honda T., et al., "Design, Synthesis, and Anti-inflammatory Activity both in Vitro and in Vivo of New Betulinic Acid Analogues Having an Enone Functionality in Ring A.," Bioorganic & Medicinal Chemistry Letters, 2006, vol. 16 (24), pp. 6306-6309.

Honda T., et al., "New Enone Derivatives of Oleanolic Acid and Ursolic Acid as inhibitors of Nitric Oxide Production in Mouse Macrophages," Bioorganic & Medicinal Chemistry Letters, 1997, vol. 7, pp. 1623-1628.

Honda T., et al., "Novel Synthetic Oleanane and Ursane Triterpenoids with Various Enone Functionalities in Ring a as inhibitors of Nitric Oxide Production in Mouse Macrophages.," Journal of Medicinal Chemistry, 2000, vol. 43 (9), pp. 1866-1877.

Honda T., et al., "Novel Synthetic Oleanane Triterpenoids: A Series of Highly Active inhibitors of Nitric Oxide Production in Mouse Macrophages.," Bioorganic & Medicinal Chemistry Letters, 1999, vol. 9 (24), pp. 3429-3434.

Honda T., et al., "Synthetic Oleanane and Ursane Triterpenoids with Modified Rings A and C: A Series of Highly Active inhibitors of Nitric Oxide Production in Mouse Macrophages.," Journal of Medicinal Chemistry, 2000, vol. 43 (22), pp. 4233-4246.

Hotamisligil GS., "Endoplasmic Reticulum Stress and the inflammatory Basis of Metabolic Disease.," Cell, 2010, vol. 140 (6), pp. 900-917.

Hotamisligil GS., "inflammation and Metabolic Disorders.," Nature, 2006, vol. 444 (7121), pp. 860-867.

International Search Report and Written Opinion for Application No. PCT/US2015/012579, mailed on Mar. 19, 2015, 11 pages.

Ishikawa K., et al., "Heme Oxygenase-1 inhibits Atherogenesis in Watanabe Heritable Hyperlipidemic Rabbits.," Circulation, 2001, vol. 104 (15), pp. 1831-1836.

IUPAC 1974 Recommendations for Section E, Fundamental Stereochemistry, Pure and Applied Chemistry, 1976, vol. 45, pp. 13-30.

Kawakami Y., et al., "A Comparative Study of Nitric Oxide, Glutathione, and Glutathione Peroxidase Activities in Cerebrospinal Fluid from Children with Convulsive Diseases/children with Aseptic Meningitis.," Brain & Development, 2006, vol. 28 (4), pp. 243-246.

Kendall-Tackett K.A., "inflammation, Cardiovascular Disease, and Metabolic Syndrome as Sequelae of Violence against Women: the Role of Depression, Hostility, and Sleep Disturbance.," Trauma, Violence & Abuse, 2007, vol. 8 (2), pp. 117-126.

Kruger A.L., et al., "Up-regulation of Heme Oxygenase Provides Vascular Protection in an Animal Model of Diabetes through Its Antioxidant Antiapoptotic Effects.," The Journal of Pharmacology and Experimental therapeutics, 2006, vol. 319 (3), pp. 1144-1152.

Lee H., et al., "Double-stranded Rna induces inos Gene Expression in Schwann Cells, Sensory Neuronal Death, and Peripheral Nerve Demyelination.," Glia, 2007, vol. 55 (7), pp. 712-722.

Lencz T., et al., "Converging Evidence for a Pseudoautosomal Cytokine Receptor Gene Locus in Schizophrenia.," Molecular Psychiatry, 2007, vol. 12 (6), pp. 572-580.

Liby K., et al., "Novel Semisynthetic Analogues of Betulinic Acid with Diverse Cytoprotective, Antiproliferative, and Proapoptotic Activites.," Molecular Cancer Therapeutics, 2007, vol. 6 (7), pp. 2113-2119.

Liby K., et al., "The Synthetic Triterpenoids, Cddo and Cddo-imidazolide, are Potent inducers of Heme Oxygenase-1 and Nrf2/are Signaling.," Cancer Research, 2005, vol. 65 (11), pp. 4789-4798.

Liby K.T., et al., "Triterpenoids and Rexinoids as Multifunctional Agents for the Prevention and Treatment of Cancer.," Nature Reviews Cancer, 2007, vol. 7 (5), pp. 357-369.

Liu X., et al., "Heme Oxygenase-1 (ho-1) inhibits Postmyocardial infarct Remodeling and Restores Ventricular Function.," Faseb Journal, 2006, vol. 20 (2), pp. 207-216.

Lu T., et al., "Tumor-infiltrating Myeloid Cells induce Tumor Cell Resistance to Cytotoxic T Cells in Mice.," The Journal of Clinical Investigation, 2011, vol. 121 (10), pp. 4015-4029.

McIver K.L., et al., "No-mediated Alterations in Skeletal Muscle Nutritive Blood Flow and Lactate Metabolism in Fibromyalgia.," Pain, 2006, vol. 120 (1-2), pp. 161-169.

Morris B.J., et al., "Association of a Functional inducible Nitric Oxide Synthase Promoter Variant with Complications in Type 2 Diabetes.," Journal of Molecular Medicine, 2002, vol. 80 (2), pp. 96-104.

Morse D., et al., "Heme Oxygenase-1: from Bench to Bedside.," American Journal of Respiratory and Critical Care Medicine, 2005, vol. 172 (6), pp. 660-670.

Morse D., et al., "Heme Oxygenase-1: the "emerging Molecule" has Arrived.," American Journal of Respiratory Cell and Molecular Biology, 2002, vol. 27 (1), pp. 8-16.

Naik A.K., et al., "Role of Oxidative Stress in Pathophysiology of Peripheral Neuropathy and Modulation by N-acetyl-l-cysteine in Rats.," European Journal of Pain, 2006, vol. 10 (7), pp. 573-579.

Pall M.L., "Nitric Oxide Synthase Partial Uncoupling as a Key Switching Mechanism for the No/onoo-Cycle.," Medical Hypotheses, 2007, vol. 69 (4), pp. 821-825.

Place A.E., et al., "The Novel Synthetic Triterpenoid, Cddo-imidazolide, inhibits inflammatory Response and Tumor Growth in Vivo.," Clinical Cancer Research, 2003, vol. 9 (7), pp. 2798-2806.

Prescott D.M., "Methods in Cell Biology", Academic Press, 1976, Table of Contents.

Rajakariar R., et al., "Hematopoietic Prostaglandin D2 Synthase Controls the onset and Resolution of Acute inflammation through Pgd2 and 15-deoxydelta12 14 Pgj2.," Proceedings of the National Academy of Sciences of the United States of America, 2007, vol. 104 (52), pp. 20979-20984.

Ross J.S., et al., "Breast Cancer Biomarkers and Molecular Medicine.," Expert Review of Molecular Diagnostics, 2003, vol. 3 (5), pp. 573-585.

Ross J.S., et al., "Her-2/neu Testing in Breast Cancer.," American Journal of Clinical Pathology, 2003, vol. 120 (Suppl), pp. S53-S71.

Ruster M., et al., "Detection of Elevated n. Epsilon-Carboxymethyllysine Levels in Muscular Tissue and in Serum of Patients with Fibromyalgia," Journal of Rheumatology, 2005, vol. 34 (6), pp. 460-463.

Sacerdoti D., et al., "Heme Oxygenase Overexpression Attenuates Glucose-mediated Oxidative Stress in Quiescent Cell Phase: Linking Heme to Hyperglycemia Complications.," Current Neurovascular Research, 2005, vol. 2 (2), pp. 103-111.

(56) References Cited

OTHER PUBLICATIONS

Salvemini D., et al., "Endogenous Nitric Oxide Enhances Prostaglandin Production in a Model of Renal inflammation.," The Journal of Clinical Investigation, 1994, vol. 93 (5), pp. 1940-1947.

Sarchielli P., et al., "Nf-kappab Activity and inos Expression in Monocytes from internal Jugular Blood of Migraine without Aura Patients During Attacks.," Cephalalgia, 2006, vol. 26 (9), pp. 1071-1079.

Satoh T., et al., "Activation of the Keap1/nrf2 Pathway for Neuroprotection by Electrophilic [correction of Electrophillic] Phase Ii inducers.," Proceedings of the National Academy of Sciences of the United States of America, 2006, vol. 103 (3), pp. 768-773.

Schulz E., et al., "Nitric Oxide, Tetrahydrobiopterin, Oxidative Stress, and Endothelial Dysfunction in Hypertension. ," Antioxidants & Redox Signaling, 2008, vol. 10 (6), pp. 1115-1126.

Shin S., et al., "Role of Nrf2 in Prevention of High-fat Diet-induced Obesity by Synthetic Triterpenoid Cddo-imidazolide.," European Journal of Pharmacology, 2009 , vol. 620 (1-3), pp. 138-144.

Smith M.B., et al., March's Advanced Organic Chemistry: Reactions, Mechanisms, and Struction, 2007, 6th Edition, Wiley-Interscience, A John Wiley and Sons, Inc., Publication, Table of Contents.

Stahl P.H., et al., eds., Handbook of Pharmaceutical Salts: Properties Selection and Use, Verlag Helvetica Chimica Acta, Wiley-VCH, 2002.

Suh N., et al., "A Novel Synthetic Oleanane Triterpenoid, 2-cyano-3,12-dioxoolean-1,9-dien-28-oic Acid, with Potent Differentiating, Antiproliferative, and Anti-inflammatory Activity.," Cancer Research, 1999, vol. 59 (2), pp. 336-341.

Suh N., et al., "Novel Triterpenoids Suppress inducible Nitric Oxide Synthase (inos) and inducible Cyclooxygenase (cox-2) in Mouse Macrophages.," Cancer Research, 1998, vol. 58 (4), pp. 717-723.

Szabo C., et al., "Peroxynitrite: Biochemistry, Pathophysiology and Development of therapeutics.," Nature Reviews. Drug Discovery, 2007, vol. 6 (8), pp. 662-680.

Takahashi M., et al., "Increased Expression of inducible and Endothelial Constitutive Nitric Oxide Synthases in Rat Colon Tumors induced by Azoxymethane.," Cancer Research, 1997, vol. 57 (7), pp. 1233-1237.

Tamir S., et al., "The Role of Nitric Oxide (no.) in the Carcinogenic Process.," Biochimica Et Biophysica Acta, 1996, vol. 1288 (2), pp. F31-F36.

Zhou Z., et al., "Carbon Monoxide Suppresses Bleomycin-induced Lung Fibrosis.," The American Journal of Pathology, 2005, vol. 166 (1), pp. 27-37.

\* cited by examiner

ARYL AND ARYLALKYL SUBSTITUTED PYRAZOLYL AND PYRIMIDINYL TRICYCLIC ENONES AS ANTIOXIDANT INFLAMMATION MODULATORS

This application claims the benefit of U.S. Provisional Patent Application No. 61/931,291, filed on Jan. 24, 2014, the entirety of which is hereby incorporated by reference.

FIELD OF THE INVENTION

The present invention relates generally to the fields of biology and medicine. More particularly, it concerns compounds, compositions and methods for the treatment and prevention of diseases such as those associated with oxidative stress and inflammation.

BACKGROUND

The anti-inflammatory and anti-proliferative activity of the naturally occurring triterpenoid, oleanolic acid, has been improved by chemical modifications. For example, 2-cyano-3,12-dioxooleana-1,9(11)-dien-28-oic acid (CDDO) and related compounds have been developed (Honda et al., 1997; Honda et al., 1998; Honda et al., 1999; Honda et al., 2000a; Honda et al., 2000b; Honda, et al., 2002; Suh et al. 1998; Suh et al., 1999; Place et al., 2003; Liby et al., 2005) and evaluated in clinical trials for the treatment of cancer, diabetic nephropathy and chronic kidney disease.

Synthetic triterpenoid analogs of oleanolic acid have also been shown to be inhibitors of cellular inflammatory processes, such as the induction by IFN-γ of inducible nitric oxide synthase (iNOS) and of COX-2 in mouse macrophages. See Honda et al. (2000a); Honda et al. (2000b), and Honda et al. (2002), which are all incorporated herein by reference. Synthetic derivatives of another triterpenoid, betulinic acid, have also been shown to inhibit cellular inflammatory processes, although these compounds have been less extensively characterized (Honda et al., 2006). The pharmacology of these synthetic triterpenoid molecules is complex. Compounds derived from oleanolic acid have been shown to affect the function of multiple protein targets and thereby modulate the activity of several important cellular signaling pathways related to oxidative stress, cell cycle control, and inflammation (e.g., Dinkova-Kostova et al., 2005; Ahmad et al., 2006; Ahmad et al., 2008; Liby et al., 2007a). Derivatives of betulinic acid, though they have shown comparable anti-inflammatory properties, also appear to have significant differences in their pharmacology compared to OA-derived compounds (Liby et al., 2007b).

In general, it is not certain that the triterpenoid starting materials employed to date have optimal properties for all applications compared to other possible starting materials. In addition, it is often necessary to synthesize triterpenoid derivatives from natural product starting materials. The production of highly purified triterpenoid starting materials can be expensive, and the plant materials that are the ultimate sources of these compounds can vary in availability, including due to adverse weather conditions, disease, and other environmental factors. Given that the biological activity profiles of known triterpenoid derivatives vary, and in view of the wide variety of diseases that may be treated or prevented with compounds having potent antioxidant and anti-inflammatory effects, and the high degree of unmet medical need represented within this variety of diseases, it is desirable to synthesize new compounds with diverse structures that may have improved biological activity profiles for the treatment of one or more indications. Therefore, the design of potent, selective antioxidant/anti-inflammatory compounds that can be readily synthesized from simple starting materials is a desirable goal.

SUMMARY OF THE INVENTION

The present disclosure provides novel synthetic triterpenoid derivatives, with anti-inflammatory and/or antioxidant properties, pharmaceutical compositions, and methods for their manufacture, and methods for their use.

In one aspect, there are provided compounds of the Formula:

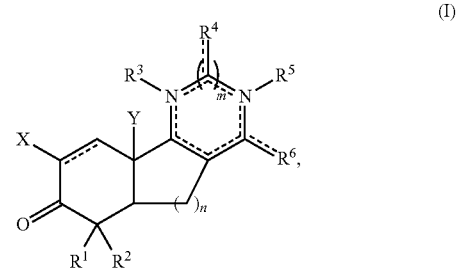

(I)

or a pharmaceutically acceptable salt thereof, wherein
----- is a single or double bond;
m is 0 or 1;
n is 1 or 2;
p is 1, 2, or 3;
q is 1, 2, or 3;
r is 1, 2, 3, or 4;
X is NC—, $F_3C$—, $R^{1x}C(O)$—, or $O_2N$—;
Y is $G^1$-, $G^1$-$(CR^aR^b)$—, $G^2$-, or $G^2$-$(CR^aR^b)$—;
$R^1$ and $R^2$ are each independently hydrogen, $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amido, amino, halogen, hydroxy, $G^{R1a}$-, $G^{R1a}$-$(CR^aR^b)_p$—, $G^{R1b}$-, $R^{1a}C(O)$—, $(R^{1a})_2N$—, $G^{R1a}NH$—, $G^{R1a}$-$(CR^aR^b)_p$—NH—, $G^{R1a}O$—, and $R^{1a}CO_2$—; or
$R^1$ and $R^2$ joined together with the carbon atom to which they are attached form a $C_3$-$C_6$-cycloalkyl, $C_3$-$C_6$-cycloalkenyl, or 4-6-membered heterocycle optionally substituted with $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;
$R^3$ is absent, hydrogen, $C_1$-$C_6$-alkyl, $C_2$-$C_4$-alkenyl, $C_1$-$C_6$-fluoroalkyl, $G^{3a}$- or $G^{3a}$-$(CR^aR^b)_q$—; provided that $R^3$ is absent when and only when the atom to which it is attached forms part of a double bond;
$R^4$ is hydrogen, $C_1$-$C_6$-alkyl, $C_2$-$C_4$-alkenyl, $C_1$-$C_6$-fluoroalkyl, amino, $C_1$-$C_6$-alkylamino, $C_1$-$C_6$-dialkylamino, $C_1$-$C_6$-alkoxy, cyano, halogen, hydroxy, $G^{4a}$-, $G^{4b}$-, $G^{4a}$-$(CR^aR^b)_p$—, $G^{4b}$-$(CR^aR^b)_p$—; $G^{4a}O$— or $G^{4a}NH$—;
$R^5$ is absent, hydrogen, $C_1$-$C_6$-alkyl, $C_2$-$C_6$-alkenyl, $C_2$-$C_6$-alkynyl, $C_1$-$C_6$-fluoroalkyl, $G^{R5a}$-, $G^{R5a}$-$(CR^aR^b)$—, $R^{5a}C(O)$—, $G^{R5a}C(O)$—, hydroxy-$C_1$-$C_6$-alkyl-$C(O)$—, $R^{5a}O_2C$—, $G^{R5a}O_2C$—, $G^{R5a}HNC(O)$—, $R^{5a}O_2CNHCH_2C(O)$—, $H_2NHCH_2C(O)$—, $R^{5a}SO_2$—, or $G^{R5a}SO_2$—; provided that $R^5$ is absent when and only when the atom to which it is attached forms part of a double bond;
$R^6$ is hydrogen, $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amino, $C_1$-$C_6$-alkylamino, $C_1$-$C_6$-dialkylamino, hydroxy, $G^{6a}$-, $G^{6a}N(R^a)$—, $G^{6a}O$— or $G^{6b}$-;
$R^a$ and $R^b$ are, at each occurrence, independently hydrogen, $C_1$-$C_6$-alkyl, or $C_1$-$C_6$-haloalkyl;

$R^{1a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$R^{1x}$ is hydroxy, $C_1$-$C_6$-alkoxy, amino, $C_1$-$C_6$-alkylamino, $C_1$-$C_6$-dialkylamino, or $C_1$-$C_6$-alkylsulfonylamino;

$R^{G1a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$R^{G1b}$ is, at each occurrence, independently $C_1$-$C_4$-alkyl, $C_2$-$C_4$-alkenyl, $C_2$-$C_4$-alkynyl or $C_1$-$C_4$-haloalkyl;

$R^{G2a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$R^{G2b}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$R^{G4a}$ is, at each occurrence, independently $C_1$-$C_4$-alkyl, $C_2$-$C_4$-alkenyl, $C_2$-$C_4$-alkynyl or $C_1$-$C_4$-haloalkyl;

$R^{5a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$R^{G6a}$ is, at each occurrence, independently $C_1$-$C_4$-alkyl, $C_2$-$C_4$-alkenyl, $C_2$-$C_4$-alkynyl or $C_1$-$C_4$-haloalkyl;

$R^{G6b}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$R^{G6c}$ is, at each occurrence, independently $C_1$-$C_4$-alkyl, $C_2$-$C_4$-alkenyl, $C_2$-$C_4$-alkynyl or $C_1$-$C_4$-haloalkyl;

$R^{G6d}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$G^1$ is phenyl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, carboxy, cyano, cyano-$C_1$-$C_6$-alkyl, halogen, halo-$C_1$-$C_6$-alkyl, hydroxy, hydroxy-$C_1$-$C_6$-alkyl, $R^{G1b}O_2C$—, $R^{G1a}HN(O)C$—, $(R^{G1a})_2N(O)C$—, $G^{1a}C(O)$—, $G^{1b}HN(O)C$—, $G^{1b}$-, $R^{G1a}C(O)N(R^{G1a})$—, $R^{G1b}O(O)CN(R^{G1a})$—, $R^{G1b}O2SN(R^{G1a})$—, $(R^{G1a})_2N$—, $G^{1b}O$—, $G^{1b}CH_2O$—, $R^{G1a}CO_2$—, $(R^{G1a})_2NCO_2$—, HS—, $R^{G1b}S$—, $R^{G1b}S(O)$—, $R^{G1b}SO_2$—, or $(R^{G1a})_2NSO_2$—;

$G^2$ is a 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, carboxy, cyano, cyano-$C_1$-$C_6$-alkyl, halogen, halo-$C_1$-$C_6$-alkyl, hydroxy, hydroxy-$C_1$-$C_6$-alkyl, $R^{G2b}CO_2$—, $R^{G2a}HNC(O)$—, $(R^{G2a})_2NC(O)$—, $G^{2a}C(O)$—, $G^{2b}HNC(O)$—, $G^{2b}$-, $R^{G2a}C(O)N(R^{G2a})$—, $R^{G2b}OC(O)N(R^{G2a})$—, $R^{G2b}SO_2N(R^{G2a})$—, $(R^{G2a})_2N$—, $G^{2b}O$—, $G^{2b}CH_2O$—, $R^{G2a}CO_2$—, $(R^{G2a})_2NCO_2$—, HS—, $R^{G2b}S$—, $R^{G2b}S(O)$—, $R^{G2b}SO_2$—, or $(R^{G2a})_2NSO_2$—;

$G^{1a}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;

$G^{1b}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{R1a}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{R1b}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;

$G^{2a}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;

$G^{2b}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{3a}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, or hydroxy;

$G^{4a}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amido, carboxy, cyano, halogen, hydroxy, $R^{G4a}O_2C$—, $R^{G4a}C(O)$—, $(R^{G4a})_2NC(O)$—, or $G^{4a1}$-;

$G^{4a1}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{4b}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;

$G^{R5a}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{6a}$ is $C_6$-$C_{10}$-aryl or 5-10-membered heteroaryl optionally substituted with 1, 2, 3, or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amino, $C_1$-$C_6$-alkylsulfonylamino, carboxy, halogen, hydroxy, hydroxy$C_1$-$C_6$-alkyl, $R^{G6a}C(O)$—, $R^{G6a}O_2C$—, $HO_2C$—$(CR^aR^b)_r$—, $R^{G6a}O_2C$—$(CR^aR^b)_r$—, $(R^{G6b})_2N(O)C$—$(CR^aR^b)_r$—, $R^{G6a}CO_2$—$(CR^aR^b)_r$—, $G^{6c}$-, or $G^{6d}$-;

$G^{6b}$ is 4-6-membered heterocycle optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, cyano, halogen, hydroxy, or oxo;

$G^{6c}$ is phenyl or 5-6-membered heteroaryl optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, amino, $C_1$-$C_6$-alkylsulfonylamino, di($C_1$-$C_6$-alkylsulfonyl)amino, $C_1$-$C_6$-alkylsulfonylamino$C_1$-$C_6$-alkyl, carboxy, cyano, halogen, hydroxy, hydroxy$C_1$-$C_6$-alkyl, $R^{G6c}C(O)$—, $R^{G6c}O_2C$—, $(R^{G6d})_2NC(O)$—, $HO_2C$—$(CR^aR^b)_r$—, $R^{G6c}O_2C$—$(CR^aR^b)_r$—, $(R^{G6d})_2NC(O)$—$(CR^aR^b)_r$—, or $R^{G6c}CO_2$—$(CR^aR^b)_r$—; and $G^{6d}$ is 4-6-membered heterocycle optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, cyano, halogen, hydroxy, or oxo.

In some aspects, there are provided pharmaceutical compositions comprising one or more of the above described compounds and an excipient. In other aspects there are provided methods of treating and/or preventing a disease or a disorder in patients in need thereof, comprising administering to such patients one or more of the above described compounds in an amount sufficient to treat and/or prevent the disease or disorder. In some embodiments, the disease has an inflammatory component. In some aspects, there are provided uses of one of more of the above described compounds in the manufacture of a medicament for the treatment of a disease with an inflammatory component. In some aspects, there are provided compounds as described above for the use in the treatment of a disease with an inflammatory component. In some aspects, there are provided compositions comprising one or more of the compounds described above for the use in the treatment of a disease with an inflammatory component.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula does not mean that it cannot also belong to another generic formula.

The compounds, compositions comprising the compounds, and methods for treating or preventing conditions and disorders by administering the compounds are further described herein.

DETAILED DESCRIPTION OF THE INVENTION

The present invention includes compounds of Formula (I):

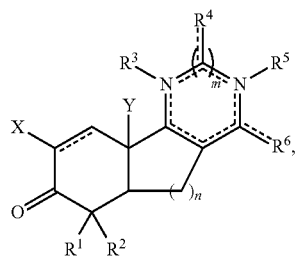

and salts thereof, wherein $R^1$, $R^2$, $R^3$, $R^4$, $R^5$, $R^6$, m, n, X and Y are as defined above in the Summary of the Invention. The invention further includes compositions comprising such compounds and methods for treating conditions and disorders using such compounds and compositions.

In various embodiments, the present invention provides at least one variable that occurs more than one time in any substituent or in the compound of the invention or any other formulae herein. Definition of a variable on each occurrence is independent of its definition at another occurrence. Further, combinations of substituents are permissible only if such combinations result in stable compounds. Stable compounds are compounds, which can be isolated from a reaction mixture.

Definitions

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" denotes a divalent group derived from a straight or branched chain hydrocarbon of 2 to 4 carbon atoms and contains at least one carbon-carbon double bond. Representative examples of alkenylene include, but are not limited to, —CH═CH— and —CH₂CH═CH—.

The term "alkoxy" refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched, saturated hydrocarbon chain containing from 1 to 10 carbon atoms. The term "lower alkyl" or "$C_{1-6}$ alkyl" means a straight or branched chain hydrocarbon containing 1 to 6 carbon atoms. The term "$C_{1-3}$-alkyl" means a straight or branched chain hydrocarbon containing 1 to 3 carbon atoms. Representative examples of alkyl include, but are not limited to, methyl, ethyl, n-propyl, isopropyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylamino" or "N-alkylamino" as used herein, means an alkyl group, as defined herein, appended to the parent molecular moiety through an amino group, as defined herein. Representative examples of alkylamino include, but are not limited to, methylamino, ethylamino, and sec-butylamino.

The term "dialkylamino" as used herein, means two independently selected alkyl groups, as defined herein, appended to the parent molecular moiety through a single amino group, as defined herein. Representative examples of dialkylamino include, but are not limited to, dimethylamino and diethylamino.

The term "alkylene" denotes a divalent group derived from a straight or branched chain hydrocarbon 1 to 10 carbon atoms. Representative examples of alkylene include, but are not limited to, —CH₂—, —CH₂CH₂—, —CH₂CH₂CH₂—, —CH₂CH₂CH₂CH₂—, and —CH₂CH(CH₃)CH₂—.

The term "alkylsulfonyl" means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylsulfonylamino" means an alkylsulfonyl group, as defined herein, appended to the parent molecular moiety through an amino group, as defined herein. Representative examples of alkylsulfonylamino include, but are not limited to, methylsulfonylamino and ethylsulfonylamino.

The term "di(alkylsulfonyl)amino" means two independent alkylsulfonyl groups, as defined herein, appended to the parent molecular moiety through a single amino group, as defined herein. Representative examples of alkylsulfonylamino include, but are not limited to, di(methylsulfonyl)amino and di(ethylsulfonyl)amino.

The term "alkylsulfonylaminoalkyl" means an alkylsulfonylamino group, as defined herein, appended to the parent molecular moiety through an alkyl group, as defined herein. Representative examples of alkylsulfonylaminoalkyl include, but are not limited to, methylsulfonylaminomethyl and methylsulfonylaminoethyl.

The term "alkynyl" as used herein, means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "amido" means an amino group appended to the parent molecular moiety through a carbonyl group, as defined herein, i.e. —C(O)NH$_2$.

The term "amino" as used herein means an —NH$_2$ group.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the biaryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present invention can be unsubstituted or substituted.

The term "arylalkyl" as used herein, means an aryl group, as defined herein, appended to the parent molecular moiety through an alkylene group, as defined herein. Representative examples of arylalkyl include, but are not limited to, benzyl, 2-phenylethyl, 3-phenylpropyl, and 2-naphth-2-ylethyl.

The term "carbonyl" means a —C(O)— group.

The term "carboxy" means a —CO$_2$H group.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1.0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system.

The term "cycloalkylalkyl" as used herein, means a cycloalkyl group appended to the parent molecular moiety through an alkyl group, as defined herein.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two or three double bonds. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring can contain one or two alkylene bridges, each consisting of one, two or three carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl can be attached to the parent molecular moiety through any substitutable atom contained within the ring systems, and can be unsubstituted or substituted.

The term "fluoroalkyl" as used herein, means an alkyl group, as defined herein, in which one, two, three, four, five, six, seven or eight hydrogen atoms are replaced by fluorine. Representative examples of haloalkyl include, but are not limited to, fluoromethyl, 2-fluoroethyl, 2,2,2-trifluoroethyl, trifluoromethyl, difluoromethyl, pentafluoroethyl, and trifluoropropyl such as 3,3,3-trifluoropropyl.

The term "halo" or "halogen" as used herein, means Cl, Br, I, or F.

The term "haloalkyl" as used herein, means an alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 3,4-dihydrobenzothienyl, 2,3-dihydroisoquinolinyl or indolinyl, 2,3-dihydroisoquinolinyl, 1,1-dioxidoisothiazolidinyl, azabicyclo[2.2.1]heptyl (including 2-azabicyclo[2.2.1]hept-2-yl), 2,3-dihydro-1H-indolyl, isoindolinyl, octahydro-1H-indolyl, octahydrocyclopenta[c] pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo [3.3.1.1$^{3,7}$]decane), and oxa-adamantane (2-oxatricyclo [3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "heteroaryl" as used herein, means a monocyclic heteroaryl or a bicyclic heteroaryl. The monocyclic heteroaryl is a five- or six-membered ring. The five-membered ring contains two double bonds. The five-membered ring can contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,2-oxazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, 2,1,3-benzothiadiazolyl, benzimidazolyl, benzoxadiazolyl, 6,7-dihydro-1,3-benzothiazolyl, furo[3,2-b]pyrrolyl, imidazo[1,2-a]pyridinyl, indazolyl, indolyl, isoindolyl, isoquinolinyl, naphthyridinyl, pyridoimidazolyl, pyrrolopyridinyl, quinolinyl, thiazolo[5,4-b]pyridin-2-yl, thiazolo[5,4-d]pyrimidin-2-yl, thienopyridinyl and 5,6,7,8-tetrahydroquinolin-5-yl. The monocyclic and bicyclic heteroaryl groups of the present invention can be substituted or unsubstituted and are connected to the parent molecular moiety through any carbon atom or any nitrogen atom contained within the ring systems.

The term "heteroarylalkyl," as used herein, means a heteroaryl group appended to the parent molecular moiety through an alkyl group, as defined herein.

The term "heteroatom" as used herein, means a nitrogen, oxygen, or sulfur atom.

The term "hydroxyl" or "hydroxy" as used herein, means an —OH group.

The term "hydroxyalkyl" as used herein, means at least one hydroxy group, as defined herein, is appended to the parent molecular moiety through an alkylene group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "nitro" as used herein, means a —NO$_2$ group.

The term "nitrogen protecting group" as used herein means those groups intended to protect a nitrogen atom against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), tert-butylacetyl, trifluoroacetyl, and triphenylmethyl (trityl). Nitrogen-protecting groups are appended onto primary or secondary amino groups by reacting the compound that contains the amine group with base, such as triethylamine, and a reagent selected from an alkyl halide, an alkyl triflate, a dialkyl anhydride, for example as represented by an alkyl anhydride (alkyl-OC=O)$_2$O, a diaryl anhydride, for example as represented by (aryl-OC=O)$_2$O, an acyl halide, an alkylchloroformate, or an alkylsulfonylhalide, an arylsulfonylhalide, or halo-CON(alkyl)$_2$, for example acetyl chloride, benzoyl chloride, benzyl bromide, benzyloxycarbonyl chloride, formylfluoride, phenylsulfonyl chloride, pivaloyl chloride, (tert-butyl-O—C=O)$_2$O, trifluoroacetic anhydride, and triphenylmethyl chloride.

The term "oxo" as used herein, means a =O group.

The term "sulfonyl" means a —SO$_2$— group.

When cycloalkyl, heterocycle, heteroaryl, aryl, and the like are "substituted", it means there are one or more substituents other than hydrogen on the respective ring. "Unsubstituted" rings have no substituents other than hydrogen.

In some instances, the number of carbon atoms in a hydrocarbon substituent (e.g., alkyl, alkenyl, alkynyl, cycloalkyl or cycloalkenyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_6$-cycloalkyl means a saturated hydrocarbon ring containing from 3 to 6 carbon ring atoms.

Compounds

Compounds of the invention have the Formula (I) as described above.

Particular values of variable groups in compounds of Formula (I) are as follows. Such values can be used where appropriate with any of the other values, definitions, claims or embodiments defined hereinbefore or hereinafter.

In one embodiment, the compounds are further defined as:

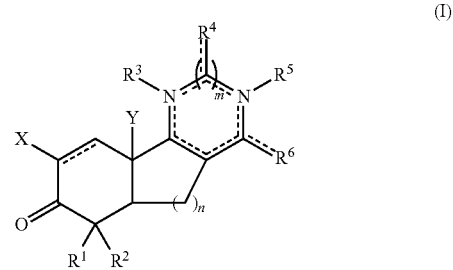

(I)

wherein, $R^1$, $R^2$, $R^3$, $R^4$, $R^5$, $R^6$, m, n, X and Y are as defined above and ----- is a single or double bond.

In one embodiment, the compounds are further defined as:

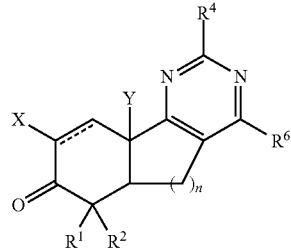

(Ia)

wherein
----- is a single or double bond;
n is 1 or 2;
p is 1, 2, or 3;
r is 1, 2, 3, or 4;
X is NC—, $F_3C$—, $R^{1x}C(O)$—, or $O_2N$—;
Y is $G^1$-, $G^1$-$(CR^aR^b)$—, $G^2$-, or $G^2$-$(CR^aR^b)$—;
$R^1$ and $R^2$ are each independently hydrogen, $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amido, amino, halogen, hydroxy, $G^{R1a}$-, $G^{R1a}$-$(CR^aR^b)_p$—, $G^{R1b}$-, $R^{1a}C(O)$—, $(R^{1a})_2N$—, $G^{R1a}NH$—, $G^{R1a}$-$(CR^aR^b)_p$—NH—, $G^{R1a}O$—, and $R^{1a}CO_2$—; or
$R^1$ and $R^2$ joined together with the carbon atom to which they are attached form a $C_3$-$C_6$-cycloalkyl, $C_3$-$C_6$-cycloalkenyl, or 4-6-membered heterocycle optionally substituted with $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;
$R^4$ is hydrogen, $C_1$-$C_6$-alkyl, $C_2$-$C_4$-alkenyl, $C_1$-$C_6$-fluoroalkyl, amino, $C_1$-$C_6$-alkylamino, $C_1$-$C_6$-dialkylamino, $C_1$-$C_6$-alkoxy, cyano, halogen, hydroxy, $G^{4a}$-, $G^{4b}$-, $G^{4a}$-$(CR^aR^b)_p$—, $G^{4b}$-$(CR^aR^b)_p$—; $G^{4a}O$— or $G^{4a}NH$—;
$R^6$ is hydrogen, $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amino, $C_1$-$C_6$-alkylamino, $C_1$-$C_6$-dialkylamino, hydroxy, $G^{6a}$-, $G^{6a}N(R^a)$—, $G^{6a}O$— or $G^{6b}$;
$R^a$ and $R^b$ are, at each occurrence, independently hydrogen, $C_1$-$C_6$-alkyl, or $C_1$-$C_6$-haloalkyl;
$R^{1a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$R^{1x}$ is hydroxy, $C_1$-$C_6$-alkoxy, amino, $C_1$-$C_6$-alkylamino, $C_1$-$C_6$-dialkylamino, or $C_1$-$C_6$-alkylsulfonylamino;
$R^{G1a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$R^{G1b}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{G2a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$R^{G2b}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{G4a}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{G6a}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{G6b}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$R^{G6c}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{G6d}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$G^1$ is phenyl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, carboxy, cyano, cyano-$C_1$-$C_6$-alkyl, halogen, halo-$C_1$-$C_6$-alkyl, hydroxy, hydroxy-$C_1$-$C_6$-alkyl, $R^{G1b}O_2C$—, $R^{G1a}HN(O)C$—, $(R^{G1a})_2N(O)C$—, $G^{1a}C(O)$—, $G^{1b}HN(O)C$—, $G^{1b}$-, $R^{G1a}C(O)N(R^{G1a})$—, $R^{G1b}O(O)CN(R^{G1a})$—, $R^{G1b}O_2SN(R^{G1a})$—, $(R^{G1a})_2N$—, $G^{1b}O$—, $G^{1b}CH_2O$—, $R^{G1a}CO_2$—, $(R^{G1a})_2NCO_2$—, HS—, $R^{G1b}S$—, $R^{G1b}S(O)$—, $R^{G1b}SO_2$—, or $(R^{G1a})_2NSO_2$—;
$G^2$ is a 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, carboxy, cyano, cyano-$C_1$-$C_6$-alkyl, halogen, halo-$C_1$-$C_6$-alkyl, hydroxy, hydroxy-$C_1$-$C_6$-alkyl, $R^{G2b}CO_2$—, $R^{G2a}HNC(O)$—, $(R^{G2a})_2NC(O)$—, $G^{2a}C(O)$—, $G^{2b}HNC(O)$—, $G^{2b}$-, $R^{G2a}C(O)N(R^{G2a})$—, $R^{G2b}OC(O)N(R^{G2a})$—, $R^{G2b}SO_2N(R^{G2a})$—, $(R^{G2a})_2N$—, $G^{2b}O$—, $G^{2b}CH_2O$—, $R^{G2a}CO_2$—, $(R^{G2a})_2NCO_2$—, HS—, $R^{G2b}S$—, $R^{G2b}S(O)$—, $R^{G2b}SO_2$—, or $(R^{G2a})_2NSO_2$—;
$G^{1a}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;
$G^{1b}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;
$G^{R1a}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;
$G^{R1b}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;
$G^{2a}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;
$G^{2b}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;
$G^{4a}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amido, carboxy, cyano, halogen, hydroxy, $R^{G4a}O_2C$—, $R^{G4a}C(O)$—, $(R^{G4a})_2NC(O)$—, or $G^{4a1}$-;
$G^{4a1}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;
$G^{4b}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;
$G^{6a}$ is $C_6$-$C_{10}$-aryl or 5-10-membered heteroaryl optionally substituted with 1, 2, 3, or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amino, $C_1$-$C_6$-alkylsulfonylamino, carboxy, halogen, hydroxy, hydroxy$C_1$-$C_6$-alkyl, $R^{G6a}C(O)$—, $R^{G6a}O_2C$—, $HO_2C$—

(CR$^a$R$^b$)$_r$—, R$^{G6a}$O$_2$C—(CR$^a$R$^b$)$_r$—, (R$^{G6b}$)$_2$N(O)C—(CR$^a$R$^b$)$_r$—, R$^{G6a}$CO$_2$—(CR$^a$R$^b$)$_r$—, G$^{6c}$-, or G$^{6d}$-;

G$^{6b}$ is 4-6-membered heterocycle optionally substituted with 1, 2, 3, or 4 C$_1$-C$_6$-alkyl, C$_2$-C$_6$-alkenyl, C$_2$-C$_6$-alkynyl, C$_1$-C$_6$-alkoxy, cyano, halogen, hydroxy, or oxo;

G$^{6c}$ is phenyl or 5-6-membered heteroaryl optionally substituted with 1, 2, 3, or 4 C$_1$-C$_6$-alkyl, C$_2$-C$_6$-alkenyl, C$_2$-C$_6$-alkynyl, C$_1$-C$_6$-alkoxy, amino, C$_1$-C$_6$-alkylsulfonylamino, di(C$_1$-C$_6$-alkylsulfonyl)amino, C$_1$-C$_6$-alkylsulfonylaminoC$_1$-C$_6$-alkyl, carboxy, cyano, halogen, hydroxy, hydroxyC$_1$-C$_6$-alkyl, R$^{G6c}$C(O)—, R$^{G6c}$O$_2$C—, (R$^{G6d}$)$_2$NC(O)—, HO$_2$C—(CR$^a$R$^b$)$_r$—, R$^{G6c}$O$_2$C—(CR$^a$R$^b$)$_r$—, (R$^{G6d}$)$_2$NC(O)—(CR$^a$R$^b$)$_r$—, or R$^{G6c}$CO$_2$—(CR$^a$R$^b$)$_r$—; and G$^{6d}$ is 4-6-membered heterocycle optionally substituted with 1, 2, 3, or 4 C$_1$-C$_6$-alkyl, C$_2$-C$_6$-alkenyl, C$_2$-C$_6$-alkynyl, C$_1$-C$_6$-alkoxy, cyano, halogen, hydroxy, or oxo.

In another embodiment, the compound is further defined as:

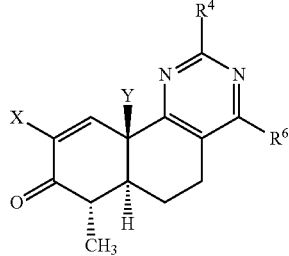

(Ia-1)

wherein,
p is 1, 2, or 3;
r is 1, 2, 3, or 4;
X is NC—, F$_3$C—, R$^{1x}$C(O)—, or O$_2$N—;
Y is G$^1$-, G$^1$-(CR$^a$R$^b$)$_p$—, G$^2$-, or G$^2$-(CR$^a$R$^b$)$_p$—;
R$^4$ is hydrogen, C$_1$-C$_6$-alkyl, C$_2$-C$_4$-alkenyl, C$_1$-C$_6$-fluoroalkyl, amino, C$_1$-C$_6$-alkylamino, C$_1$-C$_6$-dialkylamino, C$_1$-C$_6$-alkoxy, cyano, halogen, hydroxy, G$^{4a}$-, G$^{4b}$-, G$^{4a}$-(CR$^a$R$^b$)$_p$—, G$^{4b}$-(CR$^a$R$^b$)$_p$—; G$^{4a}$O— or G$^{4a}$NH—;
R$^6$ is hydrogen, C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, amino, C$_1$-C$_6$-alkylamino, C$_1$-C$_6$-dialkylamino, hydroxy, G$^{6a}$-, G$^{6a}$N(R$^a$)—, G$^{6a}$O— or G$^{6b}$-;
R$^a$ and R$^b$ are, at each occurrence, independently hydrogen, C$_1$-C$_6$-alkyl, or C$_1$-C$_6$-haloalkyl;
R$^1$ is hydroxy, C$_1$-C$_6$-alkoxy, amino, C$_1$-C$_6$-alkylamino, C$_1$-C$_6$-dialkylamino, or C$_1$-C$_6$-alkylsulfonylamino;
R$^{G1a}$ is, at each occurrence, independently hydrogen, C$_1$-C$_4$-alkyl, C$_2$-C$_4$-alkenyl, C$_2$-C$_4$-alkynyl or C$_1$-C$_4$-haloalkyl;
R$^{G1b}$ is, at each occurrence, independently C$_1$-C$_4$-alkyl, C$_2$-C$_4$-alkenyl, C$_2$-C$_4$-alkynyl or C$_1$-C$_4$-haloalkyl;
R$^{G2a}$ is, at each occurrence, independently hydrogen, C$_1$-C$_4$-alkyl, C$_2$-C$_4$-alkenyl, C$_2$-C$_4$-alkynyl or C$_1$-C$_4$-haloalkyl;
R$^{G2b}$ is, at each occurrence, independently C$_1$-C$_4$-alkyl, C$_2$-C$_4$-alkenyl, C$_2$-C$_4$-alkynyl or C$_1$-C$_4$-haloalkyl;
R$^{G4a}$ is, at each occurrence, independently C$_1$-C$_4$-alkyl, C$_2$-C$_4$-alkenyl, C$_2$-C$_4$-alkynyl or C$_1$-C$_4$-haloalkyl;
R$^{G6a}$ is, at each occurrence, independently C$_1$-C$_4$-alkyl, C$_2$-C$_4$-alkenyl, C$_2$-C$_4$-alkynyl or C$_1$-C$_4$-haloalkyl;
R$^{G6b}$ is, at each occurrence, independently hydrogen, C$_1$-C$_4$-alkyl, C$_2$-C$_4$-alkenyl, C$_2$-C$_4$-alkynyl or C$_1$-C$_4$-haloalkyl;

R$^{G6c}$ is, at each occurrence, independently C$_1$-C$_4$-alkyl, C$_2$-C$_4$-alkenyl, C$_2$-C$_4$-alkynyl or C$_1$-C$_4$-haloalkyl;
R$^{G6d}$ is, at each occurrence, independently hydrogen, C$_1$-C$_4$-alkyl, C$_2$-C$_4$-alkenyl, C$_2$-C$_4$-alkynyl or C$_1$-C$_4$-haloalkyl;
G$^1$ is phenyl optionally substituted with 1, 2, 3, 4 or 5 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, carboxy, cyano, cyano-C$_1$-C$_6$-alkyl, halogen, halo-C$_1$-C$_6$-alkyl, hydroxy, hydroxy-C$_1$-C$_6$-alkyl, R$^{G1b}$O$_2$C—, R$^{G1a}$HN(O)C—, (R$^{G1a}$)$_2$N(O)C—, G$^{1a}$C(O)—, G$^{1b}$HN(O)C—, G$^{1b}$-, R$^{G1a}$C(O)N(R$^{G1a}$)—, R$^{G1b}$O(O)CN(R$^{G1a}$)—, R$^{G1b}$O$_2$SN(R$^{G1a}$)—, (R$^{G1a}$)$_2$N—, G$^{1b}$O—, G$^{1b}$CH$_2$O—, R$^{G1a}$CO$_2$—, (R$^{G1a}$)$_2$NCO$_2$—, HS—, R$^{G1b}$S—, R$^{G1b}$S(O)—, R$^{G1b}$SO$_2$—, or (R$^{G1a}$)$_2$NSO$_2$—;
G$^2$ is a 5-6-membered heteroaryl optionally substituted with 1, 2, 3, 4 or 5 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, carboxy, cyano, cyano-C$_1$-C$_6$-alkyl, halogen, halo-C$_1$-C$_6$-alkyl, hydroxy, hydroxy-C$_1$-C$_6$-alkyl, R$^{G2b}$CO$_2$—, R$^{G2a}$HNC(O)—, (R$^{G2a}$)$_2$NC(O)—, G$^{2a}$C(O)—, G$^{2b}$HNC(O)—, G$^{2b}$-, R$^{G2a}$C(O)N(R$^{G2a}$)—R$^{G2b}$OC(O)N(R$^{G2a}$)—, R$^{G2b}$SO$_2$N(R$^{G2a}$)—, (R$^{G2a}$)$_2$N—, G$^{2b}$O—, G$^{2b}$CH$_2$O—, R$^{G2a}$CO$_2$—, (R$^{G2a}$)$_2$NCO$_2$—, HS—, R$^{G2b}$S—, R$^{G2b}$S(O)—, R$^{G2b}$SO$_2$—, or (R$^{G2a}$)$_2$NSO$_2$—;
G$^{1a}$ is a 4-6-membered heterocycle optionally substituted with 1, 2, 3 or 4 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, cyano, halogen, hydroxy, or oxo;
G$^{1b}$ is phenyl or 5-6-membered heteroaryl optionally substituted with 1, 2, 3, 4 or 5 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, cyano, halogen, hydroxy, or nitro;
G$^{2a}$ is a 4-6-membered heterocycle optionally substituted with 1, 2, 3 or 4 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, cyano, halogen, hydroxy, or oxo;
G$^{2b}$ is phenyl or 5-6-membered heteroaryl optionally substituted with 1, 2, 3, 4 or 5 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, cyano, halogen, hydroxy, or nitro;
G$^{4a}$ is phenyl or 5-6-membered heteroaryl optionally substituted with 1, 2, 3, 4 or 5 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, amido, carboxy, cyano, halogen, hydroxy, R$^{G4a}$O$_2$C—, R$^{G4a}$C(O)—, (R$^{G4a}$)$_2$NC(O)—, or G$^{4a}$-;
G$^{4a1}$ is phenyl or 5-6-membered heteroaryl optionally substituted with 1, 2, 3, 4 or 5 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, cyano, halogen, hydroxy, or nitro;
G$^{4b}$ is a 4-6-membered heterocycle optionally substituted with 1, 2, 3 or 4 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, cyano, halogen, hydroxy, or oxo;
G$^{6a}$ is C$_6$-C$_{10}$-aryl or 5-10-membered heteroaryl optionally substituted with 1, 2, 3, or 4 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, amino, C$_1$-C$_6$-alkylsulfonylamino, carboxy, halogen, hydroxy, hydroxyC$_1$-C$_6$-alkyl, R$^{G6a}$C(O)—, R$^{G6a}$O$_2$C—, HO$_2$C—(CR$^a$R$^b$)$_r$—, R$^{G6a}$O$_2$C—(CR$^a$R$^b$)$_r$—, (R$^{G6b}$)$_2$N(O)C—(CR$^a$R$^b$)$_r$—, R$^{G6a}$CO$_2$—(CR$^a$R$^b$)$_r$—, G$^{6c}$-, or G$^{6d}$-;
G$^{6b}$ is 4-6-membered heterocycle optionally substituted with 1, 2, 3, or 4 C$_1$-C$_6$-alkyl, C$_2$-C$_6$-alkenyl, C$_2$-C$_6$-alkynyl, C$_1$-C$_6$-alkoxy, cyano, halogen, hydroxy, or oxo;
G$^{6c}$ is phenyl or 5-6-membered heteroaryl optionally substituted with 1, 2, 3, or 4 C$_1$-C$_6$-alkyl, C$_2$-C$_6$-alkenyl, C$_2$-C$_6$-alkynyl, C$_1$-C$_6$-alkoxy, amino, C$_1$-C$_6$-alkylsulfonylamino, di(C$_1$-C$_6$-alkylsulfonyl)amino, C$_1$-C$_6$-alkylsulfonylaminoC$_1$-C$_6$-alkyl, carboxy, cyano, halogen, hydroxy, hydroxyC$_1$-C$_6$-alkyl, R$^{G6c}$C(O)—, R$^{G6c}$O$_2$C—, (R$^{G6d}$)$_2$NC(O)—, HO$_2$C—(CR$^a$R$^b$)$_r$—, R$^{G6c}$CO$_2$C—(CR$^a$R$^b$)$_r$—, (R$^{G6d}$)$_2$NC(O)—(CR$^a$R$^b$)$_r$—, or R$^{G6c}$CO$_2$—(CR$^a$R$^b$)$_r$—; and G$^{6d}$ is 4-6-membered heterocycle optionally substituted with 1, 2, 3, or 4 C$_1$-C$_6$-alkyl, C$_2$-C$_6$-alkenyl, C$_2$-C$_6$-alkynyl, C$_1$-C$_6$-alkoxy, cyano, halogen, hydroxy, or oxo.

In another embodiment, the compound is further defined as a compound of Formula (Ia-1) wherein:

p is 1, 2, or 3;

r is 1, 2, 3, or 4;

X is NC— or R$^{1x}$C(O)—;

Y is G$^1$- or G$^1$-(CR$^a$R$^b$)—;

R$^4$ is hydrogen, C$_1$-C$_6$-alkyl, C$_2$-C$_4$-alkenyl, C$_1$-C$_6$-fluoroalkyl, amino, C$_1$-C$_6$-alkylamino, C$_1$-C$_6$-dialkylamino, C$_1$-C$_6$-alkoxy, cyano, halogen, hydroxy, G$^{4a}$-, G$^{4b}$-, G$^{4a}$-(CR$^a$R$^b$)$_p$—, G$^{4b}$-(CR$^a$R$^b$)$_p$—; G$^{4a}$O— or G$^{4a}$NH—;

R$^6$ is hydrogen, C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, amino, C$_1$-C$_6$-alkylamino, C$_1$-C$_6$-dialkylamino, hydroxy, G$^{6a}$-, G$^{6a}$N(R$^a$)—, G$^{6a}$O— or G$^{6b}$-;

R$^a$ and R$^b$ are, at each occurrence, independently hydrogen, C$_1$-C$_6$-alkyl, or C$_1$-C$_6$-haloalkyl;

R$^{1x}$ is hydroxy, C$_1$-C$_6$-alkoxy, amino, C$_1$-C$_6$-alkylamino, C$_1$-C$_6$-dialkylamino, or C$_1$-C$_6$-alkylsulfonylamino;

R$^{G1a}$ is, at each occurrence, independently hydrogen, C$_1$-C$_4$-alkyl, C$_2$-C$_4$-alkenyl, C$_2$-C$_4$-alkynyl or C$_1$-C$_4$-haloalkyl;

R$^{G1b}$ is, at each occurrence, independently C$_1$-C$_4$-alkyl, C$_2$-C$_4$-alkenyl, C$_2$-C$_4$-alkynyl or C$_1$-C$_4$-haloalkyl;

R$^{G4a}$ is, at each occurrence, independently C$_1$-C$_4$-alkyl, C$_2$-C$_4$-alkenyl, C$_2$-C$_4$-alkynyl or C$_1$-C$_4$-haloalkyl;

R$^{G6a}$ is, at each occurrence, independently C$_1$-C$_4$-alkyl, C$_2$-C$_4$-alkenyl, C$_2$-C$_4$-alkynyl or C$_1$-C$_4$-haloalkyl;

R$^{G6b}$ is, at each occurrence, independently hydrogen, C$_1$-C$_4$-alkyl, C$_2$-C$_4$-alkenyl, C$_2$-C$_4$-alkynyl or C$_1$-C$_4$-haloalkyl;

R$^{G6c}$ is, at each occurrence, independently C$_1$-C$_4$-alkyl, C$_2$-C$_4$-alkenyl, C$_2$-C$_4$-alkynyl or C$_1$-C$_4$-haloalkyl;

R$^{G6d}$ is, at each occurrence, independently hydrogen, C$_1$-C$_4$-alkyl, C$_2$-C$_4$-alkenyl, C$_2$-C$_4$-alkynyl or C$_1$-C$_4$-haloalkyl;

G$^1$ is phenyl optionally substituted with 1, 2, 3, 4 or 5 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, carboxy, cyano, cyano-C$_1$-C$_6$-alkyl, halogen, halo-C$_1$-C$_6$-alkyl, hydroxy, hydroxy-C$_1$-C$_6$-alkyl, R$^{G1b}$O$_2$C—, R$^{G1a}$HN(O)C—, (R$^{G1a}$)$_2$N(O)C—, G$^{1a}$C(O)—, G$^{1b}$HN(O)C—, G$^{1b}$-, R$^{G1a}$C(O)N(R$^{G1a}$)—, R$^{G1b}$O(O)CN(R$^{G1a}$)—, R$^{G1b}$O$_2$SN(R$^{G1a}$)—, (R$^{G1a}$)$_2$N—, G$^{1b}$O—, G$^{1b}$CH$_2$O—, R$^{G1a}$CO$_2$—, (R$^{G1a}$)$_2$NCO$_2$—, HS—, R$^{G1b}$S—, R$^{G1b}$S(O)—, R$^{G1b}$SO$_2$—, or (R$^{G1a}$)$_2$NSO$_2$—;

G$^{1a}$ is a 4-6-membered heterocycle optionally substituted with 1, 2, 3 or 4 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, cyano, halogen, hydroxy, or oxo;

G$^{1b}$ is phenyl or 5-6-membered heteroaryl optionally substituted with 1, 2, 3, 4 or 5 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, cyano, halogen, hydroxy, or nitro;

G$^{4a}$ is phenyl or 5-6-membered heteroaryl optionally substituted with 1, 2, 3, 4 or 5 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, amido, carboxy, cyano, halogen, hydroxy, R$^{G4a}$O$_2$C—, R$^{G4a}$C(O)—, (R$^{G4a}$)$_2$NC(O)—, or G$^{4a}$-;

G$^{4a1}$ is phenyl or 5-6-membered heteroaryl optionally substituted with 1, 2, 3, 4 or 5 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, cyano, halogen, hydroxy, or nitro;

G$^{4b}$ is a 4-6-membered heterocycle optionally substituted with 1, 2, 3 or 4 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, cyano, halogen, hydroxy, or oxo;

G$^{6a}$ is C$_6$-C$_{10}$-aryl or 5-10-membered heteroaryl optionally substituted with 1, 2, 3, or 4 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, amino, C$_1$-C$_6$-alkylsulfonylamino, carboxy, halogen, hydroxy, hydroxyC$_1$-C$_6$-alkyl, R$^{G6a}$C(O)—, R$^{G6a}$O$_2$C—, HO$_2$C—(CR$^a$R$^b$)$_r$—, R$^{G6a}$O$_2$C—(CR$^a$R$^b$)$_r$—, (R$^{G6b}$)$_2$N(O)C—(CR$^a$R$^b$)$_r$—, R$^{G6a}$CO$_2$—(CR$^a$R$^b$)$_r$—, G$^{6c}$-, or G$^{6d}$-;

G$^{6b}$ is 4-6-membered heterocycle optionally substituted with 1, 2, 3, or 4 C$_1$-C$_6$-alkyl, C$_2$-C$_6$-alkenyl, C$_2$-C$_6$-alkynyl, C$_1$-C$_6$-alkoxy, cyano, halogen, hydroxy, or oxo;

G$^{6c}$ is phenyl or 5-6-membered heteroaryl optionally substituted with 1, 2, 3, or 4 C$_1$-C$_6$-alkyl, C$_2$-C$_6$-alkenyl, C$_2$-C$_6$-alkynyl, C$_1$-C$_6$-alkoxy, amino, C$_1$-C$_6$-alkylsulfonylamino, di(C$_1$-C$_6$-alkylsulfonyl)amino, C$_1$-C$_6$-alkylsulfonylaminoC$_1$-C$_6$-alkyl, carboxy, cyano, halogen, hydroxy, hydroxyC$_1$-C$_6$-alkyl, R$^{G6c}$C(O)—, R$^{G6c}$O$_2$C—, (R$^{G6d}$)$_2$NC(O)—, HO$_2$C—(CR$^a$R$^b$)$_r$—, R$^{G6c}$CO$_2$C—(CR$^a$R$^b$)$_r$—, (R$^{G6d}$)$_2$NC(O)—(CR$^a$R$^b$)$_r$—, or R$^{G6c}$CO$_2$—(CR$^a$R$^b$)$_r$—; and G$^{6d}$ is 4-6-membered heterocycle optionally substituted with 1, 2, 3, or 4 C$_1$-C$_6$-alkyl, C$_2$-C$_6$-alkenyl, C$_2$-C$_6$-alkynyl, C$_1$-C$_6$-alkoxy, cyano, halogen, hydroxy, or oxo.

In another embodiment, the compound is further defined as a compound of Formula (Ia-1) wherein:

p is 1, 2, or 3;

r is 1, 2, 3, or 4;

X is NC—;

Y is G$^1$-;

R$^4$ is hydrogen, C$_1$-C$_6$-alkyl, C$_2$-C$_4$-alkenyl, C$_1$-C$_6$-fluoroalkyl, amino, C$_1$-C$_6$-alkylamino, C$_1$-C$_6$-dialkylamino, C$_1$-C$_6$-alkoxy, cyano, halogen, hydroxy, G$^{4a}$-, G$^{4b}$-, G$^{4a}$-(CR$^a$R$^b$)$_p$—, G$^{4b}$-(CR$^a$R$^b$)$_p$—; G$^{4a}$O— or G$^{4a}$NH—;

R$^6$ is hydrogen, C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, amino, C$_1$-C$_6$-alkylamino, C$_1$-C$_6$-dialkylamino, hydroxy, G$^{6a}$-, G$^{6a}$N(R$^a$)—, G$^{6a}$O— or G$^{6b}$-;

R$^a$ and R$^b$ are, at each occurrence, independently hydrogen, C$_1$-C$_6$-alkyl, or C$_1$-C$_6$-haloalkyl;

R$^{G1a}$ is, at each occurrence, independently hydrogen, C$_1$-C$_4$-alkyl, C$_2$-C$_4$-alkenyl, C$_2$-C$_4$-alkynyl or C$_1$-C$_4$-haloalkyl;

R$^{G1b}$ is, at each occurrence, independently C$_1$-C$_4$-alkyl, C$_2$-C$_4$-alkenyl, C$_2$-C$_4$-alkynyl or C$_1$-C$_4$-haloalkyl;

R$^{G4a}$ is, at each occurrence, independently C$_1$-C$_4$-alkyl, C$_2$-C$_4$-alkenyl, C$_2$-C$_4$-alkynyl or C$_1$-C$_4$-haloalkyl;

R$^{G6a}$ is, at each occurrence, independently C$_1$-C$_4$-alkyl, C$_2$-C$_4$-alkenyl, C$_2$-C$_4$-alkynyl or C$_1$-C$_4$-haloalkyl;

R$^{G6b}$ is, at each occurrence, independently hydrogen, C$_1$-C$_4$-alkyl, C$_2$-C$_4$-alkenyl, C$_2$-C$_4$-alkynyl or C$_1$-C$_4$-haloalkyl;

R$^{G6c}$ is, at each occurrence, independently C$_1$-C$_4$-alkyl, C$_2$-C$_4$-alkenyl, C$_2$-C$_4$-alkynyl or C$_1$-C$_4$-haloalkyl;

R$^{G6d}$ is, at each occurrence, independently hydrogen, C$_1$-C$_4$-alkyl, C$_2$-C$_4$-alkenyl, C$_2$-C$_4$-alkynyl or C$_1$-C$_4$-haloalkyl;

G$^1$ is phenyl optionally substituted with 1, 2, 3, 4 or 5 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, carboxy, cyano, cyano-C$_1$-C$_6$-alkyl, halogen, halo-C$_1$-C$_6$-alkyl, hydroxy, hydroxy-C$_1$-C$_6$-alkyl, $R^{G1b}O_2C$—, $R^{G1a}HN(O)C$—, $(R^{G1a})_2N(O)C$—, $G^{1a}C(O)$—, $G^{1b}HN(O)C$—, $G^{1b}$-, $R^{G1a}C(O)N(R^{G1a})$—, $R^{G1b}O(O)CN(R^{G1a})$—, $R^{G1b}O_2SN(R^{G1a})$—, $(R^{G1a})_2N$—, $G^{1b}O$—, $G^{1b}CH_2O$—, $R^{G1a}CO_2$—, $(R^{G1a})_2NCO_2$—, HS—, $R^{G1b}S$—, $R^{G1b}S(O)$—, $R^{G1b}SO_2$—, or $(R^{G1a})_2NSO_2$—;

$G^{1a}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;

$G^{1b}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{4a}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amido, carboxy, cyano, halogen, hydroxy, $R^{G4a}O_2C$—, $R^{G4a}C(O)$—, $(R^{G4a})_2NC(O)$—, or $G^{4a1}$-;

$G^{4a1}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{4b}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;

$G^{6a}$ is $C_6$-$C_{10}$-aryl or 5-10-membered heteroaryl optionally substituted with 1, 2, 3, or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amino, $C_1$-$C_6$-alkylsulfonylamino, carboxy, halogen, hydroxy, hydroxy$C_1$-$C_6$-alkyl, $R^{G6a}C(O)$—, $R^{G6a}O_2C$—, $HO_2C$—$(CR^aR^b)_r$—, $R^{G6a}O_2C$—$(CR^aR^b)_r$—, $(R^{G6b})_2N(O)C$—$(CR^aR^b)_r$—, $R^{G6a}CO_2$—$(CR^aR^b)_r$—, $G^{6c}$-, or $G^{6d}$-;

$G^{6b}$ is 4-6-membered heterocycle optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, cyano, halogen, hydroxy, or oxo;

$G^{6c}$ is phenyl or 5-6-membered heteroaryl optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, amino, $C_1$-$C_6$-alkylsulfonylamino, di($C_1$-$C_6$-alkylsulfonyl)amino, $C_1$-$C_6$-alkylsulfonylamino$C_1$-$C_6$-alkyl, carboxy, cyano, halogen, hydroxy, hydroxy$C_1$-$C_6$-alkyl, $R^{G6c}C(O)$—, $R^{G6c}O_2C$—, $(R^{G6d})_2NC(O)$—, $HO_2C$—$(CR^aR^b)_r$—, $R^{G6c}O_2C$—$(CR^aR^b)_r$—, $(R^{G6d})_2NC(O)$—$(CR^aR^b)_r$—, or $R^{G6c}CO_2$—$(CR^aR^b)_r$—; and $G^{6d}$ is 4-6-membered heterocycle optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, cyano, halogen, hydroxy, or oxo.

In another embodiment, the compound is further defined as a compound of Formula (Ia-1) wherein:

r is 1, 2, or 3;
X is NC—;
Y is $G^1$-;
$R^4$ is hydrogen, $C_1$-$C_6$-alkyl, $C_1$-$C_6$-alkylamino, $C_1$-$C_6$-dialkylamino, $C_1$-$C_6$-alkoxy, halogen, $G^{4a}$-, $G^{4b}$-, or $G^{4a}NH$—;
$R^6$ is hydrogen, $C_1$-$C_6$-alkoxy, hydroxy, $G^{6a}$-, $G^{6a}N(R^a)$—, or $G^{6b}$-;
$R^a$ and $R^b$ are, at each occurrence, hydrogen;
$R^{G1a}$ is, at each occurrence, independently hydrogen or $C_1$-$C_4$-alkyl;
$R^{G1b}$ is, at each occurrence, $C_1$-$C_4$-alkyl;
$R^{G4a}$ is, at each occurrence, $C_1$-$C_4$-alkyl;
$R^{G6a}$ is, at each occurrence, $C_1$-$C_4$-alkyl;
$R^{G6b}$ is, at each occurrence, hydrogen;
$R^{G6c}$ is, at each occurrence, $C_1$-$C_4$-alkyl;
$R^{G6d}$ is, at each occurrence, hydrogen;

$G^1$ is phenyl optionally substituted with 1 $C_1$-$C_6$-alkyl, $C_1$-$C_6$-fluoroalkyl, $C_1$-$C_6$-alkoxy, carboxy, halogen, hydroxy, hydroxy-$C_1$-$C_6$-alkyl, $R^{G1b}O_2C$—, $R^{G1a}HN(O)C$—, $(R^{G1a})_2N(O)C$—, $G^{1a}C(O)$—, $G^{1b}HN(O)C$—, or $G^{1b}CH_2O$;

$G^{1a}$ is a 4-6-membered heterocycle;
$G^{1b}$ is phenyl;
$G^{4a}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amido, carboxy, cyano, halogen, hydroxy, $R^{G4a}O_2C$—, $R^{G4a}C(O)$—, $(R^{G4a})_2NC(O)$—, or $G^{4a1}$-;

$G^{4a1}$ is 5-6-membered heteroaryl optionally substituted with 1 $C_1$-$C_6$-alkyl;

$G^{4b}$ is a 4-6-membered heterocycle;

$G^{6a}$ is $C_6$-$C_{10}$-aryl or 5-10-membered heteroaryl optionally substituted with 1 or 2 $C_1$-$C_6$-alkyl, $C_1$-$C_6$-fluoroalkyl, $C_1$-$C_6$-alkoxy, amino, halogen, hydroxy, hydroxy$C_1$-$C_6$-alkyl, $R^{G6a}C(O)$—, $R^{G6a}O_2C$—, $HO_2C$—$(CR^aR^b)_r$—, $R^{G6a}O_2C$—$(CR^aR^b)_r$—, $(R^{G6b})_2N(O)C$—$(CR^aR^b)_r$—, $R^{G6a}CO_2$—$(CR^aR^b)_r$—, $G^{6c}$-, or $G^{6d}$-;

$G^{6b}$ is 4-6-membered heterocycle optionally substituted with 1 or 2 $C_1$-$C_6$-alkyl or oxo;

$G^{6c}$ is phenyl or 5-6-membered heteroaryl optionally substituted with 1 or 2 $C_1$-$C_6$-alkyl, amino, $C_1$-$C_6$-alkylsulfonylamino, halogen, hydroxy, $R^{G6c}O_2C$—, or $(R^{G6d})_2NC(O)$—; and $G^{6d}$ is 4-6-membered heterocycle.

In another embodiment, the compound is further defined as a compound of Formula (Ia-1) wherein:

p is 1, 2, or 3;
r is 1, 2, 3, or 4;
X is $R^{1x}C(O)$—;
Y is $G^1$-;
$R^4$ is hydrogen, $C_1$-$C_6$-alkyl, $C_2$-$C_4$-alkenyl, $C_1$-$C_6$-fluoroalkyl, amino, $C_1$-$C_6$-alkylamino, $C_1$-$C_6$-dialkylamino, $C_1$-$C_6$-alkoxy, cyano, halogen, hydroxy, $G^{4a}$-, $G^{4b}$-, $G^{4a}$-$(CR^aR^b)_p$—, $G^{4b}$-$(CR^aR^b)_p$—; $G^{4a}O$— or $G^{4a}NH$—;
$R^6$ is hydrogen, $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amino, $C_1$-$C_6$-alkylamino, $C_1$-$C_6$-dialkylamino, hydroxy, $G^{6a}$-, $G^{6a}N(R^a)$—, $G^{6a}O$— or $G^{6b}$-;
$R^{1x}$ is amino;
$R^a$ and $R^b$ are, at each occurrence, independently hydrogen, $C_1$-$C_6$-alkyl, or $C_1$-$C_6$-haloalkyl;
$R^{G1a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$R^{G1b}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{G4a}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{G6a}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{G6b}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$R^{G6c}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{G6d}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$G^1$ is phenyl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, carboxy, cyano-$C_1$-$C_6$-alkyl, halogen, halo-$C_1$-$C_6$-alkyl, hydroxy, hydroxy-$C_1$-$C_6$-alkyl, $R^{G1b}O_2C$—, $R^{G1a}HN(O)C$—, $(R^{G1a})_2N(O)C$—, $G^{1a}C$ (O)—, $G^{1b}HN(O)C$—, $G^{1b}$-, $R^{G1a}C(O)N(R^{G1a})$—, $R^{G1b}O(O)CN(R^{G1a})$—, $R^{G1b}O_2SN(R^{G1a})$—, $(R^{G1a})_2N$—, $G^{1b}O$—, $G^{1b}CH_2O$—, $R^{G1a}CO_2$—, $(R^{G1a})_2NCO_2$—, HS—, $R^{G1b}S$—, $R^{G1b}S(O)$—, $R^{G1b}SO_2$—, or $(R^{G1a})_2NSO_2$—;

$G^{1a}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;

$G^{1b}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{4a}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amido, carboxy, cyano, halogen, hydroxy, $R^{G4a}O_2C$—, $R^{G4a}C(O)$—, $(R^{G4a})_2NC(O)$—, or $G^{4a1}$-;

$G^{4a1}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{4b}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;

$G^{6a}$ is $C_6$-$C_{10}$-aryl or 5-10-membered heteroaryl optionally substituted with 1, 2, 3, or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amino, $C_1$-$C_6$-alkylsulfonylamino, carboxy, halogen, hydroxy, hydroxy$C_1$-$C_6$-alkyl, $R^{G6a}C(O)$—, $R^{G6a}O_2C$—, $HO_2C$—$(CR^aR^b)_r$—, $R^{G6a}O_2C$—$(CR^aR^b)_r$—, $(R^{G6b})_2N(O)C$—$(CR^aR^b)_r$—, $R^{G6a}CO_2$—$(CR^aR^b)_r$-$G^{6c}$-, or $G^{6d}$-;

$G^{6b}$ is 4-6-membered heterocycle optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, cyano, halogen, hydroxy, or oxo;

$G^{6c}$ is phenyl or 5-6-membered heteroaryl optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, amino, $C_1$-$C_6$-alkylsulfonylamino, di($C_1$-$C_6$-alkylsulfonyl)amino, $C_1$-$C_6$-alkylsulfonylamino$C_1$-$C_6$-alkyl, carboxy, cyano, halogen, hydroxy, hydroxy$C_1$-$C_6$-alkyl, $R^{G6c}C(O)$—, $R^{G6c}O_2C$—, $(R^{G6d})_2NC(O)$—, $HO_2C$—$(CR^aR^b)_r$—, $R^{G6c}O_2C$—$(CR^aR^b)_r$—, $(R^{G6d})_2NC(O)$—$(CR^aR^b)_r$—, or $R^{G6c}CO_2$—$(CR^aR^b)_r$—; and $G^{6d}$ is 4-6-membered heterocycle optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, cyano, halogen, hydroxy, or oxo.

In another embodiment, the compound is further defined as a compound of Formula (Ia-1) wherein:

X is $R^{1x}C(O)$—;

Y is $G^1$-;

$R^4$ is hydrogen, $C_1$-$C_6$-alkyl, $C_1$-$C_6$-fluoroalkyl, $C_1$-$C_6$-alkoxy or halogen;

$R^6$ is hydrogen, $C_1$-$C_6$-alkoxy, hydroxy, or $G^{6a}$-;

$R^{1x}$ is amino;

$R^{G1b}$ is, at each occurrence, $C_1$-$C_4$-alkyl;

$G^1$ is phenyl optionally substituted with 1 $C_1$-$C_6$-alkyl, $C_1$-$C_6$-fluoroalkyl, $C_1$-$C_6$-alkoxy, halogen, hydroxy, or $R^{G1b}O_2C$—;

$G^{6a}$ is $C_6$-$C_{10}$-aryl or 5-10-membered heteroaryl optionally substituted with 1 or 2 $C_1$-$C_6$-alkyl, $C_1$-$C_6$-fluoroalkyl, $C_1$-$C_6$-alkoxy, halogen, hydroxy, or $G^{6c}$-; and $G^{6c}$ is phenyl or 5-6-membered heteroaryl optionally substituted with 1 $C_1$-$C_6$-alkyl or halogen.

In one embodiment, the compounds are further defined as:

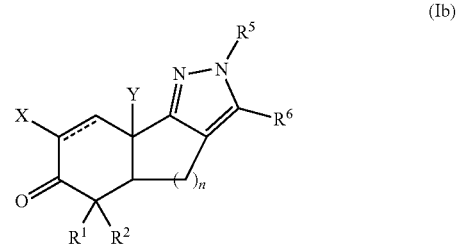

(Ib)

wherein

----- is a single or double bond;

n is 1 or 2;

p is 1, 2, or 3;

r is 1, 2, 3, or 4;

X is NC—, $F_3C$—, $R^{1x}C(O)$—, or $O_2N$—;

Y is $G^1$-, $G^1$-$(CR^aR^b)$—, $G^2$-, or $G^2$-$(CR^aR^b)$—;

$R^1$ and $R^2$ are each independently hydrogen, $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amido, amino, halogen, hydroxy, $G^{R1a}$-, $G^{R1a}$-$(CR^aR^b)_p$—, $G^{R1b}$-, $R^{1a}C(O)$—, $(R^{1a})_2N$—, $G^{R1a}NH$—, $G^{R1a}$-$(CR^aR^b)_p$—NH—, $G^{R1a}O$—, and $R^{1a}CO_2$—; or $R^1$ and $R^2$ joined together with the carbon atom to which they are attached form a $C_3$-$C_6$-cycloalkyl, $C_3$-$C_6$-cycloalkenyl, or 4-6-membered heterocycle optionally substituted with $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;

$R^5$ is hydrogen, $C_1$-$C_6$-alkyl, $C_2$-$C_6$-alkenyl, $C_2$-$C_6$-alkynyl, $C_1$-$C_6$-fluoroalkyl, $G^{R5a}$-, $G^{R5a}$-$(CR^aR^b)$—, $R^{5a}C(O)$—, $G^{R5a}C(O)$—, hydroxy-$C_1$-$C_6$-alkyl-$C(O)$—, $R^{5a}O_2C$—, $G^{R5a}O_2C$—, $G^{R5a}HNC(O)$—, $R^{5a}O_2CNHCH_2C(O)$—, $H_2NHCH_2C(O)$—, $R^{5a}SO_2$—, or $G^{R5a}SO_2$—;

$R^6$ is hydrogen, $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amino, $C_1$-$C_6$-alkylamino, $C_1$-$C_6$-dialkylamino, hydroxy, $G^{6a}$-, $G^{6a}N(R^a)$—, $G^{6a}O$— or $G^{6b}$-;

$R^a$ and $R^b$ are, at each occurrence, independently hydrogen, $C_1$-$C_6$-alkyl, or $C_1$-$C_6$-haloalkyl;

$R^{1a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$R^{1x}$ is hydroxy, $C_1$-$C_6$-alkoxy, amino, $C_1$-$C_6$-alkylamino, $C_1$-$C_6$-dialkylamino, or $C_1$-$C_6$-alkylsulfonylamino;

$R^{G1a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$R^{G1b}$ is, at each occurrence, independently $C_1$-$C_4$-alkyl, $C_2$-$C_4$-alkenyl, $C_2$-$C_4$-alkynyl or $C_1$-$C_4$-haloalkyl;

$R^{G2a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$R^{G2b}$ is, at each occurrence, independently $C_1$-$C_4$-alkyl, $C_2$-$C_4$-alkenyl, $C_2$-$C_4$-alkynyl or $C_1$-$C_4$-haloalkyl;

$R^{5a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$R^{G6a}$ is, at each occurrence, independently $C_1$-$C_4$-alkyl, $C_2$-$C_4$-alkenyl, $C_2$-$C_4$-alkynyl or $C_1$-$C_4$-haloalkyl;

$R^{G6b}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$R^{G6c}$ is, at each occurrence, independently $C_1$-$C_4$-alkyl, $C_2$-$C_4$-alkenyl, $C_2$-$C_4$-alkynyl or $C_1$-$C_4$-haloalkyl;

$R^{G6d}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$G^1$ is phenyl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, carboxy, cyano, cyano-$C_1$-$C_6$-alkyl, halogen, halo-$C_1$-$C_6$-alkyl, hydroxy, hydroxy-$C_1$-$C_6$-alkyl, $R^{G1b}O_2C$—, $R^{G1a}HN(O)C$—, $(R^{G1a})_2N(O)C$—, $G^{1a}C(O)$—, $G^{1b}HN(O)C$—, $G^{1b}$-, $R^{G1a}C(O)N(R^{G1a})$—, $R^{G1b}O(O)CN(R^{G1a})$—, $R^{G1b}O2SN(R^{G1a})$—, $(R^{G1a})_2N$—, $G^{1b}O$—, $G^{1b}CH_2O$—, $R^{G1a}CO_2$—, $(R^{G1a})_2NCO_2$—, HS—, $R^{G1b}S$—, $R^{G1b}S(O)$—, $R^{G1b}SO_2$—, or $(R^{G1a})_2NSO_2$—;

$G^2$ is a 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, carboxy, cyano, cyano-$C_1$-$C_6$-alkyl, halogen, halo-$C_1$-$C_6$-alkyl, hydroxy, hydroxy-$C_1$-$C_6$-alkyl, $R^{G2b}CO_2$—, $R^{G2a}HNC(O)$—, $(R^{G2a})_2 NC(O)$—, $G^{2a}C(O)$—, $G^{2b}HNC(O)$—, $G^{2b}$-, $R^{G2a}C(O)N(R^{G2a})$—, $R^{G2b}OC(O)N(R^{G2a})$—, $R^{G2b}SO_2N(R^{G2a})$—, $(R^{G2a})_2N$—, $G^{2b}O$—, $G^{2b}CH_2O$—, $R^{G2a}CO_2$—, $(R^{G2a})_2NCO_2$—, HS—, $R^{G2b}S$—, $R^{G2b}S(O)$—, $R^{G2b}SO_2$—, or $(R^{G2a})_2NSO_2$—;

$G^{1a}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;

$G^{1b}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{R1a}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{R1b}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;

$G^{2a}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;

$G^{2b}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{R5a}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{6a}$ is $C_6$-$C_{10}$-aryl or 5-10-membered heteroaryl optionally substituted with 1, 2, 3, or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amino, $C_1$-$C_6$-alkylsulfonylamino, carboxy, halogen, hydroxy, hydroxy$C_1$-$C_6$-alkyl, $R^{G6a}C(O)$—, $R^{G6a}O_2C$—, $HO_2C$—$(CR^aR^b)_r$—, $R^{G6a}O_2C$—$(CR^aR^b)_r$—, $(R^{G6b})_2N(O)C$—$(CR^aR^b)_r$—, $R^{G6a}CO_2$—$(CR^aR^b)_r$—, $G^{6c}$-, or $G^{6d}$-;

$G^{6b}$ is 4-6-membered heterocycle optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, cyano, halogen, hydroxy, or oxo;

$G^{6c}$ is phenyl or 5-6-membered heteroaryl optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, amino, $C_1$-$C_6$-alkylsulfonylamino, di($C_1$-$C_6$-alkylsulfonyl)amino, $C_1$-$C_6$-alkylsulfonylamino$C_1$-$C_6$-alkyl, carboxy, cyano, halogen, hydroxy, hydroxy$C_1$-$C_6$-alkyl, $R^{G6c}C(O)$—, $R^{G6c}O_2C$—, $(R^{G6d})_2NC(O)$—, $HO_2C$—$(CR^aR^b)_r$—, $R^{G6c}O_2C$—$(CR^aR^b)_r$—, $(R^{G6d})_2NC(O)$—$(CR^aR^b)_r$—, or $R^{G6c}CO_2$—$(CR^aR^b)_r$—; and $G^{6d}$ is 4-6-membered heterocycle optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, cyano, halogen, hydroxy, or oxo.

In one embodiment, the compounds are further defined as:

(Ib-1)

wherein, r is 1, 2, 3, or 4;

X is NC—, $F_3C$—, $R^{1x}C(O)$—, or $O_2N$—;

Y is $G^1$-, $G^1$-$(CR^aR^b)$—, $G^2$-, or $G^2$-$(CR^aR^b)$—;

$R^5$ is hydrogen, $C_1$-$C_6$-alkyl, $C_2$-$C_6$-alkenyl, $C_2$-$C_6$-alkynyl, $C_1$-$C_6$-fluoroalkyl, $G^{R5a}$-, $G^{R5a}$-$(CR^aR^b)$—, $R^{5a}C(O)$—, $G^{R5a}C(O)$—, hydroxy-$C_1$-$C_6$-alkyl-$C(O)$—, $R^{5a}O_2C$—, $G^{R5a}O_2C$—, $G^{R5a}HNC(O)$—, $R^{5a}O_2CNHCH_2C(O)$—, $H_2NHCH_2C(O)$—, $R^{5a}SO_2$—, or $G^{R5a}SO_2$—;

$R^6$ is hydrogen, $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amino, $C_1$-$C_6$-alkylamino, $C_1$-$C_6$-dialkylamino, hydroxy, $G^{6a}$-, $G^{6a}N(R^a)$—, $G^{6a}O$— or $G^{6b}$-;

$R^a$ and $R^b$ are, at each occurrence, independently hydrogen, $C_1$-$C_6$-alkyl, or $C_1$-$C_6$-haloalkyl;

$R^{1x}$ is hydroxy, $C_1$-$C_6$-alkoxy, amino, $C_1$-$C_6$-alkylamino, $C_1$-$C_6$-dialkylamino, or $C_1$-$C_6$-alkylsulfonylamino;

$R^{G1a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$R^{G1b}$ is, at each occurrence, independently $C_1$-$C_4$-alkyl, $C_2$-$C_4$-alkenyl, $C_2$-$C_4$-alkynyl or $C_1$-$C_4$-haloalkyl;

$R^{G2a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$R^{G2b}$ is, at each occurrence, independently $C_1$-$C_4$-alkyl, $C_2$-$C_4$-alkenyl, $C_2$-$C_4$-alkynyl or $C_1$-$C_4$-haloalkyl;

$R^{5a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$R^{G6a}$ is, at each occurrence, independently $C_1$-$C_4$-alkyl, $C_2$-$C_4$-alkenyl, $C_2$-$C_4$-alkynyl or $C_1$-$C_4$-haloalkyl;

$R^{G6b}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$R^{G6c}$ is, at each occurrence, independently $C_1$-$C_4$-alkyl, $C_2$-$C_4$-alkenyl, $C_2$-$C_4$-alkynyl or $C_1$-$C_4$-haloalkyl;

$R^{G6d}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$G^1$ is phenyl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, carboxy, cyano, cyano-$C_1$-$C_6$-alkyl, halogen, halo-$C_1$-$C_6$-alkyl, hydroxy, hydroxy-$C_1$-$C_6$-alkyl, $R^{G1b}O_2C$—, $R^{G1a}HN(O)C$—, $(R^{G1a})_2N(O)C$—, $G^{1a}C(O)$—, $G^{1b}HN(O)C$—, $G^{1b}$-, $R^{G1a}C(O)N(R^{G1a})$—, $R^{G1b}O$ (O)CN($R^{G1a}$)—, $R^{G1b}O_2SN(R^{G1a})$—, $(R^{G1a})_2N$—, $G^{1b}O$—, $G^{1b}CH_2O$—, $R^{G1a}CO_2$—, $(R^{G1a})_2NCO_2$—, HS—, $R^{G1b}S$—, $R^{G1b}S(O)$—, $R^{G1b}SO_2$—, or $(R^{G1a})_2NSO_2$—;

$G^2$ is a 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, carboxy, cyano, cyano-$C_1$-$C_6$-alkyl, halogen, halo-$C_1$-$C_6$-alkyl, hydroxy, hydroxy-$C_1$-$C_6$-alkyl, $R^{G2b}CO_2$—, $R^{G2a}HNC(O)$—, $(R^{G2a})_2NC(O)$—, $G^{2a}C(O)$—, $G^{2b}HNC(O)$—, $G^{2b}$-, $R^{G2a}C(O)N(R^{G2a})$—$R^{G2b}OC(O)N(R^{G2a})$—, $R^{G2b}SO_2N(R^{G2a})$—, $(R^{G2a})_2N$—, $G^{2b}O$—, $G^{2b}CH_2O$—, $R^{G2a}CO_2$—, $(R^{G2a})_2NCO_2$—, HS—, $R^{G2b}S$—, $R^{G2b}S(O)$—, $R^{G2b}SO_2$—, or $(R^{G2a})_2NSO_2$—;

$G^{1a}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;

$G^{1b}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{2a}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;

$G^{2b}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{R5a}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{6a}$ is $C_6$-$C_{10}$-aryl or 5-10-membered heteroaryl optionally substituted with 1, 2, 3, or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amino, $C_1$-$C_6$-alkylsulfonylamino, carboxy, halogen, hydroxy, hydroxy$C_1$-$C_6$-alkyl, $R^{G6a}C(O)$—, $R^{G6a}O_2C$—, $HO_2C$—$(CR^aR^b)_r$—, $R^{G6a}O_2C$—$(CR^aR^b)_r$—, $(R^{G6b})_2N(O)C$—$(CR^aR^b)_r$—, $R^{G6a}CO_2$—$(CR^aR^b)_r$—, $G^{6c}$-, or $G^{6d}$-;

$G^{6b}$ is 4-6-membered heterocycle optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, cyano, halogen, hydroxy, or oxo;

$G^{6c}$ is phenyl or 5-6-membered heteroaryl optionally substituted with 1, 2, 3, or 4 $C_1$-$C_6$-alkyl, $C_2$-$C_6$-alkenyl, $C_2$-$C_6$-alkynyl, $C_1$-$C_6$-alkyl, amino, $C_1$-$C_6$-alkylsulfonylamino, di($C_1$-$C_6$-alkylsulfonyl)amino, $C_1$-$C_6$-alkylsulfonylamino$C_1$-$C_6$-alkyl, carboxy, cyano, halogen, hydroxy, hydroxy$C_1$-$C_6$-alkyl, $R^{G6c}C(O)$—, $R^{G6c}O_2C$—, $(R^{G6d})_2NC(O)$—, $HO_2C$—$(CR^aR^b)_r$—, $R^{G6c}O_2C$—$(CR^aR^b)_r$—, $(R^{G6d})_2NC(O)$—$(CR^aR^b)_r$—, or $R^{G6c}CO_2$—$(CR^aR^b)_r$—; and $G^{6d}$ is 4-6-membered heterocycle optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, cyano, halogen, hydroxy, or oxo.

In another embodiment, the compound is further defined as a compound of Formula (Ib-1) wherein:

r is 1, 2, 3, or 4;

X is NC— or $R^{1x}C(O)$—;

Y is $G^1$- or $G^1$-$(CR^aR^b)$—;

$R^5$ is hydrogen, $C_1$-$C_6$-alkyl, $C_2$-$C_6$-alkenyl, $C_2$-$C_6$-alkynyl, $C_1$-$C_6$-fluoroalkyl, $G^{R5a}$-, $G^{R5a}$-$(CR^aR^b)$—, $R^{5a}C(O)$—, $G^{R5a}C(O)$—, hydroxy-$C_1$-$C_6$-alkyl-$C(O)$—, $R^{5a}O_2C$—, $G^{R5a}O_2C$—, $G^{R5a}HNC(O)$—, $R^{5a}O_2CNHCH_2C(O)$—, $H_2NHCH_2C(O)$—, $R^{5a}SO_2$—, or $G^{R5a}SO_2$—;

$R^6$ is hydrogen, $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amino, $C_1$-$C_6$-alkylamino, $C_1$-$C_6$-dialkylamino, hydroxy, $G^{6a}$-, $G^{6a}N(R^a)$—, $G^{6a}O$— or $G^{6b}$;

$R^a$ and $R^b$ are, at each occurrence, independently hydrogen, $C_1$-$C_6$-alkyl, or $C_1$-$C_6$-haloalkyl;

$R^{1x}$ is hydroxy, $C_1$-$C_6$-alkoxy, amino, $C_1$-$C_6$-alkylamino, $C_1$-$C_6$-dialkylamino, or $C_1$-$C_6$-alkylsulfonylamino;

$R^{G1a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$R^{G1b}$ is, at each occurrence, independently $C_1$-$C_4$-alkyl, $C_2$-$C_4$-alkenyl, $C_2$-$C_4$-alkynyl or $C_1$-$C_4$-haloalkyl;

$R^{5a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$R^{G6a}$ is, at each occurrence, independently $C_1$-$C_4$-alkyl, $C_2$-$C_4$-alkenyl, $C_2$-$C_4$-alkynyl or $C_1$-$C_4$-haloalkyl;

$R^{G6b}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$R^{G6c}$ is, at each occurrence, independently $C_1$-$C_4$-alkyl, $C_2$-$C_4$-alkenyl, $C_2$-$C_4$-alkynyl or $C_1$-$C_4$-haloalkyl;

$R^{G6d}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$G^1$ is phenyl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, carboxy, cyano, cyano-$C_1$-$C_6$-alkyl, halogen, halo-$C_1$-$C_6$-alkyl, hydroxy, hydroxy-$C_1$-$C_6$-alkyl, $R^{G1b}O_2C$—, $R^{G1a}HN(O)C$—, $(R^{G1a})_2N(O)C$—, $G^{1a}C(O)$—, $G^{1b}HN(O)C$—, $G^{1b}$-, $R^{G1a}C(O)N(R^{G1a})$—, $R^{G1b}O(O)CN(R^{G1a})$—, $R^{G1b}O_2SN(R^{G1a})$—, $(R^{G1a})_2N$—, $G^{1b}O$—, $G^{1b}CH_2O$—, $R^{G1a}CO_2$—, $(R^{G1a})_2NCO_2$—, HS—, $R^{G1b}S$—, $R^{G1b}S(O)$—, $R^{G1b}SO_2$—, or $(R^{G1a})_2NSO_2$—;

$G^{1a}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;

$G^{1b}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{R5a}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{6a}$ is $C_6$-$C_{10}$-aryl or 5-10-membered heteroaryl optionally substituted with 1, 2, 3, or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amino, $C_1$-$C_6$-alkylsulfonylamino, carboxy, halogen, hydroxy, hydroxy$C_1$-$C_6$-alkyl, $R^{G6a}C(O)$—, $R^{G6a}O_2C$—, $HO_2C$—$(CR^aR^b)_r$—, $R^{G6a}O_2C$—$(CR^aR^b)_r$—, $(R^{G6b})_2N(O)C$—$(CR^aR^b)_r$—, $R^{G6a}CO_2$—$(CR^aR^b)_r$—, $G^{6c}$-, or $G^{6d}$-;

$G^{6b}$ is 4-6-membered heterocycle optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, cyano, halogen, hydroxy, or oxo;

$G^{6c}$ is phenyl or 5-6-membered heteroaryl optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, amino, $C_1$-$C_6$-alkylsulfonylamino, di($C_1$-$C_6$-alkylsulfonyl)amino, $C_1$-$C_6$-alkylsulfonylamino$C_1$-$C_6$-alkyl, carboxy, cyano, halogen, hydroxy, hydroxy$C_1$-$C_6$-alkyl, $R^{G6c}C(O)$—, $R^{G6c}O_2C$—, $(R^{G6d})_2NC(O)$—, $HO_2C$—$(CR^aR^b)_r$—, $R^{G6c}O_2C$—$(CR^aR^b)_r$—, $(R^{G6d})_2NC(O)$—$(CR^aR^b)_r$—, or $R^{G6c}CO_2$—$(CR^aR^b)_r$—; and $G^{6d}$ is 4-6-membered heterocycle optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, cyano, halogen, hydroxy, or oxo.

In another embodiment, the compound is further defined as a compound of Formula (Ib-1) wherein:

r is 1, 2, 3, or 4;

X is NC—;

Y is $G^1$-;

$R^5$ is hydrogen, $C_1$-$C_6$-alkyl, $C_2$-$C_6$-alkenyl, $C_2$-$C_6$-alkynyl, $C_1$-$C_6$-fluoroalkyl, $G^{R5a}$-, $G^{R5a}$-$(CR^aR^b)$—, $R^{5a}C(O)$—, $G^{R5a}C(O)$—, hydroxy-$C_1$-$C_6$-alkyl-C(O)—, $R^{5a}O_2C$—, $G^{R5a}O_2C$—, $G^{R5a}HNC(O)$—, $R^{5a}O_2CNHCH_2C(O)$—, $H_2NHCH_2C(O)$—, $R^{5a}SO_2$—, or $G^{R5a}SO_2$—;

$R^6$ is hydrogen, $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amino, $C_1$-$C_6$-alkylamino, $C_1$-$C_6$-dialkylamino, hydroxy, $G^{6a}$-, $G^{6a}N(R^a)$—, $G^{6a}O$— or $G^{6b}$;

$R^a$ and $R^b$ are, at each occurrence, independently hydrogen, $C_1$-$C_6$-alkyl, or $C_1$-$C_6$-haloalkyl;

$R^{G1a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$R^{G1b}$ is, at each occurrence, independently $C_1$-$C_4$-alkyl, $C_2$-$C_4$-alkenyl, $C_2$-$C_4$-alkynyl or $C_1$-$C_4$-haloalkyl;

$R^{5a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$R^{G6a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$R^{G6b}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$R^{G6c}$ is, at each occurrence, independently $C_1$-$C_4$-alkyl, $C_2$-$C_4$-alkenyl, $C_2$-$C_4$-alkynyl or $C_1$-$C_4$-haloalkyl;

$R^{G6d}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;

$G^1$ is phenyl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, carboxy, cyano, cyano-$C_1$-$C_6$-alkyl, halogen, halo-$C_1$-$C_6$-alkyl, hydroxy, hydroxy-$C_1$-$C_6$-alkyl, $R^{G1b}O_2C$—, $R^{G1a}HN(O)C$—, $(R^{G1a})_2N(O)C$—, $G^{1a}C(O)$—, $G^{1b}HN(O)C$—, $G^{1b}$-, $R^{G1a}C(O)N(R^{G1a})$—, $R^{G1b}O(O)CN(R^{G1a})$—, $R^{G1b}O_2SN(R^{G1a})$—, $(R^{G1a})_2N$—, $G^{1b}O$—, $G^{1b}CH_2O$—, $R^{G1a}CO_2$—, $(R^{G1a})_2NCO_2$—, HS—, $R^{G1b}S$—, $R^{G1b}S(O)$—, $R^{G1b}SO_2$—, or $(R^{G1a})_2NSO_2$—;

$G^{1a}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;

$G^{1b}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{R5a}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{6a}$ is $C_6$-$C_{10}$-aryl or 5-10-membered heteroaryl optionally substituted with 1, 2, 3, or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amino, $C_1$-$C_6$-alkylsulfonylamino, carboxy, halogen, hydroxy, hydroxy$C_1$-$C_6$-alkyl, $R^{G6a}C(O)$—, $R^{G6a}O_2C$—, $HO_2C$—$(CR^aR^b)_r$—, $R^{G6a}O_2C$—$(CR^aR^b)_r$—, $(R^{G6b})_2N(O)C$—$(CR^aR^b)_r$—, $R^{G6a}CO_2$—$(CR^aR^b)_r$—, $G^{6c}$-, or $G^{6d}$-;

$G^{6b}$ is 4-6-membered heterocycle optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, cyano, halogen, hydroxy, or oxo;

$G^{6c}$ is phenyl or 5-6-membered heteroaryl optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, amino, $C_1$-$C_6$-alkylsulfonylamino, di($C_1$-$C_6$-alkylsulfonyl)amino, $C_1$-$C_6$-alkylsulfonylamino$C_1$-$C_6$-alkyl, carboxy, cyano, halogen, hydroxy, hydroxy$C_1$-$C_6$-alkyl, $R^{G6c}C(O)$—, $R^{G6c}O_2C$—, $(R^{G6d})_2NC(O)$—, $HO_2C$—$(CR^aR^b)_r$—, $R^{G6c}CO_2C$—$(CR^aR^b)_r$—, $(R^{G6d})_2NC(O)$—$(CR^aR^b)_r$—, or $R^{G6c}CO_2$—$(CR^aR^b)_r$—; and $G^{6d}$ is 4-6-membered heterocycle optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, cyano, halogen, hydroxy, or oxo.

In another embodiment, the compound is further defined as a compound of Formula (Ib-1) wherein:

r is 1, 2 or 3;

X is NC—;

Y is $G^1$-;

$R^5$ is hydrogen, $C_1$-$C_6$-alkyl, $C_1$-$C_6$-fluoroalkyl, $G^{R5a}$-, $G^{R5a}$-$(CR^aR^b)$—, $R^{5a}C(O)$—, $G^{R5a}C(O)$—, hydroxy-$C_1$-$C_6$-alkyl-C(O)—, $R^{5a}O_2C$—, $G^{R5a}O_2C$—, $G^{R5a}HNC(O)$—, $R^{5a}O_2CNHCH_2C(O)$—, $H_2NHCH_2C(O)$—, $R^{5a}SO_2$—, or $G^{R5a}SO_2$—;

$R^6$ is hydrogen, $C_1$-$C_6$-alkoxy or $G^{6a}$-;

$R^a$ and $R^b$ are, at each occurrence, hydrogen;

$R^{5a}$ is, at each occurrence, $C_1$-$C_4$-alkyl;

$R^{G6d}$ is, at each occurrence, hydrogen;

$G^1$ is phenyl optionally substituted with 1 or 2, $C_1$-$C_6$-alkyl, $C_1$-$C_6$-fluoroalkyl, $C_1$-$C_6$-alkoxy, carboxy, halogen, hydroxy or $R^{G1b}O_2C$—;

$G^{R5a}$ is phenyl or 5-6-membered heteroaryl;

$G^{6a}$ is $C_6$-$C_{10}$-aryl or 5-10-membered heteroaryl optionally substituted with 1 or 2 $C_1$-$C_6$-alkyl, $C_1$-$C_6$-fluoroalkyl, $C_1$-$C_6$-alkoxy, amino, $C_1$-$C_6$-alkylsulfonylamino, carboxy, halogen, hydroxy, hydroxy$C_1$-$C_6$-alkyl, $HO_2C$—$(CR^aR^b)_r$— or $G^{6c}$-;

$G^{6b}$ is 4-6-membered heterocycle optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, cyano, halogen, hydroxy, or oxo; and $G^{6c}$ is phenyl or 5-6-membered heteroaryl optionally substituted with 1 or 2 $C_1$-$C_6$-alkyl, $C_1$-$C_6$-alkoxy, amino, $C_1$-$C_6$-alkylsulfonylamino, di($C_1$-$C_6$-alkylsulfonyl)amino, $C_1$-$C_6$-alkylsulfonylamino$C_1$-$C_6$-alkyl, carboxy, cyano, halogen, hydroxy, hydroxy$C_1$-$C_6$-alkyl or $(R^{G6d})_2NC(O)$—.

In another embodiment, the compound is further defined as a compound of Formula (Ib-1) wherein:

X is NC— or $R^{1x}C(O)$—;

Y is $G^1$-$(CR^aR^b)$—;

$R^5$ is hydrogen, $C_1$-$C_6$-alkyl, $R^{5a}C(O)$— or $R^{5a}SO_2$—;

$R^6$ is hydrogen or $G^{6a}$-;

$R^a$ and $R^b$ are, at each occurrence, hydrogen;

$R^{1x}$ is amino;

$R^{G1b}$ is, at each occurrence, $C_1$-$C_4$-alkyl, $C_2$-$C_4$-alkenyl, $C_2$-$C_4$-alkynyl or $C_1$-$C_4$-haloalkyl;

$R^{5a}$ is, at each occurrence, $C_1$-$C_4$-alkyl;

$G^1$ is phenyl optionally substituted with 1 or 2 $C_1$-$C_6$-alkyl, $C_1$-$C_6$-fluoroalkyl, $C_1$-$C_6$-alkoxy, carboxy, halogen, hydroxy or $R^{G1b}O_2C$—; and $G^{6a}$ is $C_6$-$C_{10}$-aryl or 5-10-membered heteroaryl optionally substituted with 1 or 2 $C_1$-$C_6$-alkyl, $C_1$-$C_6$-fluoroalkyl, $C_1$-$C_6$-alkoxy, $C_1$-$C_6$-alkylsulfonylamino, carboxy or halogen.

In one embodiment, the compounds are further defined as:

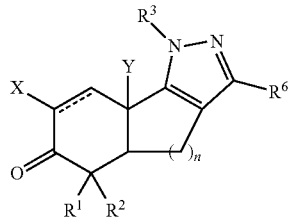

(Ic)

wherein,
----- is a single or double bond;
n is 1 or 2;
p is 1, 2, or 3;
q is 1, 2, or 3;
r is 1, 2, 3, or 4;
X is NC—, $F_3C$—, $R^{1x}C(O)$—, or $O_2N$—;
Y is $G^1$-, $G^1$-$(CR^aR^b)$—, $G^2$-, or $G^2$-$(CR^aR^b)$—;
$R^1$ and $R^2$ are each independently hydrogen, $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amido, amino, halogen, hydroxy, $G^{R1a}$-, $G^{R1a}$-$(CR^aR^b)_p$—, $G^{R1b}$-, $R^{1a}C(O)$—, $(R^{1a})_2N$—, $G^{R1a}NH$—, $G^{R1a}$-$(CR^aR^b)_p$—NH—, $G^{R1a}O$—, and $R^{1a}CO_2$—; or
$R^1$ and $R^2$ joined together with the carbon atom to which they are attached form a $C_3$-$C_6$-cycloalkyl, $C_3$-$C_6$-cycloalkenyl, or 4-6-membered heterocycle optionally substituted with $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;
$R^3$ is hydrogen, $C_1$-$C_6$-alkyl, $C_2$-$C_4$-alkenyl, $C_1$-$C_6$-fluoroalkyl, $G^{3a}$- or $G^{3a}$-$(CR^aR^b)_q$;
$R^6$ is hydrogen, $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amino, $C_1$-$C_6$-alkylamino, $C_1$-$C_6$-dialkylamino, hydroxy, $G^{6a}$-, $G^{6a}N(R^a)$—, $G^{6a}O$— or $G^{6b}$-;
$R^a$ and $R^b$ are, at each occurrence, independently hydrogen, $C_1$-$C_6$-alkyl, or $C_1$-$C_6$-haloalkyl;
$R^{1a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$R^{1x}$ is hydroxy, $C_1$-$C_6$-alkoxy, amino, $C_1$-$C_6$-alkylamino, $C_1$-$C_6$-dialkylamino, or $C_1$-$C_6$-alkylsulfonylamino;
$R^{G1a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$R^{G1b}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{G2a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$R^{G2b}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{G6a}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{G6b}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$R^{G6c}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{G6d}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$G^1$ is phenyl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, carboxy, cyano, cyano-$C_1$-$C_6$-alkyl, halogen, halo-$C_1$-$C_6$-alkyl, hydroxy, hydroxy-$C_1$-$C_6$-alkyl, $R^{G1b}O_2C$—, $R^{G1a}HN(O)C$—, $(R^{G1a})_2N(O)C$—, $G^{1a}C(O)$—, $G^{1b}HN(O)C$—, $G^{1b}$-, $R^{G1a}C(O)N(R^{G1a})$—, $R^{G1b}O(O)CN(R^{G1a})$—, $R^{G1b}O_2SN(R^{G1a})$—, $(R^{G1a})_2N$—, $G^{1b}O$—, $G^{1b}CH_2O$—, $R^{G1a}CO_2$—, $(R^{G1a})_2NCO_2$—, HS—, $R^{G1b}S$—, $R^{G1b}S(O)$—, $R^{G1b}SO_2$—, or $(R^{G1a})_2NSO_2$—;
$G^2$ is a 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, carboxy, cyano, cyano-$C_1$-$C_6$-alkyl, halogen, halo-$C_1$-$C_6$-alkyl, hydroxy, hydroxy-$C_1$-$C_6$-alkyl, $R^{G2b}CO_2$—, $R^{G2a}HNC(O)$—, $(R^{G2a})_2NC(O)$—, $G^{2a}C(O)$—, $G^{2b}HNC(O)$—, $G^{2b}$-, $R^{G2a}C(O)N(R^{G2a})$—$R^{G2b}OC(O)N(R^{G2a})$—, $R^{G2b}SO_2N(R^{G2a})$—, $(R^{G2a})_2N$—, $G^{2b}O$—, $G^{2b}CH_2O$—, $R^{G2a}CO_2$—, $(R^{G2a})_2NCO_2$—, HS—, $R^{G2b}S$—, $R^{G2b}S(O)$—, $R^{G2b}SO_2$—, or $(R^{G2a})_2NSO_2$—;
$G^{1a}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;
$G^{1b}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;
$G^{R1a}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;
$G^{R1b}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;
$G^{2a}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;
$G^{2b}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;
$G^{3a}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, or hydroxy;
$G^{6a}$ is $C_6$-$C_{10}$-aryl or 5-10-membered heteroaryl optionally substituted with 1, 2, 3, or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amino, $C_1$-$C_6$-alkylsulfonylamino, carboxy, halogen, hydroxy, hydroxy$C_1$-$C_6$-alkyl, $R^{G6a}C(O)$—, $R^{G6a}O_2C$—, $HO_2C$—$(CR^aR^b)_r$—, $R^{G6a}O_2C$—$(CR^aR^b)_r$—, $(R^{G6b})_2N(O)C$—$(CR^aR^b)_r$—, $R^{G6a}CO_2$—$(CR^aR^b)_r$—, $G^{6c}$-, or $G^{6d}$-;
$G^{6b}$ is 4-6-membered heterocycle optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, cyano, halogen, hydroxy, or oxo;
$G^{6c}$ is phenyl or 5-6-membered heteroaryl optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, amino, $C_1$-$C_6$-alkylsulfonylamino, di($C_1$-$C_6$-alkylsulfonyl)amino, $C_1$-$C_6$-alkylsulfonylamino$C_1$-$C_6$-alkyl, carboxy, cyano, halogen, hydroxy, hydroxy$C_1$-$C_6$-alkyl, $R^{G6c}C(O)$—, $R^{G6c}O_2C$—, $(R^{G6d})_2NC(O)$—, $HO_2C$—$(CR^aR^b)_r$—, $R^{G6c}CO_2C$—$(CR^aR^b)_r$—, $(R^{G6d})_2NC(O)$—$(CR^aR^b)_r$—, or $R^{G6c}CO_2$—$(CR^aR^b)_r$—; and
$G^{6d}$ is 4-6-membered heterocycle optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, cyano, halogen, hydroxy, or oxo.

In one embodiment, the compounds are further defined as:

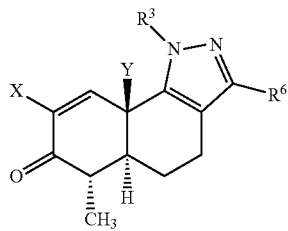

(Ic-1)

wherein,
q is 1, 2, or 3;
r is 1, 2, 3, or 4;
X is NC—, $F_3C$—, $R^{1x}C(O)$—, or $O_2N$—;
Y is $G^1$-, $G^1$-$(CR^aR^b)$—, $G^2$-, or $G^2$-$(CR^aR^b)$—;
$R^3$ is hydrogen, $C_1$-$C_6$-alkyl, $C_2$-$C_4$-alkenyl, $C_1$-$C_6$-fluoroalkyl, $G^{3a}$- or $G^{3a}$-$(CR^aR^b)_q$;
$R^6$ is hydrogen, $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amino, $C_1$-$C_6$-alkylamino, $C_1$-$C_6$-dialkylamino, hydroxy, $G^{6a}$-, $G^{6a}N(R^a)$—, $G^{6a}O$— or $G^{6b}$;
$R^a$ and $R^b$ are, at each occurrence, independently hydrogen, $C_1$-$C_6$-alkyl, or $C_1$-$C_6$-haloalkyl;
$R^{1x}$ is hydroxy, $C_1$-$C_6$-alkoxy, amino, $C_1$-$C_6$-alkylamino, $C_1$-$C_6$-dialkylamino, or $C_1$-$C_6$-alkylsulfonylamino;
$R^{G1a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$R^{G1b}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{G2a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$R^{G2b}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{G6a}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{G6b}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$R^{G6c}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{G6d}$ is, at each occurrence, independently $C_1$-$C_4$-alkyl, $C_2$-$C_4$-alkenyl, $C_2$-$C_4$-alkynyl or $C_1$-$C_4$-haloalkyl;
$G^1$ is phenyl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, carboxy, cyano, cyano-$C_1$-$C_6$-alkyl, halogen, halo-$C_1$-$C_6$-alkyl, hydroxy, hydroxy-$C_1$-$C_6$-alkyl, $R^{G1b}O_2C$—, $R^{G1a}HN(O)C$—, $(R^{G1a})_2N(O)C$—, $G^{1a}C(O)$—, $G^{1b}HN(O)C$—, $G^{1b}$-, $R^{G1a}C(O)N(R^{G1a})$—, $R^{G1b}O(O)CN(R^{G1a})$—, $R^{G1b}O_2SN(R^{G1a})$—, $(R^{G1a})_2N$—, $G^{1b}O$—, $G^{1b}CH_2O$—, $R^{G1a}CO_2$—, $(R^{G1a})_2NCO_2$—, HS—, $R^{G1b}S$—, $R^{G1b}S(O)$—, $R^{G1b}SO_2$—, or $(R^{G1a})_2NSO_2$—;
$G^2$ is a 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, carboxy, cyano, cyano-$C_1$-$C_6$-alkyl, halogen, halo-$C_1$-$C_6$-alkyl, hydroxy, hydroxy-$C_1$-$C_6$-alkyl, $R^{G2b}CO_2$—, $R^{G2a}HN(O)C$—, $(R^{G2a})_2NC(O)$—, $G^{2a}C(O)$—, $G^{2b}HNC(O)$—, $G^{2b}$-, $R^{G2a}C(O)N(R^{G2a})$, $R^{G2b}OC(O)N(R^{G2a})$—, $R^{G2b}SO_2N(R^{G2a})$—, $(R^{G2a})_2N$—, $G^{2b}O$—, $G^{2b}CH_2O$—, $R^{G2a}CO_2$—, $(R^{G2a})_2NCO_2$—, HS—, $R^{G2b}S(O)$—, $R^{G2b}SO_2$—, or $(R^{G2a})_2NSO_2$—;

$G^{1a}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;

$G^{1b}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{2a}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;

$G^{2b}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{3a}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, or hydroxy;

$G^{6a}$ is $C_6$-$C_{10}$-aryl or 5-10-membered heteroaryl optionally substituted with 1, 2, 3, or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amino, $C_1$-$C_6$-alkylsulfonylamino, carboxy, halogen, hydroxy, hydroxy$C_1$-$C_6$-alkyl, $R^{G6a}C(O)$—, $R^{G6a}O_2C$—, $HO_2C$—$(CR^aR^b)_r$—, $R^{G6a}O_2C$—$(CR^aR^b)_r$—, $(R^{G6b})_2N(O)C$—$(CR^aR^b)_r$—, $R^{G6a}CO_2$—$(CR^aR^b)_r$—, $G^{6c}$-, or $G^{6d}$-;

$G^{6b}$ is 4-6-membered heterocycle optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, cyano, halogen, hydroxy, or oxo;

$G^{6c}$ is phenyl or 5-6-membered heteroaryl optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, amino, $C_1$-$C_6$-alkylsulfonylamino, di($C_1$-$C_6$-alkylsulfonyl)amino, $C_1$-$C_6$-alkylsulfonylamino$C_1$-$C_6$-alkyl, carboxy, cyano, halogen, hydroxy, hydroxy$C_1$-$C_6$-alkyl, $R^{G6c}C(O)$—, $R^{G6c}O_2C$—, $(R^{G6d})_2NC(O)$—, $HO_2C$—$(CR^aR^b)_r$—, $R^{G6c}O_2C$—$(CR^aR^b)_r$—, $(R^{G6d})_2NC(O)$—$(CR^aR^b)_r$—, or $R^{G6c}CO_2$—$(CR^aR^b)_r$—; and $G^{6d}$ is 4-6-membered heterocycle optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, cyano, halogen, hydroxy, or oxo.

In another embodiment, the compound is further defined as a compound of Formula (Ic-1) wherein:
q is 1;
X is NC—;
Y is $G^1$-;
$R^3$ is hydrogen, $C_1$-$C_6$-alkyl or $G^{3a}$-$(CR^aR^b)_q$—;
$R^6$ is hydrogen or $G^{6a}$-;
$R^a$ and $R^b$ are, at each occurrence, hydrogen;
$R^{G1a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$R^{G1b}$ is, at each occurrence, independently $C_1$-$C_4$-alkyl, $C_2$-$C_4$-alkenyl, $C_2$-$C_4$-alkynyl or $C_1$-$C_4$-haloalkyl;
$G^1$ is phenyl optionally substituted with 1 $C_1$-$C_6$-alkyl, $C_1$-$C_6$-fluoroalkyl, $C_1$-$C_6$-alkoxy, carboxy, halogen, hydroxy, hydroxy-$C_1$-$C_6$-alkyl, $R^{G1b}O_2C$—, $R^{G1a}HN(O)C$—, $(R^{G1a})_2N(O)C$—, $G^{1a}C(O)$—, $G^{1b}HN(O)C$—, or $G^{1b}CH_2O$;
$G^{1a}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;

$G^{1b}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{3a}$ is phenyl or 5-6-membered heteroaryl optionally substituted with 1 or 2 $C_1$-$C_6$-alkyl, $C_1$-$C_6$-fluoroalkyl, $C_1$-$C_6$-alkoxy or halogen; and $G^{6a}$ is $C_6$-$C_{10}$-aryl or 5-10-membered heteroaryl optionally substituted with 1 or 2 $C_1$-$C_6$-alkyl, $C_1$-$C_6$-fluoroalkyl, $C_1$-$C_6$-alkoxy or halogen.

In another embodiment, the compound is further defined as a compound of Formula (Ic-1) wherein:

q is 1;
X is NC—;
Y is $G^1$-$(CR^aR^b)$—;
$R^3$ is hydrogen, $C_1$-$C_6$-alkyl or $G^{3a}$-$(CR^aR^b)_q$—;
$R^6$ is hydrogen or $G^{6a}$-;
$R^a$ and $R^b$ are, at each occurrence, hydrogen;
$R^{G1a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$R^{G1b}$ is, at each occurrence, independently $C_1$-$C_4$-alkyl, $C_2$-$C_4$-alkenyl, $C_2$-$C_4$-alkynyl or $C_1$-$C_4$-haloalkyl;
$G^1$ is phenyl optionally substituted with 1 $C_1$-$C_6$-alkyl, $C_1$-$C_6$-fluoroalkyl, $C_1$-$C_6$-alkoxy, carboxy, halogen, hydroxy, hydroxy-$C_1$-$C_6$-alkyl, $R^{G1b}O_2C$—, $R^{G1a}HN(O)C$—, $(R^{G1a})_2N(O)C$—, $G^{1a}C(O)$—, $G^{1b}HN(O)C$—, or $G^{1b}CH_2O$;
$G^{1a}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;
$G^{1b}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;
$G^{3a}$ is phenyl or 5-6-membered heteroaryl optionally substituted with 1 or 2 $C_1$-$C_6$-alkyl, $C_1$-$C_6$-fluoroalkyl, $C_1$-$C_6$-alkoxy or halogen; and
$G^{6a}$ is $C_6$-$C_{10}$-aryl or 5-10-membered heteroaryl optionally substituted with 1 or 2 $C_1$-$C_6$-alkyl, $C_1$-$C_6$-fluoroalkyl, $C_1$-$C_6$-alkoxy or halogen.

In one embodiment, the compounds are further defined as:

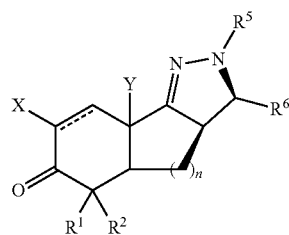

(Id)

wherein,
----- is a single or double bond;
n is 1 or 2;
p is 1, 2, or 3;
r is 1, 2, 3, or 4;
X is NC—, $F_3C$—, $R^{1x}C(O)$—, or $O_2N$—;
Y is $G^1$-, $G^1$-$(CR^aR^b)$—, $G^2$-, or $G^2$-$(CR^aR^b)$—;
$R^1$ and $R^2$ are each independently hydrogen, $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amido, amino, halogen, hydroxy, $G^{R1a}$-, $G^{R1a}$-$(CR^aR^b)_p$—, $G^{R1b}$-, $R^{1a}C(O)$—, $(R^{1a})_2N$—, $G^{R1a}NH$—, $G^{R1a}$-$(CR^aR^b)_p$—NH—, $G^{R1a}O$—, and $R^{1a}CO_2$—; or $R^1$ and $R^2$ joined together with the carbon atom to which they are attached form a $C_3$-$C_6$-cycloalkyl, $C_3$-$C_6$-cycloalkenyl, or 4-6-membered heterocycle optionally substituted with $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;
$R^5$ is hydrogen, $C_1$-$C_6$-alkyl, $C_2$-$C_6$-alkenyl, $C_2$-$C_6$-alkynyl, $C_1$-$C_6$-fluoroalkyl, $G^{R5a}$-, $G^{R5a}$-$(CR^aR^b)$—, $R^{5a}C(O)$—, $G^{R5a}C(O)$—, hydroxy-$C_1$-$C_6$-alkyl-$C(O)$—, $R^{5a}O_2C$—, $G^{R5a}O_2C$—, $G^{R5a}HNC(O)$—, $R^{5a}O_2CNHCH_2C(O)$—, $H_2NHCH_2C(O)$—, $R^{5a}SO_2$—, or $G^{R5a}SO_2$—;
$R^6$ is hydrogen, $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amino, $C_1$-$C_6$-alkylamino, $C_1$-$C_6$-dialkylamino, hydroxy, $G^{6a}$-, $G^{6a}N(R^a)$—, $G^{6a}O$— or $G^{6b}$-;
$R^a$ and $R^b$ are, at each occurrence, independently hydrogen, $C_1$-$C_6$-alkyl, or $C_1$-$C_6$-haloalkyl;
$R^{1a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$R^{1x}$ is hydroxy, $C_1$-$C_6$-alkoxy, amino, $C_1$-$C_6$-alkylamino, $C_1$-$C_6$-dialkylamino, or $C_1$-$C_6$-alkylsulfonylamino;
$R^{G1a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$R^{G1b}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{G2a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$R^{G2b}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{5a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$R^{G6a}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{G6b}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$R^{G6c}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{G6d}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$G^1$ is phenyl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, carboxy, cyano, cyano-$C_1$-$C_6$-alkyl, halogen, halo-$C_1$-$C_6$-alkyl, hydroxy, hydroxy-$C_1$-$C_6$-alkyl, $R^{G1b}O_2C$—, $R^{G1a}HN(O)C$—, $(R^{G1a})_2N(O)C$—, $G^{1a}C(O)$—, $G^{1b}HN(O)C$—, $G^{1b}$-, $R^{G1a}C(O)N(R^{G1a})$—, $R^{G1b}O(O)CN(R^{G1a})$—, $R^{G1b}O2SN(R^{G1a})$—, $(R^{G1a})_2N$—, $G^{1b}O$—, $G^{1b}CH_2O$—, $R^{G1a}CO_2$—, $(R^{G1a})_2NCO_2$—, HS—, $R^{G1b}S$—, $R^{G1b}S(O)$—, $R^{G1b}SO_2$—, or $(R^{G1a})_2NSO_2$—;
$G^2$ is a 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, carboxy, cyano, cyano-$C_1$-$C_6$-alkyl, halogen, halo-$C_1$-$C_6$-alkyl, hydroxy, hydroxy-$C_1$-$C_6$-alkyl, $R^{G2b}CO_2$—, $R^{G2a}HNC(O)$—, $(R^{G2a})_2NC(O)$—, $G^{2a}C(O)$—, $G^{2b}HNC(O)$—, $G^{2b}$-, $R^{G2a}C(O)N(R^{G2a})$—, $R^{G2b}OC(O)N(R^{G2a})$—, $R^{G2b}SO_2N(R^{G2a})$—, $(R^{G2a})_2N$—, $G^{2b}O$—, $G^{2b}CH_2O$—, $R^{G2a}CO_2$—, $(R^{G2a})_2NCO_2$—, HS—, $R^{G2b}S$—, $R^{G2b}S(O)$—, $R^{G2b}SO_2$—, or $(R^{G2a})_2NSO_2$—;
$G^{1a}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;

G$^{1b}$ is phenyl or 5-6-membered heteroaryl optionally substituted with 1, 2, 3, 4 or 5 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, cyano, halogen, hydroxy, or nitro;

G$^{R1a}$ is phenyl or 5-6-membered heteroaryl optionally substituted with 1, 2, 3, 4 or 5 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, cyano, halogen, hydroxy, or nitro;

G$^{R1b}$ is a 4-6-membered heterocycle optionally substituted with 1, 2, 3 or 4 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, cyano, halogen, hydroxy, or oxo;

G$^{2a}$ is a 4-6-membered heterocycle optionally substituted with 1, 2, 3 or 4 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, cyano, halogen, hydroxy, or oxo;

G$^{2b}$ is phenyl or 5-6-membered heteroaryl optionally substituted with 1, 2, 3, 4 or 5 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, cyano, halogen, hydroxy, or nitro;

G$^{R5a}$ is phenyl or 5-6-membered heteroaryl optionally substituted with 1, 2, 3, 4 or 5 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, cyano, halogen, hydroxy, or nitro;

G$^{6a}$ is C$_6$-C$_{10}$-aryl or 5-10-membered heteroaryl optionally substituted with 1, 2, 3, or 4 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, amino, C$_1$-C$_6$-alkylsulfonylamino, carboxy, halogen, hydroxy, hydroxyC$_1$-C$_6$-alkyl, R$^{G6a}$C(O)—, R$^{G6a}$O$_2$C—, HO$_2$C—(CR$^a$R$^b$)$_r$—, R$^{G6a}$O$_2$C—(CR$^a$R$^b$)$_r$—, (R$^{G6b}$)$_2$N(O)C—(CR$^a$R$^b$)$_r$—, R$^{G6a}$CO$_2$—(CR$^a$R$^b$)$_r$—, G$^{6c}$-, or G$^{6d}$-;

G$^{6b}$ is 4-6-membered heterocycle optionally substituted with 1, 2, 3, or 4 C$_1$-C$_6$-alkyl, C$_2$-C$_6$-alkenyl, C$_2$-C$_6$-alkynyl, C$_1$-C$_6$-alkoxy, cyano, halogen, hydroxy, or oxo;

G$^{6c}$ is phenyl or 5-6-membered heteroaryl optionally substituted with 1, 2, 3, or 4 C$_1$-C$_6$-alkyl, C$_2$-C$_6$-alkenyl, C$_2$-C$_6$-alkynyl, C$_1$-C$_6$-alkoxy, amino, C$_1$-C$_6$-alkylsulfonylamino, di(C$_1$-C$_6$-alkylsulfonyl)amino, C$_1$-C$_6$-alkylsulfonylaminoC$_1$-C$_6$-alkyl, carboxy, cyano, halogen, hydroxy, hydroxyC$_1$-C$_6$-alkyl, R$^{G6c}$C(O)—, R$^{G6c}$O$_2$C—, (R$^{G6d}$)$_2$NC(O)—, HO$_2$C—(CR$^a$R$^b$)$_r$—, R$^{G6c}$CO$_2$—(CR$^a$R$^b$)$_r$—, (R$^{G6d}$)$_2$NC(O)—(CR$^a$R$^b$)$_r$—, or R$^{G6c}$CO$_2$—(CR$^a$R$^b$)$_r$—; and G$^{6d}$ is 4-6-membered heterocycle optionally substituted with 1, 2, 3, or 4 C$_1$-C$_6$-alkyl, C$_2$-C$_6$-alkenyl, C$_2$-C$_6$-alkynyl, C$_1$-C$_6$-alkoxy, cyano, halogen, hydroxy, or oxo.

In one embodiment, the compounds are further defined as:

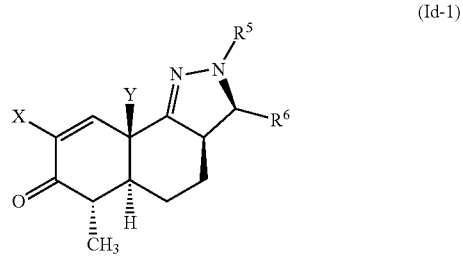

(Id-1)

wherein,
r is 1, 2, 3, or 4;
X is NC—, F$_3$C—, R$^{1x}$C(O)—, or O$_2$N—;
Y is G$^1$-, G$^1$-(CR$^a$R$^b$)$_r$—, G$^2$-, or G$^2$-(CR$^a$R$^b$)$_r$—;
R$^5$ is hydrogen, C$_1$-C$_6$-alkyl, C$_2$-C$_6$-alkenyl, C$_2$-C$_6$-alkynyl, C$_1$-C$_6$-fluoroalkyl, G$^{R5a}$-, G$^{R5a}$-(CR$^a$R$^b$)$_r$—, R$^{5a}$C(O)—, G$^{R5a}$C(O)—, hydroxy-C$_1$-C$_6$-alkyl-C(O)—, R$^{5a}$O$_2$C—, G$^{R5a}$O$_2$C—, G$^{R5a}$HNC(O)—, R$^{5a}$O$_2$CNHCH$_2$C(O)—, H$_2$NHCH$_2$C(O)—, R$^{5a}$SO$_2$—, or G$^{R5a}$SO$_2$—;

R$^6$ is hydrogen, C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, amino, C$_1$-C$_6$-alkylamino, C$_1$-C$_6$-dialkylamino, hydroxy, G$^{6a}$-, G$^{6a}$N(R$^a$)—, G$^{6a}$O— or G$^{6b}$-;

R$^a$ and R$^b$ are, at each occurrence, independently hydrogen, C$_1$-C$_6$-alkyl, or C$_1$-C$_6$-haloalkyl;

R$^{1x}$ is hydroxy, C$_1$-C$_6$-alkoxy, amino, C$_1$-C$_6$-alkylamino, C$_1$-C$_6$-dialkylamino, or C$_1$-C$_6$-alkylsulfonylamino;

R$^{G1a}$ is, at each occurrence, independently hydrogen, C$_1$-C$_4$-alkyl, C$_2$-C$_4$-alkenyl, C$_2$-C$_4$-alkynyl or C$_1$-C$_4$-haloalkyl;

R$^{G1b}$ is, at each occurrence, independently C$_1$-C$_4$-alkyl, C$_2$-C$_4$-alkenyl, C$_2$-C$_4$-alkynyl or C$_1$-C$_4$-haloalkyl;

R$^{G2a}$ is, at each occurrence, independently hydrogen, C$_1$-C$_4$-alkyl, C$_2$-C$_4$-alkenyl, C$_2$-C$_4$-alkynyl or C$_1$-C$_4$-haloalkyl;

R$^{G2b}$ is, at each occurrence, independently C$_1$-C$_4$-alkyl, C$_2$-C$_4$-alkenyl, C$_2$-C$_4$-alkynyl or C$_1$-C$_4$-haloalkyl;

R$^{5a}$ is, at each occurrence, independently hydrogen, C$_1$-C$_4$-alkyl, C$_2$-C$_4$-alkenyl, C$_2$-C$_4$-alkynyl or C$_1$-C$_4$-haloalkyl;

R$^{G6a}$ is, at each occurrence, independently C$_1$-C$_4$-alkyl, C$_2$-C$_4$-alkenyl, C$_2$-C$_4$-alkynyl or C$_1$-C$_4$-haloalkyl;

R$^{G6b}$ is, at each occurrence, independently hydrogen, C$_1$-C$_4$-alkyl, C$_2$-C$_4$-alkenyl, C$_2$-C$_4$-alkynyl or C$_1$-C$_4$-haloalkyl;

R$^{G6c}$ is, at each occurrence, independently C$_1$-C$_4$-alkyl, C$_2$-C$_4$-alkenyl, C$_2$-C$_4$-alkynyl or C$_1$-C$_4$-haloalkyl;

R$^{G6d}$ is, at each occurrence, independently hydrogen, C$_1$-C$_4$-alkyl, C$_2$-C$_4$-alkenyl, C$_2$-C$_4$-alkynyl or C$_1$-C$_4$-haloalkyl;

G$^1$ is phenyl optionally substituted with 1, 2, 3, 4 or 5 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, carboxy, cyano, cyano-C$_1$-C$_6$-alkyl, halogen, halo-C$_1$-C$_6$-alkyl, hydroxy, hydroxy-C$_1$-C$_6$-alkyl, R$^{G1b}$O$_2$C—, R$^{G1a}$HN(O)C—, (R$^{G1a}$)$_2$N(O)C—, G$^{1a}$C(O)—, R$^{G1b}$HN(O)C—, G$^{1b}$-, R$^{G1a}$C(O)N(R$^{G1a}$)—, R$^{G1b}$O(O)CN(R$^{G1a}$)—, R$^{G1b}$O$_2$SN(R$^{G1a}$)—, (R$^{G1a}$)$_2$N—, G$^{1b}$O—, G$^{1b}$CH$_2$O—, R$^{G1a}$CO$_2$—, (R$^{G1a}$)$_2$NCO$_2$—, HS—, R$^{G1b}$S—, R$^{G1b}$S(O)—, R$^{G1b}$SO$_2$—, or (R$^{G1a}$)$_2$NSO$_2$—;

G$^2$ is a 5-6-membered heteroaryl optionally substituted with 1, 2, 3, 4 or 5 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, carboxy, cyano, cyano-C$_1$-C$_6$-alkyl, halogen, halo-C$_1$-C$_6$-alkyl, hydroxy, hydroxy-C$_1$-C$_6$-alkyl, R$^{G2b}$CO$_2$—, R$^{G2a}$HNC(O)—, (R$^{G2a}$)$_2$NC(O)—, G$^{2a}$C(O)—, G$^{2b}$HNC(O)—, G$^{2b}$-, R$^{G2a}$C(O)N(R$^{G2a}$)—R$^{G2b}$OC(O)N(R$^{G2a}$)—, R$^{G2b}$SO$_2$N(R$^{G2a}$)—, (R$^{G2a}$)$_2$N—, G$^{2b}$O—, G$^{2b}$CH$_2$O—, R$^{G2a}$CO$_2$—, (R$^{G2a}$)$_2$NCO$_2$—, HS—, R$^{G2b}$S—, R$^{G2b}$S(O)—, R$^{G2b}$SO$_2$—, or (R$^{G2a}$)$_2$NSO$_2$—;

G$^{1a}$ is a 4-6-membered heterocycle optionally substituted with 1, 2, 3 or 4 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, cyano, halogen, hydroxy, or oxo;

G$^{1b}$ is phenyl or 5-6-membered heteroaryl optionally substituted with 1, 2, 3, 4 or 5 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, cyano, halogen, hydroxy, or nitro;

G$^{2a}$ is a 4-6-membered heterocycle optionally substituted with 1, 2, 3 or 4 C$_1$-C$_6$-alkyl, C$_2$-C$_6$-alkenyl, C$_2$-C$_6$-alkynyl, C$_1$-C$_6$-fluoroalkyl, C$_1$-C$_6$-alkoxy, cyano, halogen, hydroxy, or oxo;

G²ᵇ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{R5a}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{6a}$ is $C_6$-$C_{10}$-aryl or 5-10-membered heteroaryl optionally substituted with 1, 2, 3, or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amino, $C_1$-$C_6$-alkylsulfonylamino, carboxy, halogen, hydroxy, hydroxy$C_1$-$C_6$-alkyl, $R^{G6a}C(O)$—, $R^{G6a}O_2C$—, $HO_2C$—$(CR^aR^b)_r$—, $R^{G6a}O_2C$—$(CR^aR^b)_r$—, $(R^{G6b})_2N(O)C$—$(CR^aR^b)_r$—, $R^{G6a}CO_2$—$(CR^aR^b)_r$—, $G^{6c}$-, or $G^{6d}$-;

$G^{6b}$ is 4-6-membered heterocycle optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, cyano, halogen, hydroxy, or oxo;

$G^{6c}$ is phenyl or 5-6-membered heteroaryl optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, amino, $C_1$-$C_6$-alkylsulfonylamino, di($C_1$-$C_6$-alkylsulfonyl)amino, $C_1$-$C_6$-alkylsulfonylamino$C_1$-$C_6$-alkyl, carboxy, cyano, halogen, hydroxy, hydroxy$C_1$-$C_6$-alkyl, $R^{G6c}C(O)$—, $R^{G6c}O_2C$—, $(R^{G6d})_2NC(O)$—, $HO_2C$—$(CR^aR^b)_r$—, $R^{G6c}O_2C$—$(CR^aR^b)_r$—, $(R^{G6d})_2NC(O)$—$(CR^aR^b)_r$—, or $R^{G6c}CO_2$—$(CR^aR^b)_r$—; and $G^{6d}$ is 4-6-membered heterocycle optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, cyano, halogen, hydroxy, or oxo.

In another embodiment, the compound is further defined as a compound of Formula (Id-1) wherein:
r is 1, 2 or 3;
X is NC—;
Y is $G^1$-;
$R^5$ is hydrogen, $C_1$-$C_6$-alkyl, $G^{R5a}$-$(CR^aR^b)_r$—, $R^{5a}C(O)$—, $G^{R5a}C(O)$—, $R^{5a}SO_2$—, or $G^{R5a}O_2$—;
$R^6$ is hydrogen or $G^{6a}$-;
$R^a$ and $R^b$ are, at each occurrence, hydrogen;
$R^{5a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$G^1$ is phenyl optionally substituted with 1 or 2 $C_1$-$C_6$-alkyl, $C_1$-$C_6$-fluoroalkyl, $C_1$-$C_6$-alkoxy, carboxy, halogen or hydroxy;
$G^{R5a}$ is phenyl or 5-6-membered heteroaryl;
$G^{6a}$ is $C_6$-$C_{10}$-aryl or 5-10-membered heteroaryl optionally substituted with 1 or 2 $C_1$-$C_6$-alkyl, $C_1$-$C_6$-fluoroalkyl, $C_1$-$C_6$-alkoxy, amino, $C_1$-$C_6$-alkylsulfonylamino, carboxy, halogen, hydroxy, hydroxy$C_1$-$C_6$-alkyl, $HO_2C$—$(CR^aR^b)_r$— or $G^{6c}$-; and
$G^{6c}$ is phenyl or 5-6-membered heteroaryl optionally substituted with 1 or 2 $C_1$-$C_6$-alkyl, $C_1$-$C_6$-alkoxy, amino, $C_1$-$C_6$-alkylsulfonylamino, di($C_1$-$C_6$-alkylsulfonyl)amino, $C_1$-$C_6$-alkylsulfonylamino$C_1$-$C_6$-alkyl, carboxy, cyano, halogen, hydroxy.

Specific embodiments of compounds contemplated as part of the invention include, but are not limited to:
(6aS,7S,10aR)-7-methyl-8-oxo-10a-phenyl-5,6,6a,7,8,10a-hexahydrobenzo[h]quinazoline-9-carbonitrile;
rac-(5aS,6S,9aR)-2,6-dimethyl-7-oxo-3,9a-diphenyl-4,5,5a,6,7,9a-hexahydro-2H-benzo[g]indazole-8-carbonitrile;
rac-(5aS,6S,9aR)-1,6-dimethyl-7-oxo-3,9a-diphenyl-4,5,5a,6,7,9a-hexahydro-1H-benzo[g]indazole-8-carbonitrile;
rac-(5aS,6S,9aR)-9a-(4-methoxyphenyl)-2,6-dimethyl-7-oxo-4,5,5a,6,7,9a-hexahydro-2H-benzo[g]indazole-8-carbonitrile;
rac-(5aS,6S,9aR)-9a-(4-methoxyphenyl)-1,6-dimethyl-7-oxo-4,5,5a,6,7,9a-hexahydro-1H-benzo[g]indazole-8-carbonitrile;
rac-(5aS,6S,9aR)-6-methyl-7-oxo-3,9a-diphenyl-4,5,5a,6,7,9a-hexahydro-1H-benzo[g]indazole-8-carbonitrile;
(7S)-7-methyl-8-oxo-2,10a-diphenyl-5,6,6a,7,8,10a-hexahydrobenzo[h]quinazoline-9-carbonitrile;
(7S)-4-methoxy-7-methyl-8-oxo-2,10a-diphenyl-5,6,6a,7,8,10a-hexahydrobenzo[h]quinazoline-9-carbonitrile;
(7S,10aS)-2-anilino-7-methyl-8-oxo-10a-phenyl-5,6,6a,7,8,10a-hexahydrobenzo[h]quinazoline-9-carbonitrile;
(6aS,7S,10aR)-4-methoxy-2-(2-methoxyphenyl)-7-methyl-8-oxo-10a-phenyl-5,6,6a,7,8,10a-hexahydrobenzo[h]quinazoline-9-carbonitrile;
(6aS,7S,10aR)-7-methyl-8-oxo-10a-phenyl-2-(pyridin-3-yl)-5,6,6a,7,8,10a-hexahydrobenzo[h]quinazoline-9-carbonitrile;
(6aS,7S,10aR)-2-(ethylamino)-7-methyl-8-oxo-10a-phenyl-5,6,6a,7,8,10a-hexahydrobenzo[h]quinazoline-9-carbonitrile;
(6aS,7S,10aR)-4-methoxy-2,7-dimethyl-8-oxo-10a-phenyl-5,6,6a,7,8,10a-hexahydrobenzo[h]quinazoline-9-carbonitrile;
(6aS,7S,10aR)-2-anilino-4-methoxy-7-methyl-8-oxo-10a-phenyl-5,6,6a,7,8,10a-hexahydrobenzo[h]quinazoline-9-carbonitrile;
(6aS,7S,10aR)-2-[(4-bromophenyl)amino]-4-methoxy-7-methyl-8-oxo-10a-phenyl-5,6,6a,7,8,10a-hexahydrobenzo[h]quinazoline-9-carbonitrile;
(6aS,7S,10aR)-2-anilino-7-methyl-8-oxo-10a-phenyl-4-(pyrimidin-5-yl)-5,6,6a,7,8,10a-hexahydrobenzo[h]quinazoline-9-carbonitrile;
(6aS,7S,10aR)-2,7-dimethyl-4-(1-methyl-1H-imidazol-5-yl)-8-oxo-10a-phenyl-5,6,6a,7,8,10a-hexahydrobenzo[h]quinazoline-9-carbonitrile;
(6aS,7S,10aR)-2,7-dimethyl-4-(2-methyl-1,3-thiazol-5-yl)-8-oxo-10a-phenyl-5,6,6a,7,8,10a-hexahydrobenzo[h]quinazoline-9-carbonitrile;
(6aS,7S,10aR)-7-methyl-2-(morpholin-4-yl)-8-oxo-10a-phenyl-5,6,6a,7,8,10a-hexahydrobenzo[h]quinazoline-9-carbonitrile;
(6aS,7S,10aR)-4-hydroxy-2,7-dimethyl-8-oxo-10a-phenyl-5,6,6a,7,8,10a-hexahydrobenzo[h]quinazoline-9-carbonitrile;
(6aS,7S,10aR)-2,7-dimethyl-8-oxo-4,10a-diphenyl-5,6,6a,7,8,10a-hexahydrobenzo[h]quinazoline-9-carbonitrile;
(6aS,7S,10aR)-2,7-dimethyl-8-oxo-10a-phenyl-4-(pyrimidin-5-yl)-5,6,6a,7,8,10a-hexahydrobenzo[h]quinazoline-9-carbonitrile;
(6aS,7S,10aR)-4-(3-furyl)-2,7-dimethyl-8-oxo-10a-phenyl-5,6,6a,7,8,10a-hexahydrobenzo[h]quinazoline-9-carbonitrile;
(6S,9aR)-6-methyl-7-oxo-9a-phenyl-4,5,5a,6,7,9a-hexahydro-2H-benzo[g]indazole-8-carbonitrile;
(6aS,7S,10aR)-2-(2-fluorophenyl)-4-methoxy-7-methyl-8-oxo-10a-phenyl-5,6,6a,7,8,10a-hexahydrobenzo[h]quinazoline-9-carbonitrile;
(5aS,6S,9aR)-1,6-dimethyl-7-oxo-9a-phenyl-3-(pyridin-3-yl)-4,5,5a,6,7,9a-hexahydro-1H-benzo[g]indazole-8-carbonitrile;
(6aS,7S,10aR)-2,7-dimethyl-8-oxo-10a-phenyl-4-(pyridin-4-yl)-5,6,6a,7,8,10a-hexahydrobenzo[h]quinazoline-9-carbonitrile;
(6S,9aR)-2-acetyl-6-methyl-7-oxo-9a-phenyl-4,5,5a,6,7,9a-hexahydro-2H-benzo[g]indazole-8-carbonitrile;

(6aS,7S,10aR)-7-methyl-8-oxo-10a-phenyl-2-(pyridin-4-yl)-5,6,6a,7,8,10a-hexahydrobenzo[h]quinazoline-9-carbonitrile;
(6aS,7S,10aR)-2-(diethylamino)-7-methyl-8-oxo-10a-phenyl-5,6,6a,7,8,10a-hexahydrobenzo[h]quinazoline-9-carbonitrile;
(6aS,7S,10aR)-2-(2-fluorophenyl)-4-isopropoxy-7-methyl-8-oxo-10a-phenyl-5,6,6a,7,8,10a-hexahydrobenzo[h]quinazoline-9-carbonitrile;
methyl (6S,9aR)-8-cyano-6-methyl-7-oxo-9a-phenyl-4,5,5a,6,7,9a-hexahydro-2H-benzo[g]indazole-2-carboxylate;
rac-(6aS,7S,10aR)-2,7-dimethyl-8-oxo-10a-phenyl-5,6,6a,7,8,10a-hexahydrobenzo[h]quinazoline-9-carbonitrile;
(6aS,7S,10aR)-2,7-dimethyl-8-oxo-10a-phenyl-4-(1H-pyrazol-4-yl)-5,6,6a,7,8,10a-hexahydrobenzo[h]quinazoline-9-carbonitrile;
(6aS,7S,10aR)-2,7-dimethyl-4-(1-methyl-1H-pyrazol-4-yl)-8-oxo-10a-phenyl-5,6,6a,7,8,10a-hexahydrobenzo[h]quinazoline-9-carbonitrile;
(6S,9aR)-6-methyl-2-(methylsulfonyl)-7-oxo-9a-phenyl-4,5,5a,6,7,9a-hexahydro-2H-benzo[g]indazole-8-carbonitrile;
phenyl (6S,9aR)-8-cyano-6-methyl-7-oxo-9a-phenyl-4,5,5a,6,7,9a-hexahydro-2H-benzo[g]indazole-2-carboxylate;
(6S,9aR)-2-benzoyl-6-methyl-7-oxo-9a-phenyl-4,5,5a,6,7,9a-hexahydro-2H-benzo[g]indazole-8-carbonitrile;
tert-butyl {2-[(6S,9aR)-8-cyano-6-methyl-7-oxo-9a-phenyl-4,5,5a,6,7,9a-hexahydro-2H-benzo[g]indazol-2-yl]-2-oxoethyl}carbamate;
(6S,9aR)-6-methyl-7-oxo-9a-phenyl-2-(1,3-thiazol-4-ylcarbonyl)-4,5,5a,6,7,9a-hexahydro-2H-benzo[g]indazole-8-carbonitrile;
(6S,9aR)-6-methyl-7-oxo-9a-phenyl-2-(phenylsulfonyl)-4,5,5a,6,7,9a-hexahydro-2H-benzo[g]indazole-8-carbonitrile;
(6S,9aR)-2-glycoloyl-6-methyl-7-oxo-9a-phenyl-4,5,5a,6,7,9a-hexahydro-2H-benzo[g]indazole-8-carbonitrile;
(6aS,7S,10aR)-4-(3-methoxyphenyl)-2,7-dimethyl-8-oxo-10a-phenyl-5,6,6a,7,8,10a-hexahydrobenzo[h]quinazoline-9-carbonitrile;
(6aS,7S,10aR)-2,7-dimethyl-4-(1-methyl-6-oxo-1,6-dihydropyridin-3-yl)-8-oxo-10a-phenyl-5,6,6a,7,8,10a-hexahydrobenzo[h]quinazoline-9-carbonitrile;
(6aS,7S,10aR)-2,7-dimethyl-8-oxo-10a-phenyl-4-(quinolin-6-yl)-5,6,6a,7,8,10a-hexahydrobenzo[h]quinazoline-9-carbonitrile;
2-{3-[(6aS,7S,10aR)-9-cyano-2,7-dimethyl-8-oxo-10a-phenyl-5,6,6a,7,8,10a-hexahydrobenzo[h]quinazolin-4-yl]phenyl}ethyl acetate;
(6aS,7S,10aR)-4-[3-(2-hydroxyethyl)phenyl]-2,7-dimethyl-8-oxo-10a-phenyl-5,6,6a,7,8,10a-hexahydrobenzo[h]quinazoline-9-carbonitrile;
(6S,9aR)-8-cyano-6-methyl-7-oxo-9a-phenyl-N-(pyridin-3-yl)-4,5,5a,6,7,9a-hexahydro-2H-benzo[g]indazole-2-carboxamide;
(6aS,7S,10aR)-7-methyl-8-oxo-10a-phenyl-2-(pyrimidin-5-yl)-5,6,6a,7,8,10a-hexahydrobenzo[h]quinazoline-9-carbonitrile;
(6aS,7S,10aR)-10a-(4-fluorophenyl)-7-methyl-8-oxo-5,6,6a,7,8,10a-hexahydrobenzo[h]quinazoline-9-carbonitrile;
(6aS,7S,10aR)-10a-(4-fluorophenyl)-7-methyl-8-oxo-2-(pyridin-3-yl)-5,6,6a,7,8,10a-hexahydrobenzo[h]quinazoline-9-carbonitrile;
(6S,9aR)-2,6-dimethyl-7-oxo-9a-phenyl-4,5,5a,6,7,9a-hexahydro-2H-benzo[g]indazole-8-carbonitrile;
(5aS,6S,9aR)-9a-(3-fluorophenyl)-6-methyl-7-oxo-4,5,5a,6,7,9a-hexahydro-2H-benzo[g]indazole-8-carbonitrile;
(5aS,6S,9aR)-9a-(4-fluorophenyl)-6-methyl-7-oxo-4,5,5a,6,7,9a-hexahydro-2H-benzo[g]indazole-8-carbonitrile;
(6aS,7S,10aR)-10a-(3-fluorophenyl)-7-methyl-8-oxo-5,6,6a,7,8,10a-hexahydrobenzo[h]quinazoline-9-carbonitrile;
(5aS,6S,9aR)-2-benzyl-6-methyl-7-oxo-9a-phenyl-4,5,5a,6,7,9a-hexahydro-2H-benzo[g]indazole-8-carbonitrile;
(5aS,6S,9aR)-1-benzyl-6-methyl-7-oxo-9a-phenyl-4,5,5a,6,7,9a-hexahydro-1H-benzo[g]indazole-8-carbonitrile;
(5aS,6S,9aR)-9a-(4-methoxyphenyl)-6-methyl-7-oxo-4,5,5a,6,7,9a-hexahydro-2H-benzo[g]indazole-8-carbonitrile;
methyl 3-[(6aS,7S,10aR)-9-cyano-7-methyl-8-oxo-6,6a,7,8-tetrahydrobenzo[h]quinazolin-10a(5H)-yl]benzoate;
3-[(6aS,7S,10aR)-9-cyano-7-methyl-8-oxo-6,6a,7,8-tetrahydrobenzo[h]quinazolin-10a(5N)-yl]benzoic acid;
3-[(6aS,7S,10aR)-9-cyano-7-methyl-8-oxo-6,6a,7,8-tetrahydrobenzo[h]quinazolin-10a(5N)-yl]benzamide;
methyl 3-[(5aS,6S,9aR)-8-cyano-6-methyl-7-oxo-2,4,5,5a,6,7-hexahydro-9aH-benzo[g]indazol-9a-yl]benzoate;
methyl 4-[(5aS,6S,9aR)-8-cyano-6-methyl-7-oxo-2,4,5,5a,6,7-hexahydro-9aH-benzo[g]indazol-9a-yl]benzoate;
methyl 4-[(6aS,7S,10aR)-9-cyano-7-methyl-8-oxo-6,6a,7,8-tetrahydrobenzo[h]quinazolin-10a(5H)-yl]benzoate;
(5aS,6S,9aR)-1-(4-bromobenzyl)-6-methyl-7-oxo-9a-phenyl-4,5,5a,6,7,9a-hexahydro-1H-benzo[g]indazole-8-carbonitrile;
4-[(6aS,7S,10aR)-9-cyano-7-methyl-8-oxo-6,6a,7,8-tetrahydrobenzo[h]quinazolin-10a(5H)-yl]benzoic acid;
(6aS,7S,10aR)-10a-(4-methoxyphenyl)-2,7-dimethyl-8-oxo-4-(pyrimidin-5-yl)-5,6,6a,7,8,10a-hexahydrobenzo[h]quinazoline-9-carbonitrile;
(6aS,7S,10aR)-10a-(4-fluorophenyl)-2,7-dimethyl-8-oxo-4-(pyrimidin-5-yl)-5,6,6a,7,8,10a-hexahydrobenzo[h]quinazoline-9-carbonitrile;
(6aS,7S,10aR)-10a-(3-fluorophenyl)-2,7-dimethyl-8-oxo-4-(pyrimidin-5-yl)-5,6,6a,7,8,10a-hexahydrobenzo[h]quinazoline-9-carbonitrile;
(6aS,7S,10aR)-10a-(4-methoxyphenyl)-7-methyl-8-oxo-5,6,6a,7,8,10a-hexahydrobenzo[h]quinazoline-9-carbonitrile;
3-[(5aS,6S,9aR)-8-cyano-6-methyl-7-oxo-2,4,5,5a,6,7-hexahydro-9aH-benzo[g]indazol-9a-yl]benzoic acid;
(6S,9aR)-9a-(4-hydroxyphenyl)-6-methyl-7-oxo-4,5,5a,6,7,9a-hexahydro-2H-benzo[g]indazole-8-carbonitrile;
(6aS,7S,10aR)-7-methyl-8-oxo-10a-[4-(pyrrolidin-1-ylcarbonyl)phenyl]-5,6,6a,7,8,10a-hexahydrobenzo[h]quinazoline-9-carbonitrile;
(6aS,7S,10aR)-2-(2,6-difluorophenyl)-7-methyl-8-oxo-10a-phenyl-5,6,6a,7,8,10a-hexahydrobenzo[h]quinazoline-9-carbonitrile;
methyl 4-[(6aS,7S,10aR)-9-cyano-7-methyl-8-oxo-10a-phenyl-5,6,6a,7,8,10a-hexahydrobenzo[h]quinazolin-2-yl]benzoate;
(6aS,7S,10aR)-4-(1-acetyl-1H-pyrazol-4-yl)-2,7-dimethyl-8-oxo-10a-phenyl-5,6,6a,7,8,10a-hexahydrobenzo[h]quinazoline-9-carbonitrile;
4-[(6aS,7S,10aR)-9-cyano-7-methyl-8-oxo-10a-phenyl-5,6,6a,7,8,10a-hexahydrobenzo[h]quinazolin-2-yl]benzoic acid;
(6S,9aR)-9a-(3-fluorophenyl)-3-[3-(3-hydroxypropyl)phenyl]-6-methyl-7-oxo-4,5,5a,6,7,9a-hexahydro-2H-benzo[g]indazole-8-carbonitrile;
(6aS,7S,10aR)-4-[4-(4-bromo-1H-pyrazol-5-yl)phenyl]-10a-(4-methoxyphenyl)-2,7-dimethyl-8-oxo-5,6,6a,7,8,10a-hexahydrobenzo[h]quinazoline-9-carbonitrile;

(6aS,7S,10aR)-10a-(4-methoxyphenyl)-2,7-dimethyl-8-oxo-4-[4-(1H-pyrazol-5-yl)phenyl]-5,6,6a,7,8,10a-hexahydrobenzo[h]quinazoline-9-carbonitrile;

(6aS,7S,10aR)-4-[4-(4-bromo-1H-pyrazol-5-yl)phenyl]-10a-(4-fluorophenyl)-2,7-dimethyl-8-oxo-5,6,6a,7,8,10a-hexahydrobenzo[h]quinazoline-9-carbonitrile;

(5aS,6S,9aR)-9a-(4-fluorophenyl)-2-glycyl-6-methyl-7-oxo-4,5,5a,6,7,9a-hexahydro-2H-benzo[g]indazole-8-carbonitrile;

(6aS,7S,10aR)-10a-(4-fluorophenyl)-2,7-dimethyl-8-oxo-4-[4-(1H-pyrazol-5-yl)phenyl]-5,6,6a,7,8,10a-hexahydrobenzo[h]quinazoline-9-carbonitrile;

(6aS,7S,10aR)-7-methyl-8-oxo-10a-phenyl-2-(pyrazin-2-yl)-5,6,6a,7,8,10a-hexahydrobenzo[h]quinazoline-9-carbonitrile;

(6aS,7S,10aR)-2-tert-butyl-7-methyl-8-oxo-10a-phenyl-5,6,6a,7,8,10a-hexahydrobenzo[h]quinazoline-9-carbonitrile;

(6S,9aR)-6-methyl-7-oxo-9a-phenyl-3-(pyridin-3-yl)-4,5,5a,6,7,9a-hexahydro-2H-benzo[g]indazole-8-carbonitrile;

(6S,9aR)-6-methyl-7-oxo-9a-phenyl-3-(pyrimidin-5-yl)-4,5,5a,6,7,9a-hexahydro-2H-benzo[g]indazole-8-carbonitrile;

(6S,9aR)-3-(3-hydroxyphenyl)-6-methyl-7-oxo-9a-phenyl-4,5,5a,6,7,9a-hexahydro-2H-benzo[g]indazole-8-carbonitrile;

(6S,9aR)-6-methyl-3-(1-methyl-1H-pyrazol-4-yl)-7-oxo-9a-phenyl-4,5,5a,6,7,9a-hexahydro-2H-benzo[g]indazole-8-carbonitrile;

(6aS,7S,10aR)-4-(1H-benzimidazol-5-yl)-10a-(4-methoxyphenyl)-2,7-dimethyl-8-oxo-5,6,6a,7,8,10a-hexahydrobenzo[h]quinazoline-9-carbonitrile;

(6aS,7S,10aR)-4-(1H-benzimidazol-5-yl)-10a-(4-fluorophenyl)-2,7-dimethyl-8-oxo-5,6,6a,7,8,10a-hexahydrobenzo[h]quinazoline-9-carbonitrile;

(6aS,7S,10aR)-4-(3-bromo-1H-indazol-7-yl)-10a-(4-fluorophenyl)-2,7-dimethyl-8-oxo-5,6,6a,7,8,10a-hexahydrobenzo[h]quinazoline-9-carbonitrile;

(6aS,7S,10aR)-10a-(4-fluorophenyl)-4-(1H-indazol-7-yl)-2,7-dimethyl-8-oxo-5,6,6a,7,8,10a-hexahydrobenzo[h]quinazoline-9-carbonitrile;

(6aS,7S,10aR)-4-(2,4-dioxo-1,2,3,4-tetrahydropyrimidin-5-yl)-10a-(4-fluorophenyl)-2,7-dimethyl-8-oxo-5,6,6a,7,8,10a-hexahydrobenzo[h]quinazoline-9-carbonitrile;

3-[(6aS,7S,10aR)-9-cyano-7-methyl-8-oxo-6,6a,7,8-tetrahydrobenzo[h]quinazolin-10a(5H-yl]-N-phenylbenzamide;

3-[(6aS,7S,10aR)-9-cyano-7-methyl-8-oxo-6,6a,7,8-tetrahydrobenzo[h]quinazolin-10a(5N)-yl]-N-propylbenzamide;

(5aS,6S,9aR)-2,6-dimethyl-7-oxo-9a-phenyl-3-(pyridazin-4-yl)-4,5,5a,6,7,9a-hexahydro-2H-benzo[g]indazole-8-carbonitrile;

methyl 4-[(6aS,7S,10aR)-9-cyano-2,7-dimethyl-8-oxo-10a-phenyl-5,6,6a,7,8,10a-hexahydrobenzo[h]quinazolin-4-yl]-1H-pyrazole-1-carboxylate;

methyl 3-[(6aS,7S,10aR)-9-cyano-7-methyl-8-oxo-2-phenyl-6,6a,7,8-tetrahydrobenzo[h]quinazolin-10a(5N)-yl]benzoate;

3-[(6aS,7S,10aR)-9-cyano-7-methyl-8-oxo-2-phenyl-6,6a,7,8-tetrahydrobenzo[h]quinazolin-10a(5N)-yl]benzoic acid;

methyl 3-[(6aS,7S,10aR)-9-cyano-2-[4-(methoxycarbonyl)phenyl]-7-methyl-8-oxo-6,6a,7,8-tetrahydrobenzo[h]quinazolin-1a(5H)-yl]benzoate;

(6aS,7S,10aR)-2-chloro-4-methoxy-7-methyl-8-oxo-10a-phenyl-5,6,6a,7,8,10a-hexahydrobenzo[h]quinazoline-9-carbonitrile;

(6aS,7S,10aR)-2,4-dimethoxy-7-methyl-8-oxo-10a-phenyl-5,6,6a,7,8,10a-hexahydrobenzo[h]quinazoline-9-carbonitrile;

3-[(6aS,7S,10aR)-2-(4-carboxyphenyl)-9-cyano-7-methyl-8-oxo-6,6a,7,8-tetrahydrobenzo[h]quinazolin-1a(5N)-yl]benzoic acid;

(3R,3aR,5aS,6S,9aR)-2,6-dimethyl-7-oxo-3,9a-diphenyl-3,3a,4,5,5a,6,7,9a-octahydro-2H-benzo[g]indazole-8-carbonitrile;

(6S,9aR)-3-(6-aminopyridin-3-yl)-6-methyl-7-oxo-9a-phenyl-4,5,5a,6,7,9a-hexahydro-2H-benzo[g]indazole-8-carbonitrile;

(6aS,7S,10aR)-4-(imidazo[1,2-a]pyridin-6-yl)-2,7-dimethyl-8-oxo-10a-phenyl-5,6,6a,7,8,10a-hexahydrobenzo[h]quinazoline-9-carbonitrile;

(6aS,7S,10aR)-4-(4-hydroxyphenyl)-2,7-dimethyl-8-oxo-10a-phenyl-5,6,6a,7,8,10a-hexahydrobenzo[h]quinazoline-9-carbonitrile;

(6aS,7S,10aR)-4-(3-hydroxyphenyl)-2,7-dimethyl-8-oxo-10a-phenyl-5,6,6a,7,8,10a-hexahydrobenzo[h]quinazoline-9-carbonitrile;

(6aS,7S,10aR)-4-[3-(3-hydroxypropyl)phenyl]-2,7-dimethyl-8-oxo-10a-phenyl-5,6,6a,7,8,10a-hexahydrobenzo[h]quinazoline-9-carbonitrile;

(6aS,7S,10aR)-2-(5-bromo-2-hydroxyphenyl)-7-methyl-8-oxo-10a-phenyl-5,6,6a,7,8,10a-hexahydrobenzo[h]quinazoline-9-carbonitrile;

N-{4-[(6S,9aR)-8-cyano-6-methyl-7-oxo-9a-phenyl-4,5,5a,6,7,9a-hexahydro-2H-benzo[g]indazol-3-yl]phenyl}methanesulfonamide;

N-{3-[(6S,9aR)-8-cyano-6-methyl-7-oxo-9a-phenyl-4,5,5a,6,7,9a-hexahydro-2H-benzo[g]indazol-3-yl]phenyl}methanesulfonamide;

(6aS,7S,10aR)-2-(4-hydroxyphenyl)-7-methyl-8-oxo-10a-phenyl-5,6,6a,7,8,10a-hexahydrobenzo[h]quinazoline-9-carbonitrile;

(6S,9aR)-3-[4-(2-hydroxyethyl)phenyl]-6-methyl-7-oxo-9a-phenyl-4,5,5a,6,7,9a-hexahydro-2H-benzo[g]indazole-8-carbonitrile;

(6S,9aR)-3-[3-(2-hydroxyethyl)phenyl]-6-methyl-7-oxo-9a-phenyl-4,5,5a,6,7,9a-hexahydro-2H-benzo[g]indazole-8-carbonitrile;

(6S,9aR)-3-[1-(2-hydroxyethyl)-1H-pyrazol-4-yl]-6-methyl-7-oxo-9a-phenyl-4,5,5a,6,7,9a-hexahydro-2H-benzo[g]indazole-8-carbonitrile;

(6aS,7S,10aR)-4-(4'-aminobiphenyl-3-yl)-2,7-dimethyl-8-oxo-10a-phenyl-5,6,6a,7,8,10a-hexahydrobenzo[h]quinazoline-9-carbonitrile;

(6aS,7S,10aR)-4-(4'-hydroxybiphenyl-3-yl)-2,7-dimethyl-8-oxo-10a-phenyl-5,6,6a,7,8,10a-hexahydrobenzo[h]quinazoline-9-carbonitrile;

(6aS,7S,10aR)-10a-[4-(benzyloxy)phenyl]-7-methyl-8-oxo-5,6,6a,7,8,10a-hexahydrobenzo[h]quinazoline-9-carbonitrile;

(6aS,7S,10aR)-10a-(4-hydroxyphenyl)-7-methyl-8-oxo-5,6,6a,7,8,10a-hexahydrobenzo[h]quinazoline-9-carbonitrile;

(6aS,7S,10aR)-2,7-dimethyl-8-oxo-10a-phenyl-4-[4-(pyridin-4-yl)phenyl]-5,6,6a,7,8,10a-hexahydrobenzo[h]quinazoline-9-carbonitrile;

(6S,9aR)-3-[3-(3-hydroxypropyl)phenyl]-6-methyl-7-oxo-9a-phenyl-4,5,5a,6,7,9a-hexahydro-2H-benzo[g]indazole-8-carbonitrile;

N-{3'-[(6aS,7S,10aR)-9-cyano-2,7-dimethyl-8-oxo-10a-phenyl-5,6,6a,7,8,10a-hexahydrobenzo[h]quinazolin-4-yl]biphenyl-3-yl}methanesulfonamide;

3-{3-[(6aS,7S,10aR)-9-cyano-2,7-dimethyl-8-oxo-10a-phenyl-5,6,6a,7,8,10a-hexahydrobenzo[h]quinazolin-4-yl]phenyl}propyl acetate;

(6S,9aR)-3-[5-(hydroxymethyl)pyridin-3-yl]-6-methyl-7-oxo-9a-phenyl-4,5,5a,6,7,9a-hexahydro-2H-benzo[g]indazole-8-carbonitrile;

(6aS,7S,10aR)-4-[1-(2-hydroxyethyl)-1H-pyrazol-4-yl]-2,7-dimethyl-8-oxo-10a-phenyl-5,6,6a,7,8,10a-hexahydrobenzo[h]quinazoline-9-carbonitrile;

(6aS,7S,10aR)-10a-[3-(benzyloxy)phenyl]-7-methyl-8-oxo-5,6,6a,7,8,10a-hexahydrobenzo[h]quinazoline-9-carbonitrile;

(6aS,7S,10aR)-2,7-dimethyl-8-oxo-10a-phenyl-4-[4-(pyrimidin-5-yl)phenyl]-5,6,6a, 7,8,10a-hexahydrobenzo[h]quinazoline-9-carbonitrile;

(6aS,7S,10aR)-2,7-dimethyl-8-oxo-10a-phenyl-4-(pyrimidin-5-yl)-5,6,6a,7,8,10a-hexahydrobenzo[h]quinazoline-9-carboxamide;

(6aS,7S,10aR)-7-methyl-8-oxo-10a-phenyl-5,6,6a,7,8,10a-hexahydrobenzo[h]quinazoline-9-carboxamide;

(6aS,7S,10aR)-4-(5-bromo-6-hydroxypyridin-3-yl)-2,7-dimethyl-8-oxo-10a-phenyl-5,6,6a,7,8,10a-hexahydrobenzo[h]quinazoline-9-carbonitrile;

(6aS,7S,10aR)-4-(6-hydroxypyridin-3-yl)-2,7-dimethyl-8-oxo-10a-phenyl-5,6,6a,7,8,10a-hexahydrobenzo[h]quinazoline-9-carbonitrile;

methyl 3'-[(6aS,7S,10aR)-9-cyano-2,7-dimethyl-8-oxo-10a-phenyl-5,6,6a,7,8,10a-hexahydrobenzo[h]quinazolin-4-yl]biphenyl-4-carboxylate;

3'-[(6aS,7S,10aR)-9-cyano-2,7-dimethyl-8-oxo-10a-phenyl-5,6,6a,7,8,10a-hexahydrobenzo[h]quinazolin-4-yl]biphenyl-4-carboxamide;

4-[(6aS,7S,10aR)-9-cyano-7-methyl-8-oxo-10a-phenyl-5,6,6a,7,8,10a-hexahydrobenzo[h]quinazolin-2-yl]benzamide;

(6aS,7S,10aR)-10a-(3-hydroxyphenyl)-7-methyl-8-oxo-5,6,6a,7,8,10a-hexahydrobenzo[h]quinazoline-9-carbonitrile;

4-[(6aS,7S,10aR)-9-cyano-7-methyl-8-oxo-10a-phenyl-5,6,6a,7,8,10a-hexahydrobenzo[h]quinazolin-2-yl]-N,N-dimethylbenzamide;

(6aS,7S,10aR)-2,7-dimethyl-4-[4-(1-methyl-1H-imidazol-5-yl)phenyl]-8-oxo-10a-phenyl-5,6,6a,7,8,10a-hexahydrobenzo[h]quinazoline-9-carbonitrile;

(5aS,6S,9aR)-6-methyl-7-oxo-9a-phenyl-3-(pyridazin-4-yl)-4,5,5a,6,7,9a-hexahydro-2H-benzo[g]indazole-8-carbonitrile;

{4-[(6S,9aR)-8-cyano-6-methyl-7-oxo-9a-phenyl-4,5,5a,6,7,9a-hexahydro-2H-benzo[g]indazol-3-yl]-1H-pyrazol-1-yl}acetic acid;

methyl 3-[(6aS,7S,10aR)-9-carbamoyl-7-methyl-8-oxo-6,6a,7,8-tetrahydrobenzo[h]quinazolin-10a(5H)-yl]benzoate;

(5aS,6S,9aR)-2,6-dimethyl-7-oxo-9a-phenyl-3-[4-(pyridin-4-yl)phenyl]-4,5,5a,6,7,9a-hexahydro-2H-benzo[g]indazole-8-carbonitrile;

(5aS,6S,9aR)-2,6-dimethyl-7-oxo-9a-phenyl-3-[4-(pyrimidin-5-yl)phenyl]-4,5,5a,6,7,9a-hexahydro-2H-benzo[g]indazole-8-carbonitrile;

(6aS,7S,10aR)-2,7-dimethyl-8-oxo-10a-phenyl-4-[4-(pyrimidin-5-yl)phenyl]-5,6,6a,7,8,10a-hexahydrobenzo[h]quinazoline-9-carboxamide;

(6aS,7S,10aR)-4-[3-bromo-4-(morpholin-4-yl)phenyl]-2,7-dimethyl-8-oxo-10a-phenyl-5,6,6a,7,8,10a-hexahydrobenzo[h]quinazoline-9-carbonitrile;

(6aS,7S,10aR)-2,7-dimethyl-8-oxo-10a-phenyl-4-(pyridin-3-ylamino)-5,6,6a,7,8,10a-hexahydrobenzo[h]quinazoline-9-carbonitrile;

(5aS,6S,9aR)-3-(3-bromophenyl)-2,6-dimethyl-7-oxo-9a-phenyl-4,5,5a,6,7,9a-hexahydro-2H-benzo[g]indazole-8-carbonitrile;

(5aS,6S,9aR)-3-(4'-aminobiphenyl-3-yl)-2,6-dimethyl-7-oxo-9a-phenyl-4,5,5a,6,7,9a-hexahydro-2H-benzo[g]indazole-8-carbonitrile;

N-{3'-[(5aS,6S,9aR)-8-cyano-2,6-dimethyl-7-oxo-9a-phenyl-4,5,5a,6,7,9a-hexahydro-2H-benzo[g]indazol-3-yl]biphenyl-3-yl}methanesulfonamide;

(5aS,6S,9aR)-2,6-dimethyl-7-oxo-9a-phenyl-3-[3-(pyridazin-4-yl)phenyl]-4,5,5a,6,7,9a-hexahydro-2H-benzo[g]indazole-8-carbonitrile;

N-{3'-[(5aS,6S,9aR)-8-cyano-2,6-dimethyl-7-oxo-9a-phenyl-4,5,5a,6,7,9a-hexahydro-2H-benzo[g]indazol-3-yl]biphenyl-4-yl}-N-(methylsulfonyl)methanesulfonamide;

(5aS,6S,9aR)-3-[3-(2-methoxypyrimidin-5-yl)phenyl]-2,6-dimethyl-7-oxo-9a-phenyl-4,5,5a,6,7,9a-hexahydro-2H-benzo[g]indazole-8-carbonitrile;

methyl 3-{3-[(6aS,7S,10aR)-9-cyano-2,7-dimethyl-8-oxo-10a-phenyl-5,6,6a,7,8,10a-hexahydrobenzo[h]quinazolin-4-yl]phenyl}propanoate;

3-{3-[(6aS,7S,10aR)-9-cyano-2,7-dimethyl-8-oxo-10a-phenyl-5,6,6a,7,8,10a-hexahydrobenzo[h]quinazolin-4-yl]phenyl}propanoic acid;

3-{3-[(6aS,7S,10aR)-9-cyano-2,7-dimethyl-8-oxo-10a-phenyl-5,6,6a,7,8,10a-hexahydrobenzo[h]quinazolin-4-yl]phenyl}propanamide;

(5aS,6S,9aR)-3-[1-(4-cyanophenyl)-1H-pyrazol-4-yl]-6-methyl-7-oxo-9a-phenyl-4,5,5a,6,7,9a-hexahydro-2H-benzo[g]indazole-8-carbonitrile;

(5aS,6S,9aR)-6-methyl-7-oxo-9a-phenyl-3-[1-(pyridin-3-yl)-1H-pyrazol-4-yl]-4,5,5a,6,7,9a-hexahydro-2H-benzo[g]indazole-8-carbonitrile;

(5aS,6S,9aR)-6-methyl-7-oxo-9a-phenyl-3-[1-(pyridin-4-yl)-1H-pyrazol-4-yl]-4,5,5a,6,7,9a-hexahydro-2H-benzo[g]indazole-8-carbonitrile;

rac-(5aS,6S,9aR)-2,6-dimethyl-7-oxo-9a-phenyl-4,5,5a,6,7,9a-hexahydro-2H-benzo[g]indazole-8-carbonitrile;

rac-(5aS,6S,9aR)-1,6-dimethyl-7-oxo-9a-phenyl-4,5,5a,6,7,9a-hexahydro-1H-benzo[g]indazole-8-carbonitrile;

rac-(5aS,6S,9aR)-9a-benzyl-2,6-dimethyl-7-oxo-4,5,5a,6,7,9a-hexahydro-2H-benzo[g]indazole-8-carbonitrile;

rac-(5aS,6S,9aR)-9a-benzyl-1,6-dimethyl-7-oxo-4,5,5a,6,7,9a-hexahydro-1H-benzo[g]indazole-8-carbonitrile;

rac-(5aS,6S,9aR)-9a-benzyl-2,6-dimethyl-7-oxo-3-phenyl-4,5,5a,6,7,9a-hexahydro-2H-benzo[g]indazole-8-carbonitrile;

rac-(5aS,6S,9aR)-9a-benzyl-2,6-dimethyl-7-oxo-3-phenyl-4,5,5a,6,7,9a-hexahydro-2H-benzo[g]indazole-8-carboxamide;

3'-[(5aS,6S,9aR)-8-cyano-2,6-dimethyl-7-oxo-9a-phenyl-4,5,5a,6,7,9a-hexahydro-2H-benzo[g]indazol-3-yl]biphenyl-3-carboxylic acid;

(5aS,6S,9aR)-2,6-dimethyl-7-oxo-9a-phenyl-3-[3-(1H-pyrazol-4-yl)phenyl]-4,5,5a,6,7,9a-hexahydro-2H-benzo[g]indazole-8-carbonitrile;

N-({3'-[(5aS,6S,9aR)-8-cyano-2,6-dimethyl-7-oxo-9a-phenyl-4,5,5a,6,7,9a-hexahydro-2H-benzo[g]indazol-3-yl]biphenyl-4-yl}methyl)methanesulfonamide;

N-{3'-[(5aS,6S,9aR)-8-cyano-2,6-dimethyl-7-oxo-9a-phenyl-4,5,5a,6,7,9a-hexahydro-2H-benzo[g]indazol-3-yl]biphenyl-4-yl}methanesulfonamide;

(5aS,6S,9aR)-3-(4'-hydroxybiphenyl-3-yl)-2,6-dimethyl-7-oxo-9a-phenyl-4,5,5a,6,7,9a-hexahydro-2H-benzo[g]indazole-8-carbonitrile;

3'-[(5aS,6S,9aR)-8-cyano-2,6-dimethyl-7-oxo-9a-phenyl-4,5,5a,6,7,9a-hexahydro-2H-benzo[g]indazol-3-yl]biphenyl-4-carboxamide;

(6aS,7S,10aR)-2,7-dimethyl-8-oxo-10a-phenyl-4-(pyridazin-4-yl)-5,6,6a,7,8,10a-hexahydrobenzo[h]quinazoline-9-carbonitrile;

(6aS,7S,10aR)-7-methyl-2-[4-(3-methyl-1,2,4-oxadiazol-5-yl)phenyl]-8-oxo-10a-phenyl-5,6,6a,7,8,10a-hexahydrobenzo[h]quinazoline-9-carbonitrile;

(6aS,7S,10aR)-10a-(4-methoxyphenyl)-2,7-dimethyl-4-(1-methyl-1H-imidazol-5-yl)-8-oxo-5,6,6a,7,8,10a-hexahydrobenzo[h]quinazoline-9-carbonitrile;

methyl 4-[(6aS,7S,10aR)-9-cyano-2,7-dimethyl-4-(1-methyl-1H-imidazol-5-yl)-8-oxo-6,6a,7,8-tetrahydrobenzo[h]quinazolin-10a(5H)-yl]benzoate;

methyl 4-[(6aS,7S,10aR)-4-(4-bromo-1-methyl-1H-imidazol-5-yl)-9-cyano-2,7-dimethyl-8-oxo-6,6a,7,8-tetrahydrobenzo[h]quinazolin-10a(5H)-yl]benzoate;

(5aS,6S,9aR)-2,6-dimethyl-7-oxo-9a-phenyl-3-(pyrimidin-5-yl)-4,5,5a,6,7,9a-hexahydro-2H-benzo[g]indazole-8-carbonitrile;

(5aS,6S,9aR)-2,6-dimethyl-7-oxo-9a-phenyl-3-(pyridin-3-yl)-4,5,5a,6,7,9a-hexahydro-2H-benzo[g]indazole-8-carbonitrile; or (5aS,6S,9aR)-1,6-dimethyl-7-oxo-9a-phenyl-3-(pyrimidin-5-yl)-4,5,5a,6,7,9a-hexahydro-1H-benzo[g]indazole-8-carbonitrile.

Compounds of the present application can exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

The present application contemplates various stereoisomers and mixtures thereof and these are specifically included within the scope of this application. Stereoisomers include enantiomers and diastereomers, and mixtures of enantiomers or diastereomers. Individual stereoisomers of compounds of the present application can be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers can exist in the present compounds. The invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or a heterocycle are designated as being of cis or trans configuration.

Within the present invention it is to be understood that compounds disclosed herein can exhibit the phenomenon of tautomerism.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

The present invention also includes isotopically-labeled compounds, which are identical to those recited in Formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, fluorine, and chlorine, such as, but not limited to $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Compounds incorporating positron-emitting isotopes are useful in medical imaging and positron-emitting tomography (PET) studies for determining the distribution of receptors. Suitable positron-emitting isotopes that can be incorporated in compounds of Formula (I) are $^{11}C$, $^{13}N$, $^{15}O$, and $^{18}F$. Isotopically-labeled compounds of Formula (I) can generally be prepared by conventional techniques known to those skilled in the art or by processes analogous to those described in the accompanying Examples using appropriate isotopically-labeled reagent in place of non-isotopically-labeled reagent.

A. BIOLOGICAL DATA

Tissue Culture

RAW 264.7, a mouse macrophage cell line, was obtained from American Type Culture Collection (Manassas Va.) and maintained in the log phase of growth in Dulbecco's Modified Eagle's Medium (DMEM), 10% heat inactivated fetal calf serum and 100 units/mL antibiotic-antimycotic (AA). Cells were cultured and maintained in a humidified incubator at 37° C. under 5% $CO_2$ and 95% air. Cells were sub-cultured every 3 days by scraping and were not used beyond passage 20. All cell culture supplies were obtained from Life Technologies (Grand Island, N.Y.).

Nitric Oxide Suppression Assay.

RAW 264.7 cells were plated 1 day in advance of experiment at a concentration of 80,000 cells/well onto Cell-BIND® 96 well plates (Corning, N.Y.) in a total volume of 100 µL. The next day, pre-treat cells with compounds (from 3 µM to 0.3 nM serially diluted in a 10 point curve) from a 10× stock by adding 10 µL per well in complete DMEM media containing 10% fetal calf serum. The plates were centrifuged for 3 minutes at 400×g at room temperature followed by 2 hour incubation at 37° C. The cells were then incubated overnight at 37° C. with 10 µL of the insult, interferon gamma (R&D Systems, Minneapolis, Minn.), from a 10× stock for a final concentration of 20 ng/mL. The plates were centrifuged for 3 minutes at 400×g at room temperature followed by ~18 hour incubation at 37° C. The following day, transfer 50 µL cell culture supernatant from each well into a clear bottom 96 well plate and follow the instructions from Promega's Griess Detection Kit #G2930 (Madison, Wis.) which involves the addition of 50 µL of the provided sulfanilamide solution for a 5-10 minute incubation at room temperature. Next add 50 µL of the provided N-1-napthylethylenediamine dihydrochloride (NED) solution for a 5-10 minute incubation at room temperature and protected from light. If any air bubbles were introduced into the well, the plates need to be centrifuged for 5 minutes at 400×g at room temperature to avoid interference with absorbance readings. The plates were read for absorbance within 30 minutes with a filter between 520 nm and 550 nm.

For the ability of compounds to suppress the increase in nitric oxide release, the percent maximal intensity of nitric oxide detected in each well was normalized to that induced by the peak value for 20 ng/mL of interferon gamma alone and plotted against the compound concentration to calculate $IC_{50}$ values and to control for plate-to-plate variability. Concentration-response data were analyzed using GraphPad Prism (San Diego, Calif.); the $IC_{50}$ values were derived from a single curve fit to the mean data of n=2-3, in duplicates. Selected data is shown in Table 1.

All compounds were dissolved in dimethyl sulfoxide at 10 mM stock solutions and tested at a concentration that the dimethyl sulfoxide levels never exceeded 1%.

TABLE 1

Suppression of IFNγ-Induced NO Production.

| Example | $IC_{50}$ (µM) |
|---|---|
| 1 | 0.00535 |
| 2 | 0.0169 |
| 3 | 0.00719 |
| 4 | 0.114 |
| 5 | 0.0413 |
| 6 | 0.0375 |
| 7 | 0.0304 |
| 8 | 0.0963 |
| 9 | 0.00599 |
| 10 | 0.0225 |
| 11 | 0.00603 |
| 12 | 0.0241 |
| 13 | 0.0048 |
| 14 | 0.0114 |
| 15 | 0.030 |
| 16 | 0.0078 |
| 17 | 0.00325 |
| 18 | 0.00517 |
| 19 | 0.0362 |
| 20 | 0.045 |
| 21 | 0.00994 |
| 22 | 0.0318 |
| 23 | 0.00698 |
| 24 | 0.0677 |
| 25 | 0.0378 |
| 26 | 0.0013 |
| 27 | 0.0059 |
| 28 | 0.039 |
| 29 | 0.00636 |
| 30 | 0.0568 |
| 31 | 0.272 |
| 32 | 0.0259 |
| 33 | 0.023 |
| 34 | 0.00286 |
| 35 | 0.00486 |
| 36 | 0.0693 |
| 37 | 0.0605 |
| 38 | 0.0752 |
| 39 | 0.0536 |
| 40 | 0.0454 |
| 41 | 1.18 |
| 42 | 0.0342 |
| 43 | 0.0165 |
| 44 | 0.0511 |
| 45 | 0.106 |
| 46 | 0.00752 |
| 47 | 0.0188 |
| 48 | 0.0401 |

TABLE 1-continued

Suppression of IFNγ-Induced NO Production.

| Example | $IC_{50}$ (µM) |
|---|---|
| 49 | 0.00715 |
| 50 | 0.0103 |
| 51 | 0.00614 |
| 52 | 0.0532 |
| 53 | 0.0317 |
| 54 | 0.0355 |
| 55 | 0.0114 |
| 56 | 0.0932 |
| 57 | 0.022 |
| 58 | 0.0334 |
| 59 | 0.00653 |
| 60 | >3 |
| 61 | 0.591 |
| 62 | 0.0394 |
| 63 | 0.0266 |
| 64 | 0.011 |
| 65 | 0.109 |
| 66 | 0.809 |
| 67 | 0.0218 |
| 68 | 0.0336 |
| 69 | 0.0358 |
| 70 | 0.00527 |
| 71 | 1.47 |
| 72 | 0.0379 |
| 73 | 0.152 |
| 74 | 0.00926 |
| 75 | 0.0127 |
| 76 | 0.00191 |
| 77 | 0.0154 |
| 78 | 0.0218 |
| 79 | 0.0457 |
| 80 | 0.00743 |
| 81 | 0.035 |
| 82 | 0.0313 |
| 83 | 0.0164 |
| 84 | 0.00672 |
| 85 | 0.0338 |
| 86 | 0.00395 |
| 87 | 0.00418 |
| 88 | 0.0201 |
| 89 | 0.00818 |
| 90 | 0.00732 |
| 91 | 0.0136 |
| 92 | 0.0317 |
| 93 | 0.00727 |
| 94 | 0.639 |
| 95 | 0.0155 |
| 96 | 0.0782 |
| 97 | 0.015 |
| 98 | 0.0015 |
| 99 | 0.0234 |
| 100 | 0.426 |
| 101 | 0.0456 |
| 102 | 0.00397 |
| 103 | 0.0044 |
| 104 | 0.924 |
| 105 | 0.0345 |
| 106 | 0.00877 |
| 107 | 0.0107 |
| 108 | 0.00363 |
| 109 | 0.00287 |
| 110 | 0.00155 |
| 111 | 0.0123 |
| 112 | 0.0664 |
| 113 | 0.043 |
| 114 | 0.0050 |
| 115 | 0.0236 |
| 116 | 0.00925 |
| 117 | 0.0174 |
| 118 | 0.00462 |
| 119 | 0.0065 |
| 120 | 0.00544 |
| 121 | 0.00847 |
| 122 | 0.0127 |
| 123 | 0.00772 |
| 124 | 0.00135 |

TABLE 1-continued

Suppression of IFNγ-Induced NO Production.

| Example | IC$_{50}$ (µM) |
|---|---|
| 125 | 0.00469 |
| 126 | 0.00967 |
| 127 | 0.00227 |
| 128 | 0.00782 |
| 129 | 0.013 |
| 130 | >3 |
| 131 | 1.39 |
| 132 | 0.387 |
| 133 | 0.311 |
| 134 | 0.0069 |
| 135 | 0.00822 |
| 136 | 0.00337 |
| 137 | 0.00893 |
| 138 | 0.00526 |
| 139 | 0.019 |
| 140 | 0.00845 |
| 141 | 0.004 |
| 142 | 2.28 |
| 143 | 0.0693 |
| 144 | 0.0181 |
| 145 | >1 |
| 146 | 0.0522 |
| 147 | 0.048 |
| 148 | 0.0315 |
| 149 | 0.00732 |
| 150 | 0.00226 |
| 151 | 0.00681 |
| 152 | 0.0115 |
| 153 | 0.00646 |
| 154 | 0.0475 |
| 155 | 0.107 |
| 156 | 0.00357 |
| 157 | 0.0444 |
| 158 | 0.033 |
| 159 | 0.0338 |
| 160 | not tested |
| 161 | not tested |
| 162 | 0.231 |
| 163 | 0.406 |
| 164 | 0.065 |
| 165 | 0.706 |
| 166 | 0.0656 |
| 167 | 0.00327 |
| 168 | 0.0123 |
| 169 | 0.00877 |
| 170 | 0.00696 |
| 171 | 0.0139 |
| 172 | 0.0494 |
| 173 | 0.0197 |
| 174 | 0.0019 |
| 175 | 0.002 |
| 176 | 0.0128 |
| 177 | 0.0108 |
| 178 | 0.0054 |
| 179 | 0.00124 |

B. METHODS OF USING THE COMPOUNDS

Inflammation is a biological process that provides resistance to infectious or parasitic organisms and the repair of damaged tissue. Inflammation is commonly characterized by localized vasodilation, redness, swelling, and pain, the recruitment of leukocytes to the site of infection or injury, production of inflammatory cytokines such as TNF-α and IL-1, and production of reactive oxygen or nitrogen species such as hydrogen peroxide, superoxide and peroxynitrite. In later stages of inflammation, tissue remodeling, angiogenesis, and scar formation (fibrosis) may occur as part of the wound healing process. Under normal circumstances, the inflammatory response is regulated and temporary and is resolved in an orchestrated fashion once the infection or injury has been dealt with adequately. However, acute inflammation can become excessive and life-threatening if regulatory mechanisms fail. Alternatively, inflammation can become chronic and cause cumulative tissue damage or systemic complications. Based at least on the evidence presented above, the compounds of this invention may be used in the treatment or prevention of inflammation or diseases associated with inflammation.

Many serious and intractable human diseases involve dysregulation of inflammatory processes, including diseases such as cancer, melanoma, atherosclerosis, and diabetes, which were not traditionally viewed as inflammatory conditions. In the case of cancer, the inflammatory processes are associated with tumor formation, progression, metastasis, and resistance to therapy. Atherosclerosis, long viewed as a disorder of lipid metabolism, is now understood to be primarily an inflammatory condition, with activated macrophages playing an important role in the formation and eventual rupture of atherosclerotic plaques. Activation of inflammatory signaling pathways has also been shown to play a role in the development of insulin resistance, as well as in the peripheral tissue damage associated with diabetic hyperglycemia. Excessive production of reactive oxygen species and reactive nitrogen species such as superoxide, hydrogen peroxide, nitric oxide, and peroxynitrite is a hallmark of inflammatory conditions. Evidence of dysregulated peroxynitrite production has been reported in a wide variety of diseases (Szabo et al., 2007; Schulz et al., 2008; Forstermann, 2006; Pall, 2007).

Autoimmune diseases such as rheumatoid arthritis, lupus, psoriasis, and multiple sclerosis involve inappropriate and chronic activation of inflammatory processes in affected tissues, arising from dysfunction of self vs. non-self recognition and response mechanisms in the immune system. In neurodegenerative diseases such as Alzheimer's and Parkinson's diseases, neural damage is correlated with activation of microglia and elevated levels of pro-inflammatory proteins such as inducible nitric oxide synthase (iNOS). Chronic organ failure such as renal failure, heart failure, liver failure, and chronic obstructive pulmonary disease is closely associated with the presence of chronic oxidative stress and inflammation, leading to the development of fibrosis and eventual loss of organ function. Oxidative stress in vascular endothelial cells, which line major and minor blood vessels, can lead to endothelial dysfunction and is believed to be an important contributing factor in the development of systemic cardiovascular disease, complications of diabetes, chronic kidney disease and other forms of organ failure, and a number of other aging-related diseases including degenerative diseases of the central nervous system and the retina.

Many other disorders involve oxidative stress and inflammation in affected tissues, including inflammatory bowel disease; inflammatory skin diseases; mucositis related to radiation therapy and chemotherapy; eye diseases such as uveitis, glaucoma, macular degeneration, and various forms of retinopathy; transplant failure and rejection; ischemia-reperfusion injury; chronic pain; degenerative conditions of the bones and joints including osteoarthritis and osteoporosis; asthma and cystic fibrosis; seizure disorders; and neuropsychiatric conditions including schizophrenia, depression, bipolar disorder, post-traumatic stress disorder, attention deficit disorders, autism-spectrum disorders, and eating disorders such as anorexia nervosa. Dysregulation of inflammatory signaling pathways is believed to be a major factor in the pathology of muscle wasting diseases including muscular dystrophy and various forms of cachexia. Dysregulated inflammatory signaling has also been identified as a consequence of obesity, and has been reported to contribute to the development of insulin resistance, cardiovascular disease, metabolic syndrome, and other disorders that are strongly associated with obesity (see, e.g., Hotamisligil, 2010; Hotamisligil, 2006; Cai et al., 2005). Preclinical studies have indicated that Nrf2 activation can inhibit weight gain in animals provided with a high-fat diet (Shin et al., *Eur. J. Pharmacol.*, 620(1-3): 138-44.). Clinical trials have shown that, in patients with type 2 diabetes and chronic kidney disease, bardoxolone methyl treatment induced significant weight loss, with the loss being more pronounced in patients having the highest body mass index (i.e., the patients with the highest degree of obesity) (WO 2011/130302). Thus, compounds of the invention may be used in some embodiments in the prevention or treatment of clinically significant obesity and its complications.

A variety of life-threatening acute disorders also involve dysregulated inflammatory signaling, including acute organ failure involving the pancreas, kidneys, liver, or lungs, myocardial infarction or acute coronary syndrome, stroke, septic shock, trauma, severe burns, and anaphylaxis.

Many complications of infectious diseases also involve dysregulation of inflammatory responses. Although an inflammatory response can kill invading pathogens, an excessive inflammatory response can also be quite destructive and in some cases can be a primary source of damage in infected tissues. Furthermore, an excessive inflammatory response can also lead to systemic complications due to overproduction of inflammatory cytokines such as TNF-α and IL-1. This is believed to be a factor in mortality arising from severe influenza, severe acute respiratory syndrome, and sepsis.

The aberrant or excessive expression of either iNOS or cyclooxygenase-2 (COX-2) has been implicated in the pathogenesis of many disease processes. For example, it is clear that NO is a potent mutagen (Tamir and Tannebaum, 1996), and that nitric oxide can also activate COX-2 (Salvemini et al., 1994). Furthermore, there is a marked increase in iNOS in rat colon tumors induced by the carcinogen, azoxymethane (Takahashi et al., 1997). A series of synthetic triterpenoid analogs of oleanolic acid have been shown to be powerful inhibitors of cellular inflammatory processes, such as the induction by IFN-γ of inducible nitric oxide synthase (iNOS) and of COX-2 in mouse macrophages. See Honda et al. (2000a); Honda et al. (2000b), and Honda et al. (2002), which are all incorporated herein by reference.

In one aspect, compounds disclosed herein are characterized by their ability to inhibit the production of nitric oxide in macrophage-derived RAW 264.7 cells induced by exposure to γ-interferon. They are further characterized by their ability to induce the expression of antioxidant proteins such as NQO1 and reduce the expression of pro-inflammatory proteins such as COX-2 and inducible nitric oxide synthase (iNOS). These properties are relevant to the treatment of a wide array of diseases and disorders involving oxidative stress and dysregulation of inflammatory processes including cancer, complications from localized or total-body exposure to ionizing radiation, mucositis resulting from radiation therapy or chemotherapy, autoimmune diseases, cardiovascular diseases including atherosclerosis, ischemia-reperfusion injury, acute and chronic organ failure including renal failure and heart failure, respiratory diseases, insulin resistance, diabetes and complications of diabetes, severe allergies, transplant rejection, graft-versus-host disease, neurodegenerative diseases, diseases of the eye and retina, acute and chronic pain, degenerative bone diseases including osteoarthritis and osteoporosis, inflammatory bowel diseases, dermatitis and other skin diseases, sepsis, burns, seizure disorders, and neuropsychiatric disorders.

Without being bound by theory, the activation of the antioxidant/anti-inflammatory Keap1/Nrf2/ARE pathway is believed to be implicated in both the anti-inflammatory and anti-carcinogenic properties of the compounds disclosed herein.

In another aspect, compounds disclosed herein may be used for treating a subject having a condition caused by elevated levels of oxidative stress in one or more tissues. Oxidative stress results from abnormally high or prolonged levels of reactive oxygen species such as superoxide, hydrogen peroxide, nitric oxide, and peroxynitrite (formed by the reaction of nitric oxide and superoxide). The oxidative stress may be accompanied by either acute or chronic inflammation. The oxidative stress may be caused by mitochondrial dysfunction, by activation of immune cells such as macrophages and neutrophils, by acute exposure to an external agent such as ionizing radiation or a cytotoxic chemotherapy agent (e.g., doxorubicin), by trauma or other acute tissue injury, by ischemia/reperfusion, by poor circulation or anemia, by localized or systemic hypoxia or hyperoxia, by elevated levels of inflammatory cytokines and other inflammation-related proteins, and/or by other abnormal physiological states such as hyperglycemia or hypoglycemia.

In animal models of many such conditions, stimulating expression of inducible heme oxygenase (HO-1), a target gene of the Nrf2 pathway, has been shown to have a significant therapeutic effect including models of myocardial infarction, renal failure, transplant failure and rejection, stroke, cardiovascular disease, and autoimmune disease (e.g., Sacerdoti et al., 2005; Abraham & Kappas, 2005; Bach, 2006; Araujo et al., 2003; Liu et al., 2006; Ishikawa et al., 2001; Kruger et al., 2006; Satoh et al., 2006; Zhou et al., 2005; Morse and Choi, 2005; Morse and Choi, 2002). This enzyme breaks free heme down into iron, carbon monoxide (CO), and biliverdin (which is subsequently converted to the potent antioxidant molecule, bilirubin).

In another aspect, compounds of this invention may be used in preventing or treating tissue damage or organ failure, acute and chronic, resulting from oxidative stress exacerbated by inflammation. Examples of diseases that fall in this category include: heart failure, liver disease (e.g., alcoholic liver disease, fatty liver disease, non-alcoholic steatohepatitis, cirrhosis) and liver failure, transplant failure and rejection, renal failure, pancreatitis, asthma, fibrotic lung diseases (cystic fibrosis, COPD, and idiopathic pulmonary fibrosis, among others), diabetes (including complications), atherosclerosis, ischemia-reperfusion injury, glaucoma, stroke, autoimmune disease, autism, macular degeneration, and muscular dystrophy. For example, in the case of autism, studies suggest that increased oxidative stress in the central nervous system may contribute to the development of the disease (Chauhan and Chauhan, 2006).

Evidence also links oxidative stress and inflammation to the development and pathology of many other disorders of the central nervous system, including psychiatric disorders such as psychosis, major depression, and bipolar disorder; seizure disorders such as epilepsy; pain and sensory syndromes such as migraine, neuropathic pain or tinnitus; and behavioral syndromes such as the attention deficit disorders. See, e.g., Dickerson et al., 2007; Hanson et al., 2005; Kendall-Tackett, 2007; Lencz et al., 2007; Dudhgaonkar et al., 2006; Lee et al., 2007; Morris et al., 2002; Ruster et al., 2005; McIver et al., 2005; Sarchielli et al., 2006; Kawakami et al., 2006; Ross et al., 2003, which are all incorporated by reference herein. For example, elevated levels of inflammatory cytokines, including TNF, interferon-γ, and IL-6, are associated with major mental illness (Dickerson et al., 2007). Microglial activation has also been linked to major mental illness. Therefore, downregulating inflammatory cytokines and inhibiting excessive activation of microglia could be beneficial in patients with schizophrenia, major depression, bipolar disorder, autism-spectrum disorders, and other neuropsychiatric disorders.

Accordingly, in pathologies involving oxidative stress alone or oxidative stress exacerbated by inflammation, treatment may comprise administering to a subject a therapeutically effective amount of a compound of this invention, such as those described above or throughout this specification. Treatment may be administered preventively, in advance of a predictable state of oxidative stress (e.g., organ transplantation or the administration of radiation therapy to a cancer patient), or it may be administered therapeutically in settings involving established oxidative stress and inflammation.

The compounds disclosed herein may be generally applied to the treatment of inflammatory conditions, such as sepsis, dermatitis, autoimmune disease and osteoarthritis. In one aspect, the compounds of this invention may be used to treat inflammatory pain and/or neuropathic pain, for example, by inducing Nrf2 and/or inhibiting NF-κB.

In some embodiments, the compounds disclosed herein may be used in the treatment and prevention of diseases such as cancer, inflammation, Alzheimer's disease, Parkinson's disease, multiple sclerosis, autism, amyotrophic lateral sclerosis, Huntington's disease, autoimmune diseases such as rheumatoid arthritis, lupus, Crohn's disease, psoriasis, inflammatory bowel disease, melanoma, and all other diseases whose pathogenesis is believed to involve excessive production of either nitric oxide or prostaglandins, and pathologies involving oxidative stress alone or oxidative stress exacerbated by inflammation.

Another aspect of inflammation is the production of inflammatory prostaglandins such as prostaglandin E. These molecules promote vasodilation, plasma extravasation, localized pain, elevated temperature, and other symptoms of inflammation. The inducible form of the enzyme COX-2 is associated with their production, and high levels of COX-2 are found in inflamed tissues. Consequently, inhibition of COX-2 may relieve many symptoms of inflammation and a number of important anti-inflammatory drugs (e.g., ibuprofen and celecoxib) act by inhibiting COX-2 activity. Recent research, however, has demonstrated that a class of cyclopentenone prostaglandins (cyPGs) (e.g., 15-deoxy prostaglandin J2, a.k.a. PGJ2) plays a role in stimulating the orchestrated resolution of inflammation (e.g., Rajakariar et al., 2007). COX-2 is also associated with the production of cyclopentenone prostaglandins. Consequently, inhibition of COX-2 may interfere with the full resolution of inflammation, potentially promoting the persistence of activated immune cells in tissues and leading to chronic, "smoldering" inflammation. This effect may be responsible for the increased incidence of cardiovascular disease in patients using selective COX-2 inhibitors for long periods of time.

In one aspect, the compounds disclosed herein may be used to control the production of pro-inflammatory cytokines within the cell by selectively activating regulatory cysteine residues (RCRs) on proteins that regulate the activity of redox-sensitive transcription factors. Activation of RCRs by cyPGs has been shown to initiate a pro-resolution program in which the activity of the antioxidant and cytoprotective transcription factor Nrf2 is potently induced and the activities of the pro-oxidant and pro-inflammatory transcription factors NF-κB and the STATs are suppressed. In some embodiments, this increases the production of anti-oxidant and reductive molecules (NQO1, HO-1, SOD1, γ-GCS) and decreases oxidative stress and the production of pro-oxidant and pro-inflammatory molecules (iNOS, COX-2, TNF-α). In some embodiments, the compounds of this invention may cause the cells that host the inflammatory event to revert to a non-inflammatory state by promoting the resolution of inflammation and limiting excessive tissue damage to the host.

In another aspect, the compounds disclosed are useful for the treatment and prevention of immune-mediated diseases such as the resistance by transplantation of organs or tissue such as heart, kidney, liver, medulla ossium, skin, cornea, lung, pancreas, intestinum tenue, limb, muscle, nerves, duodenum, small-bowel, pancreatic-islet-cell, and the like; graft-versus-host diseases brought about by medulla ossium transplantation; autoimmune diseases such as rheumatoid arthritis, systemic lupus erythematosus, Hashimoto's thyroiditis, multiple sclerosis, myasthenia gravis, type I diabetes, uveitis, allergic encephalomyelitis, glomerulonephritis, and the like. Further uses include the treatment and prophylaxis of inflammatory and hyperproliferative skin diseases and cutaneous manifestations of immunologically-mediated illnesses, such as psoriasis, atopic dermatitis, contact dermatitis and further eczematous dermatitises, seborrhoeis dermatitis, lichen planus, pemphigus, bullous pemphigoid, epidermolysis bullosa, urticaria, angioedemas, vasculitides, erythemas, cutaneous eosinophilias, lupus erythematosus, acne and alopecia areata; various eye diseases (autoimmune and otherwise) such as keratoconjunctivitis, vernal conjunctivitis, uveitis associated with Behcet's disease, keratitis, herpetic keratitis, conical cornea, dystrophia epithelialis corneae, corneal leukoma, and ocular pemphigus. In addition reversible obstructive airway disease, which includes conditions such as asthma (for example, bronchial asthma, allergic asthma, intrinsic asthma, extrinsic asthma and dust asthma), particularly chronic or inveterate asthma (for example, late asthma and airway hyper-responsiveness), bronchitis, allergic rhinitis, and the like are targeted by compounds of this invention. The compounds disclosed are also useful in the treatment of inflammation of mucosa and blood vessels such as gastric ulcers, vascular damage caused by ischemic diseases and thrombosis. Moreover, hyperproliferative vascular diseases such as intimal smooth muscle cell hyperplasia, restenosis and vascular occlusion, particularly following biologically- or mechanically-mediated vascular injury, could be treated or prevented by the compounds of the invention.

The compounds or drugs described herein can be incorporated into stents or catheters that are constructed from or have been coated with a polymeric compound forming a drug-eluting stent or catheter, respectively. The drug-eluting stent containing the compound or drug can then be delivered to the coronary vessel by deployment from a balloon catheter. In addition to stents, other devices that can be used to introduce the drugs of this invention to the vasculature include, but are not limited to grafts, catheters, and balloons.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level can depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

Compounds of the invention can also be administered as a pharmaceutical composition comprising the compounds of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It can be understood, however, that the total daily usage of the compounds and compositions of the invention can be decided by the attending physician within the scope of sound medical judgment. The specific therapeutically effective dose level for any particular patient can depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or other animal range from about 0.01 mg/kg body weight to about 100 mg/kg body weight. More preferable doses can be in the range of from about 0.01 mg/kg body weight to about 30 mg/kg body weight. If desired, the effective daily dose can be divided into multiple doses for purposes of administration. Consequently, single dose compositions can contain such amounts or submultiples thereof to make up the daily dose.

The present invention also is directed, in part, to a use of one or more compounds and/or salts of the invention, and, optionally one or more additional therapeutic agents to prepare a medicament. In some embodiments, the medicament is for co-administration with one or more additional therapeutic agents. In some embodiments, the medicament is for treating inflammation.

This invention also is directed, in part, to one or more compounds and/or salts of the invention, and, optionally one or more additional therapeutic agents, for use as a medicament. In some embodiments, the medicament is for treating inflammation.

C. PHARMACEUTICAL COMPOSITIONS

The present invention further provides pharmaceutical compositions that comprise compounds of the present invention or a pharmaceutically acceptable salt or solvate thereof. The pharmaceutical compositions comprise compounds of the present invention that can be formulated together with one or more non-toxic pharmaceutically acceptable carriers.

In addition to being used as a monotherapy, the compounds of the present invention may also find use in combination therapies. Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

Non-limiting examples of such combination therapy include combination of one or more compounds of the invention with another anti-inflammatory agent, a chemotherapeutic agent, radiation therapy, an antidepressant, an antipsychotic agent, an anticonvulsant, a mood stabilizer, an anti-infective agent, an antihypertensive agent, a cholesterol-lowering agent or other modulator of blood lipids, an agent for promoting weight loss, an antithrombotic agent, an agent for treating or preventing cardiovascular events such as myocardial infarction or stroke, an antidiabetic agent, an agent for reducing transplant rejection or graft-versus-host disease, an anti-arthritic agent, an analgesic agent, an anti-asthmatic agent or other treatment for respiratory diseases, or an agent for treatment or prevention of skin disorders. Compounds of the invention may be combined with agents designed to improve a patient's immune response to cancer, including (but not limited to) cancer vaccines. See Lu et al. (2011), which is incorporated herein by reference.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It can also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound can be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form can also comprise buffering agents.

Solid compositions of a similar type can also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They can optionally contain opacifying agents and can also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions can also include adjuvants such as wetting agents, emulsifying and suspending agents, sweetening, flavoring and perfuming agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multilamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound can be mixed under sterile conditions with a pharmaceutically acceptable carrier and any needed preservatives, buffers or propellants which can be required. Ophthalmic formulations, eye ointments, powders and solutions are also contemplated as being within the scope of this invention.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenyl-propionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediamine, ethanolamine, diethanolamine, piperidine, piperazine and the like.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The present invention also is directed, in part, to a kit comprising one or more compounds and/or salts of the invention. The kit can optionally contain one or more additional therapeutic agents and/or instructions for, for example, using the kit.

D. GENERAL SYNTHESIS

This invention is intended to encompass compounds of the invention when prepared by synthetic processes or by metabolic processes. Preparation of the compounds by metabolic processes includes those occurring in the human or animal body (in vivo) or processes occurring in vitro.

This invention is directed, in part, to the synthetic processes for preparing compounds of Formula (I) as shown in Schemes 1-23 and the Examples below. This invention also is directed, in part, to novel intermediates that can be used to prepare the compounds of Formula (I) (and their salts) as shown in Schemes 1-23 and the Examples below. The compounds of the invention can be prepared by a variety of processes well known for the preparation of compounds of this class. For example, the compounds of the invention wherein the groups $R^1$, $R^3$, $R^4$, $R^5$, $R^6$, $R^{5a}$, $G^1$, $G^2$, $G^{4a}$, $G^{R5a}$, $G^{6a}$, $G^{6c}$, $G^{6d}$, Y, n and m, have the meanings as set forth in the Summary of the Invention section unless otherwise noted, can be synthesized as shown in Schemes 1-23.

Abbreviations: NaOAc for sodium acetate; OAc for acetate; L-Phe-OH for L-phenylalanine; L-Pro-OH for L-proline; and psi for pounds per square inch.

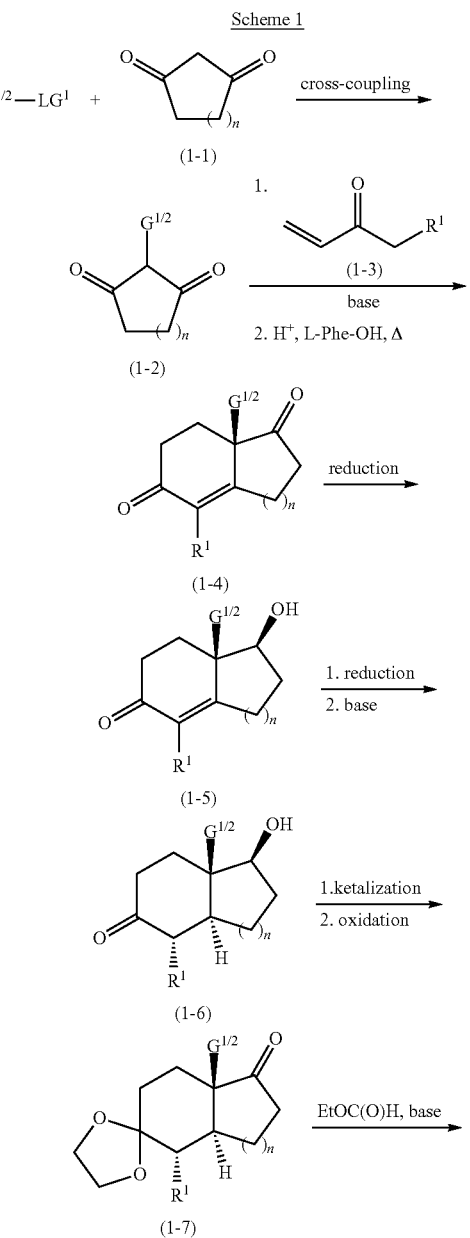

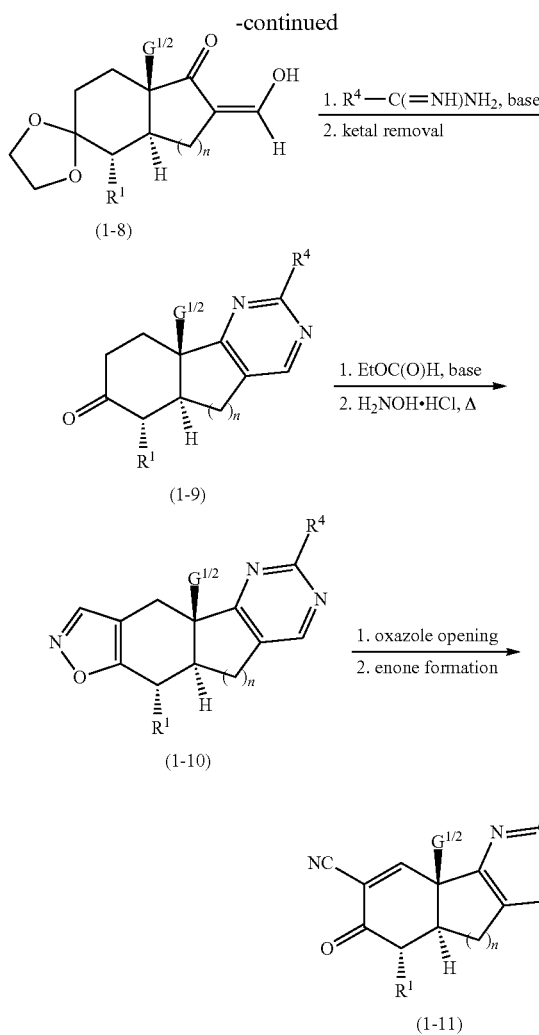

As illustrated in Scheme 1, compounds of Formula (1-11) can be prepared starting from compounds of Formula (1-1). 1,3-Diketones of Formula (1-1) can be coupled with $G^{1/2}$-$LG^1$, wherein $G^{1/2}$ represents either $G^1$ or $G^2$ as described in the Summary and $LG^1$ is chloro, bromo, iodo or a sulfonate to give compounds of Formula (1-2). The coupling can be carried out with a palladium catalyst such as palladium(II) acetate, a suitable phosphine ligand such as 2-(di-tert-butylphospino)-2'-methylbiphenyl, and a base such as potassium phosphate tribasic in a heated solvent such as a mixture of tert-amyl alcohol and dioxane. Alternatively, compounds of Formula (1-1) can be coupled with $G^{1/2}$-$LG^1$ using copper iodide, potassium carbonate, and L-proline in heated dimethyl sulfoxide to give compounds of Formula (1-2). Compounds of Formula (1-2) can be reacted first with alkyl vinyl ketones of Formula (1-3) in the presence of a base such as triethylamine in heated acetonitrile and then in the presence of an acid such as pyridinium para-toluenesulfonate or D-10-camphorsulfonic acid in a heated solvent such as acetonitrile or dimethyl sulfoxide to give compounds of Formula (1-4). The optical purity of compounds of Formula (1-4) can be enhanced by taking the compound into a solvent such as cyclohexane or ethanol (cooled to 0° C.) with stirring, removing solid racemic material by filtration, and recovering the optically enriched product from the filtrate. Compounds of Formula (1-4) can be reduced with a reagent such as sodium borohydride in ethanol or a mixture of ethanol and tetrahydrofuran to give compounds of Formula (1-5). Compounds of Formula (1-5) can be converted in a two-step process to compounds of Formula (1-6). In the first step, the double bond is reduced with hydrogen (balloon or 60-100 psi) in the presence of 5-20% palladium on carbon in solvents such as ethyl acetate or tetrahydrofuran with pyridine. The alpha alkyl group is then epimerized to a stable configuration by treatment with a diazabicyclo[5.4.0]-undec-7-ene in tetrahydrofuran or with sodium methoxide in methanol to give compounds of Formula (1-6). Another two-step process converts compounds of Formula (1-6) to compounds of Formula (1-7). The ketone of Formula (1-6) is ketalized in the presence of ethylene glycol in benzene or toluene in the presence of an acid such as p-toluenesulfonic acid under Dean-Stark conditions. Alternative ketalization conditions include a mixture of ethylene glycol and 2-ethyl-2-methyl-1,3-dioxolane in the presence of p-toluenesulfonic acid at room temperature. Subsequent oxidation of the secondary alcohol with a reagent such as pyridinium dichromate in optionally heated dichloromethane optionally containing magnesium sulfate delivers compounds of Formula (1-7). Compounds of Formula (1-7) can be treated with ethyl formate in the presence of sodium methoxide in methanol, potassium tert-butoxide in tetrahydrofuran, or sodium hydride or a mixture of sodium hydride and potassium hydride in optionally heated N,N-dimethylformamide to give compounds of Formula (1-8). Compounds of Formula (1-8) can be reacted with an amidine, $R^4$—C(=NH)NH$_2$, in the presence of a base such as piperidine in heated isopropanol optionally in a sealed tube. Subsequent exposure to hydrochloric acid in heated solvents such as methanol, dioxane, or tetrahydrofuran removes the ketal and delivers compounds of Formula (1-9). An isoxazole can be annulated onto compounds of Formula (1-9) by first reacting with ethyl formate in the presence of sodium methoxide optionally with potassium hydride in methanol or potassium tert-butoxide in tetrahydrofuran and followed by reaction with hydroxylamine hydrochloride in a heated ethanol, ethanol-water, or methanol-water to supply compounds of Formula (1-10). The isoxazole of compounds of Formula (1-10) is opened to the corresponding alpha-cyanoketone by treatment with a base such as sodium methoxide in methanol, tetrahydrofuran or a mixture of methanol and tetrahydrofuran. Exposure of compounds of Formula (1-10) to 1,3-dibromo-5,5-dimethylhydantoin in a cooled (at or near 0° C.) solvent such as N,N-dimethylformamide or N,N-dimethylacetamide followed by the addition of pyridine and heating gives compounds of Formula (1-11). Alternatively, the enone can be introduced by treatment of the intermediate alpha-cyanoketone with 2,3-dichloro-5,6-dicyano-1,4-benzoquinone (DDQ) in tetrahydrofuran or toluene. Compounds of Formula (1-11) are representative of compounds of Formula (I).

Scheme 2

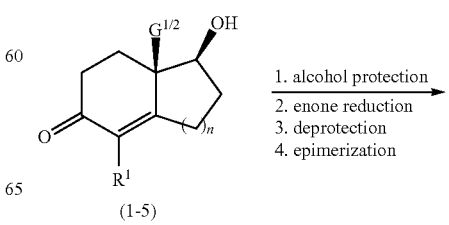

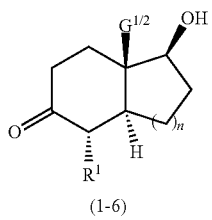

(1-6)

An alternative procedure for the conversion of compounds of Formula (1-5) to compounds of Formula (1-6) is illustrated in Scheme 2. Compounds of Formula (1-5) can be treated with dihydropyran in the presence of p-toluenesulfonic acid in dichloromethane to protect the secondary alcohol. The enone can then be reduced as previously described by hydrogenation (balloon) in the presence of 10% palladium on carbon in ethanol. Subsequent treatment with sodium methoxide in methanol epimerizes the $R^1$ group and removes the protecting tetrahydropyran group to give compounds of Formula (1-6) which can be used as described in Scheme 1.

Scheme 3

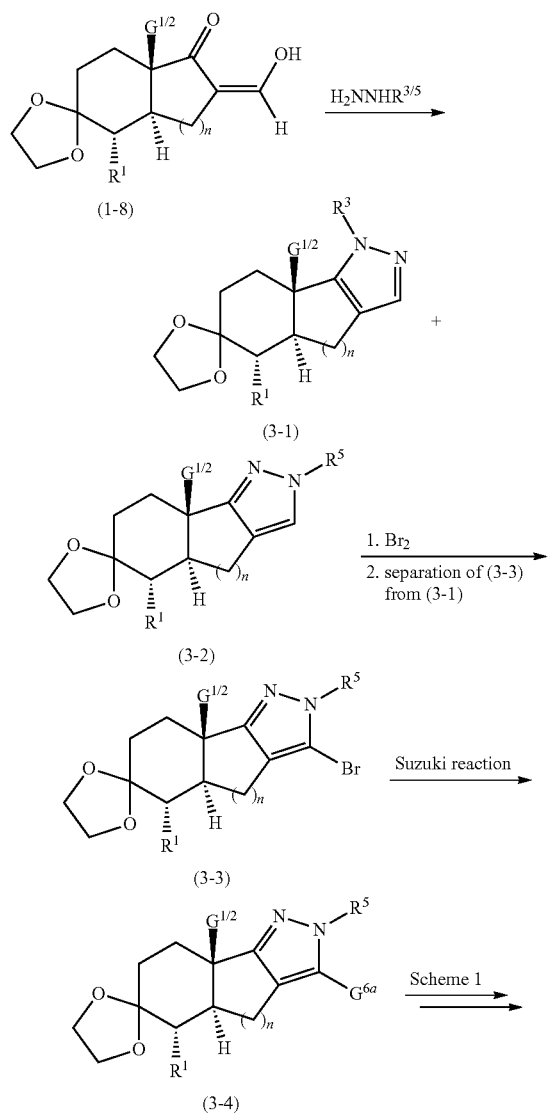

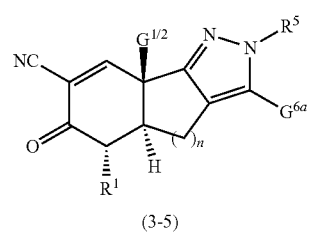

(3-5)

As shown in Scheme 3, compounds of Formula (1-8) can be transformed to compounds of Formula (3-5) which are representative of compounds of Formula (I). Compounds of Formula (1-8) can be treated with a hydrazine, $H_2NNHR^{3/5}$, wherein $R^{3/5}$ represents either $R^3$ or $R^5$ as described in the Summary in optionally heated ethanol to give a mixture of compounds of Formula (3-1) and Formula (3-2). Treatment of the mixture of compounds of Formula (3-1) and Formula (3-2) with bromine in dichloromethane gives a mixture of compounds of Formula (3-3) and unreacted compounds of Formula (3-1) which can be separated chromatographically. A Suzuki reaction can then be used to introduce the $G^{6a}$ moiety of compounds of Formula (3-4). A suitable set of reaction conditions include a boronic acid, $G^{6a}\text{-B(OH)}_2$, potassium phosphate tribasic, tetrakis(triphenylphosphine)palladium(0) in heated dimethoxyethane. The appropriate steps shown in Scheme 1 can then be used to transform compounds of Formula (3-4) to compounds of Formula (3-5). Compounds of Formula (3-5) are representative of compounds of Formula (I).

Scheme 4

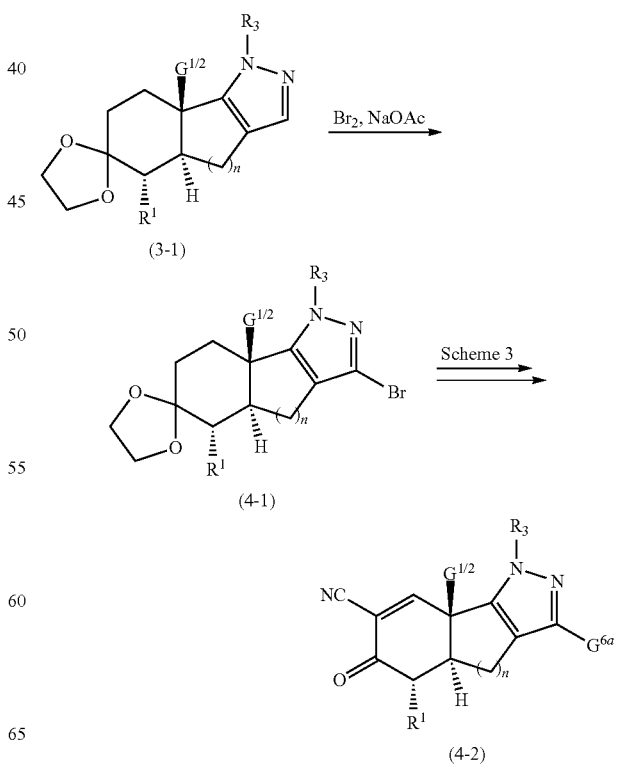

Compounds of Formula (3-1) can be brominated with bromine in the presence of sodium acetate in a mixture of ethanol and water to give compounds of Formula (4-1). Compounds of Formula (4-1) can be converted to compounds of Formula (4-2) using the steps described above for the transformation of compounds of Formula (3-3) to compounds of Formula (3-5). Compounds of Formula (4-2) are representative of compounds of Formula (I).

Scheme 5

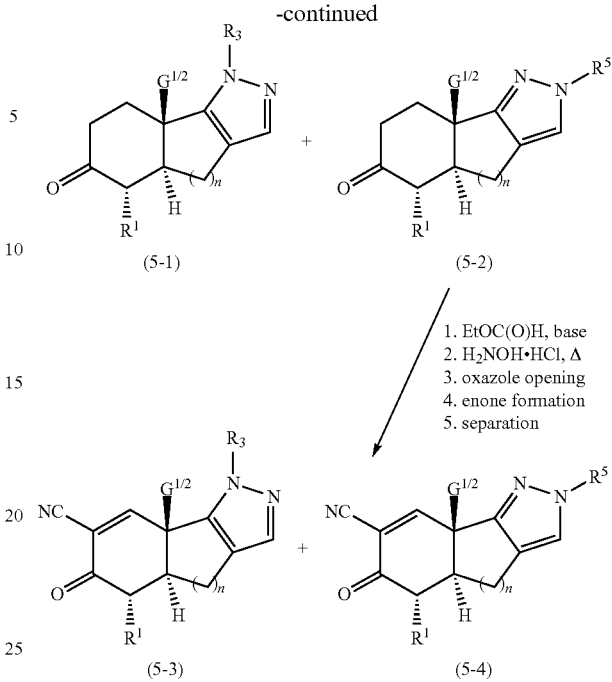

Compounds of Formula (3-1) and Formula (3-2) can also be treated with hydrochloric acid in methanol to remove the ketal moiety and give a mixture of compounds of Formula (5-1) and Formula (5-2). Compounds of Formula (5-1) and Formula (5-2) can be taken through the required steps previously illustrated in Scheme 1 to give compounds of Formula (5-3) and Formula (5-4) which can be separated chromatographically. Compounds of Formula (5-3) and Formula (5-4) are representative of compounds of Formula (I).

Scheme 6

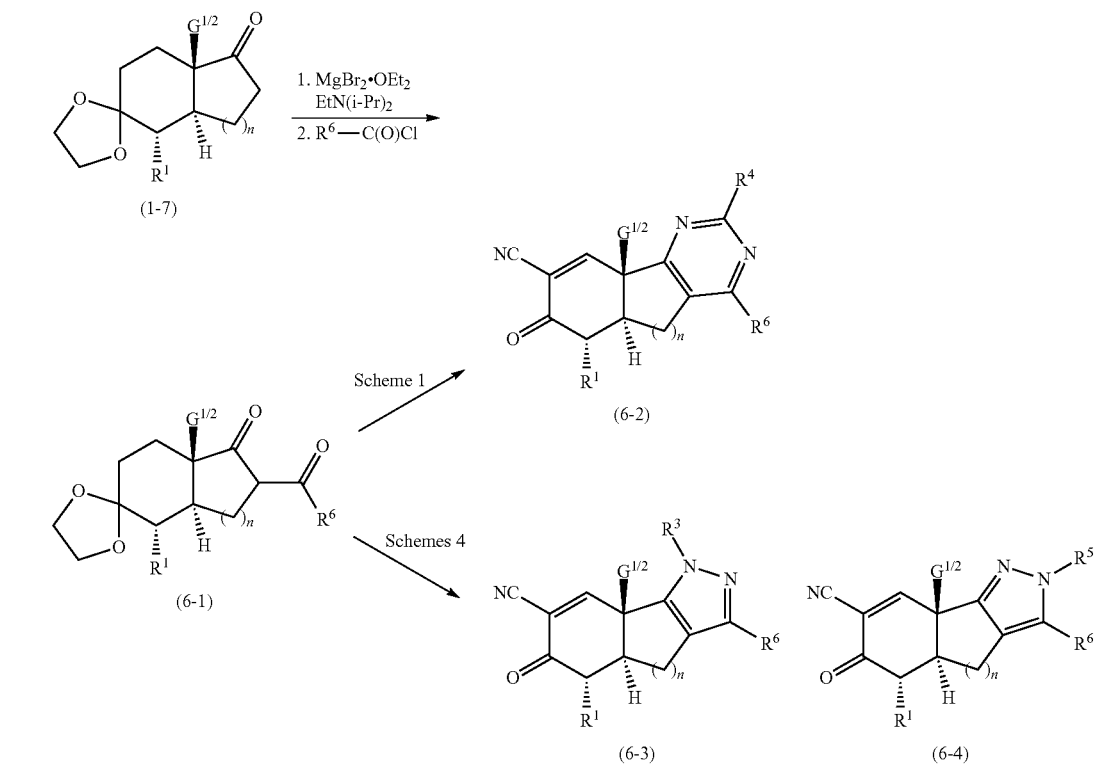

As shown in Scheme 6, compounds of Formula (1-7) are transformed into compounds of Formula (6-1) in a two-step process. First, compounds of Formula (1-7) can be treated with magnesium bromide etherate in the presence of a base such as diisopropylethylamine in dichloromethane. Then a carboxylic acid chloride, $R^6$—C(O)Cl, can be added to give compounds of Formula (6-1). Compounds of Formula (6-1) can be converted to compounds of Formula (6-2) using the appropriate steps shown in Scheme 1. Alternatively, compounds of Formula (6-1) can be treated with appropriate steps shown in Scheme 4 to give compounds of Formula (6-3) and Formula (6-4). Compounds of Formula (6-2), Formula (6-3), and Formula (6-4) are representative of compounds of Formula (I).

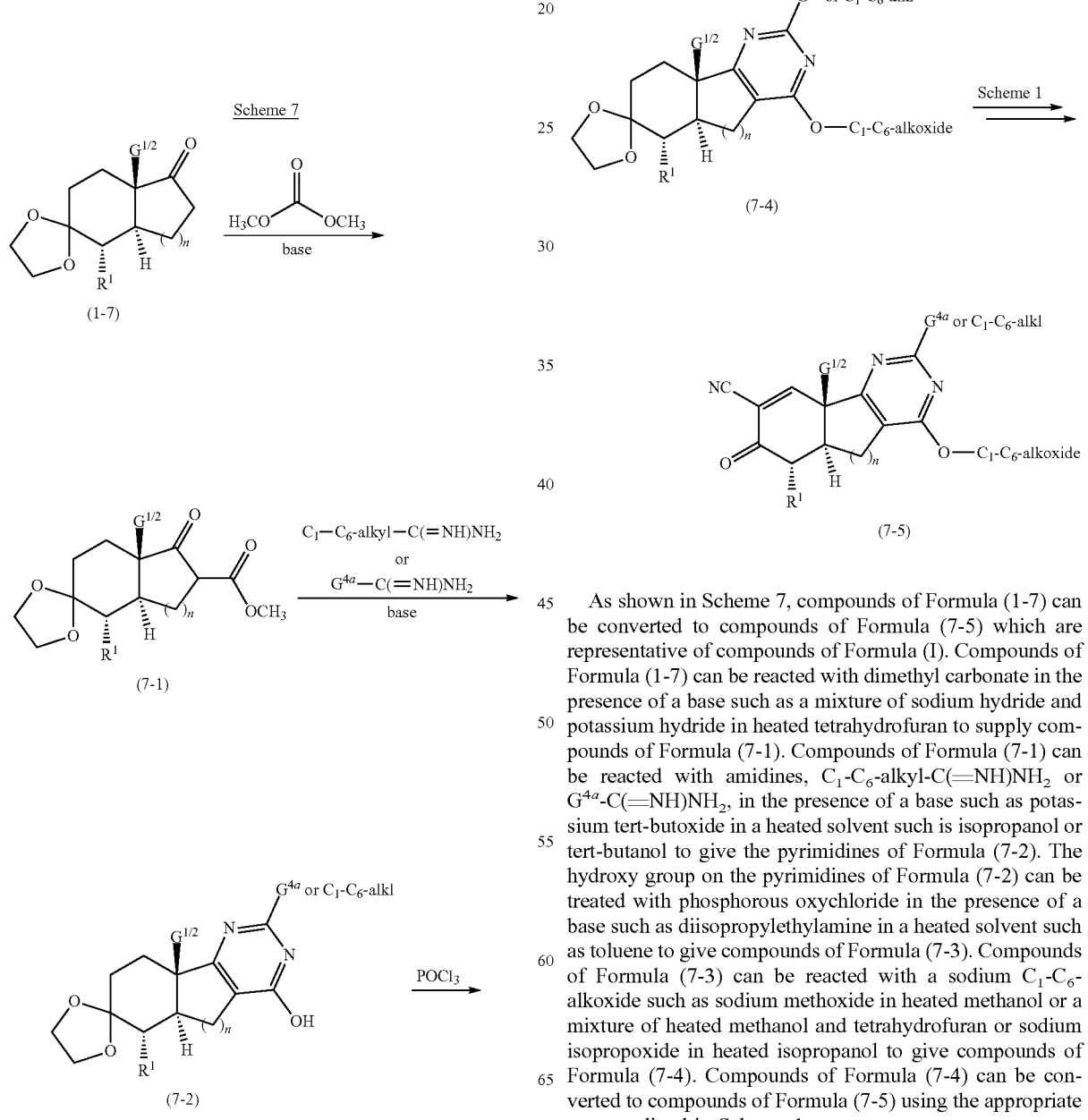

As shown in Scheme 7, compounds of Formula (1-7) can be converted to compounds of Formula (7-5) which are representative of compounds of Formula (I). Compounds of Formula (1-7) can be reacted with dimethyl carbonate in the presence of a base such as a mixture of sodium hydride and potassium hydride in heated tetrahydrofuran to supply compounds of Formula (7-1). Compounds of Formula (7-1) can be reacted with amidines, $C_1$-$C_6$-alkyl-C(=NH)NH$_2$ or $G^{4a}$-C(=NH)NH$_2$, in the presence of a base such as potassium tert-butoxide in a heated solvent such is isopropanol or tert-butanol to give the pyrimidines of Formula (7-2). The hydroxy group on the pyrimidines of Formula (7-2) can be treated with phosphorous oxychloride in the presence of a base such as diisopropylethylamine in a heated solvent such as toluene to give compounds of Formula (7-3). Compounds of Formula (7-3) can be reacted with a sodium $C_1$-$C_6$-alkoxide such as sodium methoxide in heated methanol or a mixture of heated methanol and tetrahydrofuran or sodium isopropoxide in heated isopropanol to give compounds of Formula (7-4). Compounds of Formula (7-4) can be converted to compounds of Formula (7-5) using the appropriate steps outlined in Scheme 1.

Scheme 8

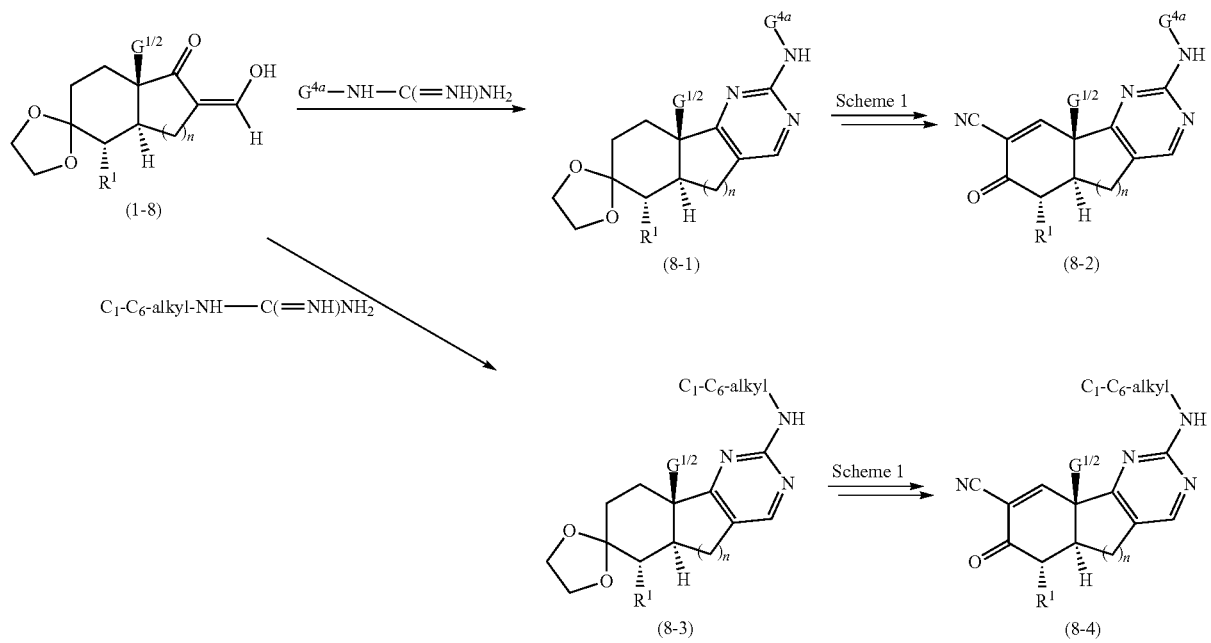

As illustrated in Scheme 8, compounds of Formula (1-8) can be reacted with guanidines, $G^{4a}$-NH—C(=NH)NH$_2$, in heated N,N-dimethylformamide to give compounds of Formula (8-1). Conversion of compounds of Formula (8-1) to compounds of Formula (8-2) has been shown analogously in Scheme 1. Compounds of Formula (1-8) can also be treated with guanidines, $C_1$-$C_6$-alkyl-NH—C(=NH)NH$_2$, in the presence of potassium tert-butoxide in heated tert-butanol to give compounds of Formula (8-3). Compounds of Formula (8-3) can be converted to compounds of Formula (8-4) using the appropriate steps shown in Scheme 1. Compounds of Formula (8-2) and Formula (8-4) are representative of compounds of Formula (I).

Scheme 9

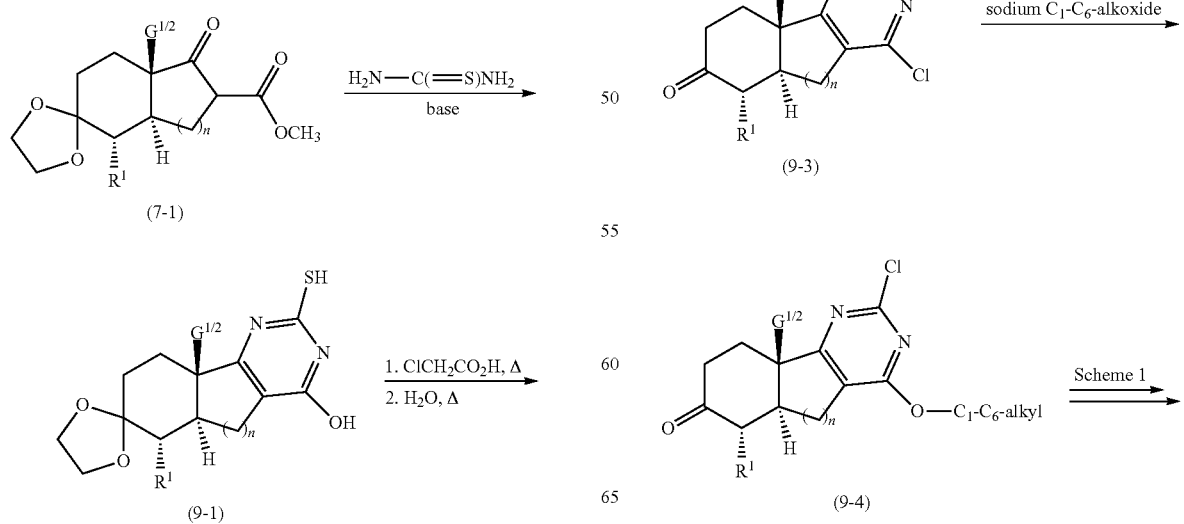

-continued

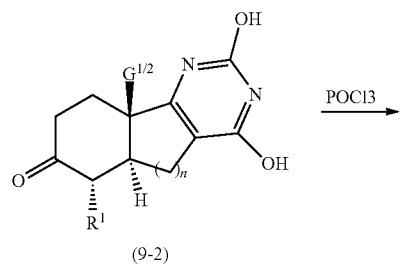

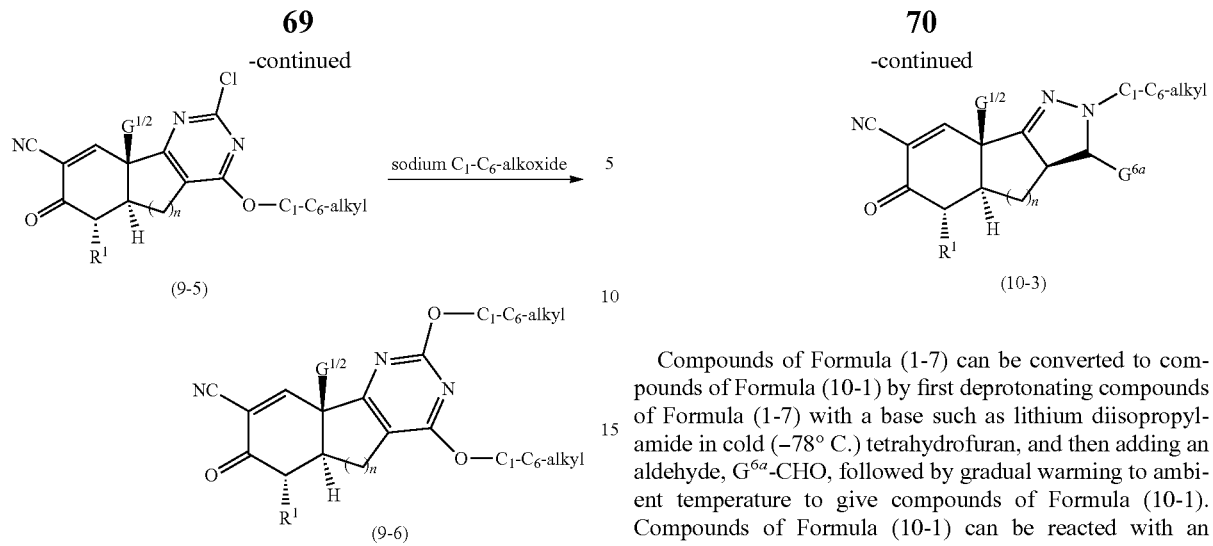

As shown in Scheme 9, compounds of Formula (1-8) can be treated with thiourea in the presence of potassium tert-butoxide in heated tert-butanol to give compounds of Formula (9-1). Compounds of Formula (9-1), can be reacted with heated chloroacetic acid and then heated again after the addition of water to give compounds of Formula (9-2). Treatment with heated phosphorous oxychloride and diisopropylethylamine delivers compounds of Formula (9-3). Compounds of Formula (9-3) can be reacted with a sodium $C_1$-$C_6$-alkoxide in a corresponding heated $C_1$-$C_6$-alcohol to give compounds of Formula (9-4). Compounds of Formula (9-4) can be converted to compounds of Formula (9-5) using the appropriate steps shown in Scheme 1. Compounds of Formula (9-5) can be reacted with a sodium $C_1$-$C_6$-alkoxide in a corresponding heated $C_1$-$C_6$-alcohol to give compounds of Formula (9-6). Compounds of Formula (9-5) and Formula (9-6) are representative of compounds of Formula (I).

Compounds of Formula (1-7) can be converted to compounds of Formula (10-1) by first deprotonating compounds of Formula (1-7) with a base such as lithium diisopropylamide in cold (−78° C.) tetrahydrofuran, and then adding an aldehyde, $G^{6a}$-CHO, followed by gradual warming to ambient temperature to give compounds of Formula (10-1). Compounds of Formula (10-1) can be reacted with an alkylhydrazine in heated isopropanol to give compounds of Formula (10-2). Compounds of Formula (10-2) can be treated with the appropriate steps shown in Scheme 1 to give compounds of Formula (10-3). Compounds of Formula (10-3) are representative of compounds of Formula (I).

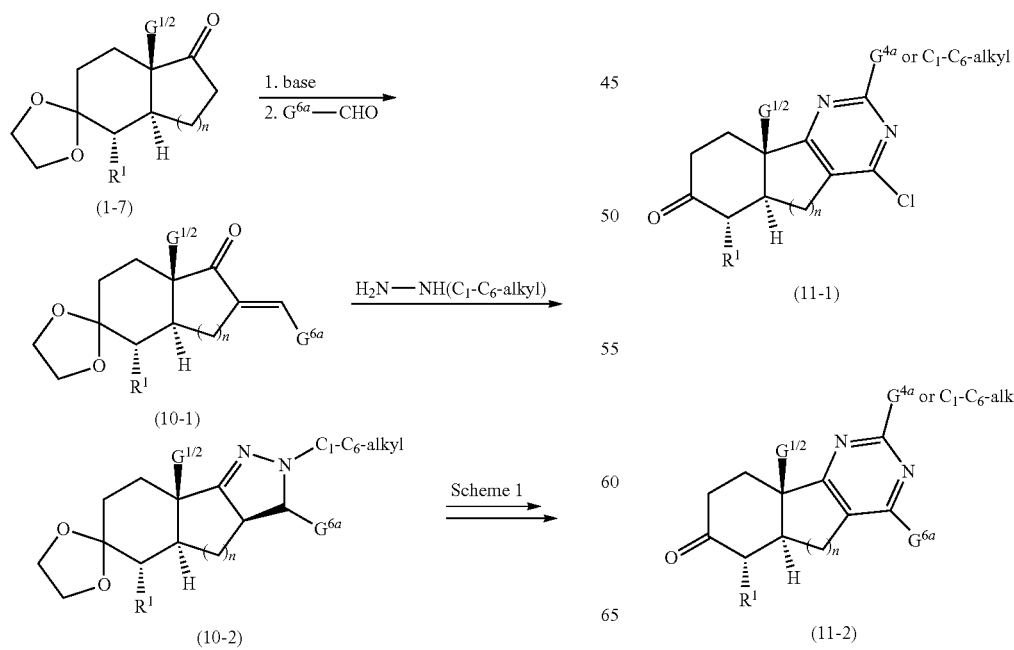

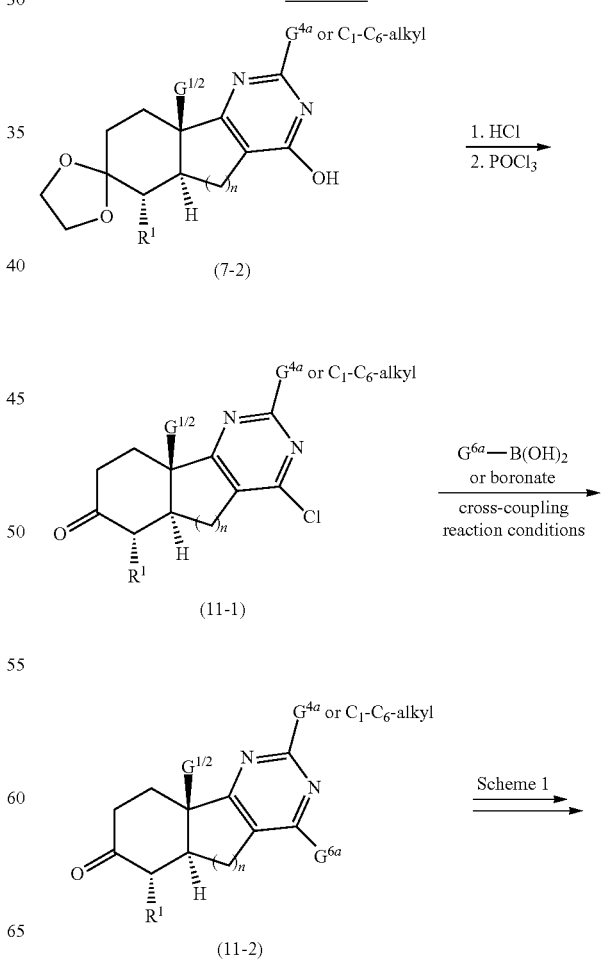

-continued

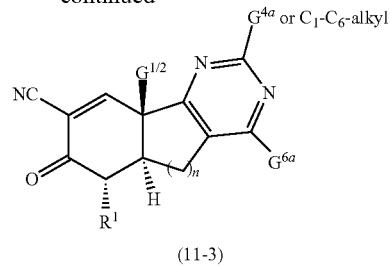

(11-3)

-continued

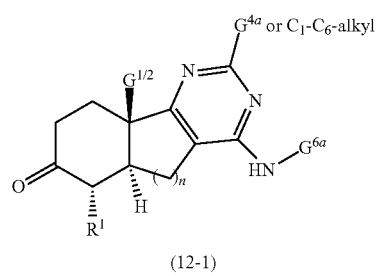

(12-1)

Scheme 1

As shown in Scheme 11, the ketal of compounds of Formula (7-2) can be removed upon treatment with aqueous acid in a solvent such as heated tetrahydrofuran and then chlorinated by treatment with phosphorous oxychloride in the presence of a base such as diisopropylethylamine in heated toluene to give compounds of Formula (11-1). A palladium catalyzed cross-coupling reaction with a boronic acid, $G^{6a}$-B(OH)$_2$, or other suitable coupling partner gives compounds of Formula (11-2). Compounds of Formula (11-1) can be converted to compounds of Formula (11-2) using the appropriate sequence of steps shown in Scheme 1 to give compounds of Formula (11-3). Compounds of Formula (11-3) are representative of compounds of Formula (I).

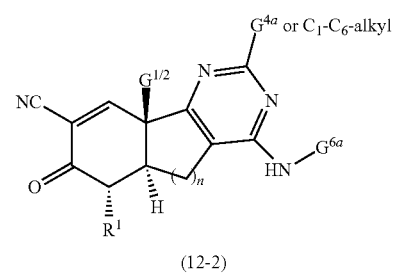

(12-2)

Scheme 12

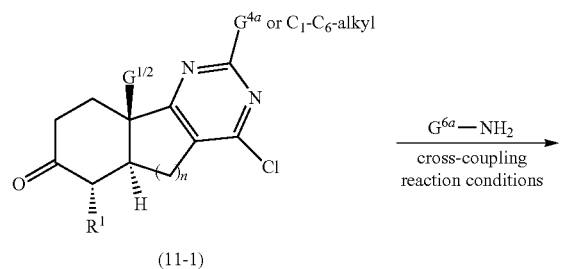

(11-1)

$G^{6a}$—NH$_2$
cross-coupling
reaction conditions

As shown in Scheme 12, compounds of Formula (11-1) can also undergo a palladium catalyzed cross-coupling reaction with amines, $G^{6a}$-NH$_2$, to deliver compounds of Formula (12-1). Compounds of Formula (12-1) can be converted to compounds of Formula (12-2) using the appropriate steps shown in Scheme 1. Compounds of Formula (12-2) are representative of compounds of Formula (I).

Scheme 13

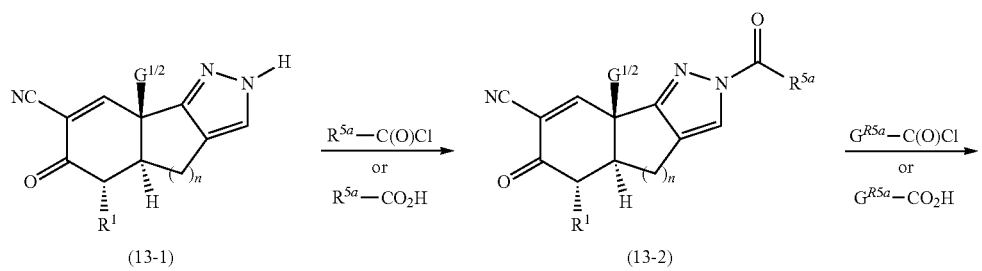

$R^{5a}$—C(O)Cl
or
$R^{5a}$—CO$_2$H $G^{R5a}$—C(O)Cl
or
$G^{R5a}$—CO$_2$H

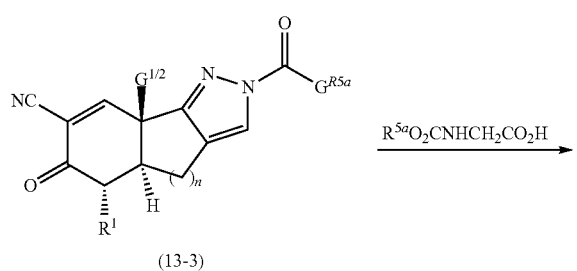

(13-3)

$R^{5a}$O$_2$CNHCH$_2$CO$_2$H

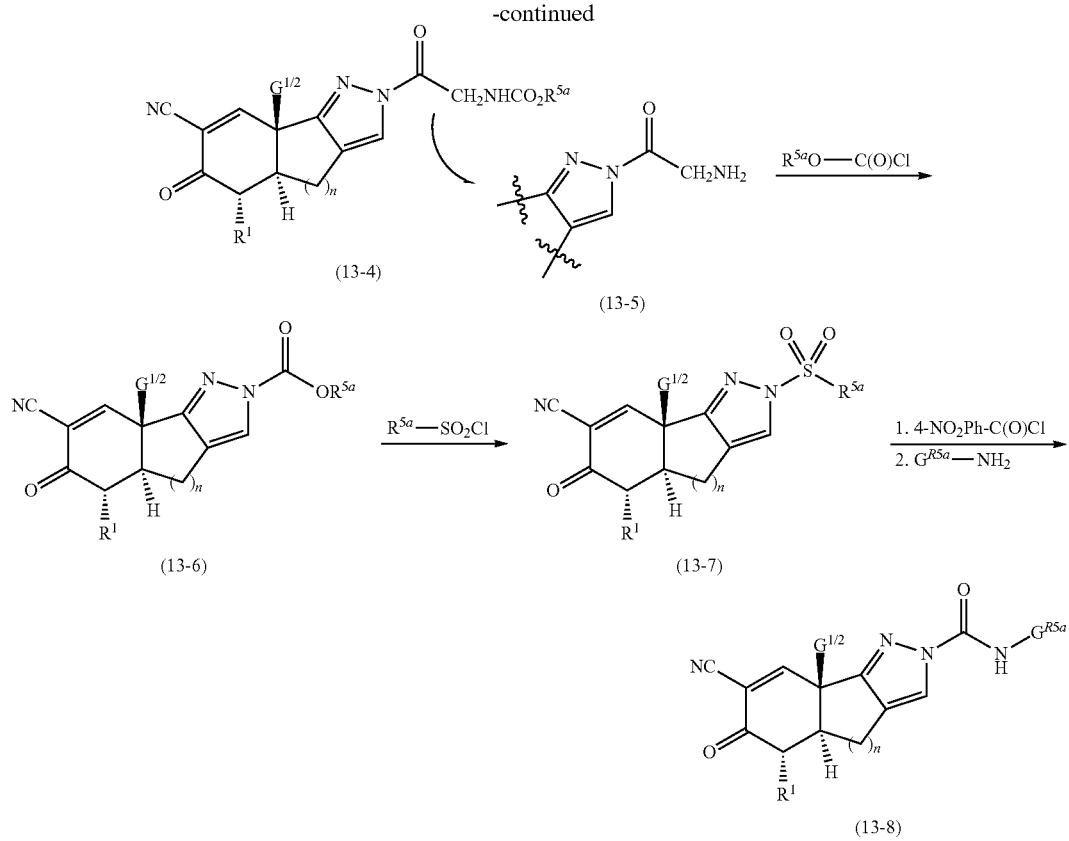

As shown in Scheme 13, the pyrazole moiety of compounds of Formula (13-1) can be modified in many ways. For instance, carboxylic acids, $R^{5a}$—$CO_2H$, can be coupled to the pyrazole moiety to give compounds of Formula (13-2). Examples of conditions known to generate amides from a mixture of a carboxylic acid and an amine of the pyrazole include but are not limited to adding a coupling reagent such as but not limited to N-(3-dimethylaminopropyl)-N-ethylcarbodiimide (EDC or EDCI), 1,3-dicyclohexyl-carbodiimide (DCC), bis(2-oxo-3-oxazolidinyl)phosphinic chloride (BOPCl), bis(dimethylamino)(3-oxido-1H-benzotriazol-1-yl)methylium hexafluorophosphate (HATU), O-benzotriazol-1-yl-N,N,N',N'-tetramethyluronium tetrafluoroborate (TBTU), and 2-(1H-benzo[d][1,2,3]triazol-1-yl)-1,1,3,3-tetramethylisouronium hexafluorophosphate(V) (HBTU). The coupling reagents can be added as a solid, a solution or as the reagent bound to a solid support resin. In addition to the coupling reagents, auxiliary-coupling reagents can facilitate the coupling reaction. Auxiliary coupling reagents that are often used in the coupling reactions include but are not limited to (dimethylamino)pyridine (DMAP), 1-hydroxy-7-azabenzotriazole (HOAT) and 1-hydroxybenzotriazole (HOBT). The reaction can be carried out optionally in the presence of a base such as triethylamine or diisopropylethylamine. The coupling reaction can be carried out in solvents such as but not limited to tetrahydrofuran, N,N-dimethylformamide, dichloromethane, and ethyl acetate. The reaction can be conducted at ambient or elevated temperatures. Alternatively, compounds of Formula (13-2) can be produced by reacting compounds of Formula (13-1) with an acid chloride, $R^{5a}$—C(O)Cl, in the presence of a tertiary amine base such as triethylamine or diisopropylethylamine in a solvent such as tetrahydrofuran or dichloromethane. Compounds of Formula (13-2) are representative of compounds of Formula (I).

Compounds of Formula (13-3) can be formed by the reaction of either $G^{R5a}$-$CO_2H$ or $G^{R5a}$-C(O)Cl under the conditions described in the above paragraph for the formation of compounds of Formula (13-2). Compounds of Formula (13-3) are representative of compounds of Formula (I).

Compounds of Formula (13-4) can be formed by coupling of a protected amino acid, $R^{5a}O_2CNHCH_2CO_2H$, to compounds of Formula (13-1) under the amide bond coupling conditions described for the formation of compounds of Formula (13-2) above. Compounds of Formula (13-4) are representative of compounds of Formula (I). Subsequently, compounds of Formula (13-4) can be converted to compounds of Formula (13-5) by removal of the protecting group under conditions known to one of skill in the art. Compounds of Formula (13-5) are representative of compounds of Formula (I).

Compounds of Formula (13-6) can be produced by reacting compounds of Formula (13-1) with $R^{5a}O$—C(O)Cl, in the presence of a tertiary amine base such as triethylamine or diisopropylethylamine in a solvent such as tetrahydrofuran or dichloromethane. Compounds of Formula (13-6) are representative of compounds of Formula (I).

Compounds of Formula (13-7) can be produced by reacting compounds of Formula (13-1) with $R^{5a}SO_2Cl$, in the presence of a tertiary amine base such as triethylamine or diisopropylethylamine in a solvent such as dichloromethane. Compounds of Formula (13-7) are representative of compounds of Formula (I).

Compounds of Formula (13-8) can be prepared from compounds of Formula (13-1) in a two-step process. The initial step involves reaction of compounds of Formula (13-1) with 4-nitrophenyl carbonochloridate in the presence of a tertiary amine base such as triethylamine or diisopropylethylamine in a solvent such as tetrahydrofuran or dichloromethane.

Subsequently, reaction of the intermediate 4-nitrophenylcarboxylate with an amine, $G^{R5a}$-NH$_2$, in dichloromethane give compounds of Formula (13-8). Compounds of Formula (13-8) are representative of compounds of Formula (I).

Compounds of Formula (14-2) can be halogenated by treatment with either 1,2 dibromotetrachloroethane or hexachloroethane and lithium hexamethyldisilazide in tetrahydrofuran at −78° C. to give compounds of Formula (14-3). Compounds of Formula (14-3) can be reacted under palladium catalyzed cross-coupling reaction conditions with $G^{6a}$-B(OH)$_2$ or other suitable coupling partner to give compounds of Formula (14-4). The ketal of compounds of Formula (14-4) can be removed under acidic conditions to

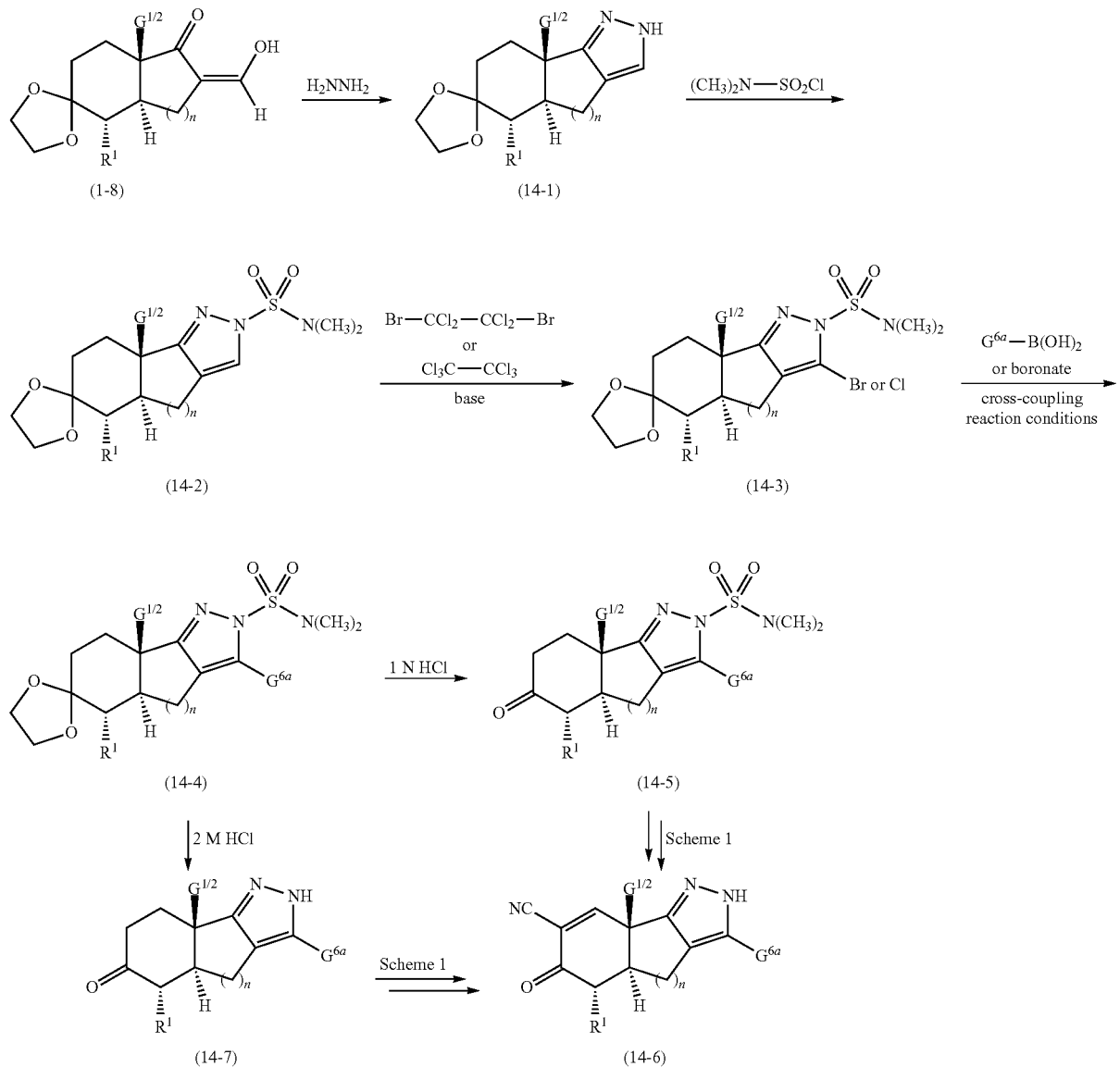

As shown in Scheme 14, compounds of Formula (14-6), which are representative of compounds of Formula (I), can be prepared from compounds of Formula (1-8). Accordingly, compounds of Formula (1-8) can be reacted with hydrazine as described in Scheme 3 to give compounds of Formula (14-1). Reaction of compounds of Formula (14-1) with dimethylsulfamoyl chloride in the presence of a base such as triethylamine in a solvent such as toluene, dichloromethane or tetrahydrofuran delivers compounds of Formula (14-2).

give compounds of Formula (14-5). Compounds of Formula (14-5) can then be transformed to compounds of Formula (14-6) using the appropriate steps described in Scheme 1. Under this sequence, the sulfonamide is cleaved with hydroxylamine. As an alternative, compounds of Formula (14-4) can be treated under stronger acid conditions to go to compounds of Formula (14-7). Then compounds of Formula (14-7) can be transformed to compounds of Formula (14-6) using the appropriate steps described in Scheme 1.

Scheme 15

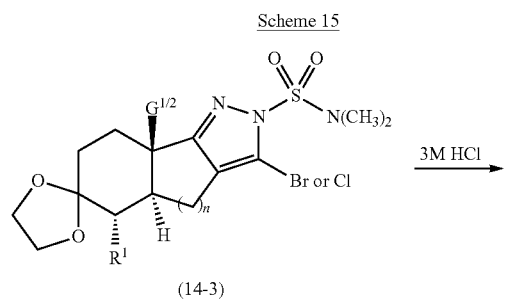

In Scheme 15, compounds of Formula (14-3) are converted to compounds of Formula (15-3) and Formula (15-4). Compounds of Formula (15-3) and Formula (15-4) are representative of compounds of Formula (I). Compounds of Formula (14-3) can be treated under acidic conditions such as 3 M HCl in heated tetrahydrofuran to deliver compounds of Formula (15-1). Compounds of Formula (15-1) can be alkylated with an alkyl halide such as methyl iodide in the presence of a base such as potassium carbonate in heated N,N-dimethylformamide to give compound of Formula (15-2). Compounds of Formula (15-2) can be treated under palladium catalyzed cross-coupling reaction conditions as described in the conversion of compounds of Formula (14-3) to compounds of Formula (14-4) to introduce a $G^{6a}$ moiety. Then use of the appropriate steps described in Scheme 1 provides compounds of Formula (15-3). The sequence used to transform compounds of Formula (15-2) to (15-3) can be applied to compounds of Formula (15-1) to give compounds of Formula (15-4).

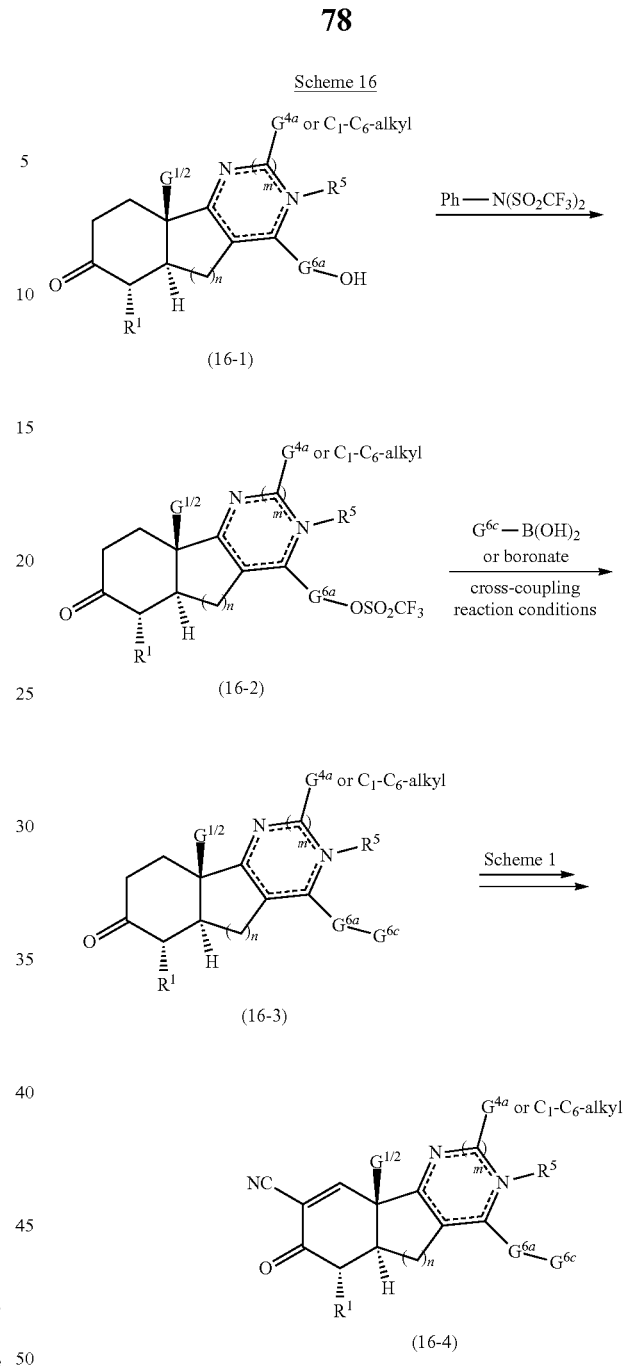

As shown in Scheme 16, compounds of Formula (16-1), which can be prepared as using methodologies described in the above Schemes, can be converted to compounds of Formula (16-4). Compounds of Formula (16-1) can be converted to compounds of Formula (16-2) by treatment with N,N-bis(trifluoromethylsulfonyl)aniline, triethylamine, and catalytic 4-dimethylaminopyridine in dichloromethane. Compounds of Formula (16-2) can be reacted under palladium catalyzed cross-coupling reaction conditions with $G^{6a}$-$B(OH)_2$ or other suitable coupling partner to give compounds of Formula (16-3). Then compounds of Formula (16-3) can be transformed to compounds of Formula (16-4) using the appropriate steps described in Scheme 1. Compounds of Formula (16-4) are representative of compounds of Formula (I).

Scheme 17

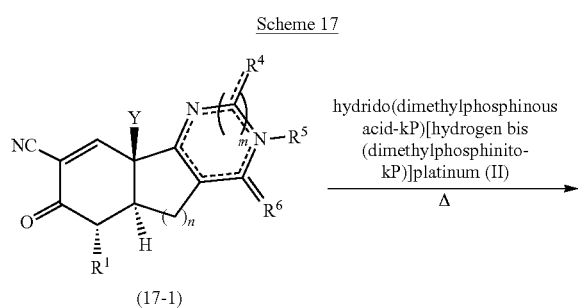

(17-1)

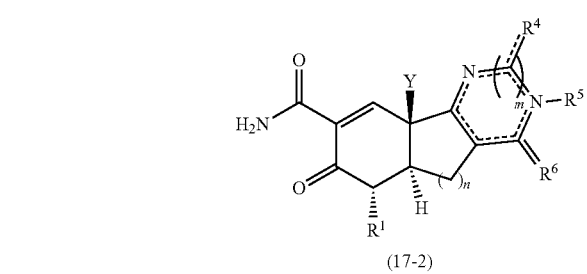

(17-2)

As shown in Scheme 17, compounds of Formula (17-1), which can be prepared as using methodologies described in the above Schemes, can be converted to compounds of Formula (17-2). Compounds of Formula (17-1) can be treated with hydrido(dimethylphosphinous acid-kP)[hydrogen bis(dimethylphosphinito-kP)]platinum (II) in heated 80% ethanol to give amide of Formula (17-2). Compounds of Formula (17-2) are representative of compounds of Formula (I).

Scheme 18

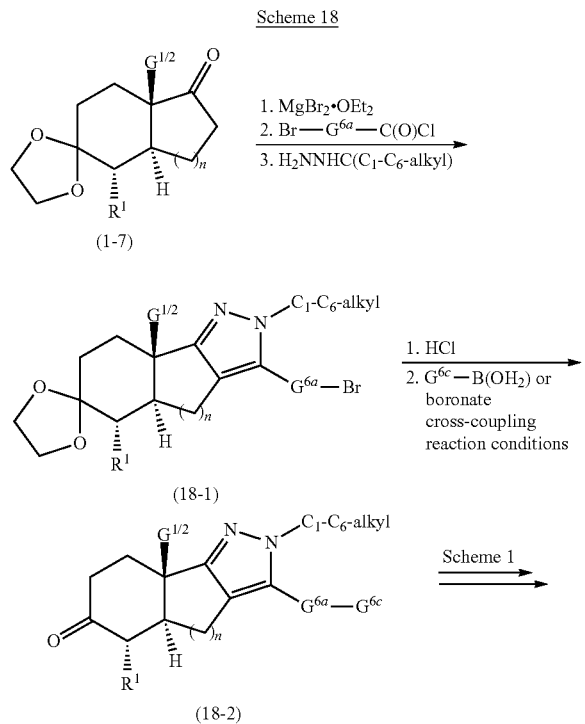

As shown in Scheme 18, compounds of Formula (1-7) can be converted to compounds of Formula (18-3). Compounds of Formula (1-7) can be treated with magnesium bromide etherate in the presence of a base such as diisopropylethylamine in dichloromethane. Then a carboxylic acid chloride, Br-$G^{6a}$-C(O)Cl, can be added to give an intermediate beta-diketone. Condensation with a hydrazine, $H_2NNH(C_1-C_6$-alkyl), as described in Scheme 3 gives compounds of Formula (18-1). The ketal of compounds of Formula (18-1) can be removed by treatment with an acid such as 4 N HCl in dioxane. Subsequent palladium catalyzed cross-coupling with a boronic acid, $G^{6c}$-B(OH)$_2$, or other suitable coupling partner supplies compounds of Formula (18-2). Compounds of Formula (18-2) can be converted to compounds of Formula (18-3) using the appropriate steps described in Scheme 1. Compounds of Formula (18-3) are representative of compounds of Formula (I).

Scheme 19

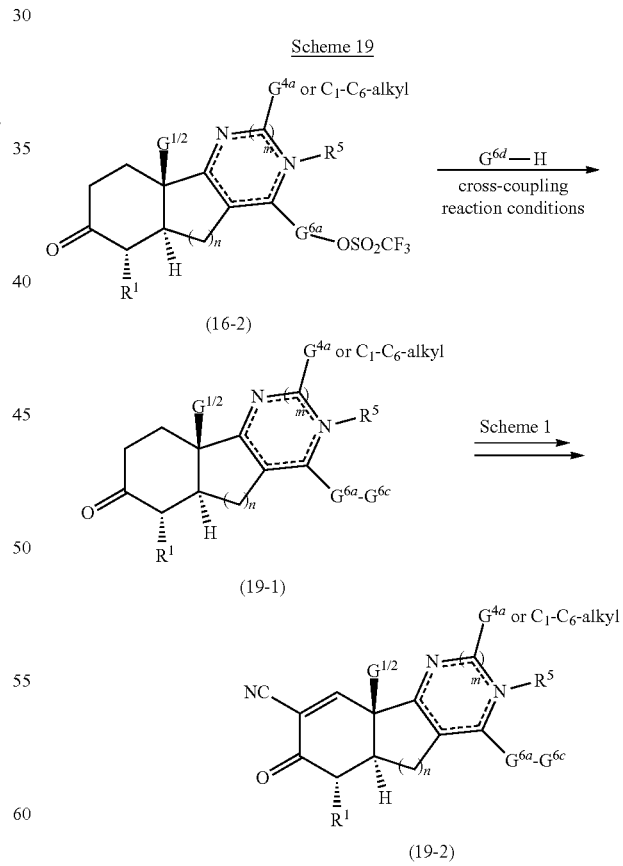

As illustrated in Scheme 19, compounds of Formula (16-2) can be transformed to compounds of Formula (19-1) which are representative of compounds of Formula (19-2). Compounds of Formula (16-2) can be reacted with heterocycle containing a secondary amine moiety as part of the heterocycle under palladium catalyzed cross-coupling reaction conditions to give compounds of Formula (19-1). Compounds of Formula (19-1) can be converted to compounds of Formula (19-2) using the appropriate reactions described in Scheme 1.

Scheme 20

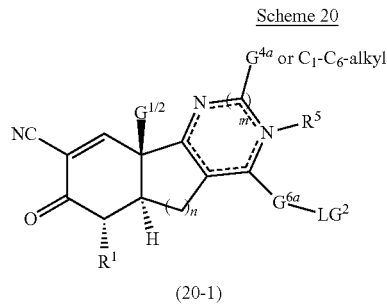

As illustrated in Scheme 20, compounds of Formula (20-1), which can be prepared using methodologies described in the above Schemes and wherein LG² is a leaving group (chlorine, bromine, iodine, sulfonate), can be reacted under palladium catalyzed cross-coupling reaction conditions with a boronic acid, $G^6C—B(OH)_2$, an analogous boronate, or other suitable coupling partner to give compounds of Formula (20-2). Compounds of Formula (20-2) are representative of compounds of Formula (I).

Scheme 21

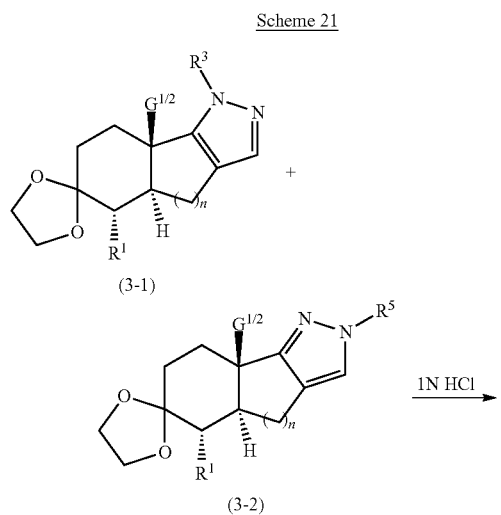

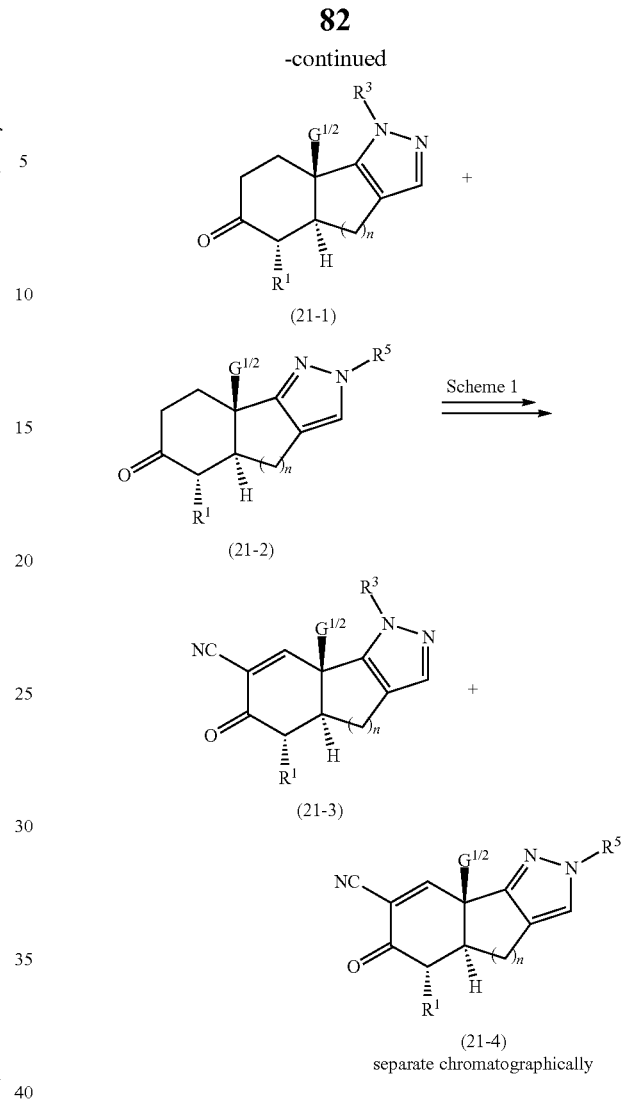

As shown in Scheme 21, compounds of Formula (3-1) and Formula (3-2) can be reacted with 1 N HCl in methanol at or near room temperature to give compounds of Formula (21-1) and Formula (21-2). The mixture of compounds of Formula (21-1) and Formula (21-2) can be taken through the appropriate steps described in Scheme 1 to give compounds of Formula (21-3) and Formula (21-4). Compounds of Formula (21-3) and Formula (21-4), which are each representative of compounds of Formula (I), can be separated chromatographically.

Scheme 22

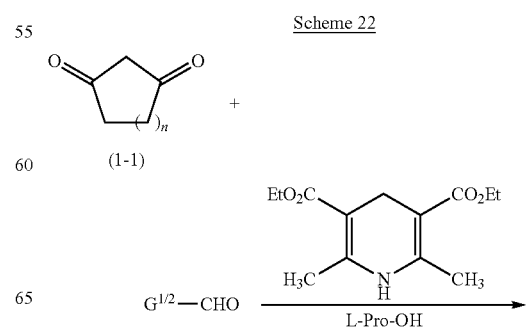

-continued

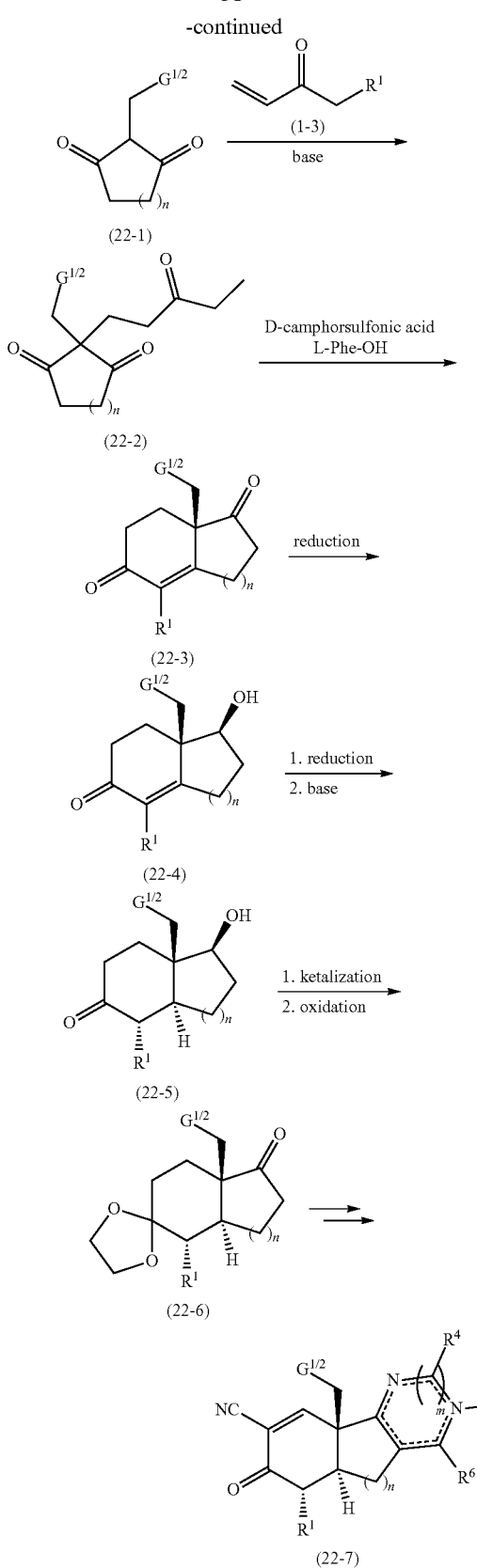

ingly, compounds of Formula (1-1) can be reacted with aldehydes, $G^{1/2}$-CHO wherein $G^{1/2}$ represents either a $G^1$ or a $G^2$ as described in the Summary, in the presence of L-proline and diludine in a solvent such as dichloromethane at or near room temperature to give compounds of Formula (22-1). Reaction of compounds of Formula (22-1) with a vinyl ketone of Formula (1-3) in the presence of a base such as triethylamine at or near room temperature in a solvent such as acetonitrile gives compounds of Formula (22-2). Compounds of Formula (22-2) can be reacted in the presence of L-phenylalanine and D-camphorsulfonic acid in heated acetonitrile to give compounds of Formula (22-3). Compounds of Formula (22-3) can be reduced with a reductant such as sodium borohydride in a solvent such as ethanol to obtain compounds of Formula (22-4). The carbon-carbon double bond in compounds of Formula (22-4) can be reduced by catalytic hydrogenation using a palladium on carbon catalyst in a solvent such as ethyl acetate. Subsequent epimerization with a base such as diazabicyclo[5.4.0]-undec-7-ene in tetrahydrofuran or with sodium methoxide in methanol gives compounds of Formula (22-5). A two-step process converts compounds of Formula (22-5) to compounds of Formula (22-6). Ketalization with ethylene glycol in benzene or toluene with a catalytic amount of p-toluenesulfonic acid under Dean-Stark conditions protects the ketone. Oxidation of the secondary alcohol with pyridinium dichromate in dichloromethane then delivers compounds of Formula (22-6). Compounds of Formula (22-6) can be converted to compounds of Formula (22-7) using methodologies described in the above Schemes.

Scheme 23

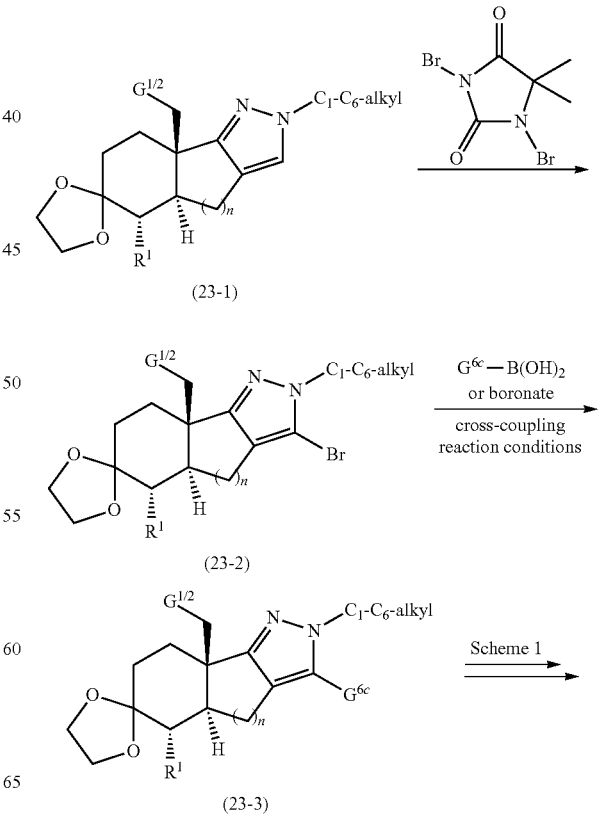

As illustrated in Scheme 22, compounds of Formula (1-1) can be transformed to compounds of Formula (22-7) which are representative of compounds of Formula (I). Accord-

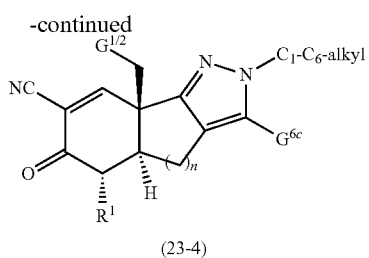

(23-4)

As shown in Scheme 23, compounds of Formula (23-1) can be converted to compounds of Formula (23-4) which are representative of compounds of Formula (I). Compounds of Formula (23-1) can be brominated with for example 1,3-dibromo-5,5-dimethylhydantoin in dichloromethane at or near 0° C. to give compounds of Formula (23-2). Compounds of Formula (23-2) can be reacted with a boronic acid, $G^{6a}$-B(OH)$_2$, or other suitable coupling partner under palladium catalyzed cross-coupling reaction conditions to give compounds of Formula (23-3). Compounds of Formula (23-3) are transformed to compounds of Formula (23-4) using the appropriate steps described in Scheme 1.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protective Groups in Organic Synthesis (3$^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

E. EXAMPLES

Abbreviations: ee for enantiomeric excess; HPLC for high-performance liquid chromatography; psig for pounds per square inch of gas; v/v for volume/volume; and w/w for weight/weight.

Example 1

(6aS,7S,10aR)-7-methyl-8-oxo-10a-phenyl-5,6,6a,7,8,10a-hexahydrobenzo[h]quinazoline-9-carbonitrile Example 1A 2-phenylcyclohexane-1,3-dione A 5 L round-bottomed flask was charged with bromobenzene (0.109 L, 1038 mmol), tert-amyl alcohol (1 L) and dioxane (2 L), and the contents were purged with $N_2$ for 45 minutes. A 5 L round-bottomed flask was charged with potassium phosphate tribasic (459 g, 2163 mmol), 1,3-cyclohexanedione (100 g, 865 mmol), palladium(II) acetate (3.59 g, 16.00 mmol) and 2-(di-tert-butylphospino)-2'-methylbiphenyl (10 g, 32.0 mmol), and the contents were purged with $N_2$ for 45 minutes. The bromobenzene solution was then transferred to 1,3-cyclohexanedione containing vessel via cannula, and the reaction was heated to reflux overnight. After cooling to room temperature, the reaction mixture was partitioned between ethyl acetate (2 L) and 10% HCl (3 L) with mixing. The lower aqueous layer was separated and extracted with ethyl acetate (2 L). The combined organic layers were washed with brine (1 L) and concentrated. The residue was taken up in toluene (1 L) and again concentrated. The residue was taken up in toluene (500 mL) and warmed to 50° C. After cooling to room temperature, the solids were collected by filtration, washed with toluene (2×100 mL) and dried in a vacuum oven at 50° C. to provide the titled compound. $^1$H NMR (400 MHz, CDCl$_3$) δ ppm 7.48-7.40 (m, 2H), 7.38-7.29 (m, 1H), 7.18 (dt, J=8.0, 1.7 Hz, 2H), 6.10 (s, 1H), 2.65-2.39 (m, 4H), 2.15-2.04 (m, 2H).

Example 1B (8aR)-5-methyl-8a-phenyl-3,4,8,8a-tetrahydronaphthalene-1,6(2H,7H)-dione A 5 L round-bottomed flask was charged with the product of Example 1A (163 g, 903 mmol) in acetonitrile (1.5 L).

Triethylamine (252 mL, 1805 mmol) and ethyl vinyl ketone (135 mL, 1.35 mol) were added, and the contents were warmed to 75° C. and stirred overnight. After cooling, the reaction mixture was concentrated. The residue was taken up in dimethyl sulfoxide (500 mL). Pyridinium para-toluenesulfonate (227 g, 903 mmol) and L-phenylalanine (149 g, 903 mmol) were added, and the contents were warmed to 45° C. for 66 hours. After cooling, the reaction mixture was poured into saturated aqueous $NH_4Cl$ (500 mL), water (500 mL), and methyl tert-butyl ether (500 mL). After mixing for 10 minutes, the solids were removed by filtration and the layers separated. The aqueous layer was extracted with methyl tert-butyl ether (500 mL). The combined organic layers were washed with water (300 mL) and brine (300 mL), dried over sodium sulfate, filtered, and concentrated. The residue was purified by chromatography over silica gel on a Teledyne Isco Combiflash Torrent® system using a 750 g RediSep® silica gel column: ethyl acetate/hexanes 0:1 (2 column volumes) up to 1:1 (gradient over 8 column volumes). Fractions containing product were combined and concentrated under reduced pressure. This 65% ee material was taken up in cyclohexane (500 mL) and stirred overnight. The racemic solids were removed by filtration rinsing with cyclohexane (2×100 mL), and the filtrate was concentrated to provide the titled compound in 95% ee determined using a Chiralpak® AS-H column (4.6 mm ID×25 cm, 5 microns) eluting with 10% ethanol in heptane at 1.0 mL/minute with the major enantiomer eluting at 10.4 minutes and the minor enantiomer eluting at 15.1 minutes. (140 g, 61%). $^1$H NMR (400 MHz, $CDCl_3$) δ ppm 7.38-7.25 (m, 3H), 7.15-7.10 (m, 2H), 2.82-2.72 (m, 1H), 2.68-2.58 (m, 1H), 2.57-2.48 (m, 1H), 2.46-2.29 (m, 3H), 2.25-2.18 (m, 1H), 2.11-2.00 (m, 1H), 1.97 (s, 3H), 1.86-1.65 (m, 2H).

Example 1C (4aR,5S)-5-hydroxy-1-methyl-4a-phenyl-4,4a,5,6,7,8-hexahydronaphthalen-2(3H)-one A 3 L jacketed round-bottomed flask was charged with the product of Example 1B (140.5 g, 552 mmol) in ethanol (1.4 L), and the solution was cooled to −5° C. A solution of sodium borohydride (6.28 g, 166 mmol) in ethanol (1.0 L) was added dropwise while maintained an internal temperature below 0° C. The resulting mixture was stirred at −5° C. for 4 hours. The reaction mixture was quenched carefully with acetic acid (100 mL) and warmed to 23° C. After stirring overnight, the mixture was concentrated. The residue was partitioned between methyl tert-butyl ether (1 L) and 10% aqueous ammonium chloride (500 mL). The layers were separated, and the organic layer was washed with 10% aqueous ammonium chloride (500 mL) and brine (200 mL). The organic solution was concentrated, taken up in ethanol (750 mL) and filtered. The product was solidified by the slow addition of water (1.125 L) and cooling the resultant slurry to 5° C. The product was collected by filtration and washed with cold 40% ethanol in water (100 mL) and dried in a vacuum oven at 50° C. to provide the titled compound (99.0 g, 70%). $^1$H NMR (400 MHz, $CDCl_3$) δ ppm 7.54-7.49 (m, 2H), 7.34-7.21 (m, 3H), 3.83 (ddd, J=10.8, 4.6, 3.6 Hz, 1H), 2.80-2.71 (m, 1H), 2.51-2.42 (m, 1H), 2.36-2.28 (m, 1H), 2.26-2.04 (m, 3H), 2.02-1.97 (m, 1H), 1.93 (d, J=1.3 Hz, 3H), 1.89-1.75 (m, 2H), 1.74-1.46 (m, 2H).

Example 1D (1S,4aS,5S,8aS)-5-hydroxy-1-methyl-4a-phenyloctahydronaphthalen-2(1H)-one A 2 L Parr stirred pressure reactor was charged with 13.2 g of 5% Pd/C (20 weight % of substrate charged). Under a stream of nitrogen, a solution of the product of Example 1C (66 g, 0.257 mol) and tetrahydrofuran (530 mL) and pyridine (130) was added to the reactor. The reactor was purged with nitrogen and hydrogen. The vessel was pressurized to and maintained at 60-100 psig with hydrogen supplied from a high-pressure reservoir. The mixture was vigorously agitated overnight while keeping the temperature between 22-25° C. The reaction mixture was carefully filtered to remove the palladium catalyst rinsing the reactor and cake with tetrahydrofuran. To the filtrate was added 1,8-diazabicyclo[5.4.0]-undec-7-ene (6 mL), and the resulting mixture was stirred at room temperature overnight. The reaction mixture was concentrated under reduced pressure, and the residue was taken up in toluene (500 mL). The resulting solution was washed with 10% HCl (2×200 mL) and brine (100 mL), dried over $Na_2SO_4$, and filtered. The toluene solution was used as is without purification.

Example 1E (1'S,4a'S,5'S,8a'S)-1'-methyl-4a'-phenyloctahydro-1'H-spiro[1,3-dioxolane-2,2'-naphthalen]-5'-ol To the toluene solution from Example 1D was added ethylene glycol (74 mL, 1.3 mol, 5 equivalents) and para-toluenesulfonic acid (5 g, 26.5 mL), and the resulting mixture was heated to reflux with Dean Stark removal of water. After reaction completion, the mixture was cooled to room temperature, and the toluene solution was washed with saturated aqueous sodium bicarbonate (2×200 mL) and brine (100 mL), dried over sodium sulfate, filtered and concentrated to provide the titled compound.

Example 1F (1'S,4a'S,8a'S)-1'-methyl-4a'-phenylhexahydro-1'H-spiro[1,3-dioxolane-2,2'-naphthalen]-5'(3'H)-one The residue of Example 1E from above was dissolved in dichloromethane (800 mL), and pyridinium dichromate (199 g, 529 mmol) and magnesium sulfate (6.4 g) were added. The resulting mixture was heated to reflux and stirred overnight. After cooling to room temperature, the mixture was filtered through a plug of silica gel (350 g) rinsing with dichloromethane (2.5 L). The filtrate was concentrated, and the remaining solids were triturated with cyclohexane (300 mL). The solids were collected by filtration, washed with cyclohexane (2×50 mL) and dried in a vacuum oven at 50° C. to provide the titled compound (45.4 g). $^1$H NMR (400 MHz, $CDCl_3$) δ ppm 7.45-7.14 (m, 5H), 4.00-3.88 (m, 4H), 2.71 (dq, J=13.0, 6.5 Hz, 1H), 2.29-2.17 (m, 1H), 2.17-2.01 (m, 4H), 2.01-1.86 (m, 3H), 1.71-1.55 (m, 2H), 1.22-1.10 (m, 1H), 1.00 (d, J=6.6 Hz, 3H).

Example 1G (1'S,4a'S,6'Z,8a'S)-6'-(hydroxymethylene)-1'-methyl-4a'-phenylhexahydro-1'H-spiro[1,3-dioxolane-2,2'-naphthalen]-5'(3'H)-one To a solution of Example 1F (28.93 g, 96 mmol) in ethyl formate (240.0 mL, 2894 mmol) cooled to below 5° C. was added 1 M potassium t-butoxide solution in tetrahydrofuran dropwise over 30 minutes. The solution was stirred at reduced temperature for an additional 30 minutes and then stirred at room temperature for 1 hour. The solution was adjusted to pH 7 by addition of 13% potassium phosphate monobasic solution, and then the volatiles were removed under vacuum. The resulting solid was collected by filtration, washed with water, and dried. The solid was re-precipitated: the crude solid was dissolved in ethyl acetate (115 mL), then heptane (800 mL) was added, and the mixture was heated until all solid was dissolved. The solution was cooled and concentrated under vacuum to 50% volume and cooled in a refrigerator below 0° C. for 20 hours. The solid was collected by filtration, washed with cold heptane (200 mL) and dried to give 29.5 g (93%) of the titled compound. $^1$H NMR (400 MHz, CDCl$_3$) δ ppm 0.99 (d, J=6.51 Hz, 3H) 1.29 (td, J=13.77, 3.69 Hz, 1H) 1.63 (dt, J=13.53, 3.48 Hz, 1H) 1.80-2.23 (m, 8H) 2.55 (dt, J=17.97, 6.47 Hz, 1H) 3.95 (s, 4H) 7.20-7.35 (m, 3H) 7.49 (d, J=7.70 Hz, 2H) 13.78 (d, J=9.87 Hz, 1H).

Example 1H (6aS,7S,10aS)-7-methyl-10a-phenyl-5,6a,7,9,10,10a-hexahydro-6H-spiro[benzo[h]quinazoline-8,2'-[1,3]dioxolane]

To a solution of Example 1G (1.2 g, 3.65 mmol) in isopropanol (25 mL) was added formamidine acetate (1.52 g, 14.62 mmol) and piperidine (1.45 g, 14.62 mmol). The reaction mixture was heated at 95° C. for 24 hours. The cooled solution was diluted with saturated aqueous NaH$_2$PO$_4$ solution, and extracted with ethyl acetate. The organic fraction was concentrated to provide the titled compound.

Example 1I (6aS,7S,10aS)-7-methyl-10a-phenyl-5,6a,7,9,10,10a-hexahydrobenzo[h]quinazolin-8(6H)-one To a solution of Example 1H (1.23 g, 3.66 mmol) in tetrahydrofuran ((20 mL) at room temperature was added 3 M HCl (7.3 mL, 21.94 mmol). The reaction mixture was stirred at room temperature for 3 hours. The solution was diluted with water, neutralized to pH 7 with saturated aqueous sodium bicarbonate solution, and extracted with ethyl acetate. The organic fraction was concentrated. The residue was purified on a Teledyne Isco Combiflash® Rf system using a 24 g RediSep® silica gel cartridge, eluting with 0-3% methanol in dichloromethane to give the titled compound (0.620 g, 58%). MS (APCI+) m/z 293 (M+H)$^+$.

Example 1J (6aS,7S,9Z,10aS)-9-(hydroxymethylene)-7-methyl-10a-phenyl-5,6a,7,9,10,10a-hexahydrobenzo[h]quinazolin-8(6H)-one To a solution of Example 1I (0.620 g, 2.12 mmol) in ethyl formate (5.18 mL, 63.6 mmol) was added 25% sodium methoxide in methanol (2.31 mL, 10.6 mmol). The reaction mixture was stirred at room temperature for 2 hours. The solution was diluted with saturated aqueous NaH$_2$PO$_4$ solution and extracted with ethyl acetate. The organic phase was dried over sodium sulfate, filtered, and concentrated to provide the titled compound. MS (APCI+) m/z 321 (M+H)$^+$.

Example 1K (6aS,7S,11aS)-7-methyl-11a-phenyl-5,6,6a,7,11,11a-hexahydro[1,2]benzoxazolo[6,5-h]quinazoline To a solution of Example 1J (0.600 g, 1.87 mmol) in ethanol (15 mL) was added hydroxylamine hydrochloride (0.521 g, 7.49 mmol). The reaction mixture was heated at 65° C. for 3 hours. The cooled solution was diluted with water, neutralized to pH 7 with saturated aqueous sodium bicarbonate solution, and extracted with ethyl acetate. The organic layer was concentrated, and the residue was purified on a Teledyne Isco Combiflash® Rf system using a RediSep® 12 g silica gel cartridge, eluting with 0-70% ethyl acetate in heptane to give the titled compound (0.284 g, 48%). MS (APCI+) m/z 318 (M+H)$^+$.

Example 1L (6aS,7S,10aS)-7-methyl-8-oxo-10a-phenyl-5,6,6a,7,8,9,10,10a-octahydrobenzo[h]quinazoline-9-carbonitrile To a solution of Example 1K (0.284 g, 0.895 mmol) in methanol (8 mL) and tetrahydrofuran (2 mL) was added 25% sodium methoxide in methanol (0.778 mL, 33.58 mmol). The reaction solution was stirred at room temperature for 3 hours, then diluted with saturated aqueous NaH$_2$PO$_4$ solution, and extracted with ethyl acetate. The organic phase was dried over sodium sulfate, filtered, and concentrated to provide the titled compound.

Example 1M (6aS,7S,10aR)-7-methyl-8-oxo-10a-phenyl-5,6,6a,7,8,10a-hexahydrobenzo[h]quinazoline-9-carbonitrile To a solution of Example 1L (0.284 g, 0.895 mmol) in dimethylformamide (10 mL) cooled to 0° C. in an ice water bath was added 1,3-dibromo-5,5-dimethylhydantoin (0.128 g, 0.447 mmol). The solution was stirred at 0° C. for 1 hour, pyridine (0.724 mL, 8.95 mmol) was added, and the solution was heated at 55° C. for 2 hours. The cooled solution was diluted with water and extracted with ethyl acetate. The organic phase was washed with brine and concentrated. The residue was purified on 12 g RediSep® silica gel cartridge using a Teledyne Isco Combiflash® Rf system eluting with 0-25% ethyl acetate in heptane to give 0.142 g (50%) of the titled compound. $^1$H NMR (400 MHz, CDCl$_3$) δ ppm 1.20 (d, J=6.61 Hz, 3H) 1.60-1.72 (m, 1H) 1.98 (dd, J=13.93, 7.54 Hz, 1H) 2.34 (td, J=12.85, 2.39 Hz, 1H) 2.46 (td, J=13.12, 6.61 Hz, 1H) 2.98-3.18 (m, 2H) 6.78 (dd, J=7.64, 1.90 Hz, 2H) 7.29-7.38 (m, 3H) 8.72 (s, 1H) 8.85 (s, 1H) 9.07 (s, 1H); MS (ESI+) m/z 316 (M+H)$^+$.

Example 2 rac-(5aS,6S,9aR)-2,6-dimethyl-7-oxo-3,9a-diphenyl-4,5,5a,6,7,9a-hexahydro-2H-benzo[g]indazole-8-carbonitrile Example 2A 2-phenylcyclohexane-1,3-dione A flask containing cyclohexane-1,3-dione (44.88 g, 400 mmol), K$_3$PO$_4$ (169 g, 797 mmol), palladium acetate (0.881 g, 3.93 mmol), and 2-(di-t-butylphosphino)biphenyl (2.0 g, 6.70 mmol) was purged with N$_2$. Bromobenzene (96 g, 611 mmol) and anhydrous dioxane (260 mL) were added, and the flask was purged with N$_2$. The reaction mixture was warmed stepwise from 50° C. to 100° C. in 10 degree increments at approximately 10 minute intervals. The reaction mixture was then heated overnight at 100° C. with stirring. The reaction mixture was cooled to about 50° C. and poured into water (1 L) and ice was added to bring the temperature to room temperature. The pH was adjusted to about 1.0 to 1.5 by careful addition of aqueous HCl (12 N), and the precipitate that formed was collected by filtration, washed with water (300 mL) and toluene (3×200 mL), and dried in a stream of air and then under high vacuum to give the titled compound 59.42 g, (79%). MS (APCI) m/z 189 (M+H)$^+$.

Example 2B 2-(3-oxopentyl)-2-phenylcyclohexane-1,3-dione

Ethyl vinyl ketone (35 g, 416 mmol) was added dropwise to a stirred mixture of Example 2A (63.63 g, 338 mmol) and acetonitrile (500 mL) under nitrogen gas. Triethylamine (75 mL, 539 mmol) was added at room temperature with continued stirring overnight. The reaction mixture was briefly warmed to 50° C., then stirred 4 days at room temperature, and concentrated under reduced pressure to a viscous oil. The oil was taken up in ethyl acetate (600 mL). The ethyl acetate mixture was washed with saturated aqueous potassium dihydrogen phosphate (2×200 mL), aqueous sodium hydroxide solution (1 N, 3×100 mL) and brine (100 mL). The organic layer was dried (MgSO$_4$), filtered, and concentrated under reduced pressure to give 50.72 g, (55%) of the titled compound. Back-extraction with ethyl acetate of the combined aqueous fractions yielded an additional fraction of 4.22 g, (5%) of the titled compound. MS (APCI) m/z 273.1 (M+H)$^+$.

Example 2C 5-methyl-8a-phenyl-3,4,8,8a-tetrahydronaphthalene-1,6(2H,7H)-dione

Example 2B (15.94 g, 58.5 mmol), (S)-phenylalanine (7.62 g, 46 mmol), D-10-camphorsulfonic acid (8.11 g, 35 mmol) and acetonitrile (200 mL) were heated to 70° C. with stirring overnight. The reaction was heated to 80° C. for an additional night. The reaction mixture was cooled and concentrated, and the residue was partitioned between water (150 mL) and ethyl acetate (300 mL). The organic layer was washed with saturated aqueous sodium bicarbonate solution (100 mL) and brine (50 mL), dried (MgSO$_4$), and concentrated under reduced pressure. The residue was purified by column chromatography (silica gel, 17% ethyl acetate in hexanes) to give 9.41 g, (63%) of the titled compound. MS (APCI) m/z 255 (M+H)$^+$.

Example 2D rac-(4aR,5S)-5-hydroxy-1-methyl-4a-phenyl-4,4a,5,6,7,8-hexahydronaphthalen-2(3H)-one A solution of Example 2C (14.58 g, 57 mmol) in ethanol (200 mL) and tetrahydrofuran (120 mL) was cooled to 0° C. A mixture of sodium borohydride (0.723 g, 19.1 mmol) in ethanol (100 mL) was added in small portions to the rapidly stirred solution over 30 minutes. Additional sodium borohydride in ethanol was added as needed to consume the starting material. When no starting material remained, the reaction was quenched by careful dropwise addition of glacial acetic acid (10 mL) in ethanol (30 mL). The reaction mixture was concentrated under reduced pressure. The concentrated reaction mixture was diluted with water (150 mL) and extracted with ethyl acetate (300 mL, then 100 mL). The combined organic fractions were washed with saturated aqueous sodium bicarbonate solution (2×100 mL), dried (MgSO$_4$), and concentrated under reduced pressure to give 14.27 g, (98%) of the titled compound. MS (APCI) m/z 257 (M+H)$^+$.

Example 2E rac-(4aR,5S)-1-methyl-4a-phenyl-5-(tetrahydro-2H-pyran-2-yloxy)-4,4a,5,6,7,8-hexahydronaphthalen-2(3H)-one A solution of Example 2D (14.23 g, 55.5 mmol), dihydropyran (7.0 mL, 82.7 mmol), and p-toluenesulfonic acid hydrate (0.160 g, 0.84 mmol) in CH$_2$Cl$_2$ (300 mL) was stirred overnight at room temperature. The reaction mixture was concentrated under reduced pressure, and residual volatiles were removed under high vacuum. Hexanes were added, and the mixture was warmed to about 50° C., and insoluble material was removed by filtration. The solution was concentrated under reduced pressure, and the residue was purified by column chromatography (silica gel, 15% ethyl acetate in hexanes) to give 16.07 g, (85%) of the titled compound. MS (APCI) m/z 341 (M+H)$^+$.

Example 2F rac-(1S,4aS,5S,8aS)-5-hydroxy-1-methyl-4a-phenyloctahydronaphthalen-2(1H)-one A flask containing a suspension of Example 2E (3.48 g, 13.6 mmol) and Pd/C (10% w/w, 0.86 g) in ethanol (80 mL) was purged with N$_2$ and H$_2$. The mixture was stirred vigorously under a balloon of hydrogen gas for 4 days. Sodium methoxide in methanol (30% w/w, 6 drops) was added, and the reaction mixture was stirred at room temperature for about 30 minutes. The catalyst was removed by filtration, and the solution was concentrated under reduced pressure. The residue was purified by column chromatography (silica gel, 20% ethyl acetate in hexanes) to give 0.70 g, (20%) of the titled compound. MS (APCI) m/z 241 (M−H$_2$O+H)$^+$.

Example 2G rac-(1'S,4a'S,5'S,8a'S)-1'-methyl-4a'-phenyloctahydro-1'H-spiro[1,3-dioxolane-2,2'-naphthalen]-5'-ol A mixture of Example 2F (1.09 g, 4.22 mmol), ethylene glycol (2.2 mL, 39.5 mmol), p-toluenesulfonic acid hydrate (0.079 g, 0.42 mmol) and toluene (70 mL) was heated to refluxed for 2.5 hours with Dean-Stark removal of water, then at room temperature overnight, and at reflux for an additional 2.5 hours. The mixture was concentrated under reduced pressure. The residue was taken up in ethyl acetate (100 mL). The ethyl acetate mixture was washed with saturated aqueous sodium bicarbonate solution (30 mL) and brine (20 mL), dried (MgSO$_4$), and concentrated under reduced pressure. The residue was purified by column chromatography (silica gel, 20% ethyl acetate in hexanes) to give 0.975 g, (76%) of the titled compound. MS (APCI) m/z 285 (M−H$_2$O+H)$^+$.

Example 2H rac-(1'S,4a'S,8a'S)-1'-methyl-4a'-phenylhexahydro-1'H-spiro[1,3-dioxolane-2,2'-naphthalen]-5'(3'H)-one Pyridinium dichromate (1.86 g, 4.95 mmol) was added to a solution of Example 2G (0.970 g, 3.2 mmol) in dichloromethane (60 mL), and the mixture was stirred overnight at room temperature. The reaction mixture was filtered through a pad of diatomaceous earth, eluting with dichloromethane until the washings ran clear. The solution was concentrated under reduced pressure, and the residue was purified by column chromatography (silica gel, 20% ethyl acetate in hexanes) to give 0.730 g, (76%) of the titled compound. MS (APCI) m/z 301 (M+H)$^+$.

Example 2I rac-(1'S,4a'S,6'Z,8a'S)-6'-(hydroxymethylene)-1'-methyl-4a'-phenylhexahydro-1'H-spiro[1,3-dioxolane-2,2'-naphthalen]-5'(3'H)-one Sodium methoxide (30% w/w in methanol, 2 mL) was added to a solution of Example 2H (0.730 g, 2.43 mmol) in ethyl formate (40 mL), and the mixture was stirred overnight at room temperature. The reaction mixture was partitioned between ethyl acetate (200 mL) and saturated aqueous potassium dihydrogen phosphate (50 mL). The organic fraction was washed with brine, dried (MgSO$_4$), and concentrated under reduced pressure to give 0.797 g, (100%) of the titled compound. MS (APCI) m/z 329 (M+H)$^+$.

Example 2J rac-(5aS,6S,9aS)-1,6-dimethyl-9a-phenyl-1,4,5,5a,6,8,9,9a-octahydrospiro[benzo[g]indazole-7,2'-[1,3]dioxolane] and rac-(5aS,6S,9aS)-2,6-dimethyl-9a-phenyl-2,4,5,5a,6,8,9,9a-octahydrospiro[benzo[g]indazole-7,2'-[1,3]dioxolane]

A solution of Example 2I (0.797 g, 2.42 mmol) and methylhydrazine (0.245 g, 5.3 mmol) in ethanol (50 mL) was stirred at room temperature for 30 minutes and was then warmed to about 65° C. for 1 hour. The reaction mixture was then stirred at 60° C. overnight and was concentrated under reduced pressure. The residue was taken up in ethanol and concentrated. This process was repeated three times. The residue was purified by column chromatography (silica gel, 50% ethyl acetate in hexanes then 5 to 10% methanol in dichloromethane) to give 0.36 g (44%) of the titled compounds.

Example 2K rac-(5aS,6S,9aS)-3-bromo-2,6-dimethyl-9a-phenyl-2,4,5,5a,6,8,9,9a-octahydrospiro[benzo[g]indazole-7,2'-[1,3]dioxolane]

A solution of Example 2J (0.5112 g, 1.51 mmol) in dichloromethane (80 mL) was cooled in to 0° C. A solution of bromine (0.263 g. 1.65 mmol) in dichloromethane (5 mL) was added dropwise until a reddish color persisted. The reaction mixture was stirred at 0° C. for 1.5 hours, and the mixture was concentrated under reduced pressure without heating. The residue was purified by column chromatography (silica gel, 50% ethyl acetate in hexanes) to give 0.216 g (34%) of the titled compound that eluted before the other more polar non-brominated N-methyl isomer (rac-(5aS,6S,9aS)-1,6-dimethyl-9a-phenyl-1,4,5,5a,6,8,9,9a-octahydrospiro[benzo[g]indazole-7,2'-[1,3]dioxolane]). MS (APCI) m/z 417, 419 (M+H)$^+$.

Example 2L rac-(5aS,6S,9aS)-2,6-dimethyl-3,9a-diphenyl-2,4,5,5a,6,8,9,9a-octahydrospiro[benzo[g]indazole-7,2'-[1,3]dioxolane]

A solution of Example 2K (0.216 g, 0.52 mmol), K$_3$PO$_4$ (0.330 g, 1.56 mmol), phenylboronic acid (0.127 g, 1.07 mmol) and dimethoxyethane (8 mL) was sparged with N$_2$ for 5 minutes. Tetrakis(triphenylphosphine)palladium(0) (0.042 g, 0.038 mmol) was added, and the solution was sparged with N$_2$ for an additional 5 minutes. The vial was tightly sealed, and the reaction mixture was heated at 85° C. overnight with stirring and then cooled to room temperature. The reaction mixture was concentrated under reduced pressure. The residue was partitioned between ethyl acetate (120 mL) and saturated aqueous sodium bicarbonate solution (50 mL), and then the organic phase was washed with brine. The organic layer was dried (MgSO$_4$) and concentrated under reduced pressure, and the residue was purified by column chromatography (silica gel, 40% ethyl acetate in hexanes) to give the titled compound (0.169 g, 78%). MS (APCI) m/z 415 (M+H)$^+$.

Example 2M rac-(5aS,6S,9aS)-2,6-dimethyl-3,9a-diphenyl-2,4,5,5a,6,8,9,9a-octahydro-7H-benzo[g]indazol-7-one Example 2L (0.169 g, 0.41 mmol) was taken up in methanol (40 mL) and aqueous hydrochloric acid (1 N, 4 mL) was added, and the mixture was stirred at room temperature for 19 hours. The reaction mixture was concentrated under reduced pressure and partitioned between ethyl acetate (150 mL) and saturated aqueous sodium bicarbonate (20 mL). The organic layer was dried (MgSO$_4$) and concentrated under reduced pressure to give the titled compound (0.136 g, 90%). MS (APCI) m/z 371 (M+H)$^+$.

Example 2N rac-(5aS,6S,8Z,9aS)-8-(hydroxymethylene)-2,6-dimethyl-3,9a-diphenyl-2,4,5,5a,6,8,9,9a-octahydro-7H-benzo[g]indazol-7-one Sodium methoxide (30% w/w, 0.6 mL) was added to a solution of Example 2M (0.132 g, 0.36 mmol) in ethyl formate (12 mL), and the mixture was stirred overnight at room temperature. The reaction mixture was diluted with ethyl acetate (100 mL) and washed with saturated aqueous potassium dihydrogen phosphate (15 mL). The organic layer was dried (MgSO$_4$) and concentrated under reduced pressure to give the titled compound (0.142 g, 100%). MS (APCI) m/z 399 (M+H)$^+$.

Example 2O rac-(5aS,6S,10aS)-2,6-dimethyl-3,10a-diphenyl-4,5,5a,6,10,10a-hexahydro-2H-indazolo[7,6-f][1,2]benzoxazole Hydroxylamine hydrochloride (0.051 g, 0.74 mmol) was added to a room temperature solution of Example 2N (0.142 g, 0.36 mmol) in ethanol/water (9/1.5 v/v, 10.5 mL), and the resultant mixture was stirred overnight. The reaction mixture was concentrated under reduced pressure and azeotroped with ethanol (3×40 mL). The residue was dissolved in ethyl acetate (80 mL), and the organic mixture was washed with saturated aqueous sodium bicarbonate (15 mL). The organic phase was dried (MgSO$_4$) and concentrated to give the titled compound (0.133 g, 93%). MS (APCI) m/z 396 (M+H)$^+$.

Example 2P rac-(5aS,6S,9aS)-2,6-dimethyl-7-oxo-3,9a-diphenyl-4,5,5a,6,7,8,9,9a-octahydro-2H-benzo[g]indazole-8-carbonitrile Sodium methoxide (30% w/w in methanol, 0.4 mL) was added to a room temperature solution of Example 2O (0.133 g, 0.34 mmol) in methanol/tetrahydrofuran (2/10 v/v, 12 mL), and the mixture was stirred overnight at room temperature. The reaction was partitioned between saturated aqueous potassium dihydrogen phosphate (15 mL) and ethyl acetate (100 mL). The organic fraction was washed with brine, dried (MgSO$_4$), and concentrated under reduced pressure to give the titled compound (0.113 g, 85%). MS (APCI) m/z 396 (M+H)$^+$.

Example 2Q rac-(5aS,6S,9aR)-2,6-dimethyl-7-oxo-3,9a-diphenyl-4,5,5a,6,7,9a-hexahydro-2H-benzo[g]indazole-8-carbonitrile 1,3-Dibromo-5,5-dimethylhydantoin (0.049 mg, 0.17 mmol) was added to a 0° C. solution of Example 2P (0.113 g, 0.29 mmol) in N,N-dimethylformamide (2 mL), and the reaction mixture was stirred at 0° C. for 1.5 hours. Pyridine (0.3 mL, 3.8 mmol) was added, and the reaction was heated to 60° C. for 3 hours. The reaction mixture was concentrated under reduced pressure, and the residue was purified by repeated column chromatography (initial: silica gel, 25% ethyl acetate in hexanes; then (2×): silica gel, 14% ethyl acetate in hexanes) to give the titled compound (0.015 g, 13%). $^1$H NMR (400 MHz, CDCl$_3$) δ ppm 8.50 (s, 1H), 7.51-7.55 (m, 2H), 7.41-7.48 (m, 3H), 7.24-7.35 (m, 3H), 6.96-7.00 (m, 2H), 3.82 (s, 3H), 2.78 (dd, J=7.0, 9.5 Hz, 1H), 2.69 (ddd, J=7.0, 11.1, 16.5 Hz, 1H), 2.46 (qd, J=6.6, 13.3 Hz, 1H), 2.38 (dt, J=2.1, 13.2 Hz, 1H), 1.80 (dd, J=7.0, 13.8 Hz, 1H), 1.49-1.58 (m, 1H), 1.16 (d, J=6.4 Hz, 3H); MS (APCI) m/z 394 (M+H)$^+$.

Example 3 rac-(5aS,6S,9aR)-1,6-dimethyl-7-oxo-3,9a-diphenyl-4,5,5a,6,7,9a-hexahydro-1H-benzo[g]indazole-8-carbonitrile Example 3A rac-(5aS,6S,9aS)-3-bromo-1,6-dimethyl-9a-phenyl-1,4,5,5a,6,8,9,9a-octahydro-7H-benzo[g]indazol-7-one Bromine (0.358 g, 2.25 mmol) was added dropwise to a solution of the more polar isomer from Example 2K (0.199 g, 0.59 mmol, rac-(5aS,6S,9aS)-1,6-dimethyl-9a-phenyl-1,4,5,5a,6,8,9,9a-octahydrospiro[benzo[g]indazole-7,2'-[1,3] dioxolane]) and sodium acetate (0.197 g, 2.4 mmol) in ethanol (10 mL) and water (3 mL). The reaction mixture was stirred at room temperature for 1.5 hours and then diluted with ethyl acetate (100 mL). The mixture was washed with brine (20 mL) and sodium thiosulfate solution, dried (MgSO$_4$), and concentrated under reduced pressure to give the titled compound (0.215 g, 98%). MS (APCI) m/z 373, 375 (M+H)$^+$.

Example 3B rac-(5aS,6S,9aS)-1,6-dimethyl-3,9a-diphenyl-1,4,5,5a,6,8,9,9a-octahydro-7H-benzo[g]indazol-7-one A solution of Example 3A (0.215 g, 0.58 mmol), K$_3$PO$_4$ (0.357 g, 1.68 mmol), phenylboronic acid (0.142 g, 1.19 mmol) and dimethoxyethane (12 mL) was sparged with N$_2$ for 5 minutes. Tetrakis(triphenylphosphine)palladium(0) (0.038 g, 0.035 mmol) was added, and the solution was sparged with N$_2$ for an additional 5 minutes. The reaction vial was tightly sealed, heated at 85° C. overnight with stirring, and cooled to room temperature. The reaction mixture was concentrated under reduced pressure, and the residue was taken into ethyl acetate (150 mL). The ethyl acetate mixture was washed with saturated aqueous sodium bicarbonate solution (20 mL) and brine (20 mL), dried (MgSO$_4$), and concentrated under reduced pressure. The residue was purified by column chromatography (silica gel, 25% ethyl acetate in hexanes) to give the titled compound (0.097 g, 45%). MS (APCI) m/z 371 (M+H)$^+$.

Example 3C rac-(5aS,6S,8Z,9aS)-8-(hydroxymethylene)-1,6-dimethyl-3,9a-diphenyl-1,4,5,5a,6,8,9,9a-octahydro-7H-benzo[g]indazol-7-one Sodium methoxide (30% w/w, 0.4 mL) was added to a room temperature solution of Example 3B (0.097 g, 0.26 mmol) in ethyl formate (15 mL). The reaction mixture was allowed to stand 4 days at room temperature. The mixture was then diluted with ethyl acetate (100 mL), washed with saturated aqueous potassium dihydrogen phosphate (15 mL), dried (MgSO$_4$), and concentrated under reduced pressure to give the titled compound (0.118 g, 100%). MS (APCI) m/z 399 (M+H)$^+$.

Example 3D rac-(5aS,6S,10aS)-1,6-dimethyl-3,10a-diphenyl-4,5,5a,6,10,10a-hexahydro-1H-indazolo[7,6-f][1,2]benzoxazole A mixture of Example 3C (all above obtained, ≤0.26 mmol) and hydroxylamine hydrochloride (0.044 g, 0.64 mmol) in ethanol/water (9/1 v/v, 10 mL) was stirred overnight at room temperature. The reaction mixture was concentrated under reduced pressure, and water was azeotropically removed with ethanol (3×40 mL). The reaction mixture was concentrated under reduced pressure, para-toluenesulfonic acid (0.025 g, 0.13 mmol) and toluene (40 mL) were added, and the mixture was heated to about 70° C. on a rotary evaporator as the mixture was concentrated to dryness. The residue was partitioned between ethyl acetate (80 mL) and saturated sodium bicarbonate solution (15 mL). The organic fraction was separated, dried (MgSO$_4$), and concentrated to give the titled compound (0.090 g, 88%). MS (APCI) m/z 396 (M+H)+.

Example 3E rac-(5aS,6S,9aS)-1,6-dimethyl-7-oxo-3,9a-diphenyl-4,5,5a,6,7,8,9,9a-octahydro-1H-benzo[g]indazole-8-carbonitrile Sodium methoxide (30% w/w, 0.3 mL) was added to a room temperature solution of Example 3D (0.090 g, 0.23 mmol) in methanol/tetrahydrofuran (1/3 v/v, 12 mL), and the resultant mixture was stirred overnight at room temperature. The mixture was diluted with ethyl acetate (80 mL), washed with saturated potassium dihydrogen phosphate (10 mL), dried (MgSO$_4$), and concentrated under reduced pressure to give the titled compound (0.097 g, 100%) that was used without further purification.

Example 3F rac-(5aS,6S,9aR)-1,6-dimethyl-7-oxo-3,9a-diphenyl-4,5,5a,6,7,9a-hexahydro-1H-benzo[g]indazole-8-carbonitrile 1,3-Dibromo-5,5-dimethylhydantoin (0.044 mg, 0.15 mmol) was added to a 0° C. solution of Example 3E (all above obtained, ≤0.23 mmol) in N,N-dimethylformamide (2.5 mL), and the reaction mixture was stirred at 0° C. for 2.5 hours. Pyridine (0.2 mL, 2.5 mmol) was added, and the reaction was heated to 60° C. for 2.5 hours. The reaction mixture was concentrated under reduced pressure, and the residue was purified by repeated column chromatography (2× silica gel, 25% ethyl acetate in hexanes) to give a solid that was triturated with ethyl acetate/hexanes (1/3) to give the titled compound (0.0084 g, 14%). $^1$H NMR (400 MHz, CDCl$_3$) δ ppm 8.17 (s, 1H), 7.75-7.77 (m, 2H), 7.43-7.47 (m, 2H), 7.33-7.40 (m, 4H), 6.88-6.91 (m, 2H), 3.58 (s, 3H), 2.98-3.04 (m, 1H), 2.89 (ddd, J=6.0, 11.8, 15.9 Hz, 1H), 2.54 (dt, J=1.8, 13.0 Hz, 1H), 2.36 (qd, J=6.7, 13.5 Hz, 1H), 1.87 (dd, J=5.9, 13.7 Hz, 1H), 1.53-1.64 (m, 1H), 1.21 (d, J=6.8 Hz, 3H); MS (APCI) m/z 394 (M+H)+.

Example 4 rac-(5aS,6S,9aR)-9a-(3-methoxyphenyl)-2,6-dimethyl-7-oxo-4,5,5a,6,7,9a-hexahydro-2H-benzo[g]indazole-8-carbonitrile Example 4A 2-(3-methoxyphenyl)cyclohexane-1,3-dione A mixture of 3-bromoanisole (18.64 g, 99.68 mmol), cyclohexane-1,3-dione (16.8 g, 138 mmol), potassium carbonate (41 g, 297 mmol), copper iodide (2.0 g, 10.5 mmol), and L-proline (2 g, 17.4 mmol) in dimethyl sulfoxide (100 mL) was heated at 90° C. for 16 hours. The reaction mixture was adjusted to pH~5 with 1 N hydrochloric and extracted with ethyl acetate (3×100 mL). The combined organic layers were washed with water and brine, dried (MgSO$_4$), and concentrated under reduced pressure. The residue was purified by column chromatography (silica gel, 25 to 75% ethyl acetate in hexanes) to give the titled compound (6.9 g, 32%). MS (APCI) m/z 219 (M+H)+.

Example 4B 2-(3-methoxyphenyl)-2-(3-oxopentyl)cyclohexane-1,3-dione

Vinyl ethyl ketone (4.0 g, 47.6 mmol) was added dropwise to a suspension of Example 4A (8.7 g, 39.8 mmol) in acetonitrile (70 mL) followed by dropwise addition of triethylamine (3.3 g, 32.6 mmol). The dark brown solution was stirred at 65° C. for 2 days. The reaction mixture was concentrated under reduced pressure and extracted with ethyl acetate (2×100 mL). The combined organic fractions were washed with saturated aqueous dihydrogen phosphate solution, dried (MgSO$_4$), and concentrated under reduced pressure. The residue was purified by column chromatography (silica gel, 25% ethyl acetate in hexanes) to give the titled compound (10.1 g, 84%). MS (APCI) m/z 303 (M+H)+.

Example 4C 8a-(3-methoxyphenyl)-5-methyl-3,4,8,8a-tetrahydronaphthalene-1,6(2H,7H)-dione Solid L-phenylalanine (4.4 g, 26.6 mmol) was added to a stirring solution of Example 4B (10.1 g, 33.4 mmol) in acetonitrile (75 mL) followed by the addition of solid (1R)-(+)-10-camphorsulfonic acid (4.6 g, 19.8 mmol). The reaction mixture was heated at 80° C. for 48 hours. The reaction mixture was concentrated under reduced pressure. The residue was treated with 200 mL of saturated aqueous potassium dihydrogen phosphate and extracted with ethyl acetate (2×100 mL). The combined organic fractions were washed with water, dried (MgSO$_4$), and concentrated under reduced pressure. The residue was purified by column chromatography (silica gel, 5 to 25% ethyl acetate in hexanes) to give the titled compound (7.5 g, 79%). MS (APCI) m/z 285 (M+H)+.

Example 4D rac-(4aR,5S)-5-hydroxy-4a-(3-methoxyphenyl)-1-methyl-4,4a,5,6,7,8-hexahydronaphthalen-2(3H)-one Sodium borohydride (0.27 g, 7.14 mmol) was added in small portions to a 0° C. solution of Example 4C (7.34 g, 25.8 mmol) in ethanol (100 mL) over a 2 hour period. The mixture was stirred an additional 3.5 hours at 0° C., quenched by the dropwise addition of acetic acid (3.1 g, 51.6 mmol), stirred at room temperature for 1 hour, and concentrated under reduced pressure. The resultant residue was dissolved into ethyl acetate (150 mL), washed with saturated sodium bicarbonate solution, dried (MgSO$_4$), and concentrated to give the titled compound (7.15 g, 96%). MS (APCI) m/z 287 (M+H)+.

Example 4E rac-(4aS,5S,8aS)-5-hydroxy-4a-(3-methoxyphenyl)-1-methyloctahydronaphthalen-2(1H)-one A flask containing a room temperature suspension of Example 4D (5.6 g, 19.56 mmol) and Pd/C (20% w/w, 0.2 g) in ethyl acetate (100 mL) was purged with N$_2$ and H$_2$. The mixture was stirred under H$_2$ (balloon pressure) at room temperature for 48 hours and then filtered. The filtrate was concentrated under reduced pressure. The resultant residue was purified by column chromatography (silica gel, 5 to 35% ethyl acetate in hexanes) to give the titled compound (3.6 g, 60%). MS (APCI) m/z 271 (M+H—H$_2$O)$^+$.

Example 4F rac-(1S,4aS,5S,8aS)-5-hydroxy-4a-(3-methoxyphenyl)-1-methyloctahydronaphthalen-2(1H)-one Sodium methoxide (30% w/w solution in methanol, 5 drops) was added to a solution of Example 4E (3.5 g, 12.1 mmol) in methanol (50 mL). The solution was stirred at room temperature under N$_2$ for 4 hours and then concentrated under reduced pressure. The residue was partitioned between ethyl acetate and saturated aqueous potassium dihydrogen phosphate solution. The organic extract was washed with water, dried (MgSO$_4$), and concentrated to give the titled compound (3.3 g, 93%). MS (APCI) m/z 271 (M+H—H$_2$O)$^+$.

Example 4G rac-(1'S,4a'S,5'S,8a'S)-4a'-(3-methoxyphenyl)-1'-methyloctahydro-1'H-spiro[1,3-dioxolane-2,2'-naphthalen]-5'-ol A solution of Example 4F (3.3 g, 11.4 mmol), ethylene glycol (4.3 g, 69.3 mmol) and p-toluenesulfonic acid monohydrate (0.25 g, 1.31 mmol) in benzene (150 mL) was refluxed under Dean-Stark conditions for 16 hours. The reaction mixture was quenched with aqueous sodium hydroxide (10% w/w, 50 mL) and extracted with ethyl acetate (2×20 mL). The combined organic fractions were washed with water, dried (MgSO$_4$), and concentrated under reduced pressure. The residue was purified by column chromatography (silica gel, 5 to 35% ethyl acetate in hexanes) to afford the titled compound (1.57 g, 41%). MS (APCI) m/z 315 (M+H—H$_2$O)$^+$.

Example 4H rac-(1'S,4a'S,8a'S)-4a'-(3-methoxyphenyl)-1'-methylhexahydro-1'H-spiro[1,3-dioxolane-2,2'-naphthalen]-5'(3'H)-one To a stirred solution of Example 4G (1.57 g, 4.7 mmol) in dichloromethane (30 mL) at room temperature was added magnesium sulfate (200 mg) and pyridinium dichromate (3.6 g, 9.57 mmol) followed by continued stirring for 24 hours. The reaction mixture was purified by column chromatography (silica gel, 30% ethyl acetate in hexanes) to give the titled compound (1.49 g, 94%). MS (APCI) m/z 331 (M+H)$^+$.

Example 4I rac-(1'S,4a'S,6'Z,8a'S)-6'-(hydroxymethylene)-4a'-(3-methoxyphenyl)-1'-methylhexahydro-1'H-spiro[1,3-dioxolane-2,2'-naphthalen]-5'(3'H)-one Sodium methoxide (30% w/w solution in methanol, 4.8 g) was added to a stirred solution of Example 4H (1.49 g, 4.5 mmol) and ethyl formate (10 mL, 124 mmol) followed by continued stirring at room temperature overnight. The reaction mixture was dissolved in ethyl acetate, washed with saturated aqueous potassium dihydrogen phosphate and water, dried (MgSO$_4$), and concentrated under reduced pressure to give the titled compound (1.5 g, 93%). MS (APCI) m/z 359 (M+H)$^+$.

Example 4J rac-(5aS,6S,9aS)-9a-(3-methoxyphenyl)-1,6-dimethyl-1,4,5,5a,6,8,9,9a-octahydrospiro[benzo[g]indazole-7,2'-[1,3]dioxolane] and rac-(5aS,6S,9aS)-9a-(3-methoxyphenyl)-2,6-dimethyl-2,4,5,5a,6,8,9,9a-octahydrospiro[benzo[g]indazole-7,2'-[1,3]dioxolane]

A mixture of the compounds of Example 4I (1.5 g, 4.18 mmol) and methyl hydrazine (300 mg, 6.52 mmol) in ethanol (10 mL) was heated to 45° C. for 6 hours. The reaction mixture was concentrated under reduced pressure, filtered through a short plug of silica eluted with ethyl acetate, and concentrated under reduced pressure to give a mixture of the titled compounds (0.85 g, 55%). MS (APCI) m/z 369 (M+H)$^+$.

Example 4K rac-(5aS,6S,9aS)-9a-(3-methoxyphenyl)-1,6-dimethyl-1,4,5,5a,6,8,9,9a-octahydro-7H-benzo[g]indazol-7-one and rac-(5aS,6S,9aS)-9a-(3-methoxyphenyl)-2,6-dimethyl-2,4,5,5a,6,8,9,9a-octahydro-7H-benzo[g]indazol-7-one A mixture of the compounds in Example 4J (0.54 g, 1.46 mmol) was taken up in methanol (10 mL), and aqueous hydrochloric acid (3 N, 3 mL) was added. The mixture was stirred for 16 hours at room temperature. The reaction mixture was quenched with saturated sodium bicarbonate solution and extracted with ethyl acetate (2×30 mL). The combined organic phases were then washed with water and concentrated under reduced pressure. The crude residue was purified by column chromatography (silica gel, 5 to 30% ethyl acetate in hexanes) to give the titled compounds (0.295 g, 62%). MS (APCI) m/z 325 (M+H)$^+$.

Example 4L rac-(5aS,6S,8Z,9aS)-8-(hydroxymethylene)-9a-(3-methoxyphenyl)-1,6-dimethyl-1,4,5,5a,6,8,9,9a-octahydro-7H-benzo[g]indazol-7-one and rac-(5aS,6S,8Z,9aS)-8-(hydroxymethylene)-9a-(3-methoxyphenyl)-2,6-dimethyl-2,4,5,5a,6,8,9,9a-octahydro-7H-benzo[g]indazol-7-one A mixture of the compounds from Example 4K (295 mg, 0.9 mmol) was taken up in ethyl formate (15 mL), and sodium methoxide (30% w/w solution in methanol, 985 mg) was added. The mixture was stirred overnight at room temperature. The reaction mixture was extracted with ethyl acetate. The organic phase was washed with saturated aqueous potassium dihydrogen phosphate, then dried (MgSO$_4$), and concentrated under reduced pressure to give the titled compounds (0.305 mg, 99%). MS (APCI) m/z 353 (M+H)$^+$.

Example 4M rac-(5aS,6S,10aS)-10a-(3-methoxyphenyl)-1,6-dimethyl-4,5,5a,6,10,10a-hexahydro-1H-indazolo[7,6-f][1,2]benzoxazole and rac-(5aS,6S,10aS)-10a-(3-methoxyphenyl)-2,6-dimethyl-4,5,5a,6,10,10a-hexahydro-2H-indazolo[7,6-f][1,2]benzoxazole A suspension of hydroxylamine hydrochloride (125 mg, 1.8 mmol) and the mixture of compounds from Example 4L (0.305 g, 0.9 mmol) in ethanol was stirred overnight at 50° C. After cooling to room temperature, the reaction mixture was concentrated under reduced pressure; the residue was partitioned between ethyl acetate and saturated aqueous sodium bicarbonate. The organic fraction was dried (MgSO$_4$) and concentrated under reduced pressure to give the titled compounds (0.300 g, 100%). MS (APCI) m/z 350 (M+H)$^+$.

Example 4N rac-(5aS,6S,9aS)-9a-(3-methoxyphenyl)-1,6-dimethyl-7-oxo-4,5,5a,6,7,8,9,9a-octahydro-1H-benzo[g]indazole-8-carbonitrile and rac-(5aS,6S,9aS)-9a-(3-methoxyphenyl)-2,6-dimethyl-7-oxo-4,5,5a,6,7,8,9,9a-octahydro-2H-benzo[g]indazole-8-carbonitrile A mixture of compounds from Example 4M (0.300 g, 0.9 mmol) was dissolved in a 3/1 methanol/tetrahydrofuran mixture (8 mL), and sodium methoxide (30% w/w solution in methanol, 1.2 g) was added. The reaction mixture was stirred at 50° C. for 6 hours and then at room temperature overnight. The reaction was quenched by addition of saturated aqueous potassium dihydrogen phosphate, and the reaction mixture was concentrated. The residue was extracted with ethyl acetate, and the combined organic fractions washed with brine, dried (MgSO$_4$), and concentrated under reduced pressure. The crude residue was purified by column chromatography (silica gel, 5 to 35% ethyl acetate in hexanes) to give the titled compounds (0.130 mg, 43%). MS (APCI) m/z 350 (M+H)$^+$.

Example 4O rac-(5aS,6S,9aR)-9a-(3-methoxyphenyl)-2,6-dimethyl-7-oxo-4,5,5a,6,7,9a-hexahydro-2H-benzo[g]indazole-8-carbonitrile The mixture of compounds from Example 4N (0.130 g, 0.37 mmol) was dissolved in dry N,N-dimethylformamide, and the solution was cooled to 0° C. 1,3-Dibromo-5,5-dimethylhydantoin (0.058 g, 0.202 mmol) was added, and the reaction stirred at 0° C. for 2 hours. Pyridine (2 mL) was added, and the reaction was allowed to warm to room temperature. The reaction mixture was then stirred at 50° C. overnight. The reaction mixture was concentrated under reduced pressure and extracted with ethyl acetate (2×25 mL). The combined organic fractions were washed with water, dried (MgSO$_4$), and concentrated under reduced pressure. The residue was purified by column chromatography (silica gel, 5 to 35% ethyl acetate in hexanes) to give the titled compound (0.050 mg, 38%) as the first eluting isomer relative to Example 5. $^1$H NMR (400 MHz, CDCl$_3$) δ ppm 8.42 (s, 1H), 7.20-7.24 (m, 2H), 6.79 (dd, J=2.5, 8.2 Hz, 1H), 6.54 (d, J=7.9 Hz, 1H), 6.42 (t, J=2.1 Hz, 1H), 3.86 (s, 3H), 3.73 (s, 3H), 2.85 (dd, J=6.7, 16.4 Hz, 1H), 2.69 (ddd, J=7.3, 11.4, 16.4 Hz, 1H), 2.48 (qd, J=6.7, 13.4 Hz, 1H), 2.31 (t, J=13.2 Hz, 1H), 1.80 (dd, J=7.1, 13.7 Hz, 1H), 1.56 (dq, J=6.7, 12.2 Hz, 1H), 1.16 (d, J=6.7 Hz, 3H); MS (APCI) m/z 277 (M+H)$^+$.

Example 5 rac-(5aS,6S,9aR)-9a-(3-methoxyphenyl)-1,6-dimethyl-7-oxo-4,5,5a,6,7,9a-hexahydro-1H-benzo[g]indazole-8-carbonitrile The titled compound (0.010 mg, 8%) was isolated during the purification of Example 4O, and was obtained as the second isomer to elute. $^1$H NMR (400 MHz, CDCl$_3$) δ ppm 8.11 (s, 1H), 7.40 (s, 1H), 7.24-7.29 (m, 2H), 6.85 (dd, J=2.5, 8.2 Hz, 1H), 6.44 (dd, J=1.6, 7.8 Hz, 1H), 3.73 (s, 3H), 3.54 (s, 3H), 2.82 (ddd, J=1.5, 5.5, 16.0 Hz, 1H), 2.63 (ddd, J=6.1, 11.9, 16.0 Hz, 1H), 2.34-2.48 (m, 2H), 1.80 (dd, J=6.1, 18.0 Hz, 1H), 1.55-1.66 (m, 1H), 1.17 (d, J=6.4 Hz, 3H); MS (APCI) m/z 277 (M+H)$^+$.

Example 6 rac-(5aS,6S,9aR)-6-methyl-7-oxo-3,9a-diphenyl-4,5,5a,6,7,9a-hexahydro-1H-benzo[g]indazole-8-carbonitrile Example 6A rac-(1'S,4a'S,8a'S)-6'-benzoyl-1'-methyl-4a'-phenyl-hexahydro-1'H-spiro[1,3-dioxolane-2,2'-naphthalen]-5'(3'H)-one Magnesium bromide etherate (2.48 g, 9.8 mmol) and diisopropylethylamine (1.98 mL, 11.5 mmol) were added sequentially to a solution of Example 2H (1.15 g, 3.8 mmol) in dichloromethane (50 mL), and the reaction mixture was stirred at room temperature for 40 minutes. A solution of benzoyl chloride (1.17 g, 4.9 mmol) in dichloromethane (50 mL) was added dropwise, and the mixture was stirred overnight at room temperature. The reaction mixture was diluted with dichloromethane (200 mL), washed with saturated aqueous sodium bicarbonate (100 mL) and saturated aqueous potassium dihydrogen phosphate (50 mL), dried (MgSO$_4$), and concentrated under reduced pressure. The residue was purified by column chromatography (silica gel, 20% ethyl acetate in hexanes) to give the titled compound (0.792 g, 52%). MS (APCI) m/z 405 (M+H)$^+$.

Example 6B rac-(5aS,6S,9aS)-6-methyl-3,9a-diphenyl-2,4,5,5a,6,8,9,9a-octahydrospiro[benzo[g]indazole-7,2'-[1,3]dioxolane]

A solution of Example 6A (0.7919 g. 1.96 mmol) and hydrazine monohydrate (0.5 mL, 10.3 mmol) in ethanol (50 mL) was heated to reflux overnight. The reaction mixture was concentrated under reduced pressure, and the residue was partitioned between ethyl acetate (150 mL) and saturated aqueous sodium bicarbonate (50 mL). The organic fraction was washed with brine (50 mL), dried (MgSO$_4$), and concentrated under reduced pressure. The residue was purified by column chromatography (silica gel, 33% to 100% ethyl acetate in hexanes) to give the titled compound (0.53 g, 68%). MS (APCI) m/z 401 (M+H)$^+$.

Example 6C rac-(5aS,6S,9aS)-6-methyl-3,9a-diphenyl-2,4,5,5a,6,8,9,9a-octahydro-7H-benzo[g]indazol-7-one Hydrochloric acid (1 N, 5 mL) was added to a room temperature solution of Example 6B (0.53 g, 1.32 mmol) in methanol (30 mL), and the mixture was stirred at room temperature for 3 days. The reaction mixture was concentrated under reduced pressure. The residue was diluted with ethyl acetate (200 mL), and the resultant solution was washed with saturated aqueous sodium bicarbonate (50 mL). The organic fraction was dried (MgSO$_4$) and concentrated under reduced pressure to give the titled compound (0.46 g, 98%). MS (APCI) m/z 357 (M+H)+.

Example 6D rac-(5aS,6S,8Z,9aS)-8-(hydroxymethylene)-6-methyl-3,9a-diphenyl-2,4,5,5a,6,8,9,9a-octahydro-7H-benzo[g]indazol-7-one Sodium methoxide (30% w/w, 7.0 mL) was added to a solution of Example 6C (0.46 g, 1.29 mmol) in ethyl formate (40 mL), and the mixture was stirred overnight at room temperature. The reaction mixture was diluted with ethyl acetate (200 mL), washed with saturated aqueous potassium dihydrogen phosphate (50 mL), dried (MgSO$_4$), and concentrated under reduced pressure to give the titled compound (0.46 g, 93%). MS (APCI) m/z 385 (M+H)+.

Example 6E rac-(5aS,6S,10aS)-6-methyl-3,10a-diphenyl-4,5,5a,6,10,10a-hexahydro-2H-indazolo[7,6-f][1,2]benzoxazole Hydroxylamine hydrochloride (0.146 g, 2.1 mmol) was added to a room temperature solution of Example 6D (0.46 g, 1.2 mmol) in ethanol/water (8/1 v/v, 27 mL), and the mixture was stirred overnight. The reaction mixture was concentrated under reduced pressure, and water was azeotropically removed with ethanol (3×50 mL). The residue was dissolved in ethyl acetate (120 mL), washed with saturated aqueous sodium bicarbonate (20 mL), dried (MgSO$_4$), and concentrated under reduced pressure to give the titled compound (0.452 g, 99%). MS (APCI) m/z 396 (M+H)+.

Example 6F rac-(5aS,6S,9aS)-6-methyl-7-oxo-3,9a-diphenyl-4,5,5a,6,7,8,9,9a-octahydro-2H-benzo[g]indazole-8-carbonitrile Sodium methoxide (30% w/w, 0.8 mL) was added to a room temperature solution of Example 6E (0.452 g, 1.18 mmol) in methanol/tetrahydrofuran (1/5 v/v, 30 mL), and the mixture was stirred overnight at room temperature. The mixture was diluted with ethyl acetate (200 mL), washed with saturated potassium dihydrogen phosphate (50 mL), dried (MgSO$_4$), and concentrated under reduced pressure to give the titled compound (0.45 g, 100%). MS (APCI) m/z 382 (M+H)+.

Example 6G rac-(5aS,6S,9aR)-6-methyl-7-oxo-3,9a-diphenyl-4,5,5a,6,7,9a-hexahydro-1H-benzo[g]indazole-8-carbonitrile 1,3-Dibromo-5,5-dimethylhydantoin (0.214 mg, 0.75 mmol) was added to a 0° C. solution of Example 6F (0.45 g, 1.18 mmol) in N,N-dimethylformamide (6 mL), and the reaction was stirred at 0° C. for 110 minutes. Pyridine (1.0 mL, 12.5 mmol) was added, and the reaction mixture was heated to 60° C. for 160 minutes. The reaction mixture was concentrated under reduced pressure. The residue was diluted with ethyl acetate (150 mL), and the resultant solution was washed with saturated aqueous potassium dihydrogen phosphate solution and brine, dried (MgSO$_4$), and concentrated under reduced pressure. The residue was purified by column chromatography (silica gel, 25% to 33% ethyl acetate in hexanes), and the titled compound (0.202 g, 45%) was obtained as a solid following trituration with ether. $^1$H NMR (400 MHz, CDCl$_3$) δ ppm 10.13 (br s, 1H), 8.47 (s, 1H), 7.57 (d, J=7.7 Hz, 2H), 7.51 (t, J=7.6 Hz, 2H), 7.42 (t, J=7.3 Hz, 1H), 7.28-7.34 (m, 3H), 6.95 (d, J=6.8 Hz, 2H), 3.06 (dd, J=6.6, 16.4 Hz, 1H), 2.92 (ddd, J=7.3, 11.2, 16.5 Hz, 1H), 2.38-2.54 (m, 2H), 1.91 (dd, J=7.2, 14.0 Hz, 1H), 1.61 (dq, J=6.4, 11.9 Hz, 1H), 1.20 (d, J=6.5 Hz, 3H); MS (APCI) m/z 380 (M+H)+.

Example 7 rac-(6aS,7S,10aR)-7-methyl-8-oxo-2,10a-diphenyl-5,6,6a,7,8,10a-hexahydrobenzo[h]quinazoline-9-carbonitrile

Example 7A rac-(6aS,7S,10aS)-7-methyl-2,10a-diphenyl-5,6a,7,9,10,10a-hexahydro-6H-spiro[benzo[h]quinazoline-8,2'-[1,3]dioxolane]

To a stirred solution of Example 21 (0.230 g, 0.70 mmol) in isopropanol (5 mL) at room temperature was added piperidine (0.277 mL, 2.80 mmol) and benzamidine (0.505 g, 4.2 mmol). The reaction mixture was heated at 95° C. for 5 hours. The cooled solution was diluted with ammonium chloride solution and extracted with dichloromethane. The organic fraction was concentrated. The residue was purified by flash chromatography on 12 g of silica gel, eluting with 0-25% ethyl acetate in heptane to provide 225 mg (78%) of the titled compound.

Example 7B rac-(6aS,7S,10aS)-7-methyl-2,10a-diphenyl-5,6a,7,9,10,10a-hexahydrobenzo[h]quinazolin-8(6H)-one To a stirred solution of Example 7A (0.225 g, 0.545 mmol) in dioxane (3 mL) at room temperature was added 3 M HCl (1.80 mL, 5.45 mmol). The reaction mixture was heated at 40° C. for 1.5 hours. The cooled solution was diluted with saturated aqueous sodium bicarbonate solution and extracted with dichloromethane. The organic fraction was dried over sodium sulfate, filtered, and concentrated to provide 0.20 g (100%) of the titled compound. $^1$H NMR (400 MHz, CDCl$_3$) δ ppm 1.21 (d, J=6.61 Hz, 3H) 2.00-2.13 (m, 1H) 2.16-2.30 (m, 2H) 2.31-2.58 (m, 3H) 2.70-2.79 (m, 1H) 2.80-2.95 (m, 2H) 3.40 (td, J=8.59, 4.61 Hz, 1H) 7.21 (t, J=7.26 Hz, 1H) 7.29 (t, J=7.54 Hz, 2H) 7.45-7.52 (m, 3H) 7.58 (d, J=7.70 Hz, 2H) 8.44-8.52 (m, 3H); MS (APCI+) m/z 369 (M+H)+.

Example 7C rac-(6aS,7S,9Z,10aS)-9-(hydroxymethylene)-7-methyl-2,10a-diphenyl-5,6a,7,9,10,10a-hexahydrobenzo[h]quinazolin-8(6H)-one To a stirred solution of Example 7B (0.200 g, 0.54 mmol) in ethyl formate (3.0 mL, 36.9 mmol) at room temperature was added 25% sodium methoxide in methanol (1.0 mL, 4.37 mmol). The reaction mixture was stirred at room temperature for 2 hours. The solution was diluted with saturated sodium phosphate tribasic solution and extracted with dichloromethane. The organic fraction was dried over sodium sulfate, filtered, and concentrated to give 0.215 g (100%) of the titled compound.

Example 7D rac-(6aS,7S,11aS)-7-methyl-2,11a-diphenyl-5,6,6a,7,
11,11a-hexahydro[1,2]benzoxazolo[6,5-h]quinazo-
line To a solution of Example 7C (0.215 g, 0.54 mmol) in ethanol (8 mL) at room temperature was added hydroxylamine hydrochloride (0.075 g, 1.085 mmol). The reaction mixture was heated at 50° C. for 2 hours. The solution was cooled, diluted with saturated aqueous sodium bicarbonate solution, and extracted with dichloromethane. The organic fraction was concentrated, and the residue was purified on a Teledyne Isco Combiflash® Rf system using a 24 g RediSep® silica gel cartridge eluting with 0-16% ethyl acetate in hexanes to give 0.125 g (59%) of the titled compound.

Example 7E rac-(6aS,7S,10aS)-7-methyl-8-oxo-2,10a-diphenyl-5,
6,6a,7,8,9,10,10a-octahydrobenzo[h]quinazoline-9-
carbonitrile To a solution of Example 7D (0.125 g, 0.318 mmol) in methanol (2.5 mL) and tetrahydrofuran (1.5 mL) at room temperature was added 25% sodium methoxide in methanol (0.36 mL, 1.59 mmol). The reaction mixture was stirred at room temperature for 18 hours, then diluted with saturated aqueous $NaH_2PO_4$ solution, and extracted with ethyl acetate. The organic fraction was dried over sodium sulfate, filtered, and concentrated to give 0.125 g (100%) of the titled compound.

Example 7F rac-(6aS,7S,10aR)-7-methyl-8-oxo-2,10a-diphenyl-
5,6,6a,7,8,10a-hexahydrobenzo[h]quinazoline-9-
carbonitrile To a solution of Example 7E (0.125 g, 0.318 mmol) in dimethylformamide (3 mL) at 0° C. was added 1,3-dibromo-5,5-dimethylhydantoin (0.045 mg, 0.159 mmol). The reaction mixture was stirred at 0° C. for 1 hour, then pyridine (0.26 mL, 3.18 mmol) was added, and the solution was heated at 55° C. for 2 hours. The cooled solution was diluted with 0.5 M HCl and extracted with ethyl acetate. The organic fraction was concentrated. The residue was purified using a 4 g RediSep® silica gel cartridge on a Teledyne Isco Combiflash® Rf system eluting with 0-50% ethyl acetate in hexanes to give 0.051 g (41%) of the titled compound. $^1$H NMR (400 MHz, $CDCl_3$) δ ppm 1.21 (d, J=6.61 Hz, 3H) 1.59-1.72 (m, 1H) 1.99 (dd, J=13.66, 7.59 Hz, 1H) 2.38 (td, J=12.88, 2.44 Hz, 1H) 2.50 (td, J=13.12, 6.61 Hz, 1H) 2.97-3.20 (m, 2H) 6.85 (dd, J=7.86, 1.79 Hz, 2H) 7.28-7.35 (m, 3H) 7.42-7.53 (m, 3H) 8.38 (dd, J=6.72, 3.04 Hz, 2H) 8.77 (s, 1H) 9.03 (s, 1H); MS (ESI+) m/z 392 (M+H)$^+$, 424 (M+$CH_3OH$+H)$^+$.

Example 8 rac-(6aS,7S,10aR)-4-methoxy-7-methyl-8-oxo-2,
10a-diphenyl-5,6,6a,7,8,10a-hexahydrobenzo[h]
quinazoline-9-carbonitrile

Example 8A rac-methyl (1'S,4a'S,8a'S)-1'-methyl-5'-oxo-4a'-phe-
nyloctahydro-1'H-spiro[1,3-dioxolane-2,2'-naphtha-
lene]-6'-carboxylate To a solution of Example 2H (0.523 g, 1.74 mmol) in tetrahydrofuran (15 mL) was added dimethyl carbonate (3.66 mL, 43.5 mmol), 95% sodium hydride (0.209 g, 8.71 mmol), and 50% potassium hydride in paraffin (0.014 g, 0.174 mmol). The mixture was heated at 70° C. for 6 hours, and then stirred at room temperature overnight. The reaction was quenched by dropwise addition of 10% acetic acid, and then the reaction mixture was partitioned between water and ethyl acetate. The organic layer was dried over sodium sulfate, filtered, and concentrated under vacuum to give 0.545 g (87%) of the titled compound. MS (APCI+) m/z 359 (M+H)$^+$.

Example 8B rac-(6aS,7S,10aS)-7-methyl-2,10a-diphenyl-5,6a,7,
9,10,10a-hexahydro-6H-spiro[benzo[h]quinazoline-
8,2'-[1,3]dioxolan]-4-ol The titled compound was prepared using the conditions described in 13B, substituting Example 8A for Example 13A and substituting benzimidamide hydrochloride for acetamidine hydrochloride and heating for 20 hours.

Example 8C rac-(6aS,7S,10aS)-4-chloro-7-methyl-2,10a-diphe-
nyl-5,6a,7,9,10,10a-hexahydrobenzo[h]quinazolin-8
(6H)-one To a solution of Example 8B (0.220 g, 0.513 mmol) in toluene (6 mL) was added Hunig's base (0.108 mL, 0.616 mmol) followed by dropwise addition of phosphorous oxychloride (0.48 mL, 5.13 mmol). The reaction mixture was heated at 90° C. for 1 hour.

The cooled, crude reaction mixture was concentrated to dryness. The residue was taken up in ethyl acetate, washed with saturated aqueous sodium bicarbonate solution, dried over sodium sulfate, and concentrated to provide the titled compound.

Example 8D rac-(6aS,7S,10aS)-4-methoxy-7-methyl-2,10a-diphe-
nyl-5,6a,7,9,10,10a-hexahydrobenzo[h]quinazolin-8
(6H)-one To a solution of Example 8C (0.200 g, 0.496 mmol) in methanol (6 mL) was added 25% sodium methoxide in methanol (0.894 mL, 4.96 mmol). The reaction mixture was heated at 50° C. for 2 hours. The cooled solution was diluted with saturated $NaH_2PO_4$ solution, extracted with ethyl acetate, and the organic phase was concentrated. The residue was purified on a Teledyne Isco Combiflash® Rf system using a 12 g RediSep® silica cartridge eluting with 0-50% ethyl acetate in hexanes to give 0.085 g (43%) of the titled compound. $^1$H NMR (400 MHz, CDCl$_3$) δ ppm 1.18 (d, J=6.72 Hz, 3H) 1.88-2.00 (m, 1H) 2.06-2.17 (m, 3H) 2.25-2.35 (m, 1H) 2.54-2.64 (m, 2H) 2.70-2.81 (m, 2H) 3.40-3.50 (m, 1H) 4.09 (s, 3H) 7.16-7.23 (m, 1H) 7.27-7.34 (m, 2H) 7.39-7.49 (m, 3H) 7.56 (d, J=8.67 Hz, 2H) 8.41-8.47 (m, 2H).

Example 8E rac-(6aS,7S,9Z,10aS)-9-(hydroxymethylene)-4-methoxy-7-methyl-2,10a-diphenyl-5,6a,7,9,10,10a-hexahydrobenzo[h]quinazolin-8(6H)-one The titled compound was prepared using the conditions described in Example 1J, substituting Example 8D for Example 1I.

Example 8F rac-(6aS,7S,11aS)-4-methoxy-7-methyl-2,11a-diphenyl-5,6,6a,7,11,11a-hexahydro[1,2]benzoxazolo[6,5-h]quinazoline The titled compound was prepared using the conditions described in Example 1K, substituting Example 8E for Example 1J.

Example 8G rac-(6aS,7S,10aS)-4-methoxy-7-methyl-8-oxo-2,10a-diphenyl-5,6,6a,7,8,9,10,10a-octahydrobenzo[h]quinazoline-9-carbonitrile The titled compound was prepared using the conditions described in Example 1L, substituting Example 8F for Example 1K.

Example 8H rac-(6aS,7S,10aR)-4-methoxy-7-methyl-8-oxo-2,10a-diphenyl-5,6,6a,7,8,10a-hexahydrobenzo[h]quinazoline-9-carbonitrile The titled compound was prepared using the conditions described in Example 1M, substituting Example 8G for Example 1L. $^1$H NMR (400 MHz, CDCl$_3$) δ ppm 1.19 (d, J=6.61 Hz, 3H) 1.45-1.55 (m, 1H) 1.89-2.00 (m, 1H) 2.28-2.39 (m, 1H) 2.45 (td, J=12.96, 6.40 Hz, 1H) 2.71-2.86 (m, 1H) 2.91-3.02 (m, 1H) 4.19 (s, 3H) 6.92 (dd, J=7.97, 1.46 Hz, 2H) 7.28-7.35 (m, 3H) 7.41-7.48 (m, 3H) 8.36-8.44 (m, 2H) 9.06 (s, 1H); MS (APCI+) m/z 422 (M+H)$^+$.

Example 9 rac-(6aS,7S,10aR)-2-anilino-7-methyl-8-oxo-10a-phenyl-5,6,6a,7,8,10a-hexahydrobenzo[h]quinazoline-9-carbonitrile

Example 9A rac-(6aS,7S)-7-methyl-N,10a-diphenyl-5,6a,7,9,10,10a-hexahydro-6H-spiro[benzo[h]quinazoline-8,2'-[1,3]dioxolan]-2-amine To a solution of the product of Example 21 (0.500 g, 1.523 mmol) in dimethylformamide (6 mL) was added phenyl guanidine carbonate salt (0.540 g, 2.74 mmol). The reaction mixture was heated at 90° C. for 18 hours. The cooled solution was diluted with NaH$_2$PO$_4$ solution and extracted with ethyl acetate. The organic fraction was dried over sodium sulfate, filtered, and concentrated.

Example 9B rac-(6aS,7S,10aS)-2-anilino-7-methyl-10a-phenyl-5,6a,7,9,10,10a-hexahydrobenzo[h]quinazolin-8(6H)-one The titled compound was prepared using the conditions described in Example 1I, substituting Example 9A for Example 1H.

Example 9C rac-(6aS,7S,9Z,10aS)-2-anilino-9-(hydroxymethylene)-7-methyl-10a-phenyl-5,6a,7,9,10,10a-hexahydrobenzo[h]quinazolin-8(6H)-one The titled compound was prepared using the conditions described in Example 1J, substituting Example 9B for Example 1I.

Example 9D rac-(6aS,7S,11aS)-7-methyl-N,11a-diphenyl-5,6,6a,7,11,11a-hexahydro[1,2]benzoxazolo[6,5-h]quinazolin-2-amine The titled compound was prepared using the conditions described in Example 1K, substituting Example 9C for Example 1J giving 0.147 g (62%). $^1$H NMR (400 MHz, CDCl$_3$) δ ppm 1.38 (d, J=6.83 Hz, 3H) 1.72-1.82 (m, 1H) 1.93-2.12 (m, 2H) 2.20-2.32 (m, 1H) 2.76-2.92 (m, 1H) 2.95-3.07 (m, 2H) 3.77 (d, J=16.81 Hz, 1H) 6.85 (dd, J=6.78, 2.98 Hz, 2H) 6.98 (t, J=7.37 Hz, 1H) 7.07 (s, 1H) 7.11-7.18 (m, 3H) 7.27 (t, J=7.92 Hz, 2H) 7.50 (d, J=7.70 Hz, 2H) 8.28 (s, 1H) 8.34 (s, 1H); MS (APCI+) m/z 409 (M+H)$^+$.

Example 9E rac-(6aS,7S,10aS)-2-anilino-7-methyl-8-oxo-10a-phenyl-5,6,6a,7,8,9,10,10a-octahydrobenzo[h]quinazoline-9-carbonitrile The titled compound was prepared using the conditions described in Example 1L, substituting Example 9D for Example 1K.

Example 9F rac-(6aS,7S,10aR)-2-anilino-7-methyl-8-oxo-10a-phenyl-5,6,6a,7,8,10a-hexahydrobenzo[h]quinazoline-9-carbonitrile The titled compound was prepared using the conditions described in Example 1M, substituting Example 9E for Example 1L, giving 0.025 g (17%). $^1$H NMR (400 MHz, CDCl$_3$) δ ppm 1.19 (d, J=6.72 Hz, 3H) 1.48-1.67 (m, 1H) 1.92 (dd, J=13.66, 7.92 Hz, 1H) 2.28-2.38 (m, 1H) 2.45 (td, J=13.20, 6.67 Hz, 1H) 2.83-3.06 (m, 2H) 6.90 (dd, J=7.92, 1.63 Hz, 2H) 6.99-7.08 (m, 2H) 7.28-7.39 (m, 5H) 7.49 (d, J=7.70 Hz, 2H) 8.41 (s, 1H) 8.78 (s, 1H); MS (ESI+) m/z 407 (M+H)⁺, 439 (M+CH₃OH+H)⁺.

Example 10

(6aS,7S,10aR)-4-methoxy-2-(2-methoxyphenyl)-7-methyl-8-oxo-10a-phenyl-5,6,6a,7,8,10a-hexahydrobenzo[h]quinazoline-9-carbonitrile

Example 10A (6aS,7S,10aS)-2-(2-methoxyphenyl)-7-methyl-10a-phenyl-5,6a,7,9,10,10a-hexahydro-6H-spiro[benzo[h]quinazoline-8,2'-[1,3]dioxolan]-4-ol To a solution of the product from Example 13A (0.850 g, 2.37 mmol) in isopropanol (10 mL) was added 2-methoxybenzimidamidine hydrochloride (0.708 g, 3.79 mmol) and 1 M potassium t-butoxide in t-butanol (3.56 mL, 3.56 mmol). The reaction mixture was heated at 90° C. for 18 hours, followed by 100° C. for 3 hours. The cooled solution was diluted with saturated aqueous NaH₂PO₄ solution and extracted with dichloromethane. The organic phase was concentrated. The residue was purified using a 24 g RediSep® silica gel cartridge on a Teledyne Isco Combiflash® Rf system eluting with 0-100% ethyl acetate in heptane to give 0.290 g (27%) of the titled compound.

Example 10B (6aS,7S,10aS)-4-chloro-2-(2-methoxyphenyl)-7-methyl-10a-phenyl-5,6a,7,9,10,10a-hexahydro-6H-spiro[benzo[h]quinazoline-8,2'-[1,3]dioxolane]

The titled compound was prepared using the conditions described in Example 8C, substituting Example 10A for Example 8B.

Example 10C (6aS,7S,10aS)-4-methoxy-2-(2-methoxyphenyl)-7-methyl-10a-phenyl-5,6a,7,9,10,10a-hexahydro-6H-spiro[benzo[h]quinazoline-8,2'-[1,3]dioxolane]

To a solution of Example 10B (0.270 g, 0.566 mmol) in tetrahydrofuran (2 mL) and methanol (2 mL) was added 25% sodium methoxide in methanol. The reaction mixture was heated at 50° C. for 3 hours. The cooled solution was diluted with saturated aqueous NaH₂PO₄ solution and extracted with ethyl acetate. The organic phase was dried over sodium sulfate, filtered, and concentrated to provide the titled compound.

Example 10D (6aS,7S,10aS)-4-methoxy-2-(2-methoxyphenyl)-7-methyl-10a-phenyl-5,6a,7,9,10,10a-hexahydrobenzo[h]quinazolin-8(6H)-one To a solution from Example 10C (0.265 g, 0.561 mmol) in tetrahydrofuran (4 mL) was added 3 M hydrochloric acid (1.86 mL, 5.61 mmol). The reaction mixture was heated at 40° C. for 1 hour. The cooled solution was diluted with water, neutralized by addition of saturated aqueous sodium bicarbonate solution, and extracted with ethyl acetate. The organic phase was dried over sodium sulfate, filtered, and concentrated to provide the titled compound.

Example 10E (6aS,7S,9Z,10aS)-9-(hydroxymethylene)-4-methoxy-2-(2-methoxyphenyl)-7-methyl-10a-phenyl-5,6a,7,9,10,10a-hexahydrobenzo[h]quinazolin-8(6H)-one To a solution of Example 10D (0.280 g, 0.653 mmol) in tetrahydrofuran (4 mL) was added ethyl formate (1.33 mL, 16.34 mmol) and 25% sodium methoxide in methanol (0.570 mL, 2.61 mmol). The reaction mixture was stirred at room temperature for 2 hours. The solution was diluted with saturated aqueous NaH₂PO₄ solution and extracted with ethyl acetate. The organic phase was dried over sodium sulfate, filtered and concentrated to provide the titled compound.

Example 10F (6aS,7S,11aS)-4-methoxy-2-(2-methoxyphenyl)-7-methyl-11a-phenyl-5,6,6a,7,11,11a-hexahydro[1,2]benzoxazolo[6,5-h]quinazoline To a solution of Example 10E (0.290 g, 0.635 mmol) in ethanol (6 mL) was added hydroxylamine hydrochloride (0.088 g, 1.27 mmol). The reaction mixture was heated at 55° C. for 24 hours. The cooled solution was concentrated, diluted with dichloromethane, and washed with saturated aqueous sodium bicarbonate solution. The organic phase was concentrated, and the residue was purified on a Teledyne Isco Combiflash® Rf system using a 12 g RediSep® silica gel cartridge eluting with 0-50% ethyl acetate in heptane to give 0.056 g (19%) of the titled compound.

Example 10G (6aS,7S,10aS)-4-methoxy-2-(2-methoxyphenyl)-7-methyl-8-oxo-10a-phenyl-5,6,6a,7,8,9,10,10a-octahydrobenzo[h]quinazoline-9-carbonitrile The titled compound was prepared using the conditions described in Example 1L, substituting Example 10F for Example 1K.

Example 10H (6aS,7S,10aR)-4-methoxy-2-(2-methoxyphenyl)-7-methyl-8-oxo-10a-phenyl-5,6,6a,7,8,10a-hexahydrobenzo[h]quinazoline-9-carbonitrile The titled compound was prepared using the conditions described in Example 1M, substituting Example 10G for Example 1L. ¹H NMR (400 MHz, CDCl₃) δ ppm 1.19 (d, J=6.61 Hz, 3H) 1.48-1.55 (m, 1H) 1.95 (dd, J=13.66, 9.00 Hz, 1H) 2.34 (td, J=12.90, 2.49 Hz, 1H) 2.45 (td, J=13.09, 6.67 Hz, 1H) 2.78 (ddd, J=18.87, 10.95, 8.02 Hz, 1H) 2.92-3.02 (m, 1H) 3.85 (s, 3H) 4.13 (s, 3H) 6.91-6.96 (m, 2H) 6.98-7.06 (m, 2H) 7.28-7.33 (m, 3H) 7.36-7.43 (m, 1H) 7.80 (dd, J=7.64, 1.68 Hz, 1H) 9.06 (s, 1H); MS (ESI+) m/z 452 (M+H)⁺, 484 (M+CH₃OH+H)⁺.

Example 11

(6aS,7S,10aR)-7-methyl-8-oxo-10a-phenyl-2-(pyridin-3-yl)-5,6,6a,7,8,10a-hexahydrobenzo[h]quinazoline-9-carbonitrile

Example 11A (6aS,7S,10aS)-7-methyl-10a-phenyl-2-(pyridin-3-yl)-5,6a,7,9,10,10a-hexahydro-6H-spiro[benzo[h]quinazoline-8,2'-[1,3]dioxolane]

The titled compound was prepared using the conditions described in Example 1H, substituting nicotinimidamide hydrochloride for formamidine acetate and heating for 2 days.

Example 11B (6aS,7S,10aS)-7-methyl-10a-phenyl-2-(pyridin-3-yl)-5,6a,7,9,10,10a-hexahydrobenzo[h]quinazolin-8(6H)-one The titled compound was prepared using the conditions described in Example 1I, substituting Example 11A for Example 1H and purifying using a 40 g RediSep® silica gel cartridge on a Teledyne Isco Combiflash® Rf system, eluting with 0-60% ethyl acetate in dichloromethane to give 0.335 g (30%). MS (APCI+) m/z 370 (M+H)$^+$.

Example 11C (6aS,7S,9Z,10aS)-9-(hydroxymethylene)-7-methyl-10a-phenyl-2-(pyridin-3-yl)-5,6a,7,9,10,10a-hexahydrobenzo[h]quinazolin-8(6H)-one To a solution of Example 11B (0.330 g, 0.893 mmol) in tetrahydrofuran (8 mL) was added ethyl formate (1.45 mL, 17.86 mmol) and 25% sodium methoxide in methanol (0.777 mL, 3.57 mmol). The reaction mixture was stirred at room temperature for 4 hours. The solution was diluted with saturated aqueous NaH$_2$PO$_4$ solution and extracted with ethyl acetate. The aqueous layer was dried over sodium sulfate, filtered and concentrated to provide the titled compound.

Example 11D (6aS,7S,11aS)-7-methyl-11a-phenyl-2-(pyridin-3-yl)-5,6,6a,7,11,11a-hexahydro[1,2]benzoxazolo[6,5-h]quinazoline The titled compound was prepared using the conditions described in Example 1K, substituting Example 11C for Example 1J, giving 0.250 g (71%).

Example 11E (6aS,7S,10aS)-7-methyl-8-oxo-10a-phenyl-2-(pyridin-3-yl)-5,6,6a,7,8,9,10,10a-octahydrobenzo[h]quinazoline-9-carbonitrile The titled compound was prepared using the conditions described in Example 1L, substituting Example 11D for Example 1K.

Example 11F (6aS,7S,10aR)-7-methyl-8-oxo-10a-phenyl-2-(pyridin-3-yl)-5,6,6a,7,8,10a-hexahydrobenzo[h]quinazoline-9-carbonitrile The titled compound was prepared using the conditions described in Example 1M, substituting Example 11E for Example 1L, heating for only 1 hour, and purifying using a 12 g silica gel RediSep® cartridge on a Teledyne Isco Combiflash® Rf system eluting with 0-70% ethyl acetate in heptane to give 0.068 g (32%). $^1$H NMR (400 MHz, CDCl$_3$) δ ppm 1.22 (d, J=6.72 Hz, 3H) 1.63-1.73 (m, 1H) 2.00 (dd, J=7.37, 5.75 Hz, 1H) 2.38 (td, J=12.82, 2.33 Hz, 1H) 2.50 (td, J=13.15, 6.56 Hz, 1H) 3.01-3.22 (m, 2H) 6.84 (dd, J=7.81, 1.73 Hz, 2H) 7.30-7.37 (m, 3H) 7.41 (dd, J=7.21, 5.04 Hz, 1H) 8.64 (d, J=7.92 Hz, 1H) 8.70 (dd, J=2.98, 1.36 Hz, 1H) 8.81 (s, 1H) 8.97 (s, 1H) 9.59 (s, 1H); MS (ESI+) m/z 393 (M+H)$^+$, 425 (M+CH$_3$OH+H)$^+$.

Example 12

(6aS,7S,10aR)-2-(ethylamino)-7-methyl-8-oxo-10a-phenyl-5,6,6a,7,8,10a-hexahydrobenzo[h]quinazoline-9-carbonitrile

Example 12A (6aS,7S,10aS)—N-ethyl-7-methyl-10a-phenyl-5,6a,7,9,10,10a-hexahydro-6H-spiro[benzo[h]quinazoline-8,2'-[1,3]dioxolan]-2-amine To a solution of the product from Example 1G (0.500 g, 1.523 mmol) in t-butanol (3 mL) was added N-ethylguanidine hydrochloride (0.376 g, 3.05 mmol) and 1 M potassium t-butoxide solution in t-butanol (3.05 mL, 3.05 mmol). The reaction mixture was heated at 85° C. for 18 hours, and then at 90° C. for 7 hours. After cooling, the solution was quenched by addition of saturated aqueous NaH$_2$PO$_4$, diluted with water, and extracted with 20% isopropanol in chloroform. The organic fraction was dried over sodium sulfate, filtered, and concentrated under vacuum to provide the titled compound.

Example 12B (6aS,7S,10aS)-2-(ethylamino)-7-methyl-10a-phenyl-5,6a,7,9,10,10a-hexahydrobenzo[h]quinazolin-8(6H)-one The titled compound was prepared using the conditions described in Example 1I, substituting Example 12A for Example 1H to give 0.205 g (45%).

Example 12C (6aS,7S,9Z,10aS)-2-(ethylamino)-9-(hydroxymethylene)-7-methyl-10a-phenyl-5,6a,7,9,10,10a-hexahydrobenzo[h]quinazolin-8(6H)-one The titled compound was prepared using the conditions described in Example 1J, substituting Example 12B for Example 1I. MS (APCI+) m/z 364 (M+H)$^+$.

Example 12D (6aS,7S,11aS)—N-ethyl-7-methyl-11a-phenyl-5,6,6a,7,11,11a-hexahydro[1,2]benzoxazolo[6,5-h]quinazolin-2-amine The titled compound was prepared using the conditions described in Example 1K, substituting Example 12C for Example 1J and purified on a Teledyne Isco Combiflash® Rf system using a 12 g RediSep® silica gel cartridge eluting with 0-70% ethyl acetate in heptane to give 0.195 g (98%).

Example 12E (6aS,7S,10aS)-2-(ethylamino)-7-methyl-8-oxo-10a-phenyl-5,6,6a,7,8,9,10,10a-octahydrobenzo[h]quinazoline-9-carbonitrile The titled compound was prepared using the conditions described in Example 1L, substituting Example 12D for Example 1K and stirring at room temperature for 18 hours.

Example 12F (6aS,7S,10aR)-2-(ethylamino)-7-methyl-8-oxo-10a-phenyl-5,6,6a,7,8,10a-hexahydrobenzo[h]quinazoline-9-carbonitrile The titled compound was prepared using the conditions described in Example 1M, substituting Example 12E for Example 1L and purifying using a 12 g RediSep® silica gel cartridge on a Teledyne Isco Combiflash® Rf system to give 0.023 g (14%). $^1$H NMR (400 MHz, CDCl$_3$) δ ppm 1.14-1.22 (m, 6H) 1.42-1.49 (m, 1H) 1.86-1.94 (m, 1H) 2.24-2.34 (m, 1H) 2.43 (td, J=13.04, 6.45 Hz, 1H) 2.77-2.98 (m, 2H) 3.40 (ddd, J=13.28, 7.05, 6.78 Hz, 2H) 6.88 (dd, J=7.75, 1.68 Hz, 2H) 7.29-7.37 (m, 3H) 8.22 (s, 1H) 8.75 (s, 1H); MS (ESI+) m/z 359 (M+H)$^+$, 390 (M+CH$_3$OH+H)$^+$.

Example 13

(6aS,7S,10aR)-4-methoxy-2,7-dimethyl-8-oxo-10a-phenyl-5,6,6a,7,8,10a-hexahydrobenzo[h]quinazoline-9-carbonitrile

Example 13A methyl (1'S,4a'S,8a'S)-1'-methyl-5'-oxo-4a'-phenyloctahydro-1'H-spiro[1,3-dioxolane-2,2'-naphthalene]-6'-carboxylate Under an atmosphere of nitrogen, Example 1F (29 g, 97 mmol) was dissolved in dry tetrahydrofuran (493 mL) followed by addition of dimethyl dicarbonate (203.3 mL, 2415 mmol), 60% sodium hydride (15.46 g, 387 mmol) and 50% potassium hydride (0.78 g, 9.76 mmol). The reaction mixture was heated to reflux (70° C.) for 5 hours followed by cooling to 50° C. where more 50% potassium hydride (0.78 g) was added. The reaction mixture was then refluxed for 20 hours. After cooling down to room temperature and neutralization with acetic acid (25 mL), the solution was diluted with ethyl acetate (500 mL) and washed with water (250 mL). The aqueous layer was further extracted with ethyl acetate (50 mL). Then the organic layers were combined and washed with 15% brine (2×250 mL). The organic layer was dried over sodium sulfate and concentrated under vacuum to dryness. The residue was dissolved in minimum amount of ethyl acetate (100 mL) with heating. Then excess heptane (500 mL) was added. The resultant solution was concentrated under vacuum to ~50% volume, cooled in an ice bath for two hours, and then stored in a refrigerator below 0° C. for 20 hours. The solid was collected by filtration, washed with cold heptane (200 mL), and dried under vacuum to give 29.9 g (86%) of the titled compound.

Example 13B (6aS,7S,10aS)-2,7-dimethyl-10a-phenyl-5,6a,7,9,10,10a-hexahydro-6H-spiro[benzo[h]quinazoline-8,2'-[1,3]dioxolan]-4-ol To a solution of Example 13A (6.0 g, 16.74 mmol) in t-butanol (9.0 mL) at room temperature was added acetamidine hydrochloride (13.17 g, 33.5 mmol) followed by 1 M potassium t-butoxide in t-butanol (33.5 mL, 35.5 mmol). The reaction was stirred at 90° C. for 48 hours. The reaction solution was diluted with ethyl acetate and washed with water. The aqueous layer was back extracted with ethyl acetate. The ethyl acetate layers were combined, washed with saturated sodium chloride, dried over magnesium sulfate, filtered, and concentrated under reduced pressure to give the titled compound which was used without further purification.

Example 13C (6aS,7S,10aS)-4-hydroxy-2,7-dimethyl-10a-phenyl-5,6a,7,9,10,10a-hexahydrobenzo[h]quinazolin-8(6H)-one To a solution of Example 13B (0.46 g, 1.26 mmol) in tetrahydrofuran (8 mL) at room temperature was added 3 M hydrochloric acid (4.2 mL, 12.6 mmol). The reaction mixture was stirred at 40° C. for 1 hour and then concentrated. The residue was dissolved in ethyl acetate and washed with saturated sodium bicarbonate and then saturated sodium chloride. The organic phase was dried over magnesium sulfate, filtered and concentrated under reduced pressure to provide the titled compound.

Example 13D (6aS,7S,10aS)-4-chloro-2,7-dimethyl-10a-phenyl-5,6a,7,9,10,10a-hexahydrobenzo[h]quinazolin-8(6H)-one To a solution of Example 13C (0.29 g, 0.91 mmol) in toluene (8 mL) was added N,N-diisopropylethylamine (0.91 mL, 1.09 mmol) followed by phosphorous oxychloride (0.85 mL, 9.12 mmol). The reaction mixture was stirred at 90° C. for 1 hour and then concentrated. The residue was dissolved in ethyl acetate and washed sequentially with saturated sodium bicarbonate and saturated sodium chloride. The organic phase was dried over magnesium sulfate, filtered and concentrated to provide the titled compound. $^1$H NMR (400 MHz, CDCl$_3$) δ ppm 1.16 (d, J=6.72 Hz, 3H) 1.95-2.16 (m, 3H) 2.23 (ddd, J=14.37, 10.14, 7.81 Hz, 1H) 2.47-2.60 (m, 3H) 2.64 (s, 3H) 2.78-2.98 (m, 2H) 3.25 (ddd, J=14.42, 6.29, 4.45 Hz, 1H) 7.19-7.33 (m, 3H) 7.39 (d, J=7.81 Hz, 2H).

Example 13E (6aS,7S,10aS)-4-methoxy-2,7-dimethyl-10a-phenyl-5,6a,7,9,10,10a-hexahydrobenzo[h]quinazolin-8(6H)-one To a solution Example 13D (0.24 g, 0.80 mmol) in tetrahydrofuran (3 mL) and methanol (3 mL) was added 25% sodium methoxide in methanol (1.75 mL, 8.0 mmol). The reaction mixture was stirred at 50° C. for 1 hour and then concentrated. The residue was dissolved in ethyl acetate, and the mixture was washed sequentially with aqueous saturated potassium phosphate monobasic and saturated sodium chloride. The organic layer was dried over magnesium sulfate, filtered and concentrated under reduced pressure to provide the titled compound.

Example 13F (6aS,7S,9Z,10aS)-9-(hydroxymethylene)-4-methoxy-2,7-dimethyl-10a-phenyl-5,6a,7,9,10,10a-hexahydrobenzo[h]quinazolin-8(6H)-one To a solution Example 13E (0.26 g, 0.77 mmol) in ethyl formate (6.2 mL, 77.0 mmol) was added 25% sodium methoxide in methanol (0.83 mL, 3.8 mmol). The reaction mixture was stirred at room temperature for 2 hours, diluted with ethyl acetate, and washed with saturated potassium phosphate monobasic and then saturated sodium chloride. The organic phase was dried over magnesium sulfate, filtered and concentrated under reduced pressure to provide the titled compound.

Example 13G (6aS,7S,11aS)-4-methoxy-2,7-dimethyl-11a-phenyl-5,6,6a,7,11,11a-hexahydro[1,2]benzoxazolo[6,5-h]quinazoline To a solution of Example 13F (0.26 g, 0.73 mmol) in ethanol (7 mL) was added hydroxylamine hydrochloride (2.02 g, 2.9 mmol). The reaction mixture was stirred at 65° C. for 2 hours and then concentrated. The residue was dissolved in ethyl acetate, and the resultant solution was washed with saturated sodium bicarbonate and then saturated sodium chloride. The organic phase was dried over magnesium sulfate, filtered and concentrated to provide the titled compound.

Example 13H (6aS,7S,10aS)-4-methoxy-2,7-dimethyl-8-oxo-10a-phenyl-5,6,6a,7,8,9,10,10a-octahydrobenzo[h]quinazoline-9-carbonitrile To a solution of Example 13G (0.24 g, 0.68 mmol) in tetrahydrofuran (3 mL) and methanol (3 mL) was added 25% sodium methoxide in methanol (0.74 mL, 3.4 mmol). The reaction mixture was stirred at room temperature for 2 hours and then concentrated. The residue was dissolved in ethyl acetate, and the resultant solution was washed with saturated sodium bicarbonate and saturated sodium chloride. The organic phase was dried over magnesium sulfate, filtered and concentrated under reduced pressure to provide the titled compound.

Example 13I (6aS,7S,10aR)-4-methoxy-2,7-dimethyl-8-oxo-10a-phenyl-5,6,6a,7,8,10a-hexahydrobenzo[h]quinazoline-9-carbonitrile To a solution of Example 13H (0.24 g, 0.68 mmol) in dimethylformamide (4 mL) at 0° C. was added 1,3-dibromo-5,5-dimethylhydantoin (0.097 g, 0.34 mmol). The reaction mixture was stirred at 0° C. for 0.5 hours. Pyridine (0.55 mL, 6.8 mmol) was then added, and the solution was heated at 50° C. for 1.5 hours and then concentrated. The residue was dissolved in ethyl acetate, and the resultant solution was washed with saturated potassium phosphate monobasic and then twice with saturated sodium chloride. The organic phase was dried over magnesium sulfate, filtered, concentrated under reduced pressure. The residue was purified by flash chromatography on silica gel eluting with 3% ethyl acetate in chloroform to give 0.067 g. (27%) of the titled compound. $^1$H NMR (400 MHz, CDCl$_3$) δ ppm 1.16 (d, J=6.72 Hz, 3H) 1.41-1.55 (m, 1H) 1.90 (dd, J=13.55, 8.67 Hz, 1H) 2.25 (td, J=12.96, 2.28 Hz, 1H) 2.40 (td, J=13.20, 6.67 Hz, 1H) 2.53 (s, 3H) 2.62-2.77 (m, 1H) 2.81-2.93 (m, 1H) 4.05 (s, 3H) 6.86 (dd, J=7.92, 1.63 Hz, 2H) 7.28-7.37 (m, 3H) 8.92 (s, 1H); MS (CI) m/z 360 (M+H)$^+$.

Example 14

(6aS,7S,10aR)-2-anilino-4-methoxy-7-methyl-8-oxo-10a-phenyl-5,6,6a,7,8,10a-hexahydrobenzo[h]quinazoline-9-carbonitrile

Example 14A (6aS,7S,10aS)-2-anilino-7-methyl-10a-phenyl-5,6a,7,9,10,10a-hexahydro-6H-spiro[benzo[h]quinazoline-8,2'-[1,3]dioxolan]-4-ol To a mixture of 13A (0.500 g, (1.395 mmol) and phenyl guanidine acetate (0.495 g, 2.51 mmol) was added 1 M potassium t-butoxide in t-butanol. The reaction mixture was heated at 95° C. for 96 hours. The cooled solution was diluted with saturated aqueous NaH$_2$PO$_4$ solution, and the resultant mixture was extracted with ethyl acetate. The organic phase was concentrated to give the titled compound.

Example 14B (6aS,7S,10aS)-2-anilino-4-hydroxy-7-methyl-10a-phenyl-5,6a,7,9,10,10a-hexahydrobenzo[h]quinazolin-8(6H)-one To a solution of Example 14A (0.600 g, 1.353 mmol) in tetrahydrofuran (6 mL) was added 3 M hydrochloric acid (2.26 mL, 6.76 mmol). The reaction mixture was heated at 48° C. for 2 hours, and then stirred at room temperature for 3 hours. The solution was diluted with water, neutralized to pH 7 with saturated aqueous sodium bicarbonate solution, and extracted with ethyl acetate. The organic phase was concentrated. Dichloromethane was added to the residue, and the solid was collected by filtration. The filtrate was concentrated, and the residue was purified using a 24 g RediSep® silica gel cartridge on a Teledyne Isco Combiflash® Rf system eluting with 0-90% ethyl acetate in heptane. The solid material and clean fractions were combined to give 0.359 g (66%) of the titled compound. MS (APCI+) m/z 400 (M+H)$^+$.

Example 14C (6aS,7S,10aS)-2-anilino-4-chloro-7-methyl-10a-phenyl-5,6a,7,9,10,10a-hexahydrobenzo[h]quinazolin-8(6H)-one The titled compound was prepared using the conditions described in Example 8C, substituting Example 14B for Example 8B, and heating at 80° C.

Example 14D (6aS,7S,10aS)-2-anilino-4-methoxy-7-methyl-10a-phenyl-5,6a,7,9,10,10a-hexahydrobenzo[h]quinazolin-8(6H)-one The titled compound was prepared using the conditions described in Example 8D, substituting Example 14C for Example 8C, and using a 1:1 mixture of methanol and tetrahydrofuran as solvent to give 0.255 g (90%).

Example 14E (6aS,7S,9Z,10aS)-2-anilino-9-(hydroxymethylene)-4-methoxy-7-methyl-10a-phenyl-5,6a,7,9,10,10a-hexahydrobenzo[h]quinazolin-8(6H)-one The titled compound was prepared using the conditions described in Example 1J, substituting Example 14D for Example 1I.

Example 14F (6aS,7S,11aS)-4-methoxy-7-methyl-N,11a-diphenyl-5,6,6a,7,11,11a-hexahydro[1,2]benzoxazolo[6,5-h]quinazolin-2-amine The titled compound was prepared using the conditions described in Example 1K, substituting Example 14E for Example 1J, and purifying using a 12 g RediSep® silica gel cartridge on a Teledyne Isco Combiflash® Rf system eluting with 0-70% ethyl acetate in heptane to give 0.058 g (22%). $^1$H NMR (400 MHz, CDCl$_3$) δ ppm 1.37 (d, J=6.83 Hz, 3H) 1.61-1.72 (m, 1H) 1.90-1.99 (m, 1H) 2.00-2.08 (m, 1H) 2.18-2.25 (m, 1H) 2.52-2.64 (m, 1H) 2.87-2.98 (m, 2H) 3.71 (d, J=16.70 Hz, 1H) 4.05 (s, 3H) 6.83 (s, 1H) 6.90-6.98 (m, 3H) 7.12-7.16 (m, 3H) 7.26 (d, J=15.94 Hz, 2H) 7.53 (d, J=7.70 Hz, 2H) 8.25 (s, 1H); MS (APCI+) m/z 439 (M+H)$^+$.

Example 14G (6aS,7S,10aS)-2-anilino-4-methoxy-7-methyl-8-oxo-10a-phenyl-5,6,6a,7,8,9,10,10a-octahydrobenzo[h]quinazoline-9-carbonitrile The titled compound was prepared using the conditions described in Example 1L, substituting Example 14F for Example 1K.

Example 14H (6aS,7S,10aR)-2-anilino-4-methoxy-7-methyl-8-oxo-10a-phenyl-5,6,6a,7,8,10a-hexahydrobenzo[h]quinazoline-9-carbonitrile The titled compound was prepared using the conditions described in Example 1M, substituting Example 14G for Example 1L. Purification was achieved using a 12 g RediSep® silica gel cartridge on a Teledyne Isco Combiflash® Rf system, eluting with 0-10% ethyl acetate in heptane. The titled compound eluted before the compound of Example 15. $^1$H NMR (400 MHz, CDCl$_3$) δ ppm 1.16 (d, J=5.75 Hz, 3H) 1.55-1.67 (m, 1H) 1.93 (dd, J=13.99, 7.05 Hz, 1H) 2.29-2.37 (m, 2H) 2.65 (ddd, J=18.49, 11.33, 7.59 Hz, 1H) 2.88 (dd, J=18.05, 6.23 Hz, 1H) 4.13 (s, 3H) 7.01 (d, J=7.37 Hz, 2H) 7.12 (t, J=7.32 Hz, 1H) 7.30-7.44 (m, 5H) 7.57 (d, J=8.02 Hz, 2H) 8.77 (s, 1H) 9.94 (s, 1H); MS (APCI+) m/z 437 (M+H)$^+$.

Example 15

(6aS,7S,10aR)-2-[(4-bromophenyl)amino]-4-methoxy-7-methyl-8-oxo-10a-phenyl-5,6,6a,7,8,10a-hexahydrobenzo[h]quinazoline-9-carbonitrile The titled compound was isolated as a byproduct from the procedure of Example 14H, eluting after the product of Example 14H. $^1$H NMR (501 MHz, CDCl$_3$) δ ppm 1.16 (d, J=6.60 Hz, 3H) 1.49 (ddd, J=24.85, 13.20, 6.88 Hz, 1H) 1.85-1.95 (m, 1H) 2.28 (td, J=12.88, 2.29 Hz, 1H) 2.39 (td, J=13.16, 6.51 Hz, 1H) 2.59-2.72 (m, 1H) 2.84 (dd, J=18.16, 6.42 Hz, 1H) 4.06 (s, 3H) 6.96 (d, J=7.89 Hz, 2H) 7.08 (s, 1H) 7.28-7.36 (m, 3H) 7.36-7.45 (m, 4H) 8.75 (s, 1H); MS (APCI+) m/z 516 (M+H)$^+$.

Example 16

(6aS,7S,10aR)-2-anilino-7-methyl-8-oxo-10a-phenyl-4-(pyrimidin-5-yl)-5,6,6a,7,8,10a-hexahydrobenzo[h]quinazoline-9-carbonitrile

Example 16A (6aS,7S,10aS)-2-anilino-7-methyl-10a-phenyl-4-(pyrimidin-5-yl)-5,6a,7,9,10,10a-hexahydrobenzo[h]quinazolin-8(6H)-one To a solution of Example 14C (0.235 g, 0.562 mmol) in dimethylformamide (2 mL) and 1,4-dioxane (3 mL) in a pressure tube was added pyrimidine-5-ylboronic acid (0.105 g, 0.843 mmol), 2 M sodium carbonate (0.703 mL, 1.406 mmol) and tetrakis(triphenylphosphine)palladium(0) (0.032 g, 0.028 mmol). Nitrogen was bubbled through the solution for 15 minutes, then the tube was sealed and the reaction mixture was heated at 90° C. for 1 hour. The cooled mixture was diluted with water and extracted with ethyl acetate. The organic layer was concentrated, and the residue was purified using a 12 g RediSep® silica gel cartridge on a Teledyne Isco Combiflash® Rf system eluting with 0-40% ethyl acetate in heptane to give 0.120 g (46%) of the titled compound. $^1$H NMR (400 MHz, CDCl$_3$) δ ppm 1.18 (d, J=6.61 Hz, 3H) 2.06-2.18 (m, 3H) 2.37-2.67 (m, 4H) 2.78-2.92 (m, 2H) 3.19-3.29 (m, 1H) 7.08 (t, J=7.37 Hz, 1H) 7.29 (d, J=7.37 Hz, 1H) 7.35 (t, J=7.81 Hz, 4H) 7.55 (d, J=7.26 Hz, 2H) 7.66 (d, J=7.70 Hz, 2H) 8.97 (s, 2H) 9.31 (s, 1H); MS (APCI+) m/z 462 (M+H)$^+$.

Example 16B (6aS,7S,9Z,10aS)-2-anilino-9-(hydroxymethylene)-7-methyl-10a-phenyl-4-(pyrimidin-5-yl)-5,6a,7,9,10,10a-hexahydrobenzo[h]quinazolin-8(6H)-one To a solution of Example 16A (0.168 g, 0.364 mmol) in methanol (2 mL) and tetrahydrofuran (2 mL) was added ethyl formate (0.741 mL, 9.10 mmol), 25% sodium methoxide in methanol (0.396 mL, 1.82 mmol) and potassium hydride (0.029 g, 0.364 mmol). The reaction mixture was stirred at room temperature for 72 hours. The solution was diluted with saturated aqueous sodium phosphate monobasic solution and extracted with ethyl acetate. The organic phase was dried over sodium sulfate, filtered, and concentrated to give 0.180 g (100%) of the titled compound.

Example 16C (6aS,7S,11aS)-7-methyl-N,11a-diphenyl-4-(pyrimidin-5-yl)-5,6,6a,7,11,11a-hexahydro[1,2]benzoxazolo[6,5-h]quinazolin-2-amine The titled compound was prepared using the conditions described in Example 1K, substituting Example 16B for Example 1J, and was purified using a 12 g RediSep® silica gel cartridge on a Teledyne Isco Combiflash® Rf system eluting with 0-30% ethyl acetate in heptane to give 0.054 g (30%). $^1$H NMR (400 MHz, CDCl$_3$) δ ppm 1.39 (d, J=6.72 Hz, 3H) 1.74-1.86 (m, 1H) 2.03-2.13 (m, 2H) 2.23-2.32 (m, 1H) 2.96-3.02 (m, 2H) 3.07 (dd, J=16.70, 2.49 Hz, 1H) 3.86-3.97 (m, 1H) 6.85-6.90 (m, 2H) 7.01 (t, J=6.99 Hz, 1H) 7.16-7.21 (m, 3H) 7.24-7.31 (m, 3H) 7.51 (d, J=8.02 Hz, 2H) 8.30 (s, 1H) 9.13 (s, 2H) 9.36 (s, 1H); MS (APCI+) m/z 487 (M+H)$^+$.

Example 16D (6aS,7S,10aS)-2-anilino-7-methyl-8-oxo-10a-phenyl-4-(pyrimidin-5-yl)-5,6,6a,7,8,9,10,10a-octahydrobenzo[h]quinazoline-9-carbonitrile The titled compound was prepared using the conditions described in Example 1L, substituting Example 16C for Example 1K.

Example 16E (6aS,7S,10aR)-2-anilino-7-methyl-8-oxo-10a-phenyl-4-(pyrimidin-5-yl)-5,6,6a,7,8,10a-hexahydrobenzo[h]quinazoline-9-carbonitrile The titled compound was prepared using the conditions described in Example 1M, substituting Example 16D for Example 1L and was purified on a Teledyne Isco Combiflash® Rf system using a 12 g RediSep® silica gel cartridge, eluting with 0-40% ethyl acetate in heptane to give 0.019 g (37%) of the titled compound. $^1$H NMR (400 MHz, CDCl$_3$) δ ppm 1.19 (d, J=6.40 Hz, 3H) 1.56-1.69 (m, 1H) 1.90-2.00 (m, 1H) 2.35-2.54 (m, 2H) 2.98 (d, J=7.05 Hz, 2H) 6.93 (d, J=6.72 Hz, 2H) 7.05 (t, J=7.43 Hz, 1H) 7.21 (s, 1H) 7.28-7.40 (m, 5H) 7.51 (d, J=8.13 Hz, 2H) 8.81 (s, 1H) 9.14 (s, 2H) 9.37 (s, 1H); MS (ESI+) m/z 485 (M+H)$^+$, 517 (M+CH$_3$OH+H)$^+$.

Example 17

(6aS,7S,10aR)-2,7-dimethyl-4-(1-methyl-1H-imidazol-5-yl)-8-oxo-10a-phenyl-5,6,6a,7,8,10a-hexahydrobenzo[h]quinazoline-9-carbonitrile

Example 17A (6aS,7S,10aS)-2,7-dimethyl-4-(1-methyl-1H-imidazol-5-yl)-10a-phenyl-5,6,6a,7,9,10,10a-hexahydrobenzo[h]quinazolin-8(6H)-one In a pressure tube, the product from Example 13D (2.4 g, 7.0 mmol), 1-methyl-5-(4,4,5,5-tetramethyl-1,3,2-dioxaborolan-2-yl)-1H-imidazole (2.20 g, 10.6 mmol), tetrakis(triphenylphosphine)palladium(0) (0.41 g, 0.35 mmol) and 2 M sodium carbonate (10.6 mL, 21.1 mmol) in dioxane (60 mL) were combined, and the mixture was sparged with nitrogen for 15 minutes. The tube was sealed and heated to 80° C. for 6 hours. The reaction was cooled to room temperature, and additional 1-methyl-5-(4,4,5,5-tetramethyl-1,3,2-dioxaborolan-2-yl)-1H-imidazole (0.60 g, 2.9 mmol) and tetrakis(triphenylphosphine)palladium(0) (0.20 g, 0.17 mmol) were added. The mixture was sparged with nitrogen for 15 minutes, the tube was sealed, and the mixture was heated to 80° C. for 16 hours. The reaction mixture was diluted with ethyl acetate and washed with water. The water was back extracted with ethyl acetate. The combined ethyl acetate layers were washed with saturated sodium chloride, dried over magnesium sulfate, filtered, and concentrated under reduced pressure. The residue was purified by flash chromatography on silica gel eluting with 5% methanol in chloroform to give 1.3 g (46%).

Example 17B (6aS,7S,9Z,10aS)-9-(hydroxymethylene)-2,7-dimethyl-4-(1-methyl-1H-imidazol-5-yl)-10a-phenyl-5,6a,7,9,10,10a-hexahydrobenzo[h]quinazolin-8(6H)-one The titled compound was prepared using the conditions described in Example 13F, substituting Example 17A for Example 13E.

Example 17C (6aS,7S,11aS)-2,7-dimethyl-4-(1-methyl-1H-imidazol-5-yl)-11a-phenyl-5,6,6a,7,11,11a-hexahydro[1,2]benzoxazolo[6,5-h]quinazoline The titled compound was prepared using the conditions described in Example 13G, substituting Example 17B for Example 13F.

Example 17D (6aS,7S,10aS)-2,7-dimethyl-4-(1-methyl-1H-imidazol-5-yl)-8-oxo-10a-phenyl-5,6,6a,7,8,9,10,10a-octahydrobenzo[h]quinazoline-9-carbonitrile The titled compound was prepared using the conditions described in Example 13H, substituting Example 17C for Example 13G. The residue was purified by flash chromatography on silica gel eluting with chloroform (97%)-methanol(3%)-ammonium hydroxide (0.2%) to give the titled compound in 72% yield.

Example 17E (6aS,7S,10aR)-2,7-dimethyl-4-(1-methyl-1H-imidazol-5-yl)-8-oxo-10a-phenyl-5,6,6a,7,8,10a-hexahydrobenzo[h]quinazoline-9-carbonitrile The titled compound was prepared using the conditions described in Example 13I, substituting Example 17D for Example 13H. The residue was purified by flash chromatography on silica gel eluting with 0-4% methanol in chloroform to give 0.5 g (72%). $^1$H NMR (400 MHz, CDCl$_3$) δ ppm 1.19 (d, J=6.61 Hz, 3H) 1.61-1.69 (m, 1H) 2.00 (dd, J=13.66, 7.81 Hz, 1H) 2.34 (td, J=12.90, 2.39 Hz, 1H) 2.46

(td, J=13.17, 6.72 Hz, 1H) 2.67 (s, 3H) 2.99-3.21 (m, 2H) 3.99 (s, 3H) 6.85 (dd, J=7.81, 1.73 Hz, 2H) 7.30-7.39 (m, 3H) 7.59 (s, 1H) 7.64 (s, 1H) 8.97 (s, 1H); MS (CI) m/z 410 (M+H)$^+$.

Example 18

(6aS,7S,10aR)-2,7-dimethyl-4-(2-methyl-1,3-thiazol-5-yl)-8-oxo-10a-phenyl-5,6,6a,7,8,10a-hexahydrobenzo[h]quinazoline-9-carbonitrile

Example 18A (6aS,7S,10aS)-2,7-dimethyl-4-(2-methyl-1,3-thiazol-5-yl)-10a-phenyl-5,6a,7,9,10,10a-hexahydrobenzo[h]quinazolin-8(6H)-one In a pressure tube, the product from Example 13D (0.4 g, 1.2 mmol), 2-methyl-5-(4,4,5,5-tetramethyl-1,3,2-dioxaborolan-2-yl)thiazole (0.32 g, 1.4 mmol), tetrakis(triphenylphosphine)palladium(0) (0.07 g, 0.06 mmol) and 2 M sodium carbonate (1.8 mL, 3.5 mmol) were combined in dioxane (8 mL) and dimethylformamide (1.5 mL). The mixture was sparged with nitrogen for 15 minutes. The pressure tube was sealed and heated to 80° C. for 2 hours. The reaction was cooled to room temperature, and additional 2-methyl-5-(4,4,5,5-tetramethyl-1,3,2-dioxaborolan-2-yl)thiazole (0.32 g, 1.4 mmol) and tetrakis(triphenylphosphine)palladium(0) (0.07 g, 0.06 mmol) were added. The mixture was sparged with nitrogen for 15 minutes and the tube was sealed followed by heating to 80° C. for 1 hour. The reaction mixture was diluted with ethyl acetate and washed with water. The aqueous layer was back extracted with ethyl acetate. The combined ethyl acetate layers were washed with saturated sodium chloride, dried over magnesium sulfate, filtered, and concentrated under reduced pressure. The residue was purified by flash chromatography on silica gel eluting with 10% acetone in heptane to give 0.47 g (82%) of the titled compound. $^1$H NMR (400 MHz, CDCl$_3$) δ ppm 1.17 (d, J=6.72 Hz, 3H) 2.02-2.22 (m, 3H) 2.25-2.37 (m, 1H) 2.50-2.59 (m, 2H) 2.59-2.64 (m, 1H) 2.66 (s, 3H) 2.75 (s, 3H) 2.90 (td, J=11.33, 5.42 Hz, 1H) 3.03-3.16 (m, 1H) 3.20-3.29 (m, 1H) 7.19-7.25 (m, 1H) 7.25-7.32 (m, 2H) 7.42 (d, J=7.92 Hz, 2H) 8.00 (s, 1H).

Example 18B (6aS,7S,9Z,10aS)-9-(hydroxymethylene)-2,7-dimethyl-4-(2-methyl-1,3-thiazol-5-yl)-10a-phenyl-5,6a,7,9,10,10a-hexahydrobenzo[h]quinazolin-8(6H)-one The titled compound was prepared using the conditions described in Example 13F, substituting Example 18A for Example 13E.

Example 18C (6aS,7S,11aS)-2,7-dimethyl-4-(2-methyl-1,3-thiazol-5-yl)-11a-phenyl-5,6,6a,7,11,11a-hexahydro[1,2]benzoxazolo[6,5-h]quinazoline The titled compound was prepared using the conditions described in Example 13G, substituting Example 18B for Example 13F.

Example 18D (6aS,7S,10aS)-2,7-dimethyl-4-(2-methyl-1,3-thiazol-5-yl)-8-oxo-10a-phenyl-5,6,6a,7,8,9,10,10a-octahydrobenzo[h]quinazoline-9-carbonitrile The titled compound was prepared using the conditions described in Example 13H, substituting Example 18C for Example 13G.

Example 18E (6aS,7S,10aR)-2,7-dimethyl-4-(2-methyl-1,3-thiazol-5-yl)-8-oxo-10a-phenyl-5,6,6a,7,8,10a-hexahydrobenzo[h]quinazoline-9-carbonitrile The titled compound was prepared using the conditions described in Example 13I, substituting Example 18D for Example 13H. The solid residue was purified by flash chromatography on silica gel eluting with 20% acetone in heptane to give the titled compound in 40% yield. $^1$H NMR (400 MHz, CDCl$_3$) δ ppm 1.21 (d, J=6.61 Hz, 3H) 1.60-1.73 (m, 1H) 2.09 (dd, J=13.66, 8.13 Hz, 1H) 2.36 (td, J=12.90, 2.17 Hz, 1H) 2.48 (td, J=13.07, 6.61 Hz, 1H) 2.66 (s, 3H) 2.79 (s, 3H) 3.05-3.25 (m, 2H) 6.84 (dd, J=7.59, 1.84 Hz, 2H) 7.29-7.37 (m, 3H) 8.21 (s, 1H) 8.95 (s, 1H); MS (CI) m/z 427 (M+H)$^+$.

Example 19

(6aS,7S,10aR)-7-methyl-2-(morpholin-4-yl)-8-oxo-10a-phenyl-5,6,6a,7,8,10a-hexahydrobenzo[h]quinazoline-9-carbonitrile

Example 19A (6aS,7S,10aS)-7-methyl-2-(morpholin-4-yl)-10a-phenyl-5,6a,7,9,10,10a-hexahydro-6H-spiro[benzo[h]quinazoline-8,2'-[1,3]dioxolane]

To a solution of Example 1G (1.10 g, 0.364 mmol) in isopropanol (30 mL) was added morpholinoformamidine hydrobromide (1.76 g, 8.37 mmol) and piperidine (0.829 mL, 8.37 mmol). The reaction mixture was heated at 90° C. for 6 hours. The cooled solution was diluted with saturated aqueous sodium phosphate monobasic solution and extracted with ethyl acetate. The organic phase was concentrated to provide the titled compound.

Example 19B (6aS,7S,10aS)-7-methyl-2-(morpholin-4-yl)-10a-phenyl-5,6a,7,9,10,10a-hexahydrobenzo[h]quinazolin-8(6H)-one The titled compound was prepared using the conditions described in Example 1I, substituting Example 19A for Example 1H, and was purified using a 40 g RediSep® silica gel cartridge on a Teledyne Isco Combiflash® Rf system, eluting with 0-40% ethyl acetate in heptane to give 0.520 g (42%). $^1$H NMR (400 MHz, CDCl$_3$) δ ppm 1.16 (d, J=6.61 Hz, 3H) 1.90-2.02 (m, 1H) 2.07-2.15 (m, 2H) 2.17-2.30 (m, 1H) 2.34-2.50 (m, 2H) 2.51-2.71 (m, 2H) 2.76 (td, J=12.71, 6.45 Hz, 1H) 3.11 (ddd, J=14.12, 5.67, 3.74 Hz, 1H) 3.77 (s, 8H) 7.21 (t, J=7.26 Hz, 1H) 7.26-7.32 (m, 2H) 7.51 (d, J=7.81 Hz, 2H) 8.04 (s, 1H) MS (ESI+) m/z 378 (M+H)$^+$.

Example 19C (6aS,7S,9Z,10aS)-9-(hydroxymethylene)-7-methyl-2-(morpholin-4-yl)-10a-phenyl-5,6a,7,9,10,10a-hexahydrobenzo[h]quinazolin-8(6H)-one The titled compound was prepared using the conditions described in Example 1J, substituting Example 19B for Example 1I and heating at 50° C. for 24 hours. MS (APCI+) m/z 406 (M+H)+.

Example 19D (6aS,7S)-7-methyl-2-(morpholin-4-yl)-11a-phenyl-5,6,6a,7,11,11a-hexahydro[1,2]benzoxazolo[6,5-h]quinazoline The titled compound was prepared using the conditions described in Example 1K, substituting Example 19C for Example 1J to give 0.228 g (42%).

Example 19E (6aS,7S)-7-methyl-2-(morpholin-4-yl)-8-oxo-10a-phenyl-5,6,6a,7,8,9,10,10a-octahydrobenzo[h]quinazoline-9-carbonitrile The titled compound was prepared using the conditions described in Example 1L, substituting Example 19D for Example 1K.

Example 19F (6aS,7S,10aR)-7-methyl-2-(morpholin-4-yl)-8-oxo-10a-phenyl-5,6,6a,7,8,10a-hexahydrobenzo[h]quinazoline-9-carbonitrile The titled compound was prepared using the conditions described in Example 1M, substituting Example 19E for Example 1L. $^1$H NMR (400 MHz, CDCl$_3$) δ ppm 1.17 (d, J=6.61 Hz, 3H) 1.46-1.54 (m, 1H) 1.88 (dd, J=14.15, 7.86 Hz, 1H) 2.28 (td, J=12.98, 2.44 Hz, 1H) 2.43 (td, J=13.15, 6.56 Hz, 1H) 2.76-2.98 (m, 2H) 3.66-3.78 (m, 8H) 6.88 (dd, J=7.64, 1.90 Hz, 2H) 7.29-7.36 (m, 3H) 8.30 (s, 1H) 8.75 (s, 1H); MS (ESI+) m/z 401 (M+H)+, 433 (M+CH$_3$OH+H)+.

Example 20

(6aS,7S,10aR)-4-hydroxy-2,7-dimethyl-8-oxo-10a-phenyl-5,6,6a,7,8,10a-hexahydrobenzo[h]quinazoline-9-carbonitrile

Example 20A (6aS,7S,9Z,10aS)-4-hydroxy-9-(hydroxymethylene)-2,7-dimethyl-10a-phenyl-5,6a,7,9,10,10a-hexahydrobenzo[h]quinazolin-8(6H)-one The titled compound was prepared using the conditions described in Example 13F, substituting Example 13C for Example 13E.

Example 20B (6aS,7S,11aS)-2,7-dimethyl-11a-phenyl-5,6,6a,7,11,11a-hexahydro[1,2]benzoxazolo[6,5-h]quinazolin-4-ol The titled compound was prepared using the conditions described in Example 13G, substituting Example 20A for Example 13F.

Example 20C (6aS,7S,10aS)-4-hydroxy-2,7-dimethyl-8-oxo-10a-phenyl-5,6,6a,7,8,9,10,10a-octahydrobenzo[h]quinazoline-9-carbonitrile The titled compound was prepared using the conditions described in Example 13H, substituting Example 20B for Example 13G.

Example 20D (6aS,7S,10aR)-4-hydroxy-2,7-dimethyl-8-oxo-10a-phenyl-5,6,6a,7,8,10a-hexahydrobenzo[h]quinazoline-9-carbonitrile The titled compound was prepared using the conditions described in Example 13I, substituting Example 20C for Example 13H and was purified by flash chromatography on silica gel eluting with 25% acetone in heptane to give 79% yield. $^1$H NMR (400 MHz, CDCl$_3$) δ ppm 1.16 (d, J=6.61 Hz, 3H) 1.40-1.54 (m, 1H) 1.91 (dd, J=14.20, 7.92 Hz, 1H) 2.24 (td, J=12.82, 2.11 Hz, 1H) 2.35 (td, J=13.15, 6.56 Hz, 1H) 2.43 (s, 3H) 2.66 (ddd, J=19.03, 10.95, 8.08 Hz, 1H) 2.84-2.98 (m, 1H) 6.99 (dd, J=7.75, 1.36 Hz, 2H) 7.31-7.41 (m, 3H) 8.78 (s, 1H) 11.89 (s, 1H); MS (CI) m/z 345 (M+NH$_4$)+.

Example 21

(6aS,7S,10aR)-2,7-dimethyl-8-oxo-4,10a-diphenyl-5,6,6a,7,8,10a-hexahydrobenzo[h]quinazoline-9-carbonitrile

Example 21A (6aS,7S,10aR)-4-chloro-2,7-dimethyl-8-oxo-10a-phenyl-5,6,6a,7,8,10a-hexahydrobenzo[h]quinazoline-9-carbonitrile The titled compound was prepared using the conditions described in Example 13D, substituting Example 20D for Example 13C. $^1$H NMR (400 MHz, CDCl$_3$) δ ppm 1.19 (d, J=6.72 Hz, 3H) 1.58-1.66 (m, 1H) 2.00 (dd, J=13.28, 8.62 Hz, 1H) 2.28 (td, J=12.93, 2.33 Hz, 1H) 2.44 (td, J=13.17, 6.72 Hz, 1H) 2.65 (s, 3H) 2.91 (ddd, J=18.87, 10.25, 8.73 Hz, 1H) 3.03-3.13 (m, 1H) 6.80 (dd, J=7.64, 1.79 Hz, 2H) 7.31-7.40 (m, 3H) 8.85 (s, 1H); MS (CI) m/z 381 (M+NH$_4$)+.

Example 21B (6aS,7S,10aR)-2,7-dimethyl-8-oxo-4,10a-diphenyl-5,6,6a,7,8,10a-hexahydrobenzo[h]quinazoline-9-carbonitrile In a pressure tube, the product from Example 21A (0.027 g, 0.074 mmol), phenylboronic acid (0.009 g, 0.074 mmol), tetrakis(triphenylphosphine)palladium(0) (0.004 g, 0.004 mmol) and 2 M sodium carbonate (0.11 mL, 0.22 mmol) were combined in dioxane (0.6 mL) and dimethylformamide (0.1 mL). The mixture was sparged with nitrogen for 15 minutes. The pressure tube was sealed and heated to 80° C. for 18 hours. The reaction was diluted with ethyl acetate and washed with water. The water layer was back washed with ethyl acetate. The combined ethyl acetate layers were washed with saturated sodium chloride, dried over magnesium sulfate, filtered, and concentrated under reduced pressure. The residue was purified by preparative thin layer chromatography eluting with 33% ethyl acetate in heptane to give the titled compound (0.007 g, 21%). $^1$H NMR (400 MHz, CDCl$_3$) δ ppm 1.16 (d, J=6.61 Hz, 3H) 1.48-1.55 (m, 1H) 1.83-1.94 (m, 1H) 2.35 (td, J=12.82, 2.33 Hz, 1H) 2.46 (td, J=13.09, 6.56 Hz, 1H) 2.71 (s, 3H) 2.96 (dd, J=8.78, 4.55 Hz, 2H) 6.85 (dd, J=7.92, 1.52 Hz, 2H) 7.30-7.37 (m, 3H) 7.47-7.60 (m, 5H) 8.99 (s, 1H); MS (CI) m/z 406 (M+H)$^+$.

Example 22

(6aS,7S,10aR)-2,7-dimethyl-8-oxo-10a-phenyl-4-(pyrimidin-5-yl)-5,6,6a,7,8,10a-hexahydrobenzo[h]quinazoline-9-carbonitrile Example 22A (6aS,7S,10aS)-2,7-dimethyl-10a-phenyl-4-(pyrimidin-5-yl)-5,6,6a,7,9,10,10a-hexahydrobenzo[h]quinazolin-8(6H)-one The titled compound was prepared using the conditions described in Example 17A, substituting pyrimidin-5-ylboronic acid for 1-methyl-5-(4,4,5,5-tetramethyl-1,3,2-dioxaborolan-2-yl)-1H-imidazole, and purified by flash chromatography on silica gel eluting with 20% acetone in heptane to give 100% yield. $^1$H NMR (400 MHz, CDCl$_3$) δ ppm 1.17 (d, J=6.51 Hz, 3H) 2.00 (td, J=11.87, 7.05 Hz, 1H) 2.06-2.23 (m, 2H) 2.28-2.45 (m, 2H) 2.46-2.54 (m, 1H) 2.63 (ddd, J=16.10, 7.92, 7.64 Hz, 1H) 2.77 (s, 3H) 2.82-2.96 (m, 2H) 3.18-3.29 (m, 1H) 7.23-7.29 (m, 1H) 7.33 (t, J=7.54 Hz, 2H) 7.54 (d, J=7.81 Hz, 2H) 8.89 (s, 2H) 9.27 (s, 1H); MS (DCI) m/z 385.1 (M+H)$^+$.

Example 22B (6aS,7S,9Z,10aS)-9-(hydroxymethylene)-2,7-dimethyl-1a-phenyl-4-(pyrimidin-5-yl)-5,6a,7,9,10,10a-hexahydrobenzo[h]quinazolin-8(6H)-one The titled compound was prepared using the conditions described in Example 13F, substituting Example 22A for Example 13E.

Example 22C (6aS,7S,11aS)-2,7-dimethyl-11a-phenyl-4-(pyrimidin-5-yl)-5,6,6a,7,11,11a-hexahydro[1,2]benzoxazolo[6,5-h]quinazoline The titled compound was prepared using the conditions described in Example 13G, substituting Example 22B for Example 13F.

Example 22D (6aS,7S,10aS)-2,7-dimethyl-8-oxo-10a-phenyl-4-(pyrimidin-5-yl)-5,6,6a,7,8,9,10,10a-octahydrobenzo[h]quinazoline-9-carbonitrile The titled compound was prepared using the conditions described in Example 13H, substituting Example 22C for Example 13G.

Example 22E (6aS,7S,10aR)-2,7-dimethyl-8-oxo-10a-phenyl-4-(pyrimidin-5-yl)-5,6,6a,7,8,10a-hexahydrobenzo[h]quinazoline-9-carbonitrile The titled compound was prepared using the conditions described in Example 13I, substituting Example 22D for Example 13H, and purified by flash chromatography on silica gel eluting with 50% ethyl acetate in heptane to give 56% yield. $^1$H NMR (400 MHz, CDCl$_3$) δ ppm 1.19 (d, J=6.61 Hz, 3H) 1.58-1.70 (m, 1H) 1.96 (dt, J=13.80, 2.97 Hz, 1H) 2.37 (td, J=12.82, 2.33 Hz, 1H) 2.48 (td, J=13.09, 6.56 Hz, 1H) 2.74 (s, 3H) 3.00-3.07 (m, 2H) 6.80-6.86 (m, 2H) 7.32-7.40 (m, 3H) 8.94 (s, 1H) 9.06 (s, 2H) 9.35 (s, 1H); MS (CI) m/z 404 (M+H)$^+$.

Example 23

(6aS,7S,10aR)-4-(3-furyl)-2,7-dimethyl-8-oxo-10a-phenyl-5,6,6a,7,8,10a-hexahydrobenzo[h]quinazoline-9-carbonitrile Example 23A (6aS,7S,10aS)-4-(3-furyl)-2,7-dimethyl-10a-phenyl-5,6a,7,9,10,10a-hexahydrobenzo[h]quinazolin-8(6H)-one In a pressure tube, the product from Example 13D (0.35 g, 1.0 mmol), 2-(furan-3-yl)-4,4,5,5-tetramethyl-1,3,2-dioxaborolane (0.20 g, 1.0 mmol), tetrakis(triphenylphosphine)palladium(0) (0.06 g, 0.05 mmol) and 2 M sodium carbonate (1.5 mL, 3.1 mmol) were combined in dioxane (7 mL) and dimethylformamide (1.3 mL). The mixture was sparged with nitrogen for 15 minutes. The pressure tube was sealed and heated to 80° C. for 18 hours. The reaction was diluted with ethyl acetate and washed with water. The aqueous layer was back extracted with ethyl acetate. The combined ethyl acetate layers were washed with saturated sodium chloride, dried over magnesium sulfate, filtered, and concentrated under reduced pressure. The residue was purified by flash chromatography on silica gel eluting with 20% ethyl acetate in heptane to the titled compound (0.34 g, 89%). $^1$H NMR (400 MHz, CDCl$_3$) δ ppm 1.16 (d, J=6.72 Hz, 3H) 2.00-2.17 (m, 3H) 2.27-2.39 (m, 1H) 2.50-2.59 (m, 2H) 2.64 (dd, J=11.66, 6.67 Hz, 1H) 2.68 (s, 3H) 2.78 (dt, J=16.83, 5.73 Hz, 1H) 2.93-3.04 (m, 1H) 3.25 (ddd, J=14.23, 6.04, 4.34 Hz, 1H) 6.96 (s, 1H) 7.22 (d, J=7.26 Hz, 1H) 7.25-7.31 (m, 2H) 7.43 (d, J=7.81 Hz, 2H) 7.51 (s, 1H) 7.86 (s, 1H); MS (ESI) m/z 373.2 (M+H)$^+$.

Example 23B (6aS,9Z,10aS)-4-(3-furyl)-9-(hydroxymethylene)-2,6a-dimethyl-10a-phenyl-5,6a,7,9,10,10a-hexahydrobenzo[h]quinazolin-8(6H)-one The titled compound was prepared using the conditions described in Example 13F, substituting Example 23A for Example 13E.

Example 23C (6aS,7S,11aS)-4-(3-furyl)-2,7-dimethyl-11a-phenyl-5,6,6a,7,11,11a-hexahydro[1,2]benzoxazolo[6,5-h]quinazoline The titled compound was prepared using the conditions described in Example 13G, substituting Example 23B for Example 13F.

Example 23D (6aS,7S,10aS)-4-(3-furyl)-2,7-dimethyl-8-oxo-10a-phenyl-5,6,6a,7,8,9,10,10a-octahydrobenzo[h]quinazoline-9-carbonitrile The titled compound was prepared using the conditions described in Example 13H, substituting Example 23C for Example 13G.

Example 23E (6aS,7S,10aR)-4-(3-furyl)-2,7-dimethyl-8-oxo-10a-phenyl-5,6,6a,7,8,10a-hexahydrobenzo[h]quinazoline-9-carbonitrile The titled compound was prepared using the conditions described in Example 13I, substituting Example 23D for Example 13H, and purified by flash chromatography on silica gel eluting with 10% acetone in heptane to give 67% yield. $^1$H NMR (400 MHz, CDCl$_3$) δ ppm 1.19 (d, J=6.61 Hz, 3H) 1.58-1.70 (m, 1H) 2.03 (dd, J=13.82, 7.86 Hz, 1H) 2.35 (td, J=12.90, 2.28 Hz, 1H) 2.47 (td, J=13.12, 6.72 Hz, 1H) 2.67 (s, 3H) 2.94-3.14 (m, 2H) 6.83 (dd, J=7.54, 1.90 Hz, 2H) 7.17 (d, J=1.30 Hz, 1H) 7.29-7.36 (m, 3H) 7.57 (s, 1H) 8.05 (s, 1H) 8.98 (s, 1H); MS (CI) m/z 396 (M+H)$^+$.

Example 24

(5aS,6S,9aR)-6-methyl-7-oxo-9a-phenyl-4,5,5a,6,7,9a-hexahydro-2H-benzo[g]indazole-8-carbonitrile

Example 24A (5aS,6S,9aS)-6-methyl-9a-phenyl-2,4,5,5a,6,8,9,9a-octahydrospiro[benzo[g]indazole-7,2'-[1,3]dioxolane]

To a solution of Example 1G (1.2 g, 3.65 mmol) in ethanol (36.5 mL) was added hydrazine (0.401 mL, 12.79 mmol). The reaction mixture was stirred at room temperature overnight. The reaction mixture was diluted with 1M NaHCO$_3$ solution and extracted with ethyl acetate. The organic fraction was dried over magnesium sulfate, filtered, and concentrated under vacuum. The residue was purified using a Biotage® SNAP silica 100 g cartridge using a gradient of 0-40% acetone in hexane to give the titled compound (1.1 g, 90% yield). $^1$H NMR (400 MHz, CDCl$_3$) δ ppm 1.01 (d, J=6.6 Hz, 3H), 1.45-1.57 (m, 2H), 1.69-1.78 (m, 1H), 2.11 (dd, J=14.0, 3.7 Hz, 1H), 2.48-2.74 (m, 4H), 3.91-3.99 (m, 5H), 7.07-7.15 (m, 1H), 7.21-7.27 (m, 3H), 7.58-7.69 (m, 2H); MS (DCI) m/z 325 (M+H)$^+$.

Example 24B (5aS,6S,9aS)-6-methyl-9a-phenyl-2,4,5,5a,6,8,9,9a-octahydro-7H-benzo[g]indazol-7-one Example 24A (1.18 g, 3.64 mmol) was dissolved in tetrahydrofuran (36.4 mL) and treated with 1 N HCl (18.19 mL, 36.4 mmol). The reaction mixture was stirred at room temperature overnight. The reaction mixture was neutralized with 1 N Na$_2$CO$_3$ and extracted with ethyl acetate. The organic fraction was dried over magnesium sulfate, filtered, and concentrated under vacuum. The residue was purified using a Biotage® SNAP silica 100 g cartridge using 0-50% acetone in hexane to give the titled compound (0.650 g, 64% yield). $^1$H NMR (400 MHz, CDCl$_3$) δ ppm 1.16 (d, J=6.8 Hz, 3H), 1.92-2.03 (m, 3H), 2.04-2.15 (m, 2H), 2.27-2.42 (m, 3H), 2.55-2.72 (m, 3H), 2.76-2.88 (m, 1H), 3.03 (ddd, J=13.8, 7.0, 4.5 Hz, 1H), 7.18 (t, J=7.2 Hz, 1H), 7.27 (t, J=7.7 Hz, 1H), 7.32 (s, 1H), 7.36 (d, J=7.7 Hz, 2H); MS (ESI) m/z 281 (M+H)$^+$.

Example 24C (5aS,6S,8Z,9aS)-8-(hydroxymethylene)-6-methyl-9a-phenyl-2,4,5,5a,6,8,9,9a-octahydro-7H-benzo[g]indazol-7-one Example 24B (0.050 g, 0.178 mmol) was dissolved in ethyl formate (2904 µL, 35.7 mmol) and treated with 25% sodium methoxide in methanol (195 µL, 0.892 mmol). The mixture was stirred at room temperature overnight. The reaction mixture was diluted with 2 N HCl and extracted with ethyl acetate. The combined organic washes were concentrated, and the titled compound was taken forward without additional purification. $^1$H NMR (400 MHz, CDCl$_3$) δ ppm 1.24 (d, J=6.5 Hz, 3H), 1.87-2.02 (m, 6H), 2.57-2.74 (m, 1H), 2.87-2.95 (m, 1H), 3.00 (d, J=15.3 Hz, 1H), 3.40-3.51 (m, 1H), 7.08 (dd, J=7.9, 1.6 Hz, 2H), 7.12-7.24 (m, 4H), 7.39 (s, 1H), 8.74 (s, 1H); MS (ESI) m/z 309 (M+H)$^+$.

Example 24D (5aS,6S,10aS)-6-methyl-10a-phenyl-4,5,5a,6,10,10a-hexahydro-2H-indazolo[7,6-f][1,2]benzoxazole Example 24C (0.504 g, 1.634 mmol) was dissolved in ethanol (16.300 mL) and treated with hydroxylamine hydrochloride (0.568 g, 8.17 mmol). The reaction mixture was stirred at 50° C. overnight. The reaction mixture was neutralized with 1 N Na$_2$CO$_3$ and extracted with ethyl acetate. The organic fraction was dried over magnesium sulfate, filtered, and concentrated under vacuum. The residue was purified using a Biotage® SNAP silica 50 g cartridge eluting with a gradient of 0-50% acetone in hexane to give the titled compound. (0.290 g, 58% yield). $^1$H NMR (400 MHz, CDCl$_3$) δ ppm 1.38 (d, J=6.8 Hz, 3H), 1.63-1.81 (m, 1H), 1.94-2.05 (m, 2H), 2.20-2.29 (m, 1H), 2.58-2.75 (m, 2H), 2.86-2.96 (m, 2H), 3.09 (dd, J=16.2, 2.5 Hz, 2H), 3.62 (d, J=16.2 Hz, 1H), 6.72-6.88 (m, 3H), 7.06-7.20 (m, 4H), 7.31 (s, 1H), 8.24 (s, 1H); MS (APCI) m/z 306 (M+H)+.

Example 24E (5aS,6S,9aS)-6-methyl-7-oxo-9a-phenyl-4,5,5a,6,7,8,9,9a-octahydro-2H-benzo[g]indazole-8-carbonitrile Example 24D (0.040 g, 0.131 mmol) was dissolved in tetrahydrofuran (1.3 mL) and treated with 25% sodium methoxide in methanol (0.143 mL, 0.655 mmol). The reaction mixture was stirred at room temperature for 2 hours. The reaction mixture was diluted with 1M $KH_2PO_3$ and extracted with ethyl acetate. The organic phase was dried over magnesium sulfate, filtered, and concentrated under vacuum. The residue was purified using a Biotage® SNAP silica 10 g cartridge using 0-50% gradient of acetone in hexane to give the titled compound (0.020 g, 50% yield).

Example 24F (6S,9aR)-6-methyl-7-oxo-9a-phenyl-4,5,5a,6,7,9a-hexahydro-2H-benzo[g]indazole-8-carbonitrile Example 24E (0.020 g, 0.065 mmol) was dissolved in tetrahydrofuran (655 µL), and the solution was sparged with nitrogen for 10 minutes. At this point, 2,3-dichloro-5,6-dicyano-1,4-benzoquinone (0.019 g, 0.085 mmol) was added, and the reaction mixture was stirred at room temperature for 10 minutes. The reaction mixture was then concentrated, and the residue was purified using a Biotage® SNAP silica 10 g cartridge using 0-80% gradient of acetone in hexane to give the titled compound (0.010 g, 10% yield). $^1$H NMR (400 MHz, $CDCl_3$) δ ppm 1.18 (d, J=6.6 Hz, 3H), 1.83 (dd, J=13.6, 7.5 Hz, 1H), 2.37 (dd, J=19.0, 6.7 Hz, 2H), 2.47 (dt, J=13.2, 6.6 Hz, 1H), 2.73 (ddd, J=36.5, 21.8, 16.0 Hz, 1H), 2.92 (dd, J=16.4, 6.6 Hz, 1H), 6.86-6.92 (m, 2H), 7.30 (d, J=7.6 Hz, 4H), 7.47 (s, 1H), 8.44 (s, 1H); MS (ESI) m/z 304 (M+H)+.

Example 25

(6aS,7S,10aR)-2-(2-fluorophenyl)-4-methoxy-7-methyl-8-oxo-10a-phenyl-5,6,6a,7,8,10a-hexahydrobenzo[h]quinazoline-9-carbonitrile

Example 25A (6aS,7S,10 aS)-2-(2-fluorophenyl)-7-methyl-10a-phenyl-5,6a,7,9,10,10a-hexahydro-6H-spiro[benzo[h]quinazoline-8,2'-[1,3]dioxolan]-4-ol To a solution of Example 13A (1.00 g, 2.79 mmol) in 1 M potassium t-butoxide (5.58 mL, 5.58 mmol) was added 2-fluorobenzimidamide hydrochloride (0.877 g, 5.02 mmol). The reaction mixture was heated at 90° C. for 72 hours. The mixture was diluted with saturated aqueous sodium phosphate monobasic solution and extracted with ethyl acetate. The organic phase was concentrated to provide the titled compound which was used without additional purification. MS (APCI+) m/z 447 (M+H)+.

Example 25B (6aS,7S,10aS)-2-(2-fluorophenyl)-4-hydroxy-7-methyl-10a-phenyl-5,6a,7,9,10,10a-hexahydrobenzo[h]quinazolin-8(6H)-one The titled compound was prepared using the conditions described in Example 1I, substituting Example 25A for Example 1H.

Example 25C (6aS,7S,10aS)-4-chloro-2-(2-fluorophenyl)-7-methyl-10a-phenyl-5,6a,7,9,10,10a-hexahydrobenzo[h]quinazolin-8(6H)-one The titled compound was prepared using the conditions described in Example 8C, substituting Example 25B for Example 8B.

Example 25D (6aS,7S,10aS)-2-(2-fluorophenyl)-4-methoxy-7-methyl-10a-phenyl-5,6a,7,9,10,10a-hexahydrobenzo[h]quinazolin-8(6H)-one The titled compound was prepared using the conditions described in Example 8D, substituting Example 25C for Example 8C. MS (APCI+) m/z 417 (M+H)+.

Example 25E (6aS,7S,9Z,10aS)-2-(2-fluorophenyl)-9-(hydroxymethylene)-4-methoxy-7-methyl-10a-phenyl-5,6a,7,9,10,10a-hexahydrobenzo[h]quinazolin-8(6H)-one The titled compound was prepared using the conditions described in Example 1J, substituting Example 25D for Example 1H.

Example 25F (6aS,7S,11aS)-2-(2-fluorophenyl)-4-methoxy-7-methyl-11a-phenyl-5,6,6a,7,11,11a-hexahydro[1,2]benzoxazolo[6,5-h]quinazoline The titled compound was prepared using the conditions described in Example 1K, substituting Example 25E for Example 1J. MS (APCI+) m/z 442 (M+H)+.

Example 25G (6aS,7S,10aS)-2-(2-fluorophenyl)-4-methoxy-7-methyl-8-oxo-10a-phenyl-5,6,6a,7,8,9,10,10a-octahydrobenzo[h]quinazoline-9-carbonitrile The titled compound was prepared using the conditions described in Example 1L, substituting Example 25F for Example 1K.

Example 25H (6aS,7S,10aR)-2-(2-fluorophenyl)-4-methoxy-7-methyl-8-oxo-10a-phenyl-5,6,6a,7,8,10a-hexahydrobenzo[h]quinazoline-9-carbonitrile The titled compound was prepared using the conditions described in Example 1M, substituting Example 25G for Example 1L and heating for 1 hour at 50° C. to give 0.050 g (21%). $^1$H NMR (400 MHz, CDCl$_3$) δ ppm 1.19 (d, J=6.61 Hz, 3H) 1.92-2.02 (m, 1H) 2.34 (td, J=12.82, 2.22 Hz, 1H) 2.44 (td, J=13.12, 6.61 Hz, 1H) 2.79 (ddd, J=19.00, 10.92, 8.13 Hz, 1H) 2.92-3.03 (m, 1H) 4.16 (s, 3H) 6.91 (d, J=7.81 Hz, 2H) 7.13 (dd, J=11.22, 8.40 Hz, 1H) 7.21 (t, J=7.97 Hz, 1H) 7.27-7.36 (m, 3H) 7.36-7.45 (m, 1H) 7.37-7.44 (m, 1H) 8.06 (td, J=7.78, 1.79 Hz, 1H) 9.00 (s, 1H); MS (APCI+) m/z 440 (M+H)$^+$.

Example 26

(5aS,6S,9aR)-1,6-dimethyl-7-oxo-9a-phenyl-3-(pyridin-3-yl)-4,5,5a,6,7,9a-hexahydro-1H-benzo[g]indazole-8-carbonitrile Example 26A (5aS,6S,9aS)-1,6-dimethyl-9a-phenyl-3-(pyridin-3-yl)-1,4,5,5a,6,8,9,9a-octahydro-7H-benzo[g]indazol-7-one The titled compound was prepared utilizing conditions described in Example 140E (49% yield) substituting Example 179A for Example 140D and substituting pyridin-3-ylboronic acid for 4-(4,4,5,5-tetramethyl-1,3,2-dioxaborolan-2-yl)pyridazine.

Example 26B (5aS,6S,8Z,9aS)-8-(hydroxymethylene)-1,6-dimethyl-9a-phenyl-3-(pyridin-3-yl)-1,4,5,5a,6,8,9,9a-octahydro-7H-benzo[g]indazol-7-one The titled compound was prepared utilizing conditions described in Example 177B (100% yield) substituting Example 26A for Example 177A.

Example 26C (5aS,6S,10aS)-1,6-dimethyl-10a-phenyl-3-(pyridin-3-yl)-4,5,5a,6,10,10a-hexahydro-1H-indazolo[7,6-f][1,2]benzoxazole The titled compound was prepared utilizing conditions described in Example 140G (100% yield) substituting Example 26B for Example 140F. MS (APCI+) m/z 397 (M+H)$^+$.

Example 26D (5aS,6S,9aS)-1,6-dimethyl-7-oxo-9a-phenyl-3-(pyridin-3-yl)-4,5,5a,6,7,8,9,9a-octahydro-1H-benzo[g]indazole-8-carbonitrile The titled compound was prepared utilizing conditions described in Example 177D (95% yield) substituting Example 26C for Example 177C.

Example 26E (5aS,6S,9aR)-1,6-dimethyl-7-oxo-9a-phenyl-3-(pyridin-3-yl)-4,5,5a,6,7,9a-hexahydro-1H-benzo[g]indazole-8-carbonitrile The titled compound was prepared utilizing conditions described in Example 97F (44% yield) substituting Example 26D for Example 97E. $^1$H NMR (400 MHz, CDCl$_3$) δ ppm 8.96 (t, J=23.0 Hz, 1H), 8.59 (d, J=4.7 Hz, 1H), 8.16 (s, 1H), 8.11 (dd, J=6.2, 1.8 Hz, 2H), 7.43-7.33 (m, 3H), 7.04-6.85 (m, 2H), 3.60 (s, 3H), 3.17-2.81 (m, 2H), 2.54 (t, J=12.1 Hz, 1H), 2.45-2.24 (m, 1H), 1.90 (dd, J=13.6, 5.6 Hz, 1H), 1.31-1.18 (m, 3H), 0.91-0.84 (m, 1H); MS (ESI+) m/z 395 (M+H)$^+$.

Example 27

(6aS,7S,10aR)-2,7-dimethyl-8-oxo-10a-phenyl-4-(pyridin-4-yl)-5,6,6a,7,8,10a-hexahydrobenzo[h]quinazoline-9-carbonitrile The titled compound was prepared using the conditions described in Example 21B substituting pyridin-4-ylboronic acid for phenylboronic acid and purified by flash chromatography on silica gel eluting with 50-80% ethyl acetate in chloroform to give 46% yield. $^1$H NMR (400 MHz, CDCl$_3$) δ ppm 1.17 (d, J=6.61 Hz, 3H) 1.50-1.64 (m, 1H) 1.88-1.95 (m, 1H) 2.35 (td, J=12.82, 2.33 Hz, 1H) 2.47 (td, J=13.12, 6.61 Hz, 1H) 2.72 (s, 3H) 2.94 (dd, J=9.43, 5.20 Hz, 2H) 6.83 (dd, J=7.70, 1.63 Hz, 2H) 7.32-7.40 (m, 3H) 7.49 (d, J=5.96 Hz, 2H) 8.80 (d, J=5.96 Hz, 2H) 8.96 (s, 1H); MS (CI) m/z 407 (M+H)$^+$.

Example 28

(5aS,6S,9aR)-2-acetyl-6-methyl-7-oxo-9a-phenyl-4,5,5a,6,7,9a-hexahydro-2H-benzo[g]indazole-8-carbonitrile The compound from Example 24F (0.010 g, 0.033 mmol) was dissolved in tetrahydrofuran (330 μL) and treated with triethylamine (9.19 μL, 0.066 mmol) and acetyl chloride (4.69 μl, 0.066 mmol). The reaction mixture was stirred at room temperature for 30 minutes. The reaction mixture was concentrated and purified by preparative thin-layer chromatography using 40% acetone/hexane to give the titled compound (0.006 g, 60% yield). $^1$H NMR (400 MHz, CDCl$_3$) δ ppm 1.11-1.23 (m, 3H), 1.79-1.92 (m, 2H), 2.26-2.38 (m, 1H), 2.43-2.54 (m, 1H), 2.64 (s, 3H), 2.69-2.86 (m, 1H), 2.90-3.01 (m, 1H), 3.49 (s, 1H), 3.71-3.80 (m, 1H), 6.87-6.94 (m, 2H), 7.31-7.38 (m, 3H), 8.14 (s, 1H), 8.44 (s, 1H); MS (ESI) m/z 346 (M+H)$^+$.

Example 29

(6aS,7S,10aR)-7-methyl-8-oxo-10a-phenyl-2-(pyridin-4-yl)-5,6,6a,7,8,10a-hexahydrobenzo[h]quinazoline-9-carbonitrile Example 29A (6aS,7S,10aS)-7-methyl-10a-phenyl-2-(pyridin-4-yl)-5,6a,7,9,10,10a-hexahydro-6H-spiro[benzo[h]quinazoline-8,2'-[1,3]dioxolane]

To a stirred solution of Example 1G (1.0 g, 0.305 mmol) in isopropanol (20 mL) at room temperature was added piperidine (0.904 mL, 9.14 mmol) and isonicotinimidamide hydrochloride (1.44 g, 9.14 mmol). The reaction mixture was heated at 95° C. for 28 hours. The cooled solution was diluted with saturated aqueous sodium phosphate monobasic solution and extracted with ethyl acetate. The ethyl acetate layer concentrated to provide the titled compound. MS (APCI+) m/z 414 (M+H)$^+$.

Example 29B (6aS,7S,10aS)-7-methyl-10a-phenyl-2-(pyridin-4-yl)-5,6a,7,9,10,10a-hexahydrobenzo[h]quinazolin-8(6H)-one The titled compound was prepared using the conditions described in Example 1I, substituting Example 29A for Example 1H and stirring at room temperature for 18 hours. The titled compound (0.450 g, 40%) was obtained following purification using a 24 g RediSep® silica gel cartridge on a Teledyne Isco Combiflash® Rf system, eluting with 0-3% methanol in dichloromethane.

Example 29C (6aS,7S,9Z,10aS)-9-(hydroxymethylene)-7-methyl-10a-phenyl-2-(pyridin-4-yl)-5,6a,7,9,10,10a-hexahydrobenzo[h]quinazolin-8(6H)-one The titled compound was prepared using the conditions described in Example 1J, substituting Example 29B for Example 1I. MS (APCI+) m/z 398 (M+H)$^+$.

Example 29D (6aS,7S,11aS)-7-methyl-11a-phenyl-2-(pyridin-4-yl)-5,6,6a,7,11,11a-hexahydro[1,2]benzoxazolo[6,5-h]quinazoline The titled compound was prepared using the conditions described in Example 1K, substituting Example 29C for Example 1J.

Example 29E (6aS,7S,10aS)-7-methyl-8-oxo-10a-phenyl-2-(pyridin-4-yl)-5,6,6a,7,8,9,10,10a-octahydrobenzo[h]quinazoline-9-carbonitrile The titled compound was prepared using the conditions described in Example 1L, substituting Example 29D for Example 1K.

Example 29F (6aS,7S,10aR)-7-methyl-8-oxo-10a-phenyl-2-(pyridin-4-yl)-5,6,6a,7,8,10a-hexahydrobenzo[h]quinazoline-9-carbonitrile The titled compound (0.081 g, 51%) was prepared using the conditions described in Example 1M, substituting Example 29E for Example 1L and purified on a Teledyne Isco Combiflash® Rf system using a 12 g RediSep® silica gel cartridge eluting with 0-50% ethyl acetate in heptane. $^1$H NMR (400 MHz, CDCl$_3$) δ ppm 1.22 (d, J=6.61 Hz, 3H) 1.44-1.50 (m, 1H) 2.00-2.09 (m, 1H) 2.38 (td, J=12.90, 2.39 Hz, 1H) 2.51 (td, J=13.12, 6.72 Hz, 1H) 3.06-3.28 (m, 2H) 6.82 (dd, J=7.43, 2.01 Hz, 2H) 7.32-7.38 (m, 3H) 8.52-8.58 (m, 2H) 8.79 (d, J=6.07 Hz, 2H) 8.90 (d, J=2.71 Hz, 2H); MS (ESI−) m/z 391 (M−H)$^−$, 423 (M+CH$_3$OH—H)$^−$.

Example 30

(6aS,7S,10aR)-2-(diethylamino)-7-methyl-8-oxo-10a-phenyl-5,6,6a,7,8,10a-hexahydrobenzo[h]quinazoline-9-carbonitrile

Example 30A (6aS,7S,10aS)—N,N-diethyl-7-methyl-10a-phenyl-5,6a,7,9,10,10a-hexahydro-6H-spiro[benzo[h]quinazoline-8,2'-[1,3]dioxolan]-2-amine To a stirred solution of Example 1G (0.750 g, 0.2.28 mmol) in isopropanol (15 mL) at room temperature was added piperidine (0.339 mL, 3.43 mmol) and 1,1-diethylguanidine hydrochloride (0.519 g, 3.43 mmol). The reaction mixture was heated at 95° C. for 28 hours. The cooled solution was diluted with saturated aqueous sodium phosphate monobasic solution and extracted with ethyl acetate. The organic phase was concentrated to provide the titled compound.

Example 30B (6aS,7S,10aS)-2-(diethylamino)-7-methyl-10a-phenyl-5,6a,7,9,10,10a-hexahydrobenzo[h]quinazolin-8(6H)-one The titled compound was prepared using the conditions described in Example 1I, substituting Example 30A for Example 1H.

Example 30C (6aS,7S,9Z,10aS)-2-(diethylamino)-9-(hydroxymethylene)-7-methyl-10a-phenyl-5,6a,7,9,10,10a-hexahydrobenzo[h]quinazolin-8(6H)-one The titled compound was prepared using the conditions described in Example 1J, substituting Example 30B for Example 1I. MS (APCI+) m/z 392 M+H)$^+$.

Example 30D (6aS,7S,11aS)—N,N-diethyl-7-methyl-11a-phenyl-5,6,6a,7,11,11a-hexahydro[1,2]benzoxazolo[6,5-h]quinazolin-2-amine The titled compound was prepared using the conditions described in Example 1K, substituting Example 30C for Example 1J. MS (APCI+) m/z 389 M+H)$^+$.

Example 30E (6aS,7S,10aS)-2-(diethylamino)-7-methyl-8-oxo-10a-phenyl-5,6,6a,7,8,9,10,10a-octahydrobenzo[h]quinazoline-9-carbonitrile The titled compound was prepared using the conditions described in Example 1L, substituting Example 30D for Example 1K.

Example 30F (6aS,7S,10aR)-2-(diethylamino)-7-methyl-8-oxo-10a-phenyl-5,6,6a,7,8,10a-hexahydrobenzo[h]quinazoline-9-carbonitrile The titled compound was prepared using the conditions described in Example 1M, substituting Example 30E for Example 1L, and purification using a 12 g RediSep® silica gel cartridge on a Teledyne Isco Combiflash® Rf system eluting with 0-10% ethyl acetate in heptane to give the titled compound (0.039 g, 48%). $^1$H NMR (400 MHz, CDCl$_3$) δ ppm 1.10 (t, J=6.89 Hz, 6H) 1.17 (d, J=6.72 Hz, 3H) 1.44-1.54 (m, 1H) 1.86 (dd, J=13.99, 7.59 Hz, 1H) 2.28 (td, J=12.85, 2.39 Hz, 1H) 2.44 (td, J=13.26, 6.78 Hz, 1H) 2.74-2.93 (m, 2H) 3.45-3.63 (m, 4H) 6.90 (dd, J=7.86, 1.57 Hz, 2H) 7.27-7.36 (m, 3H) 8.26 (s, 1H) 8.79 (s, 1H); MS (ESI+) m/z 387 (M+H)$^+$, 419 (M+CH$_3$OH+H)$^+$.

Example 31

(6aS,7S,10aR)-2-(2-fluorophenyl)-4-isopropoxy-7-methyl-8-oxo-10a-phenyl-5,6,6a,7,8,10a-hexahydrobenzo[h]quinazoline-9-carbonitrile

Example 31A (6aS,7S,10aS)-2-(2-fluorophenyl)-4-isopropoxy-7-methyl-10a-phenyl-5,6a,7,9,10,10a-hexahydrobenzo[h]quinazolin-8(6H)-one To a solution of Example 25C (0.323 g, 0.767 mmol) in isopropanol (8 mL) was added sodium isopropoxide (0.315 g, 3.84 mmol). The reaction mixture was heated at 50° C. for 2 hours. The cooled solution was diluted with saturated aqueous sodium phosphate monobasic solution and extracted with ethyl acetate. The organic phase was concentrated, and the residue was purified using a 12 g RediSep® silica gel cartridge on a Teledyne Isco Combiflash® Rf system eluting with 0-40% ethyl acetate in heptane to give the titled compound (0.035 g, 10%). MS (APCI+) m/z 445 (M+H)$^+$.

Example 31B (6aS,7S,9Z,10aS)-2-(2-fluorophenyl)-9-(hydroxymethylene)-4-isopropoxy-7-methyl-10a-phenyl-5,6a,7,9,10,10a-hexahydrobenzo[h]quinazolin-8(6H)-one The titled compound was prepared using the conditions described in Example 1J, substituting Example 31A for Example 1I and stirring at room temperature for 18 hours.

Example 31C (6aS,7S,11aS)-2-(2-fluorophenyl)-4-isopropoxy-7-methyl-11a-phenyl-5,6,6a,7,11,11a-hexahydro[1,2]benzoxazolo[6,5-h]quinazoline The titled compound was prepared using the conditions described in Example 1K, substituting Example 31B for Example 1J.

Example 31D (6aS,7S,10aS)-2-(2-fluorophenyl)-4-isopropoxy-7-methyl-8-oxo-10a-phenyl-5,6,6a,7,8,9,10,10a-octahydrobenzo[h]quinazoline-9-carbonitrile The titled compound was prepared using the conditions described in Example 1L, substituting Example 31C for Example 1K and stirring at room temperature for 18 hours.

Example 31E (6aS,7S,10aR)-2-(2-fluorophenyl)-4-isopropoxy-7-methyl-8-oxo-10a-phenyl-5,6,6a,7,8,10a-hexahydrobenzo[h]quinazoline-9-carbonitrile To a solution of the product from Example 31D (0.024 g, 0.051 mmol) in dimethylformamide (1.5 mL) cooled to 0° C. in an ice water bath was added 1,3-dibromo-5,5-dimethylhydantoin (0.007 g, 0.026 mmol). The solution was stirred at 0° C. for 30 minutes, and then pyridine (0.041 mL, 0.511 mmol) was added followed by heating at 55° C. for 1 hour. The cooled solution was diluted with water and extracted with ethyl acetate. The organic phase was washed with brine and concentrated. The residue was purified using a 12 g RediSep® silica gel cartridge on a Teledyne Isco Combiflash® Rf system, eluting with 0-10% ethyl acetate in heptane, to give the titled compound (0.013 g, 54%). $^1$H NMR (400 MHz, CDCl$_3$) δ ppm 1.18 (d, J=6.61 Hz, 3H) 1.34-1.40 (m, 1H) 1.42 (d, J=6.18 Hz, 3H) 1.50 (d, J=6.18 Hz, 3H) 1.95 (ddd, J=14.61, 7.35, 1.25 Hz, 1H) 2.33 (td, J=12.90, 2.39 Hz, 1H) 2.44 (td, J=13.17, 6.83 Hz, 1H) 2.77 (ddd, J=18.92, 10.95, 7.86 Hz, 1H) 2.89-2.98 (m, 1H) 5.59 (dt, J=12.39, 6.22 Hz, 1H) 6.90-6.95 (m, 2H) 7.09-7.24 (m, 3H) 7.28-7.35 (m, 2H) 7.36-7.44 (m, 1H) 8.03 (td, J=7.75, 1.73 Hz, 1H) 9.00 (s, 1H); MS (APCI+) m/z 468 (M+H)$^+$.

Example 32 methyl (5aS,6S,9aR)-8-cyano-6-methyl-7-oxo-9a-phenyl-4,5,5a,6,7,9a-hexahydro-2H-benzo[g]indazole-2-carboxylate The compound from Example 24F (0.110 g, 0.033 mmol) was dissolved in tetrahydrofuran (0.330 mL) and treated with triethyl amine (0.009 mL, 0.066 mmol) and methyl carbonochloridate (5.64 μL, 0.066 mmol). The reaction mixture was stirred at room temperature overnight and then concentrated. The residue was purified by reversed-phase Waters HPLC using a Nova-Pak® C18 Radial-Pak 6 μm, 60 Å, 40×100 mm, cartridge eluting with a gradient of 10-90% acetonitrile in aqueous 0.1% trifluoroacetic acid (60 mL/minute) to give the titled compound as the trifluoroacetic acid salt (0.005 g 40% yield). $^1$H NMR (400 MHz, CDCl$_3$) δ ppm 1.13-1.22 (m, 3H), 1.81-1.90 (m, 1H), 2.27-2.38 (m, 1H), 2.42-2.54 (m, 1H), 2.70-2.83 (m, 1H), 2.89-2.99 (m, 1H), 4.07 (s, 3H), 6.84-6.94 (m, 2H), 7.27-7.36 (m, 3H), 8.07 (s, 1H), 8.50 (s, 1H); MS (DCI) m/z 379 (M+NH$_4$)+.

Example 33 rac-(6aS,7S,10aR)-2,7-dimethyl-8-oxo-10a-phenyl-5,6,6a,7,8,10a-hexahydrobenzo[h]quinazoline-9-carbonitrile

Example 33A rac-(6aS,7S,10aS)-2,7-dimethyl-10a-phenyl-5,6a,7,9,10,10a-hexahydro-6H-spiro[benzo[h]quinazoline-8,2'-[1,3]dioxolane]

To a solution of acetamidine hydrochloride (0.86 g, 9.10 mmol) and piperidine (0.45 mL, 4.54 mmol) in isopropanol (10 mL), Example 21 (0.300 g, 0.913 mmol) was added. The vial was sealed, and the solution was heated to 90° C. for 4 days. The reaction mixture was cooled, concentrated under reduced pressure. The residue was partitioned between ethyl acetate and saturated potassium dihydrogen phosphate. The organic fraction was washed with brine, dried (MgSO$_4$), and concentrated under reduced pressure. The residue was purified by column chromatography (silica gel, 40% ethyl acetate in hexanes) to give the titled compound (0.141 g, 44%). MS (APCI) m/z 351 (M+H)$^+$.

Example 33B rac-(6aS,7S,10aS)-2,7-dimethyl-10a-phenyl-5,6a,7, 9,10,10a-hexahydrobenzo[h]quinazolin-8(6H)-one A solution of Example 33A (0.141 g, 0.402 mmol) and 3 N hydrochloric acid (6 mL) in methanol (10 mL) was stirred at room temperature for 16 hours. The reaction mixture was concentrated under reduced pressure, cooled to room temperature, basified with aqueous ammonium hydroxide (10% w/w), and extracted with ethyl acetate. The organic fraction was washed with brine, dried (MgSO$_4$), filtered and concentrated to give 0.098 g (80%) of the titled compound, which was used without purification in the next step. MS (APCI) m/z 307 (M+H)$^+$.

Example 33C rac-(6aS,7S,9Z,10aS)-9-(hydroxymethylene)-2,7-dimethyl-10a-phenyl-5,6a,7,9,10,10a-hexahydrobenzo[h]quinazolin-8(6H)-one Sodium methoxide (30% w/w, 0.30 mL) was added to a solution of Example 33B (0.098 g, 0.32 mmol) and ethyl formate (2.6 mL) in benzene (10 mL), and the mixture was stirred overnight at room temperature. The reaction mixture was diluted with ethyl acetate (200 mL), washed with saturated aqueous potassium dihydrogen phosphate, dried (MgSO$_4$), and concentrated under reduced pressure to give 0.091 g (85%) of the titled compound. MS (APCI) m/z 335 (M+H)$^+$.

Example 33D rac-(6aS,7S,11aS)-2,7-dimethyl-11a-phenyl-5,6,6a,7, 11,11a-hexahydro[1,2]benzoxazolo[6,5-h]quinazoline Hydroxylamine hydrochloride (0.028 g, 0.402 mmol) was added to a room temperature solution of Example 33C (0.091 g, 0.27 mmol) in methanol/water (1/1 v/v, 10 mL). The mixture was stirred at 60° C. for 2 hours and then at room temperature overnight. The reaction mixture was concentrated under reduced pressure; the residue was dissolved in ethyl acetate, washed with saturated aqueous sodium bicarbonate and brine, dried (MgSO$_4$), and concentrated under reduced pressure. The residue was used without further additional purification. MS (APCI) m/z 332 (M+H)$^+$.

Example 33E rac-(6aS,7S,10aS)-2,7-dimethyl-8-oxo-10a-phenyl-5, 6,6a,7,8,9,10,10a-octahydrobenzo[h]quinazoline-9-carbonitrile Sodium methoxide (30% w/w, 0.26 mL) was added to a room temperature solution of Example 33D (all above obtained, ≤0.27 mmol) in methanol/tetrahydrofuran (2/1 v/v, 15 mL), and stirred for 16 hours at room temperature. The mixture was concentrated under reduced pressure. The residue was diluted with ethyl acetate, washed with saturated potassium dihydrogen phosphate and brine, dried (MgSO$_4$), and concentrated under reduced pressure to give 0.103 g (100%) of the titled compound.

Example 33F rac-(6aS,7S,10aR)-2,7-dimethyl-8-oxo-10a-phenyl-5,6,6a,7,8,10a-hexahydrobenzo[h]quinazoline-9-carbonitrile A solution of 1,3-dibromo-5,5-dimethylhydantoin (0.039 g, 0.136 mmol) in N,N-dimethylformamide (5 mL) was added to a 0° C. solution of Example 33E (all above obtained, ≤0.027 mmol) in N,N-dimethylformamide (5 mL), and the reaction mixture was stirred at 0° C. for 1 hour. Pyridine (0.25 mL, 3.1 mmol) was added, the reaction was heated to 50° C. for 2 hours, and then at room temperature overnight. The reaction mixture was concentrated under reduced pressure. The residue was diluted with ethyl acetate, washed with saturated aqueous potassium dihydrogen phosphate solution and brine, dried (MgSO$_4$), and concentrated under reduced pressure. The residue was purified by column chromatography (silica gel, 60% ethyl acetate in hexanes) to give 0.018 g (20%) of a white solid. $^1$H NMR (400 MHz, CDCl$_3$) δ ppm 8.90 (s, 1H), 8.60 (s, 1H), 7.30-7.35 (m, 3H), 6.78-6.80 (m, 2H), 3.06 (dd, J=7.1, 17.9 Hz, 1H), 2.96 (ddd, J=7.6, 11.0, 18.1 Hz, 1H), 2.67 (s, 3H), 2.45 (qd, J=6.7, 13.4 Hz, 1H), 2.29 (dt, J=2.5, 12.9 Hz, 1H), 1.92-1.97 (m, 1H), 1.56-1.65 (m, 1H), 1.18 (d, J=6.7 Hz, 3H); MS (APCI) m/z 330 (M+H)$^+$.

Example 34

(6aS,7S,10aR)-2,7-dimethyl-8-oxo-10a-phenyl-4-(1H-pyrazol-4-yl)-5,6,6a,7,8,10a-hexahydrobenzo[h]quinazoline-9-carbonitrile Example 34A (6aS,7S,10aS)-2,7-dimethyl-10a-phenyl-4-(1H-pyrazol-4-yl)-5,6a,7,9,10,10a-hexahydrobenzo[h]quinazolin-8(6H)-one The titled compound was prepared using the conditions described in Example 17A, substituting 4-(4,4,5,5-tetramethyl-1,3,2-dioxaborolan-2-yl)-1H-pyrazole for 1-methyl-5-(4,4,5,5-tetramethyl-1,3,2-dioxaborolan-2-yl)-1H-imidazole and purification using flash chromatography on silica gel eluting with 20-25% acetone in heptane to give 67% yield. $^1$H NMR (400 MHz, CDCl$_3$) δ ppm 1.17 (d, J=6.72 Hz, 3H) 2.02-2.20 (m, 3H) 2.33 (ddd, J=14.29, 10.17, 7.75 Hz, 1H) 2.56 (dd, J=7.86, 4.28 Hz, 2H) 2.63 (dd, J=11.49, 6.61 Hz, 1H) 2.67 (s, 3H) 2.80-2.90 (m, 1H) 2.98-3.10 (m, 1H) 3.20-3.30 (m, 1H) 7.21 (t, J=7.26 Hz, 1H) 7.26-7.32 (m, 2H) 7.43 (d, J=7.81 Hz, 2H) 8.11 (s, 2H); MS (ESI) m/z 373.3 (M+H)$^+$.

Example 34B (6aS,9Z,10aS)-9-(hydroxymethylene)-2,6a-dimethyl-10a-phenyl-4-(1H-pyrazol-4-yl)-5,6a,7,9,10, 10a-hexahydrobenzo[h]quinazolin-8(6H)-one The titled compound was prepared using the conditions described in Example 13F, substituting Example 34A for Example 13E.

Example 34C (6aS,7S,11aS)-2,7-dimethyl-11a-phenyl-4-(1H-pyrazol-4-yl)-5,6,6a,7,11,11a-hexahydro[1,2]benzoxazolo[6,5-h]quinazoline The titled compound was prepared using the conditions described in Example 13G, substituting Example 34B for Example 13F.

Example 34D (6aS,7S,10aS)-2,7-dimethyl-8-oxo-10a-phenyl-4-(1H-pyrazol-4-yl)-5,6,6a,7,8,9,10,10a-octahydrobenzo[h]quinazoline-9-carbonitrile The titled compound was prepared using the conditions described in Example 13H, substituting Example 34C for Example 13G.

Example 34E (6aS,7S,10aR)-2,7-dimethyl-4-(1-methyl-1H-pyrazol-4-yl)-8-oxo-10a-phenyl-5,6,6a,7,8,10a-hexahydrobenzo[h]quinazoline-9-carbonitrile The titled compound was prepared using the conditions described in Example 13I, substituting Example 34D for Example 13H and purification using flash chromatography on silica gel eluting with 50-66% ethyl acetate in chloroform to give 52% yield. $^1$H NMR (400 MHz, CDCl$_3$) δ ppm 1.20 (d, J=6.61 Hz, 3H) 1.64-1.71 (m, 1H) 2.01-2.09 (m, 1H) 2.36 (td, J=12.90, 2.17 Hz, 1H) 2.47 (td, J=13.12, 6.61 Hz, 1H) 2.66 (s, 3H) 3.02-3.21 (m, 2H) 6.85 (dd, J=7.64, 1.79 Hz, 2H) 7.30-7.36 (m, 3H) 7.60 (s, 1H) 8.30 (s, 2H) 8.98 (s, 1H); MS (CI) m/z 396 (M+H)$^+$.

Example 35

(6aS,7S,10aR)-2,7-dimethyl-4-(1-methyl-1H-pyrazol-4-yl)-8-oxo-10a-phenyl-5,6,6a,7,8,10a-hexahydrobenzo[h]quinazoline-9-carbonitrile

Example 35A (6aS,7S,10aS)-2,7-dimethyl-4-(1-methyl-1H-pyrazol-4-yl)-10a-phenyl-5,6a,7,9,10,10a-hexahydrobenzo[h]quinazolin-8(6H)-one The titled compound was prepared using the conditions described in Example 23A, substituting 1-methyl-4-(4,4,5,5-tetramethyl-1,3,2-dioxaborolan-2-yl)-1H-pyrazole for 2-(furan-3-yl)-4,4,5,5-tetramethyl-1,3,2-dioxaborolane and purification by flash chromatography on silica gel eluting with 20-33% acetone in heptane to give 86% yield. $^1$H NMR (400 MHz, CDCl$_3$) δ ppm 1.16 (d, J=6.72 Hz, 3H) 2.00-2.17 (m, 3H) 2.27-2.39 (m, 1H) 2.51-2.58 (m, 2H) 2.61 (dd, J=11.49, 6.72 Hz, 1H) 2.65 (s, 3H) 2.84 (ddd, J=16.56, 5.45, 5.31 Hz, 1H) 2.98-3.08 (m, 1H) 3.19-3.29 (m, 1H) 3.97 (s, 3H) 7.21 (t, J=7.26 Hz, 1H) 7.24-7.31 (m, 2H) 7.42 (d, J=7.92 Hz, 2H) 7.94 (d, J=11.28 Hz, 2H); MS (ESI) m/z 387.3 (M+H)$^+$.

Example 35B (6aS,7S,9Z,10aS)-9-(hydroxymethylene)-2,7-dimethyl-4-(1-methyl-1H-pyrazol-4-yl)-10a-phenyl-5,6a,7,9,10,10a-hexahydrobenzo[h]quinazolin-8(6H)-one The titled compound was prepared using the conditions described in Example 13F, substituting Example 35A for Example 13E.

Example 35C (6aS,7S,11aS)-2,7-dimethyl-4-(1-methyl-1H-pyrazol-4-yl)-11a-phenyl-5,6,6a,7,11,11a-hexahydro[1,2]benzoxazolo[6,5-h]quinazoline The titled compound was prepared using the conditions described in Example 13G, substituting Example 35B for Example 13F.

Example 35D (6aS,7S,10aS)-2,7-dimethyl-4-(1-methyl-1H-pyrazol-4-yl)-8-oxo-10a-phenyl-5,6,6a,7,8,9,10,10a-octahydrobenzo[h]quinazoline-9-carbonitrile The titled compound was prepared using the conditions described in Example 13H, substituting Example 35C for Example 13G.

Example 35E (6aS,7S,10aR)-2,7-dimethyl-4-(1-methyl-1H-pyrazol-4-yl)-8-oxo-10a-phenyl-5,6,6a,7,8,10a-hexahydrobenzo[h]quinazoline-9-carbonitrile The titled compound was prepared using the conditions described in Example 13I, substituting Example 35D for Example 13H and purification by flash chromatography on silica gel eluting with 33% ethyl acetate in chloroform to give 41% yield. $^1$H NMR (400 MHz, CDCl$_3$) δ ppm 1.20 (d, J=6.61 Hz, 3H) 1.59-1.70 (m, 1H) 2.04 (dd, J=13.61, 8.29 Hz, 1H) 2.34 (td, J=12.88, 2.22 Hz, 1H) 2.47 (td, J=13.12, 6.61 Hz, 1H) 2.64 (s, 3H) 2.99-3.19 (m, 2H) 4.02 (s, 3H) 6.85 (dd, J=7.59, 1.84 Hz, 2H) 7.29-7.36 (m, 3H) 8.11 (s, 1H) 8.15 (s, 1H) 8.98 (s, 1H); MS (CI) m/z 410 (M+H)$^+$.

Example 36

(5aS,6S,9aR)-6-methyl-2-(methylsulfonyl)-7-oxo-9a-phenyl-4,5,5a,6,7,9a-hexahydro-2H-benzo[g]indazole-8-carbonitrile The compound from Example 24F (0.010 g, 0.033 mmol) was dissolved in dichloromethane (0.264 mL) and treated with triethylamine (0.009 mL, 0.066 mmol) and methanesulfonyl chloride (0.007 mL, 0.066 mmol). The reaction mixture was stirred at room temperature overnight and then concentrated. The residue was purified by reversed-phase Waters HPLC using a Nova-Pak® C18 Radial-Pak 6 μm, 60 Å, 40×100 mm, cartridge eluting with a gradient of 10-90% acetonitrile in aqueous 0.1% trifluoroacetic acid (60 mL/minute) to give the titled compound as the trifluoroacetic acid salt (0.001 g 8% yield). $^1$H NMR (400 MHz, CDCl$_3$) δ ppm 1.19 (d, J=6.7 Hz, 3H), 1.87 (dd, J=13.9, 7.8 Hz, 1H), 2.32 (t, J=12.0 Hz, 1H), 2.49 (dq, J=13.4, 6.8 Hz, 1H), 2.69-2.85 (m, 1H), 2.96 (dd, J=17.1, 6.8 Hz, 1H), 3.32 (s, 3H), 6.78-6.92 (m, 2H), 7.32 (t, J=5.6 Hz, 3H), 7.95 (s, 1H), 8.43 (s, 1H); MS (DCI) m/z 399 (M+NH$_4$)$^+$.

Example 37 phenyl (5aS,6S,9aR)-8-cyano-6-methyl-7-oxo-9a-phenyl-4,5,5a,6,7,9a-hexahydro-2H-benzo[g]indazole-2-carboxylate The compound from Example 24F (0.020 g, 0.066 mmol) was dissolved in dichloromethane (0.659 mL) and treated with triethylamine (0.027 mL, 0.198 mmol) and phenyl chloroformate (0.031 g, 0.198 mmol). The reaction mixture was stirred at room temperature overnight and concentrated. The residue was purified by reversed-phase Waters HPLC using a Nova-Pak® C18 Radial-Pak 6 µm, 60 Å, 40×100 mm, cartridge eluting with a gradient of 10-90% acetonitrile in aqueous 0.1% trifluoroacetic acid (60 mL/minute) to give the titled compound as the trifluoroacetic acid salt (0.019. g 68%). $^1$H NMR (400 MHz, CDCl$_3$) δ ppm 1.19 (t, J=5.9 Hz, 3H), 1.86-1.97 (m, 1H), 2.18 (s, 1H), 2.29-2.41 (m, 1H), 2.44-2.58 (m, 1H), 2.73-2.88 (m, 1H), 2.94-3.06 (m, 1H), 6.90-6.96 (m, 2H), 7.28-7.38 (m, 5H), 7.41-7.50 (m, 2H), 8.15-8.21 (m, 1H), 8.56 (s, 1H); MS (DCI) m/z 441 (M+NH$_4$)$^+$.

Example 38

(5aS,6S,9aR)-2-benzoyl-6-methyl-7-oxo-9a-phenyl-4,5,5a,6,7,9a-hexahydro-2H-benzo[g]indazole-8-carbonitrile The compound from Example 24F (0.020 g, 0.066 mmol) was dissolved in dichloromethane (0.659 mL) and treated with triethylamine (0.027 mL, 0.198 mmol) and benzoyl chloride (0.023 mL, 0.198 mmol). The reaction mixture was stirred at room temperature for 30 minutes and then concentrated. The residue was purified by reversed-phase Waters HPLC using a Nova-Pak® C18 Radial-Pak 6 µm, 60 Å, 40×100 mm, cartridge eluting with a gradient of 10-90% acetonitrile in aqueous 0.1% trifluoroacetic acid (60 mL/minute) to give the titled compound as the trifluoroacetic acid salt (0.024 g 89% yield). $^1$H NMR (400 MHz, CDCl$_3$) δ ppm 0.79-0.92 (m, 1H), 1.20 (d, J=6.7 Hz, 3H), 1.81-1.95 (m, 1H), 2.18 (s, 1H), 2.28-2.44 (m, 1H), 2.44-2.59 (m, 1H), 2.73-2.91 (m, 1H), 2.94-3.08 (m, 1H), 3.15-3.24 (m, 1H), 3.49 (s, 1H), 6.85-6.96 (m, 2H), 6.96-7.04 (m, 1H), 7.28-7.37 (m, 3H), 7.42-7.55 (m, 2H), 7.55-7.67 (m, 1H), 8.01-8.11 (m, 2H), 8.35 (dd, J=15.2, 4.8 Hz, 2H); MS (ESI−) m/z 406 (M−H)$^−$.

Example 39 tert-butyl {2-[(5aS,6S,9aR)-8-cyano-6-methyl-7-oxo-9a-phenyl-4,5,5a,6,7,9a-hexahydro-2H-benzo[g]indazol-2-yl]-2-oxoethyl}carbamate The compound from Example 24F (0.010 g, 0.033 mmol) was dissolved in dichloromethane (0.330 mL) and treated with triethylamine (0.009 mL, 0.066 mmol) and (O-(7-azabenzotriazol-1-yl)-N,N,N',N'-tetramethyluronium hexafluorophosphate) (0.012 g, 0.033 mmol) and 2-((tert-butoxycarbonyl)amino)acetic acid (0.005 g, 0.033 mmol). The reaction mixture was stirred at room temperature overnight. The reaction mixture was concentrated and purified using a Biotage® SNAP 10 g silica cartridge eluting with a gradient of 0-40% acetone/hexane to give the titled compound. $^1$H NMR (400 MHz, CDCl$_3$) δ ppm 1.16-1.20 (m, 3H), 1.47 (d, J=6.2 Hz, 9H), 1.50-1.65 (m, 3H), 1.80-1.91 (m, 3H), 2.24-2.38 (m, 2H), 2.42-2.57 (m, 2H), 2.89-3.04 (m, 1H), 4.59-4.72 (m, 1H), 6.82-6.93 (m, 2H), 7.29-7.38 (m, 4H), 8.08-8.15 (m, 1H); MS (APCI) m/z 461 (M+H)$^+$.

Example 40

(5aS,6S,9aR)-6-methyl-7-oxo-9a-phenyl-2-(1,3-thiazol-4-ylcarbonyl)-4,5,5a,6,7,9a-hexahydro-2H-benzo[g]indazole-8-carbonitrile The compound from Example 24F (0.015 g, 0.049 mmol) was dissolved in dichloromethane (0.494 mL) and treated with thiazole-4-carboxylic acid (0.009 mg, 0.074 mmol), triethylamine (0.021 mL, 0.148 mmol), and (O-(7-azabenzotriazol-1-yl)-N,N,N',N'-tetramethyluronium hexafluorophosphate)(0.028 g, 0.074 mmol). The reaction mixture was stirred at room temperature overnight and then concentrated. The residue was purified by reversed-phase Waters HPLC using a Nova-Pak® C18 Radial-Pak 6 µm, 60 Å, 40×100 mm, cartridge eluting with a gradient of 10-90% acetonitrile in aqueous 0.1% trifluoroacetic acid (60 mL/minute) to give the titled compound as the trifluoroacetic acid salt (0.015 g 76% yield). $^1$H NMR (400 MHz, CDCl$_3$) δ ppm 1.20 (dd, J=9.4, 4.0 Hz, 3H), 1.83-1.97 (m, 1H), 2.30-2.45 (m, 1H), 2.46-2.68 (m, 1H), 2.74-2.91 (m, 1H), 2.94-3.09 (m, 1H), 3.49 (s, 3H), 6.88-6.97 (m, 2H), 7.32-7.42 (m, 3H), 8.39-8.48 (m, 1H), 8.53 (d, J=5.4 Hz, 1H), 8.84-8.97 (m, 2H); MS (DCI) m/z 415 (M+H)$^+$.

Example 41

(5aS,6S,9aR)-6-methyl-7-oxo-9a-phenyl-2-(phenylsulfonyl)-4,5,5a,6,7,9a-hexahydro-2H-benzo[g]indazole-8-carbonitrile The compound from Example 24F (0.015 g, 0.049 mmol) was dissolved in dichloromethane (0.494 mL), and triethylamine (0.021 mL, 0.148 mmol), 4-dimethylaminopyridine (0.0006 g, 4.94 mol) and benzenesulfonyl chloride (0.019 mL, 0.148 mmol) were added. The reaction mixture was stirred for about 60 hours at room temperature. The reaction mixture was concentrated, and the residue was purified on a reversed-phase Waters HPLC using a Nova-Pak® HR C18, 6 µm, 60 Å, 40 mm×100 mm PrepPak cartridge eluting with a gradient of 10-90% acetonitrile in aqueous 0.1% trifluoroacetic acid (60 mL/minute) to provide the titled compound as the trifluoroacetic acid salt (0.004 g, 18%). $^1$H NMR (400 MHz, CDCl$_3$) δ ppm 1.15 (d, J=6.7 Hz, 3H), 1.27 (d, J=9.0 Hz, 1H), 1.37-1.51 (m, 2H), 1.81 (dd, J=13.5, 7.8 Hz, 1H), 2.25 (t, J=12.1 Hz, 1H), 2.45 (dt, J=13.5, 6.8 Hz, 1H), 2.70 (dd, J=21.7, 14.2 Hz, 1H), 2.90 (dd, J=17.0, 6.6 Hz, 1H), 6.68-6.78 (m, 2H), 7.53 (t, J=7.9 Hz, (2H), 7.66 (t, J=7.4 Hz, 1H), 7.91-8.03 (m, 3H), 8.35 (s, 1H); MS (DCI) m/z 444 (M+H)$^+$.

Example 42

(5aS,6S,9aR)-2-glycoloyl-6-methyl-7-oxo-9a-phenyl-4,5,5a,6,7,9a-hexahydro-2H-benzo[g]indazole-8-carbonitrile The compound from Example 24F (0.015 g, 0.049 mmol) was dissolved in dichloromethane (0.494 mL), and 2-hydroxyacetic acid (0.003 mg, 0.049 mmol), (O-(7-azabenzotriazol-1-yl)-N,N,N',N'-tetramethyluronium hexafluorophosphate)(0.018 mg, 0.049 mmol) and triethylamine (20.68 µL, 0.148 mmol) were added. The reaction mixture was stirred at room temperature overnight and then concentrated. The residue was purified on reversed-phase Waters HPLC using a Nova-Pak® HR C18, 6 µm, 60 Å, 40 mm×100 mm PrepPak cartridge eluting with a gradient of 10-90% acetonitrile in aqueous 0.1% trifluoroacetic acid (60 mL/minute) to give the titled compound as the trifluoroacetic acid salt (0.010 g 56%). $^1$H NMR (400 MHz, CDCl$_3$) δ ppm 0.78-0.96 (m, 1H), 1.14-1.24 (m, 3H), 1.80-1.94 (m, 1H), 2.18 (d, J=2.0 Hz, 1H), 2.23-2.37 (m, 1H), 2.40-2.57 (m, 1H), 2.69-2.87 (m, 1H), 2.90-3.05 (m, 1H), 4.88 (d, J=5.6 Hz, 2H), 6.82-6.93 (m, 2H), 7.32-7.42 (m, 3H), 8.11-8.20 (m, 1H), 8.36 (d, J=3.8 Hz, 1H); MS (DCI) m/z 362 (M+H)$^+$.

Example 43

(6aS,7S,10aR)-4-(3-methoxyphenyl)-2,7-dimethyl-8-oxo-10a-phenyl-5,6,6a,7,8,10a-hexahydrobenzo[h]quinazoline-9-carbonitrile

Example 43A (6aS,7S,10aS)-4-(3-methoxyphenyl)-2,7-dimethyl-10a-phenyl-5,6a,7,9,10,10a-hexahydrobenzo[h]quinazolin-8(6H)-one The titled compound was prepared using the conditions described in Example 23A, substituting (3-methoxyphenyl)boronic acid for 2-(furan-3-yl)-4,4,5,5-tetramethyl-1,3,2-dioxaborolane. Purification was achieved by flash chromatography on silica gel eluting with 10-20% ethyl acetate in heptane (78% yield). $^1$H NMR (400 MHz, CDCl$_3$) δ ppm 1.15 (d, J=6.61 Hz, 3H) 1.94-2.13 (m, 3H) 2.29-2.39 (m, 2H) 2.39-2.46 (m, 1H) 2.46-2.60 (m, 1H) 2.75 (s, 3H) 2.78-2.95 (m, 2H) 3.19-3.27 (m, 1H) 3.83 (s, 3H) 6.92-7.00 (m, 3H) 7.22-7.27 (m, 1H) 7.28-7.35 (m, 3H) 7.54 (d, J=7.81 Hz, 2H); MS (ESI) m/z 413.3 (M+H)$^+$.

Example 43B (6aS,7S,9Z,10aS)-9-(hydroxymethylene)-4-(3-methoxyphenyl)-2,7-dimethyl-10a-phenyl-5,6a,7,9,10,10a-hexahydrobenzo[h]quinazolin-8(6H)-one The titled compound was prepared using the conditions described in Example 13F, substituting Example 43A for Example 13E.

Example 43C (6aS,7S,11aS)-4-(3-methoxyphenyl)-2,7-dimethyl-11a-phenyl-5,6,6a,7,11,11a-hexahydro[1,2]benzoxazolo[6,5-h]quinazoline The titled compound was prepared using the conditions described in Example 13G, substituting Example 43B for Example 13F.

Example 43D (6aS,7S,10aS)-4-(3-methoxyphenyl)-2,7-dimethyl-8-oxo-10a-phenyl-5,6,6a,7,8,9,10,10a-octahydrobenzo[h]quinazoline-9-carbonitrile The titled compound was prepared using the conditions described in Example 13H, substituting Example 43C for Example 13G.

Example 43E (6aS,7S,10aR)-4-(3-methoxyphenyl)-2,7-dimethyl-8-oxo-10a-phenyl-5,6,6a,7,8,10a-hexahydrobenzo[h]quinazoline-9-carbonitrile The titled compound was prepared using the conditions described in Example 131, substituting Example 43D for Example 13H. Purification was achieved by flash chromatography on silica gel eluting with 5% ethyl acetate in chloroform (49% yield). $^1$H NMR (400 MHz, CDCl$_3$) δ ppm 1.16 (d, J=6.61 Hz, 3H) 1.47-1.55 (m, 1H) 1.81-1.92 (m, 1H) 2.34 (td, J=12.69, 1.08 Hz, 1H) 2.45 (td, J=13.07, 6.51 Hz, 1H) 2.71 (s, 3H) 2.91-3.00 (m, 2H) 3.88 (s, 3H) 6.84 (d, J=6.72 Hz, 2H) 6.99-7.15 (m, 3H) 7.29-7.39 (m, 3H) 7.42 (t, J=7.92 Hz, 1H) 8.99 (s, 1H); MS (CI) m/z 436 (M+H)$^+$.

Example 44

(6aS,7S,10aR)-2,7-dimethyl-4-(1-methyl-6-oxo-1,6-dihydropyridin-3-yl)-8-oxo-10a-phenyl-5,6,6a,7,8,10a-hexahydrobenzo[h]quinazoline-9-carbonitrile

Example 44A (6aS,7S,10aS)-2,7-dimethyl-4-(1-methyl-6-oxo-1,6-dihydropyridin-3-yl)-10a-phenyl-5,6a,7,9,10,10a-hexahydrobenzo[h]quinazolin-8(6H)-one The titled compound was prepared using the conditions described in Example 23A, substituting 1-methyl-5-(4,4,5,5-tetramethyl-1,3,2-dioxaborolan-2-yl)pyridin-2(1H)-one for 2-(furan-3-yl)-4,4,5,5-tetramethyl-1,3,2-dioxaborolane. Purification was achieved by flash chromatography on silica gel eluting with 33-66% acetone in heptane (94% yield). $^1$H NMR (400 MHz, CDCl$_3$) δ ppm 1.17 (d, J=6.61 Hz, 3H) 1.90-2.02 (m, 1H) 2.06-2.19 (m, 2H) 2.27-2.35 (m, 2H) 2.44-2.52 (m, 1H) 2.58 (ddd, J=16.02, 7.83, 7.48 Hz, 1H) 2.72 (s, 3H) 2.81-2.96 (m, 2H) 3.13-3.22 (m, 1H) 3.60 (s, 3H) 6.59 (d, J=9.32 Hz, 1H) 7.21-7.34 (m, 3H) 7.46-7.54 (m, 3H) 7.66 (d, J=2.49 Hz, 1H); MS (ESI) m/z 414.3 (M+H)$^+$.

Example 44B (6aS,7S,9Z,10aS)-9-(hydroxymethylene)-2,7-dimethyl-4-(1-methyl-6-oxo-1,6-dihydropyridin-3-yl)-10a-phenyl-5,6a,7,9,10,10a-hexahydrobenzo[h]quinazolin-8(6H)-one The titled compound was prepared using the conditions described in Example 13F, substituting Example 44A for Example 13E.

Example 44C

5-[(6aS,7S,11aS)-2,7-dimethyl-11a-phenyl-5,6,6a,7,11,11a-hexahydro[1,2]benzoxazolo[6,5-h]quinazolin-4-yl]-1-methylpyridin-2(1H)-one The titled compound was prepared using the conditions described in Example 13G, substituting Example 44B for Example 13F.

Example 44D (6aS,7S,10 aS)-2,7-dimethyl-4-(1-methyl-6-oxo-1,6-dihydropyridin-3-yl)-8-oxo-10a-phenyl-5,6,6a,7,8,9,10,10a-octahydrobenzo[h]quinazoline-9-carbonitrile The titled compound was prepared using the conditions described in Example 13H, substituting Example 44C for Example 13G.

Example 44E (6aS,7S,10aR)-2,7-dimethyl-4-(1-methyl-6-oxo-1,6-dihydropyridin-3-yl)-8-oxo-10a-phenyl-5,6,6a,7,8,10a-hexahydrobenzo[h]quinazoline-9-carbonitrile The titled compound was prepared using the conditions described in Example 13I, substituting Example 44D for Example 13H. Purification was achieved by flash chromatography on silica gel eluting with 20% acetone in chloroform (64% yield). $^1$H NMR (400 MHz, CDCl$_3$) δ ppm 1.18 (d, J=6.61 Hz, 3H) 1.58-1.68 (m, 1H) 1.92-2.00 (m, 1H) 2.34 (td, J=12.93, 2.33 Hz, 1H) 2.47 (td, J=13.17, 6.61 Hz, 1H) 2.68 (s, 3H) 3.03 (dd, J=8.51, 4.50 Hz, 2H) 3.67 (s, 3H) 6.67 (d, J=9.43 Hz, 1H) 6.80 (dd, J=7.48, 1.95 Hz, 2H) 7.30-7.37 (m, 3H) 7.72 (dd, J=9.49, 2.66 Hz, 1H) 7.86 (d, J=2.49 Hz, 1H) 8.93 (s, 1H); MS (CI) m/z 437 (M+H)$^+$.

Example 45

(6aS,7S,10aR)-2,7-dimethyl-8-oxo-10a-phenyl-4-(quinolin-6-yl)-5,6,6a,7,8,10a-hexahydrobenzo[h]quinazoline-9-carbonitrile

Example 45A (6aS,7S,10aS)-2,7-dimethyl-10a-phenyl-4-(quinolin-6-yl)-5,6a,7,9,10,10a-hexahydrobenzo[h]quinazolin-8(6H)-one The titled compound was prepared using the conditions described in Example 23A, substituting 6-(4,4,5,5-tetramethyl-1,3,2-dioxaborolan-2-yl)quinoline for 2-(furan-3-yl)-4,4,5,5-tetramethyl-1,3,2-dioxaborolane. Purification was achieved by flash chromatography on silica gel eluting with 20% acetone in heptane (93% yield). $^1$H NMR (400 MHz, CDCl$_3$) δ ppm 1.16 (d, J=6.51 Hz, 3H) 1.98-2.19 (m, 3H) 2.32-2.48 (m, 2H) 2.48-2.54 (m, 1H) 2.57-2.67 (m, 1H) 2.79 (s, 3H) 2.82-2.90 (m, 1H) 2.95 (ddd, J=16.56, 7.94, 5.20 Hz, 1H) 3.25 (td, J=8.19, 3.58 Hz, 1H) 7.34 (t, J=7.48 Hz, 3H) 7.45 (dd, J=8.24, 4.23 Hz, 1H) 7.57 (d, J=7.70 Hz, 2H) 7.80 (dd, J=8.67, 1.95 Hz, 1H) 7.93 (d, J=1.73 Hz, 1H) 8.13-8.22 (m, 2H) 8.97 (dd, J=4.28, 1.68 Hz, 1H); MS (ESI) m/z 434.3 M+H

Example 45B (6aS,7S,9Z,10aS)-9-(hydroxymethylene)-2,7-dimethyl-10a-phenyl-4-(quinolin-6-yl)-5,6a,7,9,10,10a-hexahydrobenzo[h]quinazolin-8(6H)-one The titled compound was prepared using the conditions described in Example 13F, substituting Example 45A for Example 13E.

Example 45C (6aS,7S,11aS)-2,7-dimethyl-11a-phenyl-4-(quinolin-6-yl)-5,6,6a,7,11,11a-hexahydro[1,2]benzoxazolo[6,5-h]quinazoline The titled compound was prepared using the conditions described in Example 13G, substituting Example 45B for Example 13F.

Example 45D (6aS,7S,10aS)-2,7-dimethyl-8-oxo-10a-phenyl-4-(quinolin-6-yl)-5,6,6a,7,8,9,10,10a-octahydrobenzo[h]quinazoline-9-carbonitrile The titled compound was prepared using the conditions described in Example 13H, substituting Example 45C for Example 13G.

Example 45E (6aS,7S,10aR)-2,7-dimethyl-8-oxo-10a-phenyl-4-(quinolin-6-yl)-5,6,6a,7,8,10a-hexahydrobenzo[h]quinazoline-9-carbonitrile The titled compound was prepared using the conditions described in Example 13I, substituting Example 45D for Example 13H. Purification was achieved by flash chromatography on silica gel eluting with 30% acetone in heptane (19% yield). $^1$H NMR (400 MHz, CDCl$_3$) δ ppm 1.17 (d, J=6.51 Hz, 3H) 1.60-1.65 (m, 1H) 1.90 (ddd, J=13.85, 3.31, 3.12 Hz, 1H) 2.39 (td, J=12.71, 2.22 Hz, 1H) 2.48 (td, J=13.01, 6.51 Hz, 1H) 2.75 (s, 3H) 2.99-3.05 (m, 2H) 6.87 (dd, J=8.13, 1.52 Hz, 2H) 7.31-7.41 (m, 3H) 7.51 (dd, J=8.29, 4.28 Hz, 1H) 7.93 (dd, J=8.73, 1.90 Hz, 1H) 8.07 (d, J=1.73 Hz, 1H) 8.26 (d, J=8.57 Hz, 2H) 8.98-9.06 (m, 2H); MS (CI) m/z 457 (M+H)$^+$.

Example 46

2-{3-[(6aS,7S,10aR)-9-cyano-2,7-dimethyl-8-oxo-10a-phenyl-5,6,6a,7,8,10a-hexahydrobenzo[h]quinazolin-4-yl]phenyl}ethyl acetate

Example 46A (6aS,7S,10aS)-4-[3-(2-hydroxyethyl)phenyl]-2,7-dimethyl-10a-phenyl-5,6a,7,9,10,10a-hexahydrobenzo[h]quinazolin-8(6H)-one The titled compound was prepared using the conditions described in Example 23A, substituting (3-(2-hydroxyethyl)phenyl)boronic acid for 2-(furan-3-yl)-4,4,5,5-tetramethyl-1,3,2-dioxaborolane. Purification was achieved by flash chromatography on silica gel eluting with 20-33% acetone in heptane (67% yield). $^1$H NMR (400 MHz, CDCl$_3$) δ ppm 1.15 (d, J=6.61 Hz, 3H) 1.93-2.14 (m, 3H) 2.28-2.60 (m, 4H) 2.74 (s, 3H) 2.84 (dt, J=11.71, 5.86 Hz, 2H) 2.88-2.94 (m, 2H) 3.18-3.27 (m, 1H) 3.88 (t, J=6.45 Hz, 2H) 7.20-7.42 (m, 7H) 7.54 (d, J=7.70 Hz, 2H); MS (ESI) m/z 427.3 (M+H)$^+$.

Example 46B

2-{3-[(6aS,7S,9Z,10aS)-9-(hydroxymethylene)-2,7-dimethyl-8-oxo-10a-phenyl-5,6,6a,7,8,9,10,10a-octahydrobenzo[h]quinazolin-4-yl]phenyl}ethyl acetate The titled compound was prepared using the conditions described in Example 13F, substituting Example 46A for Example 13E.

Example 46C

2-{3-[(6aS,7S,11aS)-2,7-dimethyl-11a-phenyl-5,6,6a,7,11,11a-hexahydro[1,2]benzoxazolo[6,5-h]quinazolin-4-yl]phenyl}ethyl acetate The titled compound was prepared using the conditions described in Example 13G, substituting Example 46B for Example 13F. Purification was achieved by flash chromatography on silica gel eluting with 5% acetone in chloroform (42% yield).

Example 46D

2-{3-[(6aS,7S,10aS)-9-cyano-2,7-dimethyl-8-oxo-10a-phenyl-5,6,6a,7,8,9,10,10a-octahydrobenzo[h]quinazolin-4-yl]phenyl}ethyl acetate The titled compound was prepared using the conditions described in Example 13H, substituting Example 46C for Example 13G.

Example 46E

2-{3-[(6aS,7S,10aR)-9-cyano-2,7-dimethyl-8-oxo-10a-phenyl-5,6,6a,7,8,10a-hexahydrobenzo[h]quinazolin-4-yl]phenyl}ethyl acetate The titled compound was prepared using the conditions described in Example 13I, substituting Example 46D for Example 13H. Purification was achieved by flash chromatography on silica gel eluting with 5% ethyl acetate in chloroform (90% yield). $^1$H NMR (400 MHz, CDCl$_3$) δ ppm 1.16 (d, J=6.61 Hz, 3H) 1.48-1.55 (m, 1H) 1.83-1.94 (m, 1H) 2.06 (s, 3H) 2.35 (td, J=12.79, 2.17 Hz, 1H) 2.46 (td, J=13.09, 6.45 Hz, 1H) 2.71 (s, 3H) 2.94 (dd, J=8.19, 3.85 Hz, 2H) 3.04 (t, J=7.16 Hz, 2H) 4.34 (t, J=7.16 Hz, 2H) 6.82-6.88 (m, 2H) 7.30-7.39 (m, 4H) 7.40-7.49 (m, 3H) 8.99 (s, 1H); MS (CI) m/z 492 (M+H)$^+$.

Example 47

(6aS,7S,10aR)-4-[3-(2-hydroxyethyl)phenyl]-2,7-dimethyl-8-oxo-10a-phenyl-5,6,6a,7,8,10a-hexahydrobenzo[h]quinazoline-9-carbonitrile

Example 47A (6aS,7S,10aS)-4-[3-(2-hydroxyethyl)phenyl]-2,7-dimethyl-10a-phenyl-5,6a,7,9,10,10a-hexahydrobenzo[h]quinazolin-8(6H)-one The titled compound was prepared using the conditions described in Example 23A, substituting (3-(2-hydroxyethyl)phenyl)boronic acid for 2-(furan-3-yl)-4,4,5,5-tetramethyl-1,3,2-dioxaborolane. Purification was achieved by flash chromatography on silica gel eluting with 20%-33% acetone in heptane (67% yield). $^1$H NMR (400 MHz, CDCl$_3$) δ ppm 1.15 (d, J=6.61 Hz, 3H) 1.47 (s, 1H) 1.94-2.13 (m, 3H) 2.29-2.45 (m, 2H) 2.46-2.60 (m, 2H) 2.74 (s, 3H) 2.78-2.89 (m, 2H) 2.91 (t, J=6.51 Hz, 2H) 3.19-3.27 (m, 1H) 3.88 (t, J=6.45 Hz, 2H) 7.21-7.41 (m, 7H) 7.54 (d, J=7.70 Hz, 2H); MS (APCI+) m/z 427 (M+H)$^+$.

Example 47B (6aS,7S,9Z,10aS)-4-[3-(2-hydroxyethyl)phenyl]-9-(hydroxymethylene)-2,7-dimethyl-10a-phenyl-5,6a,7,9,10,10a-hexahydrobenzo[h]quinazolin-8(6H)-one The titled compound was prepared using the conditions described in Example 13F, substituting Example 47A for Example 13E.

Example 47C

2-{3-[(6aS,7S,11aS)-2,7-dimethyl-11a-phenyl-5,6,6a,7,11,11a-hexahydro[1,2]benzoxazolo[6,5-h]quinazolin-4-yl]phenyl}ethanol The titled compound was prepared using the conditions described in Example 13G, substituting Example 47B for Example 13F. Purification was achieved by flash chromatography on silica gel eluting with 20% acetone in chloroform (32% yield).

Example 47D (6aS,7S,10aS)-4-[3-(2-hydroxyethyl)phenyl]-2,7-dimethyl-8-oxo-10a-phenyl-5,6,6a,7,8,9,10,10a-octahydrobenzo[h]quinazoline-9-carbonitrile The titled compound was prepared using the conditions described in Example 13H, substituting Example 47C for Example 13G.

Example 47E (6aS,7S,10aR)-4-[3-(2-hydroxyethyl)phenyl]-2,7-dimethyl-8-oxo-10a-phenyl-5,6,6a,7,8,10a-hexahydrobenzo[h]quinazoline-9-carbonitrile The titled compound was prepared using the conditions described in Example 13I, substituting Example 47D for Example 13H. Purification was achieved by flash chromatography on silica gel eluting with 33% ethyl acetate in chloroform (33% yield). $^1$H NMR (400 MHz, CDCl$_3$) δ ppm 1.16 (d, J=6.61 Hz, 3H) 1.51-1.55 (m, 1H) 1.84-1.92 (m, 1H) 2.35 (td, J=12.85, 2.28 Hz, 1H) 2.46 (td, J=13.15, 6.67 Hz, 1H) 2.71 (s, 3H) 2.92-3.01 (m, 4H) 3.94 (t, J=6.51 Hz, 2H) 6.85 (dd, J=7.97, 1.46 Hz, 2H) 7.31-7.39 (m, 4H) 7.41-7.50 (m, 3H) 8.98 (s, 1H); MS (CI) m/z 450 (M+H)$^+$.

Example 48

(5aS,6S,9aR)-8-cyano-6-methyl-7-oxo-9a-phenyl-N-(pyridin-3-yl)-4,5,5a,6,7,9a-hexahydro-2H-benzo[g]indazole-2-carboxamide

Example 48A 4-nitrophenyl (5aS,6S,9aR)-8-cyano-6-methyl-7-oxo-9a-phenyl-4,5,5a,6,7,9a-hexahydro-2H-benzo[g]indazole-2-carboxylate The product of Example 24F (0.020 g, 0.066 mmol) was dissolved in dichloromethane (0.659 mL) and treated with triethylamine (0.027 mL, 0.198 mmol) and 4-nitrophenyl carbonochloridate (0.013 g, 0.066 mmol). The reaction mixture was stirred at room temperature for 30 minutes and then concentrated. The residue was purified on Biotage® SNAP silica 10 g cartridge eluting with 0-50% acetone/hexane.

Example 48B (5aS,6S,9aR)-8-cyano-6-methyl-7-oxo-9a-phenyl-N-(pyridin-3-yl)-4,5,5a,6,7,9a-hexahydro-2H-benzo[g]indazole-2-carboxamide The product of Example 48A (0.025 g, 0.053 mmol) was dissolved in dichloromethane (0.534 mL) and treated with pyridin-3-amine (0.015 g, 0.160 mmol) while stirring at room temperature overnight. The reaction mixture was concentrated, and the residue was purified on reversed-phase Waters HPLC using a Nova-Pak® HR C18, 6 µm, 60 Å, 40 mm×100 mm, PrepPak cartridge eluting with a gradient of 10-90% acetonitrile in aqueous 0.1% trifluoroacetic acid (60 mL/minute) to give the titled compound as the trifluoroacetic acid salt (0.005 g, 22% yield). $^1$H NMR (400 MHz, CDCl$_3$) δ ppm 1.15-1.23 (m, 3H), 1.39-1.46 (m, 1H), 1.84-1.94 (m, 1H), 2.31-2.40 (m, 2H), 2.44-2.60 (m, 2H), 2.60-2.90 (m, 1H), 2.93-3.08 (m, 1H), 6.83-7.04 (m, 2H), 7.33-7.43 (m, 3H), 7.68-7.77 (m, 1H), 8.13-8.26 (m, 1H), 8.52-8.62 (m, 3H), 9.22-9.35 (m, 1H), 9.40-9.53 (m, 1H); MS (APCI) m/z 424 (M+H)$^+$.

Example 49

(6aS,7S,10aR)-7-methyl-8-oxo-10a-phenyl-2-(pyrimidin-5-yl)-5,6,6a,7,8,10a-hexahydrobenzo[h]quinazoline-9-carbonitrile Example 49A (6aS,7S,10aS)-7-methyl-10a-phenyl-2-(pyrimidin-5-yl)-5,6a,7,9,10,10a-hexahydro-6H-spiro[benzo[h]quinazoline-8,2'-[1,3]dioxolane]

To a stirred solution of Example 1G (0.700 g, 0.2.13 mmol) in isopropanol (05 mL) at room temperature was added piperidine (0.633 mL, 6.39 mmol) and pyrimidine-5-carboxamidine (0.781 g, 6.39 mmol). The reaction mixture was heated at 95° C. for 72 hours.

The cooled solution was diluted with saturated aqueous sodium phosphate monobasic solution, extracted with ethyl acetate, and concentrated.

Example 49B (6aS,7S,10aS)-7-methyl-10a-phenyl-2-(pyrimidin-5-yl)-5,6,6a,7,9,10,10a-hexahydrobenzo[h]quinazolin-8(6H)-one The titled compound was prepared using the conditions described in Example 1I, substituting Example 49A for Example 1H.

Example 49C (6aS,7S,9Z,10aS)-9-(hydroxymethylene)-7-methyl-10a-phenyl-2-(pyrimidin-5-yl)-5,6a,7,9,10,10a-hexahydrobenzo[h]quinazolin-8(6H)-one The titled compound was prepared using the conditions described in Example 1J, substituting Example 49B for Example 1I.

Example 49D (6aS,7S,11aS)-7-methyl-11a-phenyl-2-(pyrimidin-5-yl)-5,6,6a,7,11,11a-hexahydro[1,2]benzoxazolo[6,5-h]quinazoline The titled compound was prepared using the conditions described in Example 1K, substituting Example 49C for Example 1J. $^1$H NMR (400 MHz, CDCl$_3$) δ ppm 1.41 (d, J=6.83 Hz, 3H) 1.86 (ddd, J=19.16, 13.04, 5.96 Hz, 1H) 1.99-2.09 (m, 1H) 2.12-2.21 (m, 1H) 2.26-2.36 (m, 1H) 2.96-3.11 (m, 2H) 3.15-3.27 (m, 1H) 3.98 (d, J=16.70 Hz, 1H) 6.79 (dd, J=4.66, 3.14 Hz, 2H) 7.11-7.20 (m, 3H) 8.32 (s, 1H) 8.74 (s, 1H) 9.26 (s, 1H) 9.60 (s, 2H).

Example 49E (6aS,7S,10aS)-7-methyl-8-oxo-10a-phenyl-2-(pyrimidin-5-yl)-5,6,6a,7,8,9,10,10a-octahydrobenzo[h]quinazoline-9-carbonitrile The titled compound was prepared using the conditions described in Example 1L, substituting Example 49D for Example 1K and using only methanol as solvent.

Example 49F (6aS,7S,10aR)-7-methyl-8-oxo-10a-phenyl-2-(pyrimidin-5-yl)-5,6,6a,7,8,10a-hexahydrobenzo[h]quinazoline-9-carbonitrile To a solution of the product from Example 49E (0.030 g, 0.076 mmol) in dimethylformamide (2 mL) cooled to 0° C. in an ice water bath was added 1,3-dibromo-5,5-dimethylhydantoin (0.011 g, 0.038 mmol). The solution was stirred at 0° C. for 30 minutes, and then pyridine (0.061 mL, 0.759 mmol) was added. The resultant solution was heated at 55° C. for 1 hour. The cooled solution was diluted with water and extracted with ethyl acetate. The organic layer was washed with brine and concentrated. The residue was purified using a 12 g RediSep® cartridge on a Teledyne Isco Combiflash® Rf system, eluting with 0-70% ethyl acetate in heptane, to give 0.011 g (37%) of the titled compound. $^1$H NMR (400 MHz, CDCl$_3$) δ ppm 1.22 (d, J=6.72 Hz, 3H) 1.61-1.75 (m, 1H) 1.98-2.04 (m, 1H) 2.38 (td, J=12.77, 2.33 Hz, 1H) 2.50 (td, J=13.17, 6.61 Hz, 1H) 3.03-3.24 (m, 2H) 6.83 (dd, J=7.64, 1.79 Hz, 2H) 7.31-7.38 (m, 3H) 8.83 (s, 1H) 8.91 (s, 1H) 9.30 (s, 1H) 9.63 (s, 2H); MS (ESI+) m/z 394 (M+H)$^+$, 426 (M+CH$_3$OH+H)$^+$.

Example 50

(6aS,7S,10aR)-10a-(4-fluorophenyl)-7-methyl-8-oxo-5,6,6a,7,8,10a-hexahydrobenzo[h]quinazoline-9-carbonitrile Example 50A 2-(4-fluorophenyl)cyclohexane-1,3-dione A 1 L round-bottomed flask was charged with 4-bromofluorobenzene (28.3 mL, 45.4 mmol), tert-amyl alcohol (300 mL) and dioxane (600 mL), and the contents were purged with N$_2$ for 45 minutes. A 3 L round-bottomed flask was charged with potassium phosphate tribasic (138 g, 649 mmol), 1,3-cyclohexanedione (97 weight %, 30 g, 260 mmol), palladium(II) acetate (1.17 g, 5.2 mmol) and 2-(di-tert-butylphospino)-2'-methylbiphenyl (3.24 g, 10.4 mmol), and the contents were purged with N$_2$ for 45 minutes. The solution containing 4-bromofluorobenzene was then transferred to the mixture containing 1,3-cyclohexanedione via cannula, and the reaction mixture was heated to reflux overnight. The reaction mixture was cooled to room temperature and was partitioned between ethyl acetate (1 L) and 10% HCl (1 L) with mixing. The lower aqueous layer was separated and extracted with ethyl acetate (1 L). The combined organic layers were washed with brine (500 mL) and concentrated under reduced pressure. The residue was taken up in toluene (300 mL) and again concentrated under reduced pressure. The residue was taken up in toluene (150 mL) and warmed to 50° C. After cooling to room temperature, the solids were collected by filtration, washed with toluene (2×50 mL) and dried in the vacuum oven at 50° C. to give the titled compound (43.1 g, 81%). $^1$H NMR (400 MHz, CDCl$_3$) δ ppm 2.08 (dt, J=12.93, 6.50 Hz, 2H) 2.45-2.64 (m, 4H) 6.00 (s, 1H) 7.09-7.20 (m, 4H).

Example 50B (8aR)-8a-(4-fluorophenyl)-5-methyl-3,4,8,8a-tetra-hydronaphthalene-1,6(2H,7H)-dione A 3 L round-bottomed flask was charged with Example 50A (43.1 g, 209 mmol) in acetonitrile (300 mL). Triethylamine (58 mL, 418 mmol) and ethyl vinyl ketone (31 mL, 314 mmol) were added, and the contents were warmed to 75° C. and stirred overnight. The reaction mixture was cooled to room temperature and concentrated. The residue was taken up in dimethyl sulfoxide (125 mL). Pyridinium para-toluenesulfonate (34.1 g, 136 mmol) and L-phenylalanine (44.9 g, 272 mmol) were added, and the contents warmed to 50° C. for 66 hours. The reaction mixture was cooled to room temperature and poured into saturated aqueous NH$_4$Cl (200 mL) and methyl t-butyl ether (300 mL). After mixing for 10 minutes, the solids were removed by filtration, and the layers were separated. The organic layer was washed with saturated aqueous NH$_4$Cl (200 mL). The combined aqueous layers were extracted with methyl t-butyl ether (300 mL). The combined organic layers were washed with water (200 mL) and brine (200 mL), dried over sodium sulfate, filter, and concentrated. The residue was purified by chromatography using a 330 g RediSep® cartridge on a Teledyne Isco Torrent Combiflash® system: ethyl acetate/hexanes 0:1 (2 column volumes) up to 1:1 (gradient over 8 column volumes). Fractions containing the titled compound were combined and concentrated under reduced pressure to give the titled compound in 75% ee determined using a Chiralpak® AS-H column (4.6 mm ID×25 cm, 5 microns) eluting with 10% ethanol in heptane at 1.0 mL/minute with the major enantiomer having a retention time of 10.6 minutes and the minor enantiomer having a retention time of 9.9 minutes (36.2 g, 64%).

Example 50C (4aR,5S)-4a-(4-fluorophenyl)-5-hydroxy-1-methyl-4,4a,5,6,7,8-hexahydronaphthalen-2(3H)-one A 3 μL jacketed round bottom flask was charged with Example 50B (36.2 g, 133 mmol) in ethanol (350 mL), and the solution was cooled to −5° C. A solution of NaBH$_4$ (1.51 g, 39.9 mmol) in ethanol (350 mL) was added dropwise while maintaining an internal temperature below 0° C. The resulting mixture was stirred at −5° C. for 4 hours. The reaction mixture was quenched carefully with acetic acid (40 mL) and warmed to 23° C. After stirring overnight, the mixture was concentrated. The residue was partitioned between methyl t-butyl ether (300 mL) and 10% aqueous ammonia (150 mL). The layers were separated, and the organic layer was washed with 10% aqueous ammonia (150 mL). The combined aqueous layers were extracted with methyl t-butyl ether (300 mL). The combined organic layers were washed with brine (100 mL), dried over Na$_2$SO$_4$, filtered and concentrated. The residue was purified by chromatography over silica gel using a 330 g RediSep® cartridge on a Teledyne Isco Torrent Combiflash® system eluting with ethyl acetate/hexanes 0:1 (2 column volumes) up to 1:1 (gradient over 8 column volumes). Fractions containing the titled compound were combined and concentrated under reduced pressure (32.3 g, 89%). $^1$H NMR (400 MHz, CDCl$_3$) δ ppm 1.46-1.58 (m, 1H) 1.59-1.71 (m, 1H) 1.78-1.85 (m, 2H) 1.92 (s, 3H) 2.03-2.20 (m, 3H) 2.28-2.36 (m, 2H) 2.40-2.47 (m, 1H) 2.71-2.79 (m, 1H) 3.82 (td, J=7.65, 3.91 Hz, 1H) 6.98 (t, J=8.71 Hz, 2H) 7.53 (dd, J=8.92, 5.35 Hz, 2H).

Example 50D (1S,4aS,5S,8aS)-4a-(4-fluorophenyl)-5-hydroxy-1-methyloctahydronaphthalen-2(1H)-one A 500 mL Parr stirred pressure reactor was charged with 6.4 g of 5% Pd/C (20 weight % of substrate charged). Under a stream of nitrogen, a solution of Example 50C (32.0 g, 117 mmol), tetrahydrofuran (233 mL) and pyridine (58 mL) was added to the reactor. The reactor was purged with nitrogen and hydrogen. The vessel was pressurized to and maintained at 60-100 psig with hydrogen supplied from a high-pressure reservoir. The mixture was vigorously agitated while keeping the temperature between 22-25° C. The reaction mixture was carefully filtered to remove the palladium catalyst rinsing the reactor and cake with tetrahydrofuran. To the filtrate was added 1,8-diazobicyclo[5.4.0]undec-7-ene (3 mL), and the resulting mixture was stirred at room temperature overnight. The volatiles were removed under reduced pressure, and the residue taken up in toluene (200 mL). The resulting solution was washed with 10% HCl (2×100 mL). The combined aqueous layers were extracted with toluene (100 mL), and the combined organic layers were washed with brine (50 mL), dried over Na$_2$SO$_4$, and filtered. The resulting solution was used without purification.

Example 50E (1'S,4a'S,5'S,8a'S)-4a'-(4-fluorophenyl)-1'-methyloc-tahydro-1'H-spiro[1,3-dioxolane-2,2'-naphthalen]-5'-ol Ethylene glycol (32.5 mL, 583 mol, 5 equivalents) and p-toluenesulfonic acid (2.2 g, 11.7 mmol) were added to the toluene solution from Example 50D. The resulting mixture was heated to reflux with Dean Stark removal of water. Additional ethylene glycol (32.5 mL, 583 mol) was added after 8 hours, and refluxing was continued overnight. The mixture was cooled to room temperature, and the toluene solution was washed with saturated aqueous sodium bicarbonate (2×100 mL) and brine (50 mL), dried over sodium sulfate, filtered and concentrated. The resulting residue was used without purification.

Example 50F (1'S,4a'S,8a'S)-4a'-(4-fluorophenyl)-1'-methylhexahydro-1'H-spiro[1,3-dioxolane-2,2'-naphthalen]-5'(3'H)-one The residue from Example 50E was dissolved in dichloromethane (300 mL), and pyridinium dichromate (88 g, 234 mmol) and magnesium sulfate (2.8 g) were added. The resulting mixture was heated to reflux and stirred overnight. The reaction was cooled to room temperature, and the mixture was filtered through a plug of silica gel (150 g) rinsing with dichloromethane (1 L). The filtrate was concentrated, and the resultant solids were triturated with cyclohexane (50 mL). The solids were collected by filtration, washed with cyclohexane (2×20 mL) and dried in a vacuum oven at 50° C. to give 15.0 g, (52%) of the titled compound. $^1$H NMR (400 MHz, CDCl$_3$) δ ppm 7.42-7.33 (m, 2H), 7.04-6.94 (m, 2H), 4.00-3.88 (m, 4H), 2.63 (dq, J=13.0, 6.6 Hz, 1H), 2.26-1.86 (m, 8H), 1.71-1.57 (m, 2H), 1.12 (td, J=13.7, 4.0 Hz, 1H), 1.00 (d, J=5.2 Hz, 3H); MS (CI—NH$_3$) 336.1 m/z (M+NH$_4$)$^+$.

Example 50G (1'S,4a'S,6'Z,8a'S)-4a'-(4-fluorophenyl)-6'-(hydroxymethylene)-1'-methylhexahydro-1'H-spiro[1,3-dioxolane-2,2'-naphthalen]-5'(3'H)-one To a solution of Example 50F (2.0 g, 6.28 mmol) in dimethylformamide (20 mL) cooled to 0° C. was added 95% sodium hydride (0.397 g, 15.70 mmol) portionwise, followed by 50% potassium hydride in paraffin (0.050 g, 0.628 mmol). The mixture was stirred at room temperature for 1 hour and then re-cooled to 0° C. Ethyl formate (3.07 mL, 37.7 mmol) was added dropwise. The reaction mixture was stirred at room temperature for 2 hours, and then heated to 45° C. for 15 minutes. The cooled solution was quenched with aqueous saturated sodium phosphate monobasic, then diluted with water, and extracted with dichloromethane. The organic fraction was dried over sodium sulfate, and concentrated. Water was removed azeotropically with toluene, and the residue was dried in a vacuum oven to give 2.2 g (100%) of the titled compound. $^1$H NMR (400 MHz, CDCl$_3$) δ ppm 0.98 (d, J=6.51 Hz, 3H) 1.62-1.68 (m, 2H) 1.76-1.86 (m, 1H) 1.88-2.20 (m, 6H) 2.47 (dt, J=18.27, 6.48 Hz, 1H) 3.95 (s, 4H) 6.98 (t, J=8.67 Hz, 2H) 7.38 (d, J=9.32 Hz, 1H) 7.47 (dd, J=8.89, 5.31 Hz, 2H) 13.78 (d, J=9.76 Hz, 1H).

Example 50H (6aS,7S,10aS)-10a-(4-fluorophenyl)-7-methyl-5,6a,7,9,10,10a-hexahydro-6H-spiro[benzo[h]quinazoline-8,2'-[1,3]dioxolane]

To a solution of the product from Example 50G (0.700 g, 2.02 mmol) in isopropanol (15 mL) was added formamidine acetate (0.947 g, 9.09 mmol) and piperidine (0.900 mL, 9.09 mmol). The reaction mixture was heated at 95° C. for 24 hours. The cooled solution was diluted with a solution of saturated aqueous sodium phosphate monobasic solution and extracted with ethyl acetate. The organic layer was concentrated to provide the titled compound.

Example 50I (6aS,7S,10aS)-10a-(4-fluorophenyl)-7-methyl-5,6a,7,9,10,10a-hexahydrobenzo[h]quinazolin-8(6H)-one The titled compound was prepared using the conditions described in Example 1I, substituting Example 50H for Example 1H. Purification was achieved using a 12 g RediSep® cartridge on a Teledyne Isco Combiflash Rf® system, eluting with 0-30% ethyl acetate in heptane to give 0.458 g (73%).

Example 50J (6aS,7S,9Z,10aS)-10a-(4-fluorophenyl)-9-(hydroxymethylene)-7-methyl-5,6a,7,9,10,10a-hexahydrobenzo[h]quinazolin-8(6H)-one The titled compound was prepared using the conditions described in Example 1J, substituting Example 50I for Example 1I and using methanol as a solvent.

Example 50K (6aS,7S,11aS)-11a-(4-fluorophenyl)-7-methyl-5,6,6a,7,11,11a-hexahydro[1,2]benzoxazolo[6,5-h]quinazoline The titled compound was prepared using the conditions described in Example 1K, substituting Example 50J for Example 1J. $^1$H NMR (400 MHz, CDCl$_3$) δ ppm 1.40 (d, J=6.83 Hz, 3H) 1.71-1.84 (m, 1H) 1.95-2.04 (m, 1H) 2.08-2.19 (m, 1H) 2.20-2.31 (m, 1H) 2.93-3.05 (m, 2H) 3.09-3.17 (m, 1H) 3.81 (d, J=16.92 Hz, 1H) 6.72 (dd, J=9.00, 5.20 Hz, 2H) 6.84 (t, J=8.67 Hz, 2H) 8.26 (s, 1H) 8.66 (s, 1H) 9.03 (s, 1H); MS (APCI+) m/z 336 (M+H)$^+$.

Example 50L (6aS,7S,10aS)-10a-(4-fluorophenyl)-7-methyl-8-oxo-5,6,6a,7,8,9,10,10a-octahydrobenzo[h]quinazoline-9-carbonitrile The titled compound was prepared using the conditions described in Example 1L, substituting Example 50K for Example 1K.

Example 50M (6aS,7S,10aR)-10a-(4-fluorophenyl)-7-methyl-8-oxo-5,6,6a,7,8,10a-hexahydrobenzo[h]quinazoline-9-carbonitrile The titled compound was prepared using the conditions described in Example 1M, substituting Example 50L for Example 1L. Purification was achieved using a 12 g RediSep® cartridge on a Teledyne Isco Combiflash Rf® system, eluting with 0-50% ethyl acetate in heptane to give 0.042 g (25%). $^1$H NMR (400 MHz, CDCl$_3$) δ ppm 1.21 (d, J=6.51 Hz, 3H) 1.59-1.67 (m, 1H) 1.96-2.04 (m, 1H) 2.33 (td, J=12.66, 2.22 Hz, 1H) 2.42 (td, J=12.98, 6.56 Hz, 1H) 2.92-3.17 (m, 2H) 6.76 (dd, J=8.95, 4.93 Hz, 2H) 7.03 (t, J=8.51 Hz, 2H) 8.72 (s, 1H) 8.82 (s, 1H) 9.07 (s, 1H); MS (ESI+) m/z 334 (M+H)$^+$.

Example 51

(6aS,7S,10aR)-10a-(4-fluorophenyl)-7-methyl-8-oxo-2-(pyridin-3-yl)-5,6,6a,7,8,10a-hexahydrobenzo[h]quinazoline-9-carbonitrile

Example 51A (6aS,7S,10aS)-10a-(4-fluorophenyl)-7-methyl-2-(pyridin-3-yl)-5,6a,7,9,10,10a-hexahydro-6H-spiro[benzo[h]quinazoline-8,2'-[1,3]dioxolane]

To a solution of the Example 50G (0.700 g, 2.02 mmol) in isopropanol (15 mL) was added 3-amidinopyridinium chloride (0.955 g, 6.06 mmol) and piperidine (0.600 mL, 9.09 mmol). The reaction mixture was heated at 95° C. for 48 hours. The cooled reaction solution was diluted with a saturated aqueous solution of sodium phosphate monobasic and extracted with ethyl acetate. The organic phase concentrated to provide the titled compound. MS (APCI+) m/z 432 (M+H)$^+$.

Example 51B (6aS,7S,10aS)-10a-(4-fluorophenyl)-7-methyl-2-(pyridin-3-yl)-5,6a,7,9,10,10a-hexahydrobenzo[h]quinazolin-8(6H)-one The titled compound was prepared using the conditions described in Example 1I, substituting Example 51A for Example 1H.

Example 51C (6aS,7S,9Z,10aS)-10a-(4-fluorophenyl)-9-(hydroxymethylene)-7-methyl-2-(pyridin-3-yl)-5,6a,7,9,10,10a-hexahydrobenzo[h]quinazolin-8(6H)-one The titled compound was prepared using the conditions described in Example 1J, substituting Example 51B for Example 1I. MS (APCI+) m/z 388 (M+H)$^+$.

Example 51D (6aS,7S,11aS)-11a-(4-fluorophenyl)-7-methyl-2-(pyridin-3-yl)-5,6,6a,7,11,11a-hexahydro[1,2]benzoxazolo[6,5-h]quinazoline The titled compound was prepared using the conditions described in Example 1K, substituting Example 51C for Example 1J. MS (APCI+) m/z 413 (M+H)$^+$.

Example 51E (6aS,7S,10aS)-10a-(4-fluorophenyl)-7-methyl-8-oxo-2-(pyridin-3-yl)-5,6,6a,7,8,9,10,10a-octahydrobenzo[h]quinazoline-9-carbonitrile The titled compound was prepared using the conditions described in Example 1L, substituting Example 51D for Example 1K.

Example 51F (6aS,7S,10aR)-10a-(4-fluorophenyl)-7-methyl-8-oxo-2-(pyridin-3-yl)-5,6,6a,7,8,10a-hexahydrobenzo[h]quinazoline-9-carbonitrile The titled compound was prepared using the conditions described in Example 1M, substituting Example 51E for Example 1L and stirring at 0° C. for 35 minutes. The material was purified using a 12 g RediSep® cartridge on a Teledyne Isco Combiflash Rf® system, eluting with 0-90% ethyl acetate in heptane to give 0.019 g (16%). $^1$H NMR (400 MHz, CDCl$_3$) δ ppm 1.23 (d, J=6.40 Hz, 3H) 1.63-1.72 (m, 1H) 1.99-2.08 (m, 1H) 2.31-2.50 (m, 2H) 3.01-3.22 (m, 2H) 6.82 (dd, J=8.95, 4.93 Hz, 2H) 7.04 (t, J=8.46 Hz, 2H) 7.43-7.50 (m, 1H) 8.65-8.74 (m, 2H) 8.82 (s, 1H) 8.93 (s, 1H) 9.60 (s, 1H); MS (ESI+) m/z 411 (M+H)$^+$, 443 (M+CH$_3$OH+H)$^+$.

Example 52

(5aS,6S,9aR)-2,6-dimethyl-7-oxo-9a-phenyl-4,5,5a,6,7,9a-hexahydro-2H-benzo[g]indazole-8-carbonitrile

Example 52A (5aS,6S,9aS)-2,6-dimethyl-9a-phenyl-2,4,5,5a,6,8,9,9a-octahydrospiro[benzo[g]indazole-7,2'-[1,3]dioxolane]

The titled compound was prepared using the conditions described in Example 24A substituting hydrazine with N-methyl hydrazine. $^1$H NMR (400 MHz, CDCl$_3$) δ ppm 0.97-1.06 (m, 3H), 1.36-1.45 (m, 1H), 1.64-1.74 (m, 1H), 1.93-2.16 (m, 4H), 2.50-2.63 (m, 3H), 2.69-2.81 (m, 1H), 3.76-3.92 (m, 3H), 3.92-4.00 (m, 4H), 6.90-6.97 (m, 1H), 7.06-7.13 (m, 1H), 7.19-7.26 (m, 2H), 7.68-7.76 (m, 2H); MS (DCI) m/z 339 (M+H)$^+$

Example 52B (5aS,6S,9aS)-2,6-dimethyl-9a-phenyl-2,4,5,5a,6,8,9,9a-octahydro-7H-benzo[g]indazol-7-one The titled compound was prepared using the conditions described in Example 24B substituting Example 52A for Example 24A. MS (APCI) m/z 295 (M+H)$^+$.

Example 52C (5aS,6S,8Z,9aS)-8-(hydroxymethylene)-2,6-dimethyl-9a-phenyl-2,4,5,5a,6,8,9,9a-octahydro-7H-benzo[g]indazol-7-one The titled compound was prepared using the conditions described in Example 24C substituting Example 52B for Example 24B. MS (APCI) m/z 301 (M+H)$^+$.

Example 52D (5aS,6S,10aS)-2,6-dimethyl-10a-phenyl-4,5,5a,6,10,10a-hexahydro-2H-indazolo[7,6-f][1,2]benzoxazole The titled compound was prepared using the conditions described in Example 24D substituting Example 52C for Example 24C. MS (APCI) m/z 320 (M+H)$^+$.

Example 52E (5aS,6S,9aS)-2,6-dimethyl-7-oxo-9a-phenyl-4,5,5a,6,7,8,9,9a-octahydro-2H-benzo[g]indazole-8-carbonitrile The titled compound was prepared using the conditions described in Example 24E substituting Example 52D for Example 24D. MS (APCI) m/z 320 (M+H)$^+$.

Example 52F (5aS,6S,9aR)-2,6-dimethyl-7-oxo-9a-phenyl-4,5,5a,6,7,9a-hexahydro-2H-benzo[g]indazole-8-carbonitrile The product of Example 52E (0.022 g, 0.069 mmol) was dissolved in tetrahydrofuran (0.689 mL) and the solution was sparged with nitrogen for 10 minutes. 2,3-Dichloro-5,6-dicyano-1,4-benzoquinone (0.020 mg, 0.090 mmol) was then added with continued nitrogen sparging. The reaction mixture was stirred at room temperature for 1 hour and then concentrated. The residue was purified on reversed-phase Waters HPLC using a Nova-Pak® HR C18, 6 µm, 60 Å, 40 mm×100 mm, PrepPak cartridge eluting with a gradient of 10-90% acetonitrile in aqueous 0.1% trifluoroacetic acid (60 mL/minute) to give the titled compound as the trifluoroacetic acid salt (0.008 g, 38% yield). $^1$H NMR (400 MHz, CDCl$_3$) δ ppm 1.16 (d, J=6.6 Hz, 3H), 1.43-1.62 (m, 2H), 2.32 (t, J=11.9 Hz, 1H), 2.43 (dt, J=13.1, 6.6 Hz, 1H), 2.61-2.78 (m, 1H), 2.86 (dd, J=16.3, 6.6 Hz, 1H), 3.88 (s, 3H), 6.91 (d, J=6.7 Hz, 2H), 7.24 (s, 1H), 7.29 (dd, J=12.1, 4.3 Hz, 3H), 8.42 (s, 1H); MS (APCI) m/z 318 (M+H)$^+$.

Example 53

(5aS,6S,9aR)-9a-(3-fluorophenyl)-6-methyl-7-oxo-4,5,5a,6,7,9a-hexahydro-2H-benzo[g]indazole-8-carbonitrile

Example 53A 2-(3-fluorophenyl)cyclohexane-1,3-dione

A 1 L round-bottomed flask was charged with 3-bromofluorobenzene (34.2 mL, 311 mmol), tert-amyl alcohol (300 mL) and dioxane (600 mL), and the contents were sparged with N$_2$ for 45 minutes. A 3 L round-bottomed flask was charged with potassium phosphate tribasic (138 g, 649 mmol), 1,3-cyclohexanedione (97 weight %, 30 g, 260 mmol), palladium(II) acetate (1.17 g, 5.2 mmol) and 2-(di-tert-butylphospino)-2'-methylbiphenyl (3.24 g, 10.4 mmol), and the contents were sparged with N$_2$ for 45 minutes. The 3-bromofluorobenzene containing solution was then transferred to the 1,3-cyclohexanedione containing mixture via cannula, and the reaction mixture was heated to reflux overnight. Upon completion, the reaction mixture was cooled to room temperature, and the reaction mixture was partitioned between ethyl acetate (1 L) and 10% HCl (1 L) with mixing. The lower aqueous layer was separated and extracted with ethyl acetate (1 L). The combined organic layers were washed with brine (500 mL) and concentrated. The residue was taken up in toluene (300 mL) and again concentrated. The residue was taken up in toluene (150 mL) and warmed to 50° C. After cooling to room temperature, the solids were collected by filtration, washed with toluene (2×50 mL) and dried in a vacuum oven at 50° C. to provide the titled compound (52.4 g, 98%). $^1$H NMR (400 MHz, CDCl$_3$) δ ppm 7.45-7.33 (m, 1H), 7.09-6.99 (m, 1H), 6.99-6.88 (m, 2H), 6.26 (bs, 1H), 2.71-2.43 (m, 4H), 1.58 (bs, 2H).

Example 53B (8aR)-8a-(3-fluorophenyl)-5-methyl-3,4,8,8a-tetrahydronaphthalene-1,6(2H,7H)-dione A 3 L round-bottomed flask was charged with Example 53A (52.4 g, 254 mmol) in acetonitrile (300 mL). Triethylamine (71 mL, 508 mmol) and ethyl vinyl ketone (38 mL, 381 mmol) were added, and the contents were warmed to 75° C. with stirring overnight. Upon completion, the reaction mixture was cooled to room temperature and concentrated. The residue was taken up in dimethyl sulfoxide (125 mL). Pyridinium para-toluenesulfonate (41.5 g, 165 mmol) and L-phenylalanine (54.5 g, 330 mmol) were added, and the contents were warmed to 50° C. for 48 hours. Upon completion, the reaction mixture was cooled to room temperature and poured into saturated aqueous ammonium chloride (200 mL) and methyl t-butyl ether (300 mL). After mixing for 10 minutes, the solids were removed by filtration, and the layers separated. The organic layer was washed with saturated aqueous ammonium chloride (200 mL). The combined aqueous layers were extracted with methyl t-butyl ether (300 mL). The combined organic layers were washed with water (200 mL) and brine (200 mL), dried over sodium sulfate, filtered, and concentrated. The residue was purified by chromatography over silica gel using a 330 g RediSep® cartridge on a Teledyne Isco Torrent Combiflash® system: ethyl acetate/hexanes 0:1 (2 column volumes) up to 1:1 (gradient over 8 column volumes). Fractions containing the titled compound were combined and concentrated under reduced pressure to give the titled compound in 68% ee determined using a Chiralpak® AS-H column (4.6 mm ID×25 cm, 5 microns) eluting with 10% ethanol in heptane at 1.0 mL/minute with the major enantiomer having a retention time of 9.6 minutes and the minor enantiomer having a retention time of 11.0 minutes (32.2 g, 47%).

Example 53C (4aR,5S)-4a-(3-fluorophenyl)-5-hydroxy-1-methyl-4,4a,5,6,7,8-hexahydronaphthalen-2(3H)-one A 3 L jacketed round bottom flask was charged with Example 53B (32.2 g, 118 mmol) in ethanol (300 mL), and the solution was cooled to −5° C. A solution of sodium borohydride (1.34 g, 35.5 mmol) in ethanol (300 mL) was added dropwise while maintaining an internal temperature below 0° C. The resulting mixture was stirred at −5° C. for 4 hours. Upon completion, the reaction mixture was quenched carefully with acetic acid (40 mL) and warmed to 23° C. After stirring overnight, the mixture was concentrated. The residue was partitioned between methyl t-butyl ether (300 mL) and 10% aqueous ammonium hydroxide (150 mL). The layers were separated and the organic layer was washed with 10% aqueous ammonium hydroxide (150 mL). The combined aqueous layers were extracted with methyl t-butyl ether (300 mL). The combined organic layers were washed with brine (100 mL), dried over sodium sulfate, filtered and concentrated. The residue was purified by chromatography over silica gel using a 330 g RediSep® cartridge on a Teledyne Isco Torrent Combiflash® system: ethyl acetate/hexanes 0:1 (2 column volumes) up to 1:1 (gradient over 8 column volumes). Fractions containing the titled compound were combined and concentrated under reduced pressure (32.4 g, 100%). $^1$H NMR (400 MHz, CDCl$_3$) δ ppm 7.49-7.39 (m, 1H), 7.29-7.18 (m, 2H), 6.98-6.89 (m, 1H), 3.86-3.79 (m, 1H), 2.80-2.72 (m, 1H), 2.65-2.59 (m, 1H), 2.49-2.43 (m, 1H), 2.37-2.29 (m, 1H), 2.24-2.06 (m, 2H), 1.93 (d, J=1.2 Hz, 3H), 1.89-1.78 (m, 2H), 1.73-1.61 (m, 1H), 1.59-1.44 (m, 1H).

Example 53D (1S,4aS,5S,8aS)-4a-(3-fluorophenyl)-5-hydroxy-1-methyloctahydronaphthalen-2(1H)-one A 500 mL Parr stirred pressure reactor was charged with 8.1 g of 5% Pd/C (20 weight % of substrate charged). Under a stream of nitrogen, a solution of Example 53C (32.4 g, 118 mmol), tetrahydrofuran (295 mL) and pyridine (74 mL) was added to the reactor. The reactor was purged with nitrogen and hydrogen. The vessel was pressurized to and maintained at 60-100 psig with hydrogen supplied from a high-pressure reservoir. The mixture was vigorously agitated while keeping the temperature between 22-25° C. The reaction mixture was carefully filtered to remove the palladium catalyst rinsing the reactor and cake with tetrahydrofuran. To the filtrate was added 1,8-diazabicyclo[5.4.0]undec-7-ene (4 mL), and the resulting mixture was stirred at room temperature overnight. Upon completion, the mixture was concentrated under reduced pressure, and the residue taken up in toluene (200 mL). The resulting solution was washed with 10% hydrochloric acid (2×100 mL). The combined aqueous layers were extracted with toluene (100 mL), and the combined organic layers were washed with brine (50 mL), dried over sodium sulfate, and filtered. The resulting solution of the titled compound was used without additional purification.

Example 53E (1'S,4a'S,5'S,8a'S)-4a'-(3-fluorophenyl)-1'-methyloctahydro-1'H-spiro[1,3-dioxolane-2,2'-naphthalen]-5'-ol Ethylene glycol (45.7 g, 736 mol) and para-toluenesulfonic acid (2.8 g, 14.7 mmol) were added to the toluene solution from Example 53D, and the resulting mixture heated to reflux with Dean Stark removal of water. Additional ethylene glycol (45.7 g, 736 mol) was added after 8 hours, and refluxing was continued overnight. After reaction completion, the mixture was cooled to room temperature, and the toluene solution was washed with saturated aqueous sodium bicarbonate (2×100 mL). The combined aqueous layers were extracted with dichloromethane (100 mL). The combined organic layers were washed with brine (50 mL), dried over sodium sulfate, filtered and concentrated. The resulting residue was used without additional purification.

Example 53F (1'S,4a'S,8a'S)-4a'-(3-fluorophenyl)-1'-methylhexahydro-1'H-spiro[1,3-dioxolane-2,2'-naphthalen]-5'(3'H)-one The residue from Example 53E was dissolved in dichloromethane (300 mL) and pyridinium dichromate (111 g, 294 mmol) and magnesium sulfate (3.5 g) were added. The resulting mixture was heated to reflux and stirred overnight. The reaction was cooled to room temperature, and the mixture was filtered through a plug of silica gel (150 g) rinsing with dichloromethane (1 L). The filtrate was concentrated, and the remaining solids were triturated with cyclohexane (50 mL). The solids were collected by filtration, washed with cyclohexane (2×10 mL) and dried in a vacuum oven at 50° C. to give the titled compound. $^1$H NMR (400 MHz, CDCl$_3$) δ ppm 7.36-7.27 (m, 1H), 7.24-7.13 (m, 2H), 7.00-6.86 (m, 1H), 4.03-3.93 (m, 4H), 2.68 (dq, J=13.0, 6.6 Hz, 1H), 2.29-1.91 (m, 8H), 1.76-1.63 (m, 2H), 1.17 (td, J=13.5, 4.3 Hz, 1H), 1.04 (d, J=6.6 Hz, 3H); MS (CI—NH$_3$) m/z 336.1 (M+NH$_4$)$^+$.

Example 53G (1'S,4a'S,6'Z,8a'S)-4a'-(3-fluorophenyl)-6'-(hydroxymethylene)-1'-methylhexahydro-1'H-spiro[1,3-dioxolane-2,2'-naphthalen]-5'(3'H)-one The titled compound was prepared using the conditions described in Example 58G substituting Example 58F with Example 53F. $^1$H NMR (400 MHz, CDCl$_3$) δ ppm 1.00 (t, J=8.1 Hz, 3H), 1.27 (td, J=13.8, 3.7 Hz, 1H), 1.64 (dt, J=13.6, 3.5 Hz, 1H), 1.77-2.26 (m, 8H), 2.49 (dq, J=12.9, 6.5 Hz, 1H), 6.86-7.00 (m, 1H), 7.23 (dd, J=9.1, 6.9 Hz, 1H), 7.28 (t, J=5.6 Hz, 1H), 7.40 (d, J=9.4 Hz, 1H), 13.76 (d, J=9.6 Hz, 1H); MS (DCI) m/z 347 (M+H)$^+$.

Example 53H (5aS,6S,9aS)-9a-(3-fluorophenyl)-6-methyl-2,4,5,5a,6,8,9,9a-octahydrospiro[benzo[g]indazole-7,2'-[1,3]dioxolane]

The titled compound was prepared using the conditions described in Example 24A substituting Example 1G with Example 53G. $^1$H NMR (400 MHz, CDCl$_3$) δ ppm 1.01 (t, J=5.7 Hz, 3H), 1.47 (td, J=14.0, 3.7 Hz, 1H), 1.57-1.68 (m, 2H), 1.74 (ddd, J=18.9, 11.7, 8.3 Hz, 2H), 2.08 (dddd, J=32.6, 28.5, 16.7, 7.6 Hz, 13H), 2.44-2.56 (m, 1H), 2.56-2.76 (m, 3H), 3.91-3.98 (m, 6H), 6.64-6.99 (m, 2H), 7.02-7.16 (m, 1H), 7.16-7.24 (m, 2H), 7.28-7.32 (m, 1H), 7.32-7.40 (m, 1H), 7.43 (d, J=7.8 Hz, 1H); MS (APCI) m/z 342 (M+H)$^+$.

Example 53I (5aS,6S,9aS)-9a-(3-fluorophenyl)-6-methyl-2,4,5,5a,6,8,9,9a-octahydro-7H-benzo[g]indazol-7-one The titled compound was prepared using the conditions described in Example 24B substituting Example 24A with Example 53H. $^1$H NMR (400 MHz, CDCl$_3$) δ ppm 1.17 (d, J=6.8 Hz, 3H), 1.92-2.04 (m, 3H), 2.05-2.15 (m, 2H), 2.26-2.49 (m, 5H), 2.52-2.74 (m, 5H), 2.84 (dd, J=14.9, 4.3 Hz, 1H), 3.05 (dd, J=12.6, 5.5 Hz, 1H), 6.90 (t, J=7.7 Hz, 1H), 7.09 (d, J=11.4 Hz, 1H), 7.23 (d, J=7.8 Hz, 1H), 7.29 (d, J=5.2 Hz, 1H); MS (DCI) m/z 299 (M+H)$^+$.

Example 53J (5aS,6S,8Z,9aS)-9a-(3-fluorophenyl)-8-(hydroxymethylene)-6-methyl-2,4,5,5a,6,8,9,9a-octahydro-7H-benzo[g]indazol-7-one The titled compound was prepared using the conditions described in Example 24C substituting Example 24B with Example 53I. MS (APCI) m/z 327 (M+H)$^+$.

Example 53K (5aS,6S,10aS)-10a-(3-fluorophenyl)-6-methyl-4,5,5a,6,10,10a-hexahydro-2H-indazolo[7,6-f][1,2]benzoxazole The titled compound was prepared using the conditions described in Example 24D substituting Example 24C with Example 53J. MS (APCI) m/z 324 (M+H)$^+$.

Example 53L (5aS,6S,9aS)-9a-(3-fluorophenyl)-6-methyl-7-oxo-4,5,5a,6,7,8,9,9a-octahydro-2H-benzo[g]indazole-8-carbonitrile The titled compound was prepared using the conditions described in Example 24E substituting Example 24D with Example 53K. MS (APCI) m/z 324 (M+H)$^+$.

Example 53M (5aS,6S,9aR)-9a-(3-fluorophenyl)-6-methyl-7-oxo-4,
5,5a,6,7,9a-hexahydro-2H-benzo[g]indazole-8-carbonitrile Example 53L (0.360 g, 1.113 mmol) was dissolved in toluene (11.13 mL) and sparged with nitrogen for 10 minutes. The reaction mixture was treated with 2,3-dichloro-5,6-dicyano-1,4-benzoquinone (0.329 g, 1.447 mmol) and stirred at room temperature for 1 hour. The reaction mixture was concentrated, and the residue was purified using a Biotage® SNAP 50 g silica cartridge eluting with 0-50% acetone/hexane. The residue from the first chromatography was then purified on reversed-phase Waters HPLC using a Nova-Pak® HR C18, 6 μm, 60 Å, 40 mm×100 mm, PrepPak cartridge eluting with a gradient of 10-90% acetonitrile in aqueous 0.1% trifluoroacetic acid (60 mL/minute) to give the titled compound as the trifluoroacetic acid salt (0.015 g, 5% yield). $^1$H NMR (400 MHz, CDCl$_3$) δ ppm 1.20 (t, J=6.5 Hz, 3H), 1.55 (ddd, J=25.9, 12.1, 6.9 Hz, 1H), 1.86 (dd, J=14.2, 7.5 Hz, 1H), 2.31-2.41 (m, 2H), 2.46 (dt, J=19.7, 6.4 Hz, 2H), 2.69-2.81 (m, 2H), 2.93 (dd, J=16.5, 6.5 Hz, 1H), 6.53 (d, J=10.6 Hz, 1H), 6.74 (d, J=7.7 Hz, 1H), 6.99 (td, J=8.1, 2.3 Hz, 1H), 7.27-7.32 (m, 1H), 7.48 (s, 1H), 8.41 (s, 1H); MS (APCI) m/z 321 (M+H)$^+$.

Example 54

(5aS,6S,9aR)-9a-(4-fluorophenyl)-6-methyl-7-oxo-4,
5,5a,6,7,9a-hexahydro-2H-benzo[g]indazole-8-carbonitrile

Example 54A (5aS,6S,9aS)-9a-(4-fluorophenyl)-6-methyl-2,4,5,5a,
6,8,9,9a-octahydrospiro[benzo[g]indazole-7,2'-[1,3]
dioxolane]

The titled compound was prepared using the conditions described in Example 24A substituting Example 50G for Example 1G.

Example 54B (5aS,6S,9aS)-9a-(4-fluorophenyl)-6-methyl-2,4,5,5a,
6,8,9,9a-octahydro-7H-benzo[g]indazol-7-one The titled compound was prepared using the conditions described in Example 24B substituting Example 54A for Example 24A. MS (APCI) m/z 299 (M+H)$^+$.

Example 54C (5aS,6S,8Z,9aS)-9a-(4-fluorophenyl)-8-(hydroxymethylene)-6-methyl-2,4,5,5a,6,8,9,9a-octahydro-7H-benzo[g]indazol-7-one The titled compound was prepared using the conditions described in Example 24C substituting Example 24B with Example 54B.

Example 54D (5aS,6S,10aS)-10a-(4-fluorophenyl)-6-methyl-4,5,
5a,6,10,10a-hexahydro-2H-indazolo[7,6-f][1,2]benzoxazole The titled compound was prepared using the conditions described in Example 24D substituting Example 24C with Example 54C.

Example 54E (5aS,6S,9aS)-9a-(4-fluorophenyl)-6-methyl-7-oxo-4,
5,5a,6,7,8,9,9a-octahydro-2H-benzo[g]indazole-8-carbonitrile The titled compound was prepared using the conditions described in Example 24E substituting Example 24D with Example 54D.

Example 54F (5aS,6S,9aR)-9a-(4-fluorophenyl)-6-methyl-7-oxo-4,
5,5a,6,7,9a-hexahydro-2H-benzo[g]indazole-8-carbonitrile Example 54E (0.280 g, 0.866 mmol) was dissolved in toluene (8.66 mL) and sparged with nitrogen for 10 minutes. 2,3-Dichloro-5,6-dicyano-1,4-benzoquinone (0.256 g, 1.126 mmol) was added, and sparging with nitrogen was continued while the reaction mixture was stirred at room temperature for 1 hour. The reaction mixture was concentrated and purified on a reversed-phase Waters HPLC using a Nova-Pak® HR C18, 6 μm, 60 Å, 40 mm×100 mm, PrepPak cartridge eluting with a gradient of 10-90% acetonitrile in aqueous 0.1% trifluoroacetic acid (60 mL/minute) to give the titled compound as the trifluoroacetic acid salt (0.0150 g, 53%). $^1$H NMR (400 MHz, CDCl$_3$) δ ppm 1.14-1.21 (m, 3H), 1.80-1.91 (m, 1H), 2.31-2.46 (m, 2H), 2.66-2.80 (m, 1H), 2.87-2.97 (m, 1H), 6.81-6.89 (m, 2H), 6.97-7.04 (m, 2H), 7.43-7.51 (m, 1H), 8.39-8.45 (m, 1H); MS (DCI) m/z 339 (M+NH$_4$)$^+$.

Example 55

(6aS,7S,10aR)-10a-(3-fluorophenyl)-7-methyl-8-oxo-5,6,6a,7,8,10a-hexahydrobenzo[h]quinazoline-9-carbonitrile

Example 55A (6aS,7S,10aS)-10a-(3-fluorophenyl)-7-methyl-5,6a,
7,9,10,10a-hexahydro-6H-spiro[benzo[h]quinazoline-8,2'-[1,3]dioxolane]

To a solution of the product from Example 53G (0.500 g, 1.44 mmol) in isopropanol (10 mL) was added formamidine acetate (0.601 g, 5.77 mmol) and piperidine (0.572 mL, 5.77 mmol). The reaction mixture was heated at 95° C. for 24 hours. The cooled solution was diluted with a solution of saturated aqueous sodium phosphate monobasic and extracted with ethyl acetate. The organic phase was concentrated to give the titled compound which was used without additional purification. MS (APCI+) m/z 355 (M+H)+.

Example 55B (6aS,7S,10aS)-10a-(3-fluorophenyl)-7-methyl-5,6a, 7,9,10,10a-hexahydrobenzo[h]quinazolin-8(6H)-one The titled compound was prepared using the conditions described in Example 1I, substituting Example 55A for Example 1H. MS (APCI+) m/z 311 (M+H)+.

Example 55C (6aS,7S,9Z,10aS)-10a-(3-fluorophenyl)-9-(hydroxymethylene)-7-methyl-5,6a,7,9,10,10a-hexahydrobenzo[h]quinazolin-8(6H)-one The titled compound was prepared using the conditions described in Example 1J, substituting Example 55B for Example 1I, and heating at 45° C. for 1 hour.

Example 55D (6aS,7S,11aS)-11a-(3-fluorophenyl)-7-methyl-5,6, 6a,7,11,11a-hexahydro[1,2]benzoxazolo[6,5-h]quinazoline The titled compound was prepared using the conditions described in Example 1K, substituting Example 55C for Example 1J.

Example 55E (6aS,7S,10aS)-10a-(3-fluorophenyl)-7-methyl-8-oxo-5,6,6a,7,8,9,10,10a-octahydrobenzo[h]quinazoline-9-carbonitrile The titled compound was prepared using the conditions described in Example 1L, substituting Example 55D for Example 1K. MS (APCI+) m/z 336 (M+H)+.

Example 55F (6aS,7S,10aR)-10a-(3-fluorophenyl)-7-methyl-8-oxo-5,6,6a,7,8,10a-hexahydrobenzo[h]quinazoline-9-carbonitrile The titled compound was prepared using the conditions described in Example 1M, substituting Example 55E for Example 1L. Purification was achieved using a 12 g RediSep® cartridge on a Teledyne Isco Combiflash® Rf system, eluting with 0-10% ethyl acetate in dichloromethane to give 0.036 g (34%) of the titled compound. $^1$H NMR (400 MHz, CDCl$_3$) δ ppm 1.21 (d, J=6.61 Hz, 3H) 1.59-1.72 (m, 1H) 2.01 (dd, J=13.93, 7.64 Hz, 1H) 2.35 (td, J=12.85, 2.39 Hz, 1H) 2.45 (td, J=13.12, 6.61 Hz, 1H) 2.99-3.18 (m, 2H) 6.43 (dt, J=10.36, 2.09 Hz, 1H) 6.63 (dd, J=7.81, 1.52 Hz, 1H) 7.03 (td, J=8.19, 2.28 Hz, 1H) 7.32 (td, J=8.11, 6.23 Hz, 1H) 8.74 (s, 1H) 8.82 (s, 1H) 9.08 (s, 1H); MS (ESI+) m/z 334 (M+H)+.

Example 56

(5aS,6S,9aR)-2-benzyl-6-methyl-7-oxo-9a-phenyl-4, 5,5a,6,7,9a-hexahydro-2H-benzo[g]indazole-8-carbonitrile Example 56A (5aS,6S,9aS)-1-benzyl-6-methyl-9a-phenyl-1,4,5,5a, 6,8,9,9a-octahydrospiro[benzo[g]indazole-7,2'-[1,3] dioxolane] and (5aS,6S,9aS)-2-benzyl-6-methyl-9a-phenyl-2,4,5,5a,6,8,9,9a-octahydrospiro[benzo[g] indazole-7,2'-[1,3]dioxolane]

The titled compounds were prepared using the conditions described in Example 24A substituting hydrazine with N-benzyl hydrazine.

Example 56B (5aS,6S,9aS)-1-benzyl-6-methyl-9a-phenyl-1,4,5,5a, 6,8,9,9a-octahydro-7H-benzo[g]indazol-7-one and (5aS,6S,9aS)-2-benzyl-6-methyl-9a-phenyl-2,4,5,5a, 6,8,9,9a-octahydro-7H-benzo[g]indazol-7-one The titled compounds were prepared using the conditions described in Example 24B substituting Example 24A with Example 56A.

Example 56C (5aS,6S,8Z,9aS)-1-benzyl-8-(hydroxymethylene)-6-methyl-9a-phenyl-1,4,5,5a,6,8,9,9a-octahydro-7H-benzo[g]indazol-7-one and (5aS,6S,8Z,9aS)-2-benzyl-8-(hydroxymethylene)-6-methyl-9a-phenyl-2,4, 5,5a,6,8,9,9a-octahydro-7H-benzo[g]indazol-7-one The titled compounds were prepared using the conditions described in Example 24C substituting Example 24B with Example 56B.

Example 56D (5aS,6S,10aS)-1-benzyl-6-methyl-10a-phenyl-4,5, 5a,6,10,10a-hexahydro-1H-indazolo[7,6-f][1,2]benzoxazole and (5aS,6S,10aS)-2-benzyl-6-methyl-10a-phenyl-4,5,5a,6,10,10a-hexahydro-2H-indazolo[7,6-f][1,2]benzoxazole (1:1)

The titled compounds were prepared using the conditions described in Example 24D substituting Example 24C with Example 56C. MS (APCI) m/z 476 (M+H)+.

Example 56E (5aS,6S,9aS)-2-benzyl-6-methyl-7-oxo-9a-phenyl-4, 5,5a,6,7,8,9,9a-octahydro-2H-benzo[g]indazole-8-carbonitrile and (5aS,6S,9aS)-1-benzyl-6-methyl-7-oxo-9a-phenyl-4,5,5a,6,7,8,9,9a-octahydro-1H-benzo[g]indazole-8-carbonitrile The titled compounds were prepared using the conditions described in Example 24E substituting Example 24D with Example 56D.

Example 56F (5aS,6S,9aR)-2-benzyl-6-methyl-7-oxo-9a-phenyl-4, 5,5a,6,7,9a-hexahydro-2H-benzo[g]indazole-8-carbonitrile Example 56E (0.066 g, 0.167 mmol) was dissolved in toluene (1.67 mL), and the resultant solution was sparged with nitrogen for 10 minutes. At this point, 2,3-dichloro-5, 6-dicyano-1,4-benzoquinone (0.049 g, 0.217 mmol) was added, and the reaction mixture was stirred at room temperature nitrogen with continued nitrogen sparging for 10 minutes. The reaction mixture was concentrated, and the residue was purified on Biotage® SNAP silica 10 g cartridge using 0-50% acetone/hexane. A second chromatography was performed using a reversed-phase Waters HPLC using a Nova-Pak® HR C18, 6 μm, 60 Å, 40 mm×100 mm, PrepPak cartridge eluting with a gradient of 10-90% acetonitrile in aqueous 0.1% trifluoroacetic acid (60 mL/minute) to give 0.005 g (8% yield) of the titled compound as the second eluting isomer relative to Example 57 as the trifluoroacetic acid salt. $^1$H NMR (500 MHz, CDCl$_3$) δ ppm 1.16 (d, J=6.6 Hz, 3H), 1.53 (ddd, J=25.8, 12.1, 6.7 Hz, 1H), 1.79 (dd, J=13.8, 7.3 Hz, 1H), 2.35 (td, J=12.9, 1.9 Hz, 1H), 2.45 (dq, J=13.2, 6.6 Hz, 1H), 2.61-2.73 (m, 1H), 2.84 (dd, J=16.3, 6.5 Hz, 1H), 5.23-5.31 (m, 2H), 6.88-6.94 (m, 2H), 7.21 (d, J=6.5 Hz, 2H), 7.25-7.41 (m, 8H), 8.01-8.09 (m, 1H), 8.45 (s, 1H); MS (APCI) m/z 394 (M+H)$^+$.

Example 57

(5aS,6S,9aR)-1-benzyl-6-methyl-7-oxo-9a-phenyl-4, 5,5a,6,7,9a-hexahydro-1H-benzo[g]indazole-8-carbonitrile The titled compound was isolated to give 0.024 g (36% yield) as the first eluting compound from the reversed-phase chromatography described in Example 56F as the trifluoroacetic acid salt. $^1$H NMR (500 MHz, CDCl$_3$) δ ppm 1.15 (d, J=6.8 Hz, 3H), 1.58 (qd, J=12.5, 5.5 Hz, 1H), 1.81 (dd, J=13.8, 5.9 Hz, 1H), 2.18 (s, 1H), 2.28 (dq, J=13.6, 6.8 Hz, 1H), 2.47 (t, J=12.0 Hz, 1H), 2.69 (ddd, J=23.7, 12.8, 6.7 Hz, 1H), 2.88 (dd, J=16.0, 4.5 Hz, 1H), 4.59 (d, J=16.5 Hz, 1H), 5.21 (d, J=16.4 Hz, 1H), 6.85 (dd, J=6.4, 2.9 Hz, 2H), 6.96 (d, J=6.7 Hz, 2H), 7.25-7.41 (m, 7H), 7.46 (d, J=5.3 Hz, 1H), 7.58 (s, 1H), 7.82 (s, 1H); MS (APCI) m/z 394 (M+H)$^+$.

Example 58

(5aS,6S,9aR)-9a-(4-methoxyphenyl)-6-methyl-7-oxo-4,5,5a,6,7,9a-hexahydro-2H-benzo[g]indazole-8-carbonitrile

Example 58A 2-(4-methoxyphenyl)cyclohexane-1,3-dione

A 1 L round-bottomed flask was charged with 4-bromoanisole (39 mL, 58.2 mmol), tert-amyl alcohol (300 mL) and dioxane (600 mL), and the contents were sparged with N$_2$ for 45 minutes. A 3 L round-bottomed flask was charged with potassium phosphate tribasic (138 g, 649 mmol), 1,3-cyclohexanedione (30 g, 260 mmol), palladium(II) acetate (1.17 g, 5.2 mmol) and 2-(di-tert-butylphospino)-2'-methylbiphenyl (3.24 g, 10.4 mmol), and the contents were also sparged with N$_2$ for 45 minutes. The solution containing 4-bromoanisole was transferred to the 1,3-cyclohexanedione containing mixture via cannula, and the reaction mixture was heated to reflux overnight. Upon completion, the reaction mixture was cooled to room temperature, and the reaction mixture was partitioned between ethyl acetate (1 L) and 10% hydrochloric acid (1 L) with mixing. The lower aqueous layer was separated and extracted with ethyl acetate (1 L). The combined organic layers were washed with brine (500 mL) and concentrated. The residue was taken up in toluene (300 mL) and again concentrated under reduced pressure. The residue was taken up in toluene (150 mL) and warmed to 50° C. After cooling to room temperature, the solids were collected by filtration, washed with toluene (2×50 mL) and dried in a vacuum oven at 50° C. to give the titled compound (41.6 g, 73%).
$^1$H NMR (400 MHz, CDCl$_3$) δ ppm 7.14-7.07 (m, 2H), 7.00-6.93 (m, 2H), 6.13-5.97 (m, 1H), 3.81 (s, 3H), 2.67-2.42 (m, 4H), 1.67-1.51 (m, 2H).

Example 58B (8aR)-8a-(4-methoxyphenyl)-5-methyl-3,4,8,8a-tetrahydronaphthalene-1,6(2H,7H)-dione A 3 L round-bottomed flask was charged with Example 58A (41.6 g, 191 mmol) and acetonitrile (1.4 L). Triethylamine (53 mL, 381 mmol) and ethyl vinyl ketone (28 mL, 286 mol) were added, and the contents were warmed to 75° C. and stirred overnight. Upon completion, the reaction mixture was cooled to room temperature and concentrated. The residue was taken up in dimethyl sulfoxide (100 mL). Pyridinium para-toluenesulfonate (31.2 g, 124 mmol) and L-phenylalanine (41.0 g, 248 mmol) were added, and the contents were warmed to 45° C. for 66 hours. Upon completion, the reaction mixture was cooled to room temperature and poured into saturated aqueous ammonium chloride (200 mL) and methyl t-butyl ether (200 mL). After mixing for 10 minutes, the solids were removed by filtration and the layers separated. The organic layer was washed with saturated aqueous ammonium chloride (200 mL). The combined aqueous layers were extracted with methyl t-butyl ether (200 mL). The combined organic layers were washed with water (500 mL) and brine (200 mL), dried over Na$_2$SO$_4$, filtered, and concentrated. The residue was purified by chromatography over SiO$_2$ using a 330 g RediSep® cartridge on a Teledyne Isco Torrent Combiflash® system: ethyl acetate/hexanes 0:1 (2 column volumes) up to 1:1 (gradient over 8 column volumes). Fractions containing the titled compound were combined and concentrated under reduced pressure. The 75% ee material was taken up in ethanol (400 mL) and stirred at 0° C. for 2 hours. The solids (racemic) were removed by filtration, and the filtrate was concentrated to give the titled compound enriched to 95% ee determined using a Chiralpak® AS-H column (4.6 mm ID×25 cm, 5 microns) eluting with 10% ethanol in heptane at 1.0 mL/minute with the major enantiomer having a retention time of 15.0 minutes, and the minor enantiomer having a retention time of 17.1 minutes (32.7 g, 60%). $^1$H NMR (400 MHz, CDCl$_3$) δ ppm 7.07-6.99 (m, 2H), 6.91-6.83 (m, 2H), 3.79 (s, 3H), 2.80-2.69 (m, 1H), 2.68-2.58 (m, 1H), 2.57-2.47 (m, 1H), 2.40-2.29 (m, 3H), 2.23-2.16 (m, 1H), 2.12-2.01 (m, 1H), 1.95 (s, 3H), 1.86-1.65 (m, 2H).

Example 58C (4aR,5S)-5-hydroxy-4a-(4-methoxyphenyl)-1-methyl-4,4a,5,6,7,8-hexahydronaphthalen-2(3H)-one A 3 L jacketed round bottom flask was charged with Example 58B (32.7 g, 115 mmol) in ethanol (300 mL), and the solution was cooled to −5° C. A solution of sodium borohydride (1.31 g, 34.5 mmol) in ethanol (300 mL) was added dropwise while maintaining an internal temperature below 0° C. The resulting mixture was stirred at −5° C. for 4 hours.

Upon completion, the reaction mixture was quenched carefully with acetic acid (40 mL), and the mixture was warmed to room temperature. After stirring overnight, the mixture was concentrated. The residue was partitioned between methyl t-butyl ether (300 mL) and 10% aqueous ammonia (150 mL). The layers were separated, and the organic layer was washed with 10% aqueous ammonia (150 mL). The combined aqueous layers were extracted with methyl t-butyl ether (300 mL). The combined organic layers were washed with brine (200 mL), dried over $Na_2SO_4$, filter and concentrated. The residue was purified by chromatography over $SiO_2$ using a 330 g RediSep® cartridge on a Teledyne Isco Torrent Combiflash® system eluting with ethyl acetate/hexanes 0:1 (2 column volumes) up to 1:1 (gradient over 8 column volumes). Fractions containing the titled compound were combined and concentrated under reduced pressure (25.5 g, 77%). $^1$H NMR (400 MHz, $CDCl_3$) δ ppm 7.47-7.37 (m, 2H), 6.87-6.81 (m, 2H), 3.83-3.76 (m, 4H), 2.79-2.71 (m, 1H), 2.47-2.41 (m, 1H), 2.34-2.28 (m, 1H), 2.25-2.09 (m, 3H), 1.99 (d, J=4.8 Hz, 1H), 1.92 (d, J=0.8 Hz, 3H), 1.88-1.74 (m, 2H), 1.72-1.45 (m, 2H).

Example 58D (1S,4aS,5S,8aS)-5-hydroxy-4a-(4-methoxyphenyl)-1-methyloctahydronaphthalen-2(1H)-one A 500 mL Parr stirred pressure reactor was charged with 5.1 g of 5% Pd/C (20 weight % of substrate charged). Under a stream of nitrogen, a solution of Example 58C (25.3 g, 88 mmol), tetrahydrofuran (177 mL) and pyridine (44 mL) was added to the reactor. The reactor was purged with nitrogen and hydrogen. The vessel was pressurized to and maintained at 60-100 psig with hydrogen supplied from a high-pressure reservoir. The mixture was vigorously agitated while keeping the temperature between 22-25° C. Upon completion, the reaction mixture was carefully filtered to remove the palladium catalyst rinsing the reactor and cake with tetrahydrofuran. To the filtrate was added 1,8-diazabicyclo[5.4.0]-undec-7-ene (3 mL), and the resulting mixture was stirred at room temperature overnight. The volatiles were removed under reduces pressure, and the residue was taken up in toluene (200 mL). The resulting solution was washed with 10% hydrochloric acid (2×100 mL). The combined aqueous layers were extracted with dichloromethane (100 mL), and the combined organic layers were washed with brine (100 mL), dried over sodium sulfate, filtered and concentrated to give the titled compound which was used without additional purification.

Example 58E (1'S,4a'S,5'S,8a'S)-4a'-(4-methoxyphenyl)-1'-methyl-octahydro-1'H-spiro[1,3-dioxolane-2,2'-naphthalen]-5'-ol A solution of Example 58D in toluene (300 mL) was treated with ethylene glycol (25 mL, 440 mmol, 5 equivalents) and p-toluenesulfonic acid (1.7 g, 28.8 mmol), and the resulting mixture was heated to reflux with Dean Stark removal of water. Additional ethylene glycol (25 mL, 440 mmol, 5 equivalents) was added after 8 hours and refluxing was continued overnight. The mixture was cooled to room temperature, and the toluene solution was washed with saturated aqueous sodium bicarbonate (2×100 mL) and brine (50 mL), dried over sodium sulfate, filtered and concentrated to give the titled compound which was used without additional purification.

Example 58F (1'S,4a'S,8a'S)-4a'-(4-methoxyphenyl)-1'-methyl-hexahydro-1'H-spiro[1,3-dioxolane-2,2'-naphthalen]-5'(3'H)-one A solution of Example 58E in dichloromethane (300 mL) was treated with pyridinium dichromate (66.2 g, 176 mmol) and magnesium sulfate (2.1 g). The resulting mixture was heated to reflux and stirred overnight. Upon completion, the reaction was cooled to room temperature, and the mixture was filtered through a plug of silica gel (100 g) rinsing with dichloromethane (1 L). The filtrate was concentrated, and the remaining solids were triturated with cyclohexane (50 mL). The solids were collected by filtration, washed with cyclohexane (2×10 mL) and dried in a vacuum oven at 50° C. to give 15.0 g, (52%) of the titled compound.

Example 58G (1'S,4a'S,6'Z,8a'S)-6'-(hydroxymethylene)-4a'-(4-methoxyphenyl)-1'-methylhexahydro-1'H-spiro[1,3-dioxolane-2,2'-naphthalen]-5'(3'H)-one The product from Example 58F (2.0 g, 6.05 mmol) was dissolved in dimethylformamide and cooled in an ice bath. Sodium hydride (60% dispersion in oil) (0.605 g, 15.13 mmol) was added portion wise. The ice bath was removed, and the solution was stirred at room temperature for 1 hour. The mixture was again cooled in an ice bath, and ethyl formate (2.96 mL, 36.3 mmol) was added dropwise over a few minutes. The ice bath was removed, and the solution was stirred at room temperature overnight. The reaction mixture was then quenched with 1 M $NaH_2KO_4$ solution, poured into water, and extracted with dichloromethane. The dichloromethane layer was then washed with brine, dried over sodium sulfate, and concentrated. The residue was purified using a Biotage® SNAP 100 g cartridge eluting with 0-20% acetone/hexane to give the titled compound.

Example 58H (5aS,6S,9aS)-9a-(4-methoxyphenyl)-6-methyl-2,4,5,5a,6,8,9,9a-octahydrospiro[benzo[g]indazole-7,2'-[1,3]dioxolane]

The titled compound was prepared using the conditions described in Example 24A substituting Example 1G with Example 58G.

Example 58I (5aS,6S,9aS)-9a-(4-methoxyphenyl)-6-methyl-2,4,5,5a,6,8,9,9a-octahydro-7H-benzo[g]indazol-7-one The titled compound was prepared using the conditions described in Example 24B substituting Example 24A with Example 58H. MS (DCI) m/z 311 (M+H)$^+$.

Example 58J (5aS,6S,8Z,9aS)-8-(hydroxymethylene)-9a-(4-methoxyphenyl)-6-methyl-2,4,5,5a,6,8,9,9a-octahydro-7H-benzo[g]indazol-7-one The titled compound was prepared using the conditions described in Example 24C substituting Example 24B with Example 58I.

Example 58K (5aS,6S,10aS)-10a-(4-methoxyphenyl)-6-methyl-4,5,5a,6,10,10a-hexahydro-2H-indazolo[7,6-f][1,2]benzoxazole The titled compound was prepared using the conditions described in Example 24D substituting Example 24C with Example 58J.

Example 58L (5aS,6S,9aS)-9a-(4-methoxyphenyl)-6-methyl-7-oxo-4,5,5a,6,7,8,9,9a-octahydro-2H-benzo[g]indazole-8-carbonitrile The titled compound was prepared using the conditions described in Example 24E substituting Example 24D with Example 58K. MS (APCI) m/z 336 (M+H)+.

Example 58M (5aS,6S,9aR)-9a-(4-methoxyphenyl)-6-methyl-7-oxo-4,5,5a,6,7,9a-hexahydro-2H-benzo[g]indazole-8-carbonitrile The product of Example 58L was treated using the conditions described in Example 24F to give the desired compound. This compound was purified using a Biotage® SNAP silica 10 g cartridge eluting with 0-50% acetone/hexane. A second chromatographic purification on a reversed-phase Waters HPLC using a Nova-Pak® HR C18, 6 μm, 60 Å, 40×100 mm, PrepPak cartridge eluting with a gradient of 10-90% acetonitrile in aqueous 0.1% trifluoroacetic acid (60 mL/minute) to give 0.110 g (46% yield) of the titled compound as the trifluoroacetic acid salt. $^1$H NMR (400 MHz, CDCl$_3$) δ ppm 1.18 (d, J=6.7 Hz, 1H), 1.48-1.63 (m, 1H), 1.80-1.91 (m, 1H), 2.18 (d, J=2.3 Hz, 1H), 2.28-2.38 (m, 1H), 2.42-2.54 (m, 1H), 2.68-2.82 (m, 1H), 2.85-3.01 (m, 1H), 3.70-3.84 (m, 3H), 6.72-6.87 (m, 2H), 7.47-7.55 (m, 1H), 8.25 (s, 1H); MS (DCI) m/z 334 (M+H)+.

Example 59 methyl 3-[(6aS,7S,10aR)-9-cyano-7-methyl-8-oxo-6,6a,7,8-tetrahydrobenzo[h]quinazolin-10a(5H)-yl]benzoate

Example 59A methyl 3-(2,6-dioxocyclohexyl)benzoate 1,4-Dioxane (0.6 L) and tert-butyl alcohol (0.3 L) were charged to a 1 L round-bottomed flask. The solution was sparged with nitrogen for 30 minutes. 1,3-Cyclohexanedione (30.9 g, 267 mmol), methyl 3-bromobenzoate (142 g, 267 mmol), palladium(II) acetate (1.5 g, 6.68 mmol), potassium phosphate tribasic (58.7 g, 668 mmol), and 2-(di-tert-butylphospino)-2'-methylbiphenyl (4.18 g, 13.37 mmol) were charged into a 2 L round-bottomed flask. The flask was purged with nitrogen for 30 minutes. The liquids—via cannula—were then transferred to the flask containing the solids, and the reaction mixture was heated at 90° C. for 17 hours. The reaction mixture was partitioned between ethyl acetate (620 mL) and 10 weight % aqueous hydrochloric acid (950 mL). The layers were separated, and the aqueous layer was extracted with ethyl acetate (120 mL). The combined organics were washed with water (200 mL) and 10 weight % aqueous sodium chloride (200 mL). The organic layer was then concentrated. The residue was treated with toluene (600 mL) and concentrated. The residue was taken up in ethyl acetate (240 mL), warmed to 75° C. and then gradually cooled to ambient temperature. When the temperature was about 50° C., heptanes (500 mL) were added over 1 hour. The titled compound precipitated out of solution and was collected by filtration, washed with heptanes (2×100 mL) and dried in a vacuum oven at 50° C. (48 g, 73%). $^1$H NMR (400 MHz, CDCl$_3$) δ ppm 8.00 (dt, J=7.8, 1.5 Hz, 1H), 7.87 (t, J=1.7 Hz, 1H), 7.51 (t, J=7.7 Hz, 1H), 7.44-7.37 (m, 1H), 6.30 (s, 1H), 3.90 (s, 3H), 2.57 (s, 4H), 2.17-2.03 (m, 2H).

Example 59B methyl 3-[(4aR)-8-methyl-4,7-dioxo-1,3,4,5,6,7-hexahydronaphthalen-4a(2H)-yl]benzoate A 2 L round-bottomed flask was charged with Example 59A (80 g, 267 mmol) and acetonitrile (1.2 L). Triethylamine (115 mL, 802 mmol) and ethyl vinyl ketone (34.3 mL, 334 mmol) were added. After attaching a reflux condenser, the reaction mixture was stirred and heated at 75° C. for 16 hours. After cooling to ambient temperature, the reaction mixture was concentrated at reduced pressure. The residue was dissolved in dimethyl sulfoxide (170 mL). Pyridinium p-toluenesulfonate (37.8 g, 148 mmol) and L-phenylalanine (49.8 g, 295 mmol) were added, and the mixture was heated at 45° C. for 48 hours. The reaction mixture was cooled to ambient temperature and poured into saturated aqueous ammonium chloride (200 mL) and ethyl acetate (300 mL). After mixing for 10 minutes, the solids were removed by filtration and the layers separated. The aqueous layer was extracted with ethyl acetate (300 mL). The combined organics were washed with water (200 mL) and brine (200 mL), dried over anhydrous sodium sulfate, filtered, and concentrated. The residue was purified by flash chromatography over silica using a 330 g RediSep® column on a Teledyne Isco Torrent Combiflash® system: ethyl acetate/hexanes 1:10 to 1:3. The fractions containing the titled compound were combined and concentrated under reduced pressure (57 g, 77%). $^1$H NMR (400 MHz, CDCl$_3$) δ ppm 7.98 (dt, J=7.7, 1.4 Hz, 1H), 7.81-7.76 (m, 1H), 7.45 (t, J=7.7 Hz, 1H), 7.34 (ddd, J=7.8, 2.1, 1.2 Hz, 1H), 3.91 (s, 2H), 2.81 (ddd, J=17.4, 8.0, 5.1 Hz, 1H), 2.69-2.58 (m, 1H), 2.58-2.28 (m, 4H), 2.28-2.19 (m, 1H), 2.07-2.02 (m, 1H), 2.04-1.91 (m, 3H), 1.89-1.60 (m, 2H), 1.26 (t, J=7.1 Hz, 1H).

Example 59C methyl 3-[(4S,4aR)-4-hydroxy-8-methyl-7-oxo-1,3,4,5,6,7-hexahydronaphthalen-4a(2H)-yl]benzoate A solution of Example 59B (14.3 g, 43.8 mmol) in ethanol (70 mL) was cooled to −5° C. To the stirred solution was added dropwise a solution of sodium borohydride (6.28 g, 166 mmol) in ethanol (1.0 L)—with the internal temperature maintained below 0° C. The resulting mixture was stirred at −5° C. for 4 hours. The internal temperature of the reaction mixture was maintained below 0° C. when it was quenched by the slow addition of glacial acetic acid (13.8 mL, 241 mmol). The mixture was subsequently allowed to reach ambient temperature. After stirring overnight, the mixture was concentrated under reduced pressure. The residue was partitioned between ethyl acetate (200 mL) and 10% aqueous ammonium hydroxide (100 mL). The layers were separated, and the organic layer was washed with 10% aqueous ammonium hydroxide (100 mL) and brine (100 mL). The organic solution was concentrated and the residue was purified by flash chromatography over silica using a 120 g RediSep® cartridge on a Teledyne Isco Torrent Combiflash® system: ethyl acetate/hexanes 1:10 to 1:4. The fractions containing the titled compound were combined and concentrated under reduced pressure to give a solid. The solid was dried for 16 hours in a vacuum oven at 50° C. to give the titled compound (10.2 g, 71%).

Example 59D methyl 3-[(1S,4aS,5S,8aS)-5-hydroxy-1-methyl-2-oxooctahydronaphthalen-4a(2H)-yl]benzoate 5% Pd/C (2.1 g), corresponding to 20 weight % of substrate, was charged to a stirred 300 mL Parr pressure reactor. Under a stream of nitrogen, a solution of Example 59C (10.7 g, 32.6 mmol), tetrahydrofuran (85 mL) and pyridine (21 mL) was added to the reactor. The reactor was purged with nitrogen and, hydrogen. The vessel was pressurized to—and maintained at—60 psig with hydrogen supplied from a high-pressure reservoir. The mixture was vigorously agitated for 22 hours while the temperature was kept between 22-25° C. The reaction mixture was carefully filtered to remove the palladium catalyst. The reactor and cake were rinsed with tetrahydrofuran. 1,8-Diazabicyclo [5.4.0]undec-7-ene (0.9 mL) was added to the filtrate and the resulting mixture was stirred at room temperature overnight. The volatiles were removed by concentrating the solution under reduced pressure. The residue was taken up in toluene (200 mL) and washed with 10% aqueous hydrochloric acid (2×100 mL). The combined aqueous layers were extracted with toluene (100 mL). The combined organic layers were washed with brine (50 mL), dried over anhydrous sodium sulfate and filtered. The toluene solution of the titled compound was used without purification.

Example 59E methyl 3-[(1'S,4a'S,5'S,8a'S)-5'-hydroxy-1'-methyl-octahydro-4a'H-spiro[1,3-dioxolane-2,2'-naphthalen]-4a'-yl]benzoate Ethylene glycol (9 mL, 160 mmol, 5 equiv.) and p-toluenesulfonic acid (0.6 g, 3.2 mmol) were added to a flask containing the Example 59D toluene solution. A Dean-Stark apparatus—for removal of water—was attached to the flask whose contents were heated at reflux for 18 hours. The mixture was cooled to ambient temperature, and the toluene solution was washed with saturated aqueous sodium bicarbonate (2×100 mL) and brine (100 mL). The solution was dried over anhydrous sodium sulfate, filtered and concentrated. The residue was dissolved in dichloromethane (100 mL) and the solution of the titled compound was used in the next step without additional purification.

Example 59F methyl 3-[(1'S,4a'S,8a'S)-1'-methyl-5'-oxooctahydro-4a'H-spiro[1,3-dioxolane-2,2'-naphthalen]-4a'-yl]benzoate The dichloromethane solution containing Example 59E was mixed with pyridinium dichromate (33.8 g, 88 mmol) and magnesium sulfate (1.1 g, 8.8 mmol). The mixture was stirred at reflux for 24 hours. The mixture was cooled to ambient temperature after which it was filtered through a plug of Celite® (50 g) rinsing with dichloromethane (100 mL). The filtrate was concentrated to a residue that was then purified by flash chromatography over silica using a 120 g RediSep® column; eluted with 15% ethyl acetate in heptanes. The fractions containing the product were combined and concentrated under reduced pressure to give a solid. The solid titled compound was dried in a vacuum oven for 12 hours at 50° C. $^1$H NMR (400 MHz, CDCl$_3$) δ ppm 8.13 (d, J=1.8 Hz, 1H), 7.90 (d, J=7.7 Hz, 1H), 7.59 (dd, J=7.9, 1.9 Hz, 1H), 7.39 (t, J=7.8 Hz, 1H), 3.97-3.93 (broad s, 4H), 3.92 (s, 3H), 2.77-2.65 (m, 1H), 2.28-2.03 (m, 5H), 2.00 (d, J=3.7 Hz, 2H), 1.65-1.57 (m, 1H), 1.03 (d, J=6.5 Hz, 3H).

Example 59G methyl 3-[(1'S,4a'S,6'Z,8a'S)-6'-(hydroxymethylene)-1'-methyl-5'-oxooctahydro-4a'H-spiro[1,3-dioxolane-2,2'-naphthalen]-4a'-yl]benzoate To a solution of Example 59F (2.0 g, 5.58 mmol) in ethyl formate (13.63 mL, 167.0 mmol) at room temperature was added 1 M potassium t-butoxide in tetrahydrofuran (12.28 mL, 12.28 mmol) dropwise. The reaction mixture was stirred at room temperature for 3 hours, was then diluted with saturated aqueous sodium phosphate monobasic solution, and was extracted with ethyl acetate. The organic phase was dried over sodium sulfate and concentrated to give the titled compound.

Example 59H methyl 3-[(6aS,7S,10aS)-7-methyl-5,6,6a,7,9,10-hexahydro-10aH-spiro[benzo[h]quinazoline-8,2'-[1,3]dioxolan]-10a-yl]benzoate To a solution of the product from Example 59G (2.23 g, 5.57 mmol) in isopropanol (30 mL) was added formamidine acetate (1.74 g, 16.71 mmol) and piperidine (1.65 mL, 16.71 mmol). The reaction mixture was heated at 95° C. for 24 hours. The cooled solution was diluted with a solution of saturated aqueous sodium phosphate monobasic and extracted with ethyl acetate. The organic layer was concentrated to give the titled compound.

Example 59I methyl 3-[(6aS,7S,10aS)-7-methyl-8-oxo-6,6a,7,8,9,10-hexahydrobenzo[h]quinazolin-10a(5H)-yl]benzoate The titled compound was prepared using the conditions described in Example 1I, substituting Example 59H for Example 1H.

Example 59J ethyl 3-[(6aS,7S,9Z,10aS)-9-(hydroxymethylene)-7-methyl-8-oxo-6,6a,7,8,9,10-hexahydrobenzo[h]quinazolin-10a(5H)-yl]benzoate The titled compound was prepared using the conditions described in Example 1J, substituting Example 59I for Example 1I.

Example 59K ethyl 3-[(6aS,7S,11aS)-7-methyl-6,6a,7,11-tetrahydro[1,2]benzoxazolo[6,5-h]quinazolin-11a(5H)-yl]benzoate The titled compound was prepared using the conditions described in Example 1K, substituting Example 59J for Example 1J.

Example 59L methyl 3-[(6aS,7S,10aS)-9-cyano-7-methyl-8-oxo-6,6a,7,8,9,10-hexahydrobenzo[h]quinazolin-10a(5H)-yl]benzoate The titled compound was prepared using the conditions described in Example 1L, substituting Example 59K for Example 1K.

Example 59M methyl 3-[(6aS,7S,10aR)-9-cyano-7-methyl-8-oxo-6,6a,7,8-tetrahydrobenzo[h]quinazolin-10a(5H)-yl]benzoate To a solution of the product from Example 59F (0.560 g, 1.49 mmol) in dimethylformamide (10 mL) cooled to 0° C. in an ice water bath was added 1,3-dibromo-5,5-dimethylhydantoin (0.235 g, 0.820 mmol). The solution was stirred at 0° C. for 35 minutes, and then pyridine (1.21 mL, 14.92 mmol) was added. The resultant solution was heated at 55° C. for 1 hour. The cooled solution was diluted with water and extracted with ethyl acetate. The organic layer was washed with brine and concentrated. The residue was purified using a 12 g RediSep® cartridge on a Teledyne Isco Combiflash® Rf chromatography system, eluting with 0-70% ethyl acetate in heptane to give 0.398 g (72%) of the titled compound. $^1$H NMR (400 MHz, CDCl$_3$) δ ppm 1.20 (d, J=6.18 Hz, 3H) 1.59-1.71 (m, 1H) 2.01 (dd, J=14.20, 7.81 Hz, 1H) 2.33-2.45 (m, 2H) 2.98-3.23 (m, 2H) 3.88 (s, 3H) 6.99-7.08 (m, 1H) 7.40-7.47 (m, 2H) 7.99 (d, J=7.81 Hz, 1H) 8.75 (s, 1H) 8.85 (s, 1H) 9.07 (s, 1H); MS (APCI+) m/z 374 (M+H)$^+$.

Example 60

3-[(6aS,7S,10aR)-9-cyano-7-methyl-8-oxo-6,6a,7,8-tetrahydrobenzo[h]quinazolin-10a(5H)-yl]benzoic acid To a solution of Example 59M (0.320 g, (0.857 mmol) in tetrahydrofuran (6 mL) was added water (1.5 mL) and lithium hydroxide monohydrate (0.144 g, 3.43 mmol). The reaction mixture was stirred at room temperature for 20 hours. The solution was diluted with water, neutralized to pH 7 by dropwise addition of 1 M hydrochloric acid and extracted with 20% isopropanol in chloroform. The organic layer was concentrated, and the residue was purified using a 4 g RediSep® cartridge on a Teledyne Isco Combiflash Rf® chromatography system eluting with 0-4% methanol in dichloromethane to give 0.120 g (39%) of the titled compound. $^1$H NMR (400 MHz, DMSO-d$_6$) δ ppm 1.06 (d, J=6.61 Hz, 3H) 1.28-1.45 (m, 1H) 1.85-1.95 (m, 1H) 2.31 (td, J=13.12, 6.61 Hz, 1H) 2.55-2.69 (m, 1H) 2.93-3.15 (m, 2H) 7.18 (d, J=9.11 Hz, 1H) 7.29 (s, 1H) 7.47 (t, J=7.81 Hz, 1H) 7.86 (d, J=7.81 Hz, 1H) 8.75 (s, 1H) 8.86 (s, 1H) 9.05 (s, 1H) 13.14 (s, 1H); MS (APCI+) m/z 360 (M+H)$^+$.

Example 61

3-[(6aS,7S,10aR)-9-cyano-7-methyl-8-oxo-6,6a,7,8-tetrahydrobenzo[h]quinazolin-10a(5H)-yl]benzamide A solution of Example 59M (0.020 g, 0.054 mmol) in ammonium hydroxide (1.0 mL, 25.7 mmol) was stirred at room temperature in a sealed tube for 24 hours. The solution was concentrated under vacuum, and water was azeotropically removed with toluene. The residue was then purified using a 4 g RediSep® cartridge on a Teledyne Isco Combiflash® system eluting with 0-9% methanol in dichloromethane to give 0.009 g (50%) of the titled compound. $^1$H NMR (400 MHz, CDCl$_3$) δ ppm 1.20 (d, J=6.18 Hz, 3H) 1.60-1.75 (m, 1H) 2.01 (dd, J=14.04, 7.54 Hz, 1H) 2.31-2.46 (m, 2H) 2.99-3.25 (m, 2H) 5.58 (s, 1H) 5.91 (s, 1H) 7.05 (dd, J=8.29, 1.68 Hz, 1H) 7.26 (s, 1H) 7.44 (t, J=7.86 Hz, 1H) 7.65 (d, J=7.70 Hz, 1H) 8.75 (s, 1H) 8.85 (s, 1H) 9.07 (s, 1H); MS (APCI+) m/z 359 (M+H)$^+$.

Example 62 methyl 3-[(5aS,6S,9aR)-8-cyano-6-methyl-7-oxo-2,4,5,5a,6,7-hexahydro-9aH-benzo[g]indazol-9a-yl]benzoate

Example 62A methyl 3-[(5aS,6S,9aS)-6-methyl-4,5,5a,6,8,9-hexahydrospiro[benzo[g]indazole-7,2'-[1,3]dioxolan]-9a(2H)-yl]benzoate The titled compound was prepared using the conditions described in Example 24A substituting Example 1G with Example 59G.

Example 62B methyl 3-[(5aS,6S,9aS)-6-methyl-7-oxo-2,4,5,5a,6,7,8,9-octahydro-9aH-benzo[g]indazol-9a-yl]benzoate The titled compound was prepared using the conditions described in Example 24B substituting Example 24A with Example 62A. MS (APCI) m/z 338 (M+H)$^+$.

Example 62C methyl 3-[(5aS,6S,8Z,9aS)-8-(hydroxymethylene)-6-methyl-7-oxo-2,4,5,5a,6,7,8,9-octahydro-9aH-benzo[g]indazol-9a-yl]benzoate The titled compound was prepared using the conditions described in Example 24C substituting Example 24B with Example 62B.

Example 62D methyl 3-[(5aS,6S,10aS)-6-methyl-2,4,5,5a,6,10-hexahydro-10aH-indazolo[7,6-f][1,2]benzoxazol-10a-yl]benzoate The titled compound was prepared using the conditions described in Example 24D substituting Example 24C with Example 62C. MS (APCI) m/z 332 (M+H)$^+$.

Example 62E methyl 3-[(5aS,6S,9aS)-8-cyano-6-methyl-7-oxo-2,4,5,5a,6,7,8,9-octahydro-9aH-benzo[g]indazol-9a-yl]benzoate The titled compound was prepared using the conditions described in Example 24E substituting Example 24D with Example 62D.

Example 62F methyl 3-[(5aS,6S,9aR)-8-cyano-6-methyl-7-oxo-2,4,5,5a,6,7-hexahydro-9aH-benzo[g]indazol-9a-yl]benzoate Example 62E (0.154 g, 0.424 mmol) was dissolved in toluene (4.24 mL) and sparged with nitrogen for 10 minutes. 2,3-Dichloro-5,6-dicyano-1,4-benzoquinone (0.125 g, 0.551 mmol) was then added, and the nitrogen bubbling was continued for 1 hour. The reaction mixture was concentrated, and the residue was purified using a Biotage® SNAP 50 g silica cartridge. A second chromatography using a reversed-phase Waters HPLC using a Nova-Pak® HR C18, 6 μm, 60 Å, 40×100 mm, PrepPak cartridge eluting with a gradient of 10-90% acetonitrile in aqueous 0.1% trifluoroacetic acid (60 mL/minute) to give 0.120 g (78% yield) of the titled compound as the trifluoroacetic acid salt. $^1$H NMR (400 MHz, CDCl$_3$) δ ppm 1.14-1.20 (m, 3H), 1.81-1.92 (m, 1H), 2.18 (s, 2H), 2.35-2.44 (m, 2H), 2.69-2.84 (m, 1H), 2.91-3.02 (m, 1H), 3.89 (d, J=5.1 Hz, 3H), 7.08-7.15 (m, 1H), 7.36-7.43 (m, 1H), 7.48-7.52 (m, 1H), 7.53-7.57 (m, 1H), 7.92-7.99 (m, 1H), 8.42-8.46 (m, 1H); MS (DCI) m/z 379 (M+NH$_4$)$^+$.

Example 63 methyl 4-[(5aS,6S,9aR)-8-cyano-6-methyl-7-oxo-2,4,5,5a,6,7-hexahydro-9aH-benzo[g]indazol-9a-yl]benzoate

Example 63A ethyl 4-(2,6-dioxocyclohexyl)benzoate

The titled compound was prepared using the conditions described in Example 59A substituting ethyl-4-bromobenzoate for methyl 3-bromobenzoate.

Example 63B ethyl 4-[(4aR)-8-methyl-4,7-dioxo-1,3,4,5,6,7-hexahydronaphthalen-4a(2H)-yl]benzoate The titled compound (74% ee, determined using a Chiralpak® AS-H column (4.6 mm ID×25 cm, 5 microns) eluted with 10% ethanol in heptane at 1.0 mL/minute with the major enantiomer eluting at 17.5 minutes and the minor enantiomer eluting at 22.9 minutes) was prepared using the conditions described in Example 59B substituting Example 63A for Example 59A. $^1$H NMR (400 MHz, CDCl$_3$) δ ppm 8.08-7.96 (m, 2H), 7.26-7.18 (m, 2H), 4.45-4.30 (m, 2H), 2.88-2.71 (m, 1H), 2.70-2.56 (m, 1H), 2.56-2.29 (m, 4H), 2.29-2.17 (m, 1H), 1.98 (s, 3H), 1.86-1.64 (m, 2H), 1.39 (t, J=7.1 Hz, 3H).

Example 63C ethyl 4-[(4S,4aR)-4-hydroxy-8-methyl-7-oxo-1,3,4,5,6,7-hexahydronaphthalen-4a(2H)-yl]benzoate The titled compound was prepared using the conditions described in Example 59C substituting Example 63B for Example 59B. $^1$H NMR (400 MHz, CDCl$_3$) δ ppm 8.03-7.89 (m, 2H), 7.73-7.58 (m, 2H), 4.36 (q, J=7.1 Hz, 2H), 3.84 (dt, J=13.4, 6.6 Hz, 1H), 3.79-3.67 (m, 3H), 2.46 (dt, J=13.0, 4.3 Hz, 2H), 2.33 (dt, J=16.1, 3.6 Hz, 1H), 2.28-2.16 (m, 1H), 2.16-2.01 (m, 2H), 1.93 (d, J=1.2 Hz, 3H), 1.71-1.57 (m, 1H), 1.57-1.44 (m, 1H), 1.38 (t, J=7.1 Hz, 3H).

Example 63D ethyl 4-[(1S,4aS,5S,8aS)-5-hydroxy-1-methyl-2-oxooctahydronaphthalen-4a(2H)-yl]benzoate The titled compound was prepared using the conditions described in Example 59D substituting Example 63C for Example 59C.

Example 63E ethyl 4-[(1'S,4a'S,5'S,8a'S)-5'-hydroxy-1'-methyloctahydro-4a'H-spiro[1,3-dioxolane-2,2'-naphthalen]-4a'-yl]benzoate The titled compound was prepared using the conditions described in Example 59E substituting Example 63D for Example 59D.

Example 63F ethyl 4-[(1'S,4a'S,8a'S)-1'-methyl-5'-oxooctahydro-4a'H-spiro[1,3-dioxolane-2,2'-naphthalen]-4a'-yl]benzoate The titled compound was prepared using the conditions described in Example 59F substituting Example 63E for Example 59E. $^1$H NMR (400 MHz, CDCl$_3$) δ 7.96 (d, J=8.9 Hz, 2H), 7.48 (d, J=6.7 Hz, 2H), 4.36 (q, J=7.1 Hz, 2H), 3.94 (s, 4H), 2.67 (dq, J=13.0, 6.5 Hz, 1H), 2.21-2.09 (m, 3H), 2.09-2.00 (m, 2H), 2.00-1.88 (m, 3H), 1.72-1.55 (m, 2H), 1.38 (t, J=7.1 Hz, 3H), 1.09 (td, J=14.0, 3.7 Hz, 1H), 1.01 (d, J=6.5 Hz, 3H).

Example 63G ethyl 4-[(1'S,4a'S,6'Z,8a'S)-6'-(hydroxymethylene)-1'-methyl-5'-oxooctahydro-4a'H-spiro[1,3-dioxolane-2,2'-naphthalen]-4a'-yl]benzoate The titled compound was prepared using the conditions described in Example 58G substituting Example 58F for Example 63F.

Example 63H ethyl 4-[(5aS,6S,9aS)-6-methyl-4,5,5a,6,8,9-hexahydrospiro[benzo[g]indazole-7,2'-[1,3]dioxolan]-9a(2H)-yl]benzoate The titled compound was prepared using the conditions described in Example 24A substituting Example 1G with Example 63G.

Example 63I ethyl 4-[(5aS,6S,9aS)-6-methyl-7-oxo-2,4,5,5a,6,7,8,9-octahydro-9aH-benzo[g]indazol-9a-yl]benzoate The titled compound was prepared using the conditions described in Example 24B substituting Example 24A with Example 63H. $^1$H NMR (400 MHz, CDCl$_3$) δ ppm 1.11-1.21 (m, 3H), 1.31-1.39 (m, 3H), 2.06-2.16 (m, 1H), 2.30-2.46 (m, 2H), 2.49-2.73 (m, 3H), 2.76-2.92 (m, 1H), 2.99-3.17 (m, 1H), 4.35 (q, J=7.1 Hz, 2H), 7.30 (d, J=7.3 Hz, 1H), 7.46-7.57 (m, 2H), 7.93 (dd, J=8.6, 6.8 Hz, 2H); MS (APCI) m/z 353 (M+H)$^+$.

Example 63J ethyl 4-[(5aS,6S,8Z,9aS)-8-(hydroxymethylene)-6-methyl-7-oxo-2,4,5,5a,6,7,8,9-octahydro-9aH-benzo[g]indazol-9a-yl]benzoate The titled compound was prepared using the conditions described in Example 24C substituting Example 24B with Example 63I.

Example 63K ethyl 4-[(5aS,6S,10aS)-6-methyl-2,4,5,5a,6,10-hexahydro-10aH-indazolo[7,6-f][1,2]benzoxazol-10a-yl]benzoate The titled compound was prepared using the conditions described in Example 24D substituting Example 24C with Example 63J. MS (APCI) m/z 378 (M+H)$^+$.

Example 63L ethyl 4-[(5aS,6S,9aS)-8-cyano-6-methyl-7-oxo-2,4,5,5a,6,7,8,9-octahydro-9aH-benzo[g]indazol-9a-yl]benzoate The titled compound was prepared using the conditions described in Example 24E substituting Example 24D with Example 63K.

Example 63M methyl 4-[(5aS,6S,9aR)-8-cyano-6-methyl-7-oxo-2,4,5,5a,6,7-hexahydro-9aH-benzo[g]indazol-9a-yl]benzoate Example 63L (0.100 g, 0.275 mmol) was dissolved in toluene (2.75 mL) and sparged with nitrogen for 10 minutes. 2,3-Dichloro-5,6-dicyano-1,4-benzoquinone (0.081 g, 0.358 mmol) was then added, and sparging with nitrogen was continued for 1 hour. The reaction mixture was concentrated, and the residue was purified using a Biotage® SNAP silica 10 g cartridge eluting with 0-50% acetone/hexane to give the titled compound (0.050 g, 45% yield). $^1$H NMR (400 MHz, CDCl$_3$) δ ppm 1.14-1.21 (m, 3H), 1.80-1.90 (m, 1H), 2.35-2.46 (m, 2H), 2.69-2.83 (m, 1H), 2.90-3.00 (m, 1H), 3.90 (d, J=3.8 Hz, 4H), 6.91-7.07 (m, 3H), 7.45-7.58 (m, 1H), 7.90-8.04 (m, 2H), 8.34-8.52 (m, 1H); MS (DCI) m/z 379 (M+NH$_4$)$^+$.

Example 64 methyl 4-[(6aS,7S,10aR)-9-cyano-7-methyl-8-oxo-6,6a,7,8-tetrahydrobenzo[h]quinazolin-10a(5H)-yl]benzoate

Example 64A ethyl 4-[(6aS,7S,10aS)-7-methyl-5,6,6a,7,9,10-hexahydro-10aH-spiro[benzo[h]quinazoline-8,2'-[1,3]dioxolan]-10a-yl]benzoate To a solution Example 63G (1.25 g, 3.12 mmol) in isopropanol (25 mL) was added formamidine acetate (1.30 g, 12.49 mmol) and piperidine (1.24 mL, 12.49 mmol). The reaction mixture was heated at 90° C. for 48 hours. The cooled solution was diluted with a solution of saturated aqueous sodium phosphate monobasic and extracted with ethyl acetate.

The organic phase was separated and concentrated to give the titled compound.

Example 64B ethyl 4-[(6aS,7S,10aS)-7-methyl-8-oxo-6,6a,7,8,9,10-hexahydrobenzo[h]quinazolin-10a(5H)-yl]benzoate The titled compound was prepared using the conditions described in Example 1I, substituting Example 64A for Example 1H. MS (APCI+) m/z 365 (M+H)$^+$.

Example 64C ethyl 4-[(6aS,7S,9Z,10aS)-9-(hydroxymethylene)-7-methyl-8-oxo-6,6a,7,8,9,10-hexahydrobenzo[h]quinazolin-10a(5H)-yl]benzoate The titled compound was prepared using the conditions described in Example 1J, substituting Example 64B for Example 1I.

Example 64D ethyl 4-[(6aS,7S,11aS)-7-methyl-6,6a,7,11-tetrahydro[1,2]benzoxazolo[6,5-h]quinazolin-11a(5H)-yl]benzoate The titled compound was prepared using the conditions described in Example 1K, substituting Example 64C for Example 1J. MS (APCI+) m/z 390 (M+H)$^+$.

Example 64E methyl 4-[(6aS,7S,10aS)-9-cyano-7-methyl-8-oxo-6,6a,7,8,9,10-hexahydrobenzo[h]quinazolin-10a(5H)-yl]benzoate The titled compound was prepared using the conditions described in Example 1L, substituting Example 64D for Example 1K.

Example 64F methyl 4-[(6aS,7S,10aR)-9-cyano-7-methyl-8-oxo-6,6a,7,8-tetrahydrobenzo[h]quinazolin-10a(5H)-yl]benzoate To a solution of Example 64E (0.365 g, 0.972 mmol) in dimethylformamide (5 mL) cooled to 0° C. in an ice water bath was added 1,3-dibromo-5,5-dimethylhydantoin (0.139 g, 0.486 mmol). The solution was stirred at 0° C. for 35 minutes, and then pyridine (0.393 mL, 4.86 mmol) was added and the solution was heated at 55° C. for 1 hour. The cooled solution was diluted with water and extracted with ethyl acetate. The organic layer was washed with brine and concentrated. The residue was purified using a 12 g RediSep® cartridge on a Teledyne Isco Combiflash® Rf system, eluting with 0-70% ethyl acetate in heptane to give 0.198 g (55%) of the titled compound. $^1$H NMR (400 MHz, CDCl$_3$) δ ppm 1.20 (d, J=6.07 Hz, 3H) 1.57-1.69 (m, 1H) 2.01 (dd, J=14.64, 7.26 Hz, 1H) 2.33-2.46 (m, 2H) 3.00-3.20 (m, 2H) 3.91 (s, 3H) 6.87 (d, J=8.57 Hz, 2H) 7.98 (d, J=8.57 Hz, 2H) 8.75 (s, 1H) 8.84 (s, 1H) 9.08 (s, 1H); MS (ESI+) m/z 374 (M+H)$^+$.

Example 65

(5aS,6S,9aR)-1-(4-bromobenzyl)-6-methyl-7-oxo-9a-phenyl-4,5,5a,6,7,9a-hexahydro-1H-benzo[g]indazole-8-carbonitrile

Example 65A (5aS,6S,9aS)-1-(4-bromobenzyl)-6-methyl-9a-phenyl-1,4,5,5a,6,8,9,9a-octahydrospiro[benzo[g]indazole-7,2'-[1,3]dioxolane]

The titled compound was prepared using the conditions described in Example 24A substituting hydrazine with (4-bromobenzyl)hydrazine. MS (ESI) m/z 449 (M+H)$^+$.

Example 65B (5aS,6S,9aS)-1-(4-bromobenzyl)-6-methyl-9a-phenyl-1,4,5,5a,6,8,9,9a-octahydro-7H-benzo[g]indazol-7-one The titled compound was prepared using the conditions described in Example 24B substituting Example 24A with Example 65A.

Example 65C (5aS,6S,8Z,9aS)-1-(4-bromobenzyl)-8-(hydroxymethylene)-6-methyl-9a-phenyl-1,4,5,5a,6,8,9,9a-octahydro-7H-benzo[g]indazol-7-one The titled compound was prepared using the conditions described in Example 24C substituting Example 24B with Example 65B.

Example 65D (5aS,6S,10aS)-1-(4-bromobenzyl)-6-methyl-10a-phenyl-4,5,5a,6,10,10a-hexahydro-1H-indazolo[7,6-f][1,2]benzoxazole The titled compound was prepared using the conditions described in Example 24D substituting Example 24C with Example 65C. MS (APCI) m/z 474 (M+H)$^+$.

Example 65E (5aS,6S,9aS)-1-(4-bromobenzyl)-6-methyl-7-oxo-9a-phenyl-4,5,5a,6,7,8,9,9a-octahydro-H-benzo[g]indazole-8-carbonitrile The titled compound was prepared using the conditions described in Example 24E substituting Example 24D with Example 65D.

Example 65F (5aS,6S,9aR)-1-(4-bromobenzyl)-6-methyl-7-oxo-9a-phenyl-4,5,5a,6,7,9a-hexahydro-1H-benzo[g]indazole-8-carbonitrile Example 65E (0.060 g, 0.126 mmol) was dissolved in toluene (1.27 mL) and sparged with nitrogen. After 10 minutes, 2,3-dichloro-5,6-dicyano-1,4-benzoquinone (0.037 g, 0.164 mmol) was added with continued nitrogen sparging for 1 hour. The reaction mixture was concentrated, and the residue was purified using a Biotage® SNAP 10 g silica cartridge eluting with 0-50% acetone/hexane to give 0.045 g (75% yield). of the titled compound. $^1$H NMR (400 MHz, CDCl$_3$) δ ppm 1.15 (d, J=6.8 Hz, 3H), 1.80 (dd, J=13.9, 6.2 Hz, 1H), 2.27 (dq, J=13.4, 6.7 Hz, 1H), 2.46 (t, J=12.8 Hz, 1H), 2.60-2.76 (m, 1H), 2.86 (dd, J=16.2, 4.7 Hz, 1H), 4.67 (d, J=16.2 Hz, 1H), 5.00 (d, J=16.2 Hz, 1H), 6.82 (t, J=7.0 Hz, 4H), 7.32 (q, J=5.4 Hz, 3H), 7.38 (d, J=8.4 Hz, 2H), 7.53 (s, 1H), 7.88 (s, 1H); MS (APCI) m/z 472 (M+H)$^+$.

Example 66

4-[(6aS,7S,10aR)-9-cyano-7-methyl-8-oxo-6,6a,7,8-tetrahydrobenzo[h]quinazolin-10a(5H)-yl]benzoic acid To a solution of Example 64F (0.140 g, (0.375 mmol) in tetrahydrofuran (2 mL) was added water (1 mL) and lithium hydroxide monohydrate (0.027 g, 1.13 mmol). The reaction mixture was stirred at room temperature for 20 hours. The solution was adjusted to pH 4 by dropwise addition of 1 M hydrochloric acid. Then ethyl acetate (4 mL) was added, and the mixture stirred vigorously for 1 hour. The layers were separated, and the organic layer was concentrated. The residue was purified using a 4 g RediSep® cartridge on a Teledyne Isco Combiflash® Rf system with 0-5% methanol in dichloromethane to give 0.102 g (76%) of the titled compound. $^1$H NMR (400 MHz, CDCl$_3$) δ ppm 1.21 (d, J=5.96 Hz, 3H) 1.62 (ddd, J=24.34, 13.45, 7.21 Hz, 1H) 1.97-2.06 (m, 1H) 2.36-2.46 (m, 2H) 3.01-3.21 (m, 2H) 6.92 (d, J=8.57 Hz, 2H) 8.04 (d, J=8.57 Hz, 2H) 8.77 (s, 1H) 8.84 (s, 1H) 9.09 (s, 1H); MS (APCI+) m/z 360 (M+H)$^+$, 401 (M+H+CH$_3$CN)+.

Example 67

(6aS,7S,10aR)-10a-(4-methoxyphenyl)-2,7-dimethyl-8-oxo-4-(pyrimidin-5-yl)-5,6,6a,7,8,10a-hexahydrobenzo[h]quinazoline-9-carbonitrile

Example 67A methyl (1'S,4a'S,8a'S)-4a'-(4-methoxyphenyl)-1'-methyl-5'-oxooctahydro-1'H-spiro[1,3-dioxolane-2,2'-naphthalene]-6'-carboxylate To a solution of Example 58F (2.0 g, 6.05 mmol) in tetrahydrofuran (30.0 mL) at room temperature was added dimethyl carbonate (12.7 mL, 151 mmol) followed by 95% sodium hydride (0.61 g, 24.2 mmol) and 50% potassium hydride in paraffin (0.10 g, 1.2 mmol). The reaction was refluxed for 48 hours. The reaction mixture was cooled to room temperature, neutralized with acetic acid, diluted with ethyl acetate and washed with water. The aqueous layer was in turn washed with ethyl acetate. The combined organic layers were washed with brine, dried ($MgSO_4$) and concentrated under reduced pressure. The residue was purified by flash chromatography on silica gel eluting with 10-33% ethyl acetate in heptane to give the titled compound (1.63 g, 69%). $^1$H NMR (400 MHz, $CDCl_3$) δ ppm 0.99 (d, J=6.51 Hz, 3H) 1.11-1.22 (m, 1H) 1.60 (dt, J=13.53, 3.37 Hz, 1H) 1.93-2.03 (m, 4H) 2.03-2.19 (m, 3H) 2.68 (ddd, J=18.38, 6.72, 6.56 Hz, 1H) 3.31-3.41 (m, 1H) 3.69 (s, 3H) 3.80 (s, 3H) 3.91-3.98 (m, 4H) 6.88 (d, J=8.89 Hz, 2H) 7.30 (d, J=8.78 Hz, 2H); MS (DCI) m/z 389.1 $(M+H)^+$.

Example 67B (6aS,7S,10aS)-10a-(4-methoxyphenyl)-2,7-dimethyl-5,6a,7,9,10,10a-hexahydro-6H-spiro[benzo[h]quinazoline-8,2'-[1,3]dioxolan]-4-ol The titled compound was prepared using the conditions described in Example 13B, substituting Example 67A for Example 13A.

Example 67C (6aS,7S,10aS)-4-hydroxy-10a-(4-methoxyphenyl)-2,7-dimethyl-5,6a,7,9,10,10a-hexahydrobenzo[h]quinazolin-8(6H)-one The titled compound was prepared using the conditions described in Example 13C, substituting Example 67B for Example 13B.

Example 67D (6aS,7S,10aS)-4-chloro-10a-(4-methoxyphenyl)-2,7-dimethyl-5,6a,7,9,10,10a-hexahydrobenzo[h]quinazolin-8(6H)-one The titled compound was prepared using the conditions described in Example 13D, substituting Example 67C for Example 13C. Purification was achieved by flash chromatography on silica gel eluting with 10% ethyl acetate in chloroform (76% yield). $^1$H NMR (400 MHz, $CDCl_3$) δ ppm 1.16 (d, J=6.72 Hz, 3H) 1.94-2.25 (m, 4H) 2.50-2.58 (m, 3H) 2.63 (s, 3H) 2.83-2.90 (m, 2H) 3.18-3.27 (m, 1H) 3.77 (s, 3H) 6.82 (d, J=8.89 Hz, 2H) 7.31 (d, J=8.89 Hz, 2H); MS (DCI) m/z 371.0 $(M+H)^+$.

Example 67E (6aS,7S,10aS)-10a-(4-methoxyphenyl)-2,7-dimethyl-4-(pyrimidin-5-yl)-5,6a,7,9,10,10a-hexahydrobenzo[h]quinazolin-8(6H)-one The titled compound was prepared using the conditions described in Example 23A, substituting pyrimidin-5-ylboronic acid for 2-(furan-3-yl)-4,4,5,5-tetramethyl-1,3,2-dioxaborolane. Purification by flash chromatography on silica gel eluting with 25% acetone in heptane gave the titled compound (100% yield). $^1$H NMR (400 MHz, $CDCl_3$) δ ppm 1.16 (d, J=6.61 Hz, 3H) 1.98 (td, J=11.85, 6.99 Hz, 1H) 2.06-2.20 (m, 2H) 2.24-2.53 (m, 3H) 2.65 (ddd, J=16.13, 7.94, 7.70 Hz, 1H) 2.76 (s, 3H) 2.79-2.94 (m, 2H) 3.21 (td, J=8.92, 4.50 Hz, 1H) 3.79 (s, 3H) 6.85 (d, J=8.89 Hz, 2H) 7.46 (d, J=8.78 Hz, 2H) 8.89 (s, 2H) 9.27 (s, 1H); MS (DCI) m/z 415.1 $(M+H)^+$.

Example 67F (6aS,7S,9Z,10aS)-9-(hydroxymethylene)-10a-(4-methoxyphenyl)-2,7-dimethyl-4-(pyrimidin-5-yl)-5,6a,7,9,10,10a-hexahydrobenzo[h]quinazolin-8(6H)-one The titled compound was prepared using the conditions described in Example 13F, substituting Example 67E for Example 13E.

Example 67G (6aS,7S,11aS)-11a-(4-methoxyphenyl)-2,7-dimethyl-4-(pyrimidin-5-yl)-5,6,6a,7,11,11a-hexahydro[1,2]benzoxazolo[6,5-h]quinazoline The titled compound was prepared using the conditions described in Example 13G, substituting Example 67F for Example 13F.

Example 67H (6aS,7S,10aS)-10a-(4-methoxyphenyl)-2,7-dimethyl-8-oxo-4-(pyrimidin-5-yl)-5,6,6a,7,8,9,10,10a-octahydrobenzo[h]quinazoline-9-carbonitrile The titled compound was prepared using the conditions described in Example 13H, substituting Example 67G for Example 13G.

Example 67I (6aS,7S,10aR)-10a-(4-methoxyphenyl)-2,7-dimethyl-8-oxo-4-(pyrimidin-5-yl)-5,6,6a,7,8,10a-hexahydrobenzo[h]quinazoline-9-carbonitrile The titled compound was prepared using the conditions described in Example 13I, substituting Example 67H for Example 13H. Purification was achieved by flash chromatography on silica gel eluting with 10% acetone in chloroform (64% yield). $^1$H NMR (400 MHz, $CDCl_3$) δ ppm 1.18 (d, J=6.61 Hz, 3H) 1.58-1.67 (m, 1H) 1.95 (dt, J=13.91, 3.02 Hz, 1H) 2.33 (td, J=12.82, 2.33 Hz, 1H) 2.47 (td, J=13.12, 6.61 Hz, 1H) 2.74 (s, 3H) 2.97-3.06 (m, 2H) 3.79 (s, 3H) 6.72 (d, J=9.00 Hz, 2H) 6.87 (d, J=8.89 Hz, 2H) 8.92 (s, 1H) 9.05 (s, 2H) 9.35 (s, 1H); MS (CI) m/z 455 $(M+H)^+$.

Example 68

(6aS,7S,10aR)-10a-(4-fluorophenyl)-2,7-dimethyl-8-oxo-4-(pyrimidin-5-yl)-5,6,6a,7,8,10a-hexahydrobenzo[h]quinazoline-9-carbonitrile Example 68A methyl (1'S,4a'S,8a'S)-4a'-(4-fluorophenyl)-1'-methyl-5'-oxooctahydro-1'H-spiro[1,3-dioxolane-2,2'-naphthalene]-6'-carboxylate To a solution of Example 50F (2.0 g, 6.28 mmol) in tetrahydrofuran (30.0 mL) at room temperature was added dimethyl carbonate (13.2 mL, 157 mmol) followed by 95% sodium hydride (0.64 g, 25.1 mmol) and 50% potassium hydride in paraffin (0.05 g, 0.63 mmol). The reaction was refluxed for 18 hours. The reaction was cooled to room temperature, neutralized with acetic acid, diluted with ethyl acetate and washed with water. The aqueous layer was washed with ethyl acetate. The organic layers were combined, washed with brine, dried (MgSO$_4$) and concentrated under reduced pressure. Purification by flash chromatography on silica gel eluting with 15% ethyl acetate in heptane gave the titled compound (2.0 g, 85%). $^1$H NMR (400 MHz, CDCl$_3$) δ ppm 1.00 (d, J=6.51 Hz, 3H) 1.06-1.18 (m, 1H) 1.62 (dt, J=13.53, 3.37 Hz, 1H) 1.89-2.07 (m, 4H) 2.10-2.24 (m, 2H) 2.28-2.36 (m, 1H) 2.57-2.70 (m, 1H) 3.26-3.35 (m, 1H) 3.69 (s, 3H) 3.94 (s, 4H) 7.05 (t, J=8.62 Hz, 2H) 7.37 (dd, J=8.89, 5.20 Hz, 2H); MS (DCI) m/z 377.1 (M+H)$^+$.

Example 68B (6aS,7S,10aS)-10a-(4-fluorophenyl)-2,7-dimethyl-5,6a,7,9,10,10a-hexahydro-6H-spiro[benzo[h]quinazoline-8,2'-[1,3]dioxolan]-4-ol The titled compound was prepared using the conditions described in Example 13B, substituting Example 68A for Example 13A.

Example 68C (6aS,7S,10aS)-10a-(4-fluorophenyl)-4-hydroxy-2,7-dimethyl-5,6a,7,9,10,10a-hexahydrobenzo[h]quinazolin-8(6H)-one The titled compound was prepared using the conditions described in Example 13C, substituting Example 67B for Example 13B. Purification was achieved by flash chromatography on silica gel eluting with 20% acetone in chloroform (61% yield).

Example 68D (6aS,7S,10aS)-4-chloro-10a-(4-fluorophenyl)-2,7-dimethyl-5,6a,7,9,10,10a-hexahydrobenzo[h]quinazolin-8(6H)-one The titled compound was prepared using the conditions described in Example 13D, substituting Example 68C for Example 13C. Purification was achieved by flash chromatography on silica gel eluting with 5% ethyl acetate in chloroform (73% yield). $^1$H NMR (400 MHz, CDCl$_3$) δ ppm 1.17 (d, J=6.83 Hz, 3H) 1.97-2.27 (m, 4H) 2.43-2.61 (m, 3H) 2.64 (s, 3H) 2.84-2.95 (m, 2H) 3.22 (ddd, J=14.48, 6.61, 4.07 Hz, 1H) 6.99 (t, J=8.62 Hz, 2H) 7.38 (dd, J=8.89, 5.20 Hz, 2H); MS (DCI) m/z 359.1 (M+H)$^+$.

Example 68E (6aS,7S,10aS)-10a-(4-fluorophenyl)-2,7-dimethyl-4-(pyrimidin-5-yl)-5,6a,7,9,10,10a-hexahydrobenzo[h]quinazolin-8(6H)-one The titled compound was prepared using the conditions described in Example 23A, substituting pyrimidin-5-ylboronic acid for 2-(furan-3-yl)-4,4,5,5-tetramethyl-1,3,2-dioxaborolane. Purification was achieved by flash chromatography on silica gel eluting with 25% acetone in heptane (92% yield). $^1$H NMR (400 MHz, CDCl$_3$) δ ppm 1.17 (d, J=6.61 Hz, 3H) 1.96-2.07 (m, 1H) 2.08-2.19 (m, 2H) 2.26-2.44 (m, 2H) 2.48-2.56 (m, 1H) 2.58-2.69 (m, 1H) 2.77 (s, 3H) 2.78-2.84 (m, 1H) 2.85-2.96 (m, 1H) 3.16-3.24 (m, 1H) 7.02 (t, J=8.62 Hz, 2H) 7.48-7.56 (m, 2H) 8.90 (s, 2H) 9.28 (s, 1H); MS (DCI) m/z 403.1 (M+H)$^+$.

Example 68F (6aS,7S,9Z,10aS)-10a-(4-fluorophenyl)-9-(hydroxymethylene)-2,7-dimethyl-4-(pyrimidin-5-yl)-5,6a,7,9,10,10a-hexahydrobenzo[h]quinazolin-8(6H)-one The titled compound was prepared using the conditions described in Example 13F, substituting Example 68E for Example 13E.

Example 68G (6aS,7S,11aS)-11a-(4-fluorophenyl)-2,7-dimethyl-4-(pyrimidin-5-yl)-5,6,6a,7,11,11a-hexahydro[1,2]benzoxazolo[6,5-h]quinazoline The titled compound was prepared using the conditions described in Example 13G, substituting Example 68F for Example 13F.

Example 68H (6aS,7S,10aS)-10a-(4-fluorophenyl)-2,7-dimethyl-8-oxo-4-(pyrimidin-5-yl)-5,6,6a,7,8,9,10,10a-octahydrobenzo[h]quinazoline-9-carbonitrile The titled compound was prepared using the conditions described in Example 13H, substituting Example 68G for Example 13G.

Example 68I (6aS,7S,10aR)-10a-(4-fluorophenyl)-2,7-dimethyl-8-oxo-4-(pyrimidin-5-yl)-5,6,6a,7,8,10a-hexahydrobenzo[h]quinazoline-9-carbonitrile The titled compound was prepared using the conditions described in Example 13I, substituting Example 68H for Example 13H. Purification was achieved by flash chromatography on silica gel eluting with 10% acetone in chloroform (59% yield). $^1$H NMR (400 MHz, CDCl$_3$) δ ppm 1.20 (d, J=6.29 Hz, 3H) 1.58-1.66 (m, 1H) 1.93-2.02 (m, 1H) 2.33-2.50 (m, 2H) 2.74 (s, 3H) 2.99-3.09 (m, 2H) 6.80 (dd, J=8.84, 4.93 Hz, 2H) 7.06 (t, J=8 (M+H)$^+$. 46 Hz, 2H) 8.91 (s, 1H) 9.06 (s, 2H) 9.35 (s, 1H); MS (CI) m/z 426 (M+H)$^+$.

Example 69

(6aS,7S,10aR)-10a-(3-fluorophenyl)-2,7-dimethyl-8-oxo-4-(pyrimidin-5-yl)-5,6,6a,7,8,10a-hexahydrobenzo[h]quinazoline-9-carbonitrile Example 69A methyl (1'S,4a'S,8a'S)-4a'-(3-fluorophenyl)-1'-methyl-5'-oxooctahydro-1'H-spiro[1,3-dioxolane-2,2'-naphthalene]-6'-carboxylate To a solution of Example 53F (2.0 g, 6.28 mmol) in tetrahydrofuran (30.0 mL) at room temperature was added dimethyl carbonate (13.2 mL, 157 mmol) followed by 95% sodium hydride (0.64 g, 25.1 mmol) and 50% potassium hydride in paraffin (0.05 g, 0.63 mmol). The reaction was refluxed for 18 hours. The reaction was cooled to room temperature, neutralized with acetic acid, diluted with ethyl acetate and washed with water. The aqueous phase was washed with ethyl acetate. The organic layers were combined, washed with brine, dried (MgSO$_4$) and concentrated under reduced pressure. Purification of the residue was achieved by flash chromatography on silica gel eluting with 10-20% ethyl acetate in heptane to give the titled compound (1.4 g, 59%). $^1$H NMR (400 MHz, CDCl$_3$) δ ppm 1.00 (d, J=6.61 Hz, 3H) 1.15 (ddd, J=28.63, 14.58, 3.63 Hz, 1H) 1.63 (dt, J=13.53, 3.43 Hz, 1H) 1.90-2.10 (m, 5H) 2.10-2.23 (m, 2H) 2.66 (dt, J=18.19, 6.52 Hz, 1H) 3.27-3.34 (m, 1H) 3.70 (s, 3H) 3.95 (s, 4H) 6.96 (td, J=8.24, 2.17 Hz, 1H) 7.11-7.18 (m, 2H) 7.33 (td, J=8.11, 6.45 Hz, 1H); MS (ESI) m/z 377.0 (M+H)$^+$.

Example 69B (6aS,7S,10aS)-10a-(3-fluorophenyl)-2,7-dimethyl-5,6a,7,9,10,10a-hexahydro-6H-spiro[benzo[h]quinazoline-8,2'-[1,3]dioxolan]-4-ol The titled compound was prepared using the conditions described in Example 13B, substituting Example 69A for Example 13A.

Example 69C (6aS,7S,10aS)-10a-(3-fluorophenyl)-4-hydroxy-2,7-dimethyl-5,6a,7,9,10,10a-hexahydrobenzo[h]quinazolin-8(6H)-one The titled compound was prepared using the conditions described in Example 13C, substituting Example 69B for Example 13B. Purification was achieved by flash chromatography on silica gel eluting with 10% acetone in chloroform (32% yield).

Example 69D (6aS,7S,10aS)-4-chloro-10a-(3-fluorophenyl)-2,7-dimethyl-5,6a,7,9,10,10a-hexahydrobenzo[h]quinazolin-8(6H)-one The titled compound was prepared using the conditions described in Example 13D, substituting Example 69C for Example 13C. Purification was achieved by flash chromatography on silica gel eluting with 5% ethyl acetate in chloroform (69% yield). $^1$H NMR (400 MHz, CDCl$_3$) δ ppm 1.18 (d, J=6.72 Hz, 3H) 1.95-2.26 (m, 4H) 2.43-2.62 (m, 3H) 2.65 (s, 3H) 2.83-2.91 (m, 2H) 3.23 (ddd, J=14.42, 6.51, 3.90 Hz, 1H) 6.91-6.98 (m, 1H) 7.14 (dt, J=11.17, 2.06 Hz, 1H) 7.19-7.32 (m, 2H); MS (DCI) m/z 359.0 (M+H)$^+$.

Example 69E (6aS,7S,10aS)-10a-(3-fluorophenyl)-2,7-dimethyl-4-(pyrimidin-5-yl)-5,6a,7,9,10,10a-hexahydrobenzo[h]quinazolin-8(6H)-one The titled compound was prepared using the conditions described in Example 23A, substituting pyrimidin-5-ylboronic acid for 2-(furan-3-yl)-4,4,5,5-tetramethyl-1,3,2-dioxaborolane. Purification was achieved by flash chromatography on silica gel eluting with 25% acetone in heptane (82% yield). $^1$H NMR (400 MHz, CDCl$_3$) δ ppm 1.18 (d, J=6.61 Hz, 3H) 2.02 (td, J=11.79, 7.21 Hz, 1H) 2.10-2.22 (m, 2H) 2.26-2.44 (m, 2H) 2.48-2.57 (m, 1H) 2.59-2.70 (m, 1H) 2.78 (s, 3H) 2.80-2.97 (m, 2H) 3.21 (ddd, J=13.61, 5.37, 5.20 Hz, 1H) 6.98 (t, J=7.97 Hz, 1H) 7.21-7.40 (m, 3H) 8.90 (s, 2H) 9.28 (s, 1H); MS (DCI) m/z 403.1 (M+H)$^+$.

Example 69F (6aS,7S,9Z,10aS)-10a-(3-fluorophenyl)-9-(hydroxymethylene)-2,7-dimethyl-4-(pyrimidin-5-yl)-5,6a,7,9,10,10a-hexahydrobenzo[h]quinazolin-8(6H)-one The titled compound was prepared using the conditions described in Example 13F, substituting Example 69E for Example 13E.

Example 69G (6aS,7S,11aS)-11a-(3-fluorophenyl)-2,7-dimethyl-4-(pyrimidin-5-yl)-5,6,6a,7,11,11a-hexahydro[1,2]benzoxazolo[6,5-h]quinazoline The titled compound was prepared using the conditions described in Example 13G, substituting Example 69F for Example 13F.

Example 69H (6aS,7S,10aS)-10a-(3-fluorophenyl)-2,7-dimethyl-8-oxo-4-(pyrimidin-5-yl)-5,6,6a,7,8,9,10,10a-octahydrobenzo[h]quinazoline-9-carbonitrile The titled compound was prepared using the conditions described in Example 13H, substituting Example 69G for Example 13G.

Example 69I (6aS,7S,10aR)-10a-(3-fluorophenyl)-2,7-dimethyl-8-oxo-4-(pyrimidin-5-yl)-5,6,6a,7,8,10a-hexahydrobenzo[h]quinazoline-9-carbonitrile The titled compound was prepared using the conditions described in Example 13I, substituting Example 69H for Example 13H. Purification was achieved by flash chromatography on silica gel eluting with 10% acetone in chloroform (96% yield). $^1$H NMR (400 MHz, CDCl$_3$) δ ppm 1.20 (d, J=6.51 Hz, 3H) 1.58-1.69 (m, 1H) 1.95-2.04 (m, 1H) 2.33-2.52 (m, 2H) 2.75 (s, 3H) 3.01-3.09 (m, 2H) 6.49 (dt, J=10.27, 2.07 Hz, 1H) 6.67 (dd, J=7.75, 1.36 Hz, 1H) 7.05 (td, J=8.13, 2.28 Hz, 1H) 7.31-7.40 (m, 1H) 8.91 (s, 1H) 9.06 (s, 2H) 9.36 (s, 1H); MS (CI) m/z 426 (M+H)$^+$.

Example 70

(6aS,7S,10aR)-10a-(4-methoxyphenyl)-7-methyl-8-oxo-5,6,6a,7,8,10a-hexahydrobenzo[h]quinazoline-9-carbonitrile Example 70A (6aS,7S,10aS)-10a-(4-methoxyphenyl)-7-methyl-5,6a,7,9,10,10a-hexahydro-6H-spiro[benzo[h]quinazoline-8,2'-[1,3]dioxolane]

To a solution Example 58G (0.515 g, 1.44 mmol) in isopropanol 12 mL) was added formamidine acetate (0.598 g, 5.75 mmol) and piperidine (0.569 mL, 5.75 mmol). The reaction mixture was heated at 95° C. for 36 hours. The cooled solution was diluted with a solution of saturated aqueous sodium phosphate monobasic and extracted with ethyl acetate. The organic layer was concentrated to give the titled compound.

Example 70B (6aS,7S,10aS)-10a-(4-methoxyphenyl)-7-methyl-5, 6a,7,9,10,10a-hexahydrobenzo[h]quinazolin-8(6H)-one The titled compound was prepared using the conditions described in Example 1I, substituting Example 70A for Example 1H. $^1$H NMR (400 MHz, CDCl$_3$) δ ppm 1.17 (d, J=6.72 Hz, 3H) 2.00 (dt, J=12.23, 8.85 Hz, 1H) 2.10-2.18 (m, 2H) 2.25 (ddd, J=14.18, 10.98, 7.05 Hz, 1H) 2.44-2.59 (m, 2H) 2.67 (td, J=12.77, 6.56 Hz, 1H) 2.73-2.91 (m, 2H) 3.20 (ddd, J=14.15, 5.96, 4.07 Hz, 1H) 3.76 (s, 3H) 6.81 (d, J=8.89 Hz, 2H) 7.34 (d, J=8.89 Hz, 2H) 8.44 (s, 1H) 9.03 (s, 1H) MS (APCI+) m/z 323 (M+H)$^+$.

Example 70C (6aS,7S,9Z,10aS)-9-(hydroxymethylene)-10a-(4-methoxyphenyl)-7-methyl-5,6a,7,9,10,10a-hexahydrobenzo[h]quinazolin-8(6H)-one The titled compound was prepared using the conditions described in Example 1J, substituting Example 70B for Example 1I. In this instance, the reaction mixture was stirred overnight at room temperature.

Example 70D (6aS,7S,11aS)-11a-(4-methoxyphenyl)-7-methyl-5,6, 6a,7,11,11a-hexahydro[1,2]benzoxazolo[6,5-h]quinazoline The titled compound was prepared using the conditions described in Example 1K, substituting Example 70C for Example 1J. $^1$H NMR (400 MHz, CDCl$_3$) δ ppm 1.39 (d, J=6.94 Hz, 3H) 1.75-1.87 (m, 1H) 1.97 (ddd, J=12.88, 10.71, 2.11 Hz, 1H) 2.07-2.14 (m, 1H) 2.22-2.30 (m, 1H) 2.91-3.01 (m, 2H) 3.07-3.15 (m, 1H) 3.71 (s, 3H) 3.80 (d, J=16.92 Hz, 1H) 6.66 (s, 4H) 8.25 (s, 1H) 8.62 (s, 1H) 9.01 (s, 1H).

Example 70E (6aS,7S,10aS)-10a-(4-methoxyphenyl)-7-methyl-8-oxo-5,6,6a,7,8,9,10,10a-octahydrobenzo[h]quinazoline-9-carbonitrile The titled compound was prepared using the conditions described in Example 1L, substituting Example 70D for Example 1K and using 10 equivalents of 25% sodium methoxide in methanol.

Example 70F (6aS,7S,10aR)-10a-(4-methoxyphenyl)-7-methyl-8-oxo-5,6,6a,7,8,10a-hexahydrobenzo[h]quinazoline-9-carbonitrile To a solution of Example 70E (0.154 g, 0.443 mmol) in dimethylformamide (4 mL) cooled to 0° C. in an ice water bath was added 1,3-dibromo-5,5-dimethylhydantoin (0.063 g, 0.222 mmol). The solution was stirred at 0° C. for 35 minutes, and then pyridine (0.538 mL, 6.65 mmol) was added. The reaction solution was heated at 55° C. for 1 hour. The cooled solution was diluted with water and extracted with ethyl acetate. The organic layer was washed with brine and concentrated. The residue was purified using a 12 g RediSep® cartridge on a Teledyne Isco Combiflash® Rf, eluting with 0-55% ethyl acetate in heptane system to give 0.068 g (44%) of the titled compound. $^1$H NMR (400 MHz, CDCl$_3$) δ ppm 1.19 (d, J=6.72 Hz, 3H) 1.60-1.71 (m, 1H) 1.92-2.03 (m, 1H) 2.30 (td, J=12.93, 2.01 Hz, 1H) 2.45 (dt, J=13.04, 6.55 Hz, 1H) 2.98-3.16 (m, 2H) 3.77 (s, 3H) 6.68 (d, J=8.89 Hz, 2H) 6.84 (d, J=8.89 Hz, 2H) 8.70 (s, 1H) 8.82 (s, 1H) 9.06 (s, 1H); MS (APCI+) m/z 346 (M+H)$^+$, 387 (M+H+CH$_3$CN)+.

Example 71

3-[(5aS,6S,9aR)-8-cyano-6-methyl-7-oxo-2,4,5,5a,6, 7-hexahydro-9aH-benzo[g]indazol-9a-yl]benzoic acid Example 62F (0.078 g, 0.216 mmol) was dissolved in tetrahydrofuran (1.08 mL) and water (1.08 mL) and lithium hydroxide monohydrate (0.027 mg, 0.647 mmol) was added. The reaction mixture was stirred at room temperature overnight. The reaction mixture was neutralized with 2 M HCl (0.324 mL, 0.647 mmol) and concentrated. The residue was purified on a reversed-phase Waters HPLC using a Nova-Pak® HR C18, 6 μm, 60 Å, 40 mm×100 mm, PrepPak cartridge eluting with a gradient of 10-90% acetonitrile in aqueous 0.1% trifluoroacetic acid (60 mL/minute) to give 0.067 g (67% yield) of the titled compound as the trifluoroacetic acid salt. $^1$H NMR (400 MHz, CDCl$_3$) δ ppm 1.12-1.20 (m, 3H), 1.38-1.56 (m, 1H), 1.78-1.86 (m, 1H), 2.33-2.48 (m, 1H), 2.67-2.79 (m, 1H), 2.88-2.98 (m, 1H), 7.03-7.09 (m, 1H), 7.34-7.39 (m, 1H), 7.43 (d, J=5.9 Hz, 1H), 7.61 (s, 1H), 7.91-7.98 (m, 1H), 8.52 (d, J=4.1 Hz, 1H); MS (APCI) m/z 389 (M+CH$_3$CN)+.

Example 72

(6S,9aR)-9a-(4-hydroxyphenyl)-6-methyl-7-oxo-4,5, 5a,6,7,9a-hexahydro-2H-benzo[g]indazole-8-carbonitrile Example 72A (2Z,4aS,5S,8aS)-2-(hydroxymethylene)-8a-(4-hydroxyphenyl)-5-methylhexahydronaphthalene-1,6 (2H,5H)-dione The product of Example 58G was dissolved in dichloromethane, cooled to −10° C., treated with boron tribromide (0.018 mL, 0.176 mmol) and stirred at −10° C. for 5 hours. The reaction mixture was placed in a −20° C. freezer overnight. More boron tribromide (0.018 mL, 0.176 mmol) was added, and the reaction mixture was stirred at −10° C. for 2 hours. The reaction mixture was diluted with water and extracted with ethyl acetate. After concentration, the titled compound was used without additional purification. $^1$H NMR (400 MHz, CDCl$_3$) δ ppm 1.15 (d, J=6.6 Hz, 3H), 1.81-2.16 (m, 6H), 2.22-2.44 (m, 5H), 2.58-2.75 (m, 2H), 6.78-6.85 (m, 2H), 7.36-7.42 (m, 2H), 7.69-7.79 (m, 1H), 13.72-13.91 (m, 1H); MS (APCI) m/z 301 (M+H)$^+$.

Example 72B (5aS,6S,9aS)-9a-(4-hydroxyphenyl)-6-methyl-2,4,5,5a,6,8,9,9a-octahydro-7H-benzo[g]indazol-7-one The titled compound was prepared using the conditions described in Example 24A substituting Example 1G with Example 72A. MS (ESI) m/z 397 (M+H)$^+$.

Example 72C (5aS,6S,8Z,9aS)-8-(hydroxymethylene)-9a-(4-hydroxyphenyl)-6-methyl-2,4,5,5a,6,8,9,9a-octahydro-7H-benzo[g]indazol-7-one The titled compound was prepared using the conditions described in Example 24C substituting Example 24B with Example 72B.

Example 72D

4-[(5aS,6S,10aS)-6-methyl-2,4,5,5a,6,10-hexahydro-10aH-indazolo[7,6-][1,2]benzoxazol-10a-yl]phenol The titled compound was prepared using the conditions described in Example 24D substituting Example 24C with Example 72C. MS (APCI) m/z 322 (M+H)$^+$.

Example 72E (5aS,6S,9aS)-9a-(4-hydroxyphenyl)-6-methyl-7-oxo-4,5,5a,6,7,8,9,9a-octahydro-2H-benzo[g]indazole-8-carbonitrile The titled compound was prepared using the conditions described in Example 24E substituting Example 24D with Example 72D.

Example 72F (6S,9aR)-9a-(4-hydroxyphenyl)-6-methyl-7-oxo-4,5,5a,6,7,9a-hexahydro-2H-benzo[g]indazole-8-carbonitrile Example 72E (0.028 g, 0.087 mmol) was dissolved in tetrahydrofuran (0.290 mL) and toluene (0.581 mL) and sparged with nitrogen for 10 minutes. 2,3-Dichloro-5,6-dicyano-1,4-benzoquinone (0.21 g, 0.096 mmol) was added, and nitrogen bubbling was continued for 1 hour. The reaction mixture was concentrated and purified first using a Biotage® SNAP silica 10 g cartridge using 0-50% acetone with 5% methanol in hexane and then using a reversed-phase Waters HPLC using a Nova-Pak® HR C18, 6 µm, 60 Å, 40 mm×100 mm, PrepPak cartridge eluting with a gradient of 10-90% acetonitrile in aqueous 0.1% trifluoroacetic acid (60 mL/minute) to give 0.009 g (30% yield) of the titled compound as the trifluoroacetic acid salt. $^1$H NMR (400 MHz, CDCl$_3$) δ ppm 1.15-1.22 (m, 3H), 1.49-1.65 (m, 1H), 1.82-1.90 (m, 1H), 2.28-2.37 (m, 1H), 2.39-2.53 (m, 1H), 5.30 (s, 1H), 6.66-6.79 (m, 4H), 7.51-7.58 (m, 1H), 8.22 (d, J=5.3 Hz, 1H); MS (ESI) m/z 320 (M+H)$^+$.

Example 73

(6aS,7S,10aR)-7-methyl-8-oxo-10a-[4-(pyrrolidin-1-ylcarbonyl)phenyl]-5,6,6a,7,8,10a-hexahydrobenzo[h]quinazoline-9-carbonitrile To a solution of Example 66 (0.09 g, 0.25 mmol) in dimethylacetamide (1 mL) was added pyrrolidine (0.104 mL, 1.25 mmol), Hunig's base (1.00 mL, 5.73 mmol), and bis(dimethylamino)(3-oxido-1H-benzotriazol-1-yl)methylium hexafluorophosphate (HATU, 0.114 g, 0.301 mmol). The reaction mixture was stirred at room temperature for 5 hours, then diluted with water, and extracted with 20% isopropanol in chloroform. The reaction mixture was concentrated, and the residue was purified using a 12 g RediSep® cartridge, on a Teledyne Isco Combiflash® Rf system eluting with 0-50% ethyl acetate in heptane. A second purification was done by preparative HPLC on a Waters SunFire™ C8(2) 5 µm 100 Å column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to give 0.03 g (29%) of the titled compound. $^1$H NMR (400 MHz, CDCl$_3$) δ ppm 1.20 (d, J=6.18 Hz, 3H) 1.55-1.69 (m, 1H) 1.87-1.95 (m, 2H) 1.97-2.05 (m, 3H) 2.32-2.48 (m, 2H) 3.03-3.22 (m, 2H) 3.40 (ddd, J=23.10, 10.63, 6.61 Hz, 2H) 3.67 (t, J=6.99 Hz, 2H) 6.84 (d, J=8.46 Hz, 2H) 7.48 (d, J=8.35 Hz, 2H) 8.80 (s, 1H) 8.81 (s, 1H) 9.12 (s, 1H); MS (ESI+) m/z 413 (M+H)$^+$, m/z 445 (M+CH$_3$OH+H)$^+$.

Example 74

(6aS,7S,10aR)-2-(2,6-difluorophenyl)-7-methyl-8-oxo-10a-phenyl-5,6,6a,7,8,10a-hexahydrobenzo[h]quinazoline-9-carbonitrile

Example 74A (6aS,7S,10aS)-2-(2,6-difluorophenyl)-7-methyl-10a-phenyl-5,6a,7,9,10,10a-hexahydro-6H-spiro[benzo[h]quinazoline-8,2'-[1,3]dioxolane]

To a solution of Example 1G (0.500 g, 1.52 mmol) in isopropanol (12 mL) was added 2,6-difluorobenzenecarboximidamide (0.733 g, 3.81 mmol) and piperidine (0.377 g, 3.81 mmol). The reaction mixture was heated at 90° C. for 24 hours. The cooled solution was diluted with saturated aqueous NaH$_2$PO$_4$ solution and extracted with ethyl acetate. The organic phase was concentrated to give the titled compound. MS (APCI+) m/z 449 (M+H)$^+$.

Example 74B (6aS,7S,10 aS)-2-(2,6-difluorophenyl)-7-methyl-10a-phenyl-5,6a,7,9,10,10a-hexahydrobenzo[h]quinazolin-8(6H)-one The titled compound was prepared using the conditions described in Example 1I, substituting Example 74A for Example 1H.

Example 74C (6aS,7S,9Z,10aS)-2-(2,6-difluorophenyl)-9-(hydroxymethylene)-7-methyl-10a-phenyl-5,6a,7,9,10,10a-hexahydrobenzo[h]quinazolin-8(6H)-one The titled compound was prepared using the conditions described in Example 1J, substituting Example 74B for Example 1I. MS (APCI+) m/z 433 (M+H)$^+$.

Example 74D (6aS,7S,11aS)-2-(2,6-difluorophenyl)-7-methyl-11a-phenyl-5,6,6a,7,11,11a-hexahydro[1,2]benzoxazolo[6,5-h]quinazoline The titled compound was prepared using the conditions described in Example 1K, substituting Example 74C for Example 1J.

Example 74E (6aS,7S,10aS)-2-(2,6-difluorophenyl)-7-methyl-8-oxo-10a-phenyl-5,6,6a,7,8,9,10,10a-octahydrobenzo[h]quinazoline-9-carbonitrile The titled compound was prepared using the conditions described in Example 1L, substituting Example 74D for Example 1K and using 8 equivalents of 25% sodium methoxide in methanol.

Example 74F (6aS,7S,10aR)-2-(2,6-difluorophenyl)-7-methyl-8-oxo-10a-phenyl-5,6,6a,7,8,10a-hexahydrobenzo[h]quinazoline-9-carbonitrile The titled compound was prepared using the conditions described in Example 1M, substituting Example 74D for Example 1L (0.114 g, 46%). $^1$H NMR (400 MHz, CDCl$_3$) δ ppm 1.22 (d, J=6.61 Hz, 3H) 1.61-1.75 (m, 1H) 2.01 (dd, J=13.82, 7.54 Hz, 1H) 2.40 (td, J=12.77, 2.44 Hz, 1H) 2.50 (td, J=13.04, 6.56 Hz, 1H) 3.03-3.22 (m, 2H) 6.83 (dd, J=7.86, 1.36 Hz, 2H) 6.94-7.02 (m, 2H) 7.28-7.42 (m, 4H) 8.85 (s, 1H) 8.86 (s, 1H); MS (ESI+) m/z 428 (M+H)$^+$.

Example 75 methyl 4-[(6aS,7S,10aR)-9-cyano-7-methyl-8-oxo-10a-phenyl-5,6,6a,7,8,10a-hexahydrobenzo[h]quinazolin-2-yl]benzoate

Example 75A methyl 4-[(6aS,7S,10aS)-7-methyl-10a-phenyl-5,6a,7,9,10,10a-hexahydro-6H-spiro[benzo[h]quinazoline-8,2'-[1,3]dioxolan]-2-yl]benzoate To a solution of Example 1G (0.500 g, 1.52 mmol) in isopropanol (12 mL) was added methyl 4-carbamimidoylbenzoate (0.980 g, 4.57 mmol) and piperidine (0.452 g, 4.57 mmol).

The reaction mixture was heated at 95° C. for 72 hours. The cooled solution was diluted with saturated aqueous NaH$_2$PO$_4$ solution and extracted with ethyl acetate. The organic phase was concentrated to provide the titled compound.

Example 75B methyl 4-[(6aS,7S,10aS)-7-methyl-8-oxo-10a-phenyl-5,6,6a,7,8,9,10,10a-octahydrobenzo[h]quinazolin-2-yl]benzoate The titled compound was prepared using the conditions described in Example 1I, substituting Example 75A for Example 1H. MS (APCI+) m/z 427 (M+H)$^+$.

Example 75C ethyl 4-[(6aS,7S,9Z,10aS)-9-(hydroxymethylene)-7-methyl-8-oxo-10a-phenyl-5,6,6a,7,8,9,10,10a-octahydrobenzo[h]quinazolin-2-yl]benzoate To a solution of Example 75B (0.215 g, 0.504 mmol) in ethyl formate (1.03 mL, 12.60 mmol) was added 25% sodium methoxide in methanol (0.440 mL, 2.02 mmol). The reaction mixture was stirred at room temperature for 2 hours, then 1 M potassium t-butoxide in tetrahydrofuran was added, and the mixture was heated at 40° C. for 2 hours. The solution was diluted with saturated aqueous NaH$_2$PO$_4$ solution and extracted with ethyl acetate. The organic layer was dried over sodium sulfate, filtered, and concentrated to give 0.191 g (83%) of the titled compound.

Example 75D ethyl 4-[(6aS,7S,11aS)-7-methyl-11a-phenyl-5,6,6a,7,11,11a-hexahydro[1,2]benzoxazolo[6,5-h]quinazolin-2-yl]benzoate The titled compound was prepared using the conditions described in Example 1K, substituting Example 75C for Example 1J. MS (APCI+) m/z 466 (M+H)$^+$.

Example 75E methyl 4-[(6aS,7S,10aS)-9-cyano-7-methyl-8-oxo-10a-phenyl-5,6,6a,7,8,9,10,10a-octahydrobenzo[h]quinazolin-2-yl]benzoate The titled compound was prepared using the conditions described in Example 1L, substituting Example 75D for Example 1K.

Example 75F methyl 4-[(6aS,7S,10aR)-9-cyano-7-methyl-8-oxo-10a-phenyl-5,6,6a,7,8,10a-hexahydrobenzo[h]quinazolin-2-yl]benzoate To a solution of Example 75E (0.111 g, 0.246 mmol) in dimethylformamide (4 mL) cooled to 0° C. in an ice water bath was added 1,3-dibromo-5,5-dimethylhydantoin (0.039 g, 0.135 mmol). The solution was stirred at 0° C. for 35 minutes. Then pyridine (0.199 mL, 2.46 mmol) was added, and the solution was heated at 55° C. for 1 hour. The cooled solution was diluted with water and extracted with ethyl acetate. The organic layer was washed with brine and concentrated. The residue was purified using a 12 g RediSep® cartridge on a Teledyne Isco Combiflash® Rf system, eluting with 0-10% ethyl acetate in dichloromethane to give 0.039 g (35%) of the titled compound. $^1$H NMR (400 MHz, CDCl$_3$) δ ppm 1.22 (d, J=6.61 Hz, 3H) 1.59-1.73 (m, 1H) 2.01 (dd, J=13.66, 7.81 Hz, 1H) 2.38 (td, J=12.90, 2.39 Hz, 1H) 2.50 (td, J=13.09, 6.56 Hz, 1H) 3.00-3.21 (m, 2H) 3.95 (s, 3H) 6.85 (dd, J=7.81, 1.63 Hz, 2H) 7.29-7.38 (m, 3H) 8.12 (d, J=8.46 Hz, 2H) 8.45 (d, J=8.57 Hz, 2H) 8.81 (s, 1H) 9.00 (s, 1H); MS (ESI+) m/z 450 (M+H)$^+$.

Example 76

(6aS,7S,10aR)-4-(1-acetyl-1H-pyrazol-4-yl)-2,7-dimethyl-8-oxo-10a-phenyl-5,6,6a,7,8,10a-hexahydrobenzo[h]quinazoline-9-carbonitrile A solution of the product of Example 34E (0.0132 g, 0.033 mmol) in dichloromethane (0.4 mL) was cooled to 0°

C. and triethylamine (0.013 mL, 0.093 mmol) was added followed by acetyl chloride (0.003 mL, 0.039 mmol). The reaction solution was stirred at room temperature for 0.5 hour. The reaction mixture was then concentrated in vacuo. The residue was diluted with acetonitrile, cooled to 0° C. and neutralized with an aqueous solution of hydrochloric acid (2 N, 0.046 mL). Then this aqueous mixture was purified on a reversed-phase Waters HPLC using a Nova-Pak® HR C18, 6 μm, 60 Å, 40 mm×100 mm, PrepPak cartridge, eluted with a gradient of 30-80% $CH_3CN$ in 0.1% aqueous trifluoroacetic acid at a flow rate of 60 mL/minute over 12 minutes then hold at 100% $CH_3CN$ for 5 minutes to give the titled compound (0.005 g, 0.011 mmol, 33.6%). $^1H$ NMR (400 MHz, $CDCl_3$) δ ppm 1.20 (d, J=6.6 Hz, 3H), 1.58-1.67 (m, 1H), 2.02-2.11 (m, 1H), 2.30-2.39 (m, 1H), 2.46 (dd, J=13.2, 6.6 Hz, 1H), 2.69 (s, 3H), 2.80 (s, 3H), 3.01-3.18 (m, 2H), 6.79-6.84 (m, 2H), 7.29-7.36 (m, 3H), 8.48 (s, 1H), 8.79 (s, 1H), 8.96 (s, 1H); MS (CI) m/z 438.1 $(M+1)^+$.

Example 77

4-[(6aS,7S,10aR)-9-cyano-7-methyl-8-oxo-10a-phenyl-5,6,6a,7,8,10a-hexahydrobenzo[h]quinazolin-2-yl]benzoic acid To a solution of Example 75F (0.026 g, (0.058 mmol) in tetrahydrofuran (1.5 mL) was added water (0.5 mL) and lithium hydroxide monohydrate (0.007 g, 0.174 mmol). The reaction mixture was stirred at room temperature for 20 hours. The solution was adjusted to pH 7 by dropwise addition of 1 M hydrochloric acid, and then ethyl acetate was added and the mixture was vigorously stirred for 1 hour. The layers were separated, and the organic phase was concentrated. The residue was purified using a 4 g RediSep® cartridge on a Teledyne Isco Combiflash® Rf system, eluting with 0-10% methanol in dichloromethane to give 0.015 g (60%) of the titled compound. $^1H$ NMR (400 MHz, $CDCl_3$) δ ppm 1.22 (d, J=6.61 Hz, 3H) 1.59-1.73 (m, 1H) 1.96-2.07 (m, 1H) 2.38 (td, J=12.74, 2.17 Hz, 1H) 2.51 (td, J=13.09, 6.56 Hz, 1H) 3.01-3.22 (m, 2H) 6.85 (dd, J=7.75, 1.57 Hz, 2H) 7.30-7.38 (m, 3H) 8.18 (d, J=8.57 Hz, 2H) 8.49 (d, J=8.46 Hz, 2H) 8.82 (s, 1H) 9.00 (s, 1H); MS (ESI+) m/z 436 $(M+H)^+$.

Example 78

(6S,9aR)-9a-(3-fluorophenyl)-3-[3-(3-hydroxypropyl)phenyl]-6-methyl-7-oxo-4,5,5a,6,7,9a-hexahydro-2H-benzo[g]indazole-8-carbonitrile Example 78A (5aS,6S,9aS)-9a-(3-fluorophenyl)-N,N,6-trimethyl-4,5,5a,8,9,9a-hexahydrospiro[benzo[g]indazole-7,2'-[1,3]dioxolane]-2(6H)-sulfonamide The product of Example 53H (0.195 g, 0.569 mmol) was dissolved in toluene (6 mL) and treated with triethylamine (0.103 mL, 0.740 mmol) and dimethylsulfamoyl chloride (0.476 mL, 3.42 mmol). The reaction mixture was stirred at reflux overnight, cooled to room temperature, and concentrated. The residue was purified using a Biotage® SNAP silica 10 g cartridge using a gradient of 0-20% acetone in hexane to give the titled compound 0.247 g (96% yield). $^1H$ NMR (400 MHz, $CDCl_3$) δ ppm 0.99-1.05 (m, 3H), 1.28-1.43 (m, 1H), 1.63-1.74 (m, 1H), 1.92-2.19 (m, 4H), 2.52-2.73 (m, 5H), 2.88 (s, 6H), 3.93-3.99 (m, 4H), 6.79-6.89 (m, 1H), 7.15-7.24 (m, 1H), 7.40-7.51 (m, 2H), 7.56 (d, J=4.3 Hz, 1H); MS (APCI) m/z 450 $(M+H)^+$.

Example 78B (5aS,6S,9aS)-3-chloro-9a-(3-fluorophenyl)-N,N,6-trimethyl-4,5,5a,8,9,9a-hexahydrospiro[benzo[g]indazole-7,2'-[1,3]dioxolane]-2(6H)-sulfonamide The product of Example 78A (0.040 g, 0.089 mmol) was dissolved in tetrahydrofuran (0.890 mL) and cooled to −78° C. Lithium bis(trimethylsilyl)amide (0.311 mL, 0.311 mmol) was added, and the reaction mixture was stirred −78° C. for 1 hour. Solid hexachloroethane (0.032 g, 0.133 mmol) was then added, and the reaction mixture was stirred at −78° C. for 2 hours. Then the reaction mixture was allowed to warm to room temperature overnight. The reaction mixture was diluted with water and extracted with ethyl acetate. The organic layer was dried and concentrated. The residue was purified using a Biotage® SNAP silica 10 g cartridge eluting with 0-20% acetone/hexane.

Example 78C (5aS,6S,9aS)-9a-(3-fluorophenyl)-3-[3-(3-hydroxypropyl)phenyl]-N,N,6-trimethyl-4,5,5a,8,9,9a-hexahydrospiro[benzo[g]indazole-7,2'-[1,3]dioxolane]-2(6H)-sulfonamide The product of Example 78B (0.100 g, 0.207 mmol), cesium carbonate (0.202 g, 0.620 mmol), and 3-(3-(4,4,5,5-tetramethyl-1,3,2-dioxaborolan-2-yl)phenyl)propan-1-ol (0.217 g, 0.826 mmol) were dissolved in dioxane (4 mL) and sparged with nitrogen for 10 minutes. 1,10-Bis(di-tert-butylphosphino)ferrocene palladium dichloride (0.013 g, 0.021 mmol) was added, and the reaction mixture was heated to 100° C. overnight. The reaction mixture was concentrated, and the residue was purified using a Biotage® SNAP silica 10 g cartridge using 0-40% acetone/hexane to give the titled compound. MS (APCI) m/z 584 $(M+H)^+$.

Example 78D (5aS,6S,9aS)-9a-(3-fluorophenyl)-3-[3-(3-hydroxypropyl)phenyl]-N,N,6-trimethyl-7-oxo-4,5,5a,6,7,8,9,9a-octahydro-2H-benzo[g]indazole-2-sulfonamide The titled compound was prepared using the conditions described in Example 24B substituting Example 24A with Example 78C.

Example 78E (5aS,6S,8Z,9aS)-9a-(3-fluorophenyl)-8-(hydroxymethylene)-3-[3-(3-hydroxypropyl)phenyl]-N,N,6-trimethyl-7-oxo-4,5,5a,6,7,8,9,9a-octahydro-2H-benzo[g]indazole-2-sulfonamide The titled compound was prepared using the conditions described in Example 24C substituting Example 24B with Example 78D. MS (APCI) m/z 568 $(M+H)^+$.

Example 78F

3-{3-[(5aS,6S,10aS)-10a-(3-fluorophenyl)-6-methyl-4,5,5a,6,10,10a-hexahydro-2H-indazolo[7,6-][1,2]benzoxazol-3-yl]phenyl}propan-1-ol The titled compound was prepared using the conditions described in Example 24D substituting Example 24C with Example 78E. MS (APCI) m/z 457 (M+H)+.

Example 78G (5aS,6S,9aS)-9a-(3-fluorophenyl)-3-[3-(3-hydroxypropyl)phenyl]-6-methyl-7-oxo-4,5,5a,6,7,8,9,9a-octahydro-2H-benzo[g]indazole-8-carbonitrile The titled compound was prepared using the conditions described in Example 24E substituting Example 24D with Example 78F.

Example 78H (6S,9aR)-9a-(3-fluorophenyl)-3-[3-(3-hydroxypropyl)phenyl]-6-methyl-7-oxo-4,5,5a,6,7,9a-hexahydro-2H-benzo[g]indazole-8-carbonitrile Example 78G (0.035 g, 0.076 mmol) was dissolved in dimethylformamide (0.765 mL), and the solution was cooled to 0° C. 1,3-Dibromo-5,5-dimethylhydantoin (0.011 g, 0.038 mmol) was added, and the reaction mixture was stirred at 0° C. for 1 hour. Pyridine (0.229 mL, 2.83 mmol) was added. Then the reaction mixture was degassed with nitrogen and allowed to warm to room temperature followed by heating to 40° C. for 3 hours. The reaction mixture was concentrated, and the residue was purified on a reversed-phase Waters HPLC using a Nova-Pak® HR C18, 6 μm 60 Å, 40 mm×100 mm, PrepPak cartridge eluting with a gradient of 10-90% acetonitrile in aqueous 0.1% trifluoroacetic acid (60 mL/minute) to give 0.010 g (24%) of the titled compound as the trifluoroacetic acid salt. $^1$H NMR (400 MHz, DMSO-d$_6$) δ ppm 1.07 (d, J=6.5 Hz, 3H), 1.69-1.81 (m, 2H), 1.84 (s, 1H), 2.40 (d, J=6.7 Hz, 3H), 2.88 (s, 1H), 2.96-3.05 (m, 2H), 6.70 (d, J=10.6 Hz, 1H), 6.86 (d, J=8.5 Hz, 1H), 7.09-7.26 (m, 2H), 7.39 (d, J=6.4 Hz, 2H), 7.53 (d, J=21.4 Hz, 2H), 8.41 (s, 1H); MS (APCI) m/z 538 (M+H)+.

Example 79

(6aS,7S,10aR)-4-[4-(4-bromo-1H-pyrazol-5-yl)phenyl]-10a-(4-methoxyphenyl)-2,7-dimethyl-8-oxo-5,6,6a,7,8,10a-hexahydrobenzo[h]quinazoline-9-carbonitrile

Example 79A (6aS,7S,10aS)-10a-(4-methoxyphenyl)-2,7-dimethyl-4-[4-(1H-pyrazol-5-yl)phenyl]-5,6a,7,9,10,10a-hexahydrobenzo[h]quinazolin-8(6H)-one The titled compound was prepared using the conditions described in Example 17A, substituting (4-(1H-pyrazol-5-yl)phenyl)boronic acid for 1-methyl-5-(4,4,5,5-tetramethyl-1,3,2-dioxaborolan-2-yl)-1H-imidazole and Example 67D for Example 13D. Purification was achieved by flash chromatography on silica gel eluting with 25% acetone in chloroform (58% yield). $^1$H NMR (400 MHz, CDCl$_3$) δ ppm 1.15 (d, J=6.61 Hz, 3H) 1.93-2.11 (m, 3H) 2.26-2.54 (m, 3H) 2.55-2.66 (m, 1H) 2.75 (s, 3H) 2.78-2.86 (m, 1H) 2.88-2.99 (m, 1H) 3.21 (td, J=8.95, 4.55 Hz, 1H) 3.79 (s, 3H) 6.67 (d, J=2.28 Hz, 1H) 6.85 (d, J=8.89 Hz, 2H) 7.46 (d, J=8.89 Hz, 2H) 7.52 (d, J=8.24 Hz, 2H) 7.64 (d, J=2.28 Hz, 1H) 7.84 (d, J=8.13 Hz, 2H); MS (APCI+) m/z 479.5 (M+H)+.

Example 79B (6aS,7S,9Z,10aS)-9-(hydroxymethylene)-10a-(4-methoxyphenyl)-2,7-dimethyl-4-[4-(1H-pyrazol-5-yl)phenyl]-5,6a,7,9,10,10a-hexahydrobenzo[h]quinazolin-8(6H)-one The titled compound was prepared using the conditions described in Example 13F, substituting Example 79A for Example 13E.

Example 79C (6aS,7S,11aS)-11a-(4-methoxyphenyl)-2,7-dimethyl-4-[4-(1H-pyrazol-5-yl)phenyl]-5,6,6a,7,11,11a-hexahydro[1,2]benzoxazolo[6,5-h]quinazoline The titled compound was prepared using the conditions described in Example 13G, substituting Example 79B for Example 13F.

Example 79D (6aS,7S,10aS)-10a-(4-methoxyphenyl)-2,7-dimethyl-8-oxo-4-[4-(1H-pyrazol-5-yl)phenyl]-5,6,6a,7,8,9,10,10a-octahydrobenzo[h]quinazoline-9-carbonitrile The titled compound was prepared using the conditions described in Example 13H, substituting Example 79C for Example 13G. Purification was achieved by flash chromatography on silica gel eluting with 20% acetone in chloroform (67% yield).

Example 79E (6aS,7S,10aR)-4-[4-(4-bromo-1H-pyrazol-5-yl)phenyl]-10a-(4-methoxyphenyl)-2,7-dimethyl-8-oxo-5,6,6a,7,8,10a-hexahydrobenzo[h]quinazoline-9-carbonitrile To a solution of the product from Example 79D (0.060 g, 0.083 mmol) in dimethylformamide (0.6 mL) at 0° C. was added 1,3-dibromo-5,5-dimethylhydantoin (0.019 g, 0.066 mmol). The reaction mixture was stirred at 0° C. for 0.5 hours. Then pyridine (0.067 mL, 0.83 mmol) was added, and the solution was heated at 50° C. for 3.0 hours. After cooling, the reaction mixture was concentrated. The residue was dissolved in ethyl acetate The ethyl acetate mixture was washed with saturated potassium phosphate monobasic and then twice with saturated sodium chloride, dried (MgSO$_4$), and concentrated under reduced pressure. Purification was achieved by preparative thin layer chromatography eluting with 7% methanol in chloroform containing 0.2% ammonium hydroxide to give the titled compound (0.014 g, 25%) as the first eluting compound relative to Example 80. $^1$H NMR (400 MHz, CDCl$_3$) δ ppm 1.17 (d, J=6.61 Hz, 3H) 1.52-1.59 (m, 1H) 1.85-1.94 (m, 1H) 2.33 (td, J=12.85, 2.17 Hz, 1H) 2.46 (td, J=13.09, 6.67 Hz, 1H) 2.74 (s, 3H) 2.99 (dd, J=8.67, 4.55 Hz, 2H) 3.79 (s, 3H) 6.75 (d, J=8.89 Hz, 2H) 6.87 (d, J=9.00 Hz, 2H) 7.63-7.73 (m, 4H) 7.95 (d, J=8.13 Hz, 2H) 8.97 (s, 1H); MS (ESI) m/z 614 (M+H+methanol)$^+$.

Example 80

(6aS,7S,10aR)-10a-(4-methoxyphenyl)-2,7-dimethyl-8-oxo-4-[4-(1H-pyrazol-5-yl)phenyl]-5,6,6a,7,8,10a-hexahydrobenzo[h]quinazoline-9-carbonitrile The titled compound was isolated as the minor product and second eluting compound from the procedure described for Example 79E (0.004 g (8%). $^1$H NMR (400 MHz, CDCl$_3$) δ ppm 1.17 (d, J=6.61 Hz, 3H) 1.47-1.62 (m, J=13.23, 13.23, 9.05, 8.73 Hz, 1H) 1.84-1.93 (m, 1H) 2.28-2.39 (m, 1H) 2.46 (td, J=13.17, 6.61 Hz, 1H) 2.72 (s, 3H) 2.99 (dd, J=8.73, 4.39 Hz, 2H) 3.79 (s, 3H) 6.71-6.78 (m, 3H) 6.83-6.90 (m, 2H) 7.66 (t, J=8.24 Hz, 3H) 7.93 (d, J=8.24 Hz, 2H) 8.97 (s, 1H); MS (ESI) m/z 502 (M+H)$^+$.

Example 81

(6aS,7S,10aR)-4-[4-(4-bromo-1H-pyrazol-5-yl)phenyl]-10a-(4-fluorophenyl)-2,7-dimethyl-8-oxo-5,6,6a,7,8,10a-hexahydrobenzo[h]quinazoline-9-carbonitrile Example 81A (6aS,7S,10aS)-10a-(4-fluorophenyl)-2,7-dimethyl-4-[4-(1H-pyrazol-5-yl)phenyl]-5,6a,7,9,10,10a-hexahydrobenzo[h]quinazolin-8(6H)-one The titled compound was prepared using the conditions described in Example 17A, substituting (4-(1H-pyrazol-5-yl)phenyl)boronic acid for 1-methyl-5-(4,4,5,5-tetramethyl-1,3,2-dioxaborolan-2-yl)-1H-imidazole and Example 68D for Example 13D. Purification was achieved by flash chromatography on silica gel eluting with 15% acetone in chloroform to give the titled compound in 47% yield. $^1$H NMR (400 MHz, CDCl$_3$) δ ppm 1.16 (d, J=6.61 Hz, 3H) 1.96-2.12 (m, 3H) 2.29-2.44 (m, 2H) 2.45-2.64 (m, 2H) 2.69-2.81 (m, 4H) 2.91-3.01 (m, 1H) 3.19 (d, 1H) 6.68 (d, J=2.17 Hz, 1H) 7.01 (t, 2H) 7.48-7.55 (m, 4H) 7.65 (d, J=2.28 Hz, 1H) 7.85 (d, J=8.24 Hz, 2H); MS (APCI+) m/z 467.4 (M+H)$^+$.

Example 81B (6aS,7S,9Z,10aS)-10a-(4-fluorophenyl)-9-(hydroxymethylene)-2,7-dimethyl-4-[4-(1H-pyrazol-5-yl)phenyl]-5,6a,7,9,10,10a-hexahydrobenzo[h]quinazolin-8(6H)-one The titled compound was prepared using the conditions described in Example 13F, substituting Example 81A for Example 13E.

Example 81C

The titled compound was prepared using the conditions described in Example 13G, substituting Example 81B for Example 13F.

Example 81D (6aS,7S,11aS)-11a-(4-fluorophenyl)-2,7-dimethyl-4-[4-(1H-pyrazol-5-yl)phenyl]-5,6,6a,7,11,11a-hexahydro[1,2]benzoxazolo[6,5-h]quinazoline The titled compound was prepared using the conditions described in Example 13H, substituting Example 81C for Example 13G. Purification was achieved by flash chromatography on silica gel eluting with 20% acetone in chloroform to give the titled compound in 69% yield.

Example 81E (6aS,7S,10aR)-4-[4-(4-bromo-1H-pyrazol-5-yl)phenyl]-10a-(4-fluorophenyl)-2,7-dimethyl-8-oxo-5,6,6a,7,8,10a-hexahydrobenzo[h]quinazoline-9-carbonitrile To a solution of the product from Example 81D (0.050 g, 0.081 mmol) in dimethylformamide (0.5 mL) at 0° C. was added 1,3-dibromo-5,5-dimethylhydantoin (0.012 g, 0.059 mmol). The reaction mixture was stirred at 0° C. for 1.0 hour. Pyridine (0.067 mL, 0.83 mmol) was then added, and the solution was heated at 50° C. for 3.0 hours and then concentrated. The residue was dissolved in ethyl acetate. The organic solution was washed with saturated potassium phosphate monobasic then twice with saturated sodium chloride, dried (MgSO4), and concentrated under reduced pressure. The residue was purified by preparative thin layer chromatography eluting with 7% methanol in chloroform containing 0.2% ammonium hydroxide to give the titled compound as the first eluting compound relative to Example 83 to elute in the chromatographic purification (0.010 g, 21%). $^1$H NMR (400 MHz, CDCl$_3$) δ ppm 1.18 (d, J=6.18 Hz, 3H) 1.45-1.53 (m, 1H) 1.88-1.98 (m, 1H) 2.31-2.47 (m, 2H) 2.73 (s, 3H) 2.98-3.05 (m, 2H) 6.83 (dd, J=8.89, 4.99 Hz, 2H) 7.05 (t, J=8.51 Hz, 2H) 7.65-7.73 (m, 3H) 7.98 (d, J=8.13 Hz, 2H) 8.96 (s, 1H); MS (ESI+) m/z 568 (M+H)$^+$.

Example 82

(5aS,6S,9aR)-9a-(4-fluorophenyl)-2-glycyl-6-methyl-7-oxo-4,5,5a,6,7,9a-hexahydro-2H-benzo[g]indazole-8-carbonitrile Example 82A 9H-fluoren-9-ylmethyl {2-[(5aS,6S,9aR)-8-cyano-9a-(4-fluorophenyl)-6-methyl-7-oxo-4,5,5a,6,7,9a-hexahydro-2H-benzo[g]indazol-2-yl]-2-oxoethyl}carbamate The product of Example 54F (0.0194 g, 0.060 mmol) and N-[(9H-fluoren-9-ylmethoxy)carbonyl]glycine (0.0223 g, 0.075 mmol) were combined, and dimethylformamide (0.3 mL) was added. To the solution was added diisopropylethylamine (0.021 mL, 0.120 mmol) and O-(7-azabenzotriazol-1-yl)-N,N,N',N'-tetramethyluronium hexafluorophosphate (0.0302 g, 0.079 mmol), and the solution was stirred at room temperature for 1 hour. The reaction mixture was cooled to 0° C., diluted with acetonitrile, and neutralized with an aqueous solution of hydrochloric acid (2 N, 0.050 mL) and a 0.1% aqueous trifluoroacetic acid. Then this aqueous mixture was purified on a Waters HPLC using a Nova-Pak® HR C18, 6 μm, 60 Å, 40 mm×100 mm, PrepPak cartridge eluted with a gradient of 40-80% CH$_3$CN in 0.1% aqueous trifluoroacetic acid at a flow rate of 60 mL/minute over 12 minutes then hold at 100% CH$_3$CN for 5 minutes to give the titled compound (0.0285 g, 0.047 mmol, 79% yield). $^1$H NMR (400 MHz, CDCl$_3$) δ ppm 1.20 (d, J=6.6 Hz, 3H), 1.45-1.52 (m, 1H), 1.89 (ddd, J=12.6, 9.0, 4.1 Hz, 1H), 2.25-2.34 (m, 1H), 2.43 (dt, J=13.2, 6.5 Hz, 1H), 2.72-2.83 (m, 1H), 2.96 (dd, J=17.1, 6.5 Hz, 1H), 4.22-4.28 (m, 1H), 4.44 (d, J=7.1 Hz, 2H), 4.66-4.83 (m, 2H), 5.34-5.41 (m, 1H), 6.86 (dd, J=8.7, 5.1 Hz, 2H), 7.04 (t, J=8.5 Hz, 2H), 7.37 (dt, J=34.0, 7.4 Hz, 4H), 7.62 (d, J=7.4 Hz, 2H), 7.77 (d, J=7.5 Hz, 2H), 8.14 (s, 1H), 8.38 (s, 1H); MS (ESI+) m/z 600.9 (M+H)$^+$.

Example 82B (5aS,6S,9aR)-9a-(4-fluorophenyl)-2-glycyl-6-methyl-7-oxo-4,5,5a,6,7,9a-hexahydro-2H-benzo[g]indazole-8-carbonitrile The product of Example 82A (0.0287 g, 0.048 mmol) was dissolved in tetrahydrofuran (0.3 mL), methanol (0.15 mL) and water (0.15 mL). The solution was cooled to 0° C. and lithium hydroxide monohydrate (0.0069 g, 0.163 mmol) was added. The mixture was warm to room temperature and stirred for 1 hour. The mixture was then cooled to 0° C., diluted with CH$_3$CN, and neutralized with an aqueous solution of hydrochloric acid (2 N, 0.050 mL) and a 0.1% aqueous trifluoroacetic acid. Then this aqueous mixture was purified on a Nova-Pak® HR C18, 6 μm, 60 Å, 40 mm×100 mm, PrepPak cartridge eluted with a gradient of 40-80% CH$_3$CN in 0.1% aqueous trifluoroacetic acid at a flow rate of 60 mL/minute over 12 minutes then hold at 100% CH$_3$CN for 5 minutes to give the titled compound as a trifluoroacetic acid salt (0.0172 g, 0.033 mmol, 69.2% yield). $^1$H NMR (400 MHz, CDCl$_3$) δ ppm 1.19 (t, J=4.8 Hz, 3H), 1.45-1.57 (m, 1H), 1.82-1.90 (m, 1H), 2.39 (pd, J=13.2, 4.2 Hz, 2H), 2.74 (ddd, J=16.2, 11.7, 6.0 Hz, 1H), 2.92 (dd, J=16.4, 6.5 Hz, 1H), 4.72-5.16 (m, 4H), 6.82-6.87 (m, 2H), 6.97-7.04 (m, 2H), 7.50 (s, 1H), 8.33 (s, 1H); MS (ESI+) m/z 420.1 (M+CH$_3$CN+H)$^+$.

Example 83

(6aS,7S,10aR)-10a-(4-fluorophenyl)-2,7-dimethyl-8-oxo-4-[4-(1H-pyrazol-5-yl)phenyl]-5,6,6a,7,8,10a-hexahydrobenzo[h]quinazoline-9-carbonitrile The titled compound was isolated as a minor product (0.002 g, 5%) from the reaction conditions described in Example 81E and was the more polar compound to elute from the chromatographic purification. $^1$H NMR (400 MHz, CDCl$_3$) δ ppm 1.18 (d, J=6.07 Hz, 3H) 1.46-1.60 (m, 1H) 1.87-1.97 (m, 1H) 2.31-2.46 (m, 2H) 2.72 (s, 3H) 2.97-3.05 (m, 2H) 6.72 (d, J=1.95 Hz, 1H) 6.83 (dd, J=8.89, 4.99 Hz, 2H) 7.05 (t, J=8.46 Hz, 2H) 7.62-7.70 (m, 3H) 7.94 (d, J=8.13 Hz, 2H) 8.96 (s, 1H); MS (ESI+) m/z 522 (M+H+methanol)$^+$.

Example 84

(6aS,7S,10aR)-7-methyl-8-oxo-10a-phenyl-2-(pyrazin-2-yl)-5,6,6a,7,8,10a-hexahydrobenzo[h]quinazoline-9-carbonitrile Example 84A (6aS,7S,10aS)-7-methyl-10a-phenyl-2-(pyrazin-2-yl)-5,6a,7,9,10,10a-hexahydro-6H-spiro[benzo[h]quinazoline-8,2'-[1,3]dioxolane]

To a solution of Example 1G (0.750 g, 2.28 mmol) in isopropanol (20 mL) was added pyrazine-2-carboximidamide hydrochloride (1.09 g, 6.85 mmol) and piperidine (0.678 g, 6.85 mmol). The reaction mixture was heated at 95° C. for 72 hours. The cooled solution was diluted with saturated aqueous NaH$_2$PO$_4$ and extracted with ethyl acetate. The organic fraction was concentrated.

Example 84B (6aS,7S,10aS)-7-methyl-10a-phenyl-2-(pyrazin-2-yl)-5,6a,7,9,10,10a-hexahydrobenzo[h]quinazolin-8(6H)-one The titled compound was prepared using the conditions described in Example 1I, substituting Example 84A for Example 1H.

Example 84C (6aS,7S,9Z,10aS)-9-(hydroxymethylene)-7-methyl-10a-phenyl-2-(pyrazin-2-yl)-5,6a,7,9,10,10a-hexahydrobenzo[h]quinazolin-8(6H)-one The titled compound was prepared using the conditions described in Example 1J, substituting Example 84B for Example 1I. MS (APCI+) m/z 399 (M+H)$^+$.

Example 84D (6aS,7S,11aS)-7-methyl-11a-phenyl-2-(pyrazin-2-yl)-5,6,6a,7,11,11a-hexahydro[1,2]benzoxazolo[6,5-h]quinazoline The titled compound was prepared using the conditions described in Example 1K, substituting Example 84C for Example 1J.

Example 84E (6aS,7S,10aS)-7-methyl-8-oxo-10a-phenyl-2-(pyrazin-2-yl)-5,6,6a,7,8,9,10,10a-octahydrobenzo[h]quinazoline-9-carbonitrile The titled compound was prepared using the conditions described in Example 1L, substituting Example 84D for Example 1K. MS (APCI+) m/z 396 (M+H)$^+$.

Example 84F (6aS,7S,10aR)-7-methyl-8-oxo-10a-phenyl-2-(pyrazin-2-yl)-5,6,6a,7,8,10a-hexahydrobenzo[h]quinazoline-9-carbonitrile To a solution of Example 84E (0.151 g, 0.382 mmol) in dimethylformamide (4 mL) cooled to 0° C. in an ice water bath was added 1,3-dibromo-5,5-dimethylhydantoin (0.060 g, 0.210 mmol). The solution was stirred at 0° C. for 45 minutes, and then pyridine (0.309 mL, 3.82 mmol) was added, and the solution was heated at 55° C. for 1 hour. The cooled solution was diluted with water and extracted with ethyl acetate. The organic phase was washed with brine and concentrated. The residue was purified on a Teledyne Isco Combiflash® Rf using a 12 g RediSep® cartridge. A second chromatography by preparative HPLC on a Waters Sunfire™ C8(2) 5 μm 100 Å column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) gave 0.054 g (36%) of the titled compound. $^1$H NMR (400 MHz, CDCl$_3$) δ ppm 1.22 (d, J=6.61 Hz, 3H) 1.62-1.73 (m, 1H) 2.04 (dd, J=13.82, 7.54 Hz, 1H) 2.40 (td, J=12.82, 2.22 Hz, 1H) 2.52 (td, J=13.12, 6.61 Hz, 1H) 3.06-3.26 (m, 2H) 6.84 (dd, J=7.70, 1.73 Hz, 2H) 7.30-7.38 (m, 3H) 8.69 (d, J=2.39 Hz, 1H) 8.77 (s, 1H) 8.95 (s, 1H) 8.98 (s, 1H) 9.61 (s, 1H); MS (ESI+) m/z 394 (M+H)$^+$.

Example 85

(6aS,7S,10aR)-2-tert-butyl-7-methyl-8-oxo-10a-phenyl-5,6,6a,7,8,10a-hexahydrobenzo[h]quinazoline-9-carbonitrile

Example 85A (6aS,7S,10aS)-2-tert-butyl-7-methyl-10a-phenyl-5,6a,7,9,10,10a-hexahydro-6H-spiro[benzo[h]quinazoline-8,2'-[1,3]dioxolane]

To a solution of Example 1G (0.500 g, 1.52 mmol) in isopropanol (10 mL) was added 2,2-dimethylpropanimidamide hydrochloride (0.458 g, 3.35 mmol) and piperidine (0.332 g, 3.35 mmol). The reaction mixture was heated at 95° C. for 48 hours. The cooled solution was diluted with saturated aqueous NaH$_2$PO$_4$ solution, extracted with ethyl acetate and concentrated. MS (APCI+) m/z 393 (M+H)$^+$.

Example 85B (6aS,7S,10aS)-2-tert-butyl-7-methyl-10a-phenyl-5,6a,7,9,10,10a-hexahydrobenzo[h]quinazolin-8(6H)-one The titled compound was prepared using the conditions described in Example 1I, substituting Example 85A for Example 1H. MS (APCI+) m/z 349 (M+H)$^+$.

Example 85C (6aS,7S,9Z,10aS)-2-tert-butyl-9-(hydroxymethylene)-7-methyl-10a-phenyl-5,6a,7,9,10,10a-hexahydrobenzo[h]quinazolin-8(6H)-one The titled compound was prepared using the conditions described in Example 1J, substituting Example 85B for Example 1I.

Example 85D (6aS,7S,11aS)-2-tert-butyl-7-methyl-11a-phenyl-5,6,6a,7,11,11a-hexahydro[1,2]benzoxazolo[6,5-h]quinazoline The titled compound was prepared using the conditions described in Example 1K, substituting Example 85C for Example 1J.

Example 85E (6aS,7S,10aS)-2-tert-butyl-7-methyl-8-oxo-10a-phenyl-5,6,6a,7,8,9,10,10a-octahydrobenzo[h]quinazoline-9-carbonitrile The titled compound was prepared using the conditions described in Example 1L, substituting Example 85D for Example 1K.

Example 85F (6aS,7S,10aR)-2-tert-butyl-7-methyl-8-oxo-10a-phenyl-5,6,6a,7,8,10a-hexahydrobenzo[h]quinazoline-9-carbonitrile To a solution of Example 85E (0.169 g, 0.452 mmol) in dimethylformamide (5 mL) cooled to 0° C. in an ice water bath was added 1,3-dibromo-5,5-dimethylhydantoin (0.065 g, 0.226 mmol). The solution was stirred at 0° C. for 45 minutes, pyridine (0.366 mL, 4.52 mmol) was added, and the resultant solution was heated at 55° C. for 1 hour. The cooled solution was diluted with water and extracted with ethyl acetate. The organic phase was washed with brine and concentrated. The residue was purified on a Teledyne Isco Combiflash® Rf using a 12 g RediSep® cartridge eluting with 0-40% ethyl acetate in heptane to give 0.106 g (63%) of the titled compound. $^1$H NMR (400 MHz, CDCl$_3$) δ ppm 1.19 (d, J=6.72 Hz, 3H) 1.34 (s, 9H) 1.56-1.65 (m, 1H) 1.89-1.99 (m, 1H) 2.32 (td, J=12.90, 2.49 Hz, 1H) 2.48 (td, J=13.26, 6.89 Hz, 1H) 2.87-3.10 (m, 2H) 6.77 (dd, J=7.48, 2.06 Hz, 2H) 7.29-7.36 (m, 3H) 8.64 (s, 1H) 8.88 (s, 1H); MS (APCI+) m/z 372 (M+H)$^+$.

Example 86

(5aS,6S,9aR)-6-methyl-7-oxo-9a-phenyl-3-(pyridin-3-yl)-4,5,5a,6,7,9a-hexahydro-2H-benzo[g]indazole-8-carbonitrile

Example 86A (5aS,6S,9aS)—N,N,6-trimethyl-9a-phenyl-3-(pyridin-3-yl)-4,5,5a,8,9,9a-hexahydrospiro[benzo[g]indazole-7,2'-[1,3]dioxolane]-2(6H)-sulfonamide Compound 140C (0.035 g, 0.069 mmol), cesium carbonate (0.067 g, 0.206 mmol), and 3-(4,4,5,5-tetramethyl-1,3,2-dioxaborolan-2-yl)pyridine (56.2 mg, 0.274 mmol) were dissolved in dioxane (1.32 mL), and the mixture was sparged with nitrogen for 10 minutes. Tetrakis(triphenylphosphine)palladium(0) (0.079 g, 0.069 mmol) was then added, and the reaction mixture was heated to 100° C. for 1 hour. The reaction mixture was concentrated, and the residue was purified on Biotage® SNAP 10 g silica cartridge using acetone/hexane to give the titled compound (0.018 g 51%). MS (APCI) m/z 509 (M+H)$^+$.

Example 86B (5aS,6S,9aS)-6-methyl-9a-phenyl-3-(pyridin-3-yl)-2,4,5,5a,6,8,9,9a-octahydro-7H-benzo[g]indazol-7-one Compound 86A (0.015 g, 0.029 mmol) was dissolved in tetrahydrofuran (0.295 mL) and 2 M HCl (0.015 mL, 0.029 mmol). The resultant mixture was stirred at room temperature overnight and then heated to 50° C. for another 4 hours. The reaction mixture was neutralized with 1 N Na$_2$CO$_3$ and extracted with ethyl acetate. The organic fraction was dried and concentrated. The titled compound was taken forward without additional purification. MS (ESI) m/z 358 (M+H)$^+$.

Example 86C (5aS,6S,8Z,9aS)-8-(hydroxymethylene)-6-methyl-9a-phenyl-3-(pyridin-3-yl)-2,4,5,5a,6,8,9,9a-octahydro-7H-benzo[g]indazol-7-one The titled compound was prepared using the conditions described in Example 24C substituting Example 24B with Example 86B.

Example 86D (5aS,6S,10aS)-6-methyl-10a-phenyl-3-(pyridin-3-yl)-4,5,5a,6,10,10a-hexahydro-2H-indazolo[7,6-f][1,2]benzoxazole The titled compound was prepared using the conditions described in Example 24D substituting Example 24C with Example 86C. MS (ESI) m/z 383 (M+H)$^+$.

Example 86E (5aS,6S,9aS)-6-methyl-7-oxo-9a-phenyl-3-(pyridin-3-yl)-4,5,5a,6,7,8,9,9a-octahydro-2H-benzo[g]indazole-8-carbonitrile The titled compound was prepared using the conditions described in Example 24E substituting Example 24D with Example 86D.

Example 86F (5aS,6S,9aR)-6-methyl-7-oxo-9a-phenyl-3-(pyridin-3-yl)-4,5,5a,6,7,9a-hexahydro-2H-benzo[g]indazole-8-carbonitrile The product from Example 86E (0.003 g, 7.84 mol) was dissolved in tetrahydrofuran (0.078 mL) and sparged with nitrogen for 10 minutes. 2,3-Dichloro-5,6-dicyano-1,4-benzoquinone (0.001 g, 7.84 mol) was added, and nitrogen bubbling was continued for 10 minutes. The reaction mixture was concentrated, and the residue was purified on a reversed-phase Waters HPLC using a Nova-Pak® HR C18, 6 μm, 60 Å, 40 mm×100 mm, PrepPak cartridge eluting with a gradient of 10-90% acetonitrile in aqueous 0.1% trifluoroacetic acid (60 mL/minute) to give the titled compound as the trifluoroacetic acid salt (0.002 g, 66%). $^1$H NMR (400 MHz, DMSO-d$_6$) δ ppm 1.07 (d, J=6.7 Hz, 3H), 1.41 (dt, J=19.1, 13.0 Hz, 1H), 1.84 (dd, J=13.2, 6.9 Hz, 1H), 2.35 (dt, J=10.8, 5.4 Hz, 1H), 2.83-2.95 (m, 2H), 3.02 (dd, J=16.2, 6.3 Hz, 2H), 6.96 (d, J=7.3 Hz, 2H), 7.33 (dq, J=14.1, 7.0 Hz, 3H), 7.62 (dd, J=7.7, 5.1 Hz, 1H), 8.23 (s, 1H), 8.45 (s, 1H), 8.61 (d, J=4.3 Hz, 1H), 8.99 (s, 1H); MS (ESI+) m/z 381 (M+H)$^+$.

Example 87

(5aS,6S,9aR)-6-methyl-7-oxo-9a-phenyl-3-(pyrimidin-5-yl)-4,5,5a,6,7,9a-hexahydro-2H-benzo[g]indazole-8-carbonitrile

Example 87A (5aS,6S,9aS)—N,N,6-trimethyl-9a-phenyl-3-(pyrimidin-5-yl)-4,5,5a, 8,9,9a-hexahydrospiro[benzo[g]indazole-7,2'-[1,3]dioxolane]-2(6H)-sulfonamide The titled compound was prepared using the conditions described in Example 86A substituting 3-(4,4,5,5-tetramethyl-1,3,2-dioxaborolan-2-yl)pyridine with 5-(4,4,5,5-tetramethyl-1,3,2-dioxaborolan-2-yl)pyrimidine.

Example 87B (5aS,6S,9aS)-6-methyl-9a-phenyl-3-(pyrimidin-5-yl)-2,4,5,5a,6,8,9,9a-octahydro-7H-benzo[g]indazol-7-one The product from Example 87A (1.9 g, 3.73 mmol) was dissolved in dichloromethane (37.3 mL) and treated with trifluoroacetic acid (17.23 mL, 224 mmol). The reaction mixture was stirred at room temperature overnight and then concentrated. The residue was purified on a Biotage® SNAP 100 g silica cartridge using 0-50% acetone/hexane to give 1.1 g of the titled compound (82% yield) $^1$H NMR (400 MHz, CDCl$_3$) δ ppm 1.17 (d, J=6.8 Hz, 3H), 1.86-2.03 (m, 1H), 2.05-2.16 (m, 2H), 2.19-2.29 (m, 1H), 2.41-2.52 (m, 1H), 2.73-2.83 (m, 2H), 2.84-3.11 (m, 3H), 7.16-7.26 (m, 3H), 7.30 (q, J=7.2 Hz, 2H), 9.11-9.19 (m, 2H), 9.21 (d, J=9.4 Hz, 1H); MS (ESI) m/z 359 (M+H)$^+$.

Example 87C (5aS,6S,8Z,9aS)-8-(hydroxymethylene)-6-methyl-9a-phenyl-3-(pyrimidin-5-yl)-2,4,5,5a,6,8,9,9a-octahydro-7H-benzo[g]indazol-7-one The titled compound was prepared using the conditions described in Example 24C substituting Example 24B with Example 87B.

Example 87D (5aS,6S,10aS)-6-methyl-10a-phenyl-3-(pyrimidin-5-yl)-4,5,5a,6,10,10a-hexahydro-2H-indazolo[7,6-][1,2]benzoxazole The titled compound was prepared using the conditions described in Example 24D substituting Example 24C with Example 87C.

Example 87E (5aS,6S,9aS)-6-methyl-7-oxo-9a-phenyl-3-(pyrimidin-5-yl)-4,5,5a,6,7,8,9,9a-octahydro-2H-benzo[g]indazole-8-carbonitrile The titled compound was prepared using the conditions described in Example 24E substituting Example 24D with Example 87D.

Example 87F (5aS,6S,9aR)-6-methyl-7-oxo-9a-phenyl-3-(pyrimidin-5-yl)-4,5,5a,6,7,9a-hexahydro-2H-benzo[g]indazole-8-carbonitrile The product from Example 87E (0.048 g, 0.125 mmol) was dissolved in tetrahydrofuran (1.25 mL) and sparged with nitrogen for 10 minutes. 2,3-Dichloro-5,6-dicyano-1,4-benzoquinone (0.028 g, 0.125 mmol) was added, and sparging was continued for 15 minutes. The reaction mixture was concentrated, and the residue was purified on a reversed-phase Waters HPLC using a Nova-Pak® HR C18, 6 μm, 60 Å, 40 mm×100 mm, PrepPak cartridge eluting with a gradient of 10-90% acetonitrile in aqueous 0.1% trifluoroacetic acid (60 mL/minute) to give the titled compound as the trifluoroacetic acid salt (0.024 g, 51%). $^1$H NMR (400 MHz, DMSO-$d_6$) δ ppm 1.07 (d, J=6.7 Hz, 3H), 1.42 (d, J=6.5 Hz, 1H), 1.84 (dd, J=13.3, 7.4 Hz, 1H), 2.35 (d, J=6.7 Hz, 1H), 2.91 (dd, J=23.4, 11.9 Hz, 1H), 3.05 (dd, J=16.4, 6.7 Hz, 2H), 6.97 (d, J=7.2 Hz, 2H), 7.33 (dq, J=14.0, 6.9 Hz, 3H), 8.45 (s, 1H), 9.16 (d, J=8.2 Hz, 3H); MS (ESI+) m/z 382 (M+H)$^+$.

Example 88

(5aS,6S,9aR)-3-(3-hydroxyphenyl)-6-methyl-7-oxo-9a-phenyl-4,5,5a,6,7,9a-hexahydro-2H-benzo[g]indazole-8-carbonitrile Example 88A (5aS,6S,9aS)-3-(3-hydroxyphenyl)-N,N,6-trimethyl-9a-phenyl-4,5,5a,8,9,9a-hexahydrospiro[benzo[g]indazole-7,2'-[1,3]dioxolane]-2(6H)-sulfonamide The titled compound was prepared using the conditions described in Example 86A substituting 3-(4,4,5,5-tetramethyl-1,3,2-dioxaborolan-2-yl)pyridine with (3-hydroxyphenyl)boronic acid. MS (ESI) m/z 524 (M+H)$^+$.

Example 88B (5aS,6S,9aS)-3-(3-hydroxyphenyl)-6-methyl-9a-phenyl-2,4,5,5a,6,8,9,9a-octahydro-7H-benzo[g]indazol-7-one The titled compound was prepared using the conditions described in Example 86B substituting Example 86A with Example 88A.

Example 88C (5aS,6S,8Z,9aS)-8-(hydroxymethylene)-3-(3-hydroxyphenyl)-6-methyl-9a-phenyl-2,4,5,5a,6,8,9,9a-octahydro-7H-benzo[g]indazol-7-one The titled compound was prepared using the conditions described in Example 24C substituting Example 24B with Example 88B. MS (ESI) m/z 401 (M+H)$^+$.

Example 88D

3-[(5aS,6S,10aS)-6-methyl-10a-phenyl-4,5,5a,6,10,10a-hexahydro-2H-indazolo[7,6-f][1,2]benzoxazol-3-yl]phenol The titled compound was prepared using the conditions described in Example 24D substituting Example 24C with Example 88D.

Example 88E (5aS,6S,9aS)-3-(3-hydroxyphenyl)-6-methyl-7-oxo-9a-phenyl-4,5,5a,6,7,8,9,9a-octahydro-2H-benzo[g]indazole-8-carbonitrile The titled compound was prepared using the conditions described in Example 24E substituting Example 24D with Example 88D. MS (APCI) m/z 398 (M+H)$^+$.

Example 88F (5aS,6S,9aR)-3-(3-hydroxyphenyl)-6-methyl-7-oxo-9a-phenyl-4,5,5a,6,7,9a-hexahydro-2H-benzo[g]indazole-8-carbonitrile The product of Example 88E (0.035 g, 0.088 mmol) was dissolved in tetrahydrofuran (0.88 mL) and sparged with nitrogen for 10 minutes. 2,3-Dichloro-5,6-dicyano-1,4-benzoquinone (0.019 g, 0.088 mmol) was added, and the reaction mixture was stirred at room temperature with sparging for 20 minutes. The reaction mixture was concentrated, and the residue was purified on a reversed-phase Waters HPLC using a Nova-Pak® HR C18, 6 μm 60 Å, 40 mm×100 mm, PrepPak cartridge eluting with a gradient of 10-90% acetonitrile in aqueous 0.1% trifluoroacetic acid (60 mL/minute) to give the titled compound as the trifluoroacetic acid salt (0.004 g, 11%). $^1$H NMR (400 MHz, DMSO-$d_6$) δ ppm 1.06 (d, J=6.6 Hz, 3H), 1.30-1.48 (m, 1H), 1.75-1.87 (m, 1H), 2.33-2.37 (m, 1H), 2.79-2.88 (m, 1H), 2.93 (d, J=6.5 Hz, 1H), 6.76 (d, J=7.0 Hz, 1H), 6.95 (d, J=7.2 Hz, 2H), 7.14 (d, J=8.2 Hz, 2H), 7.23-7.39 (m, 4H), 8.43 (s, 1H); MS (ESI+) m/z 396 (M+H)$^+$.

Example 89

(5aS,6S,9aR)-6-methyl-3-(1-methyl-1H-pyrazol-4-yl)-7-oxo-9a-phenyl-4,5,5a,6,7,9a-hexahydro-2H-benzo[g]indazole-8-carbonitrile Example 89A (5aS,6S,9aS)—N,N,6-trimethyl-3-(1-methyl-1H-pyrazol-4-yl)-9a-phenyl-4,5,5a,8,9,9a-hexahydrospiro[benzo[g]indazole-7,2'-[1,3]dioxolane]-2(6H)-sulfonamide The titled compound was prepared using the conditions described in Example 86A substituting 3-(4,4,5,5-tetramethyl-1,3,2-dioxaborolan-2-yl)pyridine with 56A. 1-methyl-4-(4,4,5,5-tetramethyl-1,3,2-dioxaborolan-2-yl)-1H-pyrazole. MS (ESI) m/z 512 (M+H)$^+$.

Example 89B (5aS,6S,9aS)-6-methyl-3-(1-methyl-1H-pyrazol-4-yl)-9a-phenyl-2,4,5,5a,6,8,9,9a-octahydro-7H-benzo[g]indazol-7-one The titled compound was prepared using the conditions described in Example 86B substituting Example 86A with Example 89A.

Example 89C (5aS,6S,8Z,9aS)-8-(hydroxymethylene)-6-methyl-3-(1-methyl-1H-pyrazol-4-yl)-9a-phenyl-2,4,5,5a,6,8,9,9a-octahydro-7H-benzo[g]indazol-7-one The titled compound was prepared using the conditions described in Example 24C substituting Example 24B with Example 89B.

Example 89D (5aS,6S,10aS)-6-methyl-3-(1-methyl-1H-pyrazol-4-yl)-10a-phenyl-4,5,5a,6,10,10a-hexahydro-2H-indazolo[7,6-f][1,2]benzoxazole The titled compound was prepared using the conditions described in Example 24D substituting Example 24C with Example 89C. MS (ESI) m/z 386 (M+H)+.

Example 89E (5aS,6S,9aS)-6-methyl-3-(1-methyl-1H-pyrazol-4-yl)-7-oxo-9a-phenyl-4,5,5a,6,7,8,9,9a-octahydro-2H-benzo[g]indazole-8-carbonitrile The titled compound was prepared using the conditions described in Example 24E substituting Example 24D with Example 89D.

Example 89F (5aS,6S,9aR)-6-methyl-3-(1-methyl-1H-pyrazol-4-yl)-7-oxo-9a-phenyl-4,5,5a,6,7,9a-hexahydro-2H-benzo[g]indazole-8-carbonitrile The product from Example 89E (0.060 g, 0.156 mmol) was dissolved in tetrahydrofuran (1.56 mL) and sparged with nitrogen for 10 minutes. 2,3-Dichloro-5,6-dicyano-1,4-benzoquinone (0.035 g, 0.156 mmol) was added, and the reaction mixture was stirred at room temperature with continued sparging for 10 minutes. The reaction mixture was concentrated, and the residue was purified on a reversed-phase Waters HPLC using a Nova-Pak® HR C18, 6 μm 60 Å, 40 mm×100 mm, PrepPak cartridge eluting with a gradient of 10-90% acetonitrile in aqueous 0.1% trifluoroacetic acid (60 mL/minute) to give the titled compound as the trifluoroacetic acid salt (0.030 g 50%). $^1$H NMR (400 MHz, CDCl$_3$) δ ppm 1.04 (d, J=6.1 Hz, 3H), 2.05 (s, 3H), 6.85 (s, 2H), 7.17 (s, 4H), 7.88 (d, J=8.9 Hz, 1H), 8.07 (s, 1H), 8.31 (s, 1H), 8.61 (d, J=8.3 Hz, 2H); MS (ESI+) m/z 442 (M+CH$_3$CN+NH$_4$)+.

Example 90

(6aS,7S,10aR)-4-(1H-benzimidazol-5-yl)-10a-(4-methoxyphenyl)-2,7-dimethyl-8-oxo-5,6,6a,7,8,10a-hexahydrobenzo[h]quinazoline-9-carbonitrile

Example 90A (6aS,7S,10aS)-4-(1H-benzimidazol-5-yl)-10a-(4-methoxyphenyl)-2,7-dimethyl-5,6a,7,9,10,10a-hexahydrobenzo[h]quinazolin-8(6H)-one The titled compound was prepared using the conditions described in Example 17A, substituting 5-(4,4,5,5-tetramethyl-1,3,2-dioxaborolan-2-yl)-1H-benzo[d]imidazole for 1-methyl-5-(4,4,5,5-tetramethyl-1,3,2-dioxaborolan-2-yl)-1H-imidazole and Example 67D for Example 13D. Purification was achieved by flash chromatography on silica gel eluting with 33-75% acetone in heptane to give the titled compound in 93% yield. $^1$H NMR (400 MHz, CDCl$_3$) δ ppm 1.15 (d, J=6.61 Hz, 3H) 1.94-2.13 (m, 3H) 2.29-2.54 (m, 3H) 2.55-2.67 (m, 1H) 2.76 (s, 3H) 2.78-2.86 (m, 1H) 2.96 (ddd, J=16.26, 6.72, 6.61 Hz, 1H) 3.22 (td, J=8.70, 4.39 Hz, 1H) 3.80 (s, 3H) 6.85 (d, J=8.89 Hz, 2H) 7.39 (s, 1H) 7.47 (d, J=8.78 Hz, 2H) 7.74 (s, 2H) 8.07 (s, 1H); MS (ESI) m/z 453.3 (M+H)+.

Example 90B (6aS,7S,9Z,10aS)-4-(1H-benzimidazol-5-yl)-9-(hydroxymethylene)-10a-(4-methoxyphenyl)-2,7-dimethyl-5,6a,7,9,10,10a-hexahydrobenzo[h]quinazolin-8(6H)-one The titled compound was prepared using the conditions described in Example 13F, substituting Example 90A for Example 13E.

Example 90C (6aS,7S,11aS)-4-(1H-benzimidazol-5-yl)-11a-(4-methoxyphenyl)-2,7-dimethyl-5,6,6a,7,11,11a-hexahydro[1,2]benzoxazolo[6,5-h]quinazoline The titled compound was prepared using the conditions described in Example 13G, substituting Example 90B for Example 13F.

Example 90D (6aS,7S,10aS)-4-(1H-benzimidazol-5-yl)-10a-(4-methoxyphenyl)-2,7-dimethyl-8-oxo-5,6,6a,7,8,9,10,10a-octahydrobenzo[h]quinazoline-9-carbonitrile The titled compound was prepared using the conditions described in Example 13H, substituting Example 90C for Example 13G.

Example 90E (6aS,7S,10aR)-4-(1H-benzimidazol-5-yl)-10a-(4-methoxyphenyl)-2,7-dimethyl-8-oxo-5,6,6a,7,8,10a-hexahydrobenzo[h]quinazoline-9-carbonitrile The titled compound was prepared using the conditions described in Example 131, substituting Example 90D for Example 13H. Purification was done on a preparative HPLC on a Waters Sunfire™ C8(2) 5 μm 100 Å column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to afford the titled compound as the trifluoroacetic acid salt. The trifluoroacetic acid salt was taken up in dichloromethane (4 mL), and the mixture was washed with aqueous saturated sodium bicarbonate solution. The organic fraction was then dried over magnesium sulfate, filtered, and concentrated under vacuum to give the titled compound in 19% yield. $^1$H NMR (400 MHz, CDCl$_3$) δ ppm 1.16 (d, J=6.61 Hz, 3H) 1.47-1.59 (m, 1H) 1.83-1.92 (m, 1H) 2.34 (td, J=12.77, 2.22 Hz, 1H) 2.46 (td, J=13.07, 6.51 Hz, 1H) 2.72 (s, 3H) 3.00 (dd, J=8.73, 4.50 Hz, 2H) 3.79 (s, 3H) 6.77 (d, J=8.89 Hz, 2H) 6.84-6.90 (m, 2H) 7.52 (d, J=8.46 Hz, 1H) 7.77 (s, 1H) 7.91 (s, 1H) 8.15 (s, 1H) 8.99 (s, 1H); MS (ESI+) m/z 476 (M+H)+.

Example 91

(6aS,7S,10aR)-4-(1H-benzimidazol-5-yl)-10a-(4-fluorophenyl)-2,7-dimethyl-8-oxo-5,6,6a,7,8,10a-hexahydrobenzo[h]quinazoline-9-carbonitrile

Example 91A (6aS,7S,10aS)-4-(1H-benzimidazol-5-yl)-10a-(4-fluorophenyl)-2,7-dimethyl-5,6a,7,9,10,10a-hexahydrobenzo[h]quinazolin-8(6H)-one The titled compound was prepared using the conditions described in Example 17A, substituting 5-(4,4,5,5-tetramethyl-1,3,2-dioxaborolan-2-yl)-1H-benzo[d]imidazole for 1-methyl-5-(4,4,5,5-tetramethyl-1,3,2-dioxaborolan-2-yl)-1H-imidazole and Example 68D for Example 13D. Purification by flash chromatography on silica gel eluting with 50-80% acetone in heptane gave the titled compound in 64% yield. $^1$H NMR (400 MHz, CDCl$_3$) δ ppm 1.16 (d, J=6.61 Hz, 3H) 1.99-2.11 (m, 3H) 2.31-2.44 (m, 2H) 2.49-2.66 (m, 2H) 2.73-2.80 (m, 4H) 2.92-3.03 (m, 1H) 3.20 (td, J=7.97, 3.80 Hz, 1H) 7.02 (t, J=8.67 Hz, 2H) 7.38 (d, J=8.02 Hz, 1H) 7.53 (dd, J=8.89, 5.20 Hz, 2H) 7.69 (s, 1H) 7.77 (s, 1H) 8.05 (s, 1H); MS (ESI) m/z 441.3 (M+H)$^+$.

Example 91B (6aS,7S,9Z,10aS)-4-(1H-benzimidazol-5-yl)-10a-(4-fluorophenyl)-9-(hydroxymethylene)-2,7-dimethyl-5,6a,7,9,10,10a-hexahydrobenzo[h]quinazolin-8(6H)-one The titled compound was prepared using the conditions described in Example 13F, substituting Example 91A for Example 13E.

Example 91C (6aS,7S,11aS)-4-(1H-benzimidazol-5-yl)-11a-(4-fluorophenyl)-2,7-dimethyl-5,6,6a,7,11,11a-hexahydro[1,2]benzoxazolo[6,5-h]quinazoline The titled compound was prepared using the conditions described in Example 13G, substituting Example 91B for Example 13F.

Example 91D (6aS,7S,10aS)-4-(1H-benzimidazol-5-yl)-10a-(4-fluorophenyl)-2,7-dimethyl-8-oxo-5,6,6a,7,8,9,10,10a-octahydrobenzo[h]quinazoline-9-carbonitrile The titled compound was prepared using the conditions described in Example 13H, substituting Example 91C for Example 13G.

Example 91E (6aS,7S,10aR)-4-(1H-benzimidazol-5-yl)-10a-(4-fluorophenyl)-2,7-dimethyl-8-oxo-5,6,6a,7,8,10a-hexahydrobenzo[h]quinazoline-9-carbonitrile The titled compound was prepared using the conditions described in Example 131, substituting Example 91D for Example 13H. Purification was done by preparative HPLC on a Waters Sunfire™ C8(2) 5 μm 100 Å column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to afford the trifluoroacetic acid salt. The trifluoroacetic acid salt was taken up in dichloromethane (4 mL) and washed with aqueous saturated sodium bicarbonate solution (5 mL). The organic fraction was then dried over magnesium sulfate, filtered, and concentrated under vacuum to give the titled compound in 11% yield. MS (ESI+) m/z 496 (M+H+methanol)$^+$.

Example 92

(6aS,7S,10aR)-4-(3-bromo-1H-indazol-7-yl)-10a-(4-fluorophenyl)-2,7-dimethyl-8-oxo-5,6,6a,7,8,10a-hexahydrobenzo[h]quinazoline-9-carbonitrile

Example 92A (6aS,7S,10aS)-10a-(4-fluorophenyl)-4-(1H-indazol-7-yl)-2,7-dimethyl-5,6a,7,9,10,10a-hexahydrobenzo[h]quinazolin-8(6H)-one The titled compound was prepared using the conditions described in Example 17A, substituting (1H-indazol-7-yl) boronic acid for 1-methyl-5-(4,4,5,5-tetramethyl-1,3,2-dioxaborolan-2-yl)-1H-imidazole and Example 68D for Example 13D. Purification was achieved by flash chromatography on silica gel eluting with 20-33% acetone in heptane to give the titled compound in 100% yield. $^1$H NMR (400 MHz, CDCl$_3$) δ ppm 1.17 (d, J=6.51 Hz, 3H) 1.97-2.15 (m, 3H) 2.36-2.43 (m, 2H) 2.48-2.55 (m, 1H) 2.68-2.83 (m, 2H) 2.81 (s, 3H) 3.15-3.29 (m, 2H) 7.02 (t, J=8.62 Hz, 2H) 7.21 (t, J=7.70 Hz, 1H) 7.46-7.55 (m, 3H) 7.85 (d, J=8.02 Hz, 1H) 8.14 (s, 1H) 11.30 (s, 1H); MS (ESI) m/z 441.3 (M+H)$^+$.

Example 92B (6aS,7S,9Z,10aS)-10a-(4-fluorophenyl)-9-(hydroxymethylene)-4-(1H-indazol-7-yl)-2,7-dimethyl-5,6a,7,9,10,10a-hexahydrobenzo[h]quinazolin-8(6H)-one The titled compound was prepared using the conditions described in Example 13F, substituting Example 92A for Example 13E.

Example 92C (6aS,7S,11aS)-11a-(4-fluorophenyl)-4-(1H-indazol-7-yl)-2,7-dimethyl-5,6,6a,7,11,11a-hexahydro[1,2]benzoxazolo[6,5-h]quinazoline The titled compound was prepared using the conditions described in Example 13G, substituting Example 92B for Example 13F.

Example 92D (6aS,7S,10aS)-10a-(4-fluorophenyl)-4-(1H-indazol-7-yl)-2,7-dimethyl-8-oxo-5,6,6a,7,8,9,10,10a-octahydrobenzo[h]quinazoline-9-carbonitrile The titled compound was prepared using the conditions described in Example 13H, substituting Example 92C for Example 13G.

Example 92E (6aS,7S,10aR)-4-(3-bromo-1H-indazol-7-yl)-10a-(4-fluorophenyl)-2,7-dimethyl-8-oxo-5,6,6a,7,8,10a-hexahydrobenzo[h]quinazoline-9-carbonitrile The titled compound was prepared using the conditions described in Example 131, substituting Example 92D for Example 13H. Purification was achieved by flash chromatography on silica gel eluting with 20% acetone in heptane to give the titled compound as the first to elute compound relative to Example 93 in 12% yield. $^1$H NMR (400 MHz, CDCl$_3$) δ ppm 1.21 (d, J=5.96 Hz, 3H) 1.59-1.67 (m, 1H) 2.03 (dd, J=14.10, 7.05 Hz, 1H) 2.37-2.47 (m, 2H) 2.79 (s, 3H) 3.21-3.38 (m, 2H) 6.81 (dd, J=8.89, 4.99 Hz, 2H) 7.03 (t, J=8.46 Hz, 2H) 7.36 (t, J=7.70 Hz, 1H) 7.82 (d, J=8.02 Hz, 1H) 7.93 (d, J=7.37 Hz, 1H) 8.95 (s, 1H) 11.52 (s, 1H); MS (ESI+) m/z 574 (M+H+methanol)+.

Example 93

(6aS,7S,10aR)-10a-(4-fluorophenyl)-4-(1H-indazol-7-yl)-2,7-dimethyl-8-oxo-5,6,6a,7,8,10a-hexahydrobenzo[h]quinazoline-9-carbonitrile The titled compound was isolated from the chromatography in Example 92E as the second compound to elute in 33% yield. $^1$H NMR (400 MHz, CDCl$_3$) δ ppm 1.21 (d, J=6.07 Hz, 3H) 1.59-1.64 (m, 1H) 2.02 (dd, J=14.04, 7.21 Hz, 1H) 2.37-2.47 (m, 2H) 2.79 (s, 3H) 3.21-3.39 (m, 2H) 6.81 (dd, J=9.00, 4.99 Hz, 2H) 7.03 (t, J=8.51 Hz, 2H) 7.30 (t, J=7.70 Hz, 1H) 7.85 (d, J=7.37 Hz, 1H) 7.94 (d, J=8.02 Hz, 1H) 8.20 (s, 1H) 8.97 (s, 1H) 11.50 (s, 1H); MS (ESI+) m/z 464 (M+H)+.

Example 94

(6aS,7S,10aR)-4-(2,4-dioxo-1,2,3,4-tetrahydropyrimidin-5-yl)-10a-(4-fluorophenyl)-2,7-dimethyl-8-oxo-5,6,6a,7,8,10a-hexahydrobenzo[h]quinazoline-9-carbonitrile

Example 94A

5-[(6aS,7S,10aS)-10a-(4-fluorophenyl)-2,7-dimethyl-8-oxo-5,6,6a,7,8,9,10,10a-octahydrobenzo[h]quinazolin-4-yl]pyrimidine-2,4(1H,3H)-dione The titled compound was prepared using the conditions described in Example 17A, substituting (2,4-di-tert-butoxypyrimidin-5-yl)boronic acid for 1-methyl-5-(4,4,5,5-tetramethyl-1,3,2-dioxaborolan-2-yl)-1H-imidazole and Example 68D for Example 13D.

Purification was achieved by flash chromatography on silica gel eluting with 33-66% acetone in heptane to give the titled compound in 74% yield. $^1$H NMR (400 MHz, CDCl$_3$) δ ppm 1.16 (d, J=6.61 Hz, 3H) 1.99-2.16 (m, 3H) 2.19-2.32 (m, 1H) 2.34-2.44 (m, 1H) 2.47-2.60 (m, 2H) 2.63-2.70 (m, 1H) 2.69 (s, 3H) 2.74-2.85 (m, 1H) 3.15-3.25 (m, 1H) 6.98 (t, J=8.62 Hz, 2H) 7.46 (dd, J=8.89, 5.20 Hz, 2H) 7.55 (d, J=5.20 Hz, 1H); MS (ESI) m/z 435.3 (M+H)+.

Example 94B

5-[(6aS,7S,9Z,10aS)-10a-(4-fluorophenyl)-9-(hydroxymethylene)-2,7-dimethyl-8-oxo-5,6,6a,7,8,9,10,10a-octahydrobenzo[h]quinazolin-4-yl]pyrimidine-2,4(1H,3H)-dione The titled compound was prepared using the conditions described in Example 13F, substituting Example 94A for Example 13E.

Example 94C

5-[(6aS,7S,11aS)-11a-(4-fluorophenyl)-2,7-dimethyl-5,6,6a,7,11,11a-hexahydro[1,2]benzoxazolo[6,5-h]quinazolin-4-yl]pyrimidine-2,4(1H,3H)-dione The titled compound was prepared using the conditions described in Example 13G, substituting Example 94B for Example 13F.

Example 94D (6aS,7S,10aS)-4-(2,4-dioxo-1,2,3,4-tetrahydropyrimidin-5-yl)-10a-(4-fluorophenyl)-2,7-dimethyl-8-oxo-5,6,6a,7,8,9,10,10a-octahydrobenzo[h]quinazoline-9-carbonitrile The titled compound was prepared using the conditions described in Example 13H, substituting Example 94C for Example 13G.

Example 94E (6aS,7S,10aR)-4-(2,4-dioxo-1,2,3,4-tetrahydropyrimidin-5-yl)-10a-(4-fluorophenyl)-2,7-dimethyl-8-oxo-5,6,6a,7,8,10a-hexahydrobenzo[h]quinazoline-9-carbonitrile The titled compound was prepared using the conditions described in Example 131, substituting Example 94D for Example 13H. Purification was achieved by preparative thin layer chromatography eluting with 10% methanol in chloroform containing 0.2% ammonium hydroxide to give the titled compound in 48% yield. $^1$H NMR (400 MHz, CDCl$_3$) δ ppm 1.17 (d, J=6.18 Hz, 3H) 1.51-1.56 (m, 1H) 1.88-1.97 (m, 1H) 2.27-2.44 (m, 2H) 2.68 (s, 3H) 2.93-3.04 (m, 2H) 5.43 (s, 1H) 6.83 (dd, J=8.89, 4.99 Hz, 2H) 7.04 (t, J=8.51 Hz, 2H) 7.63 (s, 1H) 7.66 (s, 1H) 8.91 (s, 1H); MS (ESI+) m/z 458 (M+H)+.

Example 95

3-[(6aS,7S,10aR)-9-cyano-7-methyl-8-oxo-6,6a,7,8-tetrahydrobenzo[h]quinazolin-10a(5H)-yl]-N-phenylbenzamide To a solution of Example 60 (0.057 g, 0.159 mmol) in dimethylacetamide (2 mL) was added aniline (0.022 mL, 0.238 mmol), Hunig's base (0.042 mL, 0.238 mmol), and bis(dimethylamino)(3-oxido-1H-benzotriazol-1-yl)methylium hexafluorophosphate (HATU, 0.066 g, 0.174 mmol). The reaction mixture was stirred at room temperature for 24 hours, then diluted with water, and extracted with ethyl acetate. The organic fraction was concentrated, and the residue was purified by Teledyne Isco Combiflash® Rf on a 12 g RediSep® cartridge, eluting with 0-50% ethyl acetate in heptane to give 0.032 g (42%) of the titled compound. $^1$H NMR (400 MHz, CDCl$_3$) δ ppm 1.20 (d, J=6.18 Hz, 3H) 1.62-1.71 (m, 1H) 1.99-2.04 (m, 1H) 2.37-2.43 (m, 2H) 3.03-3.12 (m, 1H) 3.15-3.24 (m, 1H) 7.12 (dd, J=8.13, 1.63 Hz, 1H) 7.17 (t, J=7.43 Hz, 1H) 7.30 (s, 1H) 7.37 (t, J=7.97 Hz, 2H) 7.49 (t, J=7.86 Hz, 1H) 7.55 (d, J=7.70 Hz, 2H) 7.63

(s, 1H) 7.70 (d, J=8.24 Hz, 1H) 8.74 (s, 1H) 8.87 (s, 1H) 9.08 (s, 1H); MS ((ESI+) m/z 435 (M+H)+.

Example 96

3-[(6aS,7S,10aR)-9-cyano-7-methyl-8-oxo-6,6a,7,8-tetrahydrobenzo[h]quinazolin-10a(5H)-yl]-N-propyl-benzamide To a solution of Example 60 (0.06 g, 0.167 mmol) in dimethylacetamide (2 mL) was added propylamine (0.021 mL, 0.250 mmol), Hunig's base (0.073 mL, 0.417 mmol), and bis(dimethylamino)(3-oxido-1H-benzotriazol-1-yl)methylium hexafluorophosphate (HATU, 0.070 g, 0.184 mmol). The reaction mixture was stirred at room temperature for 24 hours, then diluted with saturated aqueous sodium phosphate monobasic solution, and extracted with ethyl acetate. The organic fraction was concentrated, and the residue was purified using a Teledyne Isco Combiflash® Rf with a 12 g RediSep® cartridge, eluting with 0-90% ethyl acetate in heptane to give 0.043 g (64%) of the titled compound. $^1$H NMR (400 MHz, CDCl$_3$) δ ppm 0.96 (t, J=7.43 Hz, 3H) 1.19 (d, J=6.07 Hz, 3H) 1.57-1.72 (m, 3H) 2.00 (dd, J=13.50, 7.21 Hz, 1H) 2.31-2.44 (m, 2H) 2.98-3.11 (m, 1H) 3.13-3.23 (m, 1H) 3.33-3.41 (m, 2H) 5.95-6.01 (m, 1H) 7.02 (dd, J=7.92, 1.63 Hz, 1H) 7.23 (s, 1H) 7.40 (t, J=7.86 Hz, 1H) 7.57 (d, J=7.70 Hz, 1H) 8.73 (s, 1H) 8.85 (s, 1H) 9.06 (s, 1H); MS (ESI+) m/z 401 (M+H)+.

Example 97

(5aS,6S,9aR)-2,6-dimethyl-7-oxo-9a-phenyl-3-(pyridazin-4-yl)-4,5,5a,6,7,9a-hexahydro-2H-benzo[g]indazole-8-carbonitrile

Example 97A (5aS,6S,9aS)-3-bromo-2,6-dimethyl-9a-phenyl-2,4,5,5a,6,8,9,9a-octahydro-7H-benzo[g]indazol-7-one Example 140D (1.8 g, 5.01 mmol) was dissolved in dimethylformamide (20 ml followed by the addition of potassium carbonate (2.08 g, 15 mmol) and methyl iodide (0.94 ml, 15 mmol), and the reaction mixture was heated at 75° C. overnight. After cooling to room temperature, water was added, and the mixture was extracted several times with ethyl acetate. The combined ethyl acetate washes were washed with brine, dried over anhydrous magnesium sulfate, filtered and concentrated. The residue was dissolved in dichloromethane and purified by flash chromatography on silica gel eluting with heptane to 30% ethyl acetate in heptane to afford the pyrazole isomer (higher R$_f$) as the titled compound (0.694 g, 38%). $^1$H NMR (400 MHz, CDCL$_3$) δ 7.47 (d, J=7.9 Hz, 2H), 7.30-7.23 (m, 2H), 7.18 (t, J=7.3 Hz, 1H), 3.81 (s, 3H), 3.09-2.96 (m, 1H), 2.64-2.41 (m, 5H), 2.30-2.21 (m, 1H), 2.11-1.95 (m, 3H), 1.16 (d, J=6.7 Hz, 3H); MS (ESI+) m/z 374 (M+H)+.

Example 97B (5aS,6S,9aS)-2,6-dimethyl-9a-phenyl-3-(pyridazin-4-yl)-2,4,5,5a,6,8,9,9a-octahydro-7H-benzo[g]indazol-7-one The titled compound was prepared utilizing conditions described in Example 140E (48% yield) substituting Example 97A for Example 140D.

Example 97C (5aS,6S,8Z,9aS)-8-(hydroxymethylene)-2,6-dimethyl-9a-phenyl-3-(pyridazin-4-yl)-2,4,5,5a,6,8,9,9a-octahydro-7H-benzo[g]indazol-7-one Example 97B (0.104 g, 0.279 mmol) was dissolved in ethyl formate (2.73 mL, 34 mmol) and the mixture was cooled to 0° C. in an ice bath followed by the addition of potassium tert butoxide (1 M in tetrahydrofuran, 2.79 ml, 0.279 mmol). The ice bath was then removed, and the mixture stirred at ambient temperature for 18 hours. A solution of 1 N aqueous potassium dihydrogen phosphate was added until neutral pH followed by extraction with ethyl acetate. The organic extracts were dried over anhydrous magnesium sulfate, filtered, and concentrated to provide the titled compound (0.112 g, 100% yield).

Example 97D (5aS,6S,10aS)-2,6-dimethyl-10a-phenyl-3-(pyridazin-4-yl)-4,5,5a,6,10,10a-hexahydro-2H-indazolo[7,6-f][1,2]benzoxazole The titled compound was prepared utilizing conditions described in Example 140G substituting Example 97C for Example 140F.

Example 97E (5aS,6S,9aS)-2,6-dimethyl-7-oxo-9a-phenyl-3-(pyridazin-4-yl)-4,5,5a,6,7,8,9,9a-octahydro-2H-benzo[g]indazole-8-carbonitrile Example 97D (0.111 g, 0.279 mmol) was dissolved in tetrahydrofuran (3 mL followed by the addition of sodium methoxide (25% NaOCH$_3$ in CH$_3$OH by weight, 0.671 mL, 2.79 mmol), and the mixture stirred at ambient temperature for 18 hours. A solution of 1 N aqueous potassium dihydrogen phosphate was added until neutral pH followed by extraction with ethyl acetate. The combined organic extracts were dried over anhydrous magnesium sulfate, filtered, and concentrated to provide the titled compound (0.08 g, 72% yield).

Example 97F (5aS,6S,9aR)-2,6-dimethyl-7-oxo-9a-phenyl-3-(pyridazin-4-yl)-4,5,5a,6,7,9a-hexahydro-2H-benzo[g]indazole-8-carbonitrile Example 97E (0.08 g, 0.201 mmol) was dissolved in dimethylformamide (3 ml) and cooled to 0° C. 1,3-Dibromo-5,5-dimethylhydantoin (0.032 g, 0.11 mmol) was added to the reaction mixture, and the resultant mixture was stirred for 1.5 hours. Pyridine (0.049 ml, 0.604 mmol) was then added dropwise, and the solution was heated at 50° C. for 18 hours. After cooling to ambient temperature, a solution of 1 N aqueous potassium dihydrogen phosphate was added followed by extraction with ethyl acetate. The combined organic extracts were dried over anhydrous magnesium sulfate, filtered, and concentrated. The resultant residue was dissolved in dichloromethane and purified by silica gel flash chromatography eluting with 0% to 90% ethyl acetate in hexanes. The residue was triturated in isopropanol/hexanes to afford the titled compound (0.03 g, 38% yield). $^1$H NMR (400 MHz, CDCl$_3$) δ ppm 9.41-9.30 (m, 2H), 8.45 (s, 1H), 7.55 (d, J=3.2 Hz, 1H), 7.33 (t, J=7.7 Hz, 3H), 6.92 (t, J=9.5 Hz, 2H), 3.94 (s, 3H), 2.93-2.71 (m, 2H), 2.47 (dq, J=13.0, 6.4 Hz, 1H), 2.36 (t, J=12.1 Hz, 1H), 1.88 (dd, J=13.7, 6.6 Hz, 1H), 1.18 (d, J=6.6 Hz, 3H), 0.90-0.81 (m, 1H); MS (DCI+) m/z 396 (M+H)+.

Example 98 methyl 4-[(6aS,7S,10aR)-9-cyano-2,7-dimethyl-8-oxo-10a-phenyl-5,6,6a,7,8,10a-hexahydrobenzo[h]quinazolin-4-yl]-1H-pyrazole-1-carboxylate To a solution of the product of Example 34E (0.0334 g, 0.085 mmol) in dichloromethane (0.8 mL) cooled to 0° C. was added diisopropylethylamine (0.037 mL, 0.212 mmol) and methyl chloroformate (0.008 mL, 0.103 mmol). The solution was stirred at room temperature for 30 minutes. The reaction mixture was diluted with ethyl acetate (50 mL) and washed with an aqueous solution of sodium bicarbonate (0.5 N, 10 mL), water (10 mL) and brine (10 mL). The combined aqueous layers were back-extracted with ethyl acetate (5 mL×3), and the combined organic layers were dried (MgSO₄), filtered, concentrated. The residue was purified chromatographically using a Biotage® SNAP 10 g silica cartridge eluted with a step gradient of acetone/heptane (3 column volume (CV) 0%, 4 CV 0-17%, 3 CV 17% then 3 CV 33%) giving the impure titled compound (0.0169 g). This material was purified again by reversed-phase Waters HPLC using a Nova-Pak® HR C18, 6 μm, 60 Å, 40 mm×100 mm, PrepPak cartridge, eluted with a gradient of 20-80% CH₃CN in 0.1% aqueous trifluoroacetic acid at flow rate of 60 mL/minute over 12 minutes then hold at 100% CH₃CN for 2 minutes and to give the titled compound (0.0106 g, 0.022 mmol, 26.2% yield). ¹H NMR (400 MHz, CDCl₃) δ ppm 1.20 (d, J=6.7 Hz, 3H), 1.61-1.71 (m, 1H), 2.04-2.12 (m, 1H), 2.31-2.39 (m, 1H), 2.43-2.51 (m, 1H), 2.69 (s, 3H), 3.02-3.18 (m, 2H), 4.16 (s, 3H), 6.83 (dd, J=7.5, 1.9 Hz, 2H), 7.30-7.34 (m, 3H), 8.50 (s, 1H), 8.75 (s, 1H), 8.96 (s, 1H); MS (ESI+) m/z 454.2 (M+H)+.

Example 99 methyl 3-[(6aS,7S,10aR)-9-cyano-7-methyl-8-oxo-2-phenyl-6,6a,7,8-tetrahydrobenzo[h]quinazolin-10a(5H)-yl]benzoate Example 99A methyl 3-[(6aS,7S,10aS)-7-methyl-2-phenyl-5,6,6a,7,9,10-hexahydro-10aH-spiro[benzo[h]quinazoline-8,2'-[1,3]dioxolan]-10a-yl]benzoate To a solution of Example 59G (0.340 g, 0.894 mmol) in isopropanol (4 mL) was added benzimidamide hydrochloride (0.266 g, 1.70 mmol) and piperidine (0.168 g, 1.70 mmol). The reaction mixture was heated at 95° C. for 24 hours. The cooled solution was diluted with saturated aqueous sodium phosphate monobasic solution and extracted with ethyl acetate. The organic fraction was concentrated to provide the titled compound. MS (APCI+) m/z 401 (M+H)+.

Example 99B methyl 3-[(6aS,7S,10aS)-7-methyl-8-oxo-2-phenyl-6,6a,7,8,9,10-hexahydrobenzo[h]quinazolin-10a(5H)-yl]benzoate The titled compound was prepared using the conditions described in Example 1I, substituting Example 99A for Example 1H.

Example 99C ethyl 3-[(6aS,7S,9Z,10aS)-9-(hydroxymethylene)-7-methyl-8-oxo-2-phenyl-6,6a,7,8,9,10-hexahydrobenzo[h]quinazolin-10a(5H)-yl]benzoate The titled compound was prepared using the conditions described in Example 1J, substituting Example 99B for Example 1I.

Example 99D ethyl 3-[(6aS,7S,11aS)-7-methyl-2-phenyl-6,6a,7,11-tetrahydro[1,2]benzoxazolo[6,5-h]quinazolin-11a(5H)-yl]benzoate The titled compound was prepared using the conditions described in Example 1K, substituting Example 99C for Example 1J. MS (APCI+) m/z 466 (M+H)+.

Example 99E methyl 3-[(6aS,7S,10aS)-9-cyano-7-methyl-8-oxo-2-phenyl-6,6a,7,8,9,10-hexahydrobenzo[h]quinazolin-10a(5H)-yl]benzoate The titled compound was prepared using the conditions described in Example 1L, substituting Example 99D for Example 1K.

Example 99F methyl 3-[(6aS,7S,10aR)-9-cyano-7-methyl-8-oxo-2-phenyl-6,6a,7,8-tetrahydrobenzo[h]quinazolin-10a(5H)-yl]benzoate To a solution of Example 99E (0.165 g, 0.365 mmol) in dimethylformamide (4 mL) and cooled to 0° C. in an ice water bath was added 1,3-dibromo-5,5-dimethylhydantoin (0.052 g, 0.183 mmol). The solution was stirred at 0° C. for 40 minutes, then pyridine (0.591 mL, 7.31 mmol) was added, and the solution was heated at 50° C. for 1 hour. The cooled solution was diluted with water and extracted with ethyl acetate. The organic phase was washed with brine and concentrated. The residue was purified using a Teledyne Isco Combiflash® Rf equipped with a 12 g RediSep® cartridge, eluting with 0-45% ethyl acetate in heptane to give 0.070 g (43%) of the titled compound. ¹H NMR (400 MHz, CDCl₃) δ ppm 1.21 (d, J=5.96 Hz, 3H) 1.57-1.69 (m, 1H) 1.98-2.06 (m, 1H) 2.36-2.47 (m, 2H) 3.00-3.23 (m, 2H) 3.88 (s, 3H) 7.05-7.11 (m, 1H) 7.42 (t, J=7.86 Hz, 1H) 7.45-7.50 (m, 3H)

7.54 (s, 1H) 7.98 (d, J=7.70 Hz, 1H) 8.34-8.42 (m, 2H) 8.80 (s, 1H) 9.03 (s, 1H); MS (APCI+) m/z 450 (M+H)+.

Example 100

3-[(6aS,7S,10aR)-9-cyano-7-methyl-8-oxo-2-phenyl-6,6a,7,8-tetrahydrobenzo[h]quinazolin-10a(5H)-yl]benzoic acid To a solution of Example 99F (0.045 g, (0.100 mmol) in tetrahydrofuran (2 mL) was added water (0.75 mL) and lithium hydroxide monohydrate (0.021 g, 0.501 mmol). The reaction mixture was stirred at room temperature for 2 hours and then heated at 40° C. for 1.5 hours. The solution was adjusted to pH 5 by dropwise addition of 1 M hydrochloric acid, then ethyl acetate (4 mL) was added, and the mixture was stirred vigorously for 1 hour. The layers were separated, and the organic fraction was concentrated. The residue was purified on a Teledyne Isco Combiflash® Rf with a 4 g RediSep® cartridge, eluting with 0-10% methanol in dichloromethane, followed by trituration with diethyl ether to give 0.017 g (38%) of the titled compound. $^1$H NMR (400 MHz, DMSO-D6) δ ppm 1.08 (d, J=6.72 Hz, 3H) 1.33-1.45 (m, 1H) 1.88-1.98 (m, 1H) 2.29-2.36 (m, 1H) 2.60-2.70 (m, 1H) 2.96-3.14 (m, 2H) 7.22 (d, J=5.31 Hz, 1H) 7.40 (s, 1H) 7.44-7.51 (m, 4H) 7.86 (d, J=7.70 Hz, 1H) 8.42 (dd, J=7.37, 2.28 Hz, 2H) 8.94 (s, 1H) 9.08 (s, 1H); MS (APCI+) m/z 436 (M+H)+.

Example 101 methyl 3-[(6aS,7S,10aR)-9-cyano-2-[4-(methoxycarbonyl)phenyl]-7-methyl-8-oxo-6,6a,7,8-tetrahydrobenzo[h]quinazolin-10a(5H)-yl]benzoate Example 101A methyl 3-{(6aS,7S,10aS)-2-[4-(ethoxycarbonyl)phenyl]-7-methyl-5,6,6a,7,9,10-hexahydro-10aH-spiro[benzo[h]quinazoline-8,2'-[1,3]dioxolan]-10a-yl}benzoate To a solution of the product from Example 59G (0.54 g, 1.35 mmol) in isopropanol (6 mL) was added ethyl-4-carbamimidoylbenzoate hydrochloride (0.617 g, 2.70 mmol) and piperidine (0.267 mL, 2.70 mmol). The reaction mixture was heated at 95° C. for 48 hours. The cooled solution was diluted with a saturated aqueous solution of sodium phosphate monobasic and extracted with ethyl acetate. The organic fraction was concentrated.

Example 101B methyl 3-[(6aS,7S,10aS)-2-[4-(ethoxycarbonyl)phenyl]-7-methyl-8-oxo-6,6a,7,8,9,10-hexahydrobenzo[h]quinazolin-10a(5H)-yl]benzoate The titled compound was prepared using the conditions described in Example 1I, substituting Example 101A for Example 1H.

Example 101C ethyl 3-[(6aS,7S,9Z,10aS)-2-[4-(ethoxycarbonyl)phenyl]-9-(hydroxymethylene)-7-methyl-8-oxo-6,6a,7,8,9,10-hexahydrobenzo[h]quinazolin-10a(5H)-yl]benzoate The titled compound was prepared using the conditions described in Example 1J, substituting Example 101B for Example 1I. MS (APCI+) m/z 541 (M+H)+.

Example 101D ethyl 3-[(6aS,7S,11aS)-2-[4-(ethoxycarbonyl)phenyl]-7-methyl-6,6a,7,11-tetrahydro[1,2]benzoxazolo[6,5-h]quinazolin-11a(5H)-yl]benzoate The titled compound was prepared using the conditions described in Example 1K, substituting Example 101C for Example 1J Example 101E methyl 3-[(6aS,7S,10aS)-9-cyano-2-[4-(methoxycarbonyl)phenyl]-7-methyl-8-oxo-6,6a,7,8,9,10-hexahydrobenzo[h]quinazolin-10a(5H)-yl]benzoate The titled compound was prepared using the conditions described in Example 1L, substituting Example 101D for Example 1K.

Example 101F methyl 3-[(6aS,7S,10aR)-9-cyano-2-[4-(methoxycarbonyl)phenyl]-7-methyl-8-oxo-6,6a,7,8-tetrahydrobenzo[h]quinazolin-10a(5H)-yl]benzoate To a solution of Example 101E (0.169 g, 0.332 mmol) in dimethylformamide (4 mL) and cooled to 0° C. in an ice water bath was added 1,3-dibromo-5,5-dimethylhydantoin (0.047 g, 0.166 mmol). The solution was stirred at 0° C. for 35 minutes, then pyridine (0.268 mL, 3.32 mmol) was added, and the solution was heated at 55° C. for 2 hours. The cooled solution was diluted with water and extracted with ethyl acetate. The organic fraction was washed with brine and concentrated. The residue was purified using a Teledyne Isco Combiflash® Rf equipped with a 12 g RediSep® cartridge, eluting with 0-45% ethyl acetate in heptane to give 0.096 g (57%) of the titled compound. $^1$H NMR (400 MHz, CDCl$_3$) δ ppm 1.21 (d, J=5.86 Hz, 3H) 1.58-1.69 (m, 1H) 1.99-2.08 (m, 1H) 2.36-2.47 (m, 2H) 3.02-3.26 (m, 2H) 3.88 (s, 3H) 3.94 (s, 3H) 7.08 (dd, J=9.00, 1.08 Hz, 1H) 7.43 (t, J=7.92 Hz, 1H) 7.53 (s, 1H) 7.99 (d, J=7.70 Hz, 1H) 8.12 (d, J=8.46 Hz, 2H) 8.45 (d, J=8.35 Hz, 2H) 8.84 (s, 1H) 9.00 (s, 1H); MS (ESI+) m/z 508 (M+H)+.

Example 102

(6aS,7S,10aR)-2-chloro-4-methoxy-7-methyl-8-oxo-10a-phenyl-5,6,6a,7,8,10a-hexahydrobenzo[h]quinazoline-9-carbonitrile Example 102A (6aS,7S,10aS)-7-methyl-10a-phenyl-2-sulfanyl-5,6a,7,9,10,10a-hexahydro-6H-spiro[benzo[h]quinazoline-8,2'-[1,3]dioxolan]-4-ol To a solution of Example 13A (0.500 g, 1.40 mmol) in t-butanol (10 mL) was added thiourea (1.06 g, 13.95 mmol) and 1 M potassium t-butoxide in t-butanol (1.40 mL, 1.40 mmol). The reaction mixture was heated at 95° C. for 24 hours, then diluted with saturated aqueous potassium phosphate monobasic solution, and extracted with ethyl acetate. The organic fraction was dried over sodium sulfate and concentrated. MS (APCI+) m/z 385 (M+H)+.

Example 102B (6aS,7S,10aS)-2,4-dihydroxy-7-methyl-10a-phenyl-5,6a,7,9,10,10a-hexahydrobenzo[h]quinazolin-8(6H)-one To chloroacetic acid (1.32 g, 13.94 mmol) was added Example 102A (0.536 g, 1.39 mmol), and the mixture was heated at 100° C. for 45 minutes. Water (3 mL) was added, and the mixture was heated at 100° C. for 4 more hours. Then concentrated hydrochloric acid (0.085 mL, 2.79 mmol) was added, and the solution was stirred at room temperature overnight. The mixture was diluted with cold water and extracted with ethyl acetate. The organic fraction was concentrated and purified on a Teledyne Isco Combiflash® Rf equipped with a 12 g RediSep® cartridge, eluting with 0-80% ethyl acetate in heptane to give 0.217 g (48%) of the titled compound. MS (APCI+) m/z 325 (M+H)+.

Example 102C (6aS,7S,10aS)-2,4-dichloro-7-methyl-10a-phenyl-5,6a,7,9,10,10a-hexahydrobenzo[h]quinazolin-8(6H)-one To phosphorous oxychloride (1.5 mL, 16.09 mmol) was added Example 102B (0.217 g, 0.669 mmol) followed by Hunig's base (0.129 mL, 0.736 mmol). The reaction mixture was heated at 90° C. for 24 hours. Toluene was added to the mixture, and it was concentrated to dryness. The residue was diluted with dichloromethane and washed with 10% sodium bicarbonate solution. The organic fraction was dried over sodium sulfate, filtered, and concentrated.

Example 102D (6aS,7S,10aS)-2-chloro-4-methoxy-7-methyl-10a-phenyl-5,6a,7,9,10,10a-hexahydrobenzo[h]quinazolin-8(6H)-one To a solution of Example 102C (0.242 g, 0.67 mmol) in methanol (5 mL) was added 25% sodium methoxide in methanol (0.50 mL, 3.43 mmol). The reaction solution was heated at 50° C. for 20 hours. The solution was diluted with saturated aqueous sodium phosphate monobasic solution and extracted with ethyl acetate. The organic fraction was concentrated, and the residue was purified using a Teledyne Isco Combiflash® Rf equipped with a 12 g RediSep® cartridge, eluting with 0-30% ethyl acetate in heptane to give 0.075 g (31%) of the titled compound. MS (APCI+) m/z 357 (M+H)+.

Example 102E (6aS,7S,9Z,10aS)-2-chloro-9-(hydroxymethylene)-4-methoxy-7-methyl-10a-phenyl-5,6a,7,9,10,10a-hexahydrobenzo[h]quinazolin-8(6H)-one The titled compound was prepared using the conditions described in Example 1J, substituting Example 102D for Example 1I.

Example 102F (6aS,7S,11aS)-2-chloro-4-methoxy-7-methyl-11a-phenyl-5,6,6a,7,11,11a-hexahydro[1,2]benzoxazolo[6,5-h]quinazoline The titled compound was prepared using the conditions described in Example 1K, substituting Example 102E for Example 1J. MS (APCI+) m/z 382 (M+H)+.

Example 102G (6aS,7S,10aS)-2-chloro-4-methoxy-7-methyl-8-oxo-10a-phenyl-5,6,6a,7,8,9,10,10a-octahydrobenzo[h]quinazoline-9-carbonitrile The titled compound was prepared using the conditions described in Example 1L, substituting Example 101F for Example 1K. The product is contaminated with a small amount of bis-methoxy byproduct.

Example 102H (6aS,7S,10aR)-2-chloro-4-methoxy-7-methyl-8-oxo-10a-phenyl-5,6,6a,7,8,10a-hexahydrobenzo[h]quinazoline-9-carbonitrile To a solution of Example 102G (0.07 g, 0.183 mmol) in dimethylformamide (2 mL) and cooled to 0° C. in an ice water bath was added 1,3-dibromo-5,5-dimethylhydantoin (0.026 g, 0.092 mmol). The solution was stirred at 0° C. for 45 minutes, then pyridine (0.297 mL, 3.67 mmol) was added, and the solution was heated at 55° C. for 1 hour. The cooled solution was diluted with water and extracted with ethyl acetate. The organic phase was washed with brine and concentrated. The residue was purified on a Teledyne Isco Combiflash® Rf equipped with a 12 g RediSep® cartridge, eluting with 0-20% ethyl acetate in heptane to give 0.009 g (13%) of the titled compound. Also isolated was a mixture of product and bis-methoxy byproduct. $^1$H NMR (400 MHz, CDCl$_3$) δ ppm 1.16 (d, J=6.72 Hz, 3H) 1.46-1.57 (m, 1H) 1.90-1.99 (m, 1H) 2.25 (td, J=12.96, 2.28 Hz, 1H) 2.39 (td, J=13.17, 6.61 Hz, 1H) 2.71 (ddd, J=18.92, 11.06, 7.97 Hz, 1H) 2.85-2.94 (m, 1H) 4.12 (s, 3H) 6.85 (dd, J=7.70, 1.84 Hz, 2H) 7.30-7.38 (m, 3H) 8.75 (s, 1H); MS (APCI+) m/z 380 (M+H)+.

Example 103

(6aS,7S,10aR)-2,4-dimethoxy-7-methyl-8-oxo-10a-phenyl-5,6,6a,7,8,10a-hexahydrobenzo[h]quinazoline-9-carbonitrile To 25% sodium methoxide in methanol (0.172 mL, 0.79 mmol) was added the mixture of product and byproduct from Example 102H (0.015 g, 0.039 mmol). The reaction mixture was stirred at room temperature overnight. The reaction mixture was diluted with water, the solid product was collected by filtration. The solid was taken up in dichloromethane and purified on a Teledyne Isco Combiflash® Rf equipped with a 4 g RediSep® cartridge eluting with 0-20% ethyl acetate in heptane to give 0.007 g, (47%) of the titled compound. $^1$H NMR (400 MHz, CDCl$_3$) δ ppm 1.16 (d, J=6.61 Hz, 3H) 1.42-1.53 (m, 1H) 1.90 (dd, J=13.17, 7.21 Hz, 1H) 2.28 (td, J=12.93, 2.33 Hz, 1H) 2.40 (td, J=13.12, 6.51 Hz, 1H) 2.66 (ddd, J=18.41, 10.98, 7.81

Hz, 1H) 2.80-2.90 (m, 1H) 3.91 (s, 3H) 4.07 (s, 3H) 6.89 (dd, J=7.64, 1.79 Hz, 2H) 7.29-7.36 (m, 3H) 8.81 (s, 1H); MS (APCI+) m/z 376 (M+H)+.

Example 104

3-[(6aS,7S,10aR)-2-(4-carboxyphenyl)-9-cyano-7-methyl-8-oxo-6,6a,7,8-tetrahydrobenzo[h]quinazolin-10a(5H)-yl]benzoic acid To a solution of Example 101F (0.060 g, (0.118 mmol) in tetrahydrofuran (2 mL) was added water (0.67 mL) and lithium hydroxide monohydrate (0.040 g, 0.946 mmol). The reaction mixture was stirred at room temperature for 24 hours. The solution was adjusted to pH 5 by dropwise addition of 1 M hydrochloric acid. Then 20% isopropanol in chloroform (4 mL) was added, and the mixture was stirred vigorously for 1 hour. The layers were separated, and the organic fraction was concentrated. The residue was purified on a Teledyne Isco Combiflash® Rf using a 4 g RediSep® cartridge eluting with 0-4% methanol in dichloromethane to give 0.030 g (53%) of the titled compound. $^1$H NMR (400 MHz, DMSO-$d_6$) δ ppm 1.08 (ddd, J=6.86, 3.63, 3.50 Hz, 3H) 1.35-1.45 (m, 1H) 1.89-1.99 (m, 1H) 2.28-2.36 (m, 1H) 2.61-2.70 (m, 1H) 2.99-3.19 (m, 2H) 7.23 (d, J=7.81 Hz, 1H) 7.40 (s, 1H) 7.48 (t, J=7.81 Hz, 1H) 7.86 (d, J=7.81 Hz, 1H) 8.02 (d, J=8.46 Hz, 2H) 8.54 (d, J=8.57 Hz, 2H) 8.99 (s, 1H) 9.10 (s, 1H); MS (APCI+) m/z 480 (M+H)+.

Example 105

(3R,3aR,5aS,6S,9aR)-2,6-dimethyl-7-oxo-3,9a-diphenyl-3,3a,4,5,5a,6,7,9a-octahydro-2H-benzo[g]indazole-8-carbonitrile

Example 105A (1'S,4a'S,6'E,8a'S)-6'-benzylidene-1'-methyl-4a'-phenylhexahydro-1'H-spiro[1,3-dioxolane-2,2'-naphthalen]-5'(3'H)-one Example 1F (1.0 g, 3.33 mmol) was dissolved in tetrahydrofuran (25 mL), and the solution was cooled to −78° C. To this mixture, a solution of lithium diisopropylamide mono tetrahydrofuran (1.5 M in tetrahydrofuran, 6.66 mL, 9.99 mmol) was added dropwise, and the mixture was stirred at −78° C. for 0.5 hour followed by the dropwise addition of benzaldehyde (1.67 mL, 16.64 mmol). The resultant solution was stirred at −78° C. for 1 hour, followed by removal of the cooling bath and warming to ambient temperature overnight. The reaction mixture was diluted with 1 N aqueous ammonium chloride and then extracted with ethyl acetate. The organic extracts were dried over anhydrous magnesium sulfate, filtered, and concentrated. The residue dissolved in dichloromethane was purified by silica gel flash chromatography eluting with 0% to 25% ethyl acetate in heptane to afford the titled compound (0.925 g, 72% yield). $^1$H NMR (400 MHz, CDCl$_3$) δ ppm 7.51 (m, 3H), 7.26 (m, 8H), 3.96 (s, 4H), 2.85 (m, 1H), 2.62 (m, 1H), 2.23 (m, 1H), 2.17 (m, 2H), 2.03 (m, 3H), 1.63 (dt, J=13.6, 3.5 Hz, 1H), 1.33 (m, 1H), 0.99 (d, J=6.5 Hz, 3H); MS (ESI+) m/z 389 (M+H)+.

Example 105B (3R,3aR,5aS,6S,9aS)-2,6-dimethyl-3,9a-diphenyl-2,3,3a,4,5,5a,6,8,9,9a-decahydrospiro[benzo[g]indazole-7,2'-[1,3]dioxolane]

Example 105A (0.150 g, 0.386 mmol) was partially dissolved in isopropanol (6 mL). Then methylhydrazine (0.163 mL, 3.09 mmol) was added, and the mixture was heated at reflux for 16 hours. After cooling to room temperature, 1 N aqueous ammonium chloride was added followed by extraction with ethyl acetate. The combined organic extracts were dried over anhydrous magnesium sulfate, filtered, and concentrated to provide (0.165 g, 100% yield) of the titled compound. MS (ESI+) m/z 417 (M+H)+.

Example 105C (3R,3aR,5aS,6S,9aS)-2,6-dimethyl-3,9a-diphenyl-2,3,3a,4,5,5a,6,8,9,9a-decahydro-7H-benzo[g]indazol-7-one Example 105B (0.160 g, 0.384 mmol) was dissolved in a solution of 4 N hydrochloric acid in dioxane (6 mL). Then water (0.6 mL) was added, and the mixture was stirred at ambient temperature for 18 hours. A solution of saturated aqueous sodium bicarbonate was added followed by extraction with ethyl acetate. The combined organic extracts were dried over anhydrous magnesium sulfate, filtered, and concentrated to provide (0.155 g, >100% yield) of the titled compound. MS (ESI+) m/z 373 (M+H)+.

Example 105D (3R,3aR,5aS,6S,10aS)-2,6-dimethyl-3,10a-diphenyl-3,3a,4,5,5a,6,10,10a-octahydro-2H-indazolo[7,6-f][1,2]benzooxazole Example 105C (0.140 g, 0.376 mmol) was dissolved in ethyl formate (1.5 mL, 18.79 mmol), and the mixture was cooled to 0° C. in an ice bath followed by the addition of 25% sodium methoxide in methanol (0.9 mL, 3.76 mmol). The ice bath was then removed, and the mixture was stirred at ambient temperature for 18 hours. A solution of 1 N aqueous potassium dihydrogen phosphate was added followed by extraction with ethyl acetate. The combined organic extracts were dried over anhydrous magnesium sulfate, filtered, and concentrated. This residue was dissolved in ethanol (4.5 mL), hydroxylamine hydrochloride (0.039 g, 0.562 mmol) was added, and the mixture was heated at 50° C. for 18 hours. After cooling to ambient temperature, the solution was concentrated. The resultant residue was purified by silica gel flash chromatography eluting with 0% to 25% ethyl acetate in heptane to afford the titled compound (0.088 g, 59%). $^1$H NMR (400 MHz, CDCl$_3$) δ ppm 7.94 (s, 1H), 7.35 (m, 4H), 7.28 (m, 4H), 7.20 (d, J=7.5 Hz, 1H), 7.16 (m, 1H), 3.49 (d, J=12.8 Hz, 1H), 3.23 (m, 1H), 3.19 (m, 1H), 3.09 (d, J=15.8 Hz, 1H), 2.80 (s, 3H), 2.76 (m, 1H), 2.15 (m, 1H), 2.01 (m, 1H), 1.92 (m, 1H), 1.80 (m, 1H), 1.53 (m, 1H), 1.47 (d, J=6.6 Hz, 3H), 1.27 (m, 1H); MS (ESI+) m/z 398 (M+H)+.

Example 105E (3R,3aR,5aS,6S,9aR)-2,6-dimethyl-7-oxo-3,9a-diphenyl-3,3a,4,5,5a,6,7,9a-octahydro-2H-benzo[g]indazole-8-carbonitrile Example 105D (0.080 g, 0.201 mmol) was dissolved in tetrahydrofuran (4.5 mL followed by the addition of sodium methoxide (25% in methanol by weight, 0.45 mL, 2.01 mmol), and the mixture was stirred at ambient temperature for 18 hours. A solution of 1 N aqueous potassium dihydrogen phosphate was added followed by extraction with ethyl acetate. The combined organic extracts were dried over anhydrous magnesium sulfate, filtered, and concentrated. This residue was then dissolved in N,N-dimethylformamide (4.5 mL). The solution was cooled in an ice bath, and 1,3-dibromo-5,5-dimethylhydantoin (0.0316 g, 0.111 mmol) was added. The mixture was stirred at 0° C. for 1.5 hours followed by the dropwise addition of pyridine (0.081 mL, 1.006 mmol). The ice bath was removed, and the resultant solution was heated at 50° C. for 18 hours. After cooling to ambient temperature, a solution of 1 N aqueous potassium dihydrogen phosphate was added followed by extraction with ethyl acetate. The organic extracts were dried over anhydrous magnesium sulfate, filtered, and concentrated. The resultant residue was purified by silica gel flash chromatography eluting with 0% to 50% ethyl acetate in heptane to afford the titled compound (0.014 g, 18%). $^1$H NMR (400 MHz, CDCl$_3$) δ ppm 8.41 (s, 1H), 7.37 (m, 8H), 7.30 (m, 2H), 3.57 (d, J=13.2 Hz, 1H), 3.00 (m, 2H), 2.78 (s, 3H), 2.30 (dt, J=12.9 Hz, 1H), 2.18 (m, 1H), 1.92 (m, 1H), 1.80 (m, 1H), 1.55 (m, 1H), 1.32 (d, J=6.7 Hz, 3H); MS (ESI+) m/z 396 (M+H)$^+$.

Example 106

(5aS,6S,9aR)-3-(6-aminopyridin-3-yl)-6-methyl-7-oxo-9a-phenyl-4,5,5a,6,7,9a-hexahydro-2H-benzo[g]indazole-8-carbonitrile Example 106A tert-butyl {5-[(5aS,6S,9aS)-6-methyl-7-oxo-9a-phenyl-4,5,5a,6,7,8,9,9a-octahydro-2H-benzo[g]indazol-3-yl]pyridin-2-yl}carbamate The titled compound was prepared using the conditions described in Example 86A substituting 3-(4,4,5,5-tetramethyl-1,3,2-dioxaborolan-2-yl)pyridine tert-butyl with 4-(4,4,5,5-tetramethyl-1,3,2-dioxaborolan-2-yl)pyridin-2-ylcarbamate and substituting Example 86A with Example 140D.

Example 106B tert-butyl {5-[(5aS,6S,8Z,9aS)-8-(hydroxymethylene)-6-methyl-7-oxo-9a-phenyl-4,5,5a,6,7,8,9,9a-octahydro-2H-benzo[g]indazol-3-yl]pyridin-2-yl}carbamate The titled compound was prepared using the conditions described in Example 24C substituting Example 24B with Example 106A. MS (APCI) m/z 501 (M+H)$^+$.

Example 106C tert-butyl {5-[(5aS,6S,10aS)-6-methyl-10a-phenyl-4,5,5a,6,10,10a-hexahydro-2H-indazolo[7,6-f][1,2]benzoxazol-3-yl]pyridin-2-yl}carbamate The titled compound was prepared using the conditions described in Example 24D substituting Example 24C with Example 106B. MS (APCI) m/z 498 (M+H)$^+$.

Example 106D tert-butyl {5-[(5aS,6S,9aS)-8-cyano-6-methyl-7-oxo-9a-phenyl-4,5,5a,6,7,8,9,9a-octahydro-2H-benzo[g]indazol-3-yl]pyridin-2-yl}carbamate The titled compound was prepared using the conditions described in Example 24E substituting Example 24D with Example 106C.

Example 106E tert-butyl {5-[(5aS,6S,9aR)-8-cyano-6-methyl-7-oxo-9a-phenyl-4,5,5a,6,7,9a-hexahydro-2H-benzo[g]indazol-3-yl]pyridin-2-yl}carbamate Example 106D (0.025 g, 0.050 mmol) was dissolved in tetrahydrofuran (0.50 mL), and the mixture was sparged with nitrogen for 10 minutes. 2,3-Dichloro-5,6-dicyano-1,4-benzoquinone (0.012 g, 0.055 mmol) was added, and the nitrogen sparging was continued for 15 minutes. The reaction mixture was concentrated, and the residue was purified on a reversed-phase Waters HPLC using a Nova-Pak® HR C18, 6 µm, 60 Å, 40 mm×100 mm, PrepPak cartridge eluting with a gradient of 10-90% acetonitrile in aqueous 0.1% trifluoroacetic acid (60 mL/minute) to give the titled compound.

Example 106F (5aS,6S,9aR)-3-(6-aminopyridin-3-yl)-6-methyl-7-oxo-9a-phenyl-4,5,5a,6,7,9a-hexahydro-2H-benzo[g]indazole-8-carbonitrile Example 106E (0.015 g, 0.030 mmol) was dissolved in 4 N hydrochloric acid in tetrahydrofuran (0.92 mL, 0.030 mmol) and dichloromethane (0.30 mL), and the reaction mixture was stirred at room temperature overnight. The reaction mixture was concentrated, and the residue was purified on a reversed-phase Waters HPLC using a Nova-Pak HR C18, 6 µm, 60 Å, 40 mm×100 mm, PrepPak cartridge eluting with a gradient of 10-90% acetonitrile in aqueous 0.1% trifluoroacetic acid (60 mL/minute) to give the titled compound as the trifluoroacetic acid salt (0.008 g, 66%). $^1$H NMR (400 MHz, DMSO-d$_6$) δ ppm 1.06 (d, J=5.9 Hz, 3H), 1.30-1.47 (m, 1H), 1.76-1.87 (m, 1H), 2.33-2.38 (m, 1H), 2.73-2.86 (m, 2H), 2.93 (dd, J=15.9, 6.2 Hz, 2H), 6.95 (d, J=7.2 Hz, 2H), 7.03 (d, J=9.1 Hz, 1H), 7.27-7.40 (m, 3H), 8.18 (s, 1H), 8.42 (s, 1H); MS (ESI+) m/z 396 (M+H)$^+$.

Example 107

(6aS,7S,10aR)-4-(imidazo[1,2-a]pyridin-6-yl)-2,7-dimethyl-8-oxo-10a-phenyl-5,6,6a,7,8,10a-hexahydrobenzo[h]quinazoline-9-carbonitrile Example 107A (6aS,7S,10aS)-4-(imidazo[1,2-a]pyridin-6-yl)-2,7-dimethyl-10a-phenyl-5,6a,7,9,10,10a-hexahydrobenzo[h]quinazolin-8(6H)-one The titled compound was prepared using the conditions described in Example 17A, substituting imidazo[1,2-a]pyridin-6-ylboronic acid for 1-methyl-5-(4,4,5,5-tetramethyl-1,3,2-dioxaborolan-2-yl)-1H-imidazole. Purification was achieved by flash chromatography on silica gel eluting with 2% methanol in chloroform to give the titled compound in 71% yield. $^1$H NMR (400 MHz, CDCl$_3$) δ ppm 1.17 (d, J=6.61 Hz, 3H) 1.94-2.05 (m, 1H) 2.06-2.20 (m, 2H) 2.30-2.53 (m, 3H) 2.56-2.67 (m, 1H) 2.77 (s, 3H) 2.84-3.01 (m, 2H) 3.22 (td, J=8.29, 3.69 Hz, 1H) 7.23-7.29 (m, 2H) 7.33 (t, J=7.48 Hz, 2H) 7.55 (d, J=7.70 Hz, 2H) 7.61-7.71 (m, 3H) 8.35 (s, 1H); MS (ESI) m/z 423.3 (M+H)$^+$.

Example 107B (6aS,7S,9Z,10aS)-9-(hydroxymethylene)-4-(imidazo[1,2-a]pyridin-6-yl)-2,7-dimethyl-10a-phenyl-5,6a,7,9,10,10a-hexahydrobenzo[h]quinazolin-8(6H)-one The titled compound was prepared using the conditions described in Example 13F, substituting Example 107A for Example 13E.

Example 107C (6aS,7S,11aS)-4-(imidazo[1,2-a]pyridin-6-yl)-2,7-dimethyl-11a-phenyl-5,6,6a,7,11,11a-hexahydro[1,3]benzoxazolo[6,5-h]quinazoline The titled compound was prepared using the conditions described in Example 13G, substituting Example 107B for Example 13F.

Example 107D (6aS,7S,10aS)-4-(imidazo[1,2-a]pyridin-6-yl)-2,7-dimethyl-8-oxo-10a-phenyl-5,6,6a,7,8,9,10,10a-octahydrobenzo[h]quinazoline-9-carbonitrile The titled compound was prepared using the conditions described in Example 13H, substituting Example 107C for Example 13G.

Example 107E (6aS,7S,10aR)-4-(imidazo[1,2-a]pyridin-6-yl)-2,7-dimethyl-8-oxo-10a-phenyl-5,6,6a,7,8,10a-hexahydrobenzo[h]quinazoline-9-carbonitrile The titled compound was prepared using the conditions described in Example 13I, substituting Example 107D for Example 13H. Purification was achieved by flash chromatography on silica gel eluting with 5% methanol in chloroform containing 0.2% ammonium hydroxide to give the titled compound in 35% yield. $^1$H NMR (400 MHz, CDCl$_3$) δ ppm 1.18 (d, J=6.61 Hz, 3H) 1.60 (tt, J=13.27, 8.85 Hz, 1H) 1.91-2.00 (m, 1H) 2.37 (td, J=12.79, 2.28 Hz, 1H) 2.48 (td, J=13.07, 6.51 Hz, 1H) 2.73 (s, 3H) 3.05 (dd, J=8.57, 4.45 Hz, 2H) 6.83 (dd, J=7.70, 1.63 Hz, 2H) 7.31-7.41 (m, 3H) 7.49 (d, J=9.22 Hz, 1H) 7.71 (s, 1H) 7.77 (s, 1H) 7.83 (d, J=9.32 Hz, 1H) 8.52 (s, 1H) 8.96 (s, 1H); MS (ESI+) m/z 478 (M+H+methanol)$^+$.

Example 108

(6aS,7S,10aR)-4-(4-hydroxyphenyl)-2,7-dimethyl-8-oxo-10a-phenyl-5,6,6a,7,8,10a-hexahydrobenzo[h]quinazoline-9-carbonitrile

Example 108A (6aS,7S,10aS)-4-(4-hydroxyphenyl)-2,7-dimethyl-10a-phenyl-5,6a,7,9,10,10a-hexahydrobenzo[h]quinazolin-8(6H)-one The titled compound was prepared using the conditions described in Example 17A, substituting (4-hydroxyphenyl)boronic acid for 1-methyl-5-(4,4,5,5-tetramethyl-1,3,2-dioxaborolan-2-yl)-1H-imidazole. Purification was achieved by flash chromatography on silica gel eluting with 5% acetone in chloroform to give the titled compound in 73% yield. $^1$H NMR (400 MHz, CDCl$_3$) δ ppm 1.15 (d, J=6.61 Hz, 3H) 1.93-2.13 (m, 3H) 2.29-2.60 (m, 4H) 2.74 (s, 3H) 2.79-2.87 (m, 1H) 2.87-2.97 (m, 1H) 3.17-3.25 (m, 1H) 5.32 (s, 1H) 6.84 (d, J=8.57 Hz, 2H) 7.20-7.38 (m, 5H) 7.53 (d, J=7.59 Hz, 2H); MS (ESI) m/z 399.3 (M+H)$^+$.

Example 108B (6aS,7S,9Z,10aS)-9-(hydroxymethylene)-4-(4-hydroxyphenyl)-2,7-dimethyl-10a-phenyl-5,6a,7,9,10,10a-hexahydrobenzo[h]quinazolin-8(6H)-one The titled compound was prepared using the conditions described in Example 13F, substituting Example 108A for Example 13E.

Example 108C

4-[(6aS,7S,11aS)-2,7-dimethyl-11a-phenyl-5,6,6a,7,11,11a-hexahydro[1,2]benzoxazolo[6,5-h]quinazolin-4-yl]phenol The titled compound was prepared using the conditions described in Example 13G, substituting Example 108B for Example 13F.

Example 108D (6aS,7S,10aS)-4-(4-hydroxyphenyl)-2,7-dimethyl-8-oxo-10a-phenyl-5,6,6a,7,8,9,10,10a-octahydrobenzo[h]quinazoline-9-carbonitrile The titled compound was prepared using the conditions described in Example 13H, substituting Example 108C for Example 13G. Purification was achieved by flash chromatography on silica gel eluting with 10-20% acetone in chloroform to give the titled compound in 54% yield.

Example 108E (6aS,7S,10aR)-4-(4-hydroxyphenyl)-2,7-dimethyl-8-oxo-10a-phenyl-5,6,6a,7,8,10a-hexahydrobenzo[h]quinazoline-9-carbonitrile A solution of Example 108D (0.059 g, 0.139 mmol) in tetrahydrofuran (1.4 mL) was sparged with nitrogen for 10 minutes. 2,3-Dichloro-5,6-dicyano-p-benzoquinone (0.032 g, 0.139 mmol) was added, and the resultant mixture was stirred at room temperature with a nitrogen sparge for 0.5 hour. The reaction mixture was concentrated, and the residue was purified on a reversed-phase Waters HPLC using a Nova-Pak HR C18, 6 μm, 60 Å, 40 mm×100 mm, PrepPak cartridge eluting with a gradient of 10-90% acetonitrile in aqueous 0.1% trifluoroacetic acid (60 mL/minute) to give the titled compound (0.039 g, 63%). $^1$H NMR (400 MHz, CDCl$_3$) δ ppm 1.17 (d, J=6.61 Hz, 3H) 1.58 (tt, J=13.27, 8.89, 8.70 Hz, 1H) 1.89-1.98 (m, 1H) 2.36 (td, J=12.79, 2.28 Hz, 1H) 2.47 (td, J=13.07, 6.61 Hz, 1H) 2.78 (s, 3H) 3.02 (dd, J=8.62, 4.50 Hz, 1H) 3.77 (s, 1H) 6.83 (dd, J=7.75, 1.68 Hz, 2H) 6.90 (d, J=8.57 Hz, 2H) 7.33-7.40 (m, 3H) 7.48 (d, J=8.57 Hz, 2H) 8.91 (s, 1H); MS (ESI+) m/z 454 (M+H+methanol)$^+$.

Example 109

(6aS,7S,10aR)-4-(3-hydroxyphenyl)-2,7-dimethyl-8-oxo-10a-phenyl-5,6,6a,7,8,10a-hexahydrobenzo[h]quinazoline-9-carbonitrile

Example 109A (6aS,7S,10aS)-4-(3-hydroxyphenyl)-2,7-dimethyl-10a-phenyl-5,6a,7,9,10,10a-hexahydrobenzo[h]quinazolin-8(6H)-one The titled compound was prepared using the conditions described in Example 17A, substituting (3-hydroxyphenyl) boronic acid for 1-methyl-5-(4,4,5,5-tetramethyl-1,3,2-dioxaborolan-2-yl)-1H-imidazole. Purification was achieved by flash chromatography on silica gel eluting with 33-50% ethyl acetate in heptane to give the titled compound in 68% yield.

Example 109B (6aS,7S,9Z,10aS)-9-(hydroxymethylene)-4-(3-hydroxyphenyl)-2,7-dimethyl-10a-phenyl-5,6a,7,9,10,10a-hexahydrobenzo[h]quinazolin-8(6H)-one The titled compound was prepared using the conditions described in Example 13F, substituting Example 109A for Example 13E.

Example 109C

3-[(6aS,7S,11aS)-2,7-dimethyl-11a-phenyl-5,6,6a,7,11,11a-hexahydro[1,2]benzoxazolo[6,5-h]quinazolin-4-yl]phenol The titled compound was prepared using the conditions described in Example 13G, substituting Example 109B for Example 13F.

Example 109D (6aS,7S,10aS)-4-(3-hydroxyphenyl)-2,7-dimethyl-8-oxo-10a-phenyl-5,6,6a,7,8,9,10,10a-octahydrobenzo[h]quinazoline-9-carbonitrile The titled compound was prepared using the conditions described in Example 13H, substituting Example 109C for Example 13G. Purification was achieved by flash chromatography on silica gel eluting with 10-20% acetone in chloroform to give the titled compound in 72% yield.

Example 109E (6aS,7S,10aR)-4-(3-hydroxyphenyl)-2,7-dimethyl-8-oxo-10a-phenyl-5,6,6a,7,8,10a-hexahydrobenzo[h]quinazoline-9-carbonitrile The titled compound was prepared using the conditions described in Example 108E, substituting Example 109D for Example 108D and purified on a reversed-phase Waters HPLC using a Nova-Pak HR C18, 6 μm, 60 Å, 40 mm×100 mm, PrepPak cartridge eluting with a gradient of 10-90% acetonitrile in aqueous 0.1% trifluoroacetic acid (60 mL/minute) to give the titled compound in 16% yield. $^1$H NMR (400 MHz, CDCl$_3$) δ ppm 1.16 (d, J=6.61 Hz, 3H) 1.55 (tt, 1H) 1.84-1.94 (m, 1H) 2.35 (td, J=12.82, 2.22 Hz, 1H) 2.46 (td, J=13.09, 6.67 Hz, 1H) 2.74 (s, 3H) 2.93-2.99 (m, 2H) 6.81-6.87 (m, 2H) 6.93 (dd, J=8.24, 2.39 Hz, 1H) 7.03 (s, 1H) 7.08 (d, J=7.59 Hz, 1H) 7.31-7.41 (m, 4H) 8.96 (s, 1H); MS (ESI+) m/z 454 (M+H+methanol)$^+$.

Example 110

(6aS,7S,10aR)-4-[3-(3-hydroxypropyl)phenyl]-2,7-dimethyl-8-oxo-10a-phenyl-5,6,6a,7,8,10a-hexahydrobenzo[h]quinazoline-9-carbonitrile

Example 110A (6aS,7S,10aS)-4-[3-(3-hydroxypropyl)phenyl]-2,7-dimethyl-10a-phenyl-5,6a,7,9,10,10a-hexahydrobenzo[h]quinazolin-8(6H)-one The titled compound was prepared using the conditions described in Example 17A, substituting (3-(3-hydroxypropyl)phenyl)boronic acid for 1-methyl-5-(4,4,5,5-tetramethyl-1,3,2-dioxaborolan-2-yl)-1H-imidazole. Purification was achieved by flash chromatography on silica gel eluting with 5-15% acetone in chloroform to give the titled compound in 76% yield. $^1$H NMR (400 MHz, CDCl$_3$) δ ppm 1.15 (d, J=6.61 Hz, 3H) 1.23-1.29 (m, 2H) 1.85-2.13 (m, 5H) 2.29-2.60 (m, 4H) 2.72-2.78 (m, 3H) 2.72-2.78 (m, 2H) 2.78-2.94 (m, 2H) 3.19-3.27 (m, 1H) 3.68 (t, J=6.34 Hz, 2H) 7.21-7.37 (m, 5H) 7.54 (d, J=7.81 Hz, 2H); MS (DCI) m/z 441.1 (M+H)$^+$.

Example 110B (6aS,7S,9Z,10aS)-9-(hydroxymethylene)-4-[3-(3-hydroxypropyl)phenyl]-2,7-dimethyl-10a-phenyl-5,6a,7,9,10,10a-hexahydrobenzo[h]quinazolin-8(6H)-one The titled compound was prepared using the conditions described in Example 13F, substituting Example 110A for Example 13E.

Example 110C

3-{3-[(6aS,7S,11aS)-2,7-dimethyl-11a-phenyl-5,6,6a,7,11,11a-hexahydro[1,2]benzoxazolo[6,5-h]quinazolin-4-yl]phenyl}propan-1-ol The titled compound was prepared using the conditions described in Example 13G, substituting Example 110B for Example 13F.

Example 110D

3-{3-[(6aS,7S,10aS)-9-cyano-2,7-dimethyl-8-oxo-10a-phenyl-5,6,6a,7,8,9,10,10a-octahydrobenzo[h]quinazolin-4-yl]phenyl}propyl acetate The titled compound was prepared using the conditions described in Example 13H, substituting Example 110C for Example 13G.

Example 110E (6aS,7S,10aS)-4-[3-(3-hydroxypropyl)phenyl]-2,7-dimethyl-8-oxo-10a-phenyl-5,6,6a,7,8,9,10,10a-octahydrobenzo[h]quinazoline-9-carbonitrile To a solution of Example 110D (0.28 g, 0.55 mmol) in methanol (5.3 mL) was added 25% sodium methoxide in methanol (0.24 mL, 0.11 mmol). The reaction mixture was stirred at room temperature for 2 hours, diluted with ethyl acetate, and washed with saturated potassium phosphate monobasic and saturated sodium chloride. The organic fraction was dried over magnesium sulfate, filtered and concentrated under reduced pressure. Purification was achieved by flash chromatography on silica gel eluting with 10-20% acetone in chloroform to give the titled compound (0.19 g, 76% yield).

Example 110F (6aS,7S,10aR)-4-[3-(3-hydroxypropyl)phenyl]-2,7-dimethyl-8-oxo-10a-phenyl-5,6,6a,7,8,10a-hexahydrobenzo[h]quinazoline-9-carbonitrile The titled compound was prepared using the conditions described in Example 131, substituting Example 107E for Example 13H. Purification was achieved by flash chromatography on silica gel eluting with 25% ethyl acetate in chloroform to give the titled compound in 51% yield. $^1$H NMR (400 MHz, CDCl$_3$) δ ppm 1.17 (d, J=6.61 Hz, 3H) 1.47-1.61 (m, 1H) 1.84-1.90 (m, 1H) 1.91-2.00 (m, 2H) 2.35 (td, J=12.77, 2.11 Hz, 1H) 2.46 (td, J=13.04, 6.67 Hz, 1H) 2.72 (s, 3H) 2.78-2.85 (m, 2H) 2.94 (dd, J=8.78, 4.45 Hz, 2H) 3.72 (t, J=6.29 Hz, 2H) 6.84 (d, J=6.61 Hz, 2H) 7.30-7.40 (m, 6H) 7.44 (t, J=7.48 Hz, 1H) 8.97 (s, 1H); MS (ESI+) m/z 496 (M+H+methanol)$^+$.

Example 111

(6aS,7S,10aR)-2-(5-bromo-2-hydroxyphenyl)-7-methyl-8-oxo-10a-phenyl-5,6,6a,7,8,10a-hexahydrobenzo[h]quinazoline-9-carbonitrile

Example 111A

2-[(6aS,7S,10aS)-7-methyl-10a-phenyl-5,6a,7,9,10,10a-hexahydro-6H-spiro[benzo[h]quinazoline-8,2'-[1,3]dioxolan]-2-yl]phenol To a solution of Example 1G (0.725 g, 2.21 mmol) in isopropanol (12 mL) was added 2-hydroxybenzimidamide sulfate (1.03 g, 4.42 mmol) and piperidine (0.481 g, 4.86 mmol). The reaction mixture was heated at 95° C. for 48 hours. The cooled solution was diluted with saturated aqueous sodium phosphate monobasic solution and extracted with ethyl acetate. The organic fraction was concentrated to provide the titled compound.

Example 111B (6aS,7S,10aS)-2-(2-hydroxyphenyl)-7-methyl-10a-phenyl-5,6a,7,9,10,10a-hexahydrobenzo[h]quinazolin-8(6H)-one The titled compound was prepared using the conditions described in Example 1I, substituting Example 111A for Example 1H. MS (APCI+) m/z 385 (M+H)$^+$.

Example 111C (6aS,7S,9Z,10aS)-9-(hydroxymethylene)-2-(2-hydroxyphenyl)-7-methyl-10a-phenyl-5,6a,7,9,10,10a-hexahydrobenzo[h]quinazolin-8(6H)-one The titled compound was prepared using the conditions described in Example 1J, substituting Example 111B for Example 1I.

Example 111D

2-[(6aS,7S,11aS)-7-methyl-11a-phenyl-5,6,6a,7,11,11a-hexahydro[1,2]benzoxazolo[6,5-h]quinazolin-2-yl]phenol The titled compound was prepared using the conditions described in Example 1K, substituting Example 111C for Example 1J

Example 111E (6aS,7S,10aS)-2-(2-hydroxyphenyl)-7-methyl-8-oxo-10a-phenyl-5,6,6a,7,8,9,10,10a-octahydrobenzo[h]quinazoline-9-carbonitrile The titled compound was prepared using the conditions described in Example 1L, substituting Example 111D for Example 1K. MS (APCI+) m/z 410 (M+H)$^+$.

Example 111F (6aS,7S,10aR)-2-(5-bromo-2-hydroxyphenyl)-7-methyl-8-oxo-10a-phenyl-5,6,6a,7,8,10a-hexahydrobenzo[h]quinazoline-9-carbonitrile To a solution of Example 111E (0.055 g, 0.134 mmol) in dimethylacetamide (2 mL) cooled to 0° C. in an ice water bath was added 1,3-dibromo-5,5-dimethylhydantoin (0.020 g, 0.067 mmol). The solution was stirred at 0° C. for 35 minutes, and then pyridine (0.109 mL, 1.34 mmol) was added, and the solution was heated at 50° C. for 2 hours. The cooled solution was diluted with water and extracted with ethyl acetate. The organic phase was washed with brine and concentrated. The residue was purified on a 4 g RediSep® cartridge using a Teledyne Isco Combiflash® Rf, eluting with 0-30% ethyl acetate in heptane. A second purification was done by preparative HPLC on a Waters Sunfire™ C8(2) 5 μm 100 Å column (30 mm×75 mm). A gradient of acetonitrile (A) and 0.1% trifluoroacetic acid in water (B) was used at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to give 0.0015 g (2.3%) of the titled compound. $^1$H NMR (400 MHz, CDCl$_3$) δ ppm 1.22 (d, J=6.61 Hz, 3H) 1.66-1.76 (m, 1H) 1.97-2.04 (m, 1H) 2.38 (td, J=12.88, 2.22 Hz, 1H) 2.50 (td, J=13.07, 6.51 Hz, 1H) 3.03-3.24 (m, 2H) 6.83 (dd, J=7.48, 1.95 Hz, 2H) 6.90 (d, J=8.78 Hz, 1H) 7.32-7.38 (m, 3H) 7.44 (dd, J=8.73, 2.66 Hz, 1H) 8.40 (d, J=2.49 Hz, 1H) 8.70 (s, 1H) 8.84 (s, 1H); MS (ESI+) m/z 486 (M+H)$^+$.

Example 112

N-{4-[(5aS,6S,9aR)-8-cyano-6-methyl-7-oxo-9a-phenyl-4,5,5a,6,7,9a-hexahydro-2H-benzo[g]indazol-3-yl]phenyl}methanesulfonamide

Example 112A (5aS,6S,9aS)—N,N,6-trimethyl-3-{4-[(methylsulfonyl)amino]phenyl}-9a-phenyl-4,5,5a,8,9,9a-hexahydrospiro[benzo[g]indazole-7,2'-[1,3]dioxolane]-2(6H)-sulfonamide The titled compound was prepared using the conditions described in Example 86A substituting compound 3-(4,4,5,5-tetramethyl-1,3,2-dioxaborolan-2-yl)pyridine with N-(4-

(4,4,5,5-tetramethyl-1,3,2-dioxaborolan-2-yl)phenyl)methanesulfonamide. MS (APCI) m/z 450 (M+H)+.

Example 112B

N-{4-[(5aS,6S,9aS)-6-methyl-7-oxo-9a-phenyl-4,5,5a,6,7,8,9,9a-octahydro-2H-benzo[g]indazol-3-yl]phenyl}methanesulfonamide The titled compound was prepared using the conditions described in Example 86B substituting Example 86A with Example 112A.

Example 112C

N-{4-[(5aS,6S,8Z,9aS)-8-(hydroxymethylene)-6-methyl-7-oxo-9a-phenyl-4,5,5a,6,7,8,9,9a-octahydro-2H-benzo[g]indazol-3-yl]phenyl}methanesulfonamide The titled compound was prepared using the conditions described in Example 24C substituting Example 24B with Example 112B. MS (APCI) m/z 478 (M+H)+.

Example 112D

N-{4-[(5aS,6S,10aS)-6-methyl-10a-phenyl-4,5,5a,6,10,10a-hexahydro-2H-indazolo[7,6-f][1,2]benzoxazol-3-yl]phenyl}methanesulfonamide The titled compound was prepared using the conditions described in Example 24D substituting Example 24C with Example 112C.

Example 112E

N-{4-[(5aS,6S,9aS)-8-cyano-6-methyl-7-oxo-9a-phenyl-4,5,5a,6,7,8,9,9a-octahydro-2H-benzo[g]indazol-3-yl]phenyl}methanesulfonamide The titled compound was prepared using the conditions described in Example 24E substituting Example 24D with Example 112D. MS (APCI) m/z 475 (M+H)+

Example 112F

N-{4-[(5aS,6S,9aR)-8-cyano-6-methyl-7-oxo-9a-phenyl-4,5,5a,6,7,9a-hexahydro-2H-benzo[g]indazol-3-yl]phenyl}methanesulfonamide Compound 112E (0.030 g, 0.063 mmol) was dissolved in tetrahydrofuran (0.63 mL), and nitrogen was sparged through the solution for 10 minutes. 2,3-Dichloro-5,6-dicyano-1,4-benzoquinone (0.014 g, 0.063 mmol) was then added, and the reaction mixture was stirred at room temperature for 10 minutes with continued nitrogen sparging. The reaction mixture was concentrated, and the residue was purified on a reversed-phase Waters HPLC using a Nova-Pak® HR C18, 6 µm, 60 Å, 40 mm×100 mm, PrepPak cartridge eluting with a gradient of 10-90% acetonitrile in aqueous 0.1% trifluoroacetic acid (60 mL/minute) to give the titled compound as the trifluoroacetic acid salt (0.007 g, 23%). $^1$H NMR (400 MHz, DMSO-$d_6$) δ ppm 1.06 (d, J=6.6 Hz, 3H), 1.38 (s, 1H), 1.81 (s, 1H), 2.36 (d, J=6.7 Hz, 1H), 2.84 (d, J=7.1 Hz, 1H), 2.92-2.99 (m, 1H), 3.03 (s, 3H), 6.95 (d, J=7.3 Hz, 2H), 7.32 (dt, J=11.1, 4.7 Hz, 6H), 7.69 (d, J=8.6 Hz, 2H), 8.43 (s, 1H), 9.91 (s, 1H); MS (ESI+) m/z 473 (M+H)+.

Example 113

N-{3-[(6S,9aR)-8-cyano-6-methyl-7-oxo-9a-phenyl-4,5,5a,6,7,9a-hexahydro-2H-benzo[g]indazol-3-yl]phenyl}methanesulfonamide Example 113A (5aS,6S,9aS)—N,N,6-trimethyl-3-{3-[(methylsulfonyl)amino]phenyl}-9a-phenyl-4,5,5a,8,9,9a-hexahydrospiro[benzo[g]indazole-7,2'-[1,3]dioxolane]-2(6H)-sulfonamide The titled compound was prepared using the conditions described in Example 86A substituting compound 3-(4,4,5,5-tetramethyl-1,3,2-dioxaborolan-2-yl)pyridine with N-(3-(4,4,5,5-tetramethyl-1,3,2-dioxaborolan-2-yl)phenyl)methanesulfonamide. MS (APCI) m/z 450 (M+H)+.

Example 113B

N-{3-[(5aS,6S,9aS)-6-methyl-7-oxo-9a-phenyl-4,5,5a,6,7,8,9,9a-octahydro-2H-benzo[g]indazol-3-yl]phenyl}methanesulfonamide The titled compound was prepared using the conditions described in Example 86B substituting Example 86A with Example 113A.

Example 113C

N-{3-[(5aS,6S,8Z,9aS)-8-(hydroxymethylene)-6-methyl-7-oxo-9a-phenyl-4,5,5a,6,7,8,9,9a-octahydro-2H-benzo[g]indazol-3-yl]phenyl}methanesulfonamide The titled compound was prepared using the conditions described in Example 24C substituting Example 24B with Example 113B. MS (APCI) m/z 478 (M+H)+.

Example 113D

N-{3-[(5aS,6S,10aS)-6-methyl-10a-phenyl-4,5,5a,6,10,10a-hexahydro-2H-indazolo[7,6-][1,2]benzoxazol-3-yl]phenyl}methanesulfonamide The titled compound was prepared using the conditions described in Example 24D substituting Example 24C with Example 113C. MS (APCI) m/z 475 (M+H)+.

Example 113E

N-{3-[(5aS,6S,9aS)-8-cyano-6-methyl-7-oxo-9a-phenyl-4,5,5a,6,7,8,9,9a-octahydro-2H-benzo[g]indazol-3-yl]phenyl}methanesulfonamide The titled compound was prepared using the conditions described in Example 24E substituting Example 24D with Example 113D.

Example 113F

N-{3-[(6S,9aR)-8-cyano-6-methyl-7-oxo-9a-phenyl-4,5,5a,6,7,9a-hexahydro-2H-benzo[g]indazol-3-yl]phenyl}methanesulfonamide Example 113E (0.030 g, 0.063 mmol) was dissolved in tetrahydrofuran (0.63 mL) and nitrogen was bubbled through the solution for 10 minutes. 2,3-Dichloro-5,6-dicyano-1,4-benzoquinone (0.014 g, 0.063 mmol) was then added, and the reaction mixture was stirred at room temperature for 10 minutes with nitrogen bubbling continued. The reaction mixture was then concentrated. The residue was purified on a reversed-phase Waters HPLC using a Nova-Pak® HR C18, 6 µm, 60 Å, 40 mm×100 mm, PrepPak cartridge eluting with a gradient of 10-90% acetonitrile in aqueous 0.1% trifluoroacetic acid (60 mL/minute) to give the titled compound as the trifluoroacetic acid salt (0.018 g, 60%). $^1$H NMR (400 MHz, DMSO-d$_6$) δ ppm 1.05-1.10 (m, 3H), 1.39 (d, J=11.7 Hz, 1H), 1.83 (d, J=12.3 Hz, 1H), 2.36 (dd, J=13.1, 6.3 Hz, 1H), 2.85 (d, J=11.1 Hz, 1H), 2.97 (s, 1H), 3.04 (s, 3H), 6.95 (d, J=7.3 Hz, 2H), 7.17 (d, J=7.2 Hz, 1H), 7.26-7.38 (m, 4H), 7.45 (dt, J=15.6, 7.8 Hz, 2H), 7.60 (s, 1H), 8.44 (s, 1H), 9.88 (s, 1H); MS (ESI+) m/z 473 (M+H)$^+$.

Example 114

(6aS,7S,10aR)-2-(4-hydroxyphenyl)-7-methyl-8-oxo-10a-phenyl-5,6,6a,7,8,10a-hexahydrobenzo[h]quinazoline-9-carbonitrile

Example 114A

4-[(6aS,7S,10aS)-7-methyl-10a-phenyl-5,6a,7,9,10,10a-hexahydro-6H-spiro[benzo[h]quinazoline-8,2'-[1,3]dioxolan]-2-yl]phenol To a solution of Example 1G (0.590 g, 1.80 mmol) in isopropanol (12 mL) was added 4-hydroxybenzamidine hydrochloride (0.620 g, 3.59 mmol) and piperidine (0.356 g, 3.59 mmol). The reaction mixture was heated at 95° C. for 48 hours. The cooled solution was diluted with saturated aqueous sodium phosphate monobasic solution and extracted with ethyl acetate. The organic fraction was concentrated to give the titled compound. MS (APCI+) m/z 429 (M+H)$^+$.

Example 114B (6aS,7S,10aS)-2-(4-hydroxyphenyl)-7-methyl-10a-phenyl-5,6a,7,9,10,10a-hexahydrobenzo[h]quinazolin-8(6H)-one The titled compound was prepared using the conditions described in Example 1I, substituting Example 114A for Example 1H.

Example 114C (6aS,7S,9Z,10aS)-9-(hydroxymethylene)-2-(4-hydroxyphenyl)-7-methyl-10a-phenyl-5,6a,7,9,10,10a-hexahydrobenzo[h]quinazolin-8(6H)-one The titled compound was prepared using the conditions described in Example 1J, substituting Example 114B for Example 1I.

Example 114D

4-[(6aS,7S,11aS)-7-methyl-11a-phenyl-5,6,6a,7,11,11a-hexahydro[1,2]benzoxazolo[6,5-h]quinazolin-2-yl]phenol The titled compound was prepared using the conditions described in Example 1K, substituting Example 114C for Example 1J. MS (APCI+) m/z 410 (M+H)$^+$.

Example 114E (6aS,7S,10aS)-2-(4-hydroxyphenyl)-7-methyl-8-oxo-10a-phenyl-5,6,6a,7,8,9,10,10a-octahydrobenzo[h]quinazoline-9-carbonitrile The titled compound was prepared using the conditions described in Example 1L, substituting Example 114D for Example 1K.

Example 114F (6aS,7S,10aR)-2-(4-hydroxyphenyl)-7-methyl-8-oxo-10a-phenyl-5,6,6a,7,8,10a-hexahydrobenzo[h]quinazoline-9-carbonitrile A solution of Example 114E (0.146 g, 0.357 mmol) in tetrahydrofuran (5 mL) at room temperature was sparged with nitrogen for 10 minutes. Then 2,3-dichloro-5,6-dicyano-1,4-benzoquinone (0.081 g, 0.357 mmol) was added. After 10 minutes, the solution was concentrated, and the residue was put directly on a 12 g RediSep® cartridge and purified using a Teledyne Isco Combiflash® Rf eluting with 0-40% ethyl acetate in heptane to give 0.068 g (47%) of the titled compound. $^1$H NMR (400 MHz, CDCl$_3$) δ ppm 1.21 (d, J=6.61 Hz, 3H) 1.59-1.69 (m, 1H) 1.98 (dd, J=13.72, 7.64 Hz, 1H) 2.36 (td, J=12.88, 2.33 Hz, 1H) 2.49 (td, J=13.17, 6.61 Hz, 1H) 2.95-3.16 (m, 2H) 5.13 (s, 1H) 6.85 (dd, J=7.75, 1.68 Hz, 2H) 6.90 (d, J=8.78 Hz, 2H) 7.28-7.36 (m, 3H) 8.29 (d, J=8.78 Hz, 2H) 8.71 (s, 1H) 9.01 (s, 1H); MS (ESI+) m/z 408 (M+H)$^+$.

Example 115

(5aS,6S,9aR)-3-[4-(2-hydroxyethyl)phenyl]-6-methyl-7-oxo-9a-phenyl-4,5,5a,6,7,9a-hexahydro-2H-benzo[g]indazole-8-carbonitrile

Example 115A (5aS,6S,9aS)-3-[4-(2-hydroxyethyl)phenyl]-N,N,6-trimethyl-9a-phenyl-4,5,5a,8,9,9a-hexahydrospiro[benzo[g]indazole-7,2'-[1,3]dioxolane]-2(6H)-sulfonamide The titled compound was prepared using the conditions described in Example 86A substituting 3-(4,4,5,5-tetramethyl-1,3,2-dioxaborolan-2-yl)pyridine with 2-(4-(4,4,5,5-tetramethyl-1,3,2-dioxaborolan-2-yl)phenyl)ethanol.

Example 115B (5aS,6S,9aS)-3-[4-(2-hydroxyethyl)phenyl]-6-methyl-9a-phenyl-2,4,5,5a,6,8,9,9a-octahydro-7H-benzo[g]indazol-7-one The titled compound was prepared using the conditions described in Example 86B substituting Example 86A with Example 115A.

Example 115C (5aS,6S,8Z,9aS)-3-[4-(2-hydroxyethyl)phenyl]-8-(hydroxymethylene)-6-methyl-9a-phenyl-2,4,5,5a,6,8,9,9a-octahydro-7H-benzo[g]indazol-7-one The titled compound was prepared using the conditions described in Example 24C substituting Example 24B with Example 115B. MS (APCI) m/z 457 (M+H)$^+$.

Example 115D

2-{4-[(5aS,6S,10aS)-6-methyl-10a-phenyl-4,5,5a,6,10,10a-hexahydro-2H-indazolo[7,6-f][1,2]benzoxazol-3-yl]phenyl}ethanol The titled compound was prepared using the conditions described in Example 24D substituting Example 24C with Example 115C. MS (APCI) m/z 426 (M+H)$^+$

Example 115E (5aS,6S,9aS)-3-[4-(2-hydroxyethyl)phenyl]-6-methyl-7-oxo-9a-phenyl-4,5,5a,6,7,8,9,9a-octahydro-2H-benzo[g]indazole-8-carbonitrile The titled compound was prepared using the conditions described in Example 24E substituting Example 24D with Example 115D.

Example 115F (5aS,6S,9aR)-3-[4-(2-hydroxyethyl)phenyl]-6-methyl-7-oxo-9a-phenyl-4,5,5a,6,7,9a-hexahydro-2H-benzo[g]indazole-8-carbonitrile Example 115E (0.040 g, 0.094 mmol) was dissolved in tetrahydrofuran (0.94 mL) and nitrogen was bubbled into the solution for 10 minutes. 2,3-Dichloro-5,6-dicyano-1,4-benzoquinone (0.021 g, 0.094 mmol) was added at this time, and the reaction mixture was stirred at room temperature for 10 minutes with nitrogen bubbling continued. The reaction mixture was concentrated, and the residue was purified on a reversed-phase Waters HPLC using a Nova-Pak® HR C18, 6 μm, 60 Å, 40 mm×100 mm, PrepPak cartridge eluting with a gradient of 10-90% acetonitrile in aqueous 0.1% trifluoroacetic acid (60 mL/minute) to give the titled compound as the trifluoroacetic acid salt (0.015 g, 37%). $^1$H NMR (400 MHz, DMSO-d$_6$) δ ppm 1.06 (d, J=6.6 Hz, 3H), 1.33-1.47 (m, 1H), 1.82 (dd, J=12.8, 6.7 Hz, 1H), 2.32-2.39 (m, 1H), 2.75 (t, J=7.0 Hz, 2H), 2.79-2.90 (m, 1H), 2.96 (dd, J=16.6, 6.2 Hz, 1H), 3.62 (t, J=7.0 Hz, 3H), 6.95 (d, J=7.4 Hz, 2H), 7.24-7.38 (m, 5H), 7.62 (d, J=8.1 Hz, 2H), 8.43 (s, 1H); MS (ESI+) m/z 424 (M+H)$^+$.

Example 116

(5aS,6S,9aR)-3-[3-(2-hydroxyethyl)phenyl]-6-methyl-7-oxo-9a-phenyl-4,5,5a,6,7,9a-hexahydro-2H-benzo[g]indazole-8-carbonitrile

Example 116A (5aS,6S,9aS)-3-[3-(2-hydroxyethyl)phenyl]-N,N,6-trimethyl-9a-phenyl-4,5,5a,8,9,9a-hexahydrospiro[benzo[g]indazole-7,2'-[1,3]dioxolane]-2(6H)-sulfonamide The titled compound was prepared using the conditions described in Example 86A substituting 3-(4,4,5,5-tetramethyl-1,3,2-dioxaborolan-2-yl)pyridine with 2-(3-(4,4,5,5-tetramethyl-1,3,2-dioxaborolan-2-yl)phenyl)ethanol.

Example 116B (5aS,6S,9aS)-3-[3-(2-hydroxyethyl)phenyl]-6-methyl-9a-phenyl-2,4,5,5a,6,8,9,9a-octahydro-7H-benzo[g]indazol-7-one The titled compound was prepared using the conditions described in Example 86B substituting Example 86A with Example 116A. MS (APCI) m/z 401 (M+H)$^+$.

Example 116C (5aS,6S,8Z,9aS)-3-[3-(2-hydroxyethyl)phenyl]-8-(hydroxymethylene)-6-methyl-9a-phenyl-2,4,5,5a,6,8,9,9a-octahydro-7H-benzo[g]indazol-7-one The titled compound was prepared using the conditions described in Example 24C substituting Example 24B with Example 116B.

Example 116D

2-{3-[(5aS,6S,10aS)-6-methyl-10a-phenyl-4,5,5a,6,10,10a-hexahydro-2H-indazolo[7,6-][1,2]benzoxazol-3-yl]phenyl}ethanol The titled compound was prepared using the conditions described in Example 24D substituting Example 24C with Example 116C. MS (APCI) m/z 426 (M+H)$^+$.

Example 116E (5aS,6S,9aS)-3-[3-(2-hydroxyethyl)phenyl]-6-methyl-7-oxo-9a-phenyl-4,5,5a,6,7,8,9,9a-octahydro-2H-benzo[g]indazole-8-carbonitrile The titled compound was prepared using the conditions described in Example 24E substituting Example 24D with Example 116D.

Example 116F (5aS,6S,9aR)-3-[3-(2-hydroxyethyl)phenyl]-6-methyl-7-oxo-9a-phenyl-4,5,5a,6,7,9a-hexahydro-2H-benzo[g]indazole-8-carbonitrile Example 116E (0.032 g, 0.075 mmol) was dissolved in tetrahydrofuran and nitrogen was bubbled through the solution for 10 minutes. 2,3-Dichloro-5,6-dicyano-1,4-benzoquinone (0.017 g, 0.075 mmol) was then added, and the reaction mixture was stirred at room temperature for 10 minutes with continued nitrogen bubbling. The reaction mixture was concentrated, and then the residue was purified on a reversed-phase Waters HPLC using a Nova-Pak® HR C18, 6 μm, 60 Å, 40 mm×100 mm, PrepPak cartridge eluting with a gradient of 10-90% acetonitrile in aqueous 0.1% trifluoroacetic acid (60 mL/minute) to give the titled compound as the trifluoroacetic acid salt (0.012 g, 38%). $^1$H NMR (400 MHz, DMSO-d$_6$) δ ppm 1.07 (d, J=6.7 Hz, 3H), 1.39 (s, 1H), 1.81 (s, 1H), 2.33-2.40 (m, 2H), 2.77 (d, J=7.0 Hz, 2H), 2.86 (s, 1H), 2.97 (d, J=10.3 Hz, 2H), 3.65 (t, J=6.9 Hz, 2H), 6.95 (d, J=7.5 Hz, 2H), 7.22 (d, J=7.3 Hz, 1H), 7.34

(ddd, J=23.5, 15.8, 7.4 Hz, 4H), 7.53 (d, J=8.3 Hz, 1H), 7.58 (s, 1H), 8.44 (s, 1H); MS (ESI) m/z 424 (M+H)$^+$.

Example 117

(5aS,6S,9aR)-3-[1-(2-hydroxyethyl)-1H-pyrazol-4-yl]-6-methyl-7-oxo-9a-phenyl-4,5,5a,6,7,9a-hexahydro-2H-benzo[g]indazole-8-carbonitrile

Example 117A

2-{4-[(5aS,6S,9aS)-2-(dimethylsulfamoyl)-6-methyl-9a-phenyl-2,4,5,5a,6,8,9,9a-octahydrospiro[benzo[g]indazole-7,2'-[1,3]dioxolan]-3-yl]-1H-pyrazol-1-yl}ethyl acetate The titled compound was prepared using the conditions described in Example 86A substituting 3-(4,4,5,5-tetramethyl-1,3,2-dioxaborolan-2-yl)pyridine with 2-(4-(4,4,5,5-tetramethyl-1,3,2-dioxaborolan-2-yl)-1H-pyrazol-1-yl)ethyl acetate.

Example 117B (5aS,6S,9aS)-3-[1-(2-hydroxyethyl)-1H-pyrazol-4-yl]-6-methyl-9a-phenyl-2,4,5,5a,6,8,9,9a-octahydro-7H-benzo[g]indazol-7-one The titled compound was prepared using the conditions described in Example 86B substituting Example 86A with Example 117A. MS (APCI) m/z 391 (M+H)$^+$.

Example 117C (5aS,6S,8Z,9aS)-3-[1-(2-hydroxyethyl)-1H-pyrazol-4-yl]-8-(hydroxymethylene)-6-methyl-9a-phenyl-2,4,5,5a,6,8,9,9a-octahydro-7H-benzo[g]indazol-7-one The titled compound was prepared using the conditions described in Example 24C substituting Example 24B with Example 117B.

Example 117D

2-{4-[(5aS,6S,10aS)-6-methyl-10a-phenyl-4,5,5a,6,10,10a-hexahydro-2H-indazolo[7,6-l][1,2]benzoxazol-3-yl]-1H-pyrazol-1-yl}ethanol The titled compound was prepared using the conditions described in Example 24D substituting Example 24C with Example 117C. MS (APCI) m/z 457 (M+H)$^+$.

Example 117E (5aS,6S,9aS)-3-[1-(2-hydroxyethyl)-1H-pyrazol-4-yl]-6-methyl-7-oxo-9a-phenyl-4,5,5a,6,7,8,9,9a-octahydro-2H-benzo[g]indazole-8-carbonitrile The titled compound was prepared using the conditions described in Example 24E substituting Example 24D with Example 117D.

Example 117F (5aS,6S,9aR)-3-[1-(2-hydroxyethyl)-1H-pyrazol-4-yl]-6-methyl-7-oxo-9a-phenyl-4,5,5a,6,7,9a-hexahydro-2H-benzo[g]indazole-8-carbonitrile Example 117E (0.025 g, 0.060 mmol) was dissolved in tetrahydrofuran and nitrogen was bubbled through the mixture for 10 minutes. 2,3-Dichloro-5,6-dicyano-1,4-benzoquinone (0.013 g, 0.060 mmol) was added, and the reaction mixture was stirred at room temperature for 10 minutes with continued nitrogen bubbling. The reaction mixture was concentrated, and then the residue was purified on a reversed-phase Waters HPLC using a Nova-Pak® HR C18, 6 µm, 60 Å, 40 mm×100 mm, PrepPak cartridge eluting with a gradient of 10-90% acetonitrile in aqueous 0.1% trifluoroacetic (60 mL/minute). Then a second chromatographic purification using preparative thin-layer chromatography eluting with 50% acetone in hexane gave the titled compound as the trifluoroacetic acid salt (0.004 g, 16%). $^1$H NMR (400 MHz, DMSO-d$_6$) δ ppm 1.06 (d, J=6.5 Hz, 3H), 1.29-1.46 (m, 1H), 1.72-1.86 (m, 1H), 2.35 (d, J=7.1 Hz, 1H), 2.68-2.76 (m, 1H), 2.85 (s, 1H), 2.91-3.04 (m, 1H), 3.75 (d, J=5.3 Hz, 2H), 4.19 (t, J=5.2 Hz, 2H), 4.96 (s, 1H), 6.94 (d, J=7.3 Hz, 2H), 7.32 (d, J=7.7 Hz, 3H), 7.83 (s, 1H), 8.06 (s, 1H), 8.40 (s, 1H); MS (ESI) m/z 414 (M+H)$^+$.

Example 118

(6aS,7S,10aR)-4-(4'-aminobiphenyl-3-yl)-2,7-dimethyl-8-oxo-10a-phenyl-5,6,6a,7,8,10a-hexahydrobenzo[h]quinazoline-9-carbonitrile

Example 118A (6aS,7S,10aS)-4-(4'-aminobiphenyl-3-yl)-2,7-dimethyl-10a-phenyl-5,6a,7,9,10,10a-hexahydrobenzo[h]quinazolin-8(6H)-one The titled compound was prepared using the conditions described in Example 119B, substituting 4-(4,4,5,5-tetramethyl-1,3,2-dioxaborolan-2-yl)aniline for (4-hydroxyphenyl)boronic acid. $^1$H NMR (400 MHz, CDCl$_3$) δ ppm 1.15 (d, J=6.61 Hz, 3H) 1.95-2.14 (m, 3H) 2.29-2.64 (m, 4H) 2.75 (s, 3H) 2.77-2.86 (m, 1H) 2.88-2.99 (m, 1H) 3.20-3.29 (m, 1H) 3.74 (s, 2H) 6.75 (d, J=8.46 Hz, 2H) 7.21-7.26 (m, 1H) 7.29-7.35 (m, 3H) 7.38-7.48 (m, 3H) 7.51-7.60 (m, 4H); MS (ESI) m/z 474.3 (M+H)$^+$.

Example 118B

N-{3'-[(6aS,7S,9Z,10aS)-9-(hydroxymethylene)-2,7-dimethyl-8-oxo-10a-phenyl-5,6,6a,7,8,9,10,10a-octahydrobenzo[h]quinazolin-4-yl]biphenyl-4-yl}formamide The titled compound was prepared using the conditions described in Example 13F, substituting Example 118A for Example 13E.

Example 118C

3'-[(6aS,7S,11aS)-2,7-dimethyl-11a-phenyl-5,6,6a,7,11,11a-hexahydro[1,2]benzoxazolo[6,5-h]quinazolin-4-yl]biphenyl-4-amine The titled compound was prepared using the conditions described in Example 13G, substituting Example 118B for Example 13F

Example 118D (6aS,7S,10aS)-4-(4'-aminobiphenyl-3-yl)-2,7-dimethyl-8-oxo-10a-phenyl-5,6,6a,7,8,9,10,10a-octahydrobenzo[h]quinazoline-9-carbonitrile The titled compound was prepared using the conditions described in Example 13H, substituting Example 118C for Example 13G.

Example 118E (6aS,7S,10aR)-4-(4'-aminobiphenyl-3-yl)-2,7-dimethyl-8-oxo-10a-phenyl-5,6,6a,7,8,10a-hexahydrobenzo[h]quinazoline-9-carbonitrile The titled compound was prepared using the conditions described in Example 108E, substituting Example 118D for Example 108D and purified on a reversed-phase Waters HPLC using a Nova-Pak® HR C18, 6 µm, 60 Å, 40 mm×100 mm, PrepPak cartridge eluting with a gradient of 10-90% acetonitrile in aqueous 0.1% trifluoroacetic (60 mL/minute) give 6% yield. $^1$H NMR (400 MHz, CDCl$_3$) δ ppm 1.16 (d, J=6.51 Hz, 3H) 1.48-1.54 (m, 1H) 1.83-1.92 (m, 1H) 2.36 (td, J=12.79, 2.06 Hz, 1H) 2.45 (td, J=12.98, 6.45 Hz, 1H) 2.72 (s, 3H) 2.98 (dd, J=8.57, 4.12 Hz, 2H) 3.78 (s, 2H) 6.78 (d, J=8.46 Hz, 2H) 6.85 (d, J=6.51 Hz, 2H) 7.28-7.38 (m, 3H) 7.42-7.49 (m, 3H) 7.53 (t, J=7.64 Hz, 1H) 7.64 (d, J=8.13 Hz, 1H) 7.68 (s, 1H) 9.00 (s, 1H); MS (ESI) m/z 529 (M+H+methanol)$^+$.

Example 119

(6aS,7S,10aR)-4-(4'-hydroxybiphenyl-3-yl)-2,7-dimethyl-8-oxo-10a-phenyl-5,6,6a,7,8,10a-hexahydrobenzo[h]quinazoline-9-carbonitrile

Example 119A

3-[(6aS,7S,10aS)-2,7-dimethyl-8-oxo-10a-phenyl-5,6,6a,7,8,9,10,10a-octahydrobenzo[h]quinazolin-4-yl]phenyl trifluoromethanesulfonate To a solution of Example 109A (0.250 g, 0.627 mmol) in dichloromethane (6 mL) was added triethylamine (0.131 mL, 0.941 mmol) and N,N-bis(trifluoromethylsulfonyl)aniline (0.291 g, 0.816 mmol) and a catalytic amount of 4-dimethylaminopyridine (0.004 g, 0.031 mmol). The reaction mixture was stirred at room temperature for 24 hours. The mixture was diluted with dichloromethane and washed with 0.5 M hydrochloric acid. The organic phase was dried over sodium sulfate, filtered, and concentrated to give the titled compound. MS (APCI+) m/z 531 (M+H)$^+$.

Example 119B (6aS,7S,10aS)-4-(4'-hydroxybiphenyl-3-yl)-2,7-dimethyl-10a-phenyl-5,6a,7,9,10,10a-hexahydrobenzo[h]quinazolin-8(6H)-one A solution of Example 119A (0.330 g, 0.622 mmol), 4-hydroxyphenyl boronic acid (0.112 g, 0.809 mmol), tetrakis(triphenylphosphine)palladium(0) (0.022 g, 0.019 mmol), potassium fluoride (0.043 g, 0.746 mmol), and potassium phosphate tribasic (0.198 g, 0.933 mmol) in 1,4-dioxane (6 mL) in a tube was sparged with nitrogen for 15 minutes, and then the tube was sealed and heated at 90° C. for 20 hours. The mixture was diluted with water and extracted with ethyl acetate. The organic fraction was concentrated, and the residue was purified using a Teledyne Isco Combiflash® system equipped with a 12 g silica gel column eluted with 0-30% ethyl acetate in heptane to give 0.190 g (64%) of the titled compound.

Example 119C (6aS,7S,9Z,10aS)-4-(4'-hydroxybiphenyl-3-yl)-9-(hydroxymethylene)-2,7-dimethyl-10a-phenyl-5,6a,7,9,10,10a-hexahydrobenzo[h]quinazolin-8(6H)-one The titled compound was prepared using the conditions described in Example 1J, substituting Example 119B for Example 1I.

Example 119D

3'-[(6aS,7S,11aS)-2,7-dimethyl-11a-phenyl-5,6,6a,7,11,11a-hexahydro[1,2]benzoxazolo[6,5-h]quinazolin-4-yl]biphenyl-4-ol The titled compound was prepared using the conditions described in Example 1K, substituting Example 119C for Example 1J. MS (APCI+) m/z 500 (M+H)$^+$.

Example 119E (6aS,7S,10aS)-4-(4'-hydroxybiphenyl-3-yl)-2,7-dimethyl-8-oxo-10a-phenyl-5,6,6a,7,8,9,10,10a-octahydrobenzo[h]quinazoline-9-carbonitrile The titled compound was prepared using the conditions described in Example 1L, substituting Example 119D for Example 1K.

Example 119F (6aS,7S,10aR)-4-(4'-hydroxybiphenyl-3-yl)-2,7-dimethyl-8-oxo-10a-phenyl-5,6,6a,7,8,10a-hexahydrobenzo[h]quinazoline-9-carbonitrile A solution of Example 119E (0.105 g, 0.210 mmol) in tetrahydrofuran (2.5 mL) at room temperature was sparged with nitrogen for 10 minutes, and then 2,3-dichloro-5,6-dicyano-1,4-benzoquinone (0.048 g, 0.210 mmol) was added. After 10 minutes, the solution was concentrated, and the residue was put directly on a 12 g RediSep® silica gel cartridge and purified using a Teledyne Isco Combiflash® Rf system eluting with 0-80% ethyl acetate in heptane. A second chromatographic purification was done by preparative HPLC on a Waters Sunfire™ C8(2) 5 µm 100 Å column (30 mm×75 mm). A gradient of acetonitrile (A) and 0.1% trifluoroacetic acid in water (B) was used, at a flow rate of 50 mL/minute (0-0.5 minute 10% A, 0.5-7.0 minutes linear gradient 10-95% A, 7.0-10.0 minutes 95% A, 10.0-12.0 minutes linear gradient 95-10% A) to give 0.055 g (53%) of the titled compound. $^1$H NMR (400 MHz, CDCl$_3$) δ ppm 1.16 (d, J=6.51 Hz, 3H) 1.48-1.52 (m, 1H) 1.88 (dd, J=15.51, 2.39 Hz, 1H) 2.36 (td, J=12.79, 2.28 Hz, 1H) 2.46 (td, J=13.01, 6.40 Hz, 1H) 2.72 (s, 3H) 2.98 (dd, J=8.46, 4.23 Hz, 2H) 6.85 (dd, J=7.92, 1.41 Hz, 2H) 6.93 (d, J=8.67 Hz, 2H) 7.33 (t, J=7.10 Hz, 3H) 7.45-7.59 (m, 4H) 7.65 (d, J=7.81 Hz, 1H) 7.69 (s, 1H) 9.00 (s, 1H); MS (ESI+) m/z 530 (M+CH$_3$OH+H)$^+$.

Example 120

(6aS,7S,10aR)-10a-[4-(benzyloxy)phenyl]-7-methyl-8-oxo-5,6,6a,7,8,10a-hexahydrobenzo[h]quinazoline-9-carbonitrile

Example 120A

2-[4-(benzyloxy)phenyl]cyclohexane-1,3-dione

A 1 L round-bottomed flask was charged with 1-(benzyloxy)-4-bromobenzene (50.0 g, 190 mmol), tert-amyl alcohol (200 mL) and dioxane (400 mL), and the contents were purged with $N_2$ for 45 minutes. A 3 L round-bottomed flask was charged with potassium phosphate tribasic (92 g, 433 mmol), 1,3-cyclohexanedione (97 weight %, 20 g, 173 mmol), palladium(II) acetate (0.78 g, 3.5 mmol) and 2-(di-tert-butylphospino)-2'-methylbiphenyl (2.16 g, 6.9 mmol), and the contents were purged with $N_2$ for 45 minutes. The 1-(benzyloxy)-4-bromobenzene containing solution was then transferred to the mixture containing 1,3-cyclohexanedione via cannula, and the reaction mixture was heated to reflux overnight. The reaction mixture was cooled to room temperature and was partitioned between ethyl acetate (600 mL) and 10% hydrochloric acid (600 mL) with mixing. The lower aqueous layer was separated and extracted with ethyl acetate (600 mL). The combined organic layers were washed with brine (2×100 mL) and concentrated under reduced pressure. The residue was taken up in toluene (300 mL) and again concentrated under reduced pressure. The residue was taken up in toluene (300 mL) and warmed to 50° C. After cooling to room temperature, the solids were collected by filtration, washed with toluene (2×50 mL) and dried in a vacuum oven at 50° C. (47.7 g, 93%). $^1$H NMR (400 MHz, DMSO-$d_6$) δ ppm 10.10 (bs, 1H), 7.51-7.23 (m, 5H), 7.07-6.96 (m, 2H), 6.92-6.82 (m, 2H), 5.07 (s, 2H), 2.48-2.40 (m, 4H), 1.96-1.85 (m, 2H); MS (CI—$NH_3$) 312.0 m/z $(M+NH_4)^+$.

Example 120B (8aR)-8a-[4-(benzyloxy)phenyl]-5-methyl-3,4,8,8a-tetrahydronaphthalene-1,6(2H,7H)-dione A 3 L round-bottomed flask was charged with Example 120A (47.4 g, 161 mmol) in acetonitrile (500 mL). Triethylamine (45 mL, 322 mmol) and ethyl vinyl ketone (20 mL, 242 mmol) were added, and the mixture was warmed to 75° C. and stirred overnight. The reaction mixture was cooled to room temperature and concentrated. The residue was taken up in dimethyl sulfoxide (75 mL), pyridinium para-toluenesulfonate (26.3 g, 105 mmol) and L-phenylalanine (34.6 g, 209 mmol) were added, and the mixture was warmed to 50° C. for 90 hours. The reaction mixture was cooled to room temperature and poured into 10% hydrochloric acid (500 mL) and methyl t-butyl ether (500 mL). After mixing for 10 minutes, the layers were separated, and the organic layer was washed with 10% hydrochloric acid (500 mL). The combined aqueous layers were extracted with methyl t-butyl ether (500 mL). The combined organic fractions were washed with brine (200 mL) and dried over sodium sulfate. The methyl t-butyl ether solution was passed through a short plug of silica gel (150 g) eluting with methyl t-butyl ether (1.5 L). The filtrate was concentrated to give a solid. The solid was triturated with methyl t-butyl ether (60 mL), collected by filtration and dried in a vacuum oven (32.6 g, 56%). $^1$H NMR (400 MHz, CDCl$_3$) δ ppm 7.46-7.29 (m, 5H), 7.08-7.00 (m, 2H), 6.97-6.90 (m, 2H), 5.05 (s, 2H), 2.79-2.69 (m, 1H), 2.68-2.57 (m, 1H), 2.57-2.47 (m, 1H), 2.41-2.28 (m, 3H), 2.24-2.16 (m, 1H), 2.12-2.01 (m, 1H), 1.95 (s, 3H), 1.87-1.75 (m, 1H), 1.75-1.65 (m, 1H); MS (CI—$NH_3$) 378.1 m/z $(M+NH_4)^+$.

Example 120C (4aR,5S)-4a-[4-(benzyloxy)phenyl]-5-hydroxy-1-methyl-4,4a,5,6,7,8-hexahydronaphthalen-2(3H)-one A 3 L jacketed round bottom flask was charged with Example 120B (34.6 g, 96 mmol) and ethanol (350 mL), and the resultant solution was cooled to −5° C. A solution of sodium borohydride (1.39 g, 36.8 mmol) in ethanol (350 mL) was added dropwise while maintaining an internal temperature below 0° C. The resulting mixture was stirred at −5° C. overnight. The reaction mixture was quenched carefully with acetic acid (20 mL) and warmed to room temperature. After stirring overnight, the mixture was concentrated under reduced pressure. The residue was partitioned between ethyl acetate (300 mL) and 10% aqueous ammonium hydroxide (250 mL). The layers were separated, and the organic layer was washed with 10% aqueous ammonium hydroxide (250 mL). The combined aqueous layers were extracted with ethyl acetate (300 mL). The combined organic layers were washed with brine (100 mL), dried over sodium sulfate, filtered and concentrated. The residue was purified by chromatography over silica gel using a 330 g RediSep® silica gel cartridge on a Teledyne Isco Torrent Combiflash® system eluted with ethyl acetate/hexanes 0:1 (2 column volumes) up to 1:1 (gradient over 8 column volumes). Fractions containing product were combined and concentrated under reduced pressure to give the titled compound (24.0 g, 69%).

Example 120D (1S,4aS,5S,8aS)-5-hydroxy-4a-(4-hydroxyphenyl)-1-methyloctahydronaphthalen-2(1H)-one A 500 mL Parr stirred pressure reactor was charged with 4.8 g of 5% Pd/C (20 weight % of substrate charged). Under a stream of nitrogen, a solution of Example 120C (23.6 g, 65 mmol) and tetrahydrofuran (170 mL) and pyridine (42 mL) was added to the reactor. The reactor was purged with nitrogen and hydrogen. The vessel was pressurized to and maintained at 60-100 psig with hydrogen supplied from a high-pressure reservoir. The mixture was vigorously agitated while keeping the temperature between 22-25° C. for 16 hours. The reaction mixture was carefully filtered to remove the palladium catalyst rinsing the reactor and cake with tetrahydrofuran. To the filtrate was added 1,8-diazabicyclo[5.4.0]undec-7-ene (3 mL), and the resulting mixture was stirred at room temperature overnight. The tetrahydrofuran and pyridine were removed by concentration under reduced pressure, and the residue was taken up in ethyl acetate (200 mL). The resulting solution was washed with 10% hydrochloric acid (2×100 mL). The combined aqueous layers were extracted with ethyl acetate (100 mL), and the combined organic layers were washed with brine (50 mL), dried over sodium sulfate, filtered and concentrated. The residue was used without further purification. $^1$H NMR (400 MHz, CDCl$_3$) δ ppm 7.49-7.26 (m, 7H), 6.97-6.88 (m, 2H), 5.02 (s, 2H), 3.86-3.72 (m, 1H), 2.81-2.69 (m, 1H), 2.48-

2.39 (m, 1H), 2.34-2.27 (m, 1H), 2.24-2.03 (m, 3H), 1.99-1.96 (m, 1H), 1.91 (s, 3H), 1.88-1.44 (m, 3H); MS (CI—NH$_3$) 380.1 m/z (M+NH$_4$)+.

Example 120E (1'S,4a'S,5'S,8a'S)-4a'-(4-hydroxyphenyl)-1'-methyl-octahydro-1'H-spiro[1,3-dioxolane-2,2'-naphthalen]-5'-ol The residue from Example 120D was taken up in 2-ethyl-2-methyl-1,3-dioxolane (37.8 g, 326 mmol) and ethylene glycol (8.1 g, 130 mol). para-Toluenesulfonic acid (1.2 g, 6.5 mmol) was added, and the resulting mixture was stirred at room temperature overnight.

The mixture was diluted with ethyl acetate (200 mL) and washed with saturated aqueous sodium bicarbonate (2×100 mL). The aqueous layer was extracted with ethyl acetate (100 mL). The combined organic layers were washed with brine (50 mL), dried over sodium sulfate, filtered and concentrated. The titled product was used without further purification.

Example 120F (1'S,4a'S,5'S,8a'S)-4a'-[4-(benzyloxy)phenyl]-1'-methyloctahydro-1'H-spiro[1,3-dioxolane-2,2'-naphthalen]-5'-ol The residue from Example 120E was taken up in acetone (200 mL) and potassium carbonate (8.6 g, 63 mmol) and benzyl bromide (10.7 g, 63 mmol) were added. The resulting mixture was stirred at room temperature overnight. The reaction mixture was partitioned between ethyl acetate (200 mL) and saturated aqueous sodium bicarbonate (100 mL), and the layers were separated. The aqueous layer was extracted with ethyl acetate (100 mL). The combined organic layers were washed with brine (50 mL), dried over sodium sulfate, filtered and concentrated. The material was purified by chromatography over silica gel using a 330 g RediSep® silica gel cartridge on a Teledyne Isco Torrent Combiflash® system eluted with ethyl acetate/hexanes 0:1 (2 column volumes) up to 1:1 (gradient over 8 column volumes). Fractions containing the titled compound were combined and concentrated under reduced pressure (15.5 g, 58%). $^1$H NMR (400 MHz, CDCl$_3$) δ ppm 7.60-7.53 (m, 2H), 7.50-7.33 (m, 5H), 6.99-6.93 (m, 2H), 5.08 (s, 2H), 4.02-3.87 (m, 4H), 3.49-3.34 (m, 1H), 2.74 (dt, J=13.7, 3.4 Hz, 1H), 2.33-2.21 (m, 1H), 1.98-1.72 (m, 3H), 1.73-1.43 (m, 4H), 1.34-1.20 (m, 1H), 1.19-1.04 (m, 2H), 0.93 (d, J=6.7 Hz, 3H).

Example 120G (1'S,4a'S,8a'S)-4a'-[4-(benzyloxy)phenyl]-1'-methyl-hexahydro-1'H-spiro[1,3-dioxolane-2,2'-naphthalen]-5'(3'H)-one Example 120F (15.5 g, 37.9 mmol) was dissolved in dichloromethane (150 mL), and pyridinium dichromate (28.5 g, 76 mmol) and magnesium sulfate (0.9 g) were added. The resulting mixture was heated to reflux and stirred overnight. The reaction was cooled to room temperature, and the mixture was filtered through a plug of silica gel (75 g) rinsing with dichloromethane (500 mL). The filtrate was concentrated, and the solid was precipitated from cyclohexane (100 mL) by heating to dissolve the solid followed by cooling to room temperature. The solid was collected by filtration, washed with cyclohexane (2×10 mL) and dried in a vacuum oven at 50° C. to give the titled compound (9.3 g, 60%).

Example 120H (1'S,4a'S,6'Z,8a'S)-4a'-[4-(benzyloxy)phenyl]-6'-(hydroxymethylene)-1'-methylhexahydro-1'H-spiro[1,3-dioxolane-2,2'-naphthalen]-5'(3'H)-one To a solution of Example 120G (2.5 g, 6.15 mmol) in ethyl formate (15.0 mL, 184.0 mmol) cooled in an ice bath was added 1 M potassium t-butoxide in tetrahydrofuran (9.22 mL, 9.228 mmol) dropwise. The reaction mixture was stirred in the ice bath for 20 minutes and then stirred at room temperature for 3 hours. The solution was quenched with aqueous sodium phosphate monobasic, diluted with water, and extracted with ethyl acetate. The organic fraction was dried over sodium sulfate, filtered, and concentrated to give the titled compound.

Example 120I (6aS,7S,10aS)-10a-[4-(benzyloxy)phenyl]-7-methyl-5,6a,7,9,10,10a-hexahydro-6H-spiro[benzo[h]quinazoline-8,2'-[1,3]dioxolane]

To a solution Example 120H (0.700 g, 1.61 mmol) in isopropanol (12 mL) was added formamidine acetate (0.503 g, 4.83 mmol) and piperidine (0.478 mL, 4.83 mmol). The reaction mixture was heated at 95° C. for 48 hours. The cooled solution was diluted with a solution of sodium phosphate monobasic and extracted with ethyl acetate. The organic fraction was concentrated to give the titled compound. MS (APCI+) m/z 443 (M+H)$^+$.

Example 120J (6aS,7S,10aS)-10a-[4-(benzyloxy)phenyl]-7-methyl-5,6a,7,9,10,10a-hexahydrobenzo[h]quinazolin-8(6H)-one The titled compound was prepared using the conditions described in Example 1I, substituting Example 120I for Example 1H. MS (APCI+) m/z 399 (M+H)$^+$.

Example 120K (6aS,7S,9Z,10aS)-10a-[4-(benzyloxy)phenyl]-9-(hydroxymethylene)-7-methyl-5,6a,7,9,10,10a-hexahydrobenzo[h]quinazolin-8(6H)-one The titled compound was prepared using the conditions described in Example 1J, substituting Example 120J for Example 1I.

Example 120L (6aS,7S,11aS)-11a-[4-(benzyloxy)phenyl]-7-methyl-5,6,6a,7,11,11a-hexahydro[1,2]benzoxazolo[6,5-h]quinazoline The titled compound was prepared using the conditions described in Example 1K, substituting Example 120K for Example 1J. MS (APCI+) m/z 424 (M+H)$^+$.

Example 120M (6aS,7S,10aS)-10a-[4-(benzyloxy)phenyl]-7-methyl-8-oxo-5,6,6a,7,8,9,10,10a-octahydrobenzo[h]quinazoline-9-carbonitrile The titled compound was prepared using the conditions described in Example 1L, substituting Example 120L for Example 1K.

Example 120N (6aS,7S,10aR)-10a-[4-(benzyloxy)phenyl]-7-methyl-8-oxo-5,6,6a,7,8,10a-hexahydrobenzo[h]quinazoline-9-carbonitrile To a solution of Example 120M (0.093 g, 0.220 mmol) in dimethylformamide (3 mL) cooled in an ice water bath to 0° C. was added 1,3-dibromo-5,5-dimethylhydantoin (0.035 g, 0.121 mmol). The solution was stirred at 0° C. for 40 minutes, pyridine (0.355 mL, 4.39 mmol) was added, and the solution was heated at 55° C. for 2 hours. The cooled solution was diluted with water and extracted with ethyl acetate. The organic phase was washed with brine and concentrated. The residue was purified using a 12 g RediSep® silica gel cartridge on a Teledyne Isco Combiflash® Rf system eluted with 0-50% ethyl acetate in heptane to give the titled compound (0.064 g (69%). $^1$H NMR (400 MHz, CDCl$_3$) δ ppm 1.19 (d, J=6.72 Hz, 3H) 1.57-1.72 (m, 1H) 1.97 (dd, J=12.96, 7.21 Hz, 1H) 2.30 (td, J=12.90, 2.39 Hz, 1H) 2.46 (td, J=13.15, 6.56 Hz, 1H) 2.94-3.15 (m, 2H) 5.02 (s, 2H) 6.67 (d, J=8.89 Hz, 2H) 6.90 (d, J=9.00 Hz, 2H) 7.30-7.42 (m, 5H) 8.70 (s, 1H) 8.82 (s, 1H) 9.06 (s, 1H); MS (ESI+) m/z 422 (M+H)$^+$.

Example 121

(6aS,7S,10aR)-10a-(4-hydroxyphenyl)-7-methyl-8-oxo-5,6,6a,7,8,10a-hexahydrobenzo[h]quinazoline-9-carbonitrile In a microwave tube Example 120N (0.038 g, 0.090 mmol) and 1-butyl-3-methylimidazolium bromide (0.400 g, 1.825 mmol) were heated until melted and homogeneous. The tube was then sealed and heated in a microwave reactor at 180° C. for 5 minutes and then at 200° C. for 3 minutes. The cooled solid mass was dissolved in 1 M hydrochloric acid (5 mL) and extracted with ethyl acetate. The organic fraction was concentrated, and the residue was purified on a Teledyne Isco Combiflash® Rf system using a 4 g RediSep® silica gel cartridge eluted with 0-20% ethyl acetate in dichloromethane to give 0.004 g (13%) of the titled compound. $^1$H NMR (400 MHz, CDCl$_3$) δ ppm 1.20 (d, J=6.72 Hz, 3H) 1.61-1.71 (m, 1H) 1.97 (dd, J=14.10, 7.26 Hz, 1H) 2.30 (td, J=12.88, 2.44 Hz, 1H) 2.45 (td, J=13.15, 6.67 Hz, 1H) 2.95-3.16 (m, 2H) 5.04 (s, 1H) 6.63 (d, J=8.78 Hz, 2H) 6.77 (d, J=8.78 Hz, 2H) 8.70 (s, 1H) 8.81 (s, 1H) 9.07 (s, 1H); MS (APCI+) m/z 332 (M+H)$^+$.

Example 122

(6aS,7S,10aR)-2,7-dimethyl-8-oxo-10a-phenyl-4-[4-(pyridin-4-yl)phenyl]-5,6,6a,7,8,10a-hexahydrobenzo[h]quinazoline-9-carbonitrile

Example 122A

4-[(6aS,7S,10aS)-2,7-dimethyl-8-oxo-10a-phenyl-5,6,6a,7,8,9,10,10a-octahydrobenzo[h]quinazolin-4-yl]phenyl trifluoromethanesulfonate The titled compound was prepared using the conditions described in Example 119A, substituting Example 108A for Example 109A. MS (APCI+) m/z 4531 (M+H)$^+$.

Example 122B (6aS,7S,10aS)-2,7-dimethyl-10a-phenyl-4-[4-(pyridin-4-yl)phenyl]-5,6a,7,9,10,10a-hexahydrobenzo[h]quinazolin-8(6H)-one The titled compound was prepared using the conditions described in Example 119B, substituting Example 122A for Example 119A and pyridine-4-ylboronic acid for 4-hydroxyphenyl boronic acid. MS (APCI+) m/z 460 (M+H)$^+$.

Example 122C (6aS,7S,9Z,10aS)-9-(hydroxymethylene)-2,7-dimethyl-10a-phenyl-4-[4-(pyridin-4-yl)phenyl]-5,6a,7,9,10,10a-hexahydrobenzo[h]quinazolin-8(6H)-one The titled compound was prepared using the conditions described in Example 1J, substituting Example 122B for Example 1I.

Example 122D (6aS,7S,11aS)-2,7-dimethyl-11a-phenyl-4-[4-(pyridin-4-yl)phenyl]-5,6,6a,7,11,11a-hexahydro[1,2]benzoxazolo[6,5-h]quinazoline The titled compound was prepared using the conditions described in Example 1K, substituting Example 122C for Example 1J

Example 122E (6aS,7S,10aS)-2,7-dimethyl-8-oxo-10a-phenyl-4-[4-(pyridin-4-yl)phenyl]-5,6,6a,7,8,9,10,10a-octahydrobenzo[h]quinazoline-9-carbonitrile The titled compound was prepared using the conditions described in Example 1L, substituting Example 122D for Example 1K.

Example 122F (6aS,7S,10aR)-2,7-dimethyl-8-oxo-10a-phenyl-4-[4-(pyridin-4-yl)phenyl]-5,6,6a,7,8,10a-hexahydrobenzo[h]quinazoline-9-carbonitrile A solution of Example 1122E (0.038 g, 0.078 mmol) in tetrahydrofuran (2 mL) at room temperature was sparged with nitrogen for 15 minutes, and then 2,3-dichloro-5,6-dicyano-1,4-benzoquinone (0.048 g, 0.210 mmol) was added. After 15 minutes with continued nitrogen bubbling, the solution was concentrated, and the residue was purified using a 12 g RediSep® silica gel cartridge on a Teledyne Isco Combiflash® Rf, system eluting with 0-80% ethyl acetate in heptane. A second purification eluting with 0-10% methanol in dichloromethane to give 0.005 g (13%) of the titled compound. $^1$H NMR (400 MHz, CDCl$_3$) δ ppm 1.18 (d, J=6.51 Hz, 3H) 1.45-1.54 (m, 1H) 1.86-1.96 (m, 1H) 2.37 (td, J=12.90, 1.84 Hz, 1H) 2.47 (td, J=12.98, 6.34 Hz, 1H) 2.73 (s, 3H) 3.02 (dd, J=8.67, 4.55 Hz, 2H) 6.86 (d, J=8.02 Hz, 2H) 7.30-7.40 (m, 3H) 7.56 (d, J=6.07 Hz, 2H) 7.69-7.75 (m, 2H) 7.76-7.82 (m, 2H) 8.72 (d, J=6.07 Hz, 2H) 8.99 (s, 1H); MS (APCI+) m/z 483 (M+H)$^+$.

Example 123

(5aS,6S,9aR)-3-[3-(3-hydroxypropyl)phenyl]-6-methyl-7-oxo-9a-phenyl-4,5,5a,6,7,9a-hexahydro-2H-benzo[g]indazole-8-carbonitrile Example 123A (5aS,6S,9aS)-3-[3-(3-hydroxypropyl)phenyl]-N,N,6-trimethyl-9a-phenyl-4,5,5a,8,9,9a-hexahydrospiro[benzo[g]indazole-7,2'-[1,3]dioxolane]-2(6H)-sulfonamide The titled compound was prepared using the conditions described in Example 86A substituting 3-(4,4,5,5-tetramethyl-1,3,2-dioxaborolan-2-yl)pyridine with 3-(3-(4,4,5,5-tetramethyl-1,3,2-dioxaborolan-2-yl)phenyl)propan-1-ol.

Example 123B (5aS,6S,9aS)-3-[3-(3-hydroxypropyl)phenyl]-6-methyl-9a-phenyl-2,4,5,5a,6,8,9,9a-octahydro-7H-benzo[g]indazol-7-one The titled compound was prepared using the conditions described in Example 86B substituting Example 86A with Example 123A. MS (APCI) m/z 415 (M+H)$^+$.

Example 123C (5aS,6S,8Z,9aS)-8-(hydroxymethylene)-3-[3-(3-hydroxypropyl)phenyl]-6-methyl-9a-phenyl-2,4,5,5a,6,8,9,9a-octahydro-7H-benzo[g]indazol-7-one The titled compound was prepared using the conditions described in Example 24C substituting Example 24B with Example 123B. MS (APCI) m/z 443 (M+H)$^+$.

Example 123D

3-{3-[(5aS,6S,10aS)-6-methyl-10a-phenyl-4,5,5a,6,10,10a-hexahydro-2H-indazolo[7,6-][1,2]benzoxazol-3-yl]phenyl}propan-1-ol The titled compound was prepared using the conditions described in Example 24D substituting Example 24C with Example 123C.

Example 123E (5aS,6S,9aS)-3-[3-(3-hydroxypropyl)phenyl]-6-methyl-7-oxo-9a-phenyl-4,5,5a,6,7,8,9,9a-octahydro-2H-benzo[g]indazole-8-carbonitrile The titled compound was prepared using the conditions described in Example 24E substituting Example 24D with Example 123D. MS (APCI) m/z 440 (M+H)$^+$.

Example 123F (5aS,6S,9aR)-3-[3-(3-hydroxypropyl)phenyl]-6-methyl-7-oxo-9a-phenyl-4,5,5a,6,7,9a-hexahydro-2H-benzo[g]indazole-8-carbonitrile Example 123E (0.050 g, 0.114 mmol) was dissolved in tetrahydrofuran (1.14 mL), and nitrogen was bubbled through the mixture for 10 minutes. 2,3-Dichloro-5,6-dicyano-1,4-benzoquinone (0.025 g, 0.114 mmol) was added, and the reaction mixture was stirred at room temperature for 10 minutes with continued nitrogen bubbling. The reaction mixture was concentrated, and the residue was purified chromatographically on a reversed-phase Waters HPLC using a Nova-Pak® HR C18, 6 μm, 60 Å, 40 mm×100 mm, PrepPak cartridge eluting with a gradient of 10-90% acetonitrile in aqueous 0.1% trifluoroacetic acid (60 mL/minute) to give the titled compound as the trifluoroacetic acid salt (0.010 g, 24%). $^1$H NMR (400 MHz, DMSO-d$_6$) δ ppm 1.07 (d, J=6.6 Hz, 3H), 1.32-1.47 (m, 1H), 1.70-1.92 (m, 3H), 2.34 (d, J=11.6 Hz, 1H), 2.79-2.92 (m, 3H), 2.95 (s, 3H), 4.53 (s, 1H), 6.95 (d, J=7.3 Hz, 2H), 7.20 (s, 1H), 7.25-7.43 (m, 4H), 7.56 (s, 2H), 8.44 (s, 1H); MS (ESI) m/z 434 (M+H)$^+$.

Example 124

N-{3'-[(6aS,7S,10aR)-9-cyano-2,7-dimethyl-8-oxo-10a-phenyl-5,6,6a,7,8,10a-hexahydrobenzo[h]quinazolin-4-yl]biphenyl-3-yl}methanesulfonamide Example 124A N-{3'-[(6aS,7S,10aS)-2,7-dimethyl-8-oxo-10a-phenyl-5,6,6a,7,8,9,10,10a-octahydrobenzo[h]quinazolin-4-yl]biphenyl-3-yl}methanesulfonamide The titled compound was prepared using the conditions described in Example 119B, substituting (3-(methylsulfonamido)phenyl)boronic acid for (4-hydroxyphenyl)boronic acid. $^1$H NMR (400 MHz, CDCl$_3$) δ ppm 1.16 (d, J=6.61 Hz, 3H) 1.96-2.19 (m, 3H) 2.30-2.64 (m, 4H) 2.76 (s, 3H) 2.84 (dd, J=12.04, 6.51 Hz, 1H) 2.87-2.98 (m, 1H) 3.03 (s, 3H) 3.20-3.29 (m, 1H) 6.45 (s, 1H) 7.17-7.27 (m, 2H) 7.32 (t, J=7.59 Hz, 2H) 7.39-7.45 (m, 4H) 7.47-7.65 (m, 5H); MS (ESI) m/z 552.3 (M+H)$^+$.

Example 124B

N-{3'-[(6aS,7S,9Z,10aS)-9-(hydroxymethylene)-2,7-dimethyl-8-oxo-10a-phenyl-5,6,6a,7,8,9,10,10a-octahydrobenzo[h]quinazolin-4-yl]biphenyl-3-yl}methanesulfonamide The titled compound was prepared using the conditions described in Example 13F, substituting Example 124A for Example 13E.

Example 124C

N-{3'-[(6aS,7S,11aS)-2,7-dimethyl-11a-phenyl-5,6,6a,7,11,11a-hexahydro[1,2]benzoxazolo[6,5-h]quinazolin-4-yl]biphenyl-3-yl}methanesulfonamide The titled compound was prepared using the conditions described in Example 13G, substituting Example 124D for Example 13F.

Example 124D

N-{3'-[(6aS,7S,10aS)-9-cyano-2,7-dimethyl-8-oxo-10a-phenyl-5,6,6a,7,8,9,10,10a-octahydrobenzo[h]quinazolin-4-yl]biphenyl-3-yl}methanesulfonamide The titled compound was prepared using the conditions described in Example 13H, substituting Example 124E for Example 13G.

Example 124E

N-{3'-[(6aS,7S,10aR)-9-cyano-2,7-dimethyl-8-oxo-10a-phenyl-5,6,6a,7,8,10a-hexahydrobenzo[h]quinazolin-4-yl]biphenyl-3-yl}methanesulfonamide The titled compound was prepared using the conditions described in Example 131, substituting Example 124D for Example 13H. Purification was done by preparative HPLC on a Waters Sunfire™ C8(2) 5 µm 100 Å column (30 mm×75 mm). A gradient of acetonitrile (A) and 0.1% trifluoroacetic acid in water (B) was used, at a flow rate of 50 mL/minute (0-0.5 minute 10% A, 0.5-7.0 minutes linear gradient 10-95% A, 7.0-10.0 minutes 95% A, 10.0-12.0 minutes linear gradient 95-10% A) to give the titled compound in 35% yield. $^1$H NMR (400 MHz, CDCl$_3$) δ ppm 1.17 (d, J=6.51 Hz, 3H) 1.49-1.55 (m, 1H) 1.86-1.93 (m, 1H) 2.37 (td, J=12.66, 2.01 Hz, 1H) 2.46 (td, J=13.07, 6.51 Hz, 1H) 2.73 (s, 3H) 2.96-3.02 (m, 2H) 3.06 (s, 3H) 6.47 (s, 1H) 6.86 (d, J=6.61 Hz, 2H) 7.18-7.23 (m, 1H) 7.30-7.38 (m, 3H) 7.43-7.49 (m, 2H) 7.51 (s, 1H) 7.54-7.63 (m, 2H) 7.69 (d, J=7.48 Hz, 1H) 7.74 (s, 1H) 8.99 (s, 1H); MS (ESI) m/z 575 (M+H)$^+$.

Example 125

3-{3-[(6aS,7S,10aR)-9-cyano-2,7-dimethyl-8-oxo-10a-phenyl-5,6,6a,7,8,10a-hexahydrobenzo[h]quinazolin-4-yl]phenyl}propyl acetate To a solution of Example 110F (0.065 g, 0.14 mmol) in dichloromethane (1.4 mL) was added triethylamine (43 µL, 0.31 mmol), acetic anhydride (15 µL, 0.15 mmol), and dimethylaminopyridine (0.003 g, 0.028 mmol). The reaction mixture was stirred at room temperature for 1 hour and then concentrated under reduced pressure. The residue was purified by flash chromatography on silica gel eluting with 5% ethyl acetate in chloroform to give the titled compound (49 mg, 67%). $^1$H NMR (400 MHz, CDCl$_3$) δ ppm 1.17 (d, J=6.61 Hz, 3H) 1.47-1.55 (m, 1H) 1.84-1.93 (m, 1H) 1.97-2.07 (m, 2H) 2.07 (s, 3H) 2.35 (td, J=12.82, 2.22 Hz, 1H) 2.46 (td, J=13.07, 6.61 Hz, 1H) 2.71 (s, 3H) 2.76-2.82 (m, 2H) 2.94 (dd, J=8.62, 4.39 Hz, 2H) 4.13 (t, J=6.56 Hz, 2H) 6.85 (d, J=6.61 Hz, 2H) 7.29-7.46 (m, 7H) 8.99 (s, 1H); MS (ESI+) m/z 506 (M+H)$^+$.

Example 126

(5aS,6S,9aR)-3-[5-(hydroxymethyl)pyridin-3-yl]-6-methyl-7-oxo-9a-phenyl-4,5,5a,6,7,9a-hexahydro-2H-benzo[g]indazole-8-carbonitrile

Example 126A (5aS,6S,9aS)-3-[5-(hydroxymethyl)pyridin-3-yl]-N,N,6-trimethyl-9a-phenyl-4,5,5a,8,9,9a-hexahydrospiro[benzo[g]indazole-7,2'-[1,3]dioxolane]-2(6H)-sulfonamide The titled compound was prepared using the conditions described in Example 86A substituting 3-(4,4,5,5-tetramethyl-1,3,2-dioxaborolan-2-yl)pyridine with (5-(4,4,5,5-tetramethyl-1,3,2-dioxaborolan-2-yl)pyridin-3-yl)methanol. MS (APCI) m/z 388 (M+H)$^+$.

Example 126B (5aS,6S,9aS)-3-[5-(hydroxymethyl)pyridin-3-yl]-6-methyl-9a-phenyl-2,4,5,5a,6,8,9,9a-octahydro-7H-benzo[g]indazol-7-one The titled compound was prepared using the conditions described in Example 86B substituting Example 86A with Example 126A.

Example 126C (5aS,6S,8Z,9aS)-8-(hydroxymethylene)-3-[5-(hydroxymethyl)pyridin-3-yl]-6-methyl-9a-phenyl-2,4,5,5a,6,8,9,9a-octahydro-7H-benzo[g]indazol-7-one The titled compound was prepared using the conditions described in Example 24C substituting Example 24B with Example 126B. MS (APCI) m/z 416 (M+H)$^+$.

Example 126D

{5-[(5aS,6S,10aS)-6-methyl-10a-phenyl-4,5,5a,6,10,10a-hexahydro-2H-indazolo[7,6-f][1,2]benzoxazol-3-yl]pyridin-3-yl}methanol The titled compound was prepared using the conditions described in Example 24D substituting Example 24C with Example 126C.

Example 126E (5aS,6S,9aS)-3-[5-(hydroxymethyl)pyridin-3-yl]-6-methyl-7-oxo-9a-phenyl-4,5,5a,6,7,8,9,9a-octahydro-2H-benzo[g]indazole-8-carbonitrile The titled compound was prepared using the conditions described in Example 24E substituting Example 24D with Example 126D. MS (APCI) m/z 413 (M+H)$^+$.

Example 126F (5aS,6S,9aR)-3-[5-(hydroxymethyl)pyridin-3-yl]-6-methyl-7-oxo-9a-phenyl-4,5,5a,6,7,9a-hexahydro-2H-benzo[g]indazole-8-carbonitrile Example 126E (0.030 g, 0.073 mmol) was dissolved in tetrahydrofuran (0.72 mL), and nitrogen was bubbled through the mixture for 10 minutes. 2,3-Dichloro-5,6-dicyano-1,4-benzoquinone (0.016 g, 0.073 mmol) was added, and the reaction mixture was stirred at room temperature for 10 minutes. The reaction mixture was concentrated, and the residue was purified on a reversed-phase Waters HPLC using a Nova-Pak® HR C18, 6 µm, 60 Å, 40 mm×100 mm, PrepPak cartridge eluting with a gradient of 10-90% acetonitrile in aqueous 0.1% trifluoroacetic acid (60 mL/minute). A second chromatographic purification by preparative thin-layer chromatography gave the titled compound as the trifluoroacetic acid salt (0.027 g, 90%). $^1$H NMR (400 MHz, DMSO-d$_6$) δ ppm 1.07 (d, J=6.7 Hz, 3H), 1.34-1.47 (m, 1H), 1.80-1.89 (m, 1H), 2.33-2.39 (m, 1H), 2.80-2.94 (m, 1H), 3.02 (dd, J=16.0, 6.2 Hz, 1H), 4.64 (s, 2H), 6.96 (d, J=7.3 Hz, 2H), 7.33 (dq, J=14.2, 7.0 Hz, 3H), 8.21 (s, 1H), 8.44 (s, 1H), 8.55 (s, 1H), 8.86 (s, 1H); MS (ESI−) m/z 409 (M−H)$^-$.

Example 127

(6aS,7S,10aR)-4-[1-(2-hydroxyethyl)-1H-pyrazol-4-yl]-2,7-dimethyl-8-oxo-10a-phenyl-5,6,6a,7,8,10a-hexahydrobenzo[h]quinazoline-9-carbonitrile Example 127A 2-{4-[(6aS,7S,10aS)-2,7-dimethyl-8-oxo-10a-phenyl-5,6,6a,7,8,9,10,10a-octahydrobenzo[h]quinazolin-4-yl]-1H-pyrazol-1-yl}ethyl acetate The product of Example 13D (0.145 g, 0.425 mmol), sodium carbonate (0.135 g, 1.274 mmol) and tetrakis(triphenylphosphine)palladium(0) (0.0491 g, 0.042 mmol) were combined, and a solution of 1-(2-acetoxyethyl)pyrazole-4-boronic acid pinacol ester (0.4 g, 1.428 mmol) in dioxane (3 mL) was cannulated into the mixture. Water (0.300 mL) was added, and the mixture was sparged with nitrogen for 30 minutes and then stirred at 80° C. overnight without further sparging. The mixture was cooled to room temperature, diluted with dichloromethane (50 mL) and washed with a saturated aqueous ammonium chloride (15 mL) and then water (10 mL). The combined aqueous layers were back-extracted with dichloromethane (10 mL×2). The combined organic layers were dried (MgSO$_4$), filtered and concentrated. The residue was purified chromatographically using a Biotage® SNAP 50 g silica cartridge eluted with a step gradient of acetone/heptane (3 column volume (CV) 0%, 4 CV 0-33%, 3 CV 33%, 3 CV 33-50% then 3 CV 50%) giving the product of Example 13D (0.15 g, 53%) and the titled compound. The titled compound was purified again chromatographically using a Biotage® SNAP 10 g silica cartridge eluted with a step gradient of ethyl acetate/heptane (3 column volume (CV) 0%, 3 CV 0-40%, 2 CV 40%, 3 CV 40-50%, 3 CV 50%, 3 CV 50-100% then 3 CV 100%) giving 0.089 g (0.195 mmol, 45.9%). $^1$H NMR (400 MHz, CDCl$_3$) δ ppm 1.17 (d, J=6.7 Hz, 3H), 2.06 (s, 3H), 2.12 (ddd, J=11.2, 9.7, 5.5 Hz, 2H), 2.27-2.37 (m, 1H), 2.47-2.57 (m, 2H), 2.61 (dd, J=12.0, 5.4 Hz, 1H), 2.65 (d, J=3.3 Hz, 3H), 2.79-2.88 (m, 1H), 2.98-3.08 (m, 1H), 3.21-3.28 (m, 1H), 4.42 (t, J=5.3 Hz, 2H), 4.49 (t, J=5.3 Hz, 2H), 7.21 (t, J=7.2 Hz, 1H), 7.26-7.31 (m, 3H), 7.43 (d, J=7.9 Hz, 2H), 7.98 (s, 1H), 8.00 (s, 1H); MS (CI) m/z 459.3 (M+H)$^+$.

Example 127B (6aS,7S,9Z,10aS)-4-[1-(2-hydroxyethyl)-1H-pyrazol-4-yl]-9-(hydroxymethylene)-2,7-dimethyl-10a-phenyl-5,6a,7,9,10,10a-hexahydrobenzo[h]quinazolin-8(6H)-one To the product of Example 127A (0.19 g, 0.417 mmol) was added ethyl formate (3.5 mL) followed by a solution of 25% sodium methanolate (0.5 mL, 2.242 mmol) in methanol at room temperature. The resulting suspension was stirred at room temperature overnight, cooled to 0° C., and quenched with a solution of aqueous hydrochloric acid (2 N, 1.12 mL). The mixture was diluted with water (10 mL) and dichloromethane (50 mL). The organic layer was separated and washed with water (10 mL). The combined aqueous layers were back-extracted with a solution of dichloromethane and dimethylformamide at a ratio of 5/1 (5 mL×2). The combined organic layers were dried (MgSO$_4$), filtered and concentrated to give the titled compound (0.219 g, 0.493 mmol, 118%).

Example 127C

2-{4-[(6aS,7S,11aS)-2,7-dimethyl-11a-phenyl-5,6,6a,7,11,11a-hexahydro[1,2]benzoxazolo[6,5-h]quinazolin-4-yl]-1H-pyrazol-1-yl}ethanol To a solution of the product of Example 127B (0.185 g, 0.416 mmol) in ethanol (3.5 mL) was added hydroxylamine hydrochloride (0.175 g, 2.52 mmol), and the mixture was stirred at 60° C. overnight. More hydroxylamine hydrochloride was added, and the mixture was stirred at 50° C. for 60 hours. The solution was cooled to room temperature, diluted with dichloromethane (30 mL), and washed with 10% aqueous sodium bicarbonate (5 mL). The organic layer was washed with water (10 mL). The aqueous layers were combined and back-extracted with dichloromethane (5 mL×3). The combined organic layers were dried (MgSO$_4$), filtered and concentrated to give the titled compound.

Example 127D (6aS,7S,10aS)-4-[1-(2-hydroxyethyl)-1H-pyrazol-4-yl]-2,7-dimethyl-8-oxo-10a-phenyl-5,6,6a,7,8,9,10,10a-octahydrobenzo[h]quinazoline-9-carbonitrile To a solution of the product of Example 127C (0.184 g, 0.417 mmol) in tetrahydrofuran (0.2 mL) and methanol (0.2 mL) was added a 25% solution of sodium methoxide (0.6 mL, 2.69 mmol) in methanol, and the mixture was stirred at room temperature overnight. The solution was cooled to 0° C., neutralized with an aqueous solution of hydrochloric acid (2 N, 1.3 mL) and partitioned between dichloromethane (50 mL) and water (10 mL). The organic layer was washed with water (10 mL) and brine (5 mL). The combined aqueous layers were back-extracted with dichloromethane (10 mL×2). The combined organic layers were dried (MgSO$_4$), filtered, and concentrated to give a brown solid. The residue was purified chromatographically using a Biotage® SNAP 10 g silica cartridge eluted with a step gradient of acetone/heptane (3 column volumes (CV) 0%, 4 CV 0-30%, 3 CV 30%, 3 CV 35-50% then 3 CV 50%) giving the titled compound (0.075 g) and impure titled compound (0.052 g). The impure titled compound was purified by preparative thin layer chromatography eluting with 50% acetone in heptane to give the pure titled compound (0.042 g). The two batches were combined to give the titled compound (0.118 g, 0.267 mmol, 64.1%).

Example 127E (6aS,7S,10aR)-4-[1-(2-hydroxyethyl)-1H-pyrazol-4-yl]-2,7-dimethyl-8-oxo-10a-phenyl-5,6,6a,7,8,10a-hexahydrobenzo[h]quinazoline-9-carbonitrile A solution of the product of Example 127D (0.029 g, 0.065 mmol) in anhydrous tetrahydrofuran (0.7 mL) was sparged with nitrogen for 10 minutes. 2,3-Dichloro-5,6-dicyano-1,4-benzoquinone (0.0148 g, 0.065 mmol) was added at room temperature, and the mixture was stirred for 20 minutes with a continued nitrogen sparge. The mixture was concentrated and diluted with dichloromethane. An insoluble solid was removed by filtration through diatomaceous earth and rinsed with dichloromethane. The filtrate was concentrated, and the residue was purified chromatographically using a Biotage® SNAP 10 g silica cartridge eluted with a step gradient of acetonitrile/chloroform (3 column volume (CV) 0%, 4 CV 0-35%, 3 CV 35%, 3 CV 35-70% then 3 CV 100%) giving the impure titled compound. This material was diluted with dichloromethane, and the insoluble solid was removed by filtration. The filtrate was concentrated to give the impure titled compound (0.0252 g). This procedure was repeated using the product of Example 127D (0.0818 g, 0.185 mmol) to give additional impure titled compound (0.082 g). All lots of the impure titled compounds were combined and purified chromatographically using a Biotage® SNAP 10 g silica cartridge eluted with a step gradient of acetone/heptane (3 column volume (CV) 0%, 5 CV 0-30%, 2 CV 30% then 3 CV 50%) giving the titled compound (0.095 g, 0.214 mmol, 86% combined yield). $^1$H NMR (400 MHz, CDCl$_3$) δ ppm 1.20 (d, J=6.6 Hz, 3H), 1.58-1.69 (m, 1H), 2.01-2.08 (m, 1H), 2.30-2.39 (m, 1H), 2.42-2.51 (m, 1H), 2.65 (s, 3H), 2.77 (t, J=5.9 Hz, 1H), 3.00-3.19 (m, 2H), 4.09 (dd, J=9.8, 5.8 Hz, 2H), 4.34-4.39 (m, 2H), 6.82-6.86 (m, 2H), 7.28-7.34 (m, 3H), 8.17 (s, 1H), 8.22 (s, 1H), 8.98 (s, 1H); MS (CI) m/z 440.2 (M+H)$^+$.

Example 128

(6aS,7S,10aR)-10a-[3-(benzyloxy)phenyl]-7-methyl-8-oxo-5,6,6a,7,8,10a-hexahydrobenzo[h]quinazoline-9-carbonitrile Example 128A 2-[3-(benzyloxy)phenyl]cyclohexane-1,3-dione A 1 L round-bottomed flask was charged with 1-(benzyloxy)-3-bromobenzene (45.5 g, 173 mmol), tert-amyl alcohol (200 mL) and dioxane (400 mL), and the contents were sparged with N$_2$ for 45 minutes. A 3 L round-bottomed flask was charged with potassium phosphate tribasic (92 g, 433 mmol), 1,3-cyclohexanedione (97 weight %, 20 g, 173 mmol), palladium(II) acetate (0.78 g, 3.5 mmol) and 2-(di-tert-butylphospino)-2'-methylbiphenyl (2.16 g, 6.9 mmol), and the contents were sparged with N$_2$ for 45 minutes. The solution of 1-(benzyloxy)-3-bromobenzene was then transferred to the 1,3-cyclohexanedione mixture via cannula, and the reaction mixture was heated to reflux overnight. The reaction mixture was cooled to room temperature and partitioned between ethyl acetate (600 mL) and 10% hydrochloric acid (600 mL) with mixing. The lower aqueous layer was separated and extracted with ethyl acetate (600 mL). The combined organic layers were washed with brine (2×100 mL) and concentrated under reduced pressure. The residue was taken up in toluene (300 mL) and again concentrated under reduced pressure. The residue was taken up in toluene (300 mL) and warmed to 50° C. After cooling to room temperature, the solids were collected by filtration, washed with toluene (2×50 mL) and dried in a vacuum oven at 50° C. to give the titled compound (44.6 g, 88%). $^1$H NMR (400 MHz, DMSO-d$_6$) δ ppm 10.54 (bs, 1H), 7.46-7.28 (m, 5H), 7.19-7.13 (m, 1H), 6.84-6.79 (m, 1H), 6.75-6.72 (m, 1H), 6.71-6.66 (m, 1H), 5.03 (s, 2H), 2.76-2.13 (m, 4H), 1.99-1.86 (m, 2H); MS (CI—NH$_3$) m/z 312.0 (M+NH$_4$)$^+$.

Example 128B (8aR)-8a-[3-(benzyloxy)phenyl]-5-methyl-3,4,8,8a-tetrahydronaphthalene-1,6(2H,7H)-dione A 3 L round-bottomed flask was charged with Example 128A (44.6 g, 152 mmol) in acetonitrile (500 mL). Triethylamine (42 mL, 303 mmol) and ethyl vinyl ketone (23 mL, 227 mmol) were added, and the mixture was warmed to 75° C. and stirred overnight. The reaction mixture was cooled to room temperature and concentrated. The residue was taken up in dimethyl sulfoxide (75 mL), pyridinium para-toluenesulfonate (24.8 g, 99 mmol) and L-phenylalanine (32.6 g, 198 mmol) were added, and the mixture was warmed to 50° C. for 168 hours. The reaction mixture was cooled to room temperature and poured into 10% hydrochloride acid (500 mL) and ethyl acetate (500 mL). After mixing for 10 minutes, the layers were separated, and the organic layer was washed with 10% hydrochloric acid (500 mL). The combined aqueous layers were extracted with ethyl acetate (500 mL). The combined organic layers were washed with brine (200 mL), dried over sodium sulfate, filtered, and concentrated. The residue was triturated with methyl t-butyl ether (100 mL), and the solids were collected, washed with methyl t-butyl ether (2×20 mL) and dried in a vacuum oven to give a first batch of the titled compound (22.7 g, 41%). The mother liquors were concentrated, and this residue was purified by chromatography over silica gel using a 330 g RediSep® cartridge on a Teledyne Isco Torrent Combiflash® system eluting with ethyl acetate/hexanes 0:1 (2 column volumes) up to 1:1 (gradient over 11 column volumes). Fractions containing product were combined and concentrated. The residue was triturated with methyl t-butyl ether (50 mL), and the solids were collected, washed with methyl t-butyl ether (2×10 mL) and dried in a vacuum oven to give a second batch of the titled compound (13.3 g, 24%). The combined batches of the titled compound gave 36.0 g (65%). $^1$H NMR (400 MHz, CDCl$_3$) δ ppm 0.41-7.23 (m, 6H), 6.93-6.89 (m, 1H), 6.73-6.68 (m, 2H), 5.02 (s, 2H), 2.75-2.64 (m, 1H), 2.59-2.43 (m, 2H), 2.43-2.27 (m, 3H), 2.23-2.15 (m, 1H), 2.11-2.00 (m, 1H), 1.93 (s, 3H), 1.81-1.61 (m, 2H).

Example 128C (4aR,5S)-4a-[3-(benzyloxy)phenyl]-5-hydroxy-1-methyl-4,4a,5,6,7,8-hexahydronaphthalen-2(3H)-one A 3 L jacketed round bottom flask was charged with Example 128B (36.0 g, 100 mmol) in ethanol (350 mL), and the solution was cooled to −5° C. A solution of sodium borohydride (1.1 g, 30.0 mmol) in ethanol (350 mL) was added dropwise while maintaining an internal temperature below 0° C. The resulting mixture was stirred at −5° C. overnight. The reaction mixture was quenched carefully with acetic acid (20 mL) and warmed to 23° C. After stirring overnight, the mixture was concentrated under reduced pressure. The residue was partitioned between ethyl acetate (300 mL) and 10% aqueous ammonium hydroxide (250 mL). The layers were separated, and the organic layer was washed with 10% aqueous ammonium hydroxide (250 mL). The combined aqueous layers were extracted with ethyl acetate (300 mL). The combined organic layers were washed with brine (100 mL), dried over sodium sulfate, filtered and concentrated. The material was purified by chromatography over silica gel using a 330 g RediSep® cartridge on a Teledyne Isco Torrent Combiflash® system eluting with ethyl acetate/hexanes 0:1 (2 column volumes) up to 1:1 (gradient over 8 column volumes). Fractions containing product were combined and concentrated under reduced pressure to give the titled compound (30.5 g, 84%). $^1$H NMR (400 MHz, CDCl$_3$) δ ppm 7.44-7.27 (m, 5H), 7.26-7.15 (m, 2H), 7.10-7.06 (m, 1H), 6.89-6.84 (m, 1H), 5.03 (d, J=6.0 Hz, 2H), 3.77 (dd, J=10.8, 3.5 Hz, 1H), 2.73-2.64 (m, 1H), 2.46-2.40 (m, 1H), 2.32-2.25 (m, 1H), 2.18-2.06 (m, 3H), 1.90 (d, J=1.3 Hz, 3H), 1.89-1.72 (m, 2H), 1.71-1.59 (m, 1H), 1.56-1.44 (m, 1H).

Example 128D (1S,4aS,5S,8aS)-5-hydroxy-4a-(3-hydroxyphenyl)-1-methyloctahydronaphthalen-2(1H)-one A 500 mL Parr stirred pressure reactor was charged with 6.0 g of 5% Pd/C (20 weight % of substrate charged). Under a stream of nitrogen, a solution of Example 128C (29.6 g, 82 mmol) and tetrahydrofuran (236 mL) and pyridine (59 mL) was added to the reactor. The reactor was purged with nitrogen and hydrogen. The vessel was pressurized to and maintained at 60-100 psig with hydrogen supplied from a high-pressure reservoir. The mixture was vigorously agitated while keeping the temperature between 22-25° C. for 16 hours. The reaction mixture was carefully filtered to remove the palladium catalyst rinsing the reactor and cake with tetrahydrofuran. To the filtrate was added 1,8-diazobicyclo[5.4.0]undec-7-ene (3 mL), and the resulting mixture was stirred at room temperature overnight. The tetrahydrofuran and pyridine were removed by concentration under reduced pressure, and the residue was taken up in ethyl acetate (200 mL). The resulting solution was washed with 10% hydrochloric acid (2×100 mL). The combined aqueous layers were extracted with ethyl acetate (100 mL), and the combined organic layers were washed with brine (50 mL), dried over sodium sulfate, filtered and concentrated. The titled compound was used without additional purification.

Example 128E (1'S,4a'S,5'S,8a'S)-4a'-(3-hydroxyphenyl)-1'-methyl-octahydro-1'H-spiro[1,3-dioxolane-2,2'-naphthalen]-5'-ol The residue from Example 128D was taken up in 2-ethyl-2-methyl-1,3-dioxolane (47.4 g, 408 mmol) and ethylene glycol (10.1 g, 163 mol). para-Toluenesulfonic acid (2.8 g, 14.7 mmol) was added, and the resulting mixture was stirred at room temperature overnight. The mixture was diluted with ethyl acetate (200 mL) and washed with saturated aqueous sodium bicarbonate (2×100 mL). The aqueous layer was extracted with ethyl acetate (100 mL). The combined organic layers were washed with brine (50 mL), dried over sodium sulfate, filtered and concentrated. The titled compound was used without additional purification.

Example 128F (1'S,4a'S,5'S,8a'S)-4a'-[3-(benzyloxy)phenyl]-1'-methyloctahydro-1'H-spiro[1,3-dioxolane-2,2'-naphthalen]-5'-ol The residue from Example 128E was taken up in acetone (200 mL), and potassium carbonate (11.1 g, 80 mmol) and benzyl bromide (13.8 g, 80 mmol) were added. The resulting mixture was stirred at room temperature overnight. The reaction mixture was poured into ethyl acetate (200 mL) and saturated aqueous sodium bicarbonate (100 mL), and the layers were separated. The aqueous layer was extracted with ethyl acetate (100 mL). The combined organic layers were washed with brine (50 mL), dried over sodium sulfate, filtered and concentrated. The material was purified by chromatography over silica gel using a 330 g RediSep® cartridge on a Teledyne Isco Torrent Combiflash® system eluting with ethyl acetate/hexanes 0:1 (2 column volumes) up to 1:1 (gradient over 8 column volumes). Fractions containing product were combined and concentrated under reduced pressure to give the titled compound (18.0 g, 58%). $^1$H NMR (400 MHz, CDCl$_3$) δ ppm 7.49-7.32 (m, 5H), 7.30-7.21 (m, 3H), 6.90-6.84 (m, 1H), 5.16-5.03 (m, 2H), 4.02-3.87 (m, 4H), 3.49-3.32 (m, 1H), 2.72 (dt, J=13.7, 3.3 Hz, 1H), 2.35-2.23 (m, 1H), 1.94-1.71 (m, 3H), 1.69-1.44 (m, 4H), 1.34-1.02 (m, 3H), 0.92 (d, J=6.7 Hz, 3H).

Example 128G (1'S,4a'S,8a'S)-4a'-[3-(benzyloxy)phenyl]-1'-methyl-hexahydro-1'H-spiro[1,3-dioxolane-2,2'-naphthalen]-5'(3'H)-one Example 128F (18.0 g, 44.1 mmol) from above was dissolved in dichloromethane (180 mL) and pyridinium dichromate (33.2 g, 88 mmol) and magnesium sulfate (1.1 g) were added. The resulting mixture was heated to reflux and stirred overnight. The reaction was cooled to room temperature, and the mixture was filtered through a plug of silica gel (75 g) rinsing with dichloromethane (500 mL). The filtrate was concentrated and the solids remaining were precipitated from cyclohexane (100 mL) by heating to dissolve and allowing cooling to room temperature. The solids were collected by filtration, washed with cyclohexane (2×10 mL) and dried in a vacuum oven at 50° C. to give the titled compound (12.0 g, 67%). $^1$H NMR (400 MHz, CDCl$_3$) δ ppm 7.50-7.32 (m, 5H), 7.30-7.20 (m, 1H), 7.02 (dd, J=4.9, 3.3 Hz, 2H), 6.89-6.83 (m, 1H), 5.12-5.01 (m, 2H), 4.04-3.93 (m, 4H), 2.71 (dq, J=13.0, 6.5 Hz, 1H), 2.24 (td, J=13.3, 6.0 Hz, 1H), 2.19-2.03 (m, 4H), 2.01-1.86 (m, 3H), 1.75-1.54 (m, 2H), 1.22 (td, J=13.1, 5.0 Hz, 1H), 1.01 (d, J=6.5 Hz, 3H); MS (CI—NH$_3$) m/z 424.2 (M+NH$_4$)$^+$.

Example 128H (1'S,4a'S,6'Z,8a'S)-4a'-[3-(benzyloxy)phenyl]-6'-(hydroxymethylene)-1'-methylhexahydro-1'H-spiro[1,3-dioxolane-2,2'-naphthalen]-5'(3'H)-one The titled compound was prepared using the conditions described in Example 58G substituting Example 58F with Example 128G.

Example 128I (6aS,7S,10aS)-10a-[3-(benzyloxy)phenyl]-7-methyl-5,6a,7,9,10,10a-hexahydro-6H-spiro[benzo[h]quinazoline-8,2'-[1,3]dioxolane]

To a solution Example 128H (1.0 g, 2.30 mmol) in isopropanol (20 mL) was added formamidine acetate (0.719 g, 6.90 mmol) and piperidine (0.684 mL, 6.90 mmol). The reaction mixture was heated at 95° C. for 48 hours. The cooled solution was diluted with a solution of sodium phosphate monobasic and extracted with ethyl acetate. The organic fraction was concentrated to give the titled compound. MS (APCI+) m/z 443 (M+H)⁺.

Example 128J (6aS,7S,10aS)-10a-[3-(benzyloxy)phenyl]-7-methyl-5,6a,7,9,10,10a-hexahydrobenzo[h]quinazolin-8 (6H)-one The titled compound was prepared using the conditions described in Example 1I, substituting Example 128I for Example 1H.

Example 128K (6aS,7S,9Z,10aS)-10a-[3-(benzyloxy)phenyl]-9-(hydroxymethylene)-7-methyl-5,6a,7,9,10,10a-hexahydrobenzo[h]quinazolin-8(6H)-one The titled compound was prepared using the conditions described in Example 1J, substituting Example 128J for Example 1I.

Example 128L (6aS,7S,11aS)-11a-[3-(benzyloxy)phenyl]-7-methyl-5,6,6a,7,11,11a-hexahydro[1,2]benzoxazolo[6,5-h]quinazoline The titled compound was prepared using the conditions described in Example 1K, substituting Example 128K for Example 1J. MS (APCI+) m/z 424 (M+H)⁺.

Example 128M (6aS,7S,10aS)-10a-[3-(benzyloxy)phenyl]-7-methyl-8-oxo-5,6,6a,7,8,9,10,10a-octahydrobenzo[h]quinazoline-9-carbonitrile The titled compound was prepared using the conditions described in Example 1L, substituting Example 128L for Example 1K.

Example 128N (6aS,7S,10aR)-10a-[3-(benzyloxy)phenyl]-7-methyl-8-oxo-5,6,6a,7,8,10a-hexahydrobenzo[h]quinazoline-9-carbonitrile To a solution of Example 128M (0.290 g, 0.685 mmol) in dimethylformamide (5 mL) cooled to 0° C. in an ice water bath was added 1,3-dibromo-5,5-dimethylhydantoin (0.108 g, 0.377 mmol). The solution was stirred at 0° C. for 1 hour, then pyridine (0.831 mL, 10.27 mmol) was added, and the solution was heated at 55° C. for 1 hour. The cooled solution was diluted with water and extracted with ethyl acetate. The organic phase was washed with brine and concentrated. The residue was purified chromatographically using a 12 g RediSep® silica gel cartridge on a Teledyne Isco Combiflash® Rf system eluting with 0-40% ethyl acetate in heptane to give 0.187 g (65%) of the titled compound. ¹H NMR (400 MHz, CDCl₃) δ ppm 1.15 (d, J=6.72 Hz, 3H) 1.48-1.54 (m, 1H) 1.86-1.97 (m, 1H) 2.26 (td, J=12.85, 2.39 Hz, 1H) 2.40 (td, J=13.15, 6.78 Hz, 1H) 2.91-2.98 (m, 2H) 4.91-5.04 (m, 2H) 6.25 (t, J=2.06 Hz, 1H) 6.37 (d, J=7.92 Hz, 1H) 6.92 (dd, J=8.19, 2.22 Hz, 1H) 7.20-7.25 (m, 1H) 7.29-7.42 (m, 5H) 8.65 (s, 1H) 8.79 (s, 1H) 9.05 (s, 1H); MS (ESI+) m/z 422 (M+H)⁺.

Example 129

(6aS,7S,10aR)-2,7-dimethyl-8-oxo-10a-phenyl-4-[4-(pyrimidin-5-yl)phenyl]-5,6,6a,7,8,10a-hexahydrobenzo[h]quinazoline-9-carbonitrile Example 129A (6aS,7S,10aS)-2,7-dimethyl-10a-phenyl-4-[4-(pyrimidin-5-yl)phenyl]-5,6a,7,9,10,10a-hexahydrobenzo[h]quinazolin-8(6H)-one The titled compound was prepared using the conditions described in Example 119B, substituting Example 122A for Example 119A and pyrimidine-5-boronic acid for 4-hydroxyphenyl boronic acid. MS (APCI+) m/z 461 (M+H)⁺.

Example 129B (6aS,7S,9Z,10aS)-9-(hydroxymethylene)-2,7-dimethyl-10a-phenyl-4-[4-(pyrimidin-5-yl)phenyl]-5,6a,7,9,10,10a-hexahydrobenzo[h]quinazolin-8(6H)-one The titled compound was prepared using the conditions described in Example 1J, substituting Example 129A for Example 1I.

Example 129C (6aS,7S,11aS)-2,7-dimethyl-11a-phenyl-4-[4-(pyrimidin-5-yl)phenyl]-5,6,6a,7,11,11a-hexahydro[1,2]benzoxazolo[6,5-h]quinazoline The titled compound was prepared using the conditions described in Example 1K, substituting Example 129B for Example 1J. MS (APCI+) m/z 486 (M+H)⁺.

Example 129D (6aS,7S,10aS)-2,7-dimethyl-8-oxo-10a-phenyl-4-[4-(pyrimidin-5-yl)phenyl]-5,6,6a,7,8,9,10,10a-octahydrobenzo[h]quinazoline-9-carbonitrile The titled compound was prepared using the conditions described in Example 1L, substituting Example 129C for Example 1K.

Example 129E (6aS,7S,10aR)-2,7-dimethyl-8-oxo-10a-phenyl-4-[4-(pyrimidin-5-yl)phenyl]-5,6,6a,7,8,10a-hexahydrobenzo[h]quinazoline-9-carbonitrile A solution of Example 129D (0.160 g, 0.330 mmol) in tetrahydrofuran (5 mL) at room temperature was sparged with nitrogen for 15 minutes, and then 2,3-dichloro-5,6-dicyano-1,4-benzoquinone (0.075 g, 0.330 mmol) was added. After 15 minutes, with continued nitrogen bubbling, the solution was concentrated, and the residue was put directly on a 12 g RediSep® silica gel cartridge and purified chromatographically on a Teledyne Isco Combiflash® Rf system eluting with 0-80% ethyl acetate in heptane to give 0.095 g (60%) of the titled compound. ¹H NMR (400 MHz, CDCl₃) δ ppm 1.18 (d, J=6.51 Hz, 3H) 1.58-1.64 (m, 1H) 1.88-1.97 (m, 1H) 2.38 (td, J=12.85, 2.17 Hz, 1H) 2.48 (td, J=13.04, 6.56 Hz, 1H) 2.73 (s, 3H) 3.02 (dd, J=8.62, 4.39 Hz, 2H) 6.86 (dd, J=7.92, 1.41 Hz, 2H) 7.30-7.40 (m, 3H) 7.72-7.79 (m, 4H) 8.99 (s, 1H) 9.02 (s, 2H) 9.27 (s, 1H); MS (ESI+) m/z 484 (M+H)⁺, 516 (M+CH₃OH+H)⁺.

Example 130

(6aS,7S,10aR)-2,7-dimethyl-8-oxo-10a-phenyl-4-(pyrimidin-5-yl)-5,6,6a,7,8,10a-hexahydrobenzo[h]quinazoline-9-carboxamide To a solution of Example 22E (0.054 g, 0.133 mmol in 80% ethanol (1.5 mL) was added hydrido(dimethylphosphinous acid-kP)[hydrogen bis(dimethylphosphinito-kP)]platinum (II) (0.011 g, 0.027 mmol). The reaction mixture was heated at a bath temperature of 90° C. for 30 minutes. The solution was concentrated and purified using a 4 g RediSep® silica gel cartridge on a Teledyne Isco Combiflash® Rf system eluting with 0-20% methanol in dichloromethane to give 0.043 g (76%) of the titled compound. ¹H NMR (400 MHz, CDCl₃) δ ppm 1.17 (d, J=6.61 Hz, 3H) 1.66-1.77 (m, 1H) 1.87-1.98 (m, 1H) 2.37 (td, J=12.71, 2.33 Hz, 1H) 2.47 (td, J=12.96, 6.51 Hz, 1H) 2.73 (s, 3H) 2.96-3.09 (m, 2H) 5.78 (d, J=3.80 Hz, 1H) 6.84 (dd, J=7.75, 1.68 Hz, 2H) 7.28-7.34 (m, 3H) 8.59 (d, J=3.69 Hz, 1H) 9.05 (s, 2H) 9.34 (s, 1H) 9.41 (s, 1H); MS (ESI+) m/z 426 (M+H)⁺.

Example 131

(6aS,7S,10aR)-7-methyl-8-oxo-10a-phenyl-5,6,6a,7,8,10a-hexahydrobenzo[h]quinazoline-9-carboxamide To a solution of Example 1M (0.050 g, 0.159 mmol in 80% ethanol (2 mL) was added hydrido(dimethylphosphinous acid-kP)[hydrogen bis(dimethylphosphinito-kP)]platinum (II) (0.014 g, 0.032 mmol). The reaction mixture was heated at a bath temperature of 90° C. for 40 minutes. The solution was concentrated and purified by 4 g RediSep® silica gel cartridge on a Teledyne Isco Combiflash® Rf system eluting with 0-4% methanol in dichloromethane to give 0.045 g (86%) of the titled compound. ¹H NMR (400 MHz, CDCl₃) δ ppm 1.18 (d, J=6.72 Hz, 3H) 1.63-1.77 (m, J=13.27, 13.27, 11.14, 6.99 Hz, 1H) 1.95 (dd, J=14.04, 7.32 Hz, 1H) 2.33 (td, J=12.85, 2.49 Hz, 1H) 2.45 (td, J=13.12, 6.61 Hz, 1H) 2.96-3.16 (m, 2H) 5.74 (s, 1H) 6.80 (dd, J=7.75, 1.79 Hz, 2H) 7.25-7.33 (m, 3H) 8.57 (s, 1H) 8.67 (s, 1H) 9.08 (s, 1H) 9.34 (s, 1H); MS (ESI+) m/z 334 (M+H)⁺.

Example 132

(6aS,7S,10aR)-4-(5-bromo-6-hydroxypyridin-3-yl)-2,7-dimethyl-8-oxo-10a-phenyl-5,6,6a,7,8,10a-hexahydrobenzo[h]quinazoline-9-carbonitrile Example 132A (6aS,7S,10aS)-4-(6-hydroxypyridin-3-yl)-2,7-dimethyl-10a-phenyl-5,6a,7,9,10,10a-hexahydrobenzo[h]quinazolin-8(6H)-one The titled compound was prepared using the conditions described in Example 17A, substituting 5-(4,4,5,5-tetramethyl-1,3,2-dioxaborolan-2-yl)pyridin-2-ol for 1-methyl-5-(4,4,5,5-tetramethyl-1,3,2-dioxaborolan-2-yl)-1H-imidazole and purified by flash chromatography on silica gel eluting with 33-66% acetone in chloroform to give the titled compound in 67% yield. ¹H NMR (400 MHz, CDCl₃) δ ppm 1.17 (d, J=6.51 Hz, 3H) 1.91-2.02 (m, 1H) 2.06-2.20 (m, 2H) 2.29-2.40 (m, 2H) 2.45-2.51 (m, 1H) 2.53-2.65 (m, 1H) 2.71 (s, 3H) 2.81-2.96 (m, 2H) 3.13-3.22 (m, 1H) 6.63 (d, J=9.54 Hz, 1H) 7.21-7.26 (m, 1H) 7.31 (t, J=7.54 Hz, 2H) 7.50 (d, J=7.70 Hz, 2H) 7.60 (d, J=2.39 Hz, 1H) 7.74 (dd, J=9.49, 2.55 Hz, 1H) 12.30 (s, 1H); MS (ESI) m/z 400.3 (M+H)⁺.

Example 132B (6aS,7S,9Z,10aS)-9-(hydroxymethylene)-4-(6-hydroxypyridin-3-yl)-2,7-dimethyl-10a-phenyl-5,6a,7,9,10,10a-hexahydrobenzo[h]quinazolin-8(6H)-one The titled compound was prepared using the conditions described in Example 13F, substituting Example 132A for Example 13E.

Example 132C

5-[(6aS,7S,11aS)-2,7-dimethyl-11a-phenyl-5,6,6a,7,11,11a-hexahydro[1,2]benzoxazolo[6,5-h]quinazolin-4-yl]pyridin-2-ol The titled compound was prepared using the conditions described in Example 13G, substituting Example 132B for Example 13F.

Example 132D (6aS,7S,10aS)-4-(6-hydroxypyridin-3-yl)-2,7-dimethyl-8-oxo-10a-phenyl-5,6,6a,7,8,9,10,10a-octahydrobenzo[h]quinazoline-9-carbonitrile The titled compound was prepared using the conditions described in Example 13H, substituting Example 132C for Example 13G and purified by flash chromatography on silica gel eluting with 5% methanol in chloroform to give the titled compound in 47% yield.

Example 132E (6aS,7S,10aR)-4-(5-bromo-6-hydroxypyridin-3-yl)-2,7-dimethyl-8-oxo-10a-phenyl-5,6,6a,7,8,10a-hexahydrobenzo[h]quinazoline-9-carbonitrile The titled compound was prepared using the conditions described in Example 131, substituting Example 132D for Example 13H and purified by flash chromatography on silica gel eluting with 25-50% acetone in chloroform to give the titled compound as the first to elute in 27% yield. ¹H NMR (400 MHz, CDCl₃) δ ppm 1.20 (d, J=6.61 Hz, 3H) 1.61-1.70 (m, 1H) 1.95-2.03 (m, 1H) 2.34 (td, J=12.93, 2.01 Hz, 1H) 2.48 (td, J=13.01, 6.51 Hz, 1H) 2.69 (s, 3H) 3.03-3.10 (m, 2H) 5.52 (s, 1H) 6.80 (dd, J=7.48, 1.84 Hz, 2H) 7.30-7.39 (m, 3H) 7.95 (d, J=2.17 Hz, 1H) 8.39 (d, J=2.28 Hz, 1H) 8.93 (s, 1H); MS (ESI) m/z 535 (M+H+methanol)⁺.

Example 133

(6aS,7S,10aR)-4-(6-hydroxypyridin-3-yl)-2,7-dimethyl-8-oxo-10a-phenyl-5,6,6a,7,8,10a-hexahydrobenzo[h]quinazoline-9-carbonitrile The titled compound was isolated as the second compound to elute from the chromatography in Example 132E in 20% yield. $^1$H NMR (400 MHz, CDCl$_3$) δ ppm 1.19 (d, J=6.61 Hz, 3H) 1.60-1.67 (m, 1H) 1.96 (ddd, J=13.91, 3.14, 3.01 Hz, 1H) 2.34 (td, J=12.85, 2.28 Hz, 1H) 2.47 (td, J=13.23, 6.83 Hz, 1H) 2.68 (s, 3H) 3.02-3.10 (m, 2H) 6.73 (d, J=9.54 Hz, 1H) 6.81 (dd, J=7.54, 1.90 Hz, 2H) 7.31-7.39 (m, 3H) 7.88 (d, J=2.49 Hz, 1H) 7.95 (dd, J=9.54, 2.49 Hz, 1H) 8.94 (s, 1H); MS (ESI) m/z 423 (M+H)$^+$.

Example 134 methyl 3'-[(6aS,7S,10aR)-9-cyano-2,7-dimethyl-8-oxo-10a-phenyl-5,6,6a,7,8,10a-hexahydrobenzo[h]quinazolin-4-yl]biphenyl-4-carboxylate

Example 134A methyl 3'-[(6aS,7S,10aS)-2,7-dimethyl-8-oxo-10a-phenyl-5,6,6a,7,8,9,10,10a-octahydrobenzo[h]quinazolin-4-yl]biphenyl-4-carboxylate The titled compound was prepared using the conditions described in Example 119B, substituting (4-(methoxycarbonyl)phenyl)boronic acid for (4-hydroxyphenyl)boronic acid and purified by flash chromatography on silica gel eluting with 10% ethyl acetate in chloroform to give the titled compound in 75% yield. $^1$H NMR (500 MHz, CDCl$_3$) δ ppm 1.16 (d, J=6.41 Hz, 3H) 1.96-2.17 (m, 3H) 2.31-2.46 (m, 2H) 2.47-2.54 (m, 1H) 2.55-2.65 (m, 1H) 2.77 (s, 3H) 2.83 (td, J=12.59, 6.56 Hz, 1H) 2.93 (ddd, J=16.48, 7.78, 5.65 Hz, 1H) 3.22-3.29 (m, 1H) 3.94 (s, 3H) 7.22-7.28 (m, 1H) 7.32 (t, J=7.63 Hz, 1H) 7.44 (d, J=7.63 Hz, 2H) 7.49-7.57 (m, 3H) 7.64-7.70 (m, 4H) 8.10 (d, J=8.54 Hz, 2H); MS (ESI) m/z 517.3 (M+H)$^+$.

Example 134 B methyl 3'-[(6aS,7S,9Z,10aS)-9-(hydroxymethylene)-2,7-dimethyl-8-oxo-10a-phenyl-5,6,6a,7,8,9,10,10a-octahydrobenzo[h]quinazolin-4-yl]biphenyl-4-carboxylate The titled compound was prepared using the conditions described in Example 13F, substituting Example 134A for Example 13E.

Example 134C methyl 3'-[(6aS,7S,11aS)-2,7-dimethyl-11a-phenyl-5,6,6a,7,11,11a-hexahydro[1,2]benzoxazolo[6,5-h]quinazolin-4-yl]biphenyl-4-carboxylate The titled compound was prepared using the conditions described in Example 13G, substituting Example 134B for Example 13F.

Example 134D methyl 3'-[(6aS,7S,10aS)-9-cyano-2,7-dimethyl-8-oxo-10a-phenyl-5,6,6a,7,8,9,10,10a-octahydrobenzo[h]quinazolin-4-yl]biphenyl-4-carboxylate The titled compound was prepared using the conditions described in Example 13H, substituting Example 134C for Example 13G and purified by flash chromatography on silica gel eluting with 25% acetone in heptane to give the titled compound in 52% yield.

Example 134E methyl 3'-[(6aS,7S,10aR)-9-cyano-2,7-dimethyl-8-oxo-10a-phenyl-5,6,6a,7,8,10a-hexahydrobenzo[h]quinazolin-4-yl]biphenyl-4-carboxylate The titled compound was prepared using the conditions described in Example 131, substituting Example 134D for Example 13H and purified by flash chromatography on silica gel eluting with 33% acetone in heptane to give the titled compound in 35% yield. $^1$H NMR (400 MHz, CDCl$_3$) δ ppm 1.16 (d, J=6.51 Hz, 3H) 1.49-1.62 (m, 1H) 1.86-1.93 (m, 1H) 2.37 (td, J=12.77, 2.22 Hz, 1H) 2.46 (td, J=12.88, 6.23 Hz, 1H) 2.73 (s, 3H) 2.96-3.01 (m, 2H) 3.96 (s, 3H) 6.85 (d, J=6.40 Hz, 2H) 7.31-7.39 (m, 3H) 7.57-7.65 (m, 2H) 7.69-7.76 (m, 3H) 7.80 (s, 1H) 8.14 (d, J=8.35 Hz, 2H) 8.99 (s, 1H); MS (ESI) m/z 540 (M+H)$^+$.

Example 135

3'-[(6aS,7S,10aR)-9-cyano-2,7-dimethyl-8-oxo-10a-phenyl-5,6,6a,7,8,10a-hexahydrobenzo[h]quinazolin-4-yl]biphenyl-4-carboxamide A solution of Example 134E (0.045 g, 0.083 mmol) in ammonium hydroxide (1.0 ml) was stirred at room temperature for 48 hours, concentrated under reduced pressure and purified by flash chromatography on silica gel eluting with 10-20% acetone in chloroform to give the titled compound (16 mg, 34%). $^1$H NMR (400 MHz, CDCl$_3$) δ ppm 1.17 (d, J=6.61 Hz, 3H) 1.50-1.61 (m, 1H) 1.86-1.93 (m, 1H) 2.37 (td, J=12.77, 2.11 Hz, 1H) 2.47 (td, J=13.01, 6.51 Hz, 1H) 2.73 (s, 3H) 2.97-3.01 (m, 2H) 5.72 (s, 1H) 6.13 (s, 1H) 6.85 (d, J=6.51 Hz, 2H) 7.31-7.39 (m, 3H) 7.55-7.66 (m, 2H) 7.72-7.76 (m, 3H) 7.79 (s, 1H) 7.93 (d, J=8.35 Hz, 2H) 8.99 (s, 1H); MS (ESI) m/z 525 (M+H)$^+$.

Example 136

4-[(6aS,7S,10aR)-9-cyano-7-methyl-8-oxo-10a-phenyl-5,6,6a,7,8,10a-hexahydrobenzo[h]quinazolin-2-yl]benzamide To 30% ammonium hydroxide solution (1.0 mL, 7.70 mmol) in a tube was added Example 75F (0.020 g, 0.044 mmol). The tube was sealed and the mixture was stirred at room temperature for 20 hours, then heated at 40° C. for 24 hours, and then stirred at room temperature for 9 days. The mixture was concentrated to dryness, and the residue was purified by preparative HPLC on a Waters Sunfire™ C8(2), 5 µm, 100 Å column (30 mm×75 mm). A gradient of acetonitrile (A) and 0.1% trifluoroacetic acid in water (B) was used, at a flow rate of 50 mL/minute (0-0.5 minute 10% A, 0.5-7.0 minutes linear gradient 10-95% A, 7.0-10.0 minutes 95% A, 10.0-12.0 minutes linear gradient 95-10% A) gave 0.0035 g (18%) of the titled compound. $^1$H NMR (400 MHz, CDCl$_3$) δ ppm 1.22 (d, J=6.61 Hz, 3H) 1.63-1.72 (m, 1H) 1.96-2.05 (m, 1H) 2.34-2.43 (m, 1H) 2.51 (td, J=13.07, 6.51 Hz, 1H) 3.02-3.21 (m, 2H) 5.62 (s, 1H) 6.13 (s, 1H) 6.85 (dd, J=7.75, 1.68 Hz, 2H) 7.30-7.37 (m, 3H) 7.90 (d, J=8.46 Hz, 2H) 8.47 (d, J=8.46 Hz, 2H) 8.81 (s, 1H) 9.00 (s, 1H); MS (APCl+) m/z 435 (M+H)$^+$.

Example 137

(6aS,7S,10aR)-10a-(3-hydroxyphenyl)-7-methyl-8-oxo-5,6,6a,7,8,10a-hexahydrobenzo[h]quinazoline-9-carbonitrile To a solution of Example 128N (0.149 g, (0.354 mmol) in dichloromethane (3 mL) cooled in an ice bath to 0° C. was added methanesulfonic acid (0.688 mL, 10.61 mmol) dropwise. The reaction solution was stirred at 0° C. for 2 hours, and then more methanesulfonic acid (0.100 mL) was added, and the stirring was continued for another 20 minutes. The reaction was quenched by dropwise addition of 1 N sodium hydroxide to pH 9, and then the pH was readjusted back to pH 6 with 1 N hydrochloric acid. The solution was extracted with 20% isopropanol in chloroform. The organic fraction was concentrated, and the residue was purified using a Teledyne Isco Combiflash® Rf system equipped with a 12 g RediSep® silica gel cartridge eluted with 0-80% ethyl acetate in heptane. Then a second purification by preparative HPLC on a Waters Sunfire™ C8(2), 5 μm, 100 Å AXIA, column (30, mm×75, mm) using a gradient of acetonitrile (A) and 0.1% trifluoroacetic acid in water (B), at a flow rate of 50 mL/minute (0-0.5 minute 10% A, 0.5-7.0 minutes linear gradient 10-95% A, 7.0-10.0 minutes 95% A, 10.0-12.0 minutes linear gradient 95-10% A) gave 0.031 g (26%) of the titled compound. $^1$H NMR (400 MHz, CDCl$_3$) δ ppm 1.20 (d, J=6.72 Hz, 3H) 1.66-1.78 (m, 1H) 1.99 (ddd, J=12.79, 7.92, 1.19 Hz, 1H) 2.32 (td, J=12.98, 2.44 Hz, 1H) 2.52 (td, J=13.28, 6.83 Hz, 1H) 2.97-3.19 (m, 2H) 6.25 (s, 1H) 6.34 (d, J=7.81 Hz, 1H) 6.77 (dd, J=8.13, 2.28 Hz, 1H) 7.19 (t, J=8.02 Hz, 1H) 8.71 (s, 1H) 8.83 (s, 1H) 9.07 (s, 1H); MS (ESI+) m/z 332 (M+H)$^+$.

Example 138

4-[(6aS,7S,10aR)-9-cyano-7-methyl-8-oxo-10a-phenyl-5,6,6a,7,8,10a-hexahydrobenzo[h]quinazolin-2-yl]-N,N-dimethylbenzamide To a solution of Example 77 (0.056 g, 0.129 mmol) in dimethylacetamide (2 mL) was added 2 M dimethylamine in methanol (0.129 mL, 2.57 mmol), Hunig's base (0.34 mL, 0.193 mmol), and bis(dimethylamino)(3-oxido-1H-benzotriazol-1-yl)methylium hexafluorophosphate (HATU, 0.059 g, 0.154 mmol). The reaction mixture was stirred at room temperature for 2 hours, then diluted with water, and extracted with ethyl acetate. The organic fraction was concentrated, and the residue was purified on a Teledyne Isco Combiflash® Rf system on a 12 g RediSep® silica gel cartridge, eluting with 0-70% ethyl acetate in heptane. Then a second purification on a 4 g silica gel column, eluting with 0-2% methanol in dichloromethane gave 0.027 g (45%) of the titled compound. $^1$H NMR (400 MHz, CDCl$_3$) δ ppm 1.21 (d, J=6.72 Hz, 3H) 1.61-1.70 (m, 1H) 1.97-2.04 (m, 1H) 2.38 (td, J=12.93, 2.55 Hz, 1H) 2.50 (td, J=13.01, 6.51 Hz, 1H) 2.98 (s, 3H) 3.03-3.20 (m, 5H) 6.85 (dd, J=7.81, 1.73 Hz, 2H) 7.30-7.36 (m, 3H) 7.51 (d, J=8.35 Hz, 2H) 8.42 (d, J=8.35 Hz, 2H) 8.79 (s, 1H) 9.01 (s, 1H); MS (ESI+) m/z 463 (M+H)$^+$, 495 (M+CH$_3$OH+H)$^+$.

Example 139

(6aS,7S,10aR)-2,7-dimethyl-4-[4-(1-methyl-1H-imidazol-5-yl)phenyl]-8-oxo-10a-phenyl-5,6,6a,7,8,10a-hexahydrobenzo[h]quinazoline-9-carbonitrile Example 139A (6aS,7S,10aS)-2,7-dimethyl-4-[4-(1-methyl-1H-imidazol-5-yl)phenyl]-10a-phenyl-5,6a,7,9,10,10a-hexahydrobenzo[h]quinazolin-8(6H)-one The titled compound was prepared using the conditions described in Example 119B, substituting Example 122A for Example 119A, 1-methyl-1H-imidazole-5-boronic acid pinacol ester for 4-hydroxyphenyl boronic acid, and heating for 5 hours.

Example 139B (6aS,7S,9Z,10aS)-9-(hydroxymethylene)-2,7-dimethyl-4-[4-(1-methyl-1H-imidazol-5-yl)phenyl]-10a-phenyl-5,6a,7,9,10,10a-hexahydrobenzo[h]quinazolin-8(6H)-one The titled compound was prepared using the conditions described in Example 1J, substituting Example 139A for Example 1I.

Example 139C (6aS,7S,11aS)-2,7-dimethyl-4-[4-(1-methyl-1H-imidazol-5-yl)phenyl]-11a-phenyl-5,6,6a,7,11,11a-hexahydro[1,2]benzoxazolo[6,5-h]quinazoline The titled compound was prepared using the conditions described in Example 1K, substituting Example 139B for Example 1J. MS (APCI+) m/z 488 (M+H)$^+$.

Example 139D (6aS,7S,10aS)-2,7-dimethyl-4-[4-(1-methyl-1H-imidazol-5-yl)phenyl]-8-oxo-10a-phenyl-5,6,6a,7,8,9,10,10a-octahydrobenzo[h]quinazoline-9-carbonitrile The titled compound was prepared using the conditions described in Example 1L, substituting Example 139C for Example 1K.

Example 139D (6aS,7S,10aR)-2,7-dimethyl-4-[4-(1-methyl-1H-imidazol-5-yl)phenyl]-8-oxo-10a-phenyl-5,6,6a,7,8,10a-hexahydrobenzo[h]quinazoline-9-carbonitrile A solution of Example 139D (0.079 g, 0.162 mmol) in tetrahydrofuran (3 mL) at room temperature was sparged with nitrogen for 15 minutes, and then 2,3-dichloro-5,6-dicyano-1,4-benzoquinone (0.037 g, 0.162 mmol) was added. After 15 minutes, with continuous nitrogen bubbling, the solution was concentrated, and the residue was purified using a 12 g RediSep® silica gel cartridge on a Teledyne Isco Combiflash® Rf, eluting with 0-90% ethyl acetate in heptane. A second purification by preparative HPLC on a Waters Sunfire™ C8(2), 5 μm, 100 Å AXIA, column (30, mm×75, mm) using a gradient of acetonitrile (A) and 0.1% trifluoroacetic acid in water (B) was used, at a flow rate of 50 mL/minute (0-0.5 minute 10% A, 0.5-7.0 minutes linear gradient 10-95% A, 7.0-10.0 minutes 95% A, 10.0-12.0 minutes linear gradient 95-10% A) gave 0.008 g (10%) of the titled compound. $^1$H NMR (400 MHz, CDCl$_3$) δ ppm 1.18 (d, J=6.61 Hz, 3H) 1.60 (tt, J=13.11, 8.69 Hz, 1H) 1.89-1.98 (m, 1H) 2.37 (td, J=12.88, 2.11 Hz, 1H) 2.48 (td, J=13.01, 6.40 Hz, 1H) 2.74 (s, 3H) 3.00 (dd, J=8.46, 4.45 Hz, 2H) 3.90 (s, 3H) 6.85 (dd, J=7.75, 1.46 Hz, 2H) 7.33-7.40 (m, 3H) 7.48 (s, 1H) 7.58 (d, J=8.13 Hz, 2H) 7.78 (d, J=8.02 Hz, 2H) 8.81 (s, 1H) 8.97 (s, 1H); MS (ESI−) m/z 484 (M−H)$^−$, 516 (M+CH$_3$OH—H)$^−$.

Example 140

(5aS,6S,9aR)-6-methyl-7-oxo-9a-phenyl-3-(pyridazin-4-yl)-4,5,5a,6,7,9a-hexahydro-2H-benzo[g]indazole-8-carbonitrile

Example 140A (5aS,6S,9aS)-6-methyl-9a-phenyl-2,4,5,5a,6,8,9,9a-octahydrospiro[benzo[g]indazole-7,2'-[1,3]dioxolane]

Example 1G (5.0 g, 15.23 mmol) was suspended in ethanol (75 ml) and cooled to 0° C. Hydrazine (1.434 ml, 45.7 mmol) was added via syringe dropwise and after 20 minutes a mostly homogeneous solution was obtained (slight haze). The mixture was warmed to room temperature and stirred overnight. The reaction was concentrated, and the residue was taken up in ethyl acetate and washed with water and brine. The organic extracts were dried over anhydrous magnesium sulfate, filtered and concentrated under reduced pressure to provide (5.09 g, >100%) of the titled compound which was utilized without further purification.

Example 140B (5aS,6S,9aS)—N,N,6-trimethyl-9a-phenyl-4,5,5a,8,9,9a-hexahydrospiro[benzo[g]indazole-7,2'-[1,3]dioxolane]-2(6H)-sulfonamide Example 140A (5.09 g, 15.69 mmol) was dissolved in toluene (75 ml) followed by addition of triethylamine (13.56 ml, 97 mmol) and dropwise addition of dimethylsulfamoyl chloride (10.04 ml, 94 mmol). The reaction was heated to reflux overnight. The reaction was concentrated, and the residue partitioned between water and ethyl acetate, and then the aqueous layer was extracted several times with ethyl acetate. The organic phase was washed with brine and separated. Any remaining undissolved flask residue was then dissolved with a solution of chloroform and isopropanol and combined with the above organic extracts. The combined organic solutions were dried over anhydrous magnesium sulfate, filtered and concentrated by rotary evaporation. The resultant residue was dissolved in dichloromethane, and the solution was loaded onto a silica gel column and was purified by flash chromatography eluting with 0% to 30% ethyl acetate in hexanes to afford the titled compound (4.91 g, 72%). $^1$H NMR (400 MHz, CDCl$_3$) δ ppm 7.71 (d, J=7.7 Hz, 2H), 7.54 (s, 1H), 7.27-7.19 (m, 2H), 7.13 (t, J=7.3 Hz, 1H), 4.02-3.82 (m, 4H), 2.88 (s, 6H), 2.75-2.48 (m, 3H), 2.19-2.01 (m, 3H), 2.00-1.90 (m, 1H), 1.67 (dt, J=13.5, 3.3 Hz, 1H), 1.43-1.19 (m, 2H), 1.04 (d, J=6.6 Hz, 3H); MS (DCI+) m/z 432 (M+H)$^+$.

Example 140C (5aS,6S,9aS)-3-bromo-N,N,6-trimethyl-9a-phenyl-4,5,5a,8,9,9a-hexahydrospiro[benzo[g]indazole-7,2'-[1,3]dioxolane]-2(6H)-sulfonamide Example 140B (4.91 g, 11.38 mmol) was dissolved in tetrahydrofuran (75 ml), and the mixture was cooled to −78° C. Lithium hexamethyldisilazide solution (1M in tetrahydrofuran, 39.8 ml, 39.8 mmol) was added by syringe over 25 minutes. The solution was allowed to stir for 1 hour at −78° C. after which time 1,2 dibromotetrachloroethane (5.56 g, 17.07 mmol) was added in one portion. After stirring for 1.5 hours at −78° C., the reaction mixture was warmed to room temperature overnight. The reaction was quenched by the addition of saturated ammonium chloride solution followed by extraction with ethyl acetate. The organic extracts were combined, washed with brine, dried over anhydrous magnesium sulfate, filtered and concentrated by rotary evaporation. The crude residue was dissolved in dichloromethane and loaded onto a silica gel column eluting with 0%-30% ethyl acetate in heptane to afford the titled compound (3.43 g, 59%). $^1$H NMR (400 MHz, CDCl$_3$) δ 7.67 (d, J=7.7 Hz, 2H), 7.28-7.21 (m, 2H), 7.14 (t, J=7.3 Hz, 1H), 3.94 (dt, J=4.9, 2.2 Hz, 4H), 3.06 (s, 6H), 2.70-2.59 (m, 2H), 2.50-2.38 (m, 2H), 2.15-2.03 (m, 2H), 1.98-1.87 (m, 1H), 1.66 (dt, J=13.6, 3.4 Hz, 1H), 1.36 (td, J=14.0, 3.5 Hz, 1H), 1.24-1.19 (m, 1H), 1.04 (d, J=6.6 Hz, 3H); MS (DCI+) m/z 510 (M+H)$^+$.

Example 140D (5aS,6S,9aS)-3-bromo-6-methyl-9a-phenyl-2,4,5,5a,6,8,9,9a-octahydro-7H-benzo[g]indazol-7-one Example 140C (0.5 g, 0.98 mmol) was dissolved in tetrahydrofuran (5 ml) followed by addition of hydrochloric acid (3 M, 9.8 mmol, 3.27 ml), and the solution was heated to 80° C. overnight. The solution was cooled to room temperature and neutralized with solid sodium bicarbonate and extracted with ethyl acetate. The organic extracts were dried over anhydrous magnesium sulfate, filtered and concentrated to give the titled compound (0.343 g, 97%).

Example 140E (5aS,6S,9aS)-6-methyl-9a-phenyl-3-(pyridazin-4-yl)-2,4,5,5a,6,8,9,9a-octahydro-7H-benzo[g]indazol-7-one Example 140D (0.193 g, 0.537 mmol) was suspended in dioxane (3 ml) and water (0.3 ml) followed by the addition of cesium carbonate (0.525 g, 1.61 mmol) and 4-(4,4,5,5-tetramethyl-1,3,2-dioxaborolan-2-yl)pyridazine (0.332 g, 1.61 mmol). The reaction mixture was sparged with nitrogen for 15 minutes followed by the addition of [1,1'-bis(diphenyl)phosphine)ferrocene]dichloropalladium(II) (0.044 g, 0.054 mmol), and the reaction mixture was heated at 85° C. for 30 hours. The cooled reaction mixture was diluted with water and extracted with ethyl acetate. The combined organic extracts were washed with saturated sodium chloride solution, dried over anhydrous magnesium sulfate, filtered and concentrated. The resulting residue was dissolved in dichloromethane and loaded onto a silica gel column and purified by flash chromatography eluting with 20% ethyl acetate in heptane to 100% ethyl acetate in heptane to afford the titled compound (0.039 g, 20%). $^1$H NMR (400 MHz, CDCl$_3$) δ 9.74-9.56 (m, 1H), 9.24-9.12 (m, 1H), 8.04 (s, 1H), 7.85-7.75 (m, 1H), 7.33-7.21 (m, 3H), 7.17 (d, J=7.4 Hz, 2H), 3.17-3.04 (m, 1H), 2.96 (ddd, J=24.1, 11.8, 6.5 Hz, 2H), 2.85-2.72 (m, 2H), 2.52-2.40 (m, 1H), 2.30-2.18 (m, 1H), 2.09-1.99 (m, 2H), 1.96-1.79 (m, 1H), 1.16 (d, J=6.9 Hz, 3H); MS (DCI+) m/z 359 (M+H)$^+$.

Example 140F (5aS,6S,8Z,9aS)-8-(hydroxymethylene)-6-methyl-9a-phenyl-3-(pyridazin-4-yl)-2,4,5,5a,6,8,9,9a-octahydro-7H-benzo[g]indazol-7-one Example 140E (0.039 g, 0.109 mmol) was dissolved in ethyl formate (1.06 mL, 13.06 mmol), and the mixture was cooled to 0° C. in an ice bath followed by the addition of sodium methoxide (25% NaOCH₃ in CH₃OH by weight, 0.522 mL, 2.18 mmol). The ice bath was then removed, and the mixture was stirred at ambient temperature for 18 hours. A solution of 1 N aqueous potassium dihydrogen phosphate was added until neutral pH followed by extraction with ethyl acetate. The organic extracts were dried over anhydrous magnesium sulfate, filtered, and concentrated by rotary evaporation to provide the titled compound (0.042 g, 100%).

Example 140G (5aS,6S,10aS)-6-methyl-10a-phenyl-3-(pyridazin-4-yl)-4,5,5a,6,10,10a-hexahydro-2H-indazolo[7,6-f][1,2]benzoxazole Example 140F (0.042 g, 0.109 mmol) was dissolved in ethanol (3 mL), and hydroxylamine hydrochloride (0.030 g, 0.434 mmol) was added. The mixture was heated at 50° C. for 18 hours. After cooling to ambient temperature, the solution was concentrated by rotary evaporation. The resultant residue was dissolved in ethyl acetate and washed with water. The organic extracts were separated and dried over anhydrous magnesium sulfate, filtered and concentrated to give the titled compound (0.04 g, 0.104 mmol) which was utilized without further purification.

Example 140H (5aS,6S,9aS)-6-methyl-7-oxo-9a-phenyl-3-(pyridazin-4-yl)-4,5,5a,6,7,8,9,9a-octahydro-2H-benzo[g]indazole-8-carbonitrile Example 140G (0.042 g, 0.110 mmol) was dissolved in tetrahydrofuran (3 mL followed by the addition of sodium methoxide (25% NaOCH₃ in CH₃OH by weight, 0.26 mL, 1.95 mmol), and the mixture stirred at ambient temperature for 18 hours. A solution of 1 N aqueous potassium dihydrogen phosphate was added until neutral pH followed by extraction with ethyl acetate. The organic extracts were dried over anhydrous magnesium sulfate, filtered, and concentrated by rotary evaporation. The crude residue was purified by reversed-phase preparative HPLC on a Waters Sunfire™ C8(2), 5 µm, 100 Å, AXIA column (30, mm×75, mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A) to give the titled compound as a trifluoroacetic acid salt. The titled compound as a trifluoroacetic acid salt was dissolved in ethyl acetate and neutralized with a saturated sodium bicarbonate solution. The organic extracts were separated, dried over anhydrous magnesium sulfate, filtered, and concentrated to afford the titled compound (0.015 g, 36%).

Example 140I (5aS,6S,9aR)-6-methyl-7-oxo-9a-phenyl-3-(pyridazin-4-yl)-4,5,5a,6,7,9a-hexahydro-2H-benzo[g]indazole-8-carbonitrile Example 140H (0.0153 g, 0.04 mmol) was dissolved in tetrahydrofuran (3 mL) and the solution was cooled in an ice bath followed by bubbling nitrogen through the solution for 10 minutes. While under a nitrogen atmosphere, 2,3-dichloro-5,6-dicyanobenzoquinone (0.0094 g, 0.04 mmol) was added, and the mixture was stirred at 0° C. for 1 hour. The reaction mixture was concentrated by rotary evaporation to give a residue which was purified by reversed-phase preparative HPLC on a Phenomenex® Luna® C8(2) 5 µm 100 Å AXIA™ column (30 mm×75 mm). A gradient of acetonitrile (A) and 0.1% trifluoroacetic acid in water (B) was used, at a flow rate of 50 mL/minute (0-0.5 minute 10% A, 0.5-7.0 minutes linear gradient 10-95% A, 7.0-10.0 minutes 95% A, 10.0-12.0 minutes linear gradient 95-10% A) to give the titled compound (0.0048 g, 29%). $^1$H NMR (400 MHz, DMSO-d₆) δ ppm 9.64 (s, 1H), 9.31 (d, J=5.4 Hz, 1H), 8.46 (s, 1H), 7.97 (dd, J=5.5, 2.3 Hz, 1H), 7.35 (dq, J=14.0, 7.0 Hz, 3H), 6.97 (d, J=7.1 Hz, 2H), 3.13 (dd, J=16.4, 6.2 Hz, 1H), 3.03-2.87 (m, 1H), 2.43-2.18 (m, 2H), 1.97-1.75 (m, 1H), 1.54-1.30 (m, 1H), 1.09 (d, J=6.7 Hz, 3H); MS (ESI+) m/z 382 (M+H)⁺.

Example 141

{4-[(5aS,6S,9aR)-8-cyano-6-methyl-7-oxo-9a-phenyl-4,5,5a,6,7,9a-hexahydro-2H-benzo[g]indazol-3-yl]-1H-pyrazol-1-yl}acetic acid Example 141A ethyl {4-[(5aS,6S,9aS)-2-(dimethylsulfamoyl)-6-methyl-9a-phenyl-2,4,5,5a,6,8,9,9a-octahydrospiro[benzo[g]indazole-7,2'-[1,3]dioxolan]-3-yl]-1H-pyrazol-1-yl}acetate The titled compound was prepared using the conditions described in Example 86A substituting 3-(4,4,5,5-tetramethyl-1,3,2-dioxaborolan-2-yl)pyridine with ethyl 2-(4-(4,4,5,5-tetramethyl-1,3,2-dioxaborolan-2-yl)-1H-pyrazol-1-yl)acetate. MS (APCI) m/z 584 (M+H)⁺.

Example 141B ethyl {4-[(5aS,6S,9aS)-6-methyl-7-oxo-9a-phenyl-4,5,5a,6,7,8,9,9a-octahydro-2H-benzo[g]indazol-3-yl]-1H-pyrazol-1-yl}acetate The titled compound was prepared using the conditions described in Example 86B substituting Example 86A with Example 141A.

Example 141C ethyl {4-[(5aS,6S,8Z,9aS)-8-(hydroxymethylene)-6-methyl-7-oxo-9a-phenyl-4,5,5a,6,7,8,9,9a-octahydro-2H-benzo[g]indazol-3-yl]-1H-pyrazol-1-yl}acetate The titled compound was prepared using the conditions described in Example 24C substituting Example 24B with Example 141B. MS (APCI) m/z 433 (M−H)⁻.

Example 141D ethyl {4-[(5aS,6S,10aS)-6-methyl-10a-phenyl-4,5,5a,6,10,10a-hexahydro-2H-indazolo[7,6-][1,2]benzoxazol-3-yl]-1H-pyrazol-1-yl}acetate The titled compound was prepared using the conditions described in Example 24D substituting Example 24C with Example 141C. MS (ESI) m/z 457 (M−H)

Example 141E

{4-[(5aS,6S,9aS)-8-cyano-6-methyl-7-oxo-9a-phenyl-4,5,5a,6,7,8,9,9a-octahydro-2H-benzo[g]indazol-3-yl]-1H-pyrazol-1-yl}acetic acid The titled compound was prepared using the conditions described in Example 24E substituting Example 24D with Example 141D.

Example 141F

{4-[(5aS,6S,9aR)-8-cyano-6-methyl-7-oxo-9a-phenyl-4,5,5a,6,7,9a-hexahydro-2H-benzo[g]indazol-3-yl]-1H-pyrazol-1-yl}acetic acid Example 141E (0.030 g, 0.070 mmol) was dissolved in tetrahydrofuran (0.70 mL) and nitrogen was bubbled through the mixture for 10 minutes. 2,3-Dichloro-5,6-dicyano-1,4-benzoquinone (0.015 g, 0.070 mmol) was added, and the reaction mixture was stirred at room temperature for 10 minutes with nitrogen bubbling continued. The reaction mixture was concentrated, and the residue was purified on a reversed-phase Waters HPLC using a Nova-Pak® HR C18, 6 µm, 60 Å, 40 mm×100 mm, PrepPak cartridge eluting with a gradient of 10-90% acetonitrile in aqueous 0.1% trifluoroacetic acid (60 mL/minute) to give the titled compound as the trifluoroacetic acid salt (0.001 g, 3%). $^1$H NMR (400 MHz, DMSO-$d_6$) δ ppm 1.07 (d, J=6.6 Hz, 3H), 1.37 (d, J=35.0 Hz, 1H), 1.77-1.88 (m, 1H), 2.34 (s, 1H), 2.90 (s, 1H), 3.03 (s, 1H), 6.96 (d, J=7.2 Hz, 2H), 7.35 (s, 4H), 8.45 (s, 1H), 9.15 (s, 3H); MS (APCI+) m/z 428 (M+H)$^+$.

Example 142 methyl 3-[(6aS,7S,10aR)-9-carbamoyl-7-methyl-8-oxo-6,6a,7,8-tetrahydrobenzo[h]quinazolin-10a(5H)-yl]benzoate To a solution of Example 59M (0.050 g, 0.134 mmol) in 80% ethanol (1.5 mL) was added hydrido(dimethylphosphinous acid-kP)[hydrogen bis(dimethylphosphinito-kP)]platinum (II) (0.011 g, 0.027 mmol). The reaction mixture was heated at 90° C. for 40 minutes. The solution was concentrated, and the residue was purified on a Teledyne Isco Combiflash® Rf system using a 4 g RediSep® silica gel cartridge, eluting with 0-70% ethyl acetate in dichloromethane to give 0.015 g (29%) of the titled compound. $^1$H NMR (400 MHz, CDCl$_3$) δ ppm 1.19 (d, J=6.18 Hz, 3H) 1.61-1.76 (m, 1H) 1.98 (dd, J=14.26, 7.97 Hz, 1H) 2.31-2.44 (m, 2H) 2.99-3.20 (m, 2H) 3.86 (s, 3H) 5.76 (d, J=4.12 Hz, 1H) 7.05 (dd, J=7.86, 1.90 Hz, 1H) 7.38 (t, J=7.86 Hz, 1H) 7.46 (s, 1H) 7.94 (d, J=7.81 Hz, 1H) 8.56 (d, J=1.74 Hz, 1H) 8.70 (s, 1H) 9.08 (s, 1H) 9.33 (s, 1H); MS (ESI+) m/z 392 (M+H)$^+$.

Example 143

(5aS,6S,9aR)-2,6-dimethyl-7-oxo-9a-phenyl-3-[4-(pyridin-4-yl)phenyl]-4,5,5a,6,7,9a-hexahydro-2H-benzo[g]indazole-8-carbonitrile

Example 143A (5aS,6S,9aS)-3-(4-bromophenyl)-2,6-dimethyl-9a-phenyl-2,4,5,5a,6,8,9,9a-octahydrospiro[benzo[g]indazole-7,2'-[1,3]dioxolane]

Example 1F (2.0 g, 6.66 mmol) was dissolved in dichloromethane (30 mL). Magnesium bromide diethyl etherate (4.30 g, 16.64 mmol) was added followed by N,N-diisopropylethylamine (3.45 mL, 19.97 mmol), and the mixture was stirred at ambient temperature for 5 minutes followed by the addition of 4-bromobenzoyl chloride (1.61 g, 7.32 mmol). The resultant solution was stirred at ambient temperature for 18 hours. A solution of 1 N aqueous potassium dihydrogen phosphate was added followed by extraction with ethyl acetate. The organic extracts were dried over anhydrous magnesium sulfate, filtered, and concentrated by rotary evaporation. This residue was partially dissolved in ethanol (75 mL), methylhydrazine (1.046 mL, 19.86 mmol) was added, and the mixture was heated at 60° C. for 18 hours. After cooling to ambient temperature, the solution was concentrated by rotary evaporation. and 1 N aqueous ammonium chloride was added to the residue followed by extraction with ethyl acetate. The organic extracts were dried over anhydrous magnesium sulfate, filtered, and concentrated by rotary evaporation. The resultant residue was dissolved in dichloromethane, and the solution was applied to a silica gel flash chromatography column eluted with 0% to 50% ethyl acetate in heptane to afford the titled compound (3.06 g, 94%). $^1$H NMR (400 MHz, CDCl$_3$) δ ppm 7.78 (d, J=7.7 Hz, 2H), 7.62 (d, J=8.5 Hz, 2H), 7.26 (m, 3H), 7.14 (d, J=8.4 Hz, 2H), 3.96 (m, 4H), 3.76 (s, 3H), 2.65 (m, 1H), 2.63 (m, 1H), 2.44 (m, 2H), 2.06 (m, 4H), 1.68 (m, 1H), 1.40 (m, 1H), 1.02 (d, J=6.6 Hz, 3H); MS (ESI+) m/z 493/495 (M+H)$^+$.

Example 143B (5aS,6S,9aS)-3-(4-bromophenyl)-2,6-dimethyl-9a-phenyl-2,4,5,5a,6,8,9,9a-octahydro-7H-benzo[g]indazol-7-one Example 143A (3.05 g, 6.18 mmol) was dissolved in a solution of 4 N hydrochloric acid in dioxane (15.5 mL). Then water (1.5 mL) was added, and the mixture was stirred at ambient temperature for 18 hours. A solution of saturated aqueous sodium bicarbonate was added followed by extraction with ethyl acetate. The organic extracts were dried over anhydrous magnesium sulfate, filtered, and concentrated by rotary evaporation to provide (2.64 g, 95%) of the titled compound. MS (ESI+) m/z 449/451 (M+H)$^+$.

Example 143C (5aS,6S,9aS)-2,6-dimethyl-9a-phenyl-3-[4-(pyridin-4-yl)phenyl]-2,4,5,5a,6,8,9,9a-octahydro-7H-benzo[g]indazol-7-one Example 143B (0.300 g, 0.668 mmol), [1,1'-bis(diphenyl)phosphine)ferrocene]dichloropalladium(II) (0.049 g, 0.067 mmol), cesium carbonate (0.653 g, 2.00 mmol), and pyridine-4-boronic acid (0.246 g, 2.00 mmol) were dissolved in dioxane (6 mL) and water (0.6 mL). Then nitrogen gas was bubbled through the mixture for 10 minutes followed by heating at 80° C. for 18 hours. After cooling to ambient temperature, 1 N aqueous ammonium chloride was added followed by extraction with ethyl acetate. The organic extracts were dried over anhydrous magnesium sulfate, filtered, and concentrated by rotary evaporation. The resultant residue was dissolved in dichloromethane, and the solution was applied to a silica gel flash chromatography column eluted with 0% to 100% ethyl acetate in heptane to afford the titled compound (0.21 g, 70%). MS (ESI+) m/z 448 (M+H)$^+$.

Example 143D (5aS,6S,10aS)-2,6-dimethyl-10a-phenyl-3-[4-(pyridin-4-yl)phenyl]-4,5,5a,6,10,10a-hexahydro-2H-indazolo[7,6-f][1,2]benzoxazole Example 143C (0.200 g, 0.447 mmol) was dissolved in ethyl formate (1.8 mL, 22.3 mmol), and the mixture was cooled to 0° C. in an ice bath followed by the addition of sodium methoxide (25% in methanol by weight, 1.0 mL, 4.47 mmol). The ice bath was then removed, and the mixture was stirred at ambient temperature for 18 hours. A solution of 1 N aqueous potassium dihydrogen phosphate was added followed by extraction with ethyl acetate. The organic extracts were dried over anhydrous magnesium sulfate, filtered, and concentrated by rotary evaporation. This residue was dissolved in ethanol (4.5 mL) and dichloroethane (1.5 mL), then hydroxylamine hydrochloride (0.041 g, 0.599 mmol) was added, and the mixture was heated at 50° C. for 18 hours. After cooling to ambient temperature, the solution was concentrated by rotary evaporation. The resultant residue was dissolved in a 3 to 1 mixture of isopropanol and chloroform and then extracted with 1 N aqueous sodium bicarbonate solution. The organic fraction was dried over anhydrous magnesium sulfate, filtered, and concentrated by rotary evaporation to a reside which was dissolved in dichloromethane. The solution was applied to a silica gel flash chromatography column eluted with 0% to 5% dichloromethane in methanol to afford the titled compound (0.138 g, 73%). $^1$H NMR (400 MHz, CDCl$_3$) δ ppm 8.72 (d, J=6.1 Hz, 2H), 8.24 (s, 1H), 7.79 (d, J=8.2 Hz, 2H), 7.55 (m, 4H), 7.15 (m, 3H), 6.93 (m, 2H), 3.85 (s, 3H), 3.69 (d, J=16.4 Hz, 1H), 3.18 (dd, J=16.5, 2.6 Hz, 1H), 2.84 (m, 1H), 2.76 (m, 1H), 2.23 (m, 1H), 2.00 (m, 2H), 1.73 (m, 1H), 1.39 (d, J=6.8 Hz, 3H); MS (ESI+) m/z 473 (M+H)$^+$.

Example 143E (5aS,6S,9aR)-2,6-dimethyl-7-oxo-9a-phenyl-3-[4-(pyridin-4-yl)phenyl]-4,5,5a,6,7,9a-hexahydro-2H-benzo[g]indazole-8-carbonitrile Example 143D (0.120 g, 0.254 mmol) was dissolved in tetrahydrofuran (4.5 mL) followed by the addition of sodium methoxide (25% in methanol by weight, 0.57 mL, 2.54 mmol), and the mixture stirred at ambient temperature for 18 hours. A solution of 1 N aqueous potassium dihydrogen phosphate was added followed by extraction with a 3 to 1 mixture of isopropanol and chloroform. The organic extracts were dried over anhydrous MgSO$_4$, filtered, and concentrated by rotary evaporation to provide a residue. This residue was then dissolved in N,N-dimethylformamide (4.5 mL), and the solution was cooled in an ice bath followed by the addition of 1,3-dibromo-5,5-dimethylhydantoin (0.0449 g, 0.157 mmol). The mixture was stirred at 0° C. for 1.5 hours followed by the dropwise addition of pyridine (0.116 mL, 1.428 mmol), removal of the ice bath, and heating the resultant solution at 50° C. for 18 hours. After cooling to ambient temperature, a solution of 1 N aqueous potassium dihydrogen phosphate was added followed by extraction with a 3 to 1 mixture of isopropanol and chloroform. The organic extracts were dried over anhydrous magnesium sulfate, filtered, and concentrated by rotary evaporation. The resultant residue was dissolved in dichloromethane, the solution applied to a silica gel flash chromatography column eluted with 0% to 100% ethyl acetate in heptane to afford the titled compound (0.069 g, 51%). $^1$H NMR (400 MHz, CDCl$_3$) δ ppm 8.73 (d, J=5.9 Hz, 2H), 8.50 (s, 1H), 7.81 (d, J=8.2 Hz, 2H), 7.58 (m, 4H), 7.33 (m, 3H), 6.98 (d, J=7.0 Hz, 2H), 3.88 (s, 3H), 2.79 (m, 2H), 2.42 (m, 2H), 1.83 (m, 1H), 1.57 (m, 1H), 1.18 (d, J=6.4 Hz, 3H); MS (ESI+) m/z 471 (M+H)$^+$.

Example 144

(5aS,6S,9aR)-2,6-dimethyl-7-oxo-9a-phenyl-3-[4-(pyrimidin-5-yl)phenyl]-4,5,5a,6,7,9a-hexahydro-2H-benzo[g]indazole-8-carbonitrile

Example 144A (5aS,6S,9aS)-2,6-dimethyl-9a-phenyl-3-[4-(pyrimidin-5-yl)phenyl]-2,4,5,5a,6,8,9,9a-octahydro-7H-benzo[g]indazol-7-one Example 143B (0.300 g, 0.668 mmol), [1,1'-bis(diphenyl)phosphine)ferrocene]dichloropalladium(II) (0.049 g, 0.067 mmol), cesium carbonate (0.653 g, 2.00 mmol), and pyrimidine-5-boronic acid (0.248 g, 2.00 mmol) were dissolved in dioxane (6 mL) and water (0.6 mL). Then nitrogen gas was bubbled through the mixture for 10 minutes followed by heating at 80° C. for 18 hours. After cooling to ambient temperature, 1 N aqueous ammonium chloride was added followed by extraction with ethyl acetate. The organic extracts were dried over anhydrous MgSO$_4$, filtered, and concentrated by rotary evaporation. The resultant residue was dissolved in dichloromethane, and the solution was applied to a silica gel flash chromatography column eluted with 0% to 100% ethyl acetate in heptane to afford the titled compound (0.239 g, 80%). $^1$H NMR (400 MHz, CDCl$_3$) δ ppm 9.25 (s, 1H), 9.01 (s, 2H), 7.69 (d, J=8.1 Hz, 2H), 7.59 (d, J=7.9 Hz, 2H), 7.51 (d, J=8.4 Hz, 2H), 7.28 (m, 2H), 7.20 (m, 1H), 3.84 (s, 3H), 3.18 (m, 1H), 2.60 (m, 6H), 2.38 (m, 1H), 2.10 (m, 2H), 1.19 (d, J=6.7 Hz, 3H); MS (ESI+) m/z 449 (M+H)$^+$.

Example 144B (5aS,6S,10aS)-2,6-dimethyl-10a-phenyl-3-[4-(pyrimidin-5-yl)phenyl]-4,5,5a,6,10,10a-hexahydro-2H-indazolo[7,6-f][1,2]benzoxazole Example 144A (0.225 g, 0.502 mmol) was dissolved in ethyl formate (2.0 mL, 25.1 mmol), and the mixture was cooled to 0° C. in an ice bath followed by the addition of sodium methoxide (25% in methanol by weight, 1.1 mL, 5.02 mmol). The ice bath was then removed, and the mixture was stirred at ambient temperature for 17 hours. A solution of 1 N aqueous potassium dihydrogen phosphate was added followed by extraction with ethyl acetate. The organic extracts were dried over anhydrous magnesium sulfate, filtered, and concentrated by rotary evaporation. This material was dissolved in ethanol (3.0 mL) and dichloroethane (3.0 mL), then hydroxylamine hydrochloride (0.051 g, 0.74 mmol) was added, and the mixture was heated at 50° C. for 18 hours. After cooling to ambient temperature, the solution was concentrated by rotary evaporation, and the resultant residue was dissolved in a 3 to 1 mixture of isopropanol and chloroform and extracted with 1 N aqueous sodium bicarbonate solution. The organic extracts were dried over anhydrous magnesium sulfate, filtered, and concentrated by rotary evaporation to a residue which was dissolved in dichloromethane. The solution was applied to a silica gel flash chromatography column eluted with 0% to 100% ethyl acetate in heptane to afford the titled compound (0.15 g, 64%). MS (ESI+) m/z 474 (M+H)+.

Example 144C (5aS,6S,9aR)-2,6-dimethyl-7-oxo-9a-phenyl-3-[4-(pyrimidin-5-yl)phenyl]-4,5,5a,6,7,9a-hexahydro-2H-benzo[g]indazole-8-carbonitrile Example 144B 0.150 g, 0.317 mmol) was dissolved in tetrahydrofuran (4.5 mL followed by the addition of sodium methoxide (25% in methanol by weight, 0.7 mL, 3.17 mmol), and the mixture was stirred at ambient temperature for 18 hours. A solution of 1 N aqueous potassium dihydrogen phosphate was added followed by extraction with a 3 to 1 mixture of isopropanol and chloroform. The organic extracts were dried over anhydrous magnesium sulfate, filtered, and concentrated by rotary evaporation to provide a residue. This material was then dissolved in N,N-dimethylformamide (4.5 mL), and the solution was cooled in an ice bath followed by the addition of 1,3-dibromo-5,5-dimethylhydantoin (0.050 g, 0.174 mmol). The mixture was stirred at 0° C. for 1.5 hours followed by the dropwise addition of pyridine (0.128 mL, 1.584 mmol), removal of the ice bath, and heating the resultant solution at 50° C. for 18 hours. After cooling to ambient temperature, a solution of 1 N aqueous potassium dihydrogen phosphate was added followed by extraction with a 3 to 1 mixture of isopropanol and chloroform. The organic extracts were dried over anhydrous magnesium sulfate, filtered, and concentrated by rotary evaporation. The resultant residue was dissolved in dichloromethane, and the solution was applied to a silica gel flash chromatography column eluted with 0% to 100% ethyl acetate in heptane to afford the titled compound as a colorless solid (0.09 g, 60%). $^1$H NMR (400 MHz, CDCl$_3$) δ ppm 9.28 (s, 1H), 9.04 (s, 2H), 8.50 (s, 1H), 7.76 (d, J=8.1 Hz, 2H), 7.60 (d, J=8.2 Hz, 2H), 7.31 (m, 3H), 6.99 (d, J=7.1 Hz, 2H), 3.88 (s, 3H), 2.80 (m, 2H), 2.42 (m, 2H), 1.81 (m, 1H), 1.57 (m, 1H), 1.18 (d, J=6.4 Hz, 3H); MS (ESI+) m/z 472 (M+H)+.

Example 145

(6aS,7S,10aR)-2,7-dimethyl-8-oxo-10a-phenyl-4-[4-(pyrimidin-5-yl)phenyl]-5,6,6a,7,8,10a-hexahydrobenzo[h]quinazoline-9-carboxamide To a solution of Example 129F (0.056 g, 0.116 mmol) in 80% ethanol (2 mL) was added hydrido(dimethylphosphinous acid-kP)[hydrogen bis(dimethylphosphinito-kP)]platinum (II) (0.010 g, 0.023 mmol). The reaction mixture was heated at 90° C. for 30 minutes. The solution was concentrated, and the residue was purified by preparative HPLC on a Waters Sunfire™ C8(2), 5 μm, 100 Å column (30 mm×75 mm). A gradient of acetonitrile (A) and 0.1% trifluoroacetic acid in water (B) was used, at a flow rate of 50 mL/minute (0-0.5 minute 10% A, 0.5-7.0 minutes linear gradient 10-95% A, 7.0-10.0 minutes 95% A, 10.0-12.0 minutes linear gradient 95-10% A) to give 0.036 g (62%) of the titled compound. $^1$H NMR (400 MHz, CDCl$_3$) δ ppm 1.17 (d, J=6.61 Hz, 3H) 1.58-1.73 (m, 1H) 1.87-1.97 (m, 1H) 2.38 (td, J=12.79, 2.17 Hz, 1H) 2.50 (td, J=13.04, 6.56 Hz, 1H) 2.76 (s, 3H) 3.00 (dd, J=8.57, 4.45 Hz, 2H) 6.86 (dd, J=7.70, 1.41 Hz, 2H) 6.98 (s, 1H) 7.30-7.37 (m, 3H) 7.76 (s, 4H) 8.93 (d, J=1.41 Hz, 1H) 9.10 (d, J=1.95 Hz, 2H) 9.31 (s, 1H) 9.46 (s, 1H); MS (ESI+) m/z 502 (M+H)+.

Example 146

(6aS,7S,10aR)-4-[3-bromo-4-(morpholin-4-yl)phenyl]-2,7-dimethyl-8-oxo-10a-phenyl-5,6,6a,7,8,10a-hexahydrobenzo[h]quinazoline-9-carbonitrile Example 146A (6aS,7S,10aS)-2,7-dimethyl-4-[4-(morpholin-4-yl)phenyl]-10a-phenyl-5,6a,7,9,10,10a-hexahydrobenzo[h]quinazolin-8(6H)-one To a solution of Example 122A (0.315 g, 0.594 mmol) in dioxane (6 mL) in a tube was added morphine (0.129 mL, 1.48 mmol), cesium carbonate (0.387 g, 1.19 mmol), palladium acetate (0.003 g, 0.012 mmol), and racemic (1,1'-binaphthalene-2,2'-diyl)bis(diphenylphosphine) (0.018 g, 0.03 mmol). The mixture was sparged with nitrogen for 15 minutes, then the tube was sealed and heated at 90° C. for 20 hours. The cooled mixture was diluted with water and extracted with ethyl acetate. The organic fraction was concentrated. The residue was purified using a 12 g RediSep® silica gel cartridge on a Teledyne Isco Combiflash® Rf system eluting with 0-2% methanol in dichloromethane to give 0.138 g (50%) of the titled compound. MS (APCI+) m/z 468 (M+H)+.

Example 146B (6aS,7S,9Z,10aS)-9-(hydroxymethylene)-2,7-dimethyl-4-[4-(morpholin-4-yl)phenyl]-10a-phenyl-5,6a,7,9,10,10a-hexahydrobenzo[h]quinazolin-8(6H)-one The titled compound was prepared using the conditions described in Example 1J, substituting Example 146A for Example 1I.

Example 146C (6aS,7S,11aS)-2,7-dimethyl-4-[4-(morpholin-4-yl)phenyl]-11a-phenyl-5,6,6a,7,11,11a-hexahydro[1,2]benzoxazolo[6,5-h]quinazoline The titled compound was prepared using the conditions described in Example 1K, substituting Example 146B for Example 1J.

Example 146D (6aS,7S,10aS)-2,7-dimethyl-4-[4-(morpholin-4-yl)phenyl]-8-oxo-10a-phenyl-5,6,6a,7,8,9,10,10a-octahydrobenzo[h]quinazoline-9-carbonitrile The titled compound was prepared using the conditions described in Example 1L, substituting Example 146C for Example 1K.

Example 146E (6aS,7S,10aR)-4-[3-bromo-4-(morpholin-4-yl)phenyl]-2,7-dimethyl-8-oxo-10a-phenyl-5,6,6a,7,8,10a-hexahydrobenzo[h]quinazoline-9-carbonitrile To a solution of Example 146D (0.059 g, 0.120 mmol) in dimethylacetamide (2 mL) cooled to 0° C. in an ice water bath was added 1,3-dibromo-5,5-dimethylhydantoin (0.017 g, 0.060 mmol). The solution was stirred at 0° C. for 45 minutes, then pyridine (0.291 mL, 3.59 mmol) was added, and the solution was heated at 55° C. for 1.5 hours. The cooled solution was diluted with water and extracted with ethyl acetate. The organic phase was washed with brine and concentrated. The residue was purified by preparative HPLC on a Waters Sunfire™ C8(2), 5 µm, 100 Å column (30 mm×75 mm). A gradient of acetonitrile (A) and 0.1% trifluoroacetic acid in water (B) was used, at a flow rate of 50 mL/minute (0-0.5 minute 10% A, 0.5-7.0 minutes linear gradient 10-95% A, 7.0-10.0 minutes 95% A, 10.0-12.0 minutes linear gradient 95-10% A) to give 0.015 g (22%) of the titled compound. $^1$H NMR (400 MHz, CDCl$_3$) δ ppm 1.17 (d, J=6.51 Hz, 3H) 1.49-1.64 (m, 1H) 1.92-1.98 (m, 1H) 2.35 (td, J=12.85, 2.17 Hz, 1H) 2.46 (td, J=13.07, 6.51 Hz, 1H) 2.70 (s, 3H) 2.99 (dd, J=8.51, 4.39 Hz, 2H) 3.13 (ddd, J=19.46, 11.49, 4.17 Hz, 4H) 3.92 (t, J=4.50 Hz, 4H) 6.82 (dd, J=7.64, 1.46 Hz, 2H) 7.15 (d, J=8.24 Hz, 1H) 7.30-7.38 (m, 3H) 7.54 (dd, J=8.19, 2.01 Hz, 1H) 7.83 (d, J=2.06 Hz, 1H) 8.96 (s, 1H); MS (ESI−) m/z 567 (M−H)$^−$, 599 (M+CH$_3$OH—H)$^−$.

Example 147

(6aS,7S,10aR)-2,7-dimethyl-8-oxo-10a-phenyl-4-(pyridin-3-ylamino)-5,6,6a,7,8,10a-hexahydrobenzo[h]quinazoline-9-carbonitrile Example 147A (6aS,7S,10aS)-2,7-dimethyl-10a-phenyl-4-(pyridin-3-ylamino)-5,6a,7,9,10,10a-hexahydrobenzo[h]quinazolin-8(6H)-one The titled compound was prepared using the conditions described in Example 146A, substituting Example 13D for Example 122A and substituting pyridine-3-amine for morpholine. MS (APCI+) m/z 399 (M+H)$^+$.

Example 147B (6aS,7S,9Z,10aS)-9-(hydroxymethylene)-2,7-dimethyl-10a-phenyl-4-(pyridin-3-ylamino)-5,6a,7,9,10,10a-hexahydrobenzo[h]quinazolin-8(6H)-one The titled compound was prepared using the conditions described in Example 1J, substituting Example 147A for Example 1I. MS (APCI+) m/z 427 (M+H)$^+$.

Example 147C (6aS,7S,11aS)-2,7-dimethyl-11a-phenyl-N-(pyridin-3-yl)-5,6,6a,7,11,11a-hexahydro[1,2]benzoxazolo[6,5-h]quinazolin-4-amine The titled compound was prepared using the conditions described in Example 1K, substituting Example 147B for Example 1J.

Example 147D (6aS,7S,10aS)-2,7-dimethyl-8-oxo-10a-phenyl-4-(pyridin-3-ylamino)-5,6,6a,7,8,9,10,10a-octahydrobenzo[h]quinazoline-9-carbonitrile The titled compound was prepared using the conditions described in Example 1L, substituting Example 147C for Example 1K.

Example 147E (6aS,7S,10aR)-2,7-dimethyl-8-oxo-10a-phenyl-4-(pyridin-3-ylamino)-5,6,6a,7,8,10a-hexahydrobenzo[h]quinazoline-9-carbonitrile A solution of Example 147D (0.190 g, 0.449 mmol) in 1,4-dioxane (6 mL) at room temperature was sparged with nitrogen for 15 minutes, and then 2,3-dichloro-5,6-dicyano-1,4-benzoquinone (0.102 g, 0.449 mmol) was added. After 15 minutes, with continuous nitrogen bubbling, the solution was concentrated. The residue was purified on a 24 g RediSep® silica gel cartridge using a Teledyne Isco Combiflash® Rf system eluting with 0-10% ethyl methanol in dichloromethane. A second purification by preparative HPLC on a Waters Sunfire™ C8(2), 5 µm, 100 Å column (30 mm×75 mm) using a gradient of acetonitrile (A) and 0.1% trifluoroacetic acid in water (B) at a flow rate of 50 mL/minute (0-0.5 minute 10% A, 0.5-7.0 minutes linear gradient 10-95% A, 7.0-10.0 minutes 95% A, 10.0-12.0 minutes linear gradient 95-10% A) to give 0.016 g (7%) of the titled compound as the trifluoroacetic acid salt. $^1$H NMR (400 MHz, CDCl$_3$) δ ppm 1.20 (d, J=6.61 Hz, 3H) 2.03-2.10 (m, 2H) 2.30 (td, J=12.96, 2.39 Hz, 1H) 2.45 (td, J=12.98, 6.13 Hz, 1H) 2.59 (s, 3H) 2.80-2.91 (m, 1H) 2.93-3.05 (m, 1H) 6.89 (d, J=8.02 Hz, 2H) 7.31-7.40 (m, 3H) 7.73-7.82 (m, 1H) 7.87 (dd, J=8.62, 5.80 Hz, 1H) 8.32 (d, J=4.99 Hz, 1H) 9.55 (dd, J=11.01, 3.85 Hz, 1H) 9.64 (s, 1H); MS (APCI+) m/z 422 (M+H)$^+$.

Example 148

(5aS,6S,9aR)-3-(3-bromophenyl)-2,6-dimethyl-7-oxo-9a-phenyl-4,5,5a,6,7,9a-hexahydro-2H-benzo[g]indazole-8-carbonitrile Example 148A (5aS,6S,9aS)-3-(3-bromophenyl)-2,6-dimethyl-9a-phenyl-2,4,5,5a,6,8,9,9a-octahydrospiro[benzo[g]indazole-7,2'-[1,3]dioxolane]

Example 1F (4.0 g, 13.32 mmol) was dissolved in dichloromethane (60 mL), magnesium bromide diethyl etherate (8.60 g, 33.3 mmol) was added followed by N,N-diisopropylethylamine (6.9 mL, 39.9 mmol), and the mixture stirred at ambient temperature for 5 minutes. Then 3-bromobenzoyl chloride (1.93 mL, 14.65 mmol) was added, and the resultant solution was stirred at ambient temperature for 18 hours. A solution of 1 N aqueous potassium dihydrogen phosphate was added followed by extraction with ethyl acetate. The organic extracts were dried over anhydrous magnesium sulfate, filtered, and concentrated by rotary evaporation. This residue was partially dissolved in ethanol (150 mL), and methylhydrazine (2.091 mL, 39.7 mmol) was added. The mixture was heated at 60° C. for 18 hours. After cooling to ambient temperature, the solution was concentrated by rotary evaporation and 1 N aqueous ammonium chloride was added followed by extraction with ethyl acetate. The organic extracts were dried over anhydrous magnesium sulfate, filtered, and concentrated by rotary evaporation. The resultant residue was dissolved in dichloromethane, the solution applied to a silica gel flash chromatography column eluted with 0% to 50% ethyl acetate in heptane to afford the titled compound (5.98 g, 92%). $^1$H NMR (400 MHz, CDCl$_3$) δ ppm 7.77 (d, J=7.7 Hz, 2H), 7.48 (d, J=8.0 Hz, 1H), 7.42 (m, 1H), 7.26 (m, 3H), 7.20 (d, J=7.8 Hz, 1H), 7.13 (t, J=7.4

Hz, 1H), 3.95 (m, 4H), 3.77 (s, 3H), 2.72 (m, 1H), 2.62 (m, 1H), 2.50 (m, 2H), 2.07 (m, 4H), 1.68 (m, 1H), 1.40 (m, 1H), 1.02 (d, J=6.6 Hz, 3H); MS (ESI+) m/z 493/495 (M+H)+.

Example 148B (5aS,6S,9aS)-3-(3-bromophenyl)-2,6-dimethyl-9a-phenyl-2,4,5,5a,6,8,9,9a-octahydro-7H-benzo[g]indazol-7-one Example 148A (5.9 g, 11.96 mmol) was dissolved in a solution of 4 N hydrochloric acid in dioxane (29.9 mL). Then water (3.0 mL) was added, and the mixture stirred at ambient temperature for 18 hours. A solution of saturated aqueous sodium bicarbonate was added followed by extraction with ethyl acetate. The organic extracts were dried over anhydrous magnesium sulfate, filtered, and concentrated by rotary evaporation to provide (4.95 g, 92%) of the titled compound. MS (ESI+) m/z 449/451 (M+H)+.

Example 148C (5aS,6S,10 aS)-3-(3-bromophenyl)-2,6-dimethyl-10a-phenyl-4,5,5a,6,10,10a-hexahydro-2H-indazolo[7,6-f][1,2]benzoxazole Example 148B (4.25 g, 9.46 mmol) was dissolved in ethyl formate (19 mL, 236 mmol), and the mixture cooled to 0° C. in an ice bath followed by the addition of sodium methoxide (25% in methanol by weight, 10.5 mL, 47.3 mmol). The ice bath was then removed, and the mixture stirred at ambient temperature for 18 hours. A solution of 1 N aqueous potassium dihydrogen phosphate was added followed by extraction with ethyl acetate. The organic extracts were dried over anhydrous magnesium sulfate, filtered, and concentrated by rotary evaporation to provide 3.18 g (70%) of a solid. This solid was dissolved in ethanol (20 mL) and dichloroethane (20 mL), then hydroxylamine hydrochloride (0.694 g, 9.99 mmol) was added, and the mixture was heated at 50° C. for 18 hours. After cooling to ambient temperature, the solution was concentrated by rotary evaporation. The resultant residue was dissolved in a 3 to 1 mixture of isopropanol and chloroform and then extracted with 1 N aqueous sodium bicarbonate solution. The organic extracts were dried over anhydrous magnesium sulfate, filtered, and concentrated by rotary evaporation to a residue which was dissolved in dichloromethane. The solution applied to a silica gel flash chromatography column eluted with 0% to 75% ethyl acetate in heptane to afford the titled compound (2.13 g, 67%). $^1$H NMR (400 MHz, CDCl$_3$) δ ppm 8.23 (s, 1H), 7.59 (m, 2H), 7.38 (m, 2H), 7.13 (m, 3H), 6.89 (m, 2H), 3.80 (s, 3H), 3.67 (d, J=16.5, 1H), 3.16 (m, 1H), 2.79 (m, 1H), 2.68 (m, 1H), 2.23 (m, 1H), 1.97 (m, 2H), 1.67 (m, 1H), 1.38 (d, J=6.8 Hz, 3H); MS (ESI+) m/z 474/476 (M+H)+.

Example 148D (5aS,6S,9aR)-3-(3-bromophenyl)-2,6-dimethyl-7-oxo-9a-phenyl-4,5,5a,6,7,9a-hexahydro-2H-benzo[g]indazole-8-carbonitrile Example 148C (2.1 g, 4.43 mmol) was dissolved in tetrahydrofuran (40 mL) followed by the addition of sodium methoxide (25% in methanol by weight, 9.9 mL, 44.3 mmol), and the mixture stirred at ambient temperature for 18 hours. A solution of 1 N aqueous potassium dihydrogen phosphate was added followed by extraction with a 3 to 1 mixture of isopropanol and chloroform. The organic extracts were dried over anhydrous magnesium sulfate, filtered, and concentrated by rotary evaporation to provide a residue. This material was then dissolved in N,N-dimethylformamide (20 mL), and the solution was cooled in an ice bath. 1,3-Dibromo-5,5-dimethylhydantoin (0.696 g, 2.435 mmol) was added, and the mixture was stirred at 0° C. for 1.5 hours. Pyridine (1.79 mL, 22.13 mmol) was then added dropwise, the ice bath was removed, and the resultant solution was heated at 50° C. for 18 hours. After cooling to ambient temperature, a solution of 1 N aqueous potassium dihydrogen phosphate was added followed by extraction with ethyl acetate. The organic extracts were dried over anhydrous magnesium sulfate, filtered, and concentrated by rotary evaporation. The resultant residue was dissolved in dichloromethane, and the solution applied to a silica gel flash chromatography column eluted with 0% to 50% ethyl acetate in heptane to afford the titled compound (1.53 g, 73%). $^1$H NMR (400 MHz, CDCl$_3$) δ ppm 8.48 (s, 1H), 7.59 (m, 2H), 7.41 (t, J=7.7 Hz, 1H), 7.32 (m, 4H), 6.95 (d, J=7.7 Hz, 2H), 3.82 (s, 3H), 2.73 (m, 2H), 2.43 (m, 1H), 1.97 (m, 1H), 1.82 (dd, J=13.7, 7.1, 1H), 1.57 (m, 1H), 1.17 (d, J=6.6 Hz, 3H); MS (ESI+) m/z 472/474 (M+H)+.

Example 149

(5aS,6S,9aR)-3-(4'-aminobiphenyl-3-yl)-2,6-dimethyl-7-oxo-9a-phenyl-4,5,5a,6,7,9a-hexahydro-2H-benzo[g]indazole-8-carbonitrile Example 148D (0.1 g, 0.212 mmol), [1,1'-bis(diphenyl)phosphine)ferrocene]dichloropalladium(II) (0.0155 g, 0.021 mmol), cesium carbonate (0.207 g, 0.635 mmol), and 4-(4,4,5,5-tetramethyl-1,3,2-dioxaborolan-2-yl)aniline (0.139 g, 0.635 mmol) were dissolved in dioxane (3 mL) and water (0.3 mL). Then nitrogen gas was bubbled through the mixture for 10 minutes followed by heating at 80° C. for 18 hours. After cooling to ambient temperature, 1 N aqueous ammonium chloride was added followed by extraction with ethyl acetate. The organic extracts were dried over anhydrous magnesium sulfate, filtered, and concentrated by rotary evaporation. The resultant residue was dissolved in dichloromethane, and the solution was applied to a silica gel flash chromatography column eluted with 0% to 60% ethyl acetate in heptane to afford the titled compound (0.076 g, 74%). $^1$H NMR (400 MHz, CDCl$_3$) δ: 8.51 (s, 1H), 7.61 (d, J=7.8 Hz, 1H), 7.55 (m, 2H), 7.46 (d, J=8.4 Hz, 2H), 7.31 (m, 4H), 6.98 (d, J=7.3 Hz, 2H), 6.80 (d, J=8.4 Hz, 2H), 3.87 (bs, 2H), 3.83 (s, 3H), 2.78 (m, 2H), 2.42 (m, 2H), 1.81 (dd, J=13.7, 6.6 Hz, 1H), 1.57 (m, 1H), 1.17 (d, J=6.3 Hz, 3H); MS (ESI+) m/z 485 (M+H)+.

Example 150

N-{3'-[(5aS,6S,9aR)-8-cyano-2,6-dimethyl-7-oxo-9a-phenyl-4,5,5a,6,7,9a-hexahydro-2H-benzo[g]indazol-3-yl]biphenyl-3-yl}methanesulfonamide Example 148D (0.05 g, 0.106 mmol), [1,1'-bis(diphenyl)phosphine)ferrocene]dichloropalladium(II) (0.0077 g, 0.0105 mmol), cesium carbonate (0.103 g, 0.318 mmol), and 3-(methylsulfonylamino)phenylboronic acid (0.068 g, 0.318 mmol) were dissolved in dioxane (3 mL) and water (0.3 mL). Then nitrogen gas was bubbled through the mixture for 10 minutes followed by heating at 80° C. for 18 hours. After cooling to ambient temperature, 1 N aqueous ammonium chloride was added followed by extraction with ethyl acetate. The organic extracts were dried over anhydrous magnesium sulfate, filtered, and concentrated by rotary evaporation. The resultant residue was dissolved in dichloromethane, and the solution was applied to a silica gel flash chromatography column eluted with 0% to 100% ethyl acetate in heptane to afford the titled compound (0.047 g, 79%). $^1$H NMR (400 MHz, CDCl$_3$) δ ppm 8.51 (s, 1H), 7.63 (m, 3H), 7.47 (m, 4H), 7.32 (m, 3H), 7.22 (m, 1H), 6.99 (d, J=7.4 Hz, 2H), 6.47 (s, 1H), 3.87 (s, 3H), 3.08 (m, 3H), 2.79 (m, 2H), 2.43 (m, 2H), 1.83 (dd, J=13.6, 6.7 Hz, 1H), 1.57 (m, 1H), 1.17 (d, J=6.4 Hz, 3H); MS (ESI+) m/z 563 (M+H)$^+$.

Example 151

(5aS,6S,9aR)-2,6-dimethyl-7-oxo-9a-phenyl-3-[3-(pyridazin-4-yl)phenyl]-4,5,5a,6,7,9a-hexahydro-2H-benzo[g]indazole-8-carbonitrile Example 148D (0.075 g, 0.159 mmol), [1,1'-bis(diphenyl)phosphine)ferrocene]dichloropalladium(II) (0.0116 g, 0.016 mmol), cesium carbonate (0.155 g, 0.476 mmol), and pyridazine-4-boronic acid pinacol ester (0.098 g, 0.476 mmol) were dissolved in dioxane (3 mL) and water (0.3 mL). Then nitrogen gas was bubbled through the mixture for 10 minutes followed by heating at 80° C. for 18 hours. After cooling to ambient temperature, 1 N aqueous ammonium chloride was added followed by extraction with ethyl acetate. The organic extracts were dried over anhydrous magnesium sulfate, filtered, and concentrated by rotary evaporation. The resultant residue was dissolved in dichloromethane, and the solution was applied to a silica gel flash chromatography column eluted with 0% to 100% ethyl acetate in heptane to afford the titled compound (0.047 g, 63%). $^1$H NMR (400 MHz, CDCl$_3$) δ ppm 9.53 (s, 1H), 9.31 (d, J=5.3 Hz, 1H), 8.50 (s, 1H), 7.72 (m, 4H), 7.59 (d, J=7.3 Hz, 1H), 7.34 (m, 3H), 6.98 (d, J=7.2 Hz, 2H), 3.87 (s, 3H), 2.79 (m, 2H), 2.42 (m, 2H), 1.82 (m, 1H), 1.57 (m, 1H), 1.17 (d, J=6.5 Hz, 3H); MS (ESI+) m/z 472 (M+H)$^+$.

Example 152

N-{3'-[(5aS,6S,9aR)-8-cyano-2,6-dimethyl-7-oxo-9a-phenyl-4,5,5a,6,7,9a-hexahydro-2H-benzo[g]indazol-3-yl]biphenyl-4-yl}-N-(methylsulfonyl)methanesulfonamide Example 149 (0.060 g, 0.124 mmol), was dissolved in dichloromethane (3 mL), and then triethylamine (0.086 mL, 0.619 mmol) and methanesulfonyl chloride (0.029 mL, 0.371 mmol) were added. The mixture was stirred at ambient temperature for 18 hours. Afterwards, 1 N aqueous sodium bicarbonate was added followed by extraction with ethyl acetate. The organic extracts were dried over anhydrous magnesium sulfate, filtered, and concentrated by rotary evaporation. The resultant residue was dissolved in dichloromethane, and the solution was applied to a silica gel flash chromatography column eluted with 0% to 75% ethyl acetate in heptane to afford the titled compound (0.064 g, 81%). $^1$H NMR (400 MHz, CDCl$_3$) δ ppm 8.50 (s, 1H), 7.71 (d, J=8.4 Hz, 2H), 7.65 (m, 3H), 7.47 (m, 3H), 7.33 (m, 3H), 6.98 (d, J=7.2 Hz, 2H), 3.87 (s, 3H), 3.46 (s, 6H), 2.79 (m, 2H), 2.42 (m, 2H), 1.84 (m, 1H), 1.57 (m, 1H), 1.17 (d, J=6.4 Hz, 3H); MS (ESI+) m/z 641 (M+H)$^+$.

Example 153

(5aS,6S,9aR)-3-[3-(2-methoxypyrimidin-5-yl)phenyl]-2,6-dimethyl-7-oxo-9a-phenyl-4,5,5a,6,7,9a-hexahydro-2H-benzo[g]indazole-8-carbonitrile Example 148D (0.075 g, 0.159 mmol), [1,1'-bis(diphenyl)phosphine)ferrocene]dichloropalladium(II) (0.0116 g, 0.016 mmol), cesium carbonate (0.155 g, 0.476 mmol), and 2-methoxypyrimidine-5-boronic acid (0.073 g, 0.476 mmol) were dissolved in dioxane (3 mL) and water (0.3 mL), and then nitrogen gas was bubbled through the mixture for 10 minutes followed by heating at 80° C. for 18 hours. After cooling to ambient temperature, 1 N aqueous ammonium chloride was added followed by extraction with ethyl acetate. The organic extracts were dried over anhydrous magnesium sulfate, filtered, and concentrated by rotary evaporation. The resultant residue was dissolved in dichloromethane, and the solution was applied to a silica gel flash chromatography column eluted with 0% to 75% ethyl acetate in heptane to afford the titled compound (0.053 g, 67%). $^1$H NMR (400 MHz, CDCl$_3$) δ ppm 8.78 (s, 2H), 8.50 (s, 1H), 7.63 (m, 2H), 7.55 (s, 1H), 7.47 (d, J=7.5 Hz, 1H), 7.34 (m, 3H), 6.98 (d, J=7.0 Hz, 2H), 4.09 (s, 3H), 3.87 (s, 3H), 2.79 (m, 2H), 2.42 (m, 2H), 1.82 (m, 1H), 1.57 (m, 1H), 1.18 (d, J=6.4 Hz, 3H); MS (ESI+) m/z 501 (M+H)$^+$.

Example 154 methyl 3-{3-[(6aS,7S,10aR)-9-cyano-2,7-dimethyl-8-oxo-10a-phenyl-5,6,6a,7,8,10a-hexahydrobenzo[h]quinazolin-4-yl]phenyl}propanoate Example 154A methyl 3-{3-[(6aS,7S,10aS)-2,7-dimethyl-8-oxo-10a-phenyl-5,6,6a,7,8,9,10,10a-octahydrobenzo[h]quinazolin-4-yl]phenyl}propanoate The titled compound was prepared using the conditions described in Example 23A, substituting (3-(3-methoxy-3-oxopropyl)phenyl)boronic acid for 2-(furan-3-yl)-4,4,5,5-tetramethyl-1,3,2-dioxaborolane and purified by flash chromatography on silica gel eluting with 10-33% ethyl acetate in heptane to give 57% yield.

Example 154 B methyl 3-{3-[(6aS,7S,9Z,10aS)-9-(hydroxymethylene)-2,7-dimethyl-8-oxo-10a-phenyl-5,6,6a,7,8,9,10,10a-octahydrobenzo[h]quinazolin-4-yl]phenyl}propanoate The titled compound was prepared using the conditions described in Example 13F, substituting Example 154 A for Example 13E.

Example 154C methyl 3-{3-[(6aS,7S,11aS)-2,7-dimethyl-11a-phenyl-5,6,6a,7,11,11a-hexahydro[1,3]benzoxazolo[6,5-h]quinazolin-4-yl]phenyl}propanoate The titled compound was prepared using the conditions described in Example 13G, substituting Example 154 B for Example 13F.

Example 154 D methyl 3-{3-[(6aS,7S,10aS)-9-cyano-2,7-dimethyl-8-oxo-10a-phenyl-5,6,6a,7,8,9,10,10a-octahydrobenzo[h]quinazolin-4-yl]phenyl}propanoate The titled compound was prepared using the conditions described in Example 13H, substituting Example 154 C for Example 13G and purified by flash chromatography on silica gel eluting with 5% acetone in chloroform to give 37% yield.

Example 154 E methyl 3-{3-[(6aS,7S,10aR)-9-cyano-2,7-dimethyl-8-oxo-10a-phenyl-5,6,6a,7,8,10a-hexahydrobenzo[h]quinazolin-4-yl]phenyl}propanoate The titled compound was prepared using the conditions described in Example 131, substituting Example 154 D for Example 13H and purified by flash chromatography on silica gel eluting with 10-33% acetone in heptane to give 67% yield. $^1$H NMR (400 MHz, CDCl$_3$) δ ppm 1.16 (d, J=6.51 Hz, 3H) 1.46-1.55 (m, 1H) 1.83-1.93 (m, 1H) 2.35 (td, J=12.79, 2.17 Hz, 1H) 2.46 (td, J=13.07, 6.51 Hz, 1H) 2.66-2.74 (m, 5H) 2.93 (dd, J=8.62, 4.50 Hz, 2H) 3.05 (t, J=7.75 Hz, 2H) 3.69 (s, 3H) 6.85 (d, J=6.61 Hz, 2H) 7.30-7.49 (m, 7H) 8.99 (s, 1H); MS (ESI+) m/z 492 (M+H)$^+$.

Example 155

3-{3-[(6aS,7S,10aR)-9-cyano-2,7-dimethyl-8-oxo-10a-phenyl-5,6,6a,7,8,10a-hexahydrobenzo[h]quinazolin-4-yl]phenyl}propanoic acid

Example 155A

3-{3-[(6aS,7S,10aS)-9-cyano-2,7-dimethyl-8-oxo-10a-phenyl-5,6,6a,7,8,9,10,10a-octahydrobenzo[h]quinazolin-4-yl]phenyl}propanoic acid The titled compound was prepared using the conditions described in Example 13H, substituting Example 154 C for Example 13G and purified by flash chromatography on silica gel eluting with 5% methanol in chloroform containing 0.2% acetic acid to give 63% yield.

Example 155 B

3-{3-[(6aS,7S,10aR)-9-cyano-2,7-dimethyl-8-oxo-10a-phenyl-5,6,6a,7,8,10a-hexahydrobenzo[h]quinazolin-4-yl]phenyl}propanoic acid The titled compound was prepared using the conditions described in Example 131, substituting Example 155 A for Example 13H and purified by flash chromatography on silica gel eluting with 10% methanol in chloroform containing 0.2% acetic acid to give 57% yield. $^1$H NMR (400 MHz, CDCl$_3$) δ ppm 1.16 (d, J=6.51 Hz, 3H) 1.47-1.60 (m, 1H) 1.83-1.92 (m, 1H) 2.35 (td, J=12.69, 2.06 Hz, 1H) 2.46 (td, J=13.12, 6.61 Hz, 1H) 2.71 (s, 3H) 2.75 (t, J=7.70 Hz, 2H) 2.93 (dd, J=8.24, 4.12 Hz, 2H) 3.06 (t, J=7.70 Hz, 2H) 6.84 (d, J=6.51 Hz, 2H) 7.30-7.49 (m, 7H) 8.98 (s, 1H); MS (ESI) m/z 510 (M+H+methanol)$^+$.

Example 156

3-{3-[(6aS,7S,10aR)-9-cyano-2,7-dimethyl-8-oxo-10a-phenyl-5,6,6a,7,8,10a-hexahydrobenzo[h]quinazolin-4-yl]phenyl}propanamide

Example 156A

3-{3-[(6aS,7S,10aR)-9-cyano-2,7-dimethyl-8-oxo-10a-phenyl-5,6,6a,7,8,10a-hexahydrobenzo[h]quinazolin-4-yl]phenyl}propanoyl chloride A solution of Example 155B (0.054 g, 0.113 mmol), oxalyl chloride (30 μL, 0.339 mmol) and dimethylformamide (0.9 μL, 0.011 mmol) in dichloromethane (1.1 mL) was stirred at room temperature for 1 hour. The reaction mixture was concentrated, and the residue was azeotroped two times with toluene to give the titled compound.

Example 156B

3-{3-[(6aS,7S,10aR)-9-cyano-2,7-dimethyl-8-oxo-10a-phenyl-5,6,6a,7,8,10a-hexahydrobenzo[h]quinazolin-4-yl]phenyl}propanamide A solution of Example 156A (0.056 g, 0.113 mmol) and ammonium hydroxide (75 μL, 1.129 mmol) in dichloromethane (1.1 mL) was stirred at room temperature for 1 hour. The mixture was concentrated, and the residue was purified by flash chromatography on silica gel eluting with 25% acetone in chloroform containing 0.2% acetic acid to give 26% yield. $^1$H NMR (400 MHz, CDCl$_3$) δ ppm 1.16 (d, J=6.61 Hz, 3H) 1.47-1.54 (m, 1H) 1.84-1.92 (m, 1H) 2.34 (td, J=12.77, 2.22 Hz, 1H) 2.46 (td, J=13.09, 6.56 Hz, 1H) 2.60 (t, J=7.64 Hz, 2H) 2.70 (s, 3H) 2.93 (dd, J=8.57, 4.45 Hz, 2H) 3.08 (t, J=7.70 Hz, 2H) 5.41 (d, J=17.78 Hz, 2H) 6.85 (d, J=6.72 Hz, 2H) 7.29-7.48 (m, 7H) 8.98 (s, 1H); MS (ESI) m/z 509 (M+H+methanol)$^+$.

Example 157

(5aS,6S,9aR)-3-[1-(4-cyanophenyl)-1H-pyrazol-4-yl]-6-methyl-7-oxo-9a-phenyl-4,5,5a,6,7,9a-hexahydro-2H-benzo[g]indazole-8-carbonitrile

Example 157A (5aS,6S,9aS)-3-[1-(4-cyanophenyl)-1H-pyrazol-4-yl]-N,N,6-trimethyl-9a-phenyl-4,5,5a,8,9,9a-hexahydrospiro[benzo[g]indazole-7,2'-[1,3]dioxolane]-2(6H)-sulfonamide The titled compound was prepared using the conditions described in Example 86A substituting 3-(4,4,5,5-tetramethyl-1,3,2-dioxaborolan-2-yl)pyridine with (1-(4-cyanophenyl)-1H-pyrazol-4-yl)boronic acid. MS (APCI) m/z 599 (M+H)$^+$.

Example 157B

4-{4-[(5aS,6S,9aS)-6-methyl-7-oxo-9a-phenyl-4,5,5a,6,7,8,9,9a-octahydro-2H-benzo[g]indazol-3-yl]-1H-pyrazol-1-yl}benzonitrile The titled compound was prepared using the conditions described in Example 86B substituting Example 86A with Example 157A. MS (APCI) m/z 448 (M+H)+.

Example 157C

4-{4-[(5aS,6S,8Z,9aS)-8-(hydroxymethylene)-6-methyl-7-oxo-9a-phenyl-4,5,5a,6,7,8,9,9a-octahydro-2H-benzo[g]indazol-3-yl]-1H-pyrazol-1-yl}benzonitrile The titled compound was prepared using the conditions described in Example 24C substituting Example 24B with Example 157B.

Example 157D

4-{4-[(5aS,6S,10aS)-6-methyl-10a-phenyl-4,5,5a,6,10,10a-hexahydro-2H-indazolo[7,6-f][1,2]benzoxazol-3-yl]-1H-pyrazol-1-yl}benzonitrile The titled compound was prepared using the conditions described in Example 24D substituting Example 24C with Example 157C. MS (APCI) m/z 473 (M+H)+.

Example 157E (5aS,6S,9aS)-3-[1-(4-cyanophenyl)-1H-pyrazol-4-yl]-6-methyl-7-oxo-9a-phenyl-4,5,5a,6,7,8,9,9a-octahydro-2H-benzo[g]indazole-8-carbonitrile The titled compound was prepared using the conditions described in Example 24E substituting Example 24D with Example 157D.

Example 157F (5aS,6S,9aR)-3-[1-(4-cyanophenyl)-1H-pyrazol-4-yl]-6-methyl-7-oxo-9a-phenyl-4,5,5a,6,7,9a-hexahydro-2H-benzo[g]indazole-8-carbonitrile Example 157E (0.055 g, 0.116 mmol) was dissolved in tetrahydrofuran (1.16 mL) and $N_2$ was bubbled through the mixture for 10 minutes. 2,3-Dichloro-5,6-dicyano-1,4-benzoquinone (0.026 g, 0.116 mmol) was then added, and the reaction mixture was stirred at room temperature with continued $N_2$ bubbling. The reaction mixture was concentrated, and the residue was purified on a reversed-phase Waters HPLC using a Nova-Pak® HR C18, 6 μm, 60 Å, 40 mm×100 mm, PrepPak cartridge eluting with a gradient of 10-90% acetonitrile in aqueous 0.1% trifluoroacetic acid (60 mL/minute) to give the titled compound as the trifluoroacetic acid salt (0.030 g, 55%). $^1$H NMR (400 MHz, DMSO-$d_6$) δ ppm 1.07 (d, J=6.6 Hz, 2H), 1.40 (d, J=8.9 Hz, 1H), 1.84 (d, J=13.2 Hz, 1H), 2.33-2.40 (m, 1H), 2.80 (d, J=8.2 Hz, 1H), 2.94-3.04 (m, 1H), 6.95 (d, J=7.3 Hz, 2H), 7.32 (dt, J=23.0, 7.1 Hz, 3H), 8.02 (d, J=8.8 Hz, 2H), 8.14 (d, J=8.8 Hz, 2H), 8.25 (s, 1H), 8.29 (s, 1H), 8.43 (s, 1H), 8.90 (s, 1H); MS (ESI) m/z 471 (M+H)+.

Example 158

(5aS,6S,9aR)-6-methyl-7-oxo-9a-phenyl-3-[1-(pyridin-3-yl)-1H-pyrazol-4-yl]-4,5,5a,6,7,9a-hexahydro-2H-benzo[g]indazole-8-carbonitrile

Example 158A (5aS,6S,9aS)—N,N,6-trimethyl-9a-phenyl-3-[1-(pyridin-3-yl)-1H-pyrazol-4-yl]-4,5,5a,8,9,9a-hexahydrospiro[benzo[g]indazole-7,2'-[1,3]dioxolane]-2(6H)-sulfonamide The titled compound was prepared using the conditions described in Example 86A substituting 3-(4,4,5,5-tetramethyl-1,3,2-dioxaborolan-2-yl)pyridine with (1-(pyridin-3-yl)-1H-pyrazol-4-yl)boronic acid. MS (APCI) m/z 575 (M+H)+.

Example 158B (5aS,6S,9aS)-6-methyl-9a-phenyl-3-[1-(pyridin-3-yl)-1H-pyrazol-4-yl]-2,4,5,5a,6,8,9,9a-octahydro-7H-benzo[g]indazol-7-one The titled compound was prepared using the conditions described in Example 86B substituting Example 86A with Example 158A.

Example 158C (5aS,6S,8Z,9aS)-8-(hydroxymethylene)-6-methyl-9a-phenyl-3-[1-(pyridin-3-yl)-1H-pyrazol-4-yl]-2,4,5,5a,6,8,9,9a-octahydro-7H-benzo[g]indazol-7-one The titled compound was prepared using the conditions described in Example 24C substituting Example 24B with Example 158B.

Example 158D (5aS,6S,10aS)-6-methyl-10a-phenyl-3-[1-(pyridin-3-yl)-1H-pyrazol-4-yl]-4,5,5a,6,10,10a-hexahydro-2H-indazolo[7,6-f][1,2]benzoxazole The titled compound was prepared using the conditions described in Example 24D substituting Example 24C with Example 158C. MS (APCI) m/z 449 (M+H)+.

Example 158E (5aS,6S,9aS)-6-methyl-7-oxo-9a-phenyl-3-[1-(pyridin-3-yl)-1H-pyrazol-4-yl]-4,5,5a,6,7,8,9,9a-octahydro-2H-benzo[g]indazole-8-carbonitrile The titled compound was prepared using the conditions described in Example 24E substituting Example 24D with example 158D.

Example 158F (5aS,6S,9aR)-6-methyl-7-oxo-9a-phenyl-3-[1-(pyridin-3-yl)-1H-pyrazol-4-yl]-4,5,5a,6,7,9a-hexahydro-2H-benzo[g]indazole-8-carbonitrile Example 158E (0.030 g, 0.067 mmol) was dissolved in tetrahydrofuran (0.70 mL) and $N_2$ was bubbled through the reaction mixture for 10 minutes. 2,3-Dichloro-5,6-dicyano-p-benzoquinone (0.015 g, 0.067 mmol) was then added, and the reaction mixture was stirred at room temperature for 10 minutes with continued $N_2$ bubbling. The reaction mixture was concentrated, and the residue was purified on a reverse phase Waters HPLC using a Nova-Pak® HR C18, 6 μm, 60 Å, 40 mm×100 mm, PrepPak cartridge eluting with a. gradient of 10-90% acetonitrile in aqueous 0.1% trifluoroacetic acid (60 mL/minute) to give the titled compound as the trifluoroacetic acid salt (0.009 g, 30%). $^1$H NMR (400 MHz, DMSO-$d_6$) δ ppm 1.04-1.10 (m, 3H), 1.40 (s, 1H), 1.83 (s, 1H), 2.35 (dd, J=12.8, 6.3 Hz, 1H), 2.83 (d, J=31.9 Hz, 2H), 2.94-3.07 (m, 2H), 6.96 (d, J=7.5 Hz, 2H), 7.25-7.40 (m, 3H), 7.60 (dd, J=8.3, 4.7 Hz, 1H), 8.23 (s, 1H), 8.29 (s, 1H), 8.33 (d, J=8.3 Hz, 1H), 8.43 (s, 1H), 8.56 (d, J=3.7 Hz, 1H), 8.85 (s, 1H), 9.18 (d, J=2.4 Hz, 1H); MS (ESI) m/z 447 (M+H)$^+$.

Example 159

(5aS,6S,9aR)-6-methyl-7-oxo-9a-phenyl-3-[1-(pyridin-4-yl)-1H-pyrazol-4-yl]-4,5,5a,6,7,9a-hexahydro-2H-benzo[g]indazole-8-carbonitrile Example 159A (5aS,6S,9aS)—N,N,6-trimethyl-9a-phenyl-3-[1-(pyridin-4-yl)-1H-pyrazol-4-yl]-4,5,5a,8,9,9a-hexahydrospiro[benzo[g]indazole-7,2'-[1,3]dioxolane]-2(6H)-sulfonamide The titled compound was prepared using the conditions described in Example 86A substituting 3-(4,4,5,5-tetramethyl-1,3,2-dioxaborolan-2-yl)pyridine with (1-(pyridin-4-yl)-1H-pyrazol-4-yl)boronic acid. MS (APCI) m/z 575 (M+H)$^+$.

Example 159B (5aS,6S,9aS)-6-methyl-9a-phenyl-3-[1-(pyridin-4-yl)-1H-pyrazol-4-yl]-2,4,5,5a,6,8,9,9a-octahydro-7H-benzo[g]indazol-7-one The titled compound was prepared using the conditions described in Example 86B substituting Example 86A with Example 159A.

Example 159C (5aS,6S,8Z,9aS)-8-(hydroxymethylene)-6-methyl-9a-phenyl-3-[1-(pyridin-4-yl)-1H-pyrazol-4-yl]-2,4,5,5a,6,8,9,9a-octahydro-7H-benzo[g]indazol-7-one The titled compound was prepared using the conditions described in Example 24C substituting Example 24B with Example 159B.

Example 159D (5aS,6S,10aS)-6-methyl-10a-phenyl-3-[1-(pyridin-4-yl)-1H-pyrazol-4-yl]-4,5,5a,6,10,10a-hexahydro-2H-indazolo[7,6-f][1,2]benzoxazole The titled compound was prepared using the conditions described in Example 24D substituting Example 24C with Example 159C. MS (APCI) m/z 449 (M+H)$^+$.

Example 159E (5aS,6S,9aS)-6-methyl-7-oxo-9a-phenyl-3-[1-(pyridin-4-yl)-1H-pyrazol-4-yl]-4,5,5a,6,7,8,9,9a-octahydro-2H-benzo[g]indazole-8-carbonitrile The titled compound was prepared using the conditions described in Example 24E substituting Example 24D with Example 159D.

Example 159F (5aS,6S,9aR)-6-methyl-7-oxo-9a-phenyl-3-[1-(pyridin-4-yl)-1H-pyrazol-4-yl]-4,5,5a,6,7,9a-hexahydro-2H-benzo[g]indazole-8-carbonitrile Example 159E (0.02 g, 0.045 mmol) was dissolved in tetrahydrofuran (0.45 mL) and $N_2$ was bubbled through the reaction mixture for 10 minutes. 2,3-Dichloro-5,6-dicyano-1,4-benzoquinone (0.010 g, 0.045 mmol) was then added, and the reaction mixture was stirred at room temperature for 10 minutes with continued $N_2$ bubbling. The reaction mixture was concentrated, and the residue was purified on a reversed-phase Waters HPLC using a Nova-Pak® HR C18, 6 μm, 60 Å, 40 mm×100 mm, PrepPak cartridge eluting with a gradient of 10-90% acetonitrile in aqueous 0.1% trifluoroacetic acid (60 mL/minute) to give the titled compound as the trifluoroacetic acid salt (0.002 g, 10%). $^1$H NMR (400 MHz, DMSO-$d_6$) δ ppm 1.09 (t, J=5.1 Hz, 3H), 1.84 (dd, J=16.5, 9.2 Hz, 1H), 2.37 (dd, J=13.4, 6.4 Hz, 1H), 2.75-2.88 (m, 1H), 2.96-3.08 (m, 1H), 6.96 (d, J=7.4 Hz, 2H), 7.25-7.43 (m, 3H), 7.95 (d, J=5.8 Hz, 2H), 8.30 (d, J=2.1 Hz, 1H), 8.45 (d, J=11.0 Hz, 1H), 8.69 (d, J=5.4 Hz, 2H), 8.94 (s, 1H); MS (ESI+) m/z 447 (M+H)$^+$.

Example 160 rac-(5aS,6S,9aR)-2,6-dimethyl-7-oxo-9a-phenyl-4,5,5a,6,7,9a-hexahydro-2H-benzo[g]indazole-8-carbonitrile Example 160A rac-(5aS,6S,9aS)-1,6-dimethyl-9a-phenyl-1,4,5,5a,6,8,9,9a-octahydrospiro[benzo[g]indazole-7,2'-[1,3]dioxolane] and rac-(5aS,6S,9aS)-2,6-dimethyl-9a-phenyl-2,4,5,5a,6,8,9,9a-octahydrospiro[benzo[g]indazole-7,2'-[1,3]dioxolane]

A solution of Example 2J (0.797 g, 2.42 mmol) and methylhydrazine (0.245 g, 5.3 mmol) in ethanol (50 mL) was stirred at room temperature for 30 minutes and was then warmed to about 65° C. for 1 hour. The reaction mixture was then stirred at 60° C. overnight. The reaction mixture was concentrated under reduced pressure. The residue was taken up in ethanol and concentrated (3×). The residue was purified by column chromatography (silica gel, 50% ethyl acetate in hexanes then 5 to 10% methanol in dichloromethane) to give 0.36 g (44%) of the titled compounds. MS (APCI) m/z 339 (M+H)$^+$.

Example 160B rac-(5aS,6S,9aS)-1,6-dimethyl-9a-phenyl-1,4,5,5a,6,8,9,9a-octahydro-7H-benzo[g]indazol-7-one and rac-(5aS,6S,9aS)-2,6-dimethyl-9a-phenyl-2,4,5,5a,6,8,9,9a-octahydro-7H-benzo[g]indazol-7-one A mixture of the compounds from Example 160A (0.36 g, 1.06 mmol) and hydrochloric acid (1 N, 6 mL) in methanol

Example 160C rac-(5aS,6S,8Z,9aS)-8-(hydroxymethylene)-1,6-dimethyl-9a-phenyl-1,4,5,5a,6,8,9,9a-octahydro-7H-benzo[g]indazol-7-one and rac-(5aS,6S,8Z,9aS)-8-(hydroxymethylene)-2,6-dimethyl-9a-phenyl-2,4,5,5a,6,8,9,9a-octahydro-7H-benzo[g]indazol-7-one Sodium methoxide (30% w/w in methanol, 2 mL) was added dropwise to a solution of the mixture from Example 160B (0.36 g, 1.22 mmol) in ethyl formate (50 mL), and the resultant mixture was stirred overnight at room temperature. The reaction mixture was partitioned between ethyl acetate (100 mL) and saturated aqueous potassium dihydrogen phosphate (20 mL). The organic layer was dried (MgSO$_4$) and concentrated under reduced pressure to give a 0.345 g (88%) of the titled compounds. MS (APCI) m/z 323 (M+H)$^+$.

Example 160D rac-(5aS,6S,10aS)-1,6-dimethyl-10a-phenyl-4,5,5a,6,10,10a-hexahydro-1H-indazolo[7,6-f][1,2]benzoxazole and rac-(5aS,6S,10aS)-2,6-dimethyl-10a-phenyl-4,5,5a,6,10,10a-hexahydro-2H-indazolo[7,6-][1,2]benzoxazole A mixture of Example 160C (0.345 g, 1.07 mmol) and 0.1 M hydroxylamine hydrochloride in ethanol/water (9/1 v/v, 16 mL, 1.6 mmol) was stirred overnight at room temperature and then was heated at 65° C. under weak vacuum until dry. The residue was taken up in ethanol and concentrated under vacuum. This process was repeated three times.

The residue was purified by column chromatography (silica gel, 50 to 100% ethyl acetate in hexanes then 4 to 5% methanol in dichloromethane) to give 0.225 g (66%) of the titled compounds. MS (APCI) m/z 320 (M+H)$^+$.

Example 160E rac-(5aS,6S,9aS)-1,6-dimethyl-7-oxo-9a-phenyl-4,5,5a,6,7,8,9,9a-octahydro-1H-benzo[g]indazole-8-carbonitrile and rac-(5aS,6S,9aS)-2,6-dimethyl-7-oxo-9a-phenyl-4,5,5a,6,7,8,9,9a-octahydro-2H-benzo[g]indazole-8-carbonitrile Sodium methoxide (30% w/w in methanol, 0.7 mL) was added to a solution of the mixture from Example 160D (0.225 g, 0.70 mmol) in methanol/tetrahydrofuran (1/1 v/v, 20 mL), and the reaction mixture was stirred overnight at room temperature. The reaction mixture was partitioned between ethyl acetate (100 mL) and saturated aqueous potassium dihydrogen phosphate (20 mL). The organic fraction was dried (MgSO$_4$) and concentrated under reduced pressure to give 0.237 g (100%) of the titled compounds.

Example 160F rac-(5aS,6S,9aR)-2,6-dimethyl-7-oxo-9a-phenyl-4,5,5a,6,7,9a-hexahydro-2H-benzo[g]indazole-8-carbonitrile The mixture from Example 161E (0.237 mg, 0.74 mmol) was dissolved in dry N,N-dimethylformamide (2 mL), and the solution was cooled to 0° C. 1,3-Dibromo-5,5-dimethylhydantoin (117 mg, 0.41 mmol) was added, and the reaction mixture was stirred at 0° C. for 1.75 hours. Pyridine (0.6 mL, 7.4 mmol) was added, and the reaction mixture was heated to 60° C. for 2.75 hours. The reaction mixture was concentrated under reduced pressure and the residue purified by column chromatography (silica gel, 30% ethyl acetate in hexanes) to give 0.014 g, 6%) the titled compound as the first to elute relative to Example 161. $^1$H NMR (400 MHz, CDCl$_3$) δ ppm 8.43 (s, 1H), 7.23-7.31 (m, 4H), 6.91 (d, J=8.0 Hz, 2H), 3.87 (s, 3H), 2.85 (dd, J=6.9, 16.6 Hz, 1H), 2.69 (ddd, J=7.4, 11.6, 16.5 Hz, 1H), 2.39-2.48 (m, 1H), 2.32 (t, J=12.7 Hz, 1H), 1.79 (dd, J=7.2, 13.6 Hz, 1H), 1.47-1.58 (m, 1H), 1.16 (d, J=6.6 Hz, 3H); MS (APCI) m/z 318 (M+H)$^+$.

Example 161 rac-(5aS,6S,9aR)-1,6-dimethyl-7-oxo-9a-phenyl-4,5,5a,6,7,9a-hexahydro-1H-benzo[g]indazole-8-carbonitrile The titled compound (0.045 g, 19%) was recovered as the second eluting component from the chromatography described in Example 160F. $^1$H NMR (400 MHz, CDCl$_3$) δ ppm 8.13 (s, 1H), 7.41 (s, 1H), 7.33-7.41 (m, 3H), 6.68 (dd, J=2.6, 7.0 Hz, 2H), 3.52 (s, 3H), 2.83 (dd, J=5.4, 16.0 Hz, 1H), 2.64 (ddd, J=6.1, 12.1, 16.0 Hz, 1H), 2.47 (t, J=12.6 Hz, 1H), 2.33 (qd, J=6.8, 13.4 Hz, 1H), 1.79 (dd, J=6.0, 13.8 Hz, 1H), 1.49-1.60 (m, 1H), 1.18 (d, J=6.7 Hz, 3H); MS (APCI) m/z 318 (M+H)$^+$.

Example 162 rac-(5aS,6S,9aR)-9a-benzyl-2,6-dimethyl-7-oxo-4,5,5a,6,7,9a-hexahydro-2H-benzo[g]indazole-8-carbonitrile

Example 162A 2-benzylcyclohexane-1,3-dione

Benzaldehyde (4.26 g, 40.1 mmol), L-proline (0.31 g, 2.68 mmol) and diludine (3.39 g, 13.4) were added sequentially to a room temperature solution of cyclohexane-1,3-dione (1.50 g, 13.4 mmol) in CH$_2$Cl$_2$ (15 mL). The mixture was stirred overnight and then filtered to give the titled compound (1.86 g, 69%) as a solid. The filtrate was concentrated under reduced pressure, and the residue was purified by column chromatography (silica gel, 2 to 4% CH$_3$OH in CH$_2$Cl$_2$) to give a second batch of the titled compound (0.67 g, 25%) as a solid. MS (APCI) m/z 203 (M+H)$^+$.

Example 162B 2-benzyl-2-(3-oxobutyl)cyclohexane-1,3-dione

Ethyl vinyl ketone (1.16 g, 13.8 mmol) and triethylamine (2.6 mL, 19 mmol) were added to a room temperature suspension of Example 162A (2.53 g, 12.5 mmol) in acetonitrile (25 mL). The mixture was stirred overnight, filtered, and concentrated under reduced pressure. The resultant residue was purified by column chromatography (silica gel, 5% ethyl acetate in $CH_2Cl_2$) to give the titled compound (2.88 g, 80%). MS(APCI) m/z 287 $(M+H)^+$.

Example 162C 8a-benzyl-5-methyl-3,4, 8, 8a-tetrahydronaphthalene-1,6(2H,7H)-dione L-Phenylalanine (1.32 g, 7.99 mmol) and D-camphorsulfonic acid (1.40 g, 6.03 mmol) were added to a solution of Example 162B (2.88 g, 10.0 mmol) in acetonitrile (40 mL). The mixture was heated at 40° C. for 1 hour, at 50° C. for 1 hour, at 70° C. overnight, and then at 80° C. for 4 hours. The mixture was concentrated under reduced pressure. The residue was diluted with water (50 mL) and extracted with ethyl acetate (2×100 mL). The combined organic fractions were washed with brine, dried ($MgSO_4$), concentrated under reduced pressure, and purified by column chromatography (silica gel 3 to 5% ethyl acetate in $CH_2Cl_2$) to give the titled compound (2.38 g, 88%). MS (APCI) 269 $(M+H)^+$.

Example 162D rac-(4aR,5S)-4a-benzyl-5-hydroxy-1-methyl-4,4a,5, 6,7,8-hexahydronaphthalen-2(3H)-one A solution of Example 162C (0.31 g, 1.16 mmol) in ethanol (10 mL) was cooled in an ice-salt bath. Sodium borohydride (12 mg, 0.31 mmol) was added in small portions over 30 minutes. After 15 minutes, another small portion of sodium borohydride (3 mg, 0.08 mmol) was added, and stirring was continued for another 20 minutes. Glacial acetic acid (3 drops) was added over several minutes until gas evolution was complete. The solution was concentrated under reduced pressure. The residue was diluted with saturated aqueous sodium bicarbonate (20 mL) and extracted with ethyl acetate (2×50 mL). The combined organic fractions were washed with brine, dried ($MgSO_4$), and concentrated under reduced pressure to give 0.31 g, (100%) of the titled compound. MS (APCI) m/z 271 $(M+H)^+$.

Example 162E rac-(1S,4aR,5S,8aS)-4a-benzyl-5-hydroxy-1-methyl-octahydronaphthalen-2(1H)-one A flask containing a suspension of Example 162D (159 mg, 0.584 mmol) and Pd/C (10% w/w, 35 mg) in ethyl acetate (5 mL) was purged with $N_2$, then $H_2$. The mixture was stirred overnight under a $H_2$ (balloon pressure). Additional Pd/C (10% w/w, 35 mg) was added, and the mixture was purged with $N_2$, then $H_2$. After an additional 24 hours, the mixture was filtered through a fine frit, and the filtrate was concentrated under reduced pressure to give a residue that was used without further purification. The residue was taken up in methanol (5 mL) and sodium methoxide (30% w/w in methanol, 2 drops) was added. The solution was stirred for 3 hours and concentrated under reduced pressure. The residue was diluted with saturated aqueous $KH_2PO_4$ (20 mL) and extracted with ethyl acetate (2×50 mL). The combined organic extracts were washed with brine, dried ($MgSO_4$), concentrated under a reduced pressure, and purified by column chromatography (silica gel, 10% ethyl acetate in $CH_2Cl_2$) to give the titled compounds (0.080 g, 50%). MS (APCI) m/z 255 $(M+H-H_2O)^+$.

Example 162F rac-(1'S,4a'R,5'S,8a'S)-4a'-benzyl-1'-methyloctahydro-1'H-spiro[1,3-dioxolane-2,2'-naphthalen]-5'-ol A solution of Example 162E (0.265 g, 0.97 mmol), ethylene glycol (0.36 g, 5.84 mmol), and p-toluenesulfonic acid (catalytic) in benzene (10 mL) was heated at reflux for 3 hours with Dean-Stark trap removal of water. The solution was cooled, diluted with saturated aqueous sodium bicarbonate solution (20 mL) and extracted with ethyl acetate (2×50 mL). The combined organic fractions were washed with brine, dried ($MgSO_4$), and concentrated under reduced pressure to give the titled compound (0.306 g, 100%). MS (APCI) m/z 299 $(M+H-H_2O)^+$.

Example 162G rac-(1'S,4a'R,8a'S)-4a'-benzyl-1'-methylhexahydro-1'H-spiro[1,3-dioxolane-2,2'-naphthalen]-5'(3'H)-one Pyridinium dichromate (0.535 g, 1.42 mmol) was added to a solution of Example 162F (300 mg, 0.95 mmol) in $CH_2Cl_2$ (15 mL). The mixture was stirred overnight and filtered through a pad of diatomaceous earth. The filtrate was concentrated under reduced pressure, and the resultant residue was purified by column chromatography (silica gel 20% ethyl acetate in hexanes) to give the titled compound (0.265 g, 89%). MS (APCI) m/z 315 $(M+H)^+$.

Example 162H rac-(1'S,4a'R,6'Z,8a'S)-benzyl-6a'-benzyl-6'-(hydroxymethylene)-1'-methylhexahydro-1'H-spiro[1,3-dioxolane-2,2'-naphthalen]-5'(3'H)-one Sodium hydride (60% w/w dispersion in mineral oil, 0.178 g, 4.45 mmol) was added to a solution of Example 162G (0.280 g, 0.89 mmol) and ethyl formate (1.32 g, 17.8 mmol) in tetrahydrofuran (15 mL). The mixture was slowly heated to 65° C. while vigorous gas was evolved for several minutes. Heating was continued for an additional 2 hour at 65° C. The reaction mixture was then cooled in an ice bath, quenched with saturated aqueous $KH_2PO_4$ (20 mL), and extracted with ethyl acetate (2×50 mL). The combined organic fractions were washed with brine, dried ($MgSO_4$), and concentrated under reduced pressure to give the titled compound (0.42 g, 100%). MS (APCI) m/z 343 $(M+H)^+$.

Example 162I rac-(5aS,6S,9aR)-9a-benzyl-2,6-dimethyl-2,4,5,5a,6, 8,9,9a-octahydrospiro[benzo[g]indazole-7,2'-[1,3] dioxolane]

A solution of Example 162H (all above obtained, ≤0.89 mmol) and methylhydrazine (0.082 g, 1.78 mmol) in ethanol (5.5 mL) was heated at 50° C. for 3 hours. Acetic acid (3 drops) was added and heating was continued at 50° C. for 2 hours. The solution was cooled, concentrated under reduced pressure, and purified by column chromatography (silica gel, 25% ethyl acetate in $CH_2Cl_2$) to give the titled compound (0.138 g, 44%)%) as the second eluting isomer (relative to Example 163A). MS (APCI) m/z 353 (M+H)⁺.

Example 162J rac-(5aS,6S,9aR)-9a-benzyl-2,6-dimethyl-2,4,5,5a,6,8,9,9a-octahydro-7H-benzo[g]indazol-7-one A solution of aqueous hydrochloric acid (1 N, 0.5 mL) was added to a room temperature solution of Example 162I (0.138 g, 0.39 mmol) in tetrahydrofuran (4 mL). The solution was stirred 2 days, diluted with saturated aqueous sodium bicarbonate (20 mL), and extracted with ethyl acetate (2×50 mL). The combined organic fractions were washed with brine (20 mL), dried (MgSO$_4$), and concentrated under reduced pressure to give the titled compound (0.120 g, 99%). MS (APCI) m/z 309 (M+H)⁺.

Example 162K rac-(5aS,6S,8Z,9aS)-9a-benzyl-8-(hydroxymethylene)-2,6-dimethyl-2,4,5,5a,6,8,9,9a-octahydro-7H-benzo[g]indazol-7-one Sodium methoxide (30% w/w in methanol, 1.2 g) was added dropwise to a 0° C. solution of Example 162J (0.21 g, 0.68 mmol) in ethyl formate (6 mL). The solution was warmed to room temperature and stirred overnight. The mixture was cooled in an ice bath, quenched by the addition of saturated aqueous KH$_2$PO$_4$ (25 mL), and extracted with ethyl acetate (2×50 mL). The combined organic extracts were washed with brine (25 mL), dried (MgSO$_4$), and concentrated under reduced pressure to give the titled compound (0.23 g, 100%). MS (APCI) m/z 337 (M+H)⁺.

Example 162L rac-(5aS,6S,10aS)-10a-benzyl-2,6-dimethyl-4,5,5a,6,10,10a-hexahydro-2H-indazolo[7,6-f][1,2]benzoxazole A mixture of hydroxylamine hydrochloride (0.071 g, 1.02 mmol) and Example 162K (0.23 g, 0.68 mmol) in ethanol (5 mL) and water (0.5 mL) was heated at 50° C. for 3 hours, cooled to room temperature, stirred overnight, and concentrated under reduced pressure. The residue was diluted with saturated aqueous sodium bicarbonate (20 mL) and extracted with ethyl acetate (2×50 mL). The combined organic fractions were washed with brine (20 mL), dried (MgSO$_4$), and concentrated under reduced pressure to give the titled compound (0.23 g, 100%). MS (APCI) m/z 334 (M+H)⁺.

Example 162M rac-(5aS,6S,9aR)-9a-benzyl-2,6-dimethyl-7-oxo-4,5,5a,6,7,8,9,9a-octahydro-2H-benzo[g]indazole-8-carbonitrile Sodium methoxide (30% w/w in methanol, 1.2 g) was added to a room temperature solution of Example 162L (0.23 g, 0.68 mmol) in tetrahydrofuran (5 mL) and methanol (1 mL). The solution was heated at 50° C. for 2 hours, cooled to room temperature, and concentrated under reduced pressure. Saturated aqueous KH$_2$PO$_4$ (25 mL) was added to the residue, and the mixture was extracted with ethyl acetate (2×50 mL). The combined organic fractions were washed with brine (20 mL), dried (MgSO$_4$), concentrated under reduced pressure, and purified by column chromatography (silica gel, 15 to 20% ethyl acetate in CH$_2$Cl$_2$) to give the titled compound (0.150 g, 66%). MS (APCI) m/z 334 (M+H)⁺.

Example 162N rac-(5aS,6S,9aR)-9a-benzyl-2,6-dimethyl-7-oxo-4,5,5a,6,7,9a-hexahydro-2H-benzo[g]indazole-8-carbonitrile A solution of Example 162M 0.150 g, 0.45 mmol) was dissolved in dry N,N-dimethylformamide (4 mL), and the solution was cooled to 0° C. 1,3-Dibromo-5,5-dimethylhydantoin (0.077 g, 0.27 mmol) was added, and the reaction mixture was stirred at 0° C. for 1.5 hours. Pyridine (0.6 mL) was added, and the reaction was heated at 60° C. for 3 hours. The reaction mixture was concentrated under reduced pressure and dried under vacuum. The crude residue was purified by column chromatography (silica gel, 5% ethyl acetate in CH$_2$Cl$_2$) to give the titled compound (0.100 g, 67%). $^1$H NMR (400 MHz, CDCl$_3$) δ ppm 8.19 (s, 1H), 7.17-7.23 (m, 3H), 7.11 (s, 1H), 6.73-6.77 (m, 2H), 3.77 (s, 3H), 3.15 (d, J=13.0 Hz, 1H), 3.07 (d, J=13.0 Hz, 1H), 2.76 (dd, J=6.8, 16.5 Hz, 1H), 2.58-2.71 (m, 2H), 2.16 (dt, J=2.9, 12.9 Hz, 1H), 1.82-2.03 (m, 2H), 1.28 (d, J=7.0 Hz, 3H); MS (APCI) m/z 332 (M+H)⁺.

Example 163 rac-(5aS,6S,9aR)-9a-benzyl-1,6-dimethyl-7-oxo-4,5,5a,6,7,9a-hexahydro-1H-benzo[g]indazole-8-carbonitrile Example 163A rac-(5aS,6S,9aR)-9a-benzyl-1,6-dimethyl-1,4,5,5a,6,8,9,9a-octahydrospiro[benzo[g]indazole-7,2'-[1,3]dioxolane]

The titled compound was isolated as the first eluting compound from the chromatography described in Example 162I: 0.078 g, (25%). MS (APCI) m/z 353 (M+H)⁺.

Example 163B rac-(5aS,6S,9aR)-9a-benzyl-1,6-dimethyl-1,4,5,5a,6,8,9,9a-octahydro-7H-benzo[g]indazol-7-one A solution of aqueous hydrochloric acid (1 N, 0.5 mL) was added to a room temperature solution of Example 163A (0.105 g, 0.30 mmol) in tetrahydrofuran (4 mL). The solution was stirred 2 days, diluted with saturated aqueous sodium bicarbonate (20 mL), and extracted with ethyl acetate (2×50 mL). The combined organic fractions were washed with brine (20 mL), dried (MgSO$_4$), and concentrated under reduced pressure to give the titled compound (0.082 g, 100%). MS (APCI) m/z 309 (M+H)⁺.

Example 163C rac-(5aS,6S,8Z,9aS)-9a-benzyl-8-(hydroxymethylene)-1,6-dimethyl-1,4,5,5a,6,8,9,9a-octahydro-7H-benzo[g]indazol-7-one Sodium methoxide (30% w/w in methanol, 0.67 g) was added dropwise to a 0° C. solution of Example 163B (0.115 g, 0.37 mmol) in ethyl formate (5 mL), and then the solution was warmed to room temperature and stirred overnight. The mixture was cooled in an ice bath, quenched by the addition of saturated aqueous $KH_2PO_4$ (20 mL), and extracted with ethyl acetate (2×50 mL). The combined organic extracts were washed with brine (20 mL), dried ($MgSO_4$), and concentrated under reduced pressure to give the titled compound (0.125 g, 100%). MS (APCI) m/z 337 $(M+H)^+$.

Example 163D rac-(5aS,6S,10aS)-10a-benzyl-1,6-dimethyl-4,5,5a,6,10,10a-hexahydro-1H-indazolo[7,6-f][1,2]benzoxazole A mixture of hydroxylamine hydrochloride (0.039 g, 0.57 mmol) and Example 163C 0.125 g, 0.37 mmol) in ethanol (4 mL) and water (0.2 mL) was heated at 50° C. for 3 hours, cooled to room temperature, stirred overnight, and concentrated under reduced pressure. The residue was diluted with saturated aqueous sodium bicarbonate (20 mL) and extracted with ethyl acetate (2×50 mL). The combined organic fractions were washed with brine (20 mL), dried ($MgSO_4$), and concentrated under reduced pressure to give the titled compound (0.125 g, 100%). MS (APCI) m/z 334 $(M+H)^+$.

Example 163E rac-(5aS,6S,9aR)-9a-benzyl-1,6-dimethyl-7-oxo-4,5,5a,6,7,8,9,9a-octahydro-1H-benzo[g]indazole-8-carbonitrile Sodium methoxide (30% w/w in methanol, 0.67 g) was added to a room temperature solution of Example 163D (all above obtained, ≤0.37 mmol) in tetrahydrofuran (4 mL) and methanol (1 mL). The solution was heated at 50° C. for 4 hours, cooled to room temperature, and concentrated under reduced pressure. Saturated aqueous $KH_2PO_4$ (25 mL) was added to the residue, and the mixture was extracted with ethyl acetate (2×50 mL). The combined organic fractions were washed with brine (20 mL), dried ($MgSO_4$), concentrated under reduced pressure, and purified by column chromatography (silica gel, 20% ethyl acetate in $CH_2Cl_2$) to give the titled compound (0.060 mg, 49%). MS (APCI) m/z 334 $(M+H)^+$.

Example 163F rac-(5aS,6S,9aR)-9a-benzyl-1,6-dimethyl-7-oxo-4,5,5a,6,7,9a-hexahydro-1H-benzo[g]indazole-8-carbonitrile A solution of Example 163E (0.060 mg, 0.18 mmol) was dissolved in dry N,N-dimethylformamide (3 mL), and the solution was cooled to 0° C. 1,3-Dibromo-5,5-dimethylhydantoin (0.031 g, 0.11 mmol) was added, and the reaction mixture was stirred at 0° C. for 1.5 hours. Pyridine (0.3 mL) was added, and the reaction was heated at 60° C. for 3 hours. The reaction mixture was concentrated under reduced pressure and dried under vacuum. The crude residue was purified by column chromatography (silica gel, 10% ethyl acetate in $CH_2Cl_2$) to give the titled compound (0.050 mg, 83%). $^1$H NMR (400 MHz, $CDCl_3$) δ ppm 8.17 (s, 1H), 7.26-7.35 (m, 4H), 6.77 (dt, J=1.6, 6.6 Hz, 2H), 3.20 (d, J=12.7 Hz, 1H), 3.14 (d, J=12.7 Hz, 1H), 2.93 (s, 3H), 2.81 (dd, J=7.2, 14.5 Hz, 1H), 2.74-2.82 (m, 1H), 2.65 (ddd, J=7.4, 11.4, 16.4 Hz, 1H), 2.28 (dt, J=2.7, 12.8 Hz, 1H), 2.10 (dd, J=8.2, 13.7 Hz, 1H), 1.87-1.99 (m, 1H), 1.37 (d, J=6.7 Hz, 3H); MS (APCI) m/z 332 $(M+H)^+$.

Example 164 rac-(5aS,6S,9aR)-9a-benzyl-2,6-dimethyl-7-oxo-3-phenyl-4,5,5a,6,7,9a-hexahydro-2H-benzo[g]indazole-8-carbonitrile Example 164A rac-(5aS,6S,9aR)-9a-benzyl-2,6-dimethyl-3-phenyl-2,4,5,5a,6,8,9,9a-octahydrospiro[benzo[g]indazole-7,2'-[1,3]dioxolane]

1,3-Dibromo-5,5-dimethylhydantoin (0.156 g, 0.55 mmol) was added to a 0° C. solution of Example 1621 (0.350 g, 0.99 mmol) in dichloromethane (15 mL), and the solution was stirred at 0° C. for 30 minutes. The solution was diluted with saturated aqueous sodium bicarbonate solution (20 mL) and extracted with ethyl acetate (2×50 mL). The combined organic fractions were washed with brine (20 mL), dried ($MgSO_4$), concentrated under reduced pressure, and purified by column chromatography (silica gel, 10% ethyl acetate in $CH_2Cl_2$) to give the titled compound (0.300 g, 70%). MS (APCI) m/z 433, 431 $(M+H)^+$.

Example 164B rac-(5aS,6S,9aR)-9a-benzyl-2,6-dimethyl-3-phenyl-2,4,5,5a,6,8,9,9a-octahydrospiro[benzo[g]indazole-7,2'-[1,3]dioxolane]

A solution of Example 164A (0.300 g, 0.70 mmol), phenylboronic acid (0.170 g, 1.39 mmol), and potassium phosphate (0.443 g, 2.09 mmol) in dimethoxyethane (6 mL) and N,N-dimethylformamide (2 mL) was sparged with $N_2$ for 10 minutes. Then tetrakis(triphenylphosphine)palladium (0) (0.056 g, 0.049 mmol) was added, and the mixture was sparged with $N_2$ for another 10 minutes. The vessel was sealed and heated at 90° C. for 24 hours. The mixture was cooled, diluted with water (25 mL), and extracted with ethyl acetate (2×50 mL). The combined organic fractions were washed with brine (20 mL), dried ($MgSO_4$), concentrated under reduced pressure, and purified by column chromatography (silica gel, 40% ethyl acetate in hexane) to give the titled compound (0.350 g, 100%). MS (APCI) m/z 429 $(M+H)^+$.

Example 164C rac-(5aS,6S,9aR)-9a-benzyl-2,6-dimethyl-3-phenyl-2,4,5,5a,6,8,9,9a-octahydro-7H-benzo[g]indazol-7-one A solution of aqueous hydrochloric acid (1 N, 1 mL) was added to a room temperature solution of Example 164C (all above obtained, ≤0.70 mmol) in tetrahydrofuran (6 mL). The solution was stirred for 2 days, diluted with aqueous saturated sodium bicarbonate (20 mL), and extracted with ethyl acetate (2×50 mL). The combined organic extracts were washed with brine (20 mL), dried ($MgSO_4$), concentrated under reduced pressure, and purified by column chromatography (silica gel, 15% to 20% ethyl acetate in $CH_2Cl_2$) to give the titled compound (0.211 g, 71%). MS (APCI) m/z 385 $(M+H)^+$.

Example 164D rac-(5aS,6S,8Z,9aS)-9a-benzyl-8-(hydroxymethyl-ene)-2,6-dimethyl-3-phenyl-2,4,5,5a,6,8,9,9a-octa-hydro-7H-benzo[g]indazol-7-one Sodium methoxide (30% w/w in methanol, 0.96 g) was added dropwise to a 0° C. solution of Example 164C (0.205 g, 0.53 mmol) in ethyl formate (10 mL), and the solution was warmed to room temperature with stirring overnight. The mixture was cooled in an ice bath, quenched by the addition of saturated aqueous $KH_2PO_4$ (25 mL), and extracted with ethyl acetate (2×50 mL). The combined organic extracts were washed with brine (25 mL), dried (MgSO4), and concentrated under reduced pressure to give the titled compound (0.225 g, 100%). MS (APCI) m/z 413 (M+H)$^+$.

Example 164E rac-(5aS,6S,10aS)-10a-benzyl-2,6-dimethyl-3-phenyl-4,5,5a,6,10,10a-hexahydro-2H-indazolo[7,6-f][1,2]benzoxazole A mixture of hydroxylamine hydrochloride (0.055 g, 0.80 mmol) and Example 164D (all above obtained, ≤0.53 mmol) in ethanol (5 mL) and water (0.5 mL) was heated at 50° C. for 3 hours, cooled to room temperature, stirred overnight, and concentrated under reduced pressure. The residue was diluted with saturated aqueous sodium bicarbonate (20 mL) and extracted with ethyl acetate (2×50 mL). The combined organic fractions were washed with brine (20 mL), dried (MgSO$_4$), and concentrated under reduced pressure to give the titled compound (0.215 g, 99%). MS (APCI) m/z 410 (M+H)$^+$.

Example 164F rac-(5aS,6S,9aR)-9a-benzyl-2,6-dimethyl-7-oxo-3-phenyl-4,5,5a,6,7,8,9,9a-octahydro-2H-benzo[g]indazole-8-carbonitrile Sodium methoxide (30% w/w in methanol, 0.96 g) was added to a room temperature solution of Example 164E (0.215 g, 0.53 mmol) in tetrahydrofuran (5 mL) and methanol (1 mL). The solution was heated at 50° C. for 4 hours, cooled to room temperature, stirred overnight, and concentrated under reduced pressure. Saturated aqueous $KH_2PO_4$ (25 mL) was added to the residue, and the mixture was extracted with ethyl acetate (2×50 mL). The combined organic fractions were washed with brine (20 mL), dried (MgSO$_4$), concentrated under reduced pressure, and purified by column chromatography (silica gel, 10% ethyl acetate in $CH_2Cl_2$) to give the titled compound (0.175 g, 81%). MS (APCI) m/z 410 (M+H)$^+$.

Example 164G rac-(5aS,6S,9aR)-9a-benzyl-2,6-dimethyl-7-oxo-3-phenyl-4,5,5a,6,7,9a-hexahydro-2H-benzo[g]indazole-8-carbonitrile A solution of Example 164F (0.175 g, 0.43 mmol) was dissolved in dry N,N-dimethylformamide (5 mL), and the solution was cooled to 0° C. 1,3-Dibromo-5,5-dimethylhydantoin (0.073 g, 0.26 mmol) was added, and the reaction stirred at 0° C. for 1 hour. Pyridine (0.6 mL) was added, and the reaction was heated at 60° C. for 4 hours. The reaction mixture was concentrated under reduced pressure and dried under vacuum. The crude residue was purified by column chromatography (silica gel, 25% ethyl acetate in $CH_2Cl_2$) to give the titled compound (0.130 g, 75%). $^1$H NMR (400 MHz, CDCl$_3$) δ ppm 8.25 (s, 1H), 7.41-7.52 (m, 3H), 7.33-7.35 (m, 2H), 7.22-7.24 (m, 3H), 6.82 (dd, J=2.8, 6.6 Hz, 2H), 3.72 (s, 3H), 3.21 (d, J=13.1 Hz, 1H), 3.13 (d, J=13.1 Hz, 1H), 2.63-2.73 (m, 2H), 2.58 (ddd, J=7.7, 10.8, 16.4 Hz, 1H), 2.21 (dt, J=2.9, 12.8 Hz, 1H), 1.83-2.04 (m, 2H), 1.27 (d, J=6.8 Hz, 3H); MS (APCI) m/z 408 (M+H)$^+$.

Example 165 rac-(5aS,6S,9aR)-9a-benzyl-2,6-dimethyl-7-oxo-3-phenyl-4,5,5a,6,7,9a-hexahydro-2H-benzo[g]indazole-8-carboxamide A mixture of Example 164G (0.040 mg, 0.0989 mmol) and hydrido(dimethylphosphinous acid-kP)[hydrogen bis(dimethylphosphinito-kP)]platinum (II) (0.013 mg, 0.0308 mmol) in ethanol (0.8 mL) and water (0.2 mL) was heated to 90° C. for 2 hours. The mixture was cooled, loaded directly onto silica gel, and purified by column chromatography (silica gel, 0% to 100% ethyl acetate in hexanes) to give the titled compound (0.036 g, 86%). $^1$H NMR (400 MHz, CDCl$_3$) δ ppm 8.89 (s, 1H), 8.44 (s, 1H), 7.39-7.52 (m, 3H), 7.32-7.34 (m, 2H), 7.15-7.20 (m, 3H), 6.83 (dd, J=2.9, 6.4 Hz, 2H), 5.59 (d, J=4.6 Hz, 1H), 3.75 (s, 3H), 3.25 (d, J=13.3 Hz, 1H), 3.10 (d, J=13.3 Hz, 1H), 2.50-2.66 (m, 3H), 2.18 (dt, J=3.0, 12.7 Hz, 1H), 1.78-1.94 (m, 2H), 1.23 (d, J=6.8 Hz, 3H); MS (APCI) m/z 426 (M+H)$^+$.

Example 166

3'-[(5aS,6S,9aR)-8-cyano-2,6-dimethyl-7-oxo-9a-phenyl-4,5,5a,6,7,9a-hexahydro-2H-benzo[g]indazol-3-yl]biphenyl-3-carboxylic acid Example 148D (0.050 g, 0.106 mmol), [1,1'-bis(diphenyl)phosphine)ferrocene]dichloropalladium(II) (0.0077 g, 0.0106 mmol), cesium carbonate (0.103 g, 0.318 mmol), and 3-boronobenzoic acid (0.053 g, 0.318 mmol) were dissolved in dioxane (3 mL) and water (0.3 mL). Then nitrogen gas was sparged through the mixture for 10 minutes followed by heating at 80° C. for 18 hours. After cooling to ambient temperature, 1 N aqueous ammonium chloride was added followed by extraction with a 3/1 mixture of/chloroform/isopropanol. The organic extracts were dried over anhydrous MgSO4, filtered, and concentrated. The resultant residue was dissolved in dichloromethane, and the solution was applied to a flash chromatography column. Purification was achieved by silica gel flash chromatography eluting with 0% to 75% ethyl acetate in heptane to afford the titled compound (0.021 g, 39% yield). $^1$H NMR (400 MHz, CDCl$_3$)™ ppm 8.51 (s, 1H), 8.37 (s, 1H), 8.15 (d, J=7.8 Hz, 1H), 7.88 (m, 1H), 7.73 (m, 1H), 7.63 (m, 3H), 7.45 (d, J=7.6 Hz, 1H), 7.32 (m, 3H), 6.99 (d, J=7.3 Hz, 2H), 3.88 (s, 3H), 2.78 (m, 2H), 2.42 (m, 2H), 1.82 (m, 1H), 1.58 (m, 1H), 1.18 (d, J=6.3 Hz, 3H); MS (ESI+) m/z 514 (M+H)$^+$.

Example 167

(5aS,6S,9aR)-2,6-dimethyl-7-oxo-9a-phenyl-3-[3-(1H-pyrazol-4-yl)phenyl]-4,5,5a,6,7,9a-hexahydro-2H-benzo[g]indazole-8-carbonitrile Example 148D (0.100 g, 0.212 mmol), [1,1'-bis(diphenyl)phosphine)ferrocene]dichloropalladium(II) (0.0155 g, 0.021 mmol), cesium carbonate (0.207 g, 0.635 mmol), and 4-(4,4,5,5-tetramethyl-1,3,2-dioxaborolan-2-yl)-1H-pyrazole (0.123 g, 0.635 mmol) were dissolved in dioxane (3 mL) and water (0.3 mL). Then nitrogen gas was bubbled through the mixture for 10 minutes followed by heating at 80° C. for 18 hours. After cooling to ambient temperature, 1 N aqueous ammonium chloride was added followed by extraction with a 3/1 mixture of chloroform/isopropanol. The organic extracts were dried over anhydrous MgSO$_4$, filtered, and concentrated. The resultant residue was dissolved in dichloromethane, and the resultant solution was applied to a flash chromatography column. Purification was achieved by silica gel flash chromatography eluting with 0% to 100% ethyl acetate in heptane to afford the titled compound (0.027 g, 28% yield). $^1$H NMR (400 MHz, CDCl$_3$)™ ppm 8.51 (s, 1H), 7.93 (s, 2H), 7.60 (d, J=8.0 Hz, 1H), 7.54 (m, 2H), 7.30 (m, 4H), 6.99 (d, J=7.2 Hz, 2H), 3.85 (s, 3H), 2.77 (m, 2H), 2.44 (m, 2H), 1.82 (m, 1H), 1.58 (m, 1H), 1.17 (d, J=6.4 Hz, 3H); MS (ESI+) m/z 460 (M+H)$^+$.

Example 168

N-({3'-[(5aS,6S,9aR)-8-cyano-2,6-dimethyl-7-oxo-9a-phenyl-4,5,5a,6,7,9a-hexahydro-2H-benzo[g]indazol-3-yl]biphenyl-4-yl}methyl)methanesulfonamide Example 148D (0.05 g, 0.106 mmol), [1,1'-bis(diphenyl)phosphine)ferrocene]dichloropalladium(II) (0.0077 g, 0.0105 mmol), cesium carbonate (0.103 g, 0.318 mmol), and (4-methanesulfonylaminomethylphenyl)boronic acid (0.073 g, 0.318 mmol) were dissolved in dioxane (3 mL) and water (0.3 mL). Then nitrogen gas was bubbled through the mixture for 10 minutes followed by heating at 80° C. for 18 hours. After cooling to ambient temperature, 1 N aqueous ammonium chloride was added followed by extraction with ethyl acetate. The organic extracts were dried over anhydrous MgSO$_4$, filtered, and concentrated. The resultant residue was dissolved in dichloromethane, and the resultant solution was applied to a flash chromatography column. Purification was achieved by silica gel flash chromatography eluting with 0% to 100% ethyl acetate in heptane to afford the titled compound (0.052 g, 85% yield). $^1$H NMR (400 MHz, CDCl$_3$)™ ppm 8.50 (s, 1H), 7.63 (m, 4H), 7.48 (d, J=8.1 Hz, 2H), 7.42 (d, J=7.6 Hz, 1H), 7.33 (m, 2H), 7.23 (d, J=8.5 Hz, 1H), 6.99 (d, J=7.1 Hz, 2H), 6.83 (d, J=8.5 Hz, 1H), 4.61 (m, 1H), 4.41 (d, J=6.2 Hz, 2H), 3.87 (s, 3H), 2.96 (s, 3H), 2.79 (m, 2H), 2.43 (m, 2H), 1.82 (m, 1H), 1.57 (m, 1H), 1.17 (d, J=6.4 Hz, 3H); MS (ESI+) m/z 577 (M+H)$^+$.

Example 169

N-{3'-[(5aS,6S,9aR)-8-cyano-2,6-dimethyl-7-oxo-9a-phenyl-4,5,5a,6,7,9a-hexahydro-2H-benzo[g]indazol-3-yl]biphenyl-4-yl}methanesulfonamide Example 148D (0.100 g, 0.212 mmol), [1,1'-bis(diphenyl)phosphine)ferrocene]dichloropalladium(II) (0.0155 g, 0.021 mmol), cesium carbonate (0.207 g, 0.635 mmol), and 4-(methanesulfonylamino)phenyl boronic acid (0.137 g, 0.635 mmol) were dissolved in dioxane (3 mL) and water (0.3 mL). Then nitrogen gas was bubbled through the mixture for 10 minutes followed by heating at 80° C. for 18 hours. After cooling to ambient temperature, 1 N aqueous ammonium chloride was added followed by extraction with a 3/1 mixture of chloroform/isopropanol. The organic extracts were dried over anhydrous MgSO$_4$, filtered, and concentrated by rotary evaporation. The resultant residue was dissolved in dichloromethane, and the solution was applied to a flash chromatography column. Purification was achieved by silica gel flash chromatography eluting with 0% to 100% ethyl acetate in heptane to afford the titled compound (0.103 g, 86% yield). $^1$H NMR (400 MHz, CDCl$_3$)™ ppm 8.50 (s, 1H), 7.62 (m, 5H), 7.41 (d, J=7.3 Hz, 1H), 7.34 (m, 4H), 6.98 (d, J=7.0 Hz, 2H), 6.46 (s, 1H), 3.87 (s, 3H), 3.08 (s, 3H), 2.77 (m, 2H), 2.44 (m, 2H), 1.82 (m, 1H), 1.56 (m, 1H), 1.17 (d, J=6.4 Hz, 3H); MS (ESI+) m/z 563 (M+H)$^+$.

Example 170

(5aS,6S,9aR)-3-(4'-hydroxybiphenyl-3-yl)-2,6-dimethyl-7-oxo-9a-phenyl-4,5,5a,6,7,9a-hexahydro-2H-benzo[g]indazole-8-carbonitrile Example 148D (0.05 g, 0.106 mmol), [1,1'-bis(diphenyl)phosphine)ferrocene]dichloropalladium(II) (0.0077 g, 0.0105 mmol), cesium carbonate (0.103 g, 0.318 mmol), and 4-hydroxyphenylboronic acid (0.044 g, 0.318 mmol) were dissolved in dioxane (3 mL) and water (0.3 mL), and then nitrogen gas was bubbled through the mixture for 10 minutes followed by heating at 80° C. for 18 hours. After cooling to ambient temperature, 1 N aqueous ammonium chloride was added followed by extraction with ethyl acetate. The organic extracts were dried over anhydrous MgSO4, filtered, and concentrated. The resultant residue was purified by silica gel flash chromatography eluting with 0% to 100% ethyl acetate in heptane to afford the titled compound (0.033 g, 64% yield). $^1$H NMR (400 MHz, CDCl$_3$) δ ppm 8.51 (s, 1H), 7.56 (m, 5H), 7.30 (m, 4H), 6.98 (d, J=7.3 Hz, 2H), 6.95 (d, J=8.6 Hz, 2H), 4.97 (s, 1H), 3.87 (s, 3H), 2.78 (m, 2H), 2.43 (m, 2H), 1.82 (m, 1H), 1.57 (m, 1H), 1.17 (d, J=6.3 Hz, 3H); MS (ESI+) m/z 486 (M+H)$^+$.

Example 171

3'-[(5aS,6S,9aR)-8-cyano-2,6-dimethyl-7-oxo-9a-phenyl-4,5,5a,6,7,9a-hexahydro-2H-benzo[g]indazol-3-yl]biphenyl-4-carboxamide Example 148D (0.05 g, 0.106 mmol), [1,1'-bis(diphenyl)phosphine)ferrocene]dichloropalladium(II) (0.0077 g, 0.0105 mmol), cesium carbonate (0.103 g, 0.318 mmol), and 4-aminocarbonylphenylboronic acid (0.052 g, 0.318 mmol) were dissolved in dioxane (3 mL) and water (0.3 mL), and then nitrogen gas was bubbled through the mixture for 10 minutes followed by heating at 80° C. for 18 hours. After cooling to ambient temperature, 1 N aqueous ammonium chloride was added followed by extraction with ethyl acetate. The organic extracts were dried over anhydrous MgSO4, filtered, and concentrated. The resultant residue was purified by silica gel flash chromatography eluting with 0% to 100% ethyl acetate in heptane to afford the titled compound (0.036 g, 66% yield). $^1$H NMR (400 MHz, CDCl$_3$) δ ppm 8.51 (s, 1H), 7.94 (d, J=8.3 Hz, 2H), 7.72 (m, 3H), 7.64 (m, 3H), 7.45 (d, J=7.6 Hz, 1H), 7.33 (m, 3H), 6.99 (d, J=7.2 Hz, 2H), 6.15 (bs, 1H), 5.62 (bs, 1H), 3.87 (s, 3H), 2.79 (m, 2H), 2.43 (m, 2H), 1.82 (m, 1H), 1.57 (m, 1H), 1.18 (d, J=6.4 Hz, 3H); MS (ESI+) m/z 513 (M+H)$^+$.

Example 172

(6aS,7S,10aR)-2,7-dimethyl-8-oxo-10a-phenyl-4-(pyridazin-4-yl)-5,6,6a,7,8,10a-hexahydrobenzo[h]quinazoline-9-carbonitrile

Example 172A (6aS,7S,10aS)-2,7-dimethyl-10a-phenyl-4-(pyridazin-4-yl)-5,6a,7,9,10,10a-hexahydrobenzo[h]quinazolin-8(6H)-one The titled compound was prepared using the conditions described in Example 23A, substituting 4-(4,4,5,5-tetramethyl-1,3,2-dioxaborolan-2-yl)pyridazine for 2-(furan-3-yl)-4,4,5,5-tetramethyl-1,3,2-dioxaborolane. Purification was achieved using a 12 g RediSep® cartridge on a Teledyne Isco Combiflash® Rf system eluting with 66-100% ethyl acetate in heptane (94% yield). $^1$H NMR (400 MHz, CDCl$_3$) δ ppm 1.17 (d, J=6.61 Hz, 3H) 2.00 (td, J=11.87, 7.16 Hz, 1H) 2.07-2.24 (m, 2H) 2.27-2.44 (m, 2H) 2.46-2.53 (m, 1H) 2.62 (ddd, J=16.16, 7.97, 7.75 Hz, 1H) 2.78 (s, 3H) 2.83-2.96 (m, 2H) 3.19-3.28 (m, 1H) 7.23-7.29 (m, 1H) 7.33 (t, J=7.54 Hz, 2H) 7.54 (d, J=7.70 Hz, 2H) 7.61 (dd, J=5.10, 2.39 Hz, 1H) 9.29-9.34 (m, 2H).

Example 172B (6aS,7S,9Z,10aS)-9-(hydroxymethylene)-2,7-dimethyl-10a-phenyl-4-(pyridazin-4-yl)-5,6a,7,9,10,10a-hexahydrobenzo[h]quinazolin-8(6H)-one The titled compound was prepared using the conditions described in Example 1J, substituting Example 172A for Example 1I.

Example 172C (6aS,7S,11aS)-2,7-dimethyl-11a-phenyl-4-(pyridazin-4-yl)-5,6,6a,7,11,11a-hexahydro[1,2]benzoxazolo[6,5-h]quinazoline The titled compound was prepared using the conditions described in Example 1K, substituting Example 172B for Example 1J.

Example 172D (6aS,7S,10aS)-2,7-dimethyl-8-oxo-10a-phenyl-4-(pyridazin-4-yl)-5,6,6a,7,8,9,10,10a-octahydrobenzo[h]quinazoline-9-carbonitrile The titled compound was prepared using the conditions described in Example 1L, substituting Example 172C for Example 1K. MS (APCI+) m/z 410 (M+H)$^+$.

Example 172E (6aS,7S,10aR)-2,7-dimethyl-8-oxo-10a-phenyl-4-(pyridazin-4-yl)-5,6,6a,7,8,10a-hexahydrobenzo[h]quinazoline-9-carbonitrile To a solution of Example 172D (0.075 g, 0.183 mmol) in N,N-dimethylacetamide (2.5 mL) cooled to 0° C. in an ice water bath was added 1,3-dibromo-5,5-dimethylhydantoin (0.029 g, 0.101 mmol). The solution was stirred at 0° C. for 45 minutes, and then pyridine (0.296 mL, 3.66 mmol) was added. The reaction solution was heated at 55° C. for 1 hour. The cooled solution was diluted with water and extracted with ethyl acetate. The organic fraction was washed with brine and concentrated. The residue was purified by flash chromatography on a Teledyne Isco Combiflash® Rf system equipped with a 12 g RediSep® cartridge eluted with 0-50% ethyl acetate in dichloromethane to give 0.027 g (36%) of the titled compound. 1H NMR (400 MHz, CDCl$_3$) δ ppm 1.19 (d, J=6.61 Hz, 3H) 1.59-1.68 (m, 1H) 1.91-2.01 (m, 1H) 2.36 (td, J=12.82, 2.33 Hz, 1H) 2.48 (td, J=13.07, 6.51 Hz, 1H) 2.74 (s, 3H) 2.97-3.06 (m, 2H) 6.81 (dd, J=7.54, 1.79 Hz, 2H) 7.32-7.41 (m, 3H) 7.75 (dd, J=5.26, 2.33 Hz, 1H) 8.93 (s, 1H) 9.41 (d, J=5.20 Hz, 1H) 9.49 (d, J=1.30 Hz, 1H); MS (ESI+) m/z 408 (M+H)$^+$, 440 (M+CH$_3$OH+H)$^+$.

Example 173

(6aS,7S,10aR)-7-methyl-2-[4-(3-methyl-1,2,4-oxadiazol-5-yl)phenyl]-8-oxo-10a-phenyl-5,6,6a,7,8,10a-hexahydrobenzo[h]quinazoline-9-carbonitrile

Example 173A

4-[(6aS,7S,10aR)-9-cyano-7-methyl-8-oxo-10a-phenyl-5,6,6a,7,8,10a-hexahydrobenzo[h]quinazolin-2-yl]-N-[(1Z)—N-hydroxyethanimidoyl]benzamide Oxalyl chloride (0.287 mL, 3.28 mmol) and one drop of N,N-dimethylformamide was added to a solution of Example 77 (0.143 g, 0.328 mmol) in dichloromethane (3 mL). The resulting solution was stirred at room temperature for 1 hour and then concentrated to dryness under vacuum. The intermediate carboxylic acid chloride was taken up in dichloromethane (3 mL). The resultant mixture was cooled in an ice bath and treated with N-hydroxyacetimidamide (0.061 g, 0.821 mmol) followed by dropwise addition of triethylamine (0.230 mL, 1.64 mmol). The ice bath was removed, and the reaction was stirred at room temperature for 2 hours. Then the reaction mixture was diluted with water and extracted with ethyl acetate. The organic fraction was dried over sodium sulfate, filtered, and concentrated to dryness to provide the titled compound.

Example 173B (6aS,7S,10aR)-7-methyl-2-[4-(3-methyl-1,2,4-oxadiazol-5-yl)phenyl]-8-oxo-10a-phenyl-5,6,6a,7,8,10a-hexahydrobenzo[h]quinazoline-9-carbonitrile To a solution of Example 173A (0.162 g, 0.330 mmol) in dioxane (4 mL) was added a 50% solution of 2,4,6-tripropyl-1,3,5,2,4,6-trioxatriphosphorinane-2,4,6-trioxide in ethyl acetate (0.577 mL, 0.989 mmol). The solution was heated at 95° C. for 6 hours and then stirred at room temperature for 3 days. The reaction solution was quenched by the slow addition of saturated sodium bicarbonate solution (5 mL), diluted with water, and extracted with ethyl acetate. The organic fraction was concentrated, and the residue was purified using a Teledyne Isco Combiflash® Rf equipped with a 12 g RediSep® cartridge eluted with 0-40% ethyl acetate in heptane to give 0.051 g (33%) of the titled compound. $^1$H NMR (400 MHz, CDCl$_3$) δ ppm 1.22 (d, J=6.61 Hz, 3H) 1.59-1.75 (m, 1H) 2.01 (dd, J=13.93, 7.75 Hz, 1H) 2.39 (td, J=12.82, 2.11 Hz, 1H) 2.45-2.57 (m, 4H) 3.01-3.24 (m, 2H) 6.85 (dd, J=7.81, 1.63 Hz, 2H) 7.29-7.38

(m, 3H) 8.21 (d, J=8.46 Hz, 2H) 8.55 (d, J=8.57 Hz, 2H) 8.82 (s, 1H) 9.00 (s, 1H); MS (ESI+) m/z 474 (M+H)+.

Example 174

(6aS,7S,10aR)-10a-(4-methoxyphenyl)-2,7-dimethyl-4-(1-methyl-1H-imidazol-5-yl)-8-oxo-5,6,6a,7,8,10a-hexahydrobenzo[h]quinazoline-9-carbonitrile Example 174A (6aS,7S,10aS)-10a-(4-methoxyphenyl)-2,7-dimethyl-4-(1-methyl-1H-imidazol-5-yl)-5,6a,7,9,10,10a-hexahydrobenzo[h]quinazolin-8(6H)-one The titled compound was prepared using the conditions described in Example 17A, substituting Example 67D for Example 13D. Purification by flash chromatography on silica gel eluted with 0-80% acetone in chloroform to give the titled compound in 40% yield. $^1$H NMR (400 MHz, CDCl$_3$) δ ppm 1.16 (d, J=6.72 Hz, 3H) 1.94-2.05 (m, 1H) 2.07-2.18 (m, 2H) 2.23-2.30 (m, 1H) 2.37-2.56 (m, 2H) 2.69 (s, 3H) 2.70-2.80 (m, 1H) 3.06 (dt, J=16.64, 7.40 Hz, 1H) 3.17-3.25 (m, 1H) 3.68-3.72 (m, 1H) 3.78 (s, 3H) 3.87 (s, 3H) 6.81-6.87 (m, 2H) 7.25-7.29 (m, 1H) 7.43 (d, J=8.89 Hz, 2H) 7.56 (s, 1H); MS (ESI) m/z 417.3 (M+H)+.

Example 174B (6aS,7S,9Z,10aS)-9-(hydroxymethylene)-10a-(4-methoxyphenyl)-2,7-dimethyl-4-(1-methyl-1H-imidazol-5-yl)-5,6a,7,9,10,10a-hexahydrobenzo[h]quinazolin-8(6H)-one The titled compound was prepared using the conditions described in Example 13F, substituting Example 174A for Example 13E.

Example 174C (6aS,7S,11aS)-11a-(4-methoxyphenyl)-2,7-dimethyl-4-(1-methyl-1H-imidazol-5-yl)-5,6,6a,7,11,11a-hexahydro[1,2]benzoxazolo[6,5-h]quinazoline The titled compound was prepared using the conditions described in Example 13G, substituting Example 174B for Example 13F.

Example 174D (6aS,7S,10aS)-10a-(4-methoxyphenyl)-2,7-dimethyl-4-(1-methyl-1H-imidazol-5-yl)-8-oxo-5,6,6a,7,8,9,10,10a-octahydrobenzo[h]quinazoline-9-carbonitrile The titled compound was prepared using the conditions described in Example 13H, substituting Example 174C for Example 13G.

Example 174E (6aS,7S,10aR)-10a-(4-methoxyphenyl)-2,7-dimethyl-4-(1-methyl-1H-imidazol-5-yl)-8-oxo-5,6,6a,7,8,10a-hexahydrobenzo[h]quinazoline-9-carbonitrile The titled compound was prepared using the conditions described in Example 131, substituting Example 174D for Example 13H. Purification was achieved by preparative thin-layer chromatography eluting with 5% methanol in chloroform containing 0.2% ammonium hydroxide to give the titled compound in 27% yield. $^1$H NMR (400 MHz, CDCl$_3$) δ ppm 1.19 (d, J=6.72 Hz, 3H) 1.23-1.34 (m, 1H) 2.00 (dd, J=13.93, 8.19 Hz, 1H) 2.30 (td, J=12.85, 2.28 Hz, 1H) 2.46 (td, J=13.15, 6.67 Hz, 1H) 2.67 (s, 3H) 3.03 (ddd, J=18.19, 10.00, 8.02 Hz, 1H) 3.10-3.20 (m, 1H) 3.78 (s, 3H) 3.99 (s, 3H) 6.75 (d, J=9.00 Hz, 2H) 6.82-6.88 (m, 2H) 7.58 (s, 1H) 7.64 (s, 1H) 8.94 (s, 1H); MS (ESI) m/z 472.3 (M+CH$_3$OH+H)+.

Example 175 methyl 4-[(6aS,7S,10aR)-9-cyano-2,7-dimethyl-4-(1-methyl-1H-imidazol-5-yl)-8-oxo-6,6a,7,8-tetrahydrobenzo[h]quinazolin-10a(5H)-yl]benzoate Example 175A methyl (1'S,4a'S,8a'S)-4a'-[4-(methoxycarbonyl)phenyl]-1'-methyl-5'-oxooctahydro-1'H-spiro[1,3-dioxolane-2,2'-naphthalene]-6'-carboxylate The titled compound was prepared using the conditions described in Example 67A, substituting Example 63F for Example 58F. Purification was achieved by flash chromatography on silica gel eluting with 0-5% acetone in chloroform to give the titled compound in 68% yield. $^1$H NMR (400 MHz, CDCl$_3$) δ ppm 1.02 (d, J=6.51 Hz, 3H) 1.10 (td, J=14.10, 3.25 Hz, 1H) 1.62 (dt, J=13.64, 3.37 Hz, 1H) 1.95-2.09 (m, 5H) 2.09-2.17 (m, 1H) 2.23 (td, J=14.31, 3.14 Hz, 1H) 2.68 (dt, J=18.13, 6.33 Hz, 1H) 3.20-3.27 (m, 1H) 3.69 (s, 3H) 3.88-3.97 (m, 7H) 7.49 (d, J=8.57 Hz, 2H) 8.02 (d, J=8.57 Hz, 2H); MS (ESI) m/z 417.0 (M+H)+.

Example 175B methyl 4-[(6aS,7S,10aS)-4-hydroxy-2,7-dimethyl-5,6,6a,7,9,10-hexahydro-10aH-spiro[benzo[h]quinazoline-8,2'-[1,3]dioxolan]-10a-yl]benzoate The titled compound was prepared using the conditions described in Example 13B, substituting Example 175A for Example 13A.

Example 175C methyl 4-[(6aS,7S,10aS)-4-hydroxy-2,7-dimethyl-8-oxo-6,6a,7,8,9,10-hexahydrobenzo[h]quinazolin-10a(5H)-yl]benzoate The titled compound was prepared using the conditions described in Example 13C, substituting Example 175B for Example 13B. $^1$H NMR (400 MHz, CDCl$_3$) δ ppm 1.11 (d, J=6.07 Hz, 3H) 1.74-1.88 (m, 1H) 1.97-2.11 (m, 3H) 2.20 (dt, J=14.58, 8.81 Hz, 1H) 2.34 (s, 3H) 2.54-2.70 (m, 3H) 2.85 (dd, J=18.60, 6.34 Hz, 1H) 3.19 (ddd, J=14.50, 7.29, 4.88 Hz, 1H) 3.90 (s, 3H) 7.43 (d, J=8.57 Hz, 2H) 7.95 (d, J=8.57 Hz, 2H) 11.49 (s, 1H); MS (ESI) m/z 381.3 (M+H)+.

Example 175D methyl 4-[(6aS,7S,10aS)-4-chloro-2,7-dimethyl-8-oxo-6,6a,7,8,9,10-hexahydrobenzo[h]quinazolin-10a(5H)-yl]benzoate The titled compound was prepared using the conditions described in Example 13D, substituting Example 175C for Example 13C.

Example 175E methyl 4-[(6aS,7S,10aS)-2,7-dimethyl-4-(1-methyl-1H-imidazol-5-yl)-8-oxo-6,6a,7,8,9,10-hexahydrobenzo[h]quinazolin-10a(5H)-yl]benzoate The titled compound was prepared using the conditions described in Example 17A, substituting Example 175D for Example 13D and purified by flash chromatography on silica gel eluting with 5% methanol in chloroform to give the titled compound in 43% yield. $^1$H NMR (400 MHz, CDCl$_3$) δ ppm 1.18 (d, J=6.61 Hz, 3H) 2.00-2.18 (m, 3H) 2.28-2.45 (m, 2H) 2.47-2.58 (m, 1H) 2.64-2.77 (m, 5H) 3.03-3.14 (m, 1H) 3.19-3.30 (m, 1H) 3.88 (s, 3H) 3.90 (s, 3H) 7.28 (s, 1H) 7.57 (s, 1H) 7.60 (d, J=8.57 Hz, 2H) 7.97 (d, J=8.46 Hz, 2H); MS (ESI) m/z 445.3 (M+H)$^+$.

Example 175F ethyl 4-[(6aS,7S,9Z,10aS)-9-(hydroxymethylene)-2,7-dimethyl-4-(1-methyl-1H-imidazol-5-yl)-8-oxo-6,6a,7,8,9,10-hexahydrobenzo[h]quinazolin-10a(5H)-yl]benzoate The titled compound was prepared using the conditions described in Example 13F, substituting Example 175E for Example 13E.

Example 175G ethyl 4-[(6aS,7S,11aS)-2,7-dimethyl-4-(1-methyl-1H-imidazol-5-yl)-6,6a,7,11-tetrahydro[1,2]benzoxazolo[6,5-h]quinazolin-11a(5H)-yl]benzoate The titled compound was prepared using the conditions described in Example 13G, substituting Example 175F for Example 13F.

Example 175H methyl 4-[(6aS,7S,10aS)-9-cyano-2,7-dimethyl-4-(1-methyl-1H-imidazol-5-yl)-8-oxo-6,6a,7,8,9,10-hexahydrobenzo[h]quinazolin-10a(5H)-yl]benzoate The titled compound was prepared using the conditions described in Example 13H, substituting Example 175G for Example 13G.

Example 175I methyl 4-[(6aS,7S,10aR)-9-cyano-2,7-dimethyl-4-(1-methyl-1H-imidazol-5-yl)-8-oxo-6,6a,7,8-tetrahydrobenzo[h]quinazolin-10a(5H)-yl]benzoate The titled compound was prepared using the conditions described in Example 13I, substituting Example 175H for Example 13H, and purified by preparative thin-layer chromatography eluting with 5% methanol in chloroform containing 0.2% ammonium hydroxide to give the titled compound in 16% yield as the more polar compound relative to Example 176. $^1$H NMR (400 MHz, CDCl$_3$) δ ppm 1.20 (d, J=6.07 Hz, 3H) 1.28-1.33 (m, 1H) 1.98-2.09 (m, 1H) 2.37-2.43 (m, 2H) 2.66 (s, 3H) 3.08 (ddd, J=18.03, 10.06, 8.13 Hz, 1H) 3.13-3.23 (m, 1H) 3.91 (s, 3H) 4.00 (s, 3H) 6.94 (d, J=8.57 Hz, 2H) 7.60 (s, 1H) 7.65 (s, 1H) 7.99 (d, J=8.57 Hz, 2H) 8.95 (s, 1H); MS (ESI) m/z 500.3 (M+CH$_3$OH+H)$^+$.

Example 176 methyl 4-[(6aS,7S,10aR)-4-(4-bromo-1-methyl-1H-imidazol-5-yl)-9-cyano-2,7-dimethyl-8-oxo-6,6a,7,8-tetrahydrobenzo[h]quinazolin-10a(5H)-yl]benzoate The titled compound was isolated as the less polar compound relative to Example 175I in the synthesis of Example 175I in 13% yield. $^1$H NMR (400 MHz, CDCl$_3$) δ ppm 1.18 (d, J=5.64 Hz, 3H) 1.28-1.34 (m, 1H) 1.58-1.66 (m, 1H) 1.90-2.02 (m, 1H) 2.32-2.48 (m, 2H) 2.63 (d, J=26.13 Hz, 1H) 2.72 (s, 3H) 3.68 (s, 3H) 3.91 (s, 3H) 6.91-7.05 (m, 2H) 7.55 (s, 1H) 8.00 (d, J=8.46 Hz, 2H) 8.97 (s, 1H); MS (ESI) m/z 578.2 (M+CH$_3$OH+H)$^+$.

Example 177

(5aS,6S,9aR)-2,6-dimethyl-7-oxo-9a-phenyl-3-(pyrimidin-5-yl)-4,5,5a,6,7,9a-hexahydro-2H-benzo[g]indazole-8-carbonitrile

Example 177A (5aS,6S,9aS)-2,6-dimethyl-9a-phenyl-3-(pyrimidin-5-yl)-2,4,5,5a,6,8,9,9a-octahydro-7H-benzo[g]indazol-7-one The titled compound was prepared utilizing conditions described in Example 140E (79% yield) substituting Example 97A for Example 140D and substituting 5-(4,4,5,5-tetramethyl-1,3,2-dioxaborolan-2-yl)pyrimidine for 4-(4,4,5,5-tetramethyl-1,3,2-dioxaborolan-2-yl)pyridazine. MS (APCI+) m/z 373 (M+H)$^+$.

Example 177B (5aS,6S,8Z,9aS)-8-(hydroxymethylene)-2,6-dimethyl-9a-phenyl-3-(pyrimidin-5-yl)-2,4,5,5a,6,8,9,9a-octahydro-7H-benzo[g]indazol-7-one Example 177A (0.158 g, 0.424 mmol) was dissolved in ethyl formate (4.14 mL, 50.9 mmol), and the mixture was cooled to 0° C. in an ice bath followed by the dropwise addition of potassium tert-butoxide (1 M in tetrahydrofuran, 4.24 mL, 4.24 mmol). The ice bath was then removed, and the mixture was stirred at ambient temperature for 18 hours. A solution of 1 N aqueous potassium dihydrogen phosphate was added until neutral pH followed by extraction with ethyl acetate. The combined organic extracts were dried over anhydrous magnesium sulfate, filtered, and concentrated to provide the titled compound (0.171 g, 100% yield).

Example 177C (5aS,6S,10aS)-2,6-dimethyl-10a-phenyl-3-(pyrimidin-5-yl)-4,5,5a,6,10,10a-hexahydro-2H-indazolo[7,6-f][1,2]benzoxazole The titled compound was prepared utilizing conditions described in Example 140G (94% yield) substituting Example 177B for Example 140F. MS (APCI+) m/z 398 (M+H)$^+$.

Example 177D (5aS,6S,9aS)-2,6-dimethyl-7-oxo-9a-phenyl-3-(pyrimidin-5-yl)-4,5,5a,6,7,8,9,9a-octahydro-2H-benzo[g]indazole-8-carbonitrile Example 177C (0.159 g, 0.400 mmol) was dissolved in tetrahydrofuran (3 mL followed by the addition of sodium methoxide (25% NaOCH$_3$ in CH$_3$OH by weight, 0.960 mL, 4.00 mmol), and the mixture was stirred at ambient temperature for 18 hours. A solution of 1 N aqueous potassium dihydrogen phosphate was added until neutral pH followed by extraction with ethyl acetate. The combined organic extracts were dried over anhydrous magnesium sulfate, filtered, and concentrated to provide the titled compound (0.159 g, 100% yield).

Example 177E (5aS,6S,9aR)-2,6-dimethyl-7-oxo-9a-phenyl-3-(pyrimidin-5-yl)-4,5,5a,6,7,9a-hexahydro-2H-benzo[g]indazole-8-carbonitrile The titled compound was prepared utilizing conditions described in Example 97F (58% yield) substituting Example 177D for Example 97E. $^1$H NMR (400 MHz, CDCl$_3$) δ ppm 9.31 (d, J=6.4 Hz, 1H), 8.87 (s, 2H), 8.46 (s, 1H), 7.38-7.28 (m, 3H), 7.02-6.89 (m, 2H), 3.88 (s, 3H), 2.76 (ddt, J=16.6, 11.1, 8.4 Hz, 2H), 2.52-2.28 (m, 1H), 1.86 (dd, J=13.9, 6.9 Hz, 1H), 1.24 (dd, J=17.8, 8.2 Hz, 1H), 1.19 (t, J=7.9 Hz, 3H), 0.92-0.79 (m, 1H); MS (ESI+) m/z 396 (M+H)$^+$.

Example 178

(5aS,6S,9aR)-2,6-dimethyl-7-oxo-9a-phenyl-3-(pyridin-3-yl)-4,5,5a,6,7,9a-hexahydro-2H-benzo[g]indazole-8-carbonitrile

Example 178A (5aS,6S,9aS)-2,6-dimethyl-9a-phenyl-3-(pyridin-3-yl)-2,4,5,5a,6,8,9,9a-octahydro-7H-benzo[g]indazol-7-one The titled compound was prepared utilizing conditions described in Example 140E (88% yield) substituting Example 97A for Example 140D and substituting pyridin-3-ylboronic acid for 4-(4,4,5,5-tetramethyl-1,3,2-dioxaborolan-2-yl)pyridazine. MS (APCI+) m/z 372 (M+H)$^+$.

Example 178B (5aS,6S,8Z,9aS)-8-(hydroxymethylene)-2,6-dimethyl-9a-phenyl-3-(pyridin-3-yl)-2,4,5,5a,6,8,9,9a-octahydro-7H-benzo[g]indazol-7-one The titled compound was prepared utilizing conditions described in Example 177B (100% yield) substituting Example 178A for Example 177A.

Example 178C (5aS,6S,10aS)-2,6-dimethyl-10a-phenyl-3-(pyridin-3-yl)-4,5,5a,6,10,10a-hexahydro-2H-indazolo[7,6-f][1,2]benzoxazole The titled compound was prepared utilizing conditions described in Example 140G (100% yield) substituting Example 178B for Example 140F. MS (APCI+) m/z 397 (M+H)$^+$.

Example 178D (5aS,6S,9aS)-2,6-dimethyl-7-oxo-9a-phenyl-3-(pyridin-3-yl)-4,5,5a,6,7,8,9,9a-octahydro-2H-benzo[g]indazole-8-carbonitrile The titled compound was prepared utilizing conditions described in Example 177D (95% yield) substituting Example 178C for Example 177C.

Example 178E (5aS,6S,9aR)-2,6-dimethyl-7-oxo-9a-phenyl-3-(pyridin-3-yl)-4,5,5a,6,7,9a-hexahydro-2H-benzo[g]indazole-8-carbonitrile The titled compound was prepared utilizing conditions described in Example 97F (51% yield) substituting Example 178D for Example 97E. $^1$H NMR (400 MHz, CDCl$_3$) δ ppm 8.79-8.61 (m, 2H), 8.48 (s, 1H), 7.77 (d, J=7.9 Hz, 1H), 7.49 (dd, J=7.7, 4.9 Hz, 1H), 7.32 (dq, J=13.8, 6.8 Hz, 3H), 6.96 (d, J=7.1 Hz, 2H), 3.89-3.76 (m, 3H), 3.48 (q, J=7.0 Hz, 1H), 2.85-2.63 (m, 2H), 2.50-2.40 (m, 2H), 1.83 (dd, J=13.9, 7.0 Hz, 1H), 1.20-1.08 (m, 3H); MS (ESI+) m/z 395 (M+H)$^+$.

Example 179

(5aS,6S,9aR)-1,6-dimethyl-7-oxo-9a-phenyl-3-(pyrimidin-5-yl)-4,5,5a,6,7,9a-hexahydro-H-benzo[g]indazole-8-carbonitrile

Example 179A (5aS,6S,9aS)-3-bromo-1,6-dimethyl-9a-phenyl-1,4,5,5a,6,8,9,9a-octahydro-7H-benzo[g]indazol-7-one The titled compound was prepared utilizing conditions described in Example 97A (20% yield) isolating the titled compound pyrazole regioisomer as the minor component exhibiting a lower R$_f$ relative to Example 97A. $^1$H NMR (400 MHz, CDCl$_3$) δ ppm 7.33-7.20 (m, 3H), 7.01-6.86 (m, 3H), 3.34 (s, 3H), 3.02 (ddd, J=13.9, 7.8, 4.1 Hz, 1H), 2.92-2.67 (m, 3H), 2.59-2.34 (m, 3H), 2.30-2.16 (m, 1H), 1.88 (dt, J=24.6, 10.6 Hz, 1H), 1.13 (t, J=7.3 Hz, 3H); MS (ESI+) m/z 374 (M+H)+.

Example 179B (5aS,6S,9aS)-1,6-dimethyl-9a-phenyl-3-(pyrimidin-5-yl)-1,4,5,5a,6,8,9,9a-octahydro-7H-benzo[g]indazol-7-one The titled compound was prepared utilizing conditions described in Example 140E (45% yield) substituting Example 179A for Example 140D and substituting 5-(4,4,5,5-tetramethyl-1,3,2-dioxaborolan-2-yl)pyrimidine for 4-(4,4,5,5-tetramethyl-1,3,2-dioxaborolan-2-yl)pyridazine. MS (APCI+) m/z 373 (M+H)+.

Example 179C (5aS,6S,8Z,9aS)-8-(hydroxymethylene)-1,6-dimethyl-9a-phenyl-3-(pyrimidin-5-yl)-1,4,5,5a,6,8,9,9a-octahydro-7H-benzo[g]indazol-7-one The titled compound was prepared utilizing conditions described in Example 177B (100% yield) substituting Example 179B for Example 177A.

Example 179D (5aS,6S,10aS)-1,6-dimethyl-10a-phenyl-3-(pyrimidin-5-yl)-4,5,5a,6,10,10a-hexahydro-1H-indazolo[7,6-f][1,2]benzoxazole The titled compound was prepared utilizing conditions described in Example 140G (96% yield) substituting Example 179C for Example 140F. MS (APCI+) m/z 398 (M+H)+.

Example 179E (5aS,6S,9aS)-1,6-dimethyl-7-oxo-9a-phenyl-3-(pyrimidin-5-yl)-4,5,5a,6,7,8,9,9a-octahydro-1H-benzo[g]indazole-8-carbonitrile The titled compound was prepared utilizing conditions described in Example 177D (84% yield) substituting Example 179D for Example 177C.

Example 179F (5aS,6S,9aR)-1,6-dimethyl-7-oxo-9a-phenyl-3-(pyrimidin-5-yl)-4,5,5a,6,7,9a-hexahydro-1H-benzo[g]indazole-8-carbonitrile The titled compound was prepared utilizing conditions described in Example 97F (69% yield) substituting Example 179E for Example 97E. $^1$H NMR (400 MHz, CDCl$_3$) δ ppm 9.17 (d, J=21.6 Hz, 1H), 9.14 (s, 2H), 8.15 (s, 1H), 7.51-7.30 (m, 3H), 6.98-6.58 (m, 2H), 3.62 (s, 3H), 3.11-2.73 (m, 2H), 2.54 (t, J=12.1 Hz, 1H), 2.46-2.20 (m, 1H), 1.98-1.84 (m, 1H), 1.28-1.11 (m, 3H), 0.92-0.72 (m, 1H); MS (ESI+) m/z 396 (M+H)+.

All of the methods disclosed and claimed herein can be made and executed without undue experimentation in light of the present disclosure. While the methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

Abraham and Kappas, *Free Radical Biol. Med.*, 39:1-25, 2005.
Ahmad et al., *Cancer Res.*, 68:2920-2926, 2008.
Ahmad et al., *J. Biol. Chem.*, 281:35764-9, 2006.
Araujo et al., *J. Immunol.*, 171(3):1572-1580, 2003.
Bach, *Hum. Immunol.*, 67(6):430-432, 2006.
Chauhan and Chauhan, *Pathophysiology*, 13(3): 171-181 2006.
Dickerson et al., *Prog Neuropsychopharmacol Biol. Psychiatry*, Mar. 6, 2007.
Dinkova-Kostova et al., *Proc. Natl. Acad. Sci. USA*, 102 (12):4584-4589, 2005.
Dudhgaonkar et al., *Eur. J. Pain*, 10(7):573-9, 2006.
Forstermann, *Biol. Chem.*, 387:1521, 2006.
Handbook of Pharmaceutical Salts: Properties, and Use, Stahl and Wermuth Eds.), Verlag Helvetica Chimica Acta, 2002.
Hanson et al., *BMC Medical Genetics*, 6(7), 2005.
Honda et al. *Bioorg. Med. Chem. Lett.*, 12:1027-1030, 2002.
Honda et al., *J. Med. Chem.*, 43:4233-4246, 2000a.
Honda, et al., *J. Med. Chem.*, 43:1866-1877, 2000b.
Honda et al., *Bioorg. Med. Chem. Lett.*, 7:1623-1628, 1997.
Honda et al., *Bioorg. Med. Chem. Lett.*, 9(24):3429-3434, 1999.
Honda et al., *Bioorg. Med. Chem. Lett.*, 8(19):2711-2714, 1998.
Honda et al., *Bioorg. Med. Chem. Lett.*, 16(24):6306-6309, 2006.
Ishikawa et al., *Circulation*, 104(15): 1831-1836, 2001.
Kawakami et al., *Brain Dev.*, 28(4):243-246, 2006.
Kendall-Tackett, *Trauma Violence Abuse*, 8(2): 117-126, 2007.
Kruger et al., *J. Pharmacol. Exp. Ther.*, 319(3): 1144-1152, 2006.
Lee et al., *Glia.*, 55(7):712-22, 2007.
Lencz et al., *Mol. Psychiatry*, 12(6):572-80, 2007.
Liby et al., *Cancer Res.*, 65(11):4789-4798, 2005.
Liby et al., *Nat. Rev. Cancer*, 7(5):357-356, 2007a.
Liby et al., *Mol. Cancer Ther.*, 6(7):2113-9, 2007b.
Liu et al., *FASEB J.*, 20(2):207-216, 2006.
Lu et al., *J. Clin. Invest.*, 121(10):4015-29, 2011.
March's Advanced Organic Chemistry: Reactions, Mechanisms, and Structure, 2007.
McIver et al., *Pain*, 120(1-2):161-9, 2005.
Morris et al., *J. Mol. Med.*, 80(2):96-104, 2002.
Morse and Choi, *Am. J. Respir. Crit. Care Med.*, 172(6): 660-670, 2005.
Morse and Choi, *Am. J. Respir. Crit. Care Med.*, 27(1):8-16, 2002.
Pall, *Med. Hypoth.*, 69:821-825, 2007.

Place et al., *Clin. Cancer Res.,* 9(7):2798-806, 2003.
Rajakariar et al., *Proc. Natl. Acad. Sci. USA,* 104(52):20979-84, 2007.
Ross et al., *Am. J. Clin. Pathol.,* 120(Suppl):S53-71, 2003.
Ross et al., *Expert Rev. Mol. Diagn.,* 3(5):573-585, 2003.
Ruster et al., *Scand. J. Rheumatol.,* 34(6):460-3, 2005.
Sacerdoti et al., *Curr Neurovasc Res.* 2(2):103-111, 2005.
Salvemini et al., *J. Clin. Invest.,* 93(5):1940-1947, 1994.
Sarchielli et al., *Cephalalgia,* 26(9):1071-1079, 2006.
Satoh et al., *Proc. Natl. Acad. Sci. USA,* 103(3):768-773, 2006.
Schulz et al., *Antioxid. Redox. Sig.,* 10:115, 2008.
Suh et al., *Cancer Res.,* 58:717-723, 1998.
Suh et al., *Cancer Res.,* 59(2):336-341, 1999.
Szabo et al., *Nature Rev. Drug Disc.,* 6:662-680, 2007.
Takahashi et al., *Cancer Res.,* 57:1233-1237, 1997.
Tamir and Tannebaum, *Biochim. Biophys. Acta,* 1288:F31-F36, 1996.
Zhou et al., *Am. J. Pathol.,* 166(1):27-37, 2005.

We claim:

1. A compound of Formula (I),

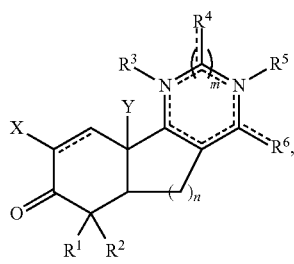

or a pharmaceutically acceptable salt thereof, wherein
⁃⁃⁃⁃⁃ is a single or double bond;
m is 0 or 1;
n is 1 or 2;
p is 1, 2, or 3;
q is 1, 2, or 3;
r is 1, 2, 3, or 4;
X is NC—, $F_3C$—, $R^{1x}C(O)$—, or $O_2N$—;
Y is $G^1$-, $G^1$-$(CR^aR^b)$—, $G^2$-, or $G^2$-$(CR^aR^b)$—;
$R^1$ and $R^2$ are each independently hydrogen, $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amido, amino, halogen, hydroxy, $G^{R1a}$-, $G^{R1a}$-$(CR^aR^b)_p$—, $G^{R1b}$-, $R^{1a}C(O)$—, $(R^{1a})_2N$—, $G^{R1a}NH$—, $G^{R1a}$-$(CR^aR^b)_p$—NH—, $G^{R1a}O$—, and $R^{1a}CO_2$—; or
$R^1$ and $R^2$ joined together with the carbon atom to which they are attached form a $C_3$-$C_6$-cycloalkyl, $C_3$-$C_6$-cycloalkenyl, or 4-6-membered heterocycle optionally substituted with $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, Or oxo;
$R^3$ is absent, hydrogen, $C_1$-$C_6$-alkyl, $C_2$-$C_4$-alkenyl, $C_1$-$C_6$-fluoroalkyl, $G^{3a}$- or $G^{3a}$-$(CR^aR^b)_q$—; provided that $R^3$ is absent when and only when the atom to which it is attached forms part of a double bond;
$R^4$ is hydrogen, $C_1$-$C_6$-alkyl, $C_2$-$C_4$-alkenyl, $C_1$-$C_6$-fluoroalkyl, amino, $C_1$-$C_6$-alkylamino, $C_1$-$C_6$-dialkylamino, $C_1$-$C_6$-alkoxy, cyano, halogen, hydroxy, $G^{4a}$-, $G^{4b}$-, $G^{4a}$-$(CR^aR^b)_p$—, $G^{4b}$-$(CR^aR^b)_p$—, $G^{4a}O$— or $G^{4a}NH$—;
$R^5$ is absent, hydrogen, $C_1$-$C_6$-alkyl, $C_2$-$C_6$-alkenyl, $C_2$-$C_6$-alkynyl, $C_1$-$C_6$-fluoroalkyl, $G^{R5a}$-, $G^{R5a}$-$(CR^aR^b)$—, $R^{5a}C(O)$—, $G^{R5a}C(O)$—, hydroxy-$C_1$-$C_6$-alkyl-$C(O)$—, $R^{5a}O_2C$—, $G^{R5a}O_2C$—, $G^{R5a}HNC(O)$—, $R^{5a}O_2CNHCH_2C(O)$—, $H_2NHCH_2C(O)$—, $R^{5a}SO_2$—, or $G^{R5a}SO_2$—; provided that $R^5$ is absent when and only when the atom to which it is attached forms part of a double bond;
$R^6$ is hydrogen, $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, amino, $C_1$-$C_6$-alkylamino, $C_1$-$C_6$-dialkylamino, hydroxy, $G^{6a}$-, $G^{6a}N(R^a)$—, $G^{6a}O$— or $G^{6b}$-;
$R^a$ and $R^b$ are, at each occurrence, independently hydrogen, $C_1$-$C_6$-alkyl, or $C_1$-$C_6$-haloalkyl;
$R^{1a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$R^{1x}$ is hydroxy, $C_1$-$C_6$-alkoxy, amino, $C_1$-$C_6$-alkylamino, $C_1$-$C_6$-dialkylamino, or $C_1$-$C_6$-alkylsulfonylamino;
$R^{G1a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$R^{G1b}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{G2a}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$R^{G2b}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{G4a}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{5a}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{G6a}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{G6b}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$R^{G6c}$ is, at each occurrence, independently $C_1$-$C_4$-alkyl, $C_2$-$C_4$-alkenyl, $C_2$-$C_4$-alkynyl or $C_1$-$C_4$-haloalkyl;
$R^{G6d}$ is, at each occurrence, independently hydrogen, $C_1$-$C_4$-alkyl, $C_2$-$C_4$-alkenyl, $C_2$-$C_4$-alkynyl or $C_1$-$C_4$-haloalkyl;
$G^1$ is phenyl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, carboxy, cyano, cyano-$C_1$-$C_6$-alkyl, halogen, halo-$C_1$-$C_6$-alkyl, hydroxy, hydroxy-$C_1$-$C_6$-alkyl, $R^{G1b}O_2C$—, $R^{G1a}HN(O)C$—, $(R^{G1a})_2N(O)C$—, $G^{1a}C(O)$—, $G^{1b}HN(O)C$—, $G^{1b}$-, $R^{G1a}C(O)N(R^{G1a})$—, $R^{G1b}(O)CN(R^{G1a})$—, $R^{G1b}O2SN(R^{G1a})$—, $(R^{G1a})_2N$—, $G^{1b}O$—, $G^{1b}CH_2O$—, $R^{G1a}CO_2$—, $(R^{G1a})_2NCO_2$—, HS—, $R^{G1b}S$—, $R^{G1b}S(O)$—, $R^{G1b}SO_2$— or $(R^{G1a})_2NSO_2$—;
$G^2$ is a 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, carboxy, cyano, cyano-$C_1$-$C_6$-alkyl, halogen, halo-$C_1$-$C_6$-alkyl, hydroxy, hydroxy-$C_1$-$C_6$-alkyl, $R^{G2b}CO_2$—, $R^{G2a}HNC(O)$—, $(R^{G2a})_2NC(O)$—, $G^{2a}C(O)$—, $G^{2b}HNC(O)$—, $G^{2b}$-, $R^{G2a}C(O)N(R^{G2a})$—, $R^{G2b}OC(O)N(R^{G2a})$—, $R^{G2b}SO_2N(R^{G2a})$—, $(R^{G2a})_2N$—, $G^{2b}O$—, $G^{2b}CH_2O$—, $R^{G2a}CO_2$—, $(R^{G2a})_2NCO_2$—, HS—, $R^{G2b}S$—, $R^{G2b}S(O)$—, $R^{G2b}SO_2$—, or $(R^{G2a})_2NSO_2$—;

$G^{1a}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;

$G^{1b}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{R1a}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{R1b}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;

$G^{2a}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;

$G^{2b}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{3a}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, or hydroxy;

$G^{4a}$ is phenyl or 5-6-membered heteroaryl optionally substituted with 1, 2, 3, 4 or 5 $C_1$-$C_2$-$C_6$-alkenyl, $C_2$-$C_6$-alkynyl, $C_1$-$C_6$-fluoroalkyl, $C_1$-$C_6$-alkoxy, amido, carboxy, cyano, halogen, hydroxy, $R^{G4a}O_2C$—, $R^{G4a}C(O)$—, $(R^{G4a})_2NC(O)$—, or $G^{4a1}$-;

$G^{4a1}$ is phenyl or 5-6-membered heteroaryl optionally substituted with 1, 2, 3, 4 or 5 $C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{4b}$ is a 4-6-membered heterocycle optionally substituted with 1, 2, 3 or 4 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or oxo;

$G^{R5a}$ is phenyl or 5-6-membered heteroaryl optionally substituted with 1, 2, 3, 4 or 5 $C_1$-$C_6$-alkyl, $C_2$-$C_6$-alkenyl, $C_2$-$C_6$-alkynyl, $C_1$-$C_6$-fluoroalkyl, $C_1$-$C_6$-alkoxy, cyano, halogen, hydroxy, or nitro;

$G^{6a}$ is $C_6$-$C_{10}$-aryl or 5-10-membered heteroaryl optionally substituted with 1, 2, 3, or 4 $C_2$-$C_6$-alkenyl, $C_2$-$C_6$-alkynyl, $C_1$-$C_6$-fluoroalkyl, $C_1$-$C_6$-alkoxy, amino, $C_1$-$C_6$-alkylsulfonylamino, carboxy, halogen, hydroxy, hydroxy$C_1$-$C_6$-alkyl, $R^{G6a}C(O)$—, $R^{G6a}O_2C$—, $HO_2C$—$(CR^aR^b)_r$—, $R^{G6a}O_2C$—$(CR^aR^b)_r$—, $(R^{G6b})_2N(O)C$—$(CR^aR^b)_r$—, $R^{G6a}CO_2$—$(CR^aR^b)_r$—, $G^{6c}$-, or $G^{6d}$-;

$G^{6b}$ is 4-6-membered heterocycle optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, cyano, halogen, hydroxy, or oxo;

$G^{6c}$ is phenyl or 5-6-membered heteroaryl optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, amino, $C_1$-$C_6$-alkylsulfonylamino, di($C_1$-$C_6$-alkylsulfonyl)amino, $C_1$-$C_6$-alkylsulfonylamino$C_1$-$C_6$-alkyl, carboxy, cyano, halogen, hydroxy, hydroxy$C_1$-$C_6$-alkyl, $R^{G6c}C(O)$—, $R^{G6c}O_2C$—, $(R^{G6d})_2NC(O)$—, $HO_2C$—$(CR^aR^b)_r$—, $R^{G6c}O_2C$—$(CR^aR^b)_r$—, $(R^{G6d})_2NC(O)$—$(CR^aR^b)_r$—, or $R^{G6c}CO_2$—$(CR^aR^b)_r$—; and $G^{6d}$ is 4-6-membered heterocycle optionally substituted with 1, 2, 3, or 4 $C_1$-$C_6$-alkyl, $C_2$-$C_6$-alkenyl, $C_2$-$C_6$-alkynyl, $C_1$-$C_6$-alkoxy, cyano, halogen, hydroxy, or oxo.

2. The compound of claim 1, or salt thereof, further defined by the Formula (Ia).

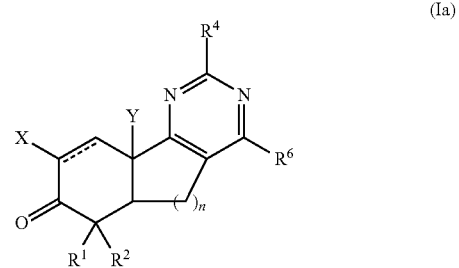

(Ia)

3. The compound of claim 2, or salt thereof, further defined by the Formula (Ia-1).

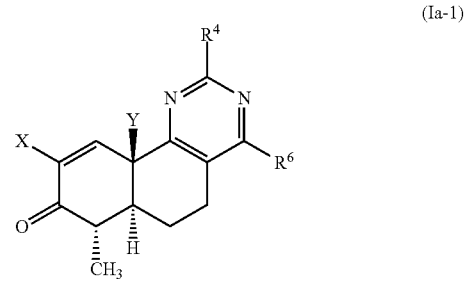

(Ia-1)

4. The compound of claim 3, or salt thereof, wherein
X is NC— or $R^{1x}C(O)$—;
Y is $G^1$- or $G^1$-$(CR^aR^b)$—; and
$R^{1x}$ is hydroxy, $C_1$-$C_6$-alkoxy, amino, $C_1$-$C_6$-alkylamino, $C_1$-$C_6$-dialkylamino, or $C_1$-$C_6$-alkylsulfonylamino.

5. The compound of claim 4, or salt thereof, wherein
X is NC—; and
Y is $G^1$-.

6. The compound of claim 5, or salt thereof, wherein
r is 1, 2, or 3;
$R^4$ is hydrogen, $C_1$-$C_6$-alkyl, $C_1$-$C_6$-alkylamino, $C_1$-$C_6$-dialkylamino, $C_1$-$C_6$-alkoxy, halogen, $G^{4a}$-, $G^{4b}$-, or $G^{4a}NH$—;
$R^6$ is hydrogen, $C_1$-$C_6$-alkoxy, hydroxy, $G^{6a}$-, $G^{6a}N(R^a)$— or $G^{6b}$-;
$R^a$ and $R^b$ are, at each occurrence, hydrogen;
$R^{G1a}$ is, at each occurrence, independently hydrogen or $C_1$-$C_4$-alkyl;
$R^{G1b}$ is, at each occurrence, $C_1$-$C_4$-alkyl;
$R^{G4a}$ is, at each occurrence, $C_1$-$C_4$-alkyl;
$R^{G6a}$ is, at each occurrence, $C_1$-$C_4$-alkyl;
$R^{G6b}$ is, at each occurrence, hydrogen;
$R^{G6c}$ is, at each occurrence, $C_1$-$C_4$-alkyl;
$R^{G6d}$ is, at each occurrence, hydrogen;
$G^1$ is phenyl optionally substituted with 1 $C_1$-$C_6$-alkyl, $C_1$-$C_6$-fluoroalkyl, $C_1$-$C_6$-alkoxy, carboxy, halogen, hydroxy, hydroxy-$C_1$-$C_6$-alkyl, $R^{G1b}O_2C$—, $R^{G1a}HN(O)C$—, $(R^{G1a})_2N(O)C$—, $G^{1a}C(O)$—, $G^{1b}HN(O)C$—, or $G^{1b}CH_2O$—;
$G^{1a}$ is a 4-6-membered heterocycle;
$G^{1b}$ is phenyl;

$G^{4a}$ is phenyl or 5-6-membered heteroaryl optionally substituted with 1 or 2 $C_1$-$C_6$-alkyl, $C_1$-$C_6$-fluoroalkyl, $C_1$-$C_6$-alkoxy, amido, carboxy, halogen, hydroxy, $R^{G4a}O_2C$—, $(R^{G4a})_2NC(O)$—, or $G^{4a1}$-;

$G^{4a1}$ is 5-6-membered heteroaryl optionally substituted with 1 $C_1$-$C_6$-alkyl;

$G^{4b}$ is a 4-6-membered heterocycle;

$G^{6a}$ is $C_6$-$C_{10}$-aryl or 5-10-membered heteroaryl optionally substituted with 1 or 2 $C_1$-$C_6$-alkyl, $C_1$-$C_6$-fluoroalkyl, $C_1$-$C_6$-alkoxy, amino, halogen, hydroxy, hydroxy$C_1$-$C_6$-alkyl, $R^{G6a}C(O)$—, $R^{G6a}O_2C$—, $HO_2C$—$(CR^aR^b)_r$—, $R^{G6a}O_2C$—$(CR^aR^b)_r$—, $(R^{G6b})_2N(O)C$—$(CR^aR^b)_r$—, $R^{G6a}CO_2$—$(CR^aR^b)_r$—, $G^{6c}$-, or $G^{6d}$-;

$G^{6b}$ is 4-6-membered heterocycle optionally substituted with 1 or 2 $C_1$-$C_6$-alkyl or oxo;

$G^{6c}$ is phenyl or 5-6-membered heteroaryl optionally substituted with 1 or 2 $C_1$-$C_6$-alkyl, amino, $C_1$-$C_6$-alkylsulfonylamino, halogen, hydroxy, $R^{G6c}O_2C$—, or $(R^{G6d})_2NC(O)$—; and $G^{6d}$ is 4-6-membered heterocycle.

7. The compound of claim 4, or salt thereof, wherein
X is $R^{1x}C(O)$—;
Y is $G^1$-; and
$R^{1x}$ is amino.

8. The compound of claim 7, or salt thereof, wherein
$R^4$ is hydrogen, $C_1$-$C_6$-alkyl, $C_1$-$C_6$-fluoroalkyl, $C_1$-$C_6$-alkoxy, or halogen;
$R^6$ is hydrogen, $C_1$-$C_6$-alkoxy, hydroxy or $G^{6a}$-;
$R^{G1b}$ is, at each occurrence, $C_1$-$C_4$-alkyl;
$G^1$ is phenyl optionally substituted with 1 $C_1$-$C_6$-alkyl, $C_1$-$C_6$-fluoroalkyl, $C_1$-$C_6$-alkoxy, halogen, hydroxy, or $R^{G1b}O_2C$—;
$G^{6a}$ is $C_6$-$C_{10}$-aryl or 5-10-membered heteroaryl optionally substituted with 1 or 2 $C_1$-$C_6$-alkyl, $C_1$-$C_6$-fluoroalkyl, $C_1$-$C_6$-alkoxy, halogen, hydroxy, or $G^{6c}$-; and
$G^{6c}$ is phenyl or 5-6-membered heteroaryl optionally substituted with 1 $C_1$-$C_6$-alkyl or halogen.

9. The compound of claim 1, or salt thereof, further defined by the Formula (Ib).

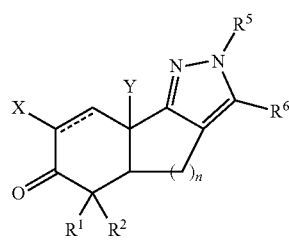

(Ib)

10. The compound of claim 9, or salt thereof, further defined by the Formula (Ib-1).

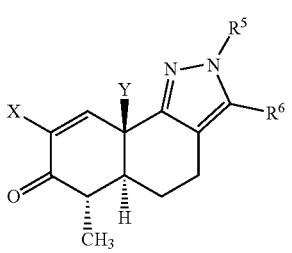

(Ib-1)

11. The compound of claim 10, or salt thereof, wherein
X is NC— or $R^{1x}C(O)$—;
Y is $G^1$- or $G^1$-$(CR^aR^b)$—; and
$R^{1x}$ is hydroxy, $C_1$-$C_6$-alkoxy, amino, $C_1$-$C_6$-alkylamino, $C_1$-$C_6$-dialkylamino, or $C_1$-$C_6$-alkylsulfonylamino.

12. The compound of claim 11, or salt thereof, wherein
X is NC—; and
Y is $G^1$-.

13. The compound of claim 12, or salt thereof, wherein
r is 1, 2 or 3;
$R^5$ is hydrogen, $C_1$-$C_6$-alkyl, $C_1$-$C_6$-fluoroalkyl, $G^{R5a}$-, $G^{R5a}$-$(CR^aR^b)$—, $R^{5a}C(O)$—, $G^{R5a}C(O)$—, hydroxy-$C_1$-$C_6$-alkyl-$C(O)$—, $R^{5a}O_2C$—, $G^{R5a}O_2C$—, $G^{R5a}HNC(O)$—, $R^{5a}O_2CNHCH_2C(O)$—, $H_2NHCH_2C(O)$—, $R^{5a}SO_2$—, or $G^{R5a}SO_2$—;
$R^6$ is hydrogen, $C_1$-$C_6$-alkoxy, or $G^{6a}$-;
$R^a$ and $R^b$ are, at each occurrence, hydrogen;
$R^{G1b}$ is, at each occurrence, $C_1$-$C_4$-alkyl;
$R^{5a}$ is, at each occurrence, $C_1$-$C_4$-alkyl;
$R^{G6d}$ is, at each occurrence, hydrogen;
$G^1$ is phenyl optionally substituted with 1 or 2 $C_1$-$C_6$-alkyl, $C_1$-$C_6$-fluoroalkyl, $C_1$-$C_6$-alkoxy, carboxy, halogen, hydroxy, or $R^{G1b}O_2C$—;
$G^{R5a}$ is phenyl or 5-6-membered heteroaryl;
$G^{6a}$ is $C_6$-$C_{10}$-aryl or 5-10-membered heteroaryl optionally substituted with 1 or 2 $C_1$-$C_6$-alkyl, $C_1$-$C_6$-fluoroalkyl, $C_1$-$C_6$-alkoxy, amino, $C_1$-$C_6$-alkylsulfonylamino, carboxy, halogen, hydroxy, hydroxy$C_1$-$C_6$-alkyl, $HO_2C$—$(CR^aR^b)_r$— or $G^{6c}$-; and
$G^{6c}$ is phenyl or 5-6-membered heteroaryl optionally substituted with 1 or 2 $C_1$-$C_6$-alkyl, $C_1$-$C_6$-alkoxy, amino, $C_1$-$C_6$-alkylsulfonylamino, di($C_1$-$C_6$-alkylsulfonyl)amino, $C_1$-$C_6$-alkylsulfonylamino$C_1$-$C_6$-alkyl, carboxy, cyano, halogen, hydroxy, hydroxy$C_1$-$C_6$-alkyl, and $(R^{G6d})_2NC(O)$—.

14. The compound of claim 11, or salt thereof, wherein
X is NC— or $R^{1x}C(O)$—;
Y is $G^1$-$(CR^aR^b)$—;
$R^5$ is hydrogen, $C_1$-$C_6$-alkyl, $R^{5a}C(O)$— or $R^{5a}SO_2$—;
$R^6$ is hydrogen or $G^{6a}$-;
$R^a$ and $R^b$ are, at each occurrence, hydrogen;
$R^{1x}$ is amino;
$R^{5a}$ is, at each occurrence, $C_1$-$C_4$-alkyl;
$G^1$ is phenyl optionally substituted with 1 or 2 $C_1$-$C_6$-alkyl, $C_1$-$C_6$-fluoroalkyl, $C_1$-$C_6$-alkoxy, carboxy, halogen, hydroxy, or $R^{G1b}O_2C$—; and
$G^{6a}$ is $C_6$-$C_{10}$-aryl or 5-10-membered heteroaryl optionally substituted with 1 or 2 $C_1$-$C_6$-alkyl, $C_1$-$C_6$-fluoroalkyl, $C_1$-$C_6$-alkoxy, $C_1$-$C_6$-alkylsulfonylamino, carboxy or halogen.

15. The compound of claim 1, or salt thereof, further defined by the Formula (Ic).

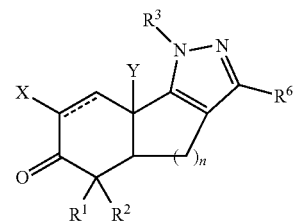

(Ic)

16. The compound of claim 15, or salt thereof, further defined by the Formula (IC-1).

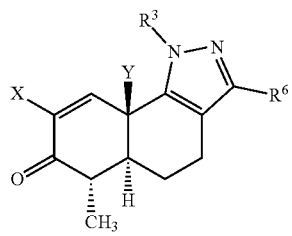

(Ic-1)

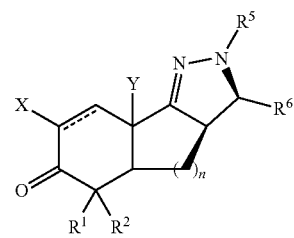

(Id)

17. The compound of claim 16, or salt thereof, wherein,
q is 1;
X is NC—;
Y is $G^1$-;
$R^3$ is hydrogen, $C_1$-$C_6$-alkyl, or $G^{3a}$-$(CR^aR^b)_q$—;
$R^6$ is hydrogen or $G^{6a}$-;
$R^a$ and $R^b$ are, at each occurrence, hydrogen;
$R^{G1a}$ is, at each occurrence, independently hydrogen or $C_1$-$C_4$-alkyl;
$R^{G1b}$ is, at each occurrence, $C_1$-$C_4$-alkyl;
$G^1$ is phenyl optionally substituted with 1 $C_1$-$C_6$-alkyl, $C_1$-$C_6$-fluoroalkyl, $C_1$-$C_6$-alkoxy, carboxy, halogen, hydroxy, hydroxy-$C_1$-$C_6$-alkyl, $R^{G1b}O_2C$—, $R^{G1a}$HN(O)C—, $(R^{G1a})_2$N(O)C—, $G^{1a}$C(O)—, $G^{1b}$HN(O)C—, or $G^{1b}$CH$_2$O;
$G^{1a}$ is a 4-6-membered heterocycle;
$G^{1b}$ is phenyl;
$G^{3a}$ is phenyl or 5-6-membered heteroaryl optionally substituted with 1 or 2 $C_1$-$C_6$-alkyl, $C_1$-$C_6$-fluoroalkyl, $C_1$-$C_6$-alkoxy or halogen; and
$G^{6a}$ is $C_6$-$C_{10}$-aryl or 5-10-membered heteroaryl optionally substituted with 1 or 2 $C_1$-$C_6$-alkyl, $C_1$-$C_6$-fluoroalkyl, $C_1$-$C_6$-alkoxy or halogen.

18. The compound of claim 16, or salt thereof, wherein,
q is 1;
X is NC—;
Y is $G^1$-$(CR^aR^b)$—;
$R^3$ is hydrogen, $C_1$-$C_6$-alkyl, or $G^{3a}$-$(CR^aR^b)_q$—;
$R^6$ is hydrogen or $G^{6a}$-;
$R^a$ and $R^b$ are, at each occurrence, hydrogen;
$R^{G1a}$ is, at each occurrence, independently hydrogen or $C_1$-$C_4$-alkyl;
$R^{G1b}$ is, at each occurrence, $C_1$-$C_4$-alkyl;
$G^1$ is phenyl optionally substituted with 1 $C_1$-$C_6$-alkyl, $C_1$-$C_6$-fluoroalkyl, $C_1$-$C_6$-alkoxy, carboxy, halogen, hydroxy, hydroxy-$C_1$-$C_6$-alkyl, $R^{G1b}O_2C$—, $R^{G1a}$HN(O)C—, $(R^{G1a})_2$N(O)C—, $G^{1a}$C(O)—, $G^{1b}$HN(O)C—, or $G^{1b}$CH$_2$O;
$G^{1a}$ is a 4-6-membered heterocycle;
$G^{1b}$ is phenyl;
$G^{3a}$ is phenyl or 5-6-membered heteroaryl optionally substituted with 1 or 2 $C_1$-$C_6$-alkyl, $C_1$-$C_6$-fluoroalkyl, $C_1$-$C_6$-alkoxy or halogen; and
$G^{6a}$ is $C_6$-$C_{10}$-aryl or 5-10-membered heteroaryl optionally substituted with 1 or 2 $C_1$-$C_6$-alkyl, $C_1$-$C_6$-fluoroalkyl, $C_1$-$C_6$-alkoxy or halogen.

19. The compound of claim 1, or a salt thereof, further defined by the Formula (Id).

20. The compound of claim 19, or salt thereof, further defined by the Formula (Id-1).

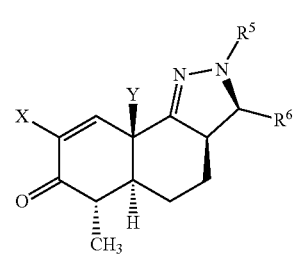

(Id-1)

21. The compound of claim 20, or salt thereof, wherein,
X is NC—; and
Y is $G^1$-;
r is 1, 2 or 3;
$R^5$ is hydrogen, $C_1$-$C_6$-alkyl, $G^{R5a}$-$(CR^aR^b)$—, $R^{5a}$C(O)—, $G^{R5a}$C(O)—, $R^{5a}$SO$_2$—, or $G^{R5a}$SO$_2$—;
$R^6$ is hydrogen or $G^{6a}$-;
$R^a$ and $R^b$ are, at each occurrence, hydrogen;
$R^{5a}$ is, at each occurrence, $C_1$-$C_4$-alkyl;
$G^1$ is phenyl optionally substituted with 1 or 2 $C_1$-$C_6$-alkyl, $C_1$-$C_6$-fluoroalkyl, $C_1$-$C_6$-alkoxy, carboxy, halogen or hydroxy;
$G^{R5a}$ is phenyl or 5-6-membered heteroaryl;
$G^{6a}$ is $C_6$-$C_{10}$-aryl or 5-10-membered heteroaryl optionally substituted with 1 or 2 $C_1$-$C_6$-alkyl, $C_1$-$C_6$-fluoroalkyl, $C_1$-$C_6$-alkoxy, amino, $C_1$-$C_6$-alkylsulfonylamino, carboxy, halogen, hydroxy, hydroxy$C_1$-$C_6$-alkyl, HO$_2$C—$(CR^aR^b)_r$— or $G^{6c}$-; and
$G^{6c}$ is phenyl or 5-6-membered heteroaryl optionally substituted with 1 or 2 $C_1$-$C_6$-alkyl, $C_1$-$C_6$-alkoxy, amino, $C_1$-$C_6$-alkylsulfonylamino, di($C_1$-$C_6$-alkylsulfonyl)amino, $C_1$-$C_6$-alkylsulfonylamino$C_1$-$C_6$-alkyl, carboxy, cyano, halogen and hydroxy.

22. The compound of claim 1, or a salt thereof, wherein the compound is selected from the group consisting of:
(6aS,7S,10aR)-7-methyl-8-oxo-10a-phenyl-5,6,6a,7,8,10a-hexahydrobenzo[h]quinazoline-9-carbonitrile;
rac-(5aS,6S,9aR)-2,6-dimethyl-7-oxo-3,9a-diphenyl-4,5,5a,6,7,9a-hexahydro-2H-benzo[g]indazole-8-carbonitrile;
rac-(5aS,6S,9aR)-1,6-dimethyl-7-oxo-3,9a-diphenyl-4,5,5a,6,7,9a-hexahydro-1H-benzo[g]indazole-8-carbonitrile;
rac-(5aS,6S,9aR)-9a-(4-methoxyphenyl)-2,6-dimethyl-7-oxo-4,5,5a,6,7,9a-hexahydro-2H-benzo[g]indazole-8-carbonitrile;
rac-(5aS,6S,9aR)-9a-(4-methoxyphenyl)-1,6-dimethyl-7-oxo-4,5,5a,6,7,9a-hexahydro-1H-benzo[g]indazole-8-carbonitrile;

rac-(5aS,6S,9aR)-6-methyl-7-oxo-3,9a-diphenyl-4,5,5a,6,7,9a-hexahydro-1H-benzo[g]indazole-8-carbonitrile;
(7S)-7-methyl-8-oxo-2,10a-diphenyl-5,6,6a,7,8,10a-hexahydrobenzo[h]quinazoline-9-carbonitrile;
(7S)-4-methoxy-7-methyl-8-oxo-2,10a-diphenyl-5,6,6a,7,8,10a-hexahydrobenzo[h]quinazoline-9-carbonitrile;
(7S,10aS)-2-anilino-7-methyl-8-oxo-10a-phenyl-5,6,6a,7,8,10a-hexahydrobenzo[h]quinazoline-9-carbonitrile;
(6aS,7S,10aR)-4-methoxy-2-(2-methoxyphenyl)-7-methyl-8-oxo-10a-phenyl-5,6,6a,7,8,10a-hexahydrobenzo[h]quinazoline-9-carbonitrile;
(6aS,7S,10aR)-7-methyl-8-oxo-10a-phenyl-2-(pyridin-3-yl)-5,6,6a,7,8,10a-hexahydrobenzo[h]quinazoline-9-carbonitrile;
(6aS,7S,10aR)-2-(ethylamino)-7-methyl-8-oxo-10a-phenyl-5,6,6a,7,8,10a-hexahydrobenzo[h]quinazoline-9-carbonitrile;
(6aS,7S,10aR)-4-methoxy-2,7-dimethyl-8-oxo-10a-phenyl-5,6,6a,7,8,10a-hexahydrobenzo[h]quinazoline-9-carbonitrile;
(6aS,7S,10aR)-2-anilino-4-methoxy-7-methyl-8-oxo-10a-phenyl-5,6,6a,7,8,10a-hexahydrobenzo[h]quinazoline-9-carbonitrile;
(6aS,7S,10aR)-2-[(4-bromophenyl)amino]-4-methoxy-7-methyl-8-oxo-10a-phenyl-5,6,6a,7,8,10a-hexahydrobenzo[h]quinazoline-9-carbonitrile;
(6aS,7S,10aR)-2-anilino-7-methyl-8-oxo-10a-phenyl-4-(pyrimidin-5-yl)-5,6,6a,7,8,10a-hexahydrobenzo[h]quinazoline-9-carbonitrile;
(6aS,7S,10aR)-2,7-dimethyl-4-(1-methyl-1H-imidazol-5-yl)-8-oxo-10a-phenyl-5,6,6a,7,8,10a-hexahydrobenzo[h]quinazoline-9-carbonitrile;
(6aS,7S,10aR)-2,7-dimethyl-4-(2-methyl-1,3-thiazol-5-yl)-8-oxo-10a-phenyl-5,6,6a,7,8,10a-hexahydrobenzo[h]quinazoline-9-carbonitrile;
(6aS,7S,10aR)-7-methyl-2-(morpholin-4-yl)-8-oxo-10a-phenyl-5,6,6a,7,8,10a-hexahydrobenzo[h]quinazoline-9-carbonitrile;
(6aS,7S,10aR)-4-hydroxy-2,7-dimethyl-8-oxo-10a-phenyl-5,6,6a,7,8,10a-hexahydrobenzo[h]quinazoline-9-carbonitrile;
(6aS,7S,10aR)-2,7-dimethyl-8-oxo-4,10a-diphenyl-5,6,6a,7,8,10a-hexahydrobenzo[h]quinazoline-9-carbonitrile;
(6aS,7S,10aR)-2,7-dimethyl-8-oxo-10a-phenyl-4-(pyrimidin-5-yl)-5,6,6a,7,8,10a-hexahydrobenzo[h]quinazoline-9-carbonitrile;
(6aS,7S,10aR)-4-(3-furyl)-2,7-dimethyl-8-oxo-10a-phenyl-5,6,6a,7,8,10a-hexahydrobenzo[h]quinazoline-9-carbonitrile;
(6S,9aR)-6-methyl-7-oxo-9a-phenyl-4,5,5a,6,7,9a-hexahydro-2H-benzo[g]indazole-8-carbonitrile;
(6aS,7S,10aR)-2-(2-fluorophenyl)-4-methoxy-7-methyl-8-oxo-10a-phenyl-5,6,6a,7,8,10a-hexahydrobenzo[h]quinazoline-9-carbonitrile;
(5aS,6S,9aR)-1,6-dimethyl-7-oxo-9a-phenyl-3-(pyridin-3-yl)-4,5,5a,6,7,9a-hexahydro-1H-benzo[g]indazole-8-carbonitrile;
(6aS,7S,10aR)-2,7-dimethyl-8-oxo-10a-phenyl-4-(pyridin-4-yl)-5,6,6a,7,8,10a-hexahydrobenzo[h]quinazoline-9-carbonitrile;
(6S,9aR)-2-acetyl-6-methyl-7-oxo-9a-phenyl-4,5,5a,6,7,9a-hexahydro-2H-benzo[g]indazole-8-carbonitrile;
(6aS,7S,10aR)-7-methyl-8-oxo-10a-phenyl-2-(pyridin-4-yl)-5,6,6a,7,8,10a-hexahydrobenzo[h]quinazoline-9-carbonitrile;
(6aS,7S,10aR)-2-(diethylamino)-7-methyl-8-oxo-10a-phenyl-5,6,6a,7,8,10a-hexahydrobenzo[h]quinazoline-9-carbonitrile;
(6aS,7S,10aR)-2-(2-fluorophenyl)-4-isopropoxy-7-methyl-8-oxo-10a-phenyl-5,6,6a,7,8,10a-hexahydrobenzo[h]quinazoline-9-carbonitrile;
methyl (6S,9aR)-8-cyano-6-methyl-7-oxo-9a-phenyl-4,5,5a,6,7,9a-hexahydro-2H-benzo[g]indazole-2-carboxylate;
rac-(6aS,7S,10aR)-2,7-dimethyl-8-oxo-10a-phenyl-5,6,6a,7,8,10a-hexahydrobenzo[h]quinazoline-9-carbonitrile;
(6aS,7S,10aR)-2,7-dimethyl-8-oxo-10a-phenyl-4-(1H-pyrazol-4-yl)-5,6,6a,7,8,10a-hexahydrobenzo[h]quinazoline-9-carbonitrile;
(6aS,7S,10aR)-2,7-dimethyl-4-(1-methyl-1H-pyrazol-4-yl)-8-oxo-10a-phenyl-5,6,6a,7,8,10a-hexahydrobenzo[h]quinazoline-9-carbonitrile;
(6S,9aR)-6-methyl-2-(methylsulfonyl)-7-oxo-9a-phenyl-4,5,5a,6,7,9a-hexahydro-2H-benzo[g]indazole-8-carbonitrile;
phenyl (6S,9aR)-8-cyano-6-methyl-7-oxo-9a-phenyl-4,5,5a,6,7,9a-hexahydro-2H-benzo[g]indazole-2-carboxylate;
(6S,9aR)-2-benzoyl-6-methyl-7-oxo-9a-phenyl-4,5,5a,6,7,9a-hexahydro-2H-benzo[g]indazole-8-carbonitrile;
tert-butyl {2-[(6S,9aR)-8-cyano-6-methyl-7-oxo-9a-phenyl-4,5,5a,6,7,9a-hexahydro-2H-benzo[g]indazol-2-yl]-2-oxoethyl}carbamate;
(6S,9aR)-6-methyl-7-oxo-9a-phenyl-2-(1,3-thiazol-4-ylcarbonyl)-4,5,5a,6,7,9a-hexahydro-2H-benzo[g]indazole-8-carbonitrile;
(6S,9aR)-6-methyl-7-oxo-9a-phenyl-2-(phenylsulfonyl)-4,5,5a,6,7,9a-hexahydro-2H-benzo[g]indazole-8-carbonitrile;
(6S,9aR)-2-glycoloyl-6-methyl-7-oxo-9a-phenyl-4,5,5a,6,7,9a-hexahydro-2H-benzo[g]indazole-8-carbonitrile;
(6aS,7S,10aR)-4-(3-methoxyphenyl)-2,7-dimethyl-8-oxo-10a-phenyl-5,6,6a,7, 8,10a-hexahydrobenzo[h]quinazoline-9-carbonitrile;
(6aS,7S,10aR)-2,7-dimethyl-4-(1-methyl-6-oxo-1,6-dihydropyridin-3-yl)-8-oxo-10a-phenyl-5,6,6a,7,8,10a-hexahydrobenzo[h]quinazoline-9-carbonitrile;
(6aS,7S,10aR)-2,7-dimethyl-8-oxo-10a-phenyl-4-(quinolin-6-yl)-5,6,6a,7,8,10a-hexahydrobenzo[h]quinazoline-9-carbonitrile;
2-{3-[(6aS,7S,10aR)-9-cyano-2,7-dimethyl-8-oxo-10a-phenyl-5,6,6a,7,8, 0a-hexahydrobenzo[h]quinazolin-4-yl]phenyl}ethyl acetate;
(6aS,7S,10aR)-4-[3-(2-hydroxyethyl)phenyl]-2,7-dimethyl-8-oxo-10a-phenyl-5,6,6a,7,8,10a-hexahydrobenzo[h]quinazoline-9-carbonitrile;
(6S,9aR)-8-cyano-6-methyl-7-oxo-9a-phenyl-N-(pyridin-3-yl)-4,5,5a,6,7,9a-hexahydro-2H-benzo[g]indazole-2-carboxamide;
(6aS,7S,10aR)-7-methyl-8-oxo-10a-phenyl-2-(pyrimidin-5-yl)-5,6,6a,7, 8,10a-hexahydrobenzo[h]quinazoline-9-carbonitrile;
(6aS,7S,10aR)-10a-(4-fluorophenyl)-7-methyl-8-oxo-5,6,6a,7,8,10a-hexahydrobenzo[h]quinazoline-9-carbonitrile;
(6aS,7S,10aR)-10a-(4-fluorophenyl)-7-methyl-8-oxo-2-(pyridin-3-yl)-5,6,6a,7,8,10a-hexahydrobenzo[h]quinazoline-9-carbonitrile;
(6S,9aR)-2,6-dimethyl-7-oxo-9a-phenyl-4,5,5a,6,7,9a-hexahydro-2H-benzo[g]indazole-8-carbonitrile;

(5aS,6S,9aR)-9a-(3-fluorophenyl)-6-methyl-7-oxo-4,5,5a,6,7,9a-hexahydro-2H-benzo[g]indazole-8-carbonitrile;

(5aS,6S,9aR)-9a-(4-fluorophenyl)-6-methyl-7-oxo-4,5,5a,6,7,9a-hexahydro-2H-benzo[g]indazole-8-carbonitrile;

(6aS,7S,10aR)-10a-(3-fluorophenyl)-7-methyl-8-oxo-5,6,6a,7,8,10a-hexahydrobenzo[h]quinazoline-9-carbonitrile;

(5aS,6S,9aR)-2-benzyl-6-methyl-7-oxo-9a-phenyl-4,5,5a,6,7,9a-hexahydro-2H-benzo[g]indazole-8-carbonitrile;

(5aS,6S,9aR)-1-benzyl-6-methyl-7-oxo-9a-phenyl-4,5,5a,6,7,9a-hexahydro-1H-benzo[g]indazole-8-carbonitrile;

(5aS,6S,9aR)-9a-(4-methoxyphenyl)-6-methyl-7-oxo-4,5,5a,6,7,9a-hexahydro-2H-benzo[g]indazole-8-carbonitrile;

methyl 3-[(6aS,7S,10aR)-9-cyano-7-methyl-8-oxo-6,6a,7,8-tetrahydrobenzo[h]quinazolin-10a(5H)-yl]benzoate;

3-[(6aS,7S,10aR)-9-cyano-7-methyl-8-oxo-6,6a,7,8-tetrahydrobenzo[h]quinazolin-10a(5H)-yl]benzoic acid;

3-[(6aS,7S,10aR)-9-cyano-7-methyl-8-oxo-6,6a,7,8-tetrahydrobenzo[h]quinazolin-10a(5H)-yl]benzamide;

methyl 3-[(5aS,6S,9aR)-8-cyano-6-methyl-7-oxo-2,4,5,5a,6,7-hexahydro-9aH-benzo[g]indazol-9a-yl]benzoate;

methyl 4-[(5aS,6S,9aR)-8-cyano-6-methyl-7-oxo-2,4,5,5a,6,7-hexahydro-9aH-benzo[g]indazol-9a-yl]benzoate;

methyl 4-[(6aS,7S,10aR)-9-cyano-7-methyl-8-oxo-6,6a,7,8-tetrahydrobenzo[h]quinazolin-10a(5H)-yl]benzoate;

(5aS,6S,9aR)-1-(4-bromobenzyl)-6-methyl-7-oxo-9a-phenyl-4,5,5a,6,7,9a-hexahydro-1H-benzo[g]indazole-8-carbonitrile;

4-[(6aS,7S,10aR)-9-cyano-7-methyl-8-oxo-6,6a,7,8-tetrahydrobenzo[h]quinazolin-10a(5H)-yl]benzoic acid;

(6aS,7S,10aR)-10a-(4-methoxyphenyl)-2,7-dimethyl-8-oxo-4-(pyrimidin-5-yl)-5,6,6a,7,8,10a-hexahydrobenzo[h]quinazoline-9-carbonitrile;

(6aS,7S,10aR)-10a-(4-fluorophenyl)-2,7-dimethyl-8-oxo-4-(pyrimidin-5-yl)-5,6,6a,7,8,10a-hexahydrobenzo[h]quinazoline-9-carbonitrile;

(6aS,7S,10aR)-10a-(3-fluorophenyl)-2,7-dimethyl-8-oxo-4-(pyrimidin-5-yl)-5,6,6a,7,8,10a-hexahydrobenzo[h]quinazoline-9-carbonitrile;

(6aS,7S,10aR)-10a-(4-methoxyphenyl)-7-methyl-8-oxo-5,6,6a,7,8,10a-hexahydrobenzo[h]quinazoline-9-carbonitrile;

3-[(5aS,6S,9aR)-8-cyano-6-methyl-7-oxo-2,4,5,5a,6,7-hexahydro-9aH-benzo[g]indazol-9a-yl]benzoic acid;

(6S,9aR)-9a-(4-hydroxyphenyl)-6-methyl-7-oxo-4,5,5a,6,7,9a-hexahydro-2H-benzo[g]indazole-8-carbonitrile;

(6aS,7S,10aR)-7-methyl-8-oxo-10a-[4-(pyrrolidin-1-ylcarbonyl)phenyl]-5,6,6a,7,8,10a-hexahydrobenzo[h]quinazoline-9-carbonitrile;

(6aS,7S,10aR)-2-(2,6-difluorophenyl)-7-methyl-8-oxo-10a-phenyl-5,6,6a,7,8,10a-hexahydrobenzo[h]quinazoline-9-carbonitrile;

methyl 4-[(6aS,7S,10aR)-9-cyano-7-methyl-8-oxo-10a-phenyl-5,6,6a,7,8,10a-hexahydrobenzo[h]quinazolin-2-yl]benzoate;

(6aS,7S,10aR)-4-(1-acetyl-1H-pyrazol-4-yl)-2,7-dimethyl-8-oxo-10a-phenyl-5,6,6a,7,8,10a-hexahydrobenzo[h]quinazoline-9-carbonitrile;

4-[(6aS,7S,10aR)-9-cyano-7-methyl-8-oxo-10a-phenyl-5,6,6a,7,8,10a-hexahydrobenzo[h]quinazolin-2-yl]benzoic acid;

(6S,9aR)-9a-(3-fluorophenyl)-3-[3-(3-hydroxypropyl)phenyl]-6-methyl-7-oxo-4,5,5a,6,7,9a-hexahydro-2H-benzo[g]indazole-8-carbonitrile;

(6aS,7S,10aR)-4-[4-(4-bromo-1H-pyrazol-5-yl)phenyl]-10a-(4-methoxyphenyl)-2,7-dimethyl-8-oxo-5,6,6a,7,8,10a-hexahydrobenzo[h]quinazoline-9-carbonitrile;

(6aS,7S,10aR)-10a-(4-methoxyphenyl)-2,7-dimethyl-8-oxo-4-[4-(1H-pyrazol-5-yl)phenyl]-5,6,6a,7,8,10a-hexahydrobenzo[h]quinazoline-9-carbonitrile;

(6aS,7S,10aR)-4-[4-(4-bromo-1H-pyrazol-5-yl)phenyl]-10a-(4-fluorophenyl)-2,7-dimethyl-8-oxo-5,6,6a,7,8,10a-hexahydrobenzo[h]quinazoline-9-carbonitrile;

(5aS,6S,9aR)-9a-(4-fluorophenyl)-2-glycyl-6-methyl-7-oxo-4,5,5a,6,7,9a-hexahydro-2H-benzo[g]indazole-8-carbonitrile;

(6aS,7S,10aR)-10a-(4-fluorophenyl)-2,7-dimethyl-8-oxo-4-[4-(1H-pyrazol-5-yl)phenyl]-5,6,6a,7,8,10a-hexahydrobenzo[h]quinazoline-9-carbonitrile;

(6aS,7S,10aR)-7-methyl-8-oxo-10a-phenyl-2-(pyrazin-2-yl)-5,6,6a,7,8,10a-hexahydrobenzo[h]quinazoline-9-carbonitrile;

(6aS,7S,10aR)-2-tert-butyl-7-methyl-8-oxo-10a-phenyl-5,6,6a,7,8,10a-hexahydrobenzo[h]quinazoline-9-carbonitrile;

(6S,9aR)-6-methyl-7-oxo-9a-phenyl-3-(pyridin-3-yl)-4,5,5a,6,7,9a-hexahydro-2H-benzo[g]indazole-8-carbonitrile;

(6S,9aR)-6-methyl-7-oxo-9a-phenyl-3-(pyrimidin-5-yl)-4,5,5a,6,7,9a-hexahydro-2H-benzo[g]indazole-8-carbonitrile;

(6S,9aR)-3-(3-hydroxyphenyl)-6-methyl-7-oxo-9a-phenyl-4,5,5a,6,7,9a-hexahydro-2H-benzo[g]indazole-8-carbonitrile;

(6S,9aR)-6-methyl-3-(1-methyl-1H-pyrazol-4-yl)-7-oxo-9a-phenyl-4,5,5a,6,7,9a-hexahydro-2H-benzo[g]indazole-8-carbonitrile;

(6aS,7S,10aR)-4-(1H-benzimidazol-5-yl)-10a-(4-methoxyphenyl)-2,7-dimethyl-8-oxo-5,6,6a,7,8,10a-hexahydrobenzo[h]quinazoline-9-carbonitrile;

(6aS,7S,10aR)-4-(1H-benzimidazol-5-yl)-10a-(4-fluorophenyl)-2,7-dimethyl-8-oxo-5,6,6a,7,8,10a-hexahydrobenzo[h]quinazoline-9-carbonitrile;

(6aS,7S,10aR)-4-(3-bromo-1H-indazol-7-yl)-10a-(4-fluorophenyl)-2,7-dimethyl-8-oxo-5,6,6a,7,8,10a-hexahydrobenzo[h]quinazoline-9-carbonitrile;

(6aS,7S,10aR)-10a-(4-fluorophenyl)-4-(1H-indazol-7-yl)-2,7-dimethyl-8-oxo-5,6,6a,7,8,10a-hexahydrobenzo[h]quinazoline-9-carbonitrile;

(6aS,7S,10aR)-4-(2,4-dioxo-1,2,3,4-tetrahydropyrimidin-5-yl)-10a-(4-fluorophenyl)-2,7-dimethyl-8-oxo-5,6,6a,7,8,10a-hexahydrobenzo[h]quinazoline-9-carbonitrile;

3-[(6aS,7S,10aR)-9-cyano-7-methyl-8-oxo-6,6a,7,8-tetrahydrobenzo[h]quinazolin-10a(5H)-yl]-N-phenylbenzamide;

3-[(6aS,7S,10aR)-9-cyano-7-methyl-8-oxo-6,6a,7,8-tetrahydrobenzo[h]quinazolin-10a(5H)-yl]-N-propylbenzamide;

(5aS,6S,9aR)-2,6-dimethyl-7-oxo-9a-phenyl-3-(pyridazin-4-yl)-4,5,5a,6,7,9a-hexahydro-2H-benzo[g]indazole-8-carbonitrile;

methyl 4-[(6aS,7S,10aR)-9-cyano-2,7-dimethyl-8-oxo-10a-phenyl-5,6,6a,7,8,10a-hexahydrobenzo[h]quinazolin-4-yl]-1H-pyrazole-1-carboxylate;

methyl 3-[(6aS,7S,10aR)-9-cyano-7-methyl-8-oxo-2-phenyl-6,6a,7,8-tetrahydrobenzo[h]quinazolin-10a (5H)-yl]benzoate;
3-[(6aS,7S,10aR)-9-cyano-7-methyl-8-oxo-2-phenyl-6,6a,7,8-tetrahydrobenzo[h]quinazolin-10a(5H)-yl]benzoic acid;
methyl 3-[(6aS,7S,10aR)-9-cyano-2-[4-(methoxycarbonyl)phenyl]-7-methyl-8-oxo-6,6a,7,8-tetrahydrobenzo[h]quinazolin-10a(5H)-yl]benzoate;
(6aS,7S,10aR)-2-chloro-4-methoxy-7-methyl-8-oxo-10a-phenyl-5,6,6a,7,8,10a-hexahydrobenzo[h]quinazoline-9-carbonitrile;
(6aS,7S,10aR)-2,4-dimethoxy-7-methyl-8-oxo-10a-phenyl-5,6,6a,7,8,10a-hexahydrobenzo[h]quinazoline-9-carbonitrile;
3-[(6aS,7S,10aR)-2-(4-carboxyphenyl)-9-cyano-7-methyl-8-oxo-6,6a,7,8-tetrahydrobenzo[h]quinazolin-10a(5H)-yl]benzoic acid;
(3R,3aR,5aS,6S,9aR)-2,6-dimethyl-7-oxo-3,9a-diphenyl-3,3a,4,5,5a,6,7,9a-octahydro-2H-benzo[g]indazole-8-carbonitrile;
(6S,9aR)-3-(6-aminopyridin-3-yl)-6-methyl-7-oxo-9a-phenyl-4,5,5a,6,7,9a-hexahydro-2H-benzo[g]indazole-8-carbonitrile;
(6aS,7S,10aR)-4-(imidazo[1,2-a]pyridin-6-yl)-2,7-dimethyl-8-oxo-10a-phenyl-5,6,6a,7,8,10a-hexahydrobenzo[h]quinazoline-9-carbonitrile;
(6aS,7S,10aR)-4-(4-hydroxyphenyl)-2,7-dimethyl-8-oxo-10a-phenyl-5,6,6a,7,8,10a-hexahydrobenzo[h]quinazoline-9-carbonitrile;
(6aS,7S,10aR)-4-(3-hydroxyphenyl)-2,7-dimethyl-8-oxo-10a-phenyl-5,6,6a,7,8,10a-hexahydrobenzo[h]quinazoline-9-carbonitrile;
(6aS,7S,10aR)-4-[3-(3-hydroxypropyl)phenyl]-2,7-dimethyl-8-oxo-10a-phenyl-5,6,6a,7,8,10a-hexahydrobenzo[h]quinazoline-9-carbonitrile;
(6aS,7S,10aR)-2-(5-bromo-2-hydroxyphenyl)-7-methyl-8-oxo-10a-phenyl-5,6,6a,7,8,10a-hexahydrobenzo[h]quinazoline-9-carbonitrile;
N-{4-[(6S,9aR)-8-cyano-6-methyl-7-oxo-9a-phenyl-4,5,5a,6,7,9a-hexahydro-2H-benzo[g]indazol-3-yl]phenyl}methanesulfonamide;
N-{3-[(6S,9aR)-8-cyano-6-methyl-7-oxo-9a-phenyl-4,5,5a,6,7,9a-hexahydro-2H-benzo[g]indazol-3-yl]phenyl}methanesulfonamide;
(6aS,7S,10aR)-2-(4-hydroxyphenyl)-7-methyl-8-oxo-10a-phenyl-5,6,6a,7,8,10a-hexahydrobenzo[h]quinazoline-9-carbonitrile;
(6S,9aR)-3-[4-(2-hydroxyethyl)phenyl]-6-methyl-7-oxo-9a-phenyl-4,5,5a,6,7,9a-hexahydro-2H-benzo[g]indazole-8-carbonitrile;
(6S,9aR)-3-[3-(2-hydroxyethyl)phenyl]-6-methyl-7-oxo-9a-phenyl-4,5,5a,6,7,9a-hexahydro-2H-benzo[g]indazole-8-carbonitrile;
(6S,9aR)-3-[1-(2-hydroxyethyl)-1H-pyrazol-4-yl]-6-methyl-7-oxo-9a-phenyl-4,5,5a,6,7,9a-hexahydro-2H-benzo[g]indazole-8-carbonitrile;
(6aS,7S,10aR)-4-(4'-aminobiphenyl-3-yl)-2,7-dimethyl-8-oxo-10a-phenyl-5,6,6a,7,8,10a-hexahydrobenzo[h]quinazoline-9-carbonitrile;
(6aS,7S,10aR)-4-(4'-hydroxybiphenyl-3-yl)-2,7-dimethyl-8-oxo-10a-phenyl-5,6,6a,7,8,10a-hexahydrobenzo[h]quinazoline-9-carbonitrile;
(6aS,7S,10aR)-10a-[4-(benzyloxy)phenyl]-7-methyl-8-oxo-5,6,6a,7,8,10a-hexahydrobenzo[h]quinazoline-9-carbonitrile;
(6aS,7S,10aR)-10a-(4-hydroxyphenyl)-7-methyl-8-oxo-5,6,6a,7,8,10a-hexahydrobenzo[h]quinazoline-9-carbonitrile;
(6aS,7S,10aR)-2,7-dimethyl-8-oxo-10a-phenyl-4-[4-(pyridin-4-yl)phenyl]-5,6,6a,7,8,10a-hexahydrobenzo[h]quinazoline-9-carbonitrile;
(6S,9aR)-3-[3-(3-hydroxypropyl)phenyl]-6-methyl-7-oxo-9a-phenyl-4,5,5a,6,7,9a-hexahydro-2H-benzo[g]indazole-8-carbonitrile;
N-{3'-[(6aS,7S,10aR)-9-cyano-2,7-dimethyl-8-oxo-10a-phenyl-5,6,6a,7,8,10a-hexahydrobenzo[h]quinazolin-4-yl]biphenyl-3-yl}methanesulfonamide;
3-{3-[(6aS,7S,10aR)-9-cyano-2,7-dimethyl-8-oxo-10a-phenyl-5,6,6a,7,8,10a-hexahydrobenzo[h]quinazolin-4-yl]phenyl}propyl acetate;
(6S,9aR)-3-[5-(hydroxymethyl)pyridin-3-yl]-6-methyl-7-oxo-9a-phenyl-4,5,5a,6,7,9a-hexahydro-2H-benzo[g]indazole-8-carbonitrile;
(6aS,7S,10aR)-4-[1-(2-hydroxyethyl)-1H-pyrazol-4-yl]-2,7-dimethyl-8-oxo-10a-phenyl-5,6,6a,7,8,10a-hexahydrobenzo[h]quinazoline-9-carbonitrile;
(6aS,7S,10aR)-10a-[3-(benzyloxy)phenyl]-7-methyl-8-oxo-5,6,6a,7,8,10a-hexahydrobenzo[h]quinazoline-9-carbonitrile;
(6aS,7S,10aR)-2,7-dimethyl-8-oxo-10a-phenyl-4-[4-(pyrimidin-5-yl)phenyl]-5,6,6a,7,8,10a-hexahydrobenzo[h]quinazoline-9-carbonitrile;
(6aS,7S,10aR)-2,7-dimethyl-8-oxo-10a-phenyl-4-(pyrimidin-5-yl)-5,6,6a,7,8,10a-hexahydrobenzo[h]quinazoline-9-carboxamide;
(6aS,7S,10aR)-7-methyl-8-oxo-10a-phenyl-5,6,6a,7,8,10a-hexahydrobenzo[h]quinazoline-9-carboxamide;
(6aS,7S,10aR)-4-(5-bromo-6-hydroxypyridin-3-yl)-2,7-dimethyl-8-oxo-10a-phenyl-5,6,6a,7,8,10a-hexahydrobenzo[h]quinazoline-9-carbonitrile;
(6aS,7S,10aR)-4-(6-hydroxypyridin-3-yl)-2,7-dimethyl-8-oxo-10a-phenyl-5,6,6a,7,8,10a-hexahydrobenzo[h]quinazoline-9-carbonitrile;
methyl 3'-[(6aS,7S,10aR)-9-cyano-2,7-dimethyl-8-oxo-10a-phenyl-5,6,6a,7,8,10a-hexahydrobenzo[h]quinazolin-4-yl]biphenyl-4-carboxylate;
3'-[(6aS,7S,10aR)-9-cyano-2,7-dimethyl-8-oxo-10a-phenyl-5,6,6a,7,8,10a-hexahydrobenzo[h]quinazolin-4-yl]biphenyl-4-carboxamide;
4-[(6aS,7S,10aR)-9-cyano-7-methyl-8-oxo-10a-phenyl-5,6,6a,7,8,10a-hexahydrobenzo[h]quinazolin-2-yl]benzamide;
(6aS,7S,10aR)-10a-(3-hydroxyphenyl)-7-methyl-8-oxo-5,6,6a,7,8,10a-hexahydrobenzo[h]quinazoline-9-carbonitrile;
4-[(6aS,7S,10aR)-9-cyano-7-methyl-8-oxo-10a-phenyl-5,6,6a,7,8,10a-hexahydrobenzo[h]quinazolin-2-yl]-N,N-dimethylbenzamide;
(6aS,7S,10aR)-2,7-dimethyl-4-[4-(1-methyl-1H-imidazol-5-yl)phenyl]-8-oxo-10a-phenyl-5,6,6a,7,8,10a-hexahydrobenzo[h]quinazoline-9-carbonitrile;
(5aS,6S,9aR)-6-methyl-7-oxo-9a-phenyl-3-(pyridazin-4-yl)-4,5,5a,6,7,9a-hexahydro-2H-benzo[g]indazole-8-carbonitrile;
{4-[(6S,9aR)-8-cyano-6-methyl-7-oxo-9a-phenyl-4,5,5a,6,7,9a-hexahydro-2H-benzo[g]indazol-3-yl]-1H-pyrazol-1-yl}acetic acid;
methyl 3-[(6aS,7S,10aR)-9-carbamoyl-7-methyl-8-oxo-6,6a,7,8-tetrahydrobenzo[h]quinazolin-10a(5H)-yl]benzoate;

(5aS,6S,9aR)-2,6-dimethyl-7-oxo-9a-phenyl-3-[4-(pyridin-4-yl)phenyl]-4,5,5a,6,7,9a-hexahydro-2H-benzo[g]indazole-8-carbonitrile;
(5aS,6S,9aR)-2,6-dimethyl-7-oxo-9a-phenyl-3-[4-(pyrimidin-5-yl)phenyl]-4,5,5a,6,7,9a-hexahydro-2H-benzo[g]indazole-8-carbonitrile;
(6aS,7S,10aR)-2,7-dimethyl-8-oxo-10a-phenyl-4-[4-(pyrimidin-5-yl)phenyl]-5,6,6a,7,8,10a-hexahydrobenzo[h]quinazoline-9-carboxamide;
(6aS,7S,10aR)-4-[3-bromo-4-(morpholin-4-yl)phenyl]-2,7-dimethyl-8-oxo-10a-phenyl-5,6,6a,7,8,10a-hexahydrobenzo[h]quinazoline-9-carbonitrile;
(6aS,7S,10aR)-2,7-dimethyl-8-oxo-10a-phenyl-4-(pyridin-3-ylamino)-5,6,6a,7,8,10a-hexahydrobenzo[h]quinazoline-9-carbonitrile;
(5aS,6S,9aR)-3-(3-bromophenyl)-2,6-dimethyl-7-oxo-9a-phenyl-4,5,5a,6,7,9a-hexahydro-2H-benzo[g]indazole-8-carbonitrile;
(5aS,6S,9aR)-3-(4'-aminobiphenyl-3-yl)-2,6-dimethyl-7-oxo-9a-phenyl-4,5,5a,6,7,9a-hexahydro-2H-benzo[g]indazole-8-carbonitrile;
N-{3'-[(5aS,6S,9aR)-8-cyano-2,6-dimethyl-7-oxo-9a-phenyl-4,5,5a,6,7,9a-hexahydro-2H-benzo[g]indazol-3-yl]biphenyl-3-yl}methanesulfonamide;
(5aS,6S,9aR)-2,6-dimethyl-7-oxo-9a-phenyl-3-[3-(pyridazin-4-yl)phenyl]-4,5,5a,6,7,9a-hexahydro-2H-benzo[g]indazole-8-carbonitrile;
N-{3'-[(5aS,6S,9aR)-8-cyano-2,6-dimethyl-7-oxo-9a-phenyl-4,5,5a,6,7,9a-hexahydro-2H-benzo[g]indazol-3-yl]biphenyl-4-yl}-N-(methylsulfonyl)methanesulfonamide;
(5aS,6S,9aR)-3-[3-(2-methoxypyrimidin-5-yl)phenyl]-2,6-dimethyl-7-oxo-9a-phenyl-4,5,5a,6,7,9a-hexahydro-2H-benzo[g]indazole-8-carbonitrile;
methyl 3-{3-[(6aS,7S,10aR)-9-cyano-2,7-dimethyl-8-oxo-10a-phenyl-5,6,6a,7,8,10a-hexahydrobenzo[h]quinazolin-4-yl]phenyl}propanoate;
3-{3-[(6aS,7S,10aR)-9-cyano-2,7-dimethyl-8-oxo-10a-phenyl-5,6,6a,7,8,10a-hexahydrobenzo[h]quinazolin-4-yl]phenyl}propanoic acid;
3-{3-[(6aS,7S,10aR)-9-cyano-2,7-dimethyl-8-oxo-10a-phenyl-5,6,6a,7,8,10a-hexahydrobenzo[h]quinazolin-4-yl]phenyl}propanamide;
(5aS,6S,9aR)-3-[1-(4-cyanophenyl)-1H-pyrazol-4-yl]-6-methyl-7-oxo-9a-phenyl-4,5,5a,6,7,9a-hexahydro-2H-benzo[g]indazole-8-carbonitrile;
(5aS,6S,9aR)-6-methyl-7-oxo-9a-phenyl-3-[1-(pyridin-3-yl)-1H-pyrazol-4-yl]-4,5,5a,6,7,9a-hexahydro-2H-benzo[g]indazole-8-carbonitrile;
(5aS,6S,9aR)-6-methyl-7-oxo-9a-phenyl-3-[1-(pyridin-4-yl)-1H-pyrazol-4-yl]-4,5,5a,6,7,9a-hexahydro-2H-benzo[g]indazole-8-carbonitrile;
rac-(5aS,6S,9aR)-2,6-dimethyl-7-oxo-9a-phenyl-4,5,5a,6,7,9a-hexahydro-2H-benzo[g]indazole-8-carbonitrile;
rac-(5aS,6S,9aR)-1,6-dimethyl-7-oxo-9a-phenyl-4,5,5a,6,7,9a-hexahydro-1H-benzo[g]indazole-8-carbonitrile;
rac-(5aS,6S,9aR)-9a-benzyl-2,6-dimethyl-7-oxo-4,5,5a,6,7,9a-hexahydro-2H-benzo[g]indazole-8-carbonitrile;
rac-(5aS,6S,9aR)-9a-benzyl-1,6-dimethyl-7-oxo-4,5,5a,6,7,9a-hexahydro-1H-benzo[g]indazole-8-carbonitrile;
rac-(5aS,6S,9aR)-9a-benzyl-2,6-dimethyl-7-oxo-3-phenyl-4,5,5a,6,7,9a-hexahydro-2H-benzo[g]indazole-8-carbonitrile;
rac-(5aS,6S,9aR)-9a-benzyl-2,6-dimethyl-7-oxo-3-phenyl-4,5,5a,6,7,9a-hexahydro-2H-benzo[g]indazole-8-carboxamide;
3'-[(5aS,6S,9aR)-8-cyano-2,6-dimethyl-7-oxo-9a-phenyl-4,5,5a,6,7,9a-hexahydro-2H-benzo[g]indazol-3-yl]biphenyl-3-carboxylic acid;
(5aS,6S,9aR)-2,6-dimethyl-7-oxo-9a-phenyl-3-[3-(1H-pyrazol-4-yl)phenyl]-4,5,5a,6,7,9a-hexahydro-2H-benzo[g]indazole-8-carbonitrile;
N-({3'-[(5aS,6S,9aR)-8-cyano-2,6-dimethyl-7-oxo-9a-phenyl-4,5,5a,6,7,9a-hexahydro-2H-benzo[g]indazol-3-yl]biphenyl-4-yl}methyl)methanesulfonamide;
N-{3'-[(5aS,6S,9aR)-8-cyano-2,6-dimethyl-7-oxo-9a-phenyl-4,5,5a,6,7,9a-hexahydro-2H-benzo[g]indazol-3-yl]biphenyl-4-yl}methanesulfonamide;
(5aS,6S,9aR)-3-(4'-hydroxybiphenyl-3-yl)-2,6-dimethyl-7-oxo-9a-phenyl-4,5,5a,6,7,9a-hexahydro-2H-benzo[g]indazole-8-carbonitrile;
3'-[(5aS,6S,9aR)-8-cyano-2,6-dimethyl-7-oxo-9a-phenyl-4,5,5a,6,7,9a-hexahydro-2H-benzo[g]indazol-3-yl]biphenyl-4-carboxamide;
(6aS,7S,10aR)-2,7-dimethyl-8-oxo-10a-phenyl-4-(pyridazin-4-yl)-5,6,6a,7,8,10a-hexahydrobenzo[h]quinazoline-9-carbonitrile;
(6aS,7S,10aR)-7-methyl-2-[4-(3-methyl-1,2,4-oxadiazol-5-yl)phenyl]-8-oxo-10a-phenyl-5,6,6a,7,8,10a-hexahydrobenzo[h]quinazoline-9-carbonitrile;
(6aS,7S,10aR)-10a-(4-methoxyphenyl)-2,7-dimethyl-4-(1-methyl-1H-imidazol-5-yl)-8-oxo-5,6,6a,7,8,10a-hexahydrobenzo[h]quinazoline-9-carbonitrile;
methyl 4-[(6aS,7S,10aR)-9-cyano-2,7-dimethyl-4-(1-methyl-1H-imidazol-5-yl)-8-oxo-6,6a,7,8-tetrahydrobenzo[h]quinazolin-10a(5H)-yl]benzoate;
methyl 4-[(6aS,7S,10aR)-4-(4-bromo-1-methyl-1H-imidazol-5-yl)-9-cyano-2,7-dimethyl-8-oxo-6,6a,7,8-tetrahydrobenzo[h]quinazolin-10a(5H)-yl]benzoate;
(5aS,6S,9aR)-2,6-dimethyl-7-oxo-9a-phenyl-3-(pyrimidin-5-yl)-4,5,5a,6,7,9a-hexahydro-2H-benzo[g]indazole-8-carbonitrile;
(5aS,6S,9aR)-2,6-dimethyl-7-oxo-9a-phenyl-3-(pyridin-3-yl)-4,5,5a,6,7,9a-hexahydro-2H-benzo[g]indazole-8-carbonitrile; and
(5aS,6S,9aR)-1,6-dimethyl-7-oxo-9a-phenyl-3-(pyrimidin-5-yl)-4,5,5a,6,7,9a-hexahydro-1H-benzo[g]indazole-8-carbonitrile.

23. The compound, or a salt thereof, of claim 1, wherein the salt is a pharmaceutically acceptable salt.

24. A pharmaceutical composition comprising a therapeutically effective amount of claim 1, or a pharmaceutically acceptable salt thereof, in combination with a pharmaceutically acceptable carrier.

* * * * *

UNITED STATES PATENT AND TRADEMARK OFFICE
CERTIFICATE OF CORRECTION

PATENT NO.         : 9,464,082 B2
APPLICATION NO.    : 14/604129
DATED              : October 11, 2016
INVENTOR(S)        : Pamela Donner et al.

It is certified that error appears in the above-identified patent and that said Letters Patent is hereby corrected as shown below:

In the Claims

In Claim 1, Column 309, Line 56, delete "Or" and insert -- or -- therefor.

In Claim 1, Column 310, Line 51, delete "$R^{G1b}(O)CN(R^{G1a})$—" and insert -- $R^{G1b}OC(O)N(R^{G1a})$— -- therefor.

In Claim 1, Column 310, Line 52, delete "$R^{G1b}O2SN(R^{G1a})$—" and insert -- $R^{G1b}O_2SN(R^{G1a})$— -- therefor.

In Claim 1, Column 311, Line 31, delete "$C_1$-$C_2$-$C_6$-alkenyl" and insert -- $C_1$-$C_6$-alkyl, $C_2$-$C_6$-alkenyl -- therefor.

In Claim 1, Column 311, Line 36, delete "$C_6$-alkyl" and insert -- $C_1$-$C_6$-alkyl -- therefor.

In Claim 1, Column 311, Line 48, before the term $C_2$-$C_6$-alkenyl, insert -- $C_1$-$C_6$-alkyl, --.

In Claim 22, Column 318, Line 49, delete "5,6,6a,7,8, 0a" and insert -- 5,6,6a,7,8,10a -- therefor.

In Claim 24, Column 324, Line 55, before the term claim, insert -- a compound of --.

Signed and Sealed this
Twenty-third Day of May, 2017

Michelle K. Lee
*Director of the United States Patent and Trademark Office*